US011492335B2

(12) United States Patent
Han et al.

(10) Patent No.: US 11,492,335 B2
(45) Date of Patent: *Nov. 8, 2022

(54) ARYL OR HETEROARYL TRIAZOLONE DERIVATIVES OR SALTS THEREOF, OR PHARMACEUTICAL COMPOSITIONS COMPRISING THE SAME

(71) Applicant: YUHAN CORPORATION, Seoul (KR)

(72) Inventors: Tae Dong Han, Yongin-si (KR); Hee Jae Tak, Yongin-si (KR); Eun Kyung Kim, Hwaseong-si (KR); Su Bin Choi, Yongin-si (KR); Dong Hoon Kim, Suwon-si (KR); Sol Park, Yongin-si (KR); Eun Hye Jung, Yongin-si (KR); Hyun Ho Choi, Suwon-si (KR); Tae Wang Kim, Yongin-si (KR); Mi Kyeong Ju, Suwon-si (KR); Na Ry Ha, Seoul (KR)

(73) Assignee: YUHAN CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/104,557

(22) Filed: Nov. 25, 2020

(65) Prior Publication Data

US 2021/0147368 A1    May 20, 2021

Related U.S. Application Data

(63) Continuation of application No. 16/721,020, filed on Dec. 19, 2019, now Pat. No. 10,899,719, which is a continuation of application No. 16/359,984, filed on Mar. 20, 2019, now Pat. No. 10,562,865.

(30) Foreign Application Priority Data

Mar. 21, 2018  (KR) .................. 10-2018-0032554

(51) Int. Cl.
| | |
|---|---|
| C07D 401/14 | (2006.01) |
| C07D 403/04 | (2006.01) |
| C07D 403/14 | (2006.01) |
| C07D 409/10 | (2006.01) |
| C07D 413/14 | (2006.01) |
| C07D 417/04 | (2006.01) |
| C07D 417/14 | (2006.01) |
| C07D 249/08 | (2006.01) |
| C07D 401/04 | (2006.01) |
| C07D 405/10 | (2006.01) |
| C07D 407/14 | (2006.01) |
| C07D 401/10 | (2006.01) |
| C07D 403/10 | (2006.01) |
| C07D 405/14 | (2006.01) |
| C07D 413/10 | (2006.01) |
| C07D 417/10 | (2006.01) |
| C07D 249/12 | (2006.01) |

(52) U.S. Cl.
CPC ......... *C07D 249/08* (2013.01); *C07D 249/12* (2013.01); *C07D 401/04* (2013.01); *C07D 401/10* (2013.01); *C07D 401/14* (2013.01); *C07D 403/04* (2013.01); *C07D 403/10* (2013.01); *C07D 403/14* (2013.01); *C07D 405/10* (2013.01); *C07D 405/14* (2013.01); *C07D 407/14* (2013.01); *C07D 409/10* (2013.01); *C07D 413/10* (2013.01); *C07D 413/14* (2013.01); *C07D 417/04* (2013.01); *C07D 417/10* (2013.01); *C07D 417/14* (2013.01)

(58) Field of Classification Search
CPC .. C07D 401/14; C07D 403/04; C07D 403/14; C07D 409/10; C07D 413/14; C07D 417/04; C07D 417/14
See application file for complete search history.

(56) References Cited

U.S. PATENT DOCUMENTS

| | | | |
|---|---|---|---|
| 10,562,865 B2 | 2/2020 | Han et al. | |
| 10,899,719 B2 | 1/2021 | Han et al. | |
| 2005/0096360 A1 | 5/2005 | Salter-Cid et al. | |
| 2007/0293548 A1 | 12/2007 | Wang et al. | |
| 2008/0249151 A1 | 10/2008 | Sweeney et al. | |
| 2010/0029697 A1 | 2/2010 | Debenham et al. | |
| 2010/0298330 A1 | 11/2010 | McDonald et al. | |
| 2012/0225878 A1 | 9/2012 | Bouillot et al. | |
| 2015/0158813 A1 | 6/2015 | Deodhar et al. | |
| 2016/0009721 A1 | 1/2016 | Wu et al. | |
| 2017/0360756 A1 | 12/2017 | Brown et al. | |
| 2018/0104198 A1 | 4/2018 | Rippmann et al. | |
| 2018/0297987 A1 | 10/2018 | Coates et al. | |

(Continued)

FOREIGN PATENT DOCUMENTS

| | | |
|---|---|---|
| EP | 0000014 A1 | 12/1978 |
| WO | WO-2005/014583 A1 | 2/2005 |

(Continued)

OTHER PUBLICATIONS

Dobosz, et al., "Synthesis of 1-(3-Amino-2-Hydroksypropyl)-4-Phenyl-1,2,4-Triazolin-5-One and 1-(3-Amino-2-Hydroksypropyl)-3,4-Diphenyl-1,2,4-Triazolin-5-One Derivatives", Acta Poloniae Pharmaceutica—Drug Research 57(5): 363-368 (2000).

(Continued)

*Primary Examiner* — Laura L Stockton
(74) *Attorney, Agent, or Firm* — Sheppard Mullin Richter & Hampton LLP

(57) ABSTRACT

The present technology provides aryl or heteroaryl triazolone derivatives or pharmaceutically acceptable salts thereof, preparation processes thereof, pharmaceutical compositions comprising the same, and the use thereof. The aryl or heteroaryl triazolone derivatives or their pharmaceutically acceptable salts exhibit selective inhibitory activity on VAP-1 and therefore can be usefully applied, e.g., for the treatment and prophylaxis of nonalcoholic hepatosteatosis (NASH).

17 Claims, No Drawings

(56) References Cited

U.S. PATENT DOCUMENTS

| | | |
|---|---|---|
| 2019/0308944 A1 | 10/2019 | Han et al. |
| 2019/0322655 A1 | 10/2019 | Han et al. |
| 2020/0223808 A1 | 7/2020 | Han et al. |
| 2020/0223827 A1 | 7/2020 | Han et al. |
| 2020/0223844 A1 | 7/2020 | Han et al. |
| 2021/0317110 A1 | 10/2021 | Han et al. |

FOREIGN PATENT DOCUMENTS

| | | |
|---|---|---|
| WO | WO-2006/138695 A1 | 12/2006 |
| WO | WO-2007120528 | 10/2007 |
| WO | WO-2008/119662 A1 | 10/2008 |
| WO | WO-2009/066152 A2 | 5/2009 |
| WO | WO-2010/096722 A1 | 8/2010 |
| WO | WO-2013/134562 A1 | 9/2013 |
| WO | WO-2013/163675 A1 | 11/2013 |
| WO | WO-2016/106106 A2 | 6/2016 |
| WO | WO-2017/046738 A1 | 3/2017 |
| WO | WO-2017/136870 A1 | 8/2017 |
| WO | WO-2017/191112 A1 | 11/2017 |
| WO | WO-2018/073154 A1 | 4/2018 |
| WO | WO-2018/157190 A1 | 9/2018 |
| WO | WO-2018196677 | 11/2018 |
| WO | WO-2018233633 | 12/2018 |
| WO | WO-2019101086 | 5/2019 |
| WO | WO-2019129213 | 7/2019 |
| WO | WO-2019/180644 A1 | 9/2019 |
| WO | WO-2019/180646 A1 | 9/2019 |
| WO | WO-2020/063854 A1 | 4/2020 |
| WO | WO-2020/069330 A2 | 4/2020 |
| WO | WO-2020/069335 A2 | 4/2020 |
| WO | WO-2020/083264 A1 | 4/2020 |
| WO | WO-2020/086747 A2 | 4/2020 |
| WO | WO-2020063696 | 4/2020 |
| WO | WO-2020/121261 A1 | 6/2020 |
| WO | WO-2020/121263 A1 | 6/2020 |
| WO | WO-2020/143763 A1 | 7/2020 |

OTHER PUBLICATIONS

International Search Report and Written Opinion on PCT/IB2019/060736 dated Apr. 6, 2020.
International Search Report and Written Opinion on PCT/IB2019/060738 dated Apr. 6, 2020.
International Search Report and Written Opinion, issued in Int'l. App. No. PCT/IB2019/052276, 13 pages (dated Aug. 1, 2019).
International Search Report and Written Opinion, issued in Int'l. App. No. PCT/IB2019/052278, 12 pages (dated Aug. 1, 2019).
Kirton, et al., "Function-blocking antibodies to human vascular adhesion protein-1: A potential anti-inflammatory therapy", Eur. J. Immunol. 35: 3119-3130 (2005).
McDonald, et al., "Semicarbazide Sensitive Amine Oxidase and Vascular Adhesion Protein-1: One Protein Being Validated as a Therapeutic Target for Inflammatory Diseases", Chapter 15, Annual Reports in Medicinal Chemistry 42: 229-243 (2007).
Noda, et al., "Inhibition of vascular adhesion protein-1 suppresses endotoxin-induced uveitis", The FASEB Journal 22(4): 1094-1103 (2008).
Notice of Allowance on U.S. Appl. No. 16/359,984 dated Sep. 27, 2019.
Notice of Allowance on U.S. Appl. No. 16/721,020 dated Aug. 27, 2020.
Salmi, et al., "VAP-1: an adhesin and an enzyme", Trends in Immunology 22(4): 211-216 (2001).
Salter-Cid, et al., "Anti-Inflammatory Effects of Inhibiting the Amine Oxidase Activity of Semicarbazide-Sensitive Amine Oxidase", J. Pharmacol. Exp. Ther. 315(2): 553-562 (2005).
Sheng, et al., "Design and synthesis of novel triazole antifungal derivatives by structure-based bioisosterism", Eur. J. Med. Chem. 46(11): 5276-5282 (2011).
Still, et al., "Rapid Chromatographic Technique for Preparative Separations with Moderate Resolution", J. Org. Chem. 43(14): 2923-2925 (1978).
Stolen, et al., "Absence of the Endothelial Oxidase AOC3 Leads to Abnormal Leukocyte Traffic In Vivo", Immunity 22: 105-115 (2005).
Sun, et al., "Discovery of triazolone derivatives as novel, potent stearoyl-CoA desaturase-1 (SCD1) inhibitors", Bioorganic & Medicinal Chemistry 23(3): 455-465 (2015).
Weston, et al., "Vascular adhesion protein-1 promotes liver inflammation and drives hepatic fibrosis", The Journal of Clinical Investigation 125(2): 501-520 (2015).
Chemical Abstracts STN Registry Database record for RN 1700586-71-5, entered into STN on May 7, 2015. 1 page.
Extended European Search Report for European Application No. 19770858.9 dated Nov. 3, 2021. 6 pages.
Extended European Search Report for European Application No. 19772403.2 dated Nov. 18, 2021. 7 pages.
Salmi et al., Vascular Adhesion Protein-1: A Cell Surface Amine Oxidase in Translation. Antioxidants & Redox Signaling 2019, vol. 30, pp. 314-332.

ARYL OR HETEROARYL TRIAZOLONE DERIVATIVES OR SALTS THEREOF, OR PHARMACEUTICAL COMPOSITIONS COMPRISING THE SAME

CROSS-REFERENCE TO RELATED APPLICATIONS

This application is a continuation of U.S. patent application Ser. No. 16/721,020, filed on Dec. 19, 2019, and issued as U.S. Pat. No. 10,899,719, which is a continuation of U.S. patent application Ser. No. 16/359,984, filed on Mar. 20, 2019, and issued as U.S. Pat. No. 10,562,865, which claims priority to Korean Patent Application No. 10-2018-0032554, filed on Mar. 21, 2018, all of which are incorporated by reference herein in their entireties.

FIELD

The present technology relates to aryl or heteroaryl triazolone derivatives or pharmaceutically acceptable salts thereof having inhibitory activity on vascular adhesion protein (VAP-1), a process for the preparation thereof, a pharmaceutical composition comprising the same, and uses thereof.

BACKGROUND

Vascular adhesion protein-1 (VAP-1) is a semicarbazide-sensitive amine oxidase (SSAO), which is abundantly present in human plasma. VAP-1 is an ectoenzyme comprising a short cytoplasmic tail, a single transmembrane domain, and an extracellular domain with large and high glycosylation containing the center of activity. In addition, VAP-1 exists not only as a membrane-bound form in the endothelium, but also as a soluble form in serums (soluble VAP-1, sVAP-1). This form was shown to be a product cleaved from the membrane-bound VAP-1, and appears to have similar properties as the tissue-bound form. It has been also reported that VAP-1 is normally stored in intracellular granules within endothelial cells, but when an inflammatory response is evoked in response to inflammatory stimuli, it is translocated onto the cell membrane, and its expression is upregulated, and therefore, it is expressed more strongly in inflamed tissues than in normal tissues.

Substrates for VAP-1 include endogenous methylamine and aminoacetone as well as some xenobiotic amines such as tyramine and benzylamine.

VAP-1 has two physiological functions: the first is amine oxidase activity stated earlier in this section, and the second is cell adhesion activity. Due to these two activities, VAP-1 has been shown to play a key role in the leakage of inflammatory cells as it acts as an adhesion protein for leukocytes in inflamed sites [*Trends Immunol.* (2001) 22: 211]. VAP-1-deficient transgenic mice are healthy, develop normally, and fertile, and phenotypically normal, but exhibit a marked decrease in the inflammatory responses evoked in response to various inflammatory stimuli [*Immunity.* (2005) 22: 105].

In addition, inhibitory activity of VAP-1 in multiple animal models of human diseases (e.g., carrageenan-induced paw inflammation, oxazolone-induced colitis, lipopolysaccharide-induced lung inflammation, collagen-induced arthritis, endotoxin-induced uveitis) by the use of antibodies or small molecules has been shown to prevent leukocyte from rolling, adhering, and leaking, and reduce levels of inflammatory cytokines and chemokines, thereby reducing the severity of the disease [*Eur J Immunol.* (2005) 35: 3119; *J Pharmacol Exp Ther.* (2005) 315: 553; *Annu Rep Med Chem.* (2007) 42: 229; *FASEB J.* (2008) 22: 1094]. Inflammation is the first reaction of the immune system to infection or stimulus and in such a process, the movement of leukocytes into the tissue through circulation is an important step. The leukocytes are first bound to adhesion proteins and then adhered to the endothelium before they start to pass through blood vessel walls. VAP-1 is highly expressed in endothelial venules (HEV) such as high endothelial venules in lymphoid organs, as well as hepatic sinusoidal endothelial cells, (HSEC), smooth muscle cells, and adipocytes. The VAP-1 expression on the cell surface of endothelial cells is strictly regulated and is increased during inflammation. VAP-1 activates NF-κB when it is present in the substrate, and the NF-κB is activated within the HSEC while E-selectin and chemokine IL-8 that are other adhesion molecules are upregulated ex vivo. This suggests that VAP-1 may be a key factor for the regulation of the inflammatory response, and it seems therefore likely that VAP-1 inhibitors may be effective anti-inflammatory drugs in a wide range of human diseases.

Nonalcoholic fatty liver disease (NAFLD), histologically, encompasses simple steatosis, nonalcoholic hepatosteatosis (NASH), and liver cirrhosis. Among these, unlike simple steatosis (non-alcoholic fatty liver, NAFL), NASH potentially progresses to liver cirrhosis and hepatoma (hepatocellular carcinoma). In NASH, insulin resistance is known to play an important role in the progression of disease, along with oxidative stress, inflammatory cascade, and fibrosis. In patients with NAFLD, sVAP-1 levels were found to be elevated, and in VAP-1 knockout (K/O) mice, carbon tetrachloride-induced liver fibrosis was reduced compared with that in wild type animals. In addition, improvement of liver fibrosis by VAP-1 inhibition following administration of VAP-1 antibody was identified by histological changes [*J Clin Invest* (2015) 125: 501]. Thus, VAP-1 was found to be associated with NASH in clinical studies and animal models of diseases. Inhibitory activity of VAP-1 in the carbon tetrachloride-induced animal model appears to be due to a reduction in infiltration of leukocytes such as T cells, B cells, NKT cells, and NK cells observed in liver fibrosis, and VAP-1 inhibitors have the potential for treating fibrotic diseases.

Thus, a substance that inhibits VAP-1 may be applied to prevention and treatment of various inflammatory diseases and fibrotic diseases.

SUMMARY

The present inventors found that specific aryl or heteroaryl triazolone derivatives having fluoroallylamine groups or their pharmaceutically acceptable salts exhibit selective inhibitory activity on VAP-1. Therefore, the aryl or heteroaryl triazolone derivatives and their salts can be usefully used in the treatment and prophylaxis of various VAP-1 mediated disease, for example, nonalcoholic hepatosteatosis (NASH).

Therefore, the present technology provides the aryl or heteroaryl triazolone derivatives or their pharmaceutically acceptable salts, preparation processes thereof, pharmaceutical compositions comprising the same, and the use thereof.

In accordance with one aspect of the present technology, there is provided an aryl or heteroaryl triazolone derivative or its pharmaceutically acceptable salt.

In accordance with another aspect of the present technology, there is provided a preparation process of the aryl or heteroaryl triazolone derivative.

In accordance with another aspect of the present technology, there is provided a pharmaceutical composition comprising the aryl or heteroaryl triazolone derivative as an active ingredient.

In accordance with another aspect of the present technology, there is provided a method of treatment comprising administering the aryl or heteroaryl triazolone derivative.

In accordance with another aspect of the present technology, there is provided the use of the aryl or heteroaryl triazolone derivative or its pharmaceutically acceptable salt in the manufacture of a medicament for selective inhibition of vascular adhesion protein-1.

It was found by the present technology that specific aryl or heteroaryl triazolone derivatives having fluoroallylamine groups, or their pharmaceutically acceptable salts, exhibit selective inhibitory activity on VAP-1. Therefore, the compounds according to the present technology or pharmaceutically acceptable salts thereof can be usefully applied for the treatment and prophylaxis of VAP-1 mediated various diseases, for example, nonalcoholic hepatosteatosis (NASH).

In another aspect, provided herein are compounds of Formula X

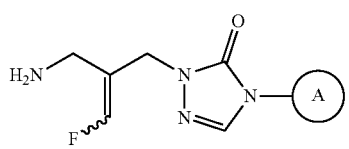

(Formula X)

or an isomer thereof, or a pharmaceutically acceptable salt thereof; wherein A is an aryl or heteroaryl group, said heteroaryl group has 1 to 5 heteroatom ring members chosen from O, N, or S, and said aryl or heteroaryl group is optionally substituted with one to three substituents chosen from $C_{1-3}$ alkyl, $C_{1-3}$ alkoxy, halogen, benzyloxy, —R, —CH$_2$—R, —CH=CH—R, and —C≡C—R; and R is substituted or unsubstituted cyclic ring, optionally containing 1 to 5 heteroatom ring members chosen from O, N, or S, and the cyclic ring is aromatic or non-aromatic. In some embodiments, A is selected from phenyl, naphthalene, pyridine, pyrimidine, pyrazine, triazine, thiazole, thiophene, pyrrole, pyrazole, imidazole, triazole, tetrazole, furan, oxazole, isoxazole, oxadiazole, and thiadiazole. In some embodiments, A is selected from phenyl, pyridine, pyrazine, and thiazole.

In another aspect, provided herein are compounds of Formula 1 below

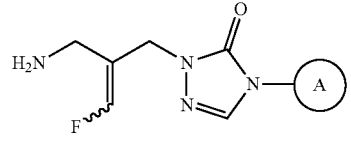

(Formula 1)

or an isomer thereof, or a pharmaceutically acceptable salt thereof; wherein A is an aryl or heteroaryl group selected from the group consisting of phenyl, pyridine, pyrazine, and thiazole, wherein said aryl or heteroaryl group is optionally substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R, wherein said R is a cyclic ring selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydropyrido[3,2-b][1,4]oxazine, pyrido[2,3-b][1,4]oxazin-2-one, pyrido[3,2-b][1,4]oxazin-3-one, and dibenzo[b,d]furan, wherein said cyclic ring is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$ alkyl sulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, oxazolyl, oxadiazolyl, cyclopropyl-oxadiazolyl, $C_{1-6}$ alkyl-oxadiazolyl, and oxadiazol-5-onyl. In some embodiments, A is pyridine. In some embodiments, said aryl or heteroaryl group is substituted with one or two substituents selected from the group consisting of $C_{1-3}$ alkyl, halogen, —R, and —C≡C—R. In some embodiments, said R is a cyclic ring selected from the group consisting of benzene, pyridine, and pyrazole. In some embodiments, said cyclic ring is unsubstituted; or substituted with a substituent selected from the group consisting of $C_{1-6}$ alkyl, trifluoromethyl, and oxazolyl. In some embodiments, A is pyridine, wherein said pyridine is substituted with one or two substituents selected from the group consisting of $C_{1-3}$ alkyl, halogen, —R, and —C≡C—R, wherein said R is a cyclic ring selected from the group consisting of benzene, pyridine, and pyrazole, wherein said cyclic ring is unsubstituted; or substituted with a substituent selected from the group consisting of $C_{1-6}$ alkyl, trifluoromethyl, and oxazolyl. In some embodiments, the compound is selected from Table 1, or an isomer thereof, or a pharmaceutically acceptable salt thereof.

In another aspect, provided herein are compounds of Formula 10:

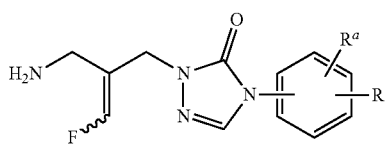

(Formula 10)

or an isomer thereof, or a pharmaceutically acceptable salt thereof, wherein R is a substituted or unsubstituted cyclic ring, optionally containing at least one heteroatom, and the cyclic ring is aromatic or non-aromatic; and $R^a$ is hydrogen, $C_{1-3}$ alkyl, $C_{1-3}$ alkoxy, or halogen. In some embodiments, the compound is of Formula 10a:

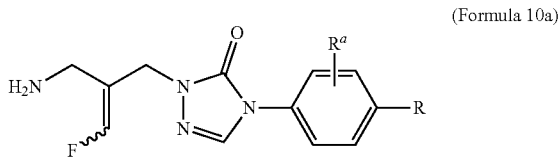
(Formula 10a)

or an isomer thereof, or a pharmaceutically acceptable salt thereof. In some embodiments, the compound is of Formula 10b:

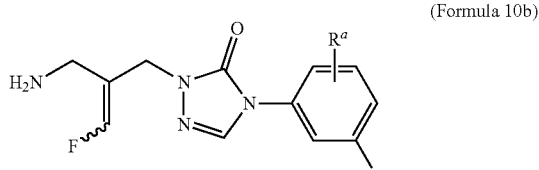
(Formula 10b)

or an isomer thereof, or a pharmaceutically acceptable salt thereof.

In another aspect, provided herein are compounds of Formula 11:

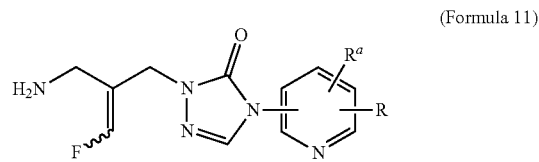
(Formula 11)

or an isomer thereof, or a pharmaceutically acceptable salt thereof, wherein R is a substituted or unsubstituted cyclic ring, optionally containing at least one heteroatom, and the cyclic ring is aromatic or non-aromatic; and $R^a$ is hydrogen, $C_{1-3}$ alkyl, $C_{1-3}$ alkoxy, or halogen. In some embodiments, the compound is of Formula 11a:

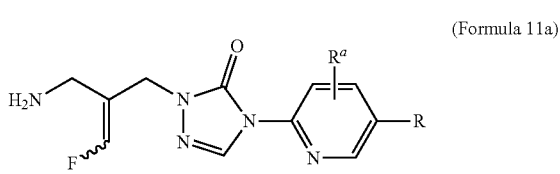
(Formula 11a)

or an isomer thereof, or a pharmaceutically acceptable salt thereof. In some embodiments, the compound is of Formula 11b:

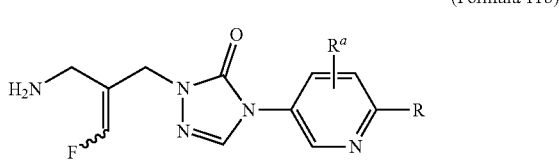
(Formula 11b)

or an isomer thereof, or a pharmaceutically acceptable salt thereof. In some embodiments, the compound is of Formula 11c:

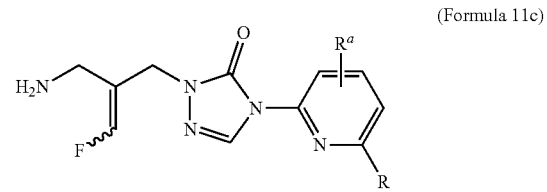
(Formula 11c)

or an isomer thereof, or a pharmaceutically acceptable salt thereof. In some embodiments, the compound is of Formula 11d:

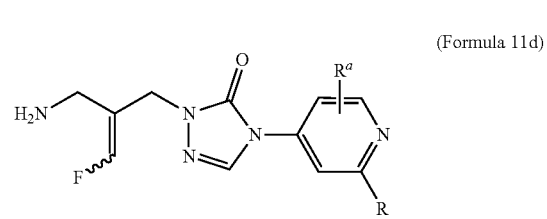
(Formula 11d)

or an isomer thereof, or a pharmaceutically acceptable salt thereof. In some embodiments, the compound is of Formula 11e:

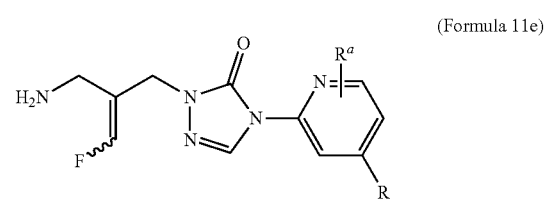
(Formula 11e)

or an isomer thereof, or a pharmaceutically acceptable salt thereof.

In another aspect, provided herein are compounds of Formula 12:

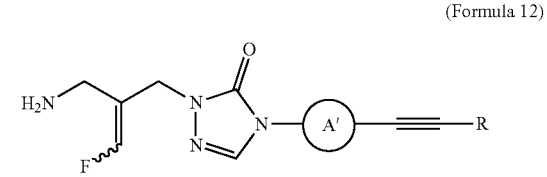
(Formula 12)

or an isomer thereof, or a pharmaceutically acceptable salt thereof, wherein A' is pyridine; and R is a substituted or unsubstituted cyclic ring, optionally containing at least one heteroatom, and the cyclic ring is aromatic or non-aromatic.

In some embodiments of the compound of Formulae X, 10, 10a, 10b, 11, 11a, 11b, 11c, 11d, 11e, and 12, R is selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido

[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan; and R is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$alkylsulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, isoxazolyl, oxazolyl, oxadiazolyl, cyclopropyl-oxadiazolyl, $C_{1-6}$ alkyl-oxadiazolyl, and oxadiazol-5-onyl.

In another aspect, provided herein are pharmaceutical compositions comprising a compound disclosed herein and at least one pharmaceutically acceptable excipient.

In another aspect, provided herein are methods of selectively inhibiting vascular adhesion protein (VAP-1), comprising administering, to a mammal, a therapeutically effective amount of a compound disclosed herein.

In another aspect, provided herein are methods of treating NASH in a subject in need thereof, the method comprising administering to the subject a therapeutically effective amount of a compound disclosed herein, or a therapeutically effective amount of a pharmaceutical composition disclosed herein.

In another aspect, provided herein are uses of a compound disclosed herein for the manufacture of a medicament for the treatment of NASH.

In another aspect, provided herein are compounds disclosed herein for use in treating NASH.

In another aspect, provided herein are compositions disclosed herein for use in treating NASH.

In another aspect, provided herein are compounds disclosed herein for use in selectively inhibiting VAP-1.

In another aspect, provided herein are compositions disclosed herein for use in selectively inhibiting VAP-1.

In another aspect, provided herein are methods of treating a disease mediated by VAP-1 in a subject in need thereof, the method comprising administering to the subject a therapeutically effective amount of a compound disclosed herein or a therapeutically effective amount of a pharmaceutical composition disclosed herein. In some embodiments, the disease mediated by VAP-1 is selected from the group consisting of lipid and lipoprotein disorders, conditions and diseases which result from chronic fatty and fibrotic degeneration of organs due to accumulated lipid and specifically triglyceride accumulation and subsequent activation of profibrotic pathways, Type I or Type II Diabetes and clinical complications of Type I and Type II Diabetes, chronic intrahepatic or some forms of extrahepatic cholestatic conditions, liver fibrosis, acute intraheptic cholestatic conditions, obstructive or chronic inflammatory disorders that arise out of improper bile composition, gastrointestinal conditions with a reduced uptake of dietary fat and fat-soluble dietary vitamins, inflammatory bowel diseases, obesity and metabolic syndrome (combined conditions of dyslipidemia, diabetes and abnormally high body-mass index), persistent infections by intracellular bacteria or parasitic protozoae, non-malignant hyperproliferative disorders, malignant hyperproliferative disorders, colon adenocarcinoma and hepatocellular carcinoma in particular, liver steatosis and associated syndromes, Hepatitis B infection, Hepatitis C infection and/or of cholestatic and fibrotic effects that are associated with alcohol-induced cirrhosis or with viral-borne forms of hepatitis, liver failure or liver malfunction as an outcome of chronic liver diseases or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

In another aspect, provided herein are methods of preparing a compound of Formula 1a, or an isomer thereof, or a pharmaceutically acceptable salt thereof,

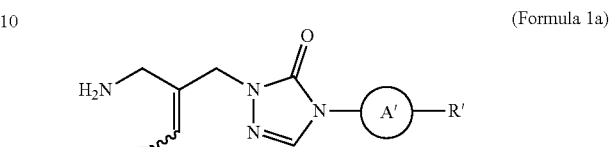
(Formula 1a)

the method comprising (a) reacting a compound of Formula 2 with a compound of Formula 3a or a compound of Formula 3b to obtain a compound of Formula 1aa;

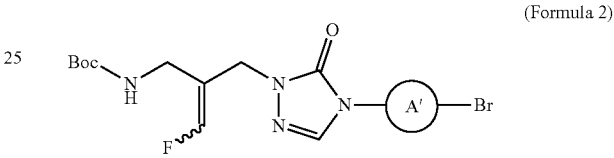
(Formula 2)

(Formula 3a)

(Formula 3b)

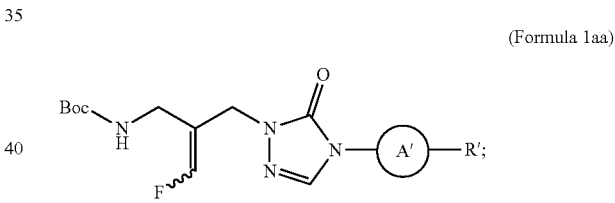
(Formula 1aa)

wherein Boc is an amine protecting group; A' is an aryl or heteroaryl group selected from the group consisting of phenyl, pyridine, pyrazine, and thiazole; Z is hydroxy or $C_{1-3}$ alkoxy, or two Z together with the boron to which they are attached form

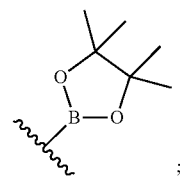 [SMILES: *B1OC(C)(C)C(C)(C)O1]

R' is one to three groups independently selected from the group consisting of —R, —CH$_2$—R, —CH═CH—R, and —C≡C—R; and R is a substituted or unsubstituted cyclic ring, optionally containing at least one heteroatom, and the cyclic ring is aromatic or non-aromatic; and (b) removing Boc from the compound of Formula 1aa under reaction conditions to obtain the compound of Formula 1a, or the isomer thereof, or the pharmaceutically acceptable salt thereof.

In some embodiments, the cyclic ring is selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan; wherein said cyclic ring is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$ alkyl sulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, isoxazolyl, oxazolyl, oxadiazolyl, cyclopropyl-oxadiazolyl, $C_{1-6}$ alkyl-oxadiazolyl, and oxadiazol-5-onyl.

DETAILED DESCRIPTION

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "comprising" or "comprises" is intended to mean that the compositions and methods include the recited elements, but not excluding others. A composition or method "consisting essentially" of the elements as defined herein would not exclude other materials or steps that do not materially affect the basic and novel characteristic(s) of the claimed technology. "Consisting of" shall mean excluding more than trace elements of other ingredients and substantial method steps. Embodiments defined by each of these transition terms are within the scope of this technology. When an embodiment is defined by one of these terms (e.g., "comprising") it should be understood that this disclosure also includes alternative embodiments, such as "consisting essentially of" and "consisting of" for said embodiment.

"Substantially" or "essentially" means nearly totally or completely, for instance, 95%, 96%, 97%, 98%, 99% or greater of some given quantity.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Where a range of values is provided, it is understood that each intervening value, to the tenth of the unit of the lower limit unless the context clearly dictates otherwise, between the upper and lower limit of that range and any other stated or intervening value in that stated range, is encompassed within the present technology. The upper and lower limits of these smaller ranges may independently be included in the smaller ranges and are also encompassed within the present technology, subject to any specifically excluded limit in the stated range. Where the stated range includes one or both of the limits, ranges excluding either or both of those included limits are also included in the present technology.

In general, "substituted" refers to an organic group (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. The present disclosure is understood to include embodiments where, for instance a "substituted alkyl" optionally contains one or more alkene and/or alkyne. A substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; aryl groups; heteroaryl groups; cycloalkyl groups; heterocyclyl groups; carbonyls (oxo); carboxyls; esters; carbamates; urethanes; ureas; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cyclic, substituted cycloalkyl, substituted aryl, substituted heterocyclic and substituted heteroaryl groups also include rings and fused ring systems in which a bond to a hydrogen atom is replaced with a bond to a carbon atom. Therefore, substituted cyclic, substituted cycloalkyl, substituted aryl, substituted heterocyclic and substituted heteroaryl groups may also be substituted with substituted or unsubstituted alkyl, alkenyl, and alkynyl groups as defined below.

As used herein, the term "cyclic ring" refers to an aromatic or non-aromatic ring, optionally containing one or more heteroatoms. Exemplary heteroatoms include, but are not limited to, N, O, S, or B. In some embodiments, the cyclic ring optionally contains 1 to 5 heteroatom ring members chosen from O, N, or S. In some embodiments, the cyclic ring optionally contains 1 to 4 heteroatom ring members chosen from O, N, or S. In some embodiments, the cyclic ring optionally contains 1 to 3 heteroatom ring members chosen from O, N, or S. Cyclic rings include aryl, cycloalkyl, and heterocyclic groups.

As used herein, an "aryl group" refers to a cyclic aromatic hydrocarbon that does not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

As used herein, the term "cycloalkyl group" refers to a cyclic alkyl group such as, but not limited to, cyclopropyl, cyclobutyl, cyclopentyl, cyclohexyl, cycloheptyl, and cyclooctyl groups. In some embodiments, the cycloalkyl group has 3 to 8 carbon ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-di-substituted cyclohexyl groups, which may be substituted with substituents such as those listed above. In some embodiments, a cycloalkyl group has one or more alkene bonds, but is not aromatic.

As used herein, the term "heterocyclic group" includes aromatic (also referred to as heteroaryl) and non-aromatic ring compounds containing 3 or more ring members, of which one or more is a heteroatom such as, but not limited to, N, O, S or B. In some embodiments, heterocyclic groups include 3 to 20 ring members, whereas other such groups have 3 to 6, 3 to 10, 3 to 12, or 3 to 15 ring members. Heterocyclic groups encompass unsaturated, partially saturated and saturated ring systems, such as, for example, imidazolyl, imidazolinyl and imidazolidinyl groups. The phrase "heterocyclic group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclic groups that have other groups, such as alkyl, oxo or halo groups, bonded to one of the ring members. Rather, these are referred to as "substituted heterocyclic groups". Heterocyclic groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclic groups may be mono-substituted or substituted more than once, such as, but not limited to, pyridyl or piperazinyl groups, which are 2-, 3-, 4-, 5-, or 6-substituted, or disubstituted with various substituents such as those listed above.

As used herein, the term "heteroaryl group" refers to an aromatic ring compound containing 5 or more ring members, of which, one or more is a heteroatom such as, but not limited to, N, O, S or B. In some embodiments, one or more heteroatoms are chosen from N, O, or S. In some embodiments, 1 to 4 heteroatoms are chosen from N, O, or S. In some embodiments, 1 to 5 heteroatoms are chosen from N, O, or S. In some embodiments, heteroaryl groups include 5 to 14 ring members, whereas other such groups have 5 to 6, 5 to 9, 5 to 10, 6 to 9, 6 to 10, or 6 to 14 ring members. For example, a 5-membered heteroaryl group has 5 ring members; a 6-membered heteroaryl group has 6 ring members; and a 9-membered heteroaryl group has 9 ring members (such as, but not limited to, benzothiophene). Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above. An azolyl group is a 5-membered heteroaryl group containing a nitrogen atom and at least one other atom selected from nitrogen, sulfur, and oxygen as part of the ring. Azolyl groups include imidazole, pyrazole, 1,2,3-triazole, 1,2,4-triazole, tetrazole, pentazole, oxazole, isoxazole, 1,2,4-oxadiazole, 1,2,5-oxadiazole, 1,3,4-oxadiazole, thiazole, isothiazole, 1,2,3-thiadiazole, 1,2,4-thiadiazole, 1,2,5-thiadiazole, and 1,3,4-thiadiazole.

As used herein, the term "alkyl" refers to an aliphatic hydrocarbon radical, which encompasses both straight and branched hydrocarbon radicals. In some embodiments, alkyl has from 1 to about 20 carbon atoms, from 1 to 12 carbons, from 1 to 8 carbons, 1 to 6 carbons, or 1 to 4 carbon atoms.

For example, $C_{1-6}$ alkyl refers to an aliphatic hydrocarbon having 1 to 6 carbons, which includes methyl, ethyl, propyl, n-butyl, n-pentyl, n-hexyl, isopropyl, isobutyl, sec-butyl, tert-butyl, neopentyl, isopentyl, and the like.

As used herein, the term "hydroxy" is defined as OH.

As used herein, the term "alkoxy," unless particularly defined herein, refers to a radical formed by substituting the hydrogen atom of a hydroxyl group with an alkyl, as defined above. For example, $C_{1-6}$ alkoxy includes methoxy, ethoxy, propoxy, n-butoxy, n-pentyloxy, isopropoxy, sec-butoxy, tert-butoxy, neopentyloxy, isopentyloxy, and the like.

In addition, the term "halogen" refers to fluorine, bromine, chlorine, and iodine.

In addition, the term "amino" is defined as —$NH_2$, and the term "alkylamino" refers to a mono- or di-alkyl substituted amino. For example, $C_{1-6}$ alkylamino includes mono- or di-$C_{1-6}$ alkyl substituted amino.

In addition, the term "alkylthio" is defined as —SR* (wherein R* is alkyl), and the term "cyano" is defined as —CN.

Those of skill in the art will appreciate that compounds of the present technology may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the present technology encompasses any tautomeric, conformational isomeric, optical isomeric and/or geometric isomeric forms of the compounds having one or more of the utilities described herein, as well as mixtures of these various different forms. As used herein, "isomer" refers to a tautomer, conformation isomer, optical isomer, geometric isomer, or any combination thereof, of a compound. Structural isomers are not included in the meaning of "isomer" as used herein.

As readily understood by one skilled in the art, a wide variety of functional groups and other structures may exhibit tautomerism, and all tautomers of compounds as described herein are within the scope of the present technology.

Stereoisomers of compounds, also known as "optical isomers," include all chiral, diastereomeric, and racemic forms of a structure, unless the specific stereochemistry is expressly indicated. Thus, compounds used in the present technology include enriched or resolved optical isomers at any or all stereogenic atoms as are apparent from the depictions. Both racemic and diastereomeric mixtures, as well as the individual optical isomers can be isolated or synthesized so as to be substantially free of their enantiomeric or diastereomeric partners, and these are all within the scope of the present technology.

By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

Generally, reference to a certain moiety capable of being protected (such as hydroxy, amine, carbonyl, etc.) includes the protected groups in some embodiments of the disclosure. For example, in some embodiments, an OH moiety as included herein also includes OP, where P is a protecting group. Protecting groups, as referred to herein may be selected by one of ordinary skill in the art, and include the groups and strategies set forth in the art, for example, those such as described in R. Larock, *Comprehensive Organic Transformations*, VCH Publishers (1989); T. W. Greene and P. G. M. Wuts, *Greene's protective groups in organic synthesis*, John Wiley & Sons (2006); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

"Subject" refers to an animal, such as a mammal (including a human), that has been or will be the object of treatment, observation or experiment. "Subject" and "patient" may be used interchangeably, unless otherwise indicated. The methods described herein may be useful in human therapy and/or veterinary applications. In some embodiments, the subject is a mammal. In some embodiments, the subject is a human.

The terms "therapeutically effective amount" and "effective amount" are used interchangeably and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease, or the manner of administration as determined by a qualified prescriber or care giver.

The term "treatment" or "treating" means administering a compound disclosed herein for the purpose of: (i) delaying the onset of a disease, that is, causing the clinical symptoms of the disease not to develop or delaying the development thereof; (ii) inhibiting the disease, that is, arresting the development of clinical symptoms; and/or (iii) relieving the disease, that is, causing the regression of clinical symptoms or the severity thereof.

Unless defined otherwise, all technical and scientific terms used herein have the same meaning as commonly understood by one of ordinary skill in the art to which this present technology belongs. Although any methods and materials similar or equivalent to those described herein can also be used in the practice or testing of the present technology, representative illustrative methods and materials are described herein.

In one aspect, the present technology provides a compound of Formula X, or an isomer thereof, or a pharmaceutically acceptable salt thereof:

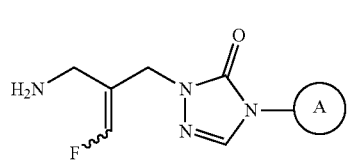

(Formula X)

wherein

A is an aryl or heteroaryl group, said heteroaryl group has 1 to 5 heteroatom ring members chosen from O, N, or S, and said aryl or heteroaryl group is optionally substituted with one to three substituents chosen from $C_{1-3}$ alkyl, $C_{1-3}$ alkoxy, halogen, benzyloxy, —R, —$CH_2$—R, —CH=CH—R, and —C≡C—R; and R is substituted or unsubstituted cyclic ring, optionally containing 1 to 5 heteroatom ring members chosen from O, N, or S, and the cyclic ring is aromatic or non-aromatic.

In some embodiments of a compound of Formula X, or an isomer thereof, or a pharmaceutically acceptable salt thereof, A is an aryl group, and said aryl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments of a compound of Formula X, or an isomer thereof, or a pharmaceutically acceptable salt thereof, A is a $C_{6-10}$ aryl group, and said $C_{6-10}$ aryl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments of a compound of Formula X, or an isomer thereof, or a pharmaceutically acceptable salt thereof, A is a phenyl group, and said phenyl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments of a compound of Formula X, or an isomer thereof, or a pharmaceutically acceptable salt thereof, A is a naphthyl group, and said naphthyl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R.

In some embodiments of a compound of Formula X, or an isomer thereof, or a pharmaceutically acceptable salt thereof, A is a heteroaryl group, said heteroaryl group has 1 to 5 heteroatom ring members chosen from O, N, or S, and said heteroaryl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments of a compound of Formula X, or an isomer thereof, or a pharmaceutically acceptable salt thereof, A is a 5- to 10-membered heteroaryl group, and said heteroaryl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments of a compound of Formula X, or an isomer thereof, or a pharmaceutically acceptable salt thereof, A is a 5- to 9-membered heteroaryl group, and said heteroaryl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments of a compound of Formula X, or an isomer thereof, or a pharmaceutically acceptable salt thereof, A is a 5- or 6-membered heteroaryl group, and said heteroaryl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R.

In some embodiments of a compound of Formula X, or an isomer thereof, or a pharmaceutically acceptable salt thereof, A is a 5-membered heteroaryl group, said heteroaryl group has 1 to 4 heteroatom ring members chosen from O, N, or S, and said heteroaryl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments, the 5-membered heteroaryl group is selected from thiazole, thiophene, pyrrole, pyrazole, imidazole, triazole, tetrazole, furan, oxazole, isoxazole, oxadiazole, and thiadiazole. In some embodiments of a compound of Formula X, or an isomer thereof, or a pharmaceutically acceptable salt thereof, A is an azolyl group, and said azolyl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R.

In some embodiments of a compound of Formula X, or an isomer thereof, or a pharmaceutically acceptable salt thereof, A is a 6-membered heteroaryl group, said heteroaryl group has 1 to 3 heteroatom ring members chosen from O, N, or S, and said heteroaryl group is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments, the 6-membered heteroaryl group is selected from pyridine, pyrimidine, pyrazine, and triazine. In some embodiments of a compound of Formula X, or an isomer thereof, or a pharmaceutically acceptable salt thereof, A is a pyridine, and said pyridine is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments of a compound of Formula X, or an isomer thereof, or a pharmaceutically acceptable salt thereof, A is a pyrimidine, and said pyrimidine is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments of a compound of Formula X, or an isomer thereof, or a pharmaceutically acceptable salt thereof, A is a pyrazine, and said pyrazine is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R. In some embodiments of a compound of Formula X, or an isomer thereof, or a pharmaceutically acceptable salt thereof, A is a triazine, and said triazine is substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R.

In another aspect, the present technology provides a compound having selective inhibitory activity on VAP-1 or its salt, that is, a compound of Formula 1 below, an isomer thereof, or a pharmaceutically acceptable salt thereof:

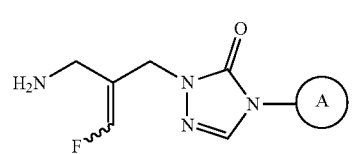

(Formula 1)

wherein

A is an aryl or heteroaryl group selected from the group consisting of phenyl, pyridine, pyrazine, and thiazole, wherein said aryl or heteroaryl group is optionally substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R, wherein said R is a cyclic ring selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin- 2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan, wherein said cyclic ring is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$alkylsulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, oxazolyl, oxadiazolyl, cyclopropyl-oxadiazolyl, $C_{1-6}$ alkyl-oxadiazolyl, and oxadiazol-5-onyl.

In another aspect, provided herein is a compound of Formula 10, or an isomer thereof, or a pharmaceutically acceptable salt thereof:

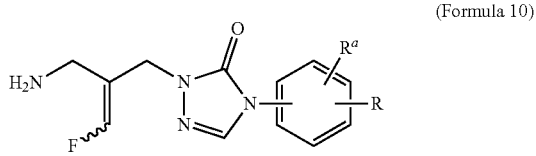

(Formula 10)

wherein

R is a substituted or unsubstituted cyclic ring, optionally containing at least one heteroatom, and the cyclic ring is aromatic or non-aromatic; and $R^a$ is hydrogen, $C_{1-3}$ alkyl, $C_{1-3}$ alkoxy, or halogen.

In some embodiments, the compound of Formula 10 is a compound of Formula 10a:

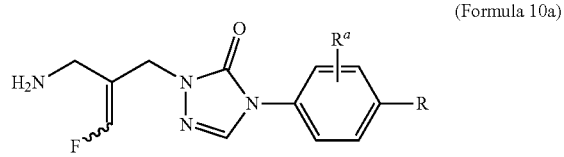

(Formula 10a)

or an isomer thereof, or a pharmaceutically acceptable salt thereof, wherein R and $R^a$ are as defined for Formula 10.

In some embodiments, the compound of Formula 10 is a compound of Formula 10b:

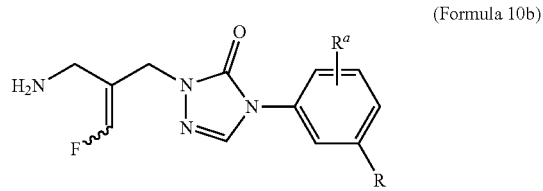

(Formula 10b)

or an isomer thereof, or a pharmaceutically acceptable salt thereof, wherein R and $R^a$ are as defined for Formula 10.

In another aspect, provided herein is a compound of Formula 11, or an isomer thereof, or a pharmaceutically acceptable salt thereof:

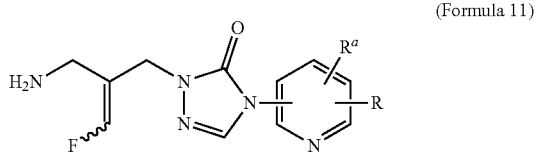

(Formula 11)

wherein

R is a substituted or unsubstituted cyclic ring, optionally containing at least one heteroatom, and the cyclic ring is aromatic or non-aromatic; and $R^a$ is hydrogen, $C_{1-3}$ alkyl, $C_{1-3}$ alkoxy, or halogen.

In some embodiments, the compound of Formula 11 is a compound of Formula 11a:

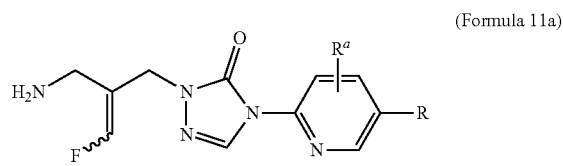

(Formula 11a)

or an isomer thereof, or a pharmaceutically acceptable salt thereof, wherein R and $R^a$ are as defined for Formula 11.

In some embodiments, the compound of Formula 11 is a compound of Formula 11b:

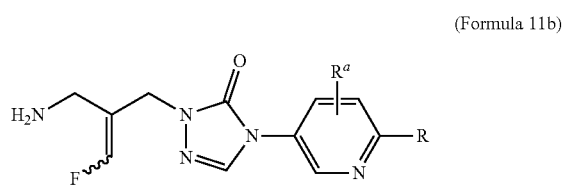

(Formula 11b)

or an isomer thereof, or a pharmaceutically acceptable salt thereof, wherein R and $R^a$ are as defined for Formula 11.

In some embodiments, the compound of Formula 11 is a compound of Formula 11c:

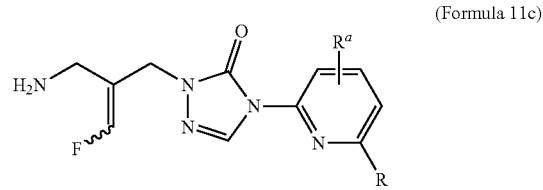

(Formula 11c)

or an isomer thereof, or a pharmaceutically acceptable salt thereof, wherein R and $R^a$ are as defined for Formula 11.

In some embodiments, the compound of Formula 11 is a compound of Formula 11d:

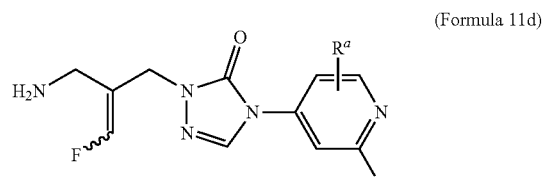

(Formula 11d)

or an isomer thereof, or a pharmaceutically acceptable salt thereof, wherein R and $R^a$ are as defined for Formula 11.

In some embodiments, the compound of Formula 11 is a compound of Formula 11e:

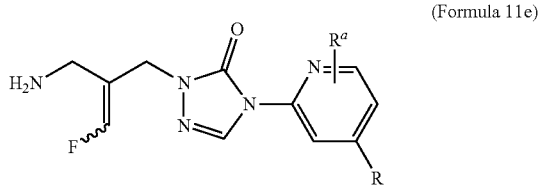

(Formula 11e)

or an isomer thereof, or a pharmaceutically acceptable salt thereof, wherein R and $R^a$ are as defined for Formula 11.

In another aspect, provided herein is a compound of Formula 12, or an isomer thereof, or a pharmaceutically acceptable salt thereof:

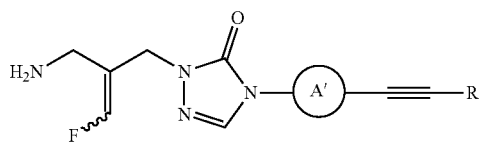

(Formula 12)

wherein
A' is pyridine; and
R is a substituted or unsubstituted cyclic ring, optionally containing at least one heteroatom, and the cyclic ring is aromatic or non-aromatic.

In some embodiments, A' is

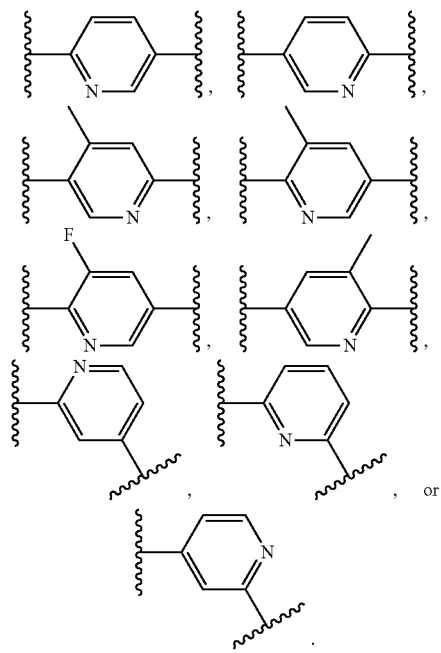

, or

In some embodiments, A' is

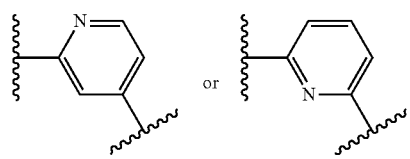

or .

In some embodiments of a compound of Formulae X, 10, 10a, 10b, 11, 11a, 11b, 11c, 11d, 11e, or 12, or an isomer thereof, or a pharmaceutically acceptable salt thereof, R is selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan.

In some embodiments of a compound of Formulae X, 10, 10a, 10b, 11, 11a, 11b, 11c, 11d, 11e, or 12, or an isomer thereof, or a pharmaceutically acceptable salt thereof, R is selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan; and R is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$alkylsulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, isoxazolyl, oxazolyl, oxadiazolyl, cyclopropyl-oxadiazolyl, $C_{1-6}$ alkyl-oxadiazolyl, and oxadiazol-5-onyl.

The compounds provided in the description are inhibitors of VAP-1. VAP-1 inhibition may be measured, for example, by determining the half maximal inhibitory concentration ($IC_{50}$). One method for determining an $IC_{50}$ for VAP-1 is provided herein.

In one embodiment, the compounds are selective inhibitors of VAP-1. Selectivity may be determined, for example, by comparing inhibition of VAP-1 to inhibition of other aminooxidaxes such as MAO-A (monoamine oxidase-A), MAO-B (monoamine oxidase-B), and DAO (diamine oxidase). In one embodiment, said "significantly high inhibitory activity" means $IC_{50}$ for VAP-1 obtained from the in vitro enzyme analysis (in vitro enzyme assay) test is at least 3000 times lower than $IC_{50}$ of MAO-A, at least 100 times lower than $IC_{50}$ of MAO-B, or at least 100 times lower than $IC_{50}$ of DAO. In an alternative embodiment, "significantly high inhibitory activity" means the $IC_{50}$ for VAP-1 obtained from the in vitro enzyme analysis (in vitro enzyme assay) test is at least 3000 times lower than $IC_{50}$ of MAO-A, at least 100 times lower than $IC_{50}$ of MAO-B, and at least 100 times lower than $IC_{50}$ of DAO.

In the compound of Formula 1 or its pharmaceutically acceptable salt thereof according to the present technology, A may preferably be pyridine. In some embodiments of a compound of Formula 1, an isomer thereof, or a pharmaceutically acceptable salt thereof, A is phenyl. In some embodiments of a compound of Formula 1, an isomer thereof, or a pharmaceutically acceptable salt thereof, A is pyrazine. In some embodiments of a compound of Formula 1, an isomer thereof, or a pharmaceutically acceptable salt thereof, A is thiazole.

In some embodiments of Formula X or Formula 1, an isomer thereof, or a pharmaceutically acceptable salt thereof, A is

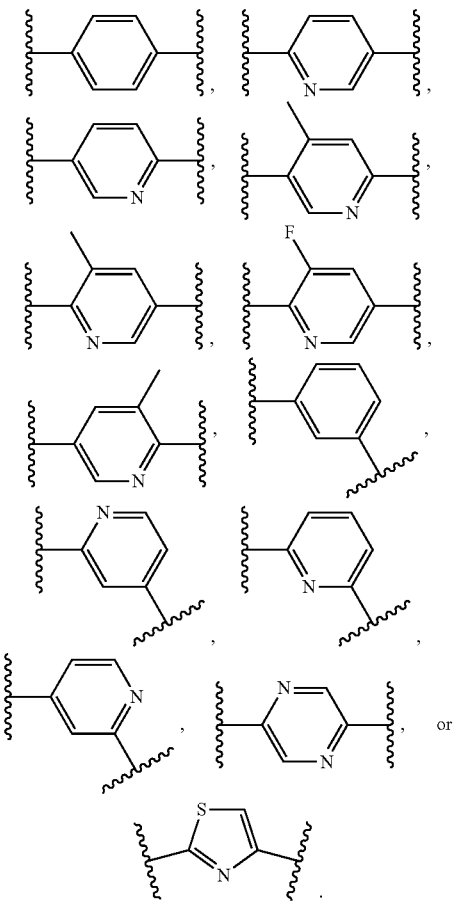

In some embodiments of Formula X or Formula 1, an isomer thereof, or a pharmaceutically acceptable salt thereof, A is

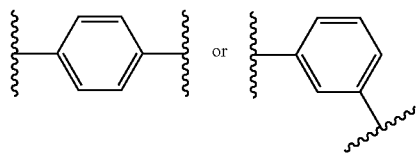 or 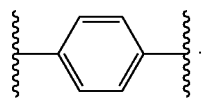.

In some embodiments of Formula X or Formula 1, an isomer thereof, or a pharmaceutically acceptable salt thereof, A is

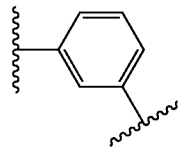 [SMILES: *c1cccc(*)c1]

In some embodiments of Formula X or Formula 1, an isomer thereof, or a pharmaceutically acceptable salt thereof, A is

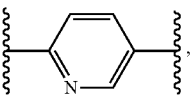 [SMILES: *c1ccc(*)nc1],

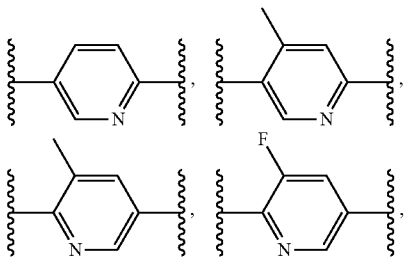

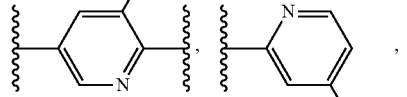

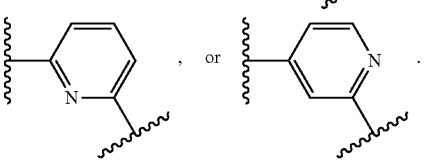 or .

In some embodiments of the compound of Formula X, or an isomer thereof, or a pharmaceutically acceptable salt thereof, said aryl or heteroaryl group is substituted with one to two substituents selected from the group consisting of $C_{1-3}$ alkyl, halogen, —R, and —C≡C—R. In further embodiments of the compound of Formula X, or an isomer thereof, or a pharmaceutically acceptable salt thereof, R is a cyclic ring selected from the group consisting of benzene, pyridine, and pyrazole. In still further embodiments of the compound of Formula X, or an isomer thereof, or a pharmaceutically acceptable salt thereof, said cyclic ring is unsubstituted; or substituted with a substituent selected from the group consisting of $C_{1-6}$ alkyl, trifluoromethyl, and oxazolyl.

Further, in the compound of Formula 1 or its pharmaceutically acceptable salt thereof according to the present technology, said aryl or heteroaryl group can be optionally substituted with one to two substituents selected from the group consisting of $C_{1-3}$ alkyl, halogen, —R, and —C≡C—R. Preferably, said R may be a cyclic ring selected from the group consisting of benzene, pyridine, and pyrazole. More preferably, said cyclic ring may be unsubstituted; or substituted with a substituent selected from the group consisting of $C_{1-6}$ alkyl, trifluoromethyl, and oxazolyl.

In some embodiments of a compound of Formula X or 1, an isomer thereof, or a pharmaceutically acceptable salt thereof, said aryl or heteroaryl group is substituted with $C_{1-3}$ alkyl, $C_{1-3}$ alkoxy, halogen, benzyloxy, —R, —CH$_2$—R, —CH=CH—R, or —C≡C—R. In some embodiments of a compound of Formula X or 1, an isomer thereof, or a pharmaceutically acceptable salt thereof, said aryl or heteroaryl group is substituted with $C_{1-3}$ alkyl. In some embodiments of a compound of Formula X or 1, an isomer thereof, or a pharmaceutically acceptable salt thereof, said aryl or heteroaryl group is substituted with $C_{1-3}$ alkoxy. In some embodiments of a compound of Formula X or 1, an isomer thereof, or a pharmaceutically acceptable salt thereof, said aryl or heteroaryl group is substituted with halogen. In some embodiments of a compound of Formula X or 1, an isomer thereof, or a pharmaceutically acceptable salt thereof, said aryl or heteroaryl group is substituted with benzyloxy. In some embodiments of a compound of Formula X or 1, an isomer thereof, or a pharmaceutically acceptable salt thereof, said aryl or heteroaryl group is substituted with —R. In some embodiments of a compound of Formula X or 1, an isomer thereof, or a pharmaceutically acceptable salt thereof, said aryl or heteroaryl group is substituted with —CH$_2$—R. In some embodiments of a compound of Formula X or 1, an isomer thereof, or a pharmaceutically acceptable salt thereof, said aryl or heteroaryl group is substituted with —CH=CH—R. In some embodiments of a compound of Formula X or 1, an isomer thereof, or a pharmaceutically acceptable salt thereof, said aryl or heteroaryl group is substituted with —C≡C—R.

In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted benzene. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted phenylbenzene. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted pyridine. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted tetrahydropyridine. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted pyridin-2-one. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted pyrimidine. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted thiophene. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted thiazole. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted imidazole. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted pyrazole. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted piperazine. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted morpholine. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted benzodioxole. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted benzoxadiazole. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted benzothiophene. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted benzothiazole. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted 2,3-dihydro-benzodioxine. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted indazole. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted indole. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted 1,3-dihydroindol-2-one. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted 1,2-dihydroindol-3-one. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted quinoline. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted isoquinoline. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted quinolin-2-one. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted 3,4-dihydroquinolin-2-one. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted 3,4-dihydro-1,4-benzoxazine. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted 1,4-benzoxazin-3-one. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted 3,1-benzoxazin-2-one. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted 2,3-dihydro-imidazo[4,5-b]pyridine. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted oxazolo[4,5-b]pyridin-2-one. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted 2,3-dihydro-pyrido[2,3-b][1,4]oxazine. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted 3,4-dihydro-pyrido[3,2-b][1,4]oxazine. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted pyrido[2,3-b][1,4]oxazin-2-one. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted pyrido[3,2-b][1,4]oxazin-3-one. In some embodiments of a compound of Formulae X, 1, 10, 10a, 10b, 11, 11a, 11b, 11c, 11d, 11e, or 12, an isomer thereof, or a pharmaceutically acceptable salt thereof, said R is substituted or unsubstituted dibenzo[b,d]furan.

In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is unsubstituted. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$alkylsulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, isoxazolyl, oxazolyl, oxadiazolyl, cyclopropyl-oxadiazolyl, $C_{1-6}$ alkyl-oxadiazolyl, or oxadiazol-5-onyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with hydroxyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with halogen. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with $C_{1-6}$ alkyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with trifluoromethyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with $C_{1-6}$ alkoxy. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with trifluoromethoxy. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with amino. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with mono- or di-$C_{1-6}$ alkylamino. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with mono-$C_{1-6}$ alkylamino. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with di-$C_{1-6}$ alkylamino. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with $C_{1-6}$ alkylcarbonylamino. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with $C_{1-6}$ alkylthio. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with mono- or di-$C_{1-6}$ alkylaminosulfonyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with mono-$C_{1-6}$ alkylaminosulfonyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with di-$C_{1-6}$ alkylaminosulfonyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with $C_{1-6}$alkylsulfonyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with $C_{1-6}$ alkylcarbonyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with morpholinylcarbonyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with benzodioxolyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with pyrrolidinyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with piperazinyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with acetylpiperazinyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with morpholinyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with tetrahydropyranyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with triazolyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with tetrazolyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with oxazolyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with isoxazolyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with oxadiazolyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with cyclopropyl-oxadiazolyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with $C_{1-6}$ alkyl-oxadiazolyl. In some embodiments of a compound of Formulae X, 1, 10, 10a, 10b, 11, 11a, 11b, 11c, 11d, 11e, or 12, an isomer thereof, or a pharmaceutically acceptable salt thereof, R is a cyclic ring, and said cyclic ring is substituted with oxadiazol-5-onyl.

In one embodiment of the present technology, a compound, wherein A is pyridine; said pyridine is substituted with one or two substituents selected from the group consisting of $C_{1-3}$ alkyl, halogen, —R, and —C≡C—R; said R is a cyclic ring selected from the group consisting of benzene, pyridine, and pyrazole; and said cyclic ring is unsubstituted or substituted with a substituent selected from the group consisting of $C_{1-6}$ alkyl, trifluoromethyl, and oxazolyl; or a pharmaceutically acceptable salt thereof is provided.

In another aspect, a compound of Formula X or Formula 1, or an isomer thereof, or a pharmaceutically acceptable salt thereof, is selected from the following compounds, or an isomer thereof, or a pharmaceutically acceptable salt thereof:

2-[(2Z)-2-(aminomethyl)-3-fluoroprop-2-en-1-yl]-4-(4-bromophenyl)-2,4-dihydro-3H-1,2,4-triazol-3-one;
2-[(2E)-2-(aminomethyl)-3-fluoroprop-2-en-1-yl]-4-(4-bromophenyl)-2,4-dihydro-3H-1,2,4-triazol-3-one;
2-[(2Z)-2-(aminomethyl)-3-fluoroprop-2-en-1-yl]-4-(3-bromophenyl)-2,4-dihydro-3H-1,2,4-triazol-3-one hydrochloride;
2-[(2E)-2-(aminomethyl)-3-fluoroprop-2-en-1-yl]-4-(3-bromophenyl)-2,4-dihydro-3H-1,2,4-triazol-3-one hydrochloride;
2-[(2Z)-2-(aminomethyl)-3-fluoroprop-2-en-1-yl]-4-(4-fluorophenyl)-2,4-dihydro-3H-1,2,4-triazol-3-one;
2-[(2E)-2-(aminomethyl)-3-fluoroprop-2-en-1-yl]-4-(4-fluorophenyl)-2,4-dihydro-3H-1,2,4-triazol-3-one hydrochloride;
2-[(2Z)-2-(aminomethyl)-3-fluoroprop-2-en-1-yl]-4-[4-(benzyloxy)phenyl]-2,4-dihydro-3H-1,2,4-triazol-3-one;
2-[(2E)-2-(aminomethyl)-3-fluoroprop-2-en-1-yl]-4-[4-(benzyloxy)phenyl]-2,4-dihydro-3H-1,2,4-triazol-3-one hydrochloride;
2-[(2Z)-2-(aminomethyl)-3-fluoroprop-2-en-1-yl]-4-(3,4-difluorophenyl)-2,4-dihydro-3H-1,2,4-triazol-3-one;
2-[(2E)-2-(aminomethyl)-3-fluoroprop-2-en-1-yl]-4-(3,4-difluorophenyl)-2,4-dihydro-3H-1,2,4-triazol-3-one hydrochloride;
2-[(2Z)-2-(aminomethyl)-3-fluoroprop-2-en-1-yl]-4-(4-bromo-2-fluorophenyl)-2,4-dihydro-3H-1,2,4-triazol-3-one hydrochloride;
2-[(2E)-2-(aminomethyl)-3-fluoroprop-2-en-1-yl]-4-(4-bromo-2-fluorophenyl)-2,4-dihydro-3H-1,2,4-triazol-3-one hydrochloride;
2-[(2Z)-2-(aminomethyl)-3-fluoroprop-2-en-1-yl]-4-(4-bromo-3-fluorophenyl)-2,4-dihydro-3H-1,2,4-triazol-3-one;
2-[(2E)-2-(aminomethyl)-3-fluoroprop-2-en-1-yl]-4-(4-bromo-3-fluorophenyl)-2,4-dihydro-3H-1,2,4-triazol-3-one hydrochloride;
2-[(2Z)-2-(aminomethyl)-3-fluoroprop-2-en-1-yl]-4-(4-bromo-3-methylphenyl)-2,4-dihydro-3H-1,2,4-triazol-3-one;
2-[(2E)-2-(aminomethyl)-3-fluoroprop-2-en-1-yl]-4-(4-bromo-3-methylphenyl)-2,4-dihydro-3H-1,2,4-triazol-3-one hydrochloride;
2-[(2Z)-2-(aminomethyl)-3-fluoroprop-2-en-1-yl]-4-(4-bromo-3-methoxyphenyl)-2,4-dihydro-3H-1,2,4-triazol-3-one;
2-[(2E)-2-(aminomethyl)-3-fluoroprop-2-en-1-yl]-4-(4-bromo-3-methoxyphenyl)-2,4-dihydro-3H-1,2,4-triazol-3-one hydrochloride;
2-[(2Z)-2-(aminomethyl)-3-fluoroprop-2-en-1-yl]-4-(4-bromo-3,5-difluorophenyl)-2,4-dihydro-3H-1,2,4-triazol-3-one;
2-[(2E)-2-(aminomethyl)-3-fluoroprop-2-en-1-yl]-4-(4-bromo-3,5-difluorophenyl)-2,4-dihydro-3H-1,2,4-triazol-3-one hydrochloride;
2-[(2Z)-2-(aminomethyl)-3-fluoroprop-2-en-1-yl]-4-(4-bromo-2,6-difluorophenyl)-2,4-dihydro-3H-1,2,4-triazol-3-one hydrochloride;
2-[(2E)-2-(aminomethyl)-3-fluoroprop-2-en-1-yl]-4-(4-bromo-2,6-difluorophenyl)-2,4-dihydro-3H-1,2,4-triazol-3-one hydrochloride;
2-[(2E)-2-(aminomethyl)-3-fluoroprop-2-en-1-yl]-4-(4-bromo-2,5-difluorophenyl)-2,4-dihydro-3H-1,2,4-triazol-3-one hydrochloride;
2-[(2Z)-2-(aminomethyl)-3-fluoroprop-2-en-1-yl]-4-(6-bromopyridin-3-yl)-2,4-dihydro-3H-1,2,4-triazol-3-one;
2-[(2E)-2-(aminomethyl)-3-fluoroprop-2-en-1-yl]-4-(6-bromopyridin-3-yl)-2,4-dihydro-3H-1,2,4-triazol-3-one hydrochloride;

2-[(2Z)-2-(aminomethyl)-3-fluoroprop-2-en-1-yl]-4-(6-bromo-5-methylpyridin-3-yl)-2,4-dihydro-3H-1,2,4-triazol-3-one hydrochloride;

2-[(2E)-2-(aminomethyl)-3-fluoroprop-2-en-1-yl]-4-(6-bromo-5-methylpyridin-3-yl)-2,4-dihydro-3H-1,2,4-triazol-3-one hydrochloride;

2-[(2E)-2-(aminomethyl)-3-fluoroprop-2-en-1-yl]-4-(6-bromo-4-methylpyridin-3-yl)-2,4-dihydro-3H-1,2,4-triazol-3-one hydrochloride;

2-[(2Z)-2-(aminomethyl)-3-fluoroprop-2-en-1-yl]-4-(5-bromopyridin-2-yl)-2,4-dihydro-3H-1,2,4-triazol-3-one hydrochloride;

2-[(2E)-2-(aminomethyl)-3-fluoroprop-2-en-1-yl]-4-(5-bromopyridin-2-yl)-2,4-dihydro-3H-1,2,4-triazol-3-one hydrochloride;

2-[(2Z)-2-(aminomethyl)-3-fluoroprop-2-en-1-yl]-4-(5-bromo-3-methylpyridin-2-yl)-2,4-dihydro-3H-1,2,4-triazol-3-one hydrochloride;

2-[(2E)-2-(aminomethyl)-3-fluoroprop-2-en-1-yl]-4-(5-bromo-3-methylpyridin-2-yl)-2,4-dihydro-3H-1,2,4-triazol-3-one hydrochloride;

2-[(2Z)-2-(aminomethyl)-3-fluoroprop-2-en-1-yl]-4-(5-bromo-4-methylpyridin-2-yl)-2,4-dihydro-3H-1,2,4-triazol-3-one hydrochloride;

2-[(2E)-2-(aminomethyl)-3-fluoroprop-2-en-1-yl]-4-(5-bromo-4-methylpyridin-2-yl)-2,4-dihydro-3H-1,2,4-triazol-3-one hydrochloride;

2-[(2Z)-2-(aminomethyl)-3-fluoroprop-2-en-1-yl]-4-(5-bromo-3-fluoropyridin-2-yl)-2,4-dihydro-3H-1,2,4-triazol-3-one hydrochloride;

2-[(2E)-2-(aminomethyl)-3-fluoroprop-2-en-1-yl]-4-(5-bromo-3-fluoropyridin-2-yl)-2,4-dihydro-3H-1,2,4-triazol-3-one hydrochloride;

2-[(2E)-2-(aminomethyl)-3-fluoroprop-2-en-1-yl]-4-(6-bromopyridin-2-yl)-2,4-dihydro-3H-1,2,4-triazol-3-one;

2-[(2E)-2-(aminomethyl)-3-fluoroprop-2-en-1-yl]-4-(5-bromopyrazin-2-yl)-2,4-dihydro-3H-1,2,4-triazol-3-one;

2-[(2Z)-2-(aminomethyl)-3-fluoroprop-2-en-1-yl]-4-(1,3-thiazol-2-yl)-2,4-dihydro-3H-1,2,4-triazol-3-one hydrochloride;

2-[(2Z)-2-(aminomethyl)-3-fluoroprop-2-en-1-yl]-4-(5-bromo-1,3-thiazol-2-yl)-2,4-dihydro-3H-1,2,4-triazol-3-one hydrochloride;

2-[(2E)-2-(aminomethyl)-3-fluoroprop-2-en-1-yl]-4-(5-bromo-1,3-thiazol-2-yl)-2,4-dihydro-3H-1,2,4-triazol-3-one hydrochloride;

4-[4-(5-acetylthiophen-2-yl)phenyl]-2-[(2Z)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-[3-fluoro-4'-(4H-1,2,4-triazol-3-yl)biphenyl-4-yl]-2,4-dihydro-3H-1,2,4-triazol-3-one;

2-[(2E)-2-(aminomethyl)-3-fluoroprop-2-en-1-yl]-4-[3-fluoro-3'-(4H-1,2,4-triazol-3-yl)biphenyl-4-yl]-2,4-dihydro-3H-1,2,4-triazol-3-one;

2-[(2E)-2-(aminomethyl)-3-fluoroprop-2-en-1-yl]-4-[4-(1,3-benzodioxol-5-yl)-2-fluorophenyl]-2,4-dihydro-3H-1,2,4-triazol-3-one hydrochloride;

2-[(2E)-2-(aminomethyl)-3-fluoroprop-2-en-1-yl]-4-[4-(2,1,3-benzoxadiazol-5-yl)-2-fluorophenyl]-2,4-dihydro-3H-1,2,4-triazol-3-one hydrochloride;

2-[(2E)-2-(aminomethyl)-3-fluoroprop-2-en-1-yl]-4-[5-bromo-2-methoxy-4-(morpholin-4-yl)phenyl]-2,4-dihydro-3H-1,2,4-triazol-3-one hydrochloride;

2-[(2E)-2-(aminomethyl)-3-fluoroprop-2-en-1-yl]-4-[3-(1,2,3,6-tetrahydropyridin-4-yl)phenyl]-2,4-dihydro-3H-1,2,4-triazol-3-one dihydrochloride;

4-[3-(5-acetylthiophen-2-yl)phenyl]-2-[(2E)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-[4'-(trifluoromethoxy)biphenyl-3-yl]-2,4-dihydro-3H-1,2,4-triazol-3-one hydrochloride;

2-[(2E)-2-(aminomethyl)-3-fluoroprop-2-en-1-yl]-4-[4'-(dimethylamino)biphenyl-3-yl]-2,4-dihydro-3H-1,2,4-triazol-3-one hydrochloride;

2-[(2E)-2-(aminomethyl)-3-fluoroprop-2-en-1-yl]-4-[4'-(propan-2-ylsulfanyl)biphenyl-3-yl]-2,4-dihydro-3H-1,2,4-triazol-3-one hydrochloride;

2-[(2Z)-2-(aminomethyl)-3-fluoroprop-2-en-1-yl]-4-[4'-(methylsulfonyl)biphenyl-3-yl]-2,4-dihydro-3H-1,2,4-triazol-3-one hydrochloride;

2-[(2E)-2-(aminomethyl)-3-fluoroprop-2-en-1-yl]-4-[4'-(methylsulfonyl)biphenyl-3-yl]-2,4-dihydro-3H-1,2,4-triazol-3-one hydrochloride;

3'-{1-[(2E)-2-(aminomethyl)-3-fluoroprop-2-en-1-yl]-5-oxo-1,5-dihydro-4H-1,2,4-triazol-4-yl}-N,N-dimethylbiphenyl-4-sulfonamide hydrochloride;

N-(3'-{1-[(2Z)-2-(aminomethyl)-3-fluoroprop-2-en-1-yl]-5-oxo-1,5-dihydro-4H-1,2,4-triazol-4-yl}biphenyl-4-yl)acetamide hydrochloride;

N-(3'-{1-[(2E)-2-(aminomethyl)-3-fluoroprop-2-en-1-yl]-5-oxo-1,5-dihydro-4H-1,2,4-triazol-4-yl}biphenyl-4-yl)acetamide hydrochloride;

2-[(2Z)-2-(aminomethyl)-3-fluoroprop-2-en-1-yl]-4-[4'-(4H-1,2,4-triazol-3-yl)biphenyl-3-yl]-2,4-dihydro-3H-1,2,4-triazol-3-one;

2-[(2E)-2-(aminomethyl)-3-fluoroprop-2-en-1-yl]-4-[4'-(4H-1,2,4-triazol-3-yl)biphenyl-3-yl]-2,4-dihydro-3H-1,2,4-triazol-3-one;

2-[(2Z)-2-(aminomethyl)-3-fluoroprop-2-en-1-yl]-4-[3'-(4H-1,2,4-triazol-3-yl)biphenyl-3-yl]-2,4-dihydro-3H-1,2,4-triazol-3-one;

2-[(2E)-2-(aminomethyl)-3-fluoroprop-2-en-1-yl]-4-[4'-(1,2,4-oxadiazol-3-yl)biphenyl-3-yl]-2,4-dihydro-3H-1,2,4-triazol-3-one;

2-[(2E)-2-(aminomethyl)-3-fluoroprop-2-en-1-yl]-4-[3'-(1,2,4-oxadiazol-3-yl)biphenyl-3-yl]-2,4-dihydro-3H-1,2,4-triazol-3-one;

2-[(2E)-2-(aminomethyl)-3-fluoroprop-2-en-1-yl]-4-[4'-(5-cyclopropyl-1,2,4-oxadiazol-3-yl)biphenyl-3-yl]-2,4-dihydro-3H-1,2,4-triazol-3-one hydrochloride;

2-[(2E)-2-(aminomethyl)-3-fluoroprop-2-en-1-yl]-4-{4'-[5-(propan-2-yl)-1,2,4-oxadiazol-3-yl]biphenyl-3-yl}-2,4-dihydro-3H-1,2,4-triazol-3-one hydrochloride;

2-[(2E)-2-(aminomethyl)-3-fluoroprop-2-en-1-yl]-4-{3'-[5-(propan-2-yl)-1,2,4-oxadiazol-3-yl]biphenyl-3-yl}-2,4-dihydro-3H-1,2,4-triazol-3-one hydrochloride;

2-[(2E)-2-(aminomethyl)-3-fluoroprop-2-en-1-yl]-4-[4"-(methylsulfonyl)-1,1': 4',1"-terphenyl-3-yl]-2,4-dihydro-3H-1,2,4-triazol-3-one hydrochloride;

2-[(2E)-2-(aminomethyl)-3-fluoroprop-2-en-1-yl]-4-[4"-(methylsulfonyl)-1,1':3',1"-terphenyl-3-yl]-2,4-dihydro-3H-1,2,4-triazol-3-one;

N-(3"-{1-[(2E)-2-(aminomethyl)-3-fluoroprop-2-en-1-yl]-5-oxo-1,5-dihydro-4H-1,2,4-triazol-4-yl}-1,1':4',1"-terphenyl-4-yl)acetamide hydrochloride;

N-(3"-{1-[(2E)-2-(aminomethyl)-3-fluoroprop-2-en-1-yl]-5-oxo-1,5-dihydro-4H-1,2,4-triazol-4-yl}-1,1':3',1"-terphenyl-4-yl)acetamide hydrochloride;

2-[(2E)-2-(aminomethyl)-3-fluoroprop-2-en-1-yl]-4-[4'-(1,3-benzodioxol-5-yl)biphenyl-3-yl]-2,4-dihydro-3H-1,2,4-triazol-3-one hydrochloride;

2-[(2E)-2-(aminomethyl)-3-fluoroprop-2-en-1-yl]-4-[3'-(1,
3-benzodioxol-5-yl)biphenyl-3-yl]-2,4-dihydro-3H-1,2,
4-triazol-3-one hydrochloride;

4-[4'-(4-acetylpiperazine-1-yl)biphenyl-3-yl]-2-[(2E)-2-
(aminomethyl)-3-fluoroprop-2-en-1-yl]-2,4-dihydro-3H-
1,2,4-triazol-3-one hydrochloride;

2-[(2E)-2-(aminomethyl)-3-fluoroprop-2-en-1-yl]-4-[4'-
(tetrahydro-2H-pyran-4-yl)biphenyl-3-yl]-2,4-dihydro-
3H-1,2,4-triazol-3-one hydrochloride;

2-[(2E)-2-(aminomethyl)-3-fluoroprop-2-en-1-yl]-4-[4'-
(morpholin-4-yl)biphenyl-3-yl]-2,4-dihydro-3H-1,2,4-
triazol-3-one hydrochloride;

2-[(2E)-2-(aminomethyl)-3-fluoroprop-2-en-1-yl]-4-[3'-
fluoro-4'-(morpholin-4-yl)biphenyl-3-yl]-2,4-dihydro-
3H-1,2,4-triazol-3-one hydrochloride;

2-[(2E)-2-(aminomethyl)-3-fluoroprop-2-en-1-yl]-4-[3'-
chloro-4'-(morpholin-4-yl)biphenyl-3-yl]-2,4-dihydro-
3H-1,2,4-triazol-3-one hydrochloride;

2-[(2E)-2-(aminomethyl)-3-fluoroprop-2-en-1-yl]-4-[3'-
methyl-4'-(morpholin-4-yl)biphenyl-3-yl]-2,4-dihydro-
3H-1,2,4-triazol-3-one hydrochloride;

2-[(2E)-2-(aminomethyl)-3-fluoroprop-2-en-1-yl]-4-[4'-
(morpholin-4-ylcarbonyl)biphenyl-3-yl]-2,4-dihydro-3H-
1,2,4-triazol-3-one hydrochloride;

2-[(2E)-2-(aminomethyl)-3-fluoroprop-2-en-1-yl]-4-[3-(2-
methoxypyridin-4-yl)phenyl]-2,4-dihydro-3H-1,2,4-tri-
azol-3-one hydrochloride;

N-[4-(3-{1-[(2Z)-2-(aminomethyl)-3-fluoroprop-2-en-1-
yl]-5-oxo-1,5-dihydro-4H-1,2,4-triazol-4-yl}phenyl)pyri-
din-2-yl]acetamide hydrochloride;

N-[4-(3-{1-[(2E)-2-(aminomethyl)-3-fluoroprop-2-en-1-
yl]-5-oxo-1,5-dihydro-4H-1,2,4-triazol-4-yl}phenyl)pyri-
din-2-yl]acetamide hydrochloride;

2-[(2E)-2-(aminomethyl)-3-fluoroprop-2-en-1-yl]-4-[3-
(pyridin-3-yl)phenyl]-2,4-dihydro-3H-1,2,4-triazol-3-one
hydrochloride;

2-[(2E)-2-(aminomethyl)-3-fluoroprop-2-en-1-yl]-4-[3-(6-
methoxypyridin-3-yl)phenyl]-2,4-dihydro-3H-1,2,4-tri-
azol-3-one hydrochloride;

2-[(2E)-2-(aminomethyl)-3-fluoroprop-2-en-1-yl]-4-{3-[6-
(trifluoromethyl)pyridin-3-yl]phenyl}-2,4-dihydro-3H-1,
2,4-triazol-3-one hydrochloride;

2-[(2E)-2-(aminomethyl)-3-fluoroprop-2-en-1-yl]-4-[3-(6-
chloropyridin-3-yl)phenyl]-2,4-dihydro-3H-1,2,4-triazol-
3-one hydrochloride;

2-[(2E)-2-(aminomethyl)-3-fluoroprop-2-en-1-yl]-4-{3-[6-
(morpholin-4-yl)pyridin-3-yl]phenyl}-2,4-dihydro-3H-1,
2,4-triazol-3-one hydrochloride;

2-[(2E)-2-(aminomethyl)-3-fluoroprop-2-en-1-yl]-4-{3-[6-
methoxy-5-(trifluoromethyl)pyridin-3-yl]phenyl}-2,4-di-
hydro-3H-1,2,4-triazol-3-one hydrochloride;

2-[(2E)-2-(aminomethyl)-3-fluoroprop-2-en-1-yl]-4-{3-[6-
hydroxy-5-(trifluoromethyl)pyridin-3-yl]phenyl}-2,4-di-
hydro-3H-1,2,4-triazol-3-one hydrochloride;

5-(3-{1-[(2E)-2-(aminomethyl)-3-fluoroprop-2-en-1-yl]-5-
oxo-1,5-dihydro-4H-1,2,4-triazol-4-yl}phenyl)-1,3-dim-
ethylpyridin-2(1H)-one hydrochloride;

5-(3-{1-[(2E)-2-(aminomethyl)-3-fluoroprop-2-en-1-yl]-5-
oxo-1,5-dihydro-4H-1,2,4-triazol-4-yl}phenyl)-1-(pro-
pan-2-yl)pyridin-2(1H)-one hydrochloride;

2-[(2E)-2-(aminomethyl)-3-fluoroprop-2-en-1-yl]-4-[3-(2-
methylpyrimidin-5-yl)phenyl]-2,4-dihydro-3H-1,2,4-tri-
azol-3-one hydrochloride;

2-[(2Z)-2-(aminomethyl)-3-fluoroprop-2-en-1-yl]-4-[3-(1,
3-benzodioxol-5-yl)phenyl]-2,4-dihydro-3H-1,2,4-tri-
azol-3-one hydrochloride;

2-[(2E)-2-(aminomethyl)-3-fluoroprop-2-en-1-yl]-4-[3-(1,
3-benzodioxol-5-yl)phenyl]-2,4-dihydro-3H-1,2,4-tri-
azol-3-one hydrochloride;

2-[(2Z)-2-(aminomethyl)-3-fluoroprop-2-en-1-yl]-4-[3-(2,
3-dihydro-1,4-benzodioxin-6-yl)phenyl]-2,4-dihydro-
3H-1,2,4-triazol-3-one hydrochloride;

2-[(2E)-2-(aminomethyl)-3-fluoroprop-2-en-1-yl]-4-[3-(2,
3-dihydro-1,4-benzodioxin-6-yl)phenyl]-2,4-dihydro-
3H-1,2,4-triazol-3-one hydrochloride;

2-[(2E)-2-(aminomethyl)-3-fluoroprop-2-en-1-yl]-4-[3-(2,
1,3-benzoxadiazol-5-yl)phenyl]-2,4-dihydro-3H-1,2,4-
triazol-3-one hydrochloride;

2-[(2E)-2-(aminomethyl)-3-fluoroprop-2-en-1-yl]-4-[3-
(1H-indazol-6-yl)phenyl]-2,4-dihydro-3H-1,2,4-triazol-
3-one hydrochloride;

2-[(2E)-2-(aminomethyl)-3-fluoroprop-2-en-1-yl]-4-[3-
(1H-indol-4-yl)phenyl]-2,4-dihydro-3H-1,2,4-triazol-3-
one hydrochloride;

4-[3-(2-amino-1,3-benzothiazol-5-yl)phenyl]-2-[(2E)-2-
(aminomethyl)-3-fluoroprop-2-en-1-yl]-2,4-dihydro-3H-
1,2,4-triazol-3-one hydrochloride;

2-[(2E)-2-(aminomethyl)-3-fluoroprop-2-en-1-yl]-4-[3-
(1H-indol-3-yl)phenyl]-2,4-dihydro-3H-1,2,4-triazol-3-
one hydrochloride;

2-[(2E)-2-(aminomethyl)-3-fluoroprop-2-en-1-yl]-4-[3-(1-
benzothiophen-2-yl)phenyl]-2,4-dihydro-3H-1,2,4-tri-
azol-3-one hydrochloride;

6-(3-{1-[(2E)-2-(aminomethyl)-3-fluoroprop-2-en-1-yl]-5-
oxo-1,5-dihydro-4H-1,2,4-triazol-4-yl}phenyl)-8-
methyl-3,4-dihydroquinolin-2(1H)-one hydrochloride;

6-(3-{1-[(2E)-2-(aminomethyl)-3-fluoroprop-2-en-1-yl]-5-
oxo-1,5-dihydro-4H-1,2,4-triazol-4-yl}phenyl)-2H-1,4-
benzoxazin-3(4H)-one hydrochloride;

2-[(2E)-2-(aminomethyl)-3-fluoroprop-2-en-1-yl]-4-[3-
(isoquinolin-4-yl)phenyl]-2,4-dihydro-3H-1,2,4-triazol-
3-one hydrochloride;

2-[(2E)-2-(aminomethyl)-3-fluoroprop-2-en-1-yl]-4-[3-(8-
methylquinolin-5-yl)phenyl]-2,4-dihydro-3H-1,2,4-tri-
azol-3-one hydrochloride;

2-[(2E)-2-(aminomethyl)-3-fluoroprop-2-en-1-yl]-4-[2-
methyl-4'-(methylsulfonyl)biphenyl-3-yl]-2,4-dihydro-
3H-1,2,4-triazol-3-one;

N-(3'-{1-[(2E)-2-(aminomethyl)-3-fluoroprop-2-en-1-yl]-5-
oxo-1,5-dihydro-4H-1,2,4-triazol-4-yl}-2'-methylbiphe-
nyl-4-yl)acetamide;

2-[(2E)-2-(aminomethyl)-3-fluoroprop-2-en-1-yl]-4-[2-
methyl-4'-(1,2-oxazol-3-yl)biphenyl-3-yl]-2,4-dihydro-
3H-1,2,4-triazol-3-one;

N-[4-(3-{1-[(2E)-2-(aminomethyl)-3-fluoroprop-2-en-1-
yl]-5-oxo-1,5-dihydro-4H-1,2,4-triazol-4-yl}-2-meth-
ylphenyl)pyridin-2-yl]acetamide;

2-[(2E)-2-(aminomethyl)-3-fluoroprop-2-en-1-yl]-4-{2-
methyl-3-[6-(morpholin-4-yl)pyridin-3-yl]phenyl}-2,4-
dihydro-3H-1,2,4-triazol-3-one;

2-[(2E)-2-(aminomethyl)-3-fluoroprop-2-en-1-yl]-4-[3-(1,
3-benzodioxol-5-yl)-2-methylphenyl]-2,4-dihydro-3H-1,
2,4-triazol-3-one;

2-[(2E)-2-(aminomethyl)-3-fluoroprop-2-en-1-yl]-4-[3-(2,
3-dihydro-1,4-benzodioxin-6-yl)-2-methylphenyl]-2,4-
dihydro-3H-1,2,4-triazol-3-one;

2-[(2E)-2-(aminomethyl)-3-fluoroprop-2-en-1-yl]-4-[3-(2,
1,3-benzoxadiazol-5-yl)-2-methylphenyl]-2,4-dihydro-
3H-1,2,4-triazol-3-one;

4-[3-(2-amino-1,3-benzothiazol-5-yl)-2-methylphenyl]-2-
[(2E)-2-(aminomethyl)-3-fluoroprop-2-en-1-yl]-2,4-di-
hydro-3H-1,2,4-triazol-3-one;

2-[(2E)-2-(aminomethyl)-3-fluoroprop-2-en-1-yl]-4-{5-methyl-6-[4-(1H-1,2,4-triazol-3-yl)phenyl]pyridin-3-yl}-2,4-dihydro-3H-1,2,4-triazol-3-one;

2-[(2E)-2-(aminomethyl)-3-fluoroprop-2-en-1-yl]-4-{5-methyl-6-[3-(1H-1,2,4-triazol-3-yl)phenyl]pyridin-3-yl}-2,4-dihydro-3H-1,2,4-triazol-3-one;

2-[(2E)-2-(aminomethyl)-3-fluoroprop-2-en-1-yl]-4-[6-(1,3-benzodioxol-5-yl)-5-methylpyridin-3-yl]-2,4-dihydro-3H-1,2,4-triazol-3-one;

4-[6-(2-amino-1,3-benzothiazol-5-yl)-5-methylpyridin-3-yl]-2-[(2E)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-{4-methyl-6-[4-(methylsulfonyl)phenyl]pyridin-3-yl}-2,4-dihydro-3H-1,2,4-triazol-3-one;

N-[4-(5-{1-[(2E)-2-(aminomethyl)-3-fluoroprop-2-en-1-yl]-5-oxo-1,5-dihydro-4H-1,2,4-triazol-4-yl}-4-methylpyridin-2-yl)phenyl]acetamide;

2-[(2E)-2-(aminomethyl)-3-fluoroprop-2-en-1-yl]-4-{4-methyl-6-[4-(1H-1,2,4-triazol-3-yl)phenyl]pyridin-3-yl}-2,4-dihydro-3H-1,2,4-triazol-3-one;

2-[(2E)-2-(aminomethyl)-3-fluoroprop-2-en-1-yl]-4-{4-methyl-6-[3-(1H-1,2,4-triazol-3-yl)phenyl]pyridin-3-yl}-2,4-dihydro-3H-1,2,4-triazol-3-one;

N-(5-{1-[(2E)-2-(aminomethyl)-3-fluoroprop-2-en-1-yl]-5-oxo-1,5-dihydro-4H-1,2,4-triazol-4-yl}-4-methyl-2,4'-bipyridin-2'-yl)acetamide;

2-[(2E)-2-(aminomethyl)-3-fluoroprop-2-en-1-yl]-4-[4-methyl-6'-(morpholin-4-yl)-2,3'-bipyridin-5-yl]-2,4-dihydro-3H-1,2,4-triazol-3-one;

2-[(2E)-2-(aminomethyl)-3-fluoroprop-2-en-1-yl]-4-[6-(2,1,3-benzoxadiazol-5-yl)-4-methylpyridin-3-yl]-2,4-dihydro-3H-1,2,4-triazol-3-one;

2-[(2E)-2-(aminomethyl)-3-fluoroprop-2-en-1-yl]-4-[6-(1H-indazol-6-yl)-4-methylpyridin-3-yl]-2,4-dihydro-3H-1,2,4-triazol-3-one;

4-[6-(2-amino-1,3-benzothiazol-5-yl)-4-methylpyridin-3-yl]-2-[(2E)-2-(aminomethyl)-3-fluoroprop-2-en-1-yl]-2,4-dihydro-3H-1,2,4-triazol-3-one;

N-[5-(5-{1-[(2E)-2-(aminomethyl)-3-fluoroprop-2-en-1-yl]-5-oxo-1,5-dihydro-4H-1,2,4-triazol-4-yl}-4-methylpyridin-2-yl)-1,3-benzothiazol-2-yl]acetamide;

2-[(2Z)-2-(aminomethyl)-3-fluoroprop-2-en-1-yl]-4-{5-[4-(methylsulfonyl)phenyl]pyridin-2-yl}-2,4-dihydro-3H-1,2,4-triazol-3-one hydrochloride;

N-[4-(6-{1-[(2Z)-2-(aminomethyl)-3-fluoroprop-2-en-1-yl]-5-oxo-1,5-dihydro-4H-1,2,4-triazol-4-yl}pyridin-3-yl)phenyl]acetamide hydrochloride;

2-[(2E)-2-(aminomethyl)-3-fluoroprop-2-en-1-yl]-4-[3-methyl-5-(piperazin-1-yl)pyridin-2-yl]-2,4-dihydro-3H-1,2,4-triazol-3-one;

4-[5-(5-acetylthiophen-2-yl)-3-methylpyridin-2-yl]-2-[(2E)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-{3-methyl-5-[4-(methylsulfonyl)phenyl]pyridin-2-yl}-2,4-dihydro-3H-1,2,4-triazol-3-one hydrochloride;

N-[4-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)phenyl]acetamide hydrochloride;

2-[(2Z)-2-(aminomethyl)-3-fluoroprop-2-en-1-yl]-4-{3-methyl-5-[4-(4H-1,2,4-triazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{3-methyl-5-[4-(4H-1,2,4-triazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{3-methyl-5-[3-(4H-1,2,4-triazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{3-methyl-5-[4-(1,2,5-oxadiazol-3-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{3-methyl-5-[4-(1,2,4-oxadiazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{3-methyl-5-[3-(1,2,4-oxadiazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{5-[4-(5-cyclopropyl-1,2,4-oxadiazol-3-yl)phenyl]-3-methylpyridin-2-yl}-2,4-dihydro-3H-1,2,4-triazol-3-one hydrochloride;

2-[(2E)-2-(aminomethyl)-3-fluoroprop-2-en-1-yl]-4-(3-methyl-5-{4-[5-(propane-2-yl)-1,2,4-oxadiazol-3-yl]phenyl}pyridin-2-yl)-2,4-dihydro-3H-1,2,4-triazol-3-one hydrochloride;

2-[(2E)-2-(aminomethyl)-3-fluoroprop-2-en-1-yl]-4-(3-methyl-5-{3-[5-(propan-2-yl)-1,2,4-oxadiazol-3-yl]phenyl}pyridin-2-yl)-2,4-dihydro-3H-1,2,4-triazol-3-one hydrochloride;

2-[(2E)-2-(aminomethyl)-3-fluoroprop-2-en-1-yl]-4-{3-methyl-5-[3-(1H-tetrazol-5-yl)phenyl]pyridin-2-yl}-2,4-dihydro-3H-1,2,4-triazol-3-one;

2-[(2E)-2-(aminomethyl)-3-fluoroprop-2-en-1-yl]-4-{3-methyl-5-[4-(piperazin-1-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{3-methyl-5-[4-(morpholin-4-ylcarbonyl)phenyl]pyridin-2-yl}-2,4-dihydro-3H-1,2,4-triazol-3-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-2H-1,4-benzoxazin-3(4H)-one hydrochloride;

2-[(2E)-2-(aminomethyl)-3-fluoroprop-2-en-1-yl]-4-[5-methyl-6'-(trifluoromethyl)-3,3'-bipyridin-6-yl]-2,4-dihydro-3H-1,2,4-triazol-3-one hydrochloride;

2-[(2E)-2-(aminomethyl)-3-fluoroprop-2-en-1-yl]-4-[5-methyl-6'-(morpholin-4-yl)-3,3'-bipyridin-6-yl]-2,4-dihydro-3H-1,2,4-triazol-3-one hydrochloride;

2-[(2E)-2-(aminomethyl)-3-fluoroprop-2-en-1-yl]-4-[5-(2H-1,3-benzodioxol-5-yl)-3-methylpyridin-2-yl]-2,4-dihydro-3H-1,2,4-triazol-3-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-1,3-dihydro-2H-indol-2-one;

2-[(2E)-2-(aminomethyl)-3-fluoroprop-2-en-1-yl]-4-[5-(2,1,3-benzoxadiazol-5-yl)-3-methylpyridin-2-yl]-2,4-dihydro-3H-1,2,4-triazol-3-one hydrochloride;

2-[(2E)-2-(aminomethyl)-3-fluoroprop-2-en-1-yl]-4-[5-(1H-indazol-6-yl)-3-methylpyridin-2-yl]-2,4-dihydro-3H-1,2,4-triazol-3-one;

6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-8-methyl-3,4-dihydroquinolin-2(1H)-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-2H-1,4-benzoxazin-3(4H)-one hydrochloride;

7-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-1,4-dihydro-2H-3,1-benzoxazin-2-one hydrochloride;

2-[(2E)-2-(aminomethyl)-3-fluoroprop-2-en-1-yl]-4-{4-methyl-5-[4-(1H-1,2,4-triazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{4-methyl-5-[3-(1H-1,2,4-triazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-[5-(1,3-benzodioxol-5-yl)-4-methylpyridin-2-yl]-2,4-dihydro-3H-1,2,4-triazol-3-one;

2-[(2E)-2-(aminomethyl)-3-fluoroprop-2-en-1-yl]-4-[5-(1H-indazol-6-yl)-4-methylpyridin-2-yl]-2,4-dihydro-3H-1,2,4-triazol-3-one;

4-[5-(2-amino-1,3-benzothiazol-5-yl)-4-methylpyridin-2-yl]-2-[(2E)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-[5-(1,3-benzodioxol-5-yl)-3-fluoropyridin-2-yl]-2,4-dihydro-3H-1,2,4-triazol-3-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-fluoropyridin-3-yl)-1,2-dihydro-3H-indol-3-one;

4-[5-(2-amino-1,3-benzothiazol-5-yl)-3-fluoropyridin-2-yl]-2-[(2E)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-{4-[4-(methylsulfonyl)phenyl]pyridin-2-yl}-2,4-dihydro-3H-1,2,4-triazol-3-one;

N-[4-(2-{1-[(2E)-2-(aminomethyl)-3-fluoroprop-2-en-1-yl]-5-oxo-1,5-dihydro-4H-1,2,4-triazol-4-yl}pyridin-4-yl)phenyl]acetamide;

2-[(2E)-2-(aminomethyl)-3-fluoroprop-2-en-1-yl]-4-{4-[4-(1,2-oxazol-3-yl)phenyl]pyridin-2-yl}-2,4-dihydro-3H-1,2,4-triazol-3-one;

N-(2'-{1-[(2E)-2-(aminomethyl)-3-fluoroprop-2-en-1-yl]-5-oxo-1,5-dihydro-4H-1,2,4-triazol-4-yl}-4,4'-bipyridin-2-yl)acetamide;

2-[(2E)-2-(aminomethyl)-3-fluoroprop-2-en-1-yl]-4-[6-(morpholin-4-yl)-3,4'-bipyridin-2'-yl]-2,4-dihydro-3H-1,2,4-triazol-3-one;

2-[(2E)-2-(aminomethyl)-3-fluoroprop-2-en-1-yl]-4-[4-(1,3-benzodioxol-5-yl)pyridin-2-yl]-2,4-dihydro-3H-1,2,4-triazol-3-one;

2-[(2E)-2-(aminomethyl)-3-fluoroprop-2-en-1-yl]-4-[4-(2,3-dihydro-1,4-benzodioxin-6-yl)pyridin-2-yl]-2,4-dihydro-3H-1,2,4-triazol-3-one;

2-[(2E)-2-(aminomethyl)-3-fluoroprop-2-en-1-yl]-4-[4-(2,1,3-benzoxadiazol-5-yl)pyridin-2-yl]-2,4-dihydro-3H-1,2,4-triazol-3-one;

4-[4-(2-amino-1,3-benzothiazol-5-yl)pyridin-2-yl]-2-[(2E)-2-(aminomethyl)-3-fluoroprop-2-en-1-yl]-2,4-dihydro-3H-1,2,4-triazol-3-one;

2-[(2E)-2-(aminomethyl)-3-fluoroprop-2-en-1-yl]-4-{6-[3-(dimethylamino)phenyl]pyridin-2-yl}-2,4-dihydro-3H-1,2,4-triazol-3-one hydrochloride;

N-[4-(6-{1-[(2E)-2-(aminomethyl)-3-fluoroprop-2-en-1-yl]-5-oxo-1,5-dihydro-4H-1,2,4-triazol-4-yl}pyridin-2-yl)phenyl]acetamide;

2-[(2E)-2-(aminomethyl)-3-fluoroprop-2-en-1-yl]-4-{6-[4-(1,2-oxazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{6-[4-(1,2,5-oxadiazol-3-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[4-(5-cyclopropyl-1,2,4-oxadiazol-3-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[3-(5-cyclopropyl-1,2,4-oxadiazol-3-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-(6-{4-[5-(propan-2-yl)-1,2,4-oxadiazol-3-yl]phenyl}pyridin-2-yl)-2,4-dihydro-3H-1,2,4-triazol-3-one;

2-[(2E)-2-(aminomethyl)-3-fluoroprop-2-en-1-yl]-4-(6-{3-[5-(propan-2-yl)-1,2,4-oxadiazol-3-yl]phenyl}pyridin-2-yl)-2,4-dihydro-3H-1,2,4-triazol-3-one;

3-[4-(6-{1-[(2E)-2-(aminomethyl)-3-fluoroprop-2-en-1-yl]-5-oxo-1,5-dihydro-4H-1,2,4-triazol-4-yl}pyridin-2-yl)phenyl]-1,2,4-oxadiazol-5(4H)-one hydrochloride;

2-[(2E)-2-(aminomethyl)-3-fluoroprop-2-en-1-yl]-4-{6-[4-(pyrrolidin-1-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[4-(piperazin-1-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[3-(piperazin-1-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[4-(morpholin-4-ylcarbonyl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-[6'-(trifluoromethyl)-2,3'-bipyridin-6-yl]-2,4-dihydro-3H-1,2,4-triazol-3-one hydrochloride;

2-[(2E)-2-(aminomethyl)-3-fluoroprop-2-en-1-yl]-4-[6'-(dimethylamino)-2,3'-bipyridin-6-yl]-2,4-dihydro-3H-1,2,4-triazol-3-one hydrochloride;

2-[(2E)-2-(aminomethyl)-3-fluoroprop-2-en-1-yl]-4-[6'-(morpholin-4-yl)-2,3'-bipyridin-6-yl]-2,4-dihydro-3H-1,2,4-triazol-3-one;

2-[(2E)-2-(aminomethyl)-3-fluoroprop-2-en-1-yl]-4-(6'-fluoro-5'-methyl-2,3'-bipyridin-6-yl)-2,4-dihydro-3H-1,2,4-triazol-3-one hydrochloride;

2-[(2E)-2-(aminomethyl)-3-fluoroprop-2-en-1-yl]-4-[6'-(dimethylamino)-5'-fluoro-2,3'-bipyridin-6-yl]-2,4-dihydro-3H-1,2,4-triazol-3-one hydrochloride;

2-[(2E)-2-(aminomethyl)-3-fluoroprop-2-en-1-yl]-4-{6-[1-methyl-3-(trifluoromethyl)-1H-pyrazol-5-yl]pyridin-2-yl}-2,4-dihydro-3H-1,2,4-triazol-3-one hydrochloride;

2-[(2E)-2-(aminomethyl)-3-fluoroprop-2-en-1-yl]-4-{6-(1,3-benzodioxol-5-yl)pyridin-2-yl}-2,4-dihydro-3H-1,2,4-triazol-3-one;

2-[(2E)-2-(aminomethyl)-3-fluoroprop-2-en-1-yl]-4-[6-(2,3-dihydro-1,4-benzodioxin-6-yl)pyridin-2-yl]-2,4-dihydro-3H-1,2,4-triazol-3-one;

2-[(2E)-2-(aminomethyl)-3-fluoroprop-2-en-1-yl]-4-[6-(2,1,3-benzoxadiazol-5-yl)pyridin-2-yl]-2,4-dihydro-3H-1,2,4-triazol-3-one;

4-[6-(2-amino-1,3-benzothiazol-5-yl)pyridin-2-yl]-2-[(2E)-2-(aminomethyl)-3-fluoroprop-2-en-1-yl]-2,4-dihydro-3H-1,2,4-triazol-3-one;

6-(6-{1-[(2E)-2-(aminomethyl)-3-fluoroprop-2-en-1-yl]-5-oxo-1,5-dihydro-4H-1,2,4-triazol-4-yl}pyridin-2-yl)-8-methyl-3,4-dihydroquinolin-2(1H)-one hydrochloride;

6-[6-[1-[(E)-2-(aminomethyl)-3-fluoro-allyl]-5-oxo-1,2,4-triazol-4-yl]-2-pyridyl]-1-methyl-3,4-dihydroquinolin-2-one hydrochloride;

6-(3-{1-[(2E)-2-(aminomethyl)-3-fluoroprop-2-en-1-yl]-5-oxo-1,5-dihydro-4H-1,2,4-triazol-4-yl}pyridin-2-yl)-2H-1,4-benzoxazin-3(4H)-one hydrochloride;

7-(6-{1-[(2E)-2-(aminomethyl)-3-fluoroprop-2-en-1-yl]-5-oxo-1,5-dihydro-4H-1,2,4-triazol-4-yl}pyridin-2-yl)-1,4-dihydro-2H-3,1-benzoxazin-2-one hydrochloride;

5-(6-{1-[(2E)-2-(aminomethyl)-3-fluoroprop-2-en-1-yl]-5-oxo-1,5-dihydro-4H-1,2,4-triazol-4-yl}pyridin-2-yl)quinolin-2(1H)-one hydrochloride;

2-[(2E)-2-(aminomethyl)-3-fluoroprop-2-en-1-yl]-4-[6-(4-methyl-3,4-dihydro-2H-1,4-benzoxazin-7-yl)pyridin-2-yl]-2,4-dihydro-3H-1,2,4-triazol-3-one hydrochloride;

2-[(2E)-2-(aminomethyl)-3-fluoroprop-2-en-1-yl]-4-[6-(dibenzo[b,d]furan-4-yl)pyridin-2-yl]-2,4-dihydro-3H-1,2,4-triazol-3-one hydrochloride;

2-[(2E)-2-(aminomethyl)-3-fluoroprop-2-en-1-yl]-4-{6-[4-(5-cyclopropyl-1,2,4-oxadiazol-3-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-(2-{4-[5-(propan-2-yl)-1,2,4-oxadiazol-3-yl]phenyl}pyridin-4-yl)-2,4-dihydro-3H-1,2,4-triazol-3-one hydrochloride;

2-[(2E)-2-(aminomethyl)-3-fluoroprop-2-en-1-yl]-4-(2-{3-[5-(propan-2-yl)-1,2,4-oxadiazol-3-yl]phenyl}pyridin-4-yl)-2,4-dihydro-3H-1,2,4-triazol-3-one hydrochloride;

2-[(2E)-2-(aminomethyl)-3-fluoroprop-2-en-1-yl]-4-{2-[4-(morpholin-4-yl)phenyl]pyridin-4-yl}-2,4-dihydro-3H-1,2,4-triazol-3-one hydrochloride;

2-[(2E)-2-(aminomethyl)-3-fluoroprop-2-en-1-yl]-4-{2-[4-(morpholin-4-ylcarbonyl)phenyl]pyridin-4-yl}-2,4-dihydro-3H-1,2,4-triazol-3-one hydrochloride;

2-[(2E)-2-(aminomethyl)-3-fluoroprop-2-en-1-yl]-4-[2-(1,3-benzodioxol-5-yl)pyridin-4-yl]-2,4-dihydro-3H-1,2,4-triazol-3-one hydrochloride;

2-[(2E)-2-(aminomethyl)-3-fluoroprop-2-en-1-yl]-4-{6-[3-(5-cyclopropyl-1,2,4-oxadiazol-3-yl)phenyl]-3-methylpyridin-2-yl}-2,4-dihydro-3H-1,2,4-triazol-3-one hydrochloride;

2-[(2E)-2-(aminomethyl)-3-fluoroprop-2-en-1-yl]-4-{3-methyl-6-[4-(morpholin-4-ylcarbonyl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-(6'-methoxy-5-methyl-2,3'-bipyridin-6-yl)-2,4-dihydro-3H-1,2,4-triazol-3-one hydrochloride;

2-[(2E)-2-(aminomethyl)-3-fluoroprop-2-en-1-yl]-4-[6-(1,3-benzodioxol-5-yl)-3-methylpyridin-2-yl]-2,4-dihydro-3H-1,2,4-triazol-3-one hydrochloride;

2-[(2E)-2-(aminomethyl)-3-fluoroprop-2-en-1-yl]-4-[6-(1H-indazol-6-yl)-3-methylpyridin-2-yl]-2,4-dihydro-3H-1,2,4-triazol-3-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-methylpyridin-2-yl)-8-methyl-3,4-dihydroquinolin-2(1H)-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-methylpyridin-2-yl)-2H-1,4-benzoxazin-3(4H)-one hydrochloride;

2-[(2E)-2-(aminomethyl)-3-fluoroprop-2-en-1-yl]-4-{5-[4-(methylsulfonyl)phenyl]pyrazin-2-yl}-2,4-dihydro-3H-1,2,4-triazol-3-one;

2-[(2E)-2-(aminomethyl)-3-fluoroprop-2-en-1-yl]-4-{5-[4-(1H-1,2,4-triazol-3-yl)phenyl]pyrazin-2-yl}-2,4-dihydro-3H-1,2,4-triazol-3-one;

2-[(2E)-2-(aminomethyl)-3-fluoroprop-2-en-1-yl]-4-{5-[3-(1H-1,2,4-triazol-3-yl)phenyl]pyrazin-2-yl}-2,4-dihydro-3H-1,2,4-triazol-3-one;

N-[4-(5-{1-[(2E)-2-(aminomethyl)-3-fluoroprop-2-en-1-yl]-5-oxo-1,5-dihydro-4H-1,2,4-triazol-4-yl}pyrazin-2-yl)pyridin-2-yl]acetamide;

2-[(2E)-2-(aminomethyl)-3-fluoroprop-2-en-1-yl]-4-{5-[6-(morpholin-4-yl)pyridin-3-yl]pyrazin-2-yl}-2,4-dihydro-3H-1,2,4-triazol-3-one;

2-[(2E)-2-(aminomethyl)-3-fluoroprop-2-en-1-yl]-4-[5-(2,1,3-benzoxadiazol-5-yl)pyrazin-2-yl]-2,4-dihydro-3H-1,2,4-triazol-3-one;

2-[(2E)-2-(aminomethyl)-3-fluoroprop-2-en-1-yl]-4-[5-(1H-indazol-6-yl)pyrazin-2-yl]-2,4-dihydro-3H-1,2,4-triazol-3-one;

4-[5-(2-amino-1,3-benzothiazol-5-yl)pyrazin-2-yl]-2-[(2E)-2-(aminomethyl)-3-fluoroprop-2-en-1-yl]-2,4-dihydro-3H-1,2,4-triazol-3-one;

N-[5-(5-{1-[(2E)-2-(aminomethyl)-3-fluoroprop-2-en-1-yl]-5-oxo-1,5-dihydro-4H-1,2,4-triazol-4-yl}pyrazin-2-yl)-1,3-benzothiazol-2-yl]acetamide;

2-[(2Z)-2-(aminomethyl)-3-fluoroprop-2-en-1-yl]-4-{5-[4-(methylsulfonyl)phenyl]-1,3-thiazol-2-yl}-2,4-dihydro-3H-1,2,4-triazol-3-one hydrochloride;

2-[(2E)-2-(aminomethyl)-3-fluoroprop-2-en-1-yl]-4-{5-[4-(4H-1,2,4-triazol-3-yl)phenyl]-1,3-thiazol-2-yl}-2,4-dihydro-3H-1,2,4-triazol-3-one;

2-[(2E)-2-(aminomethyl)-3-fluoroprop-2-en-1-yl]-4-{5-[3-(4H-1,2,4-triazol-3-yl)phenyl]-1,3-thiazol-2-yl}-2,4-dihydro-3H-1,2,4-triazol-3-one;

2-[(2E)-2-(aminomethyl)-3-fluoroprop-2-en-1-yl]-4-{5-[4-(4H-1,2,4-oxadiazol-3-yl)phenyl]-1,3-thiazol-2-yl}-2,4-dihydro-3H-1,2,4-triazol-3-one;

2-[(2E)-2-(aminomethyl)-3-fluoroprop-2-en-1-yl]-4-{5-[3-(1H-tetrazol-5-yl)phenyl]-1,3-thiazol-2-yl}-2,4-dihydro-3H-1,2,4-triazol-3-one;

N-[4-(2-{1-[(2E)-2-(aminomethyl)-3-fluoroprop-2-en-1-yl]-5-oxo-1,5-dihydro-4H-1,2,4-triazol-4-yl}-1,3-thiazol-5-yl)pyridin-2-yl]acetamide;

2-[(2Z)-2-(aminomethyl)-3-fluoroprop-2-en-1-yl]-4-[5-(1,3-benzodioxol-5-yl)-1,3-thiazol-2-yl]-2,4-dihydro-3H-1,2,4-triazol-3-one hydrochloride;

6-(2-{1-[(2E)-2-(aminomethyl)-3-fluoroprop-2-en-1-yl]-5-oxo-1,5-dihydro-4H-1,2,4-triazol-4-yl}-1,3-thiazol-5-yl)-1,3-dihydro-2H-indol-2-one;

2-[(2Z)-2-(aminomethyl)-3-fluoroprop-2-en-1-yl]-4-[5-(2,1,3-benzoxadiazol-5-yl)-1,3-thiazol-2-yl]-2,4-dihydro-3H-1,2,4-triazol-3-one hydrochloride;

N-[5-(4-{1-[(2E)-2-(aminomethyl)-3-fluoroprop-2-en-1-yl]-5-oxo-1,5-dihydro-4H-1,2,4-triazol-4-yl}benzyl)-1,3-thiazol-2-yl]acetamide hydrochloride;

2-[(2E)-2-(aminomethyl)-3-fluoroprop-2-en-1-yl]-4-{4-[(E)-2-phenylethenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[(E)-2-(thiophen-3-yl)ethenyl]pyridin-2-yl}-2,4-dihydro-3H-1,2,4-triazol-3-one;

2-[(2E)-2-(aminomethyl)-3-fluoroprop-2-en-1-yl]-4-(6-{(E)-2-[4-(trifluoromethyl)phenyl]ethenyl}pyridin-2-yl)-2,4-dihydro-3H-1,2,4-triazol-3-one hydrochloride;

2-[(E)-2-(aminomethyl)-3-fluoro-allyl]-4-[6-[(E)-2-[4-(dimethylamino)phenyl]vinyl]-2-pyridyl]-1,2,4-triazol-3-one hydrochloride;

2-[(E)-2-(aminomethyl)-3-fluoro-allyl]-4-[6-[(E)-2-(3-methyl-1,2-dihydroimidazo[4,5-b]pyridin-6-yl)vinyl]-2-pyridyl]-1,2,4-triazol-3-one hydrochloride;

7-[(E)-2-[6-[1-[(E)-2-(aminomethyl)-3-fluoro-allyl]-5-oxo-1,2,4-triazol-4-yl]-2-pyridyl]vinyl]-1H-pyrido[2,3-b][1,4]oxazin-2-one hydrochloride;

6-[(E)-2-[6-[1-[(E)-2-(aminomethyl)-3-fluoro-allyl]-5-oxo-1,2,4-triazol-4-yl]-2-pyridyl]vinyl]-3H-oxazolo[4,5-b]pyridin-2-one hydrochloride;

2-[(2E)-2-(aminomethyl)-3-fluoroprop-2-en-1-yl]-4-[3-(pyridin-3-ylethynyl)phenyl]-2,4-dihydro-3H-1,2,4-triazol-3-one hydrochloride;

2-[(2E)-2-(aminomethyl)-3-fluoroprop-2-en-1-yl]-4-[4-(pyridin-2-ylethynyl)pyridin-2-yl]-2,4-dihydro-3H-1,2,4-triazol-3-one hydrochloride;
2-[(2E)-2-(aminomethyl)-3-fluoroprop-2-en-1-yl]-4-[4-(pyridin-3-ylethynyl)pyridin-2-yl]-2,4-dihydro-3H-1,2,4-triazol-3-one hydrochloride;
2-[(2E)-2-(aminomethyl)-3-fluoroprop-2-en-1-yl]-4-[4-(pyridin-4-ylethynyl)pyridin-2-yl]-2,4-dihydro-3H-1,2,4-triazol-3-one hydrochloride;
2-[(2E)-2-(aminomethyl)-3-fluoroprop-2-en-1-yl]-4-{6-[(6-methoxypyridin-3-yl)ethynyl]pyridin-2-yl}-2,4-dihydro-3H-1,2,4-triazol-3-one;
2-[(E)-2-(aminomethyl)-3-fluoro-allyl]-4-[6-[2-[6-(dimethylamino)-3-pyridyl]ethynyl]-2-pyridyl]-1,2,4-triazol-3-one;
2-[(E)-2-(aminomethyl)-3-fluoro-allyl]-4-[6-[2-(6-morpholino-3-pyridyl)ethynyl]-2-pyridyl]-1,2,4-triazol-3-one;
2-[(E)-2-(aminomethyl)-3-fluoro-allyl]-4-[6-[2-(3,4-dihydro-2H-1,4-benzoxazin-6-yl)ethynyl]-2-pyridyl]-1,2,4-triazol-3-one;
2-[(E)-2-(aminomethyl)-3-fluoro-allyl]-4-[6-[2-(2,3-dihydro-1H-pyrido[2,3-b][1,4]oxazin-7-yl)ethynyl]-2-pyridyl]-1,2,4-triazol-3-one;
2-[(E)-2-(aminomethyl)-3-fluoro-allyl]-4-[6-[2-(3,4-dihydro-2H-pyrido[3,2-b][1,4]oxazin-7-yl)ethynyl]-2-pyridyl]-1,2,4-triazol-3-one;
2-[(E)-2-(aminomethyl)-3-fluoro-allyl]-4-[6-[2-(2,3-dihydro-1H-pyrido[2,3-b][1,4]oxazin-6-yl)ethynyl]-2-pyridyl]-1,2,4-triazol-3-one;
6-[2-[6-[1-[(E)-2-(aminomethyl)-3-fluoro-allyl]-5-oxo-1,2,4-triazol-4-yl]-2-pyridyl]ethynyl]-3,4-dihydro-1H-quinolin-2-one;
7-[2-[6-[1-[(E)-2-(aminomethyl)-3-fluoro-allyl]-5-oxo-1,2,4-triazol-4-yl]-2-pyridyl]ethynyl]-4H-pyrido[3,2-b][1,4]oxazin-3-one;
2-[(E)-2-(aminomethyl)-3-fluoro-allyl]-4-[6-[2-(3-methylimidazol-4-yl)ethynyl]-2-pyridyl]-1,2,4-triazol-3-one;
2-[(2E)-2-(aminomethyl)-3-fluoroprop-2-en-1-yl]-4-{6-[(1-methyl-1H-pyrazol-4-yl)ethynyl]pyridin-2-yl}-2,4-dihydro-3H-1,2,4-triazol-3-one hydrochloride;
7-[2-[6-[1-[(E)-2-(aminomethyl)-3-fluoro-allyl]-5-oxo-1,2,4-triazol-4-yl]-2-pyridyl]ethynyl]-1H-pyrido[2,3-b][1,4]oxazin-2-one; and
2-[(E)-2-(aminomethyl)-3-fluoro-allyl]-4-[3-methyl-5-(6-piperazin-1-yl-3-pyridyl)-2-pyridyl]-1,2,4-triazol-3-one.

As for the compound of Formula 1, or the isomer thereof, or a pharmaceutically acceptable salt thereof, the preferred compound may be a compound selected from the group consisting of the following compounds, or an isomer thereof, or a pharmaceutically acceptable salt thereof:
2-[(2Z)-2-(aminomethyl)-3-fluoroprop-2-en-1-yl]-4-(4-bromophenyl)-2,4-dihydro-3H-1,2,4-triazol-3-one;
2-[(2E)-2-(aminomethyl)-3-fluoroprop-2-en-1-yl]-4-(4-bromophenyl)-2,4-dihydro-3H-1,2,4-triazol-3-one;
2-[(2Z)-2-(aminomethyl)-3-fluoroprop-2-en-1-yl]-4-(3-bromophenyl)-2,4-dihydro-3H-1,2,4-triazol-3-one hydrochloride;
2-[(2E)-2-(aminomethyl)-3-fluoroprop-2-en-1-yl]-4-(3-bromophenyl)-2,4-dihydro-3H-1,2,4-triazol-3-one hydrochloride;
2-[(2Z)-2-(aminomethyl)-3-fluoroprop-2-en-1-yl]-4-(4-fluorophenyl)-2,4-dihydro-3H-1,2,4-triazol-3-one;
2-[(2E)-2-(aminomethyl)-3-fluoroprop-2-en-1-yl]-4-(4-fluorophenyl)-2,4-dihydro-3H-1,2,4-triazol-3-one hydrochloride;
2-[(2Z)-2-(aminomethyl)-3-fluoroprop-2-en-1-yl]-4-[4-(benzyloxy)phenyl]-2,4-dihydro-3H-1,2,4-triazol-3-one;
2-[(2E)-2-(aminomethyl)-3-fluoroprop-2-en-1-yl]-4-[4-(benzyloxy)phenyl]-2,4-dihydro-3H-1,2,4-triazol-3-one hydrochloride;
2-[(2Z)-2-(aminomethyl)-3-fluoroprop-2-en-1-yl]-4-(3,4-difluorophenyl)-2,4-dihydro-3H-1,2,4-triazol-3-one;
2-[(2E)-2-(aminomethyl)-3-fluoroprop-2-en-1-yl]-4-(3,4-difluorophenyl)-2,4-dihydro-3H-1,2,4-triazol-3-one hydrochloride;
2-[(2Z)-2-(aminomethyl)-3-fluoroprop-2-en-1-yl]-4-(4-bromo-2-fluorophenyl)-2,4-dihydro-3H-1,2,4-triazol-3-one hydrochloride;
2-[(2E)-2-(aminomethyl)-3-fluoroprop-2-en-1-yl]-4-(4-bromo-2-fluorophenyl)-2,4-dihydro-3H-1,2,4-triazol-3-one hydrochloride;
2-[(2Z)-2-(aminomethyl)-3-fluoroprop-2-en-1-yl]-4-(4-bromo-3-fluorophenyl)-2,4-dihydro-3H-1,2,4-triazol-3-one;
2-[(2E)-2-(aminomethyl)-3-fluoroprop-2-en-1-yl]-4-(4-bromo-3-fluorophenyl)-2,4-dihydro-3H-1,2,4-triazol-3-one hydrochloride;
2-[(2Z)-2-(aminomethyl)-3-fluoroprop-2-en-1-yl]-4-(4-bromo-3-methylphenyl)-2,4-dihydro-3H-1,2,4-triazol-3-one;
2-[(2E)-2-(aminomethyl)-3-fluoroprop-2-en-1-yl]-4-(4-bromo-3-methylphenyl)-2,4-dihydro-3H-1,2,4-triazol-3-one hydrochloride;
2-[(2Z)-2-(aminomethyl)-3-fluoroprop-2-en-1-yl]-4-(4-bromo-3-methoxyphenyl)-2,4-dihydro-3H-1,2,4-triazol-3-one;
2-[(2E)-2-(aminomethyl)-3-fluoroprop-2-en-1-yl]-4-(4-bromo-3-methoxyphenyl)-2,4-dihydro-3H-1,2,4-triazol-3-one hydrochloride;
2-[(2Z)-2-(aminomethyl)-3-fluoroprop-2-en-1-yl]-4-(4-bromo-3,5-difluorophenyl)-2,4-dihydro-3H-1,2,4-triazol-3-one;
2-[(2E)-2-(aminomethyl)-3-fluoroprop-2-en-1-yl]-4-(4-bromo-3,5-difluorophenyl)-2,4-dihydro-3H-1,2,4-triazol-3-one hydrochloride;
2-[(2Z)-2-(aminomethyl)-3-fluoroprop-2-en-1-yl]-4-(4-bromo-2,6-difluorophenyl)-2,4-dihydro-3H-1,2,4-triazol-3-one hydrochloride;
2-[(2E)-2-(aminomethyl)-3-fluoroprop-2-en-1-yl]-4-(4-bromo-2,6-difluorophenyl)-2,4-dihydro-3H-1,2,4-triazol-3-one hydrochloride;
2-[(2E)-2-(aminomethyl)-3-fluoroprop-2-en-1-yl]-4-(4-bromo-2,5-difluorophenyl)-2,4-dihydro-3H-1,2,4-triazol-3-one hydrochloride;
2-[(2Z)-2-(aminomethyl)-3-fluoroprop-2-en-1-yl]-4-(6-bromopyridin-3-yl)-2,4-dihydro-3H-1,2,4-triazol-3-one;
2-[(2E)-2-(aminomethyl)-3-fluoroprop-2-en-1-yl]-4-(6-bromopyridin-3-yl)-2,4-dihydro-3H-1,2,4-triazol-3-one hydrochloride;
2-[(2Z)-2-(aminomethyl)-3-fluoroprop-2-en-1-yl]-4-(6-bromo-5-methylpyridin-3-yl)-2,4-dihydro-3H-1,2,4-triazol-3-one hydrochloride;
2-[(2E)-2-(aminomethyl)-3-fluoroprop-2-en-1-yl]-4-(6-bromo-5-methylpyridin-3-yl)-2,4-dihydro-3H-1,2,4-triazol-3-one hydrochloride;
2-[(2E)-2-(aminomethyl)-3-fluoroprop-2-en-1-yl]-4-(6-bromo-4-methylpyridin-3-yl)-2,4-dihydro-3H-1,2,4-triazol-3-one hydrochloride;
2-[(2Z)-2-(aminomethyl)-3-fluoroprop-2-en-1-yl]-4-(5-bromopyridin-2-yl)-2,4-dihydro-3H-1,2,4-triazol-3-one hydrochloride;

2-[(2E)-2-(aminomethyl)-3-fluoroprop-2-en-1-yl]-4-(5-bromopyridin-2-yl)-2,4-dihydro-3H-1,2,4-triazol-3-one hydrochloride;
2-[(2Z)-2-(aminomethyl)-3-fluoroprop-2-en-1-yl]-4-(5-bromo-3-methylpyridin-2-yl)-2,4-dihydro-3H-1,2,4-triazol-3-one hydrochloride;
2-[(2E)-2-(aminomethyl)-3-fluoroprop-2-en-1-yl]-4-(5-bromo-3-methylpyridin-2-yl)-2,4-dihydro-3H-1,2,4-triazol-3-one hydrochloride;
2-[(2Z)-2-(aminomethyl)-3-fluoroprop-2-en-1-yl]-4-(5-bromo-4-methylpyridin-2-yl)-2,4-dihydro-3H-1,2,4-triazol-3-one hydrochloride;
2-[(2E)-2-(aminomethyl)-3-fluoroprop-2-en-1-yl]-4-(5-bromo-4-methylpyridin-2-yl)-2,4-dihydro-3H-1,2,4-triazol-3-one hydrochloride;
2-[(2Z)-2-(aminomethyl)-3-fluoroprop-2-en-1-yl]-4-(5-bromo-3-fluoropyridin-2-yl)-2,4-dihydro-3H-1,2,4-triazol-3-one hydrochloride;
2-[(2E)-2-(aminomethyl)-3-fluoroprop-2-en-1-yl]-4-(5-bromo-3-fluoropyridin-2-yl)-2,4-dihydro-3H-1,2,4-triazol-3-one hydrochloride;
2-[(2E)-2-(aminomethyl)-3-fluoroprop-2-en-1-yl]-4-(6-bromopyridin-2-yl)-2,4-dihydro-3H-1,2,4-triazol-3-one;
2-[(2E)-2-(aminomethyl)-3-fluoroprop-2-en-1-yl]-4-(5-bromopyrazin-2-yl)-2,4-dihydro-3H-1,2,4-triazol-3-one;
2-[(2Z)-2-(aminomethyl)-3-fluoroprop-2-en-1-yl]-thiazol-2-yl)-2,4-dihydro-3H-1,2,4-triazol-3-one hydrochloride;
2-[(2Z)-2-(aminomethyl)-3-fluoroprop-2-en-1-yl]-4-(5-bromo-1,3-thiazol-2-yl)-2,4-dihydro-3H-1,2,4-triazol-3-one hydrochloride;
2-[(2E)-2-(aminomethyl)-3-fluoroprop-2-en-1-yl]-4-(5-bromo-1,3-thiazol-2-yl)-2,4-dihydro-3H-1,2,4-triazol-3-one hydrochloride;
4-[4-(5-acetylthiophen-2-yl)phenyl]-2-[(2Z)-2-(aminomethyl)-3-fluoroprop-2-en-1-yl]-2,4-dihydro-3H-1,2,4-triazol-3-one hydrochloride;
2-[(2E)-2-(aminomethyl)-3-fluoroprop-2-en-1-yl]-4-[3-fluoro-4'-(4H-1,2,4-triazol-3-yl)biphenyl-4-yl]-2,4-dihydro-3H-1,2,4-triazol-3-one;
2-[(2E)-2-(aminomethyl)-3-fluoroprop-2-en-1-yl]-4-[3-fluoro-3'-(4H-1,2,4-triazol-3-yl)biphenyl-4-yl]-2,4-dihydro-3H-1,2,4-triazol-3-one;
2-[(2E)-2-(aminomethyl)-3-fluoroprop-2-en-1-yl]-4-[4-(1,3-benzodioxol-5-yl)-2-fluorophenyl]-2,4-dihydro-3H-1,2,4-triazol-3-one hydrochloride;
2-[(2E)-2-(aminomethyl)-3-fluoroprop-2-en-1-yl]-4-[4-(2,1,3-benzoxadiazol-5-yl)-2-fluorophenyl]-2,4-dihydro-3H-1,2,4-triazol-3-one hydrochloride;
2-[(2E)-2-(aminomethyl)-3-fluoroprop-2-en-1-yl]-4-[5-bromo-2-methoxy-4-(morpholin-4-yl)phenyl]-2,4-dihydro-3H-1,2,4-triazol-3-one hydrochloride;
2-[(2E)-2-(aminomethyl)-3-fluoroprop-2-en-1-yl]-4-[3-(1,2,3,6-tetrahydropyridin-4-yl)phenyl]-2,4-dihydro-3H-1,2,4-triazol-3-one dihydrochloride;
4-[3-(5-acetylthiophen-2-yl)phenyl]-2-[(2E)-2-(aminomethyl)-3-fluoroprop-2-en-1-yl]-2,4-dihydro-3H-1,2,4-triazol-3-one hydrochloride;
2-[(2E)-2-(aminomethyl)-3-fluoroprop-2-en-1-yl]-4-[4'-(trifluoromethoxy)biphenyl-3-yl]-2,4-dihydro-3H-1,2,4-triazol-3-one hydrochloride;
2-[(2E)-2-(aminomethyl)-3-fluoroprop-2-en-1-yl]-4-[4'-(dimethylamino)biphenyl-3-yl]-2,4-dihydro-3H-1,2,4-triazol-3-one hydrochloride;
2-[(2E)-2-(aminomethyl)-3-fluoroprop-2-en-1-yl]-4-[4'-(propan-2-ylsulfanyl)biphenyl-3-yl]-2,4-dihydro-3H-1,2,4-triazol-3-one hydrochloride;
2-[(2Z)-2-(aminomethyl)-3-fluoroprop-2-en-1-yl]-4-[4'-(methylsulfonyl)biphenyl-3-yl]-2,4-dihydro-3H-1,2,4-triazol-3-one hydrochloride;
2-[(2E)-2-(aminomethyl)-3-fluoroprop-2-en-1-yl]-4-[4'-(methylsulfonyl)biphenyl-3-yl]-2,4-dihydro-3H-1,2,4-triazol-3-one hydrochloride;
3'-{1-[(2E)-2-(aminomethyl)-3-fluoroprop-2-en-1-yl]-5-oxo-1,5-dihydro-4H-1,2,4-triazol-4-yl}-N,N-dimethylbiphenyl-4-sulfonamide hydrochloride;
N-(3'-{1-[(2Z)-2-(aminomethyl)-3-fluoroprop-2-en-1-yl]-5-oxo-1,5-dihydro-4H-1,2,4-triazol-4-yl}biphenyl-4-yl)acetamide hydrochloride;
N-(3'-{1-[(2E)-2-(aminomethyl)-3-fluoroprop-2-en-1-yl]-5-oxo-1,5-dihydro-4H-1,2,4-triazol-4-yl}biphenyl-4-yl)acetamide hydrochloride;
2-[(2Z)-2-(aminomethyl)-3-fluoroprop-2-en-1-yl]-4-[4'-(4H-1,2,4-triazol-3-yl)biphenyl-3-yl]-2,4-dihydro-3H-1,2,4-triazol-3-one;
2-[(2E)-2-(aminomethyl)-3-fluoroprop-2-en-1-yl]-4-[4'-(4H-1,2,4-triazol-3-yl)biphenyl-3-yl]-2,4-dihydro-3H-1,2,4-triazol-3-one;
2-[(2Z)-2-(aminomethyl)-3-fluoroprop-2-en-1-yl]-4-[3'-(4H-1,2,4-triazol-3-yl)biphenyl-3-yl]-2,4-dihydro-3H-1,2,4-triazol-3-one;
2-[(2E)-2-(aminomethyl)-3-fluoroprop-2-en-1-yl]-4-[4'-(1,2,4-oxadiazol-3-yl)biphenyl-3-yl]-2,4-dihydro-3H-1,2,4-triazol-3-one;
2-[(2E)-2-(aminomethyl)-3-fluoroprop-2-en-1-yl]-4-[3'-(1,2,4-oxadiazol-3-yl)biphenyl-3-yl]-2,4-dihydro-3H-1,2,4-triazol-3-one;
2-[(2E)-2-(aminomethyl)-3-fluoroprop-2-en-1-yl]-4-[4'-(5-cyclopropyl-1,2,4-oxadiazol-3-yl)biphenyl-3-yl]-2,4-dihydro-3H-1,2,4-triazol-3-one hydrochloride;
2-[(2E)-2-(aminomethyl)-3-fluoroprop-2-en-1-yl]-4-{4'-[5-(propan-2-yl)-1,2,4-oxadiazol-3-yl]biphenyl-3-yl}-2,4-dihydro-3H-1,2,4-triazol-3-one hydrochloride;
2-[(2E)-2-(aminomethyl)-3-fluoroprop-2-en-1-yl]-4-{3'-[5-(propan-2-yl)-1,2,4-oxadiazol-3-yl]biphenyl-3-yl}-2,4-dihydro-3H-1,2,4-triazol-3-one hydrochloride;
2-[(2E)-2-(aminomethyl)-3-fluoroprop-2-en-1-yl]-4-[4''-(methylsulfonyl)-1,1':4',1''-terphenyl-3-yl]-2,4-dihydro-3H-1,2,4-triazol-3-one hydrochloride;
2-[(2E)-2-(aminomethyl)-3-fluoroprop-2-en-1-yl]-4-[4''-(methylsulfonyl)-1,1':3',1''-terphenyl-3-yl]-2,4-dihydro-3H-1,2,4-triazol-3-one;
N-(3''-{1-[(2E)-2-(aminomethyl)-3-fluoroprop-2-en-1-yl]-5-oxo-1,5-dihydro-4H-1,2,4-triazol-4-yl}-1,1':4',1''-terphenyl-4-yl)acetamide hydrochloride;
N-(3''-{1-[(2E)-2-(aminomethyl)-3-fluoroprop-2-en-1-yl]-5-oxo-1,5-dihydro-4H-1,2,4-triazol-4-yl}-1,1':3',1''-terphenyl-4-yl)acetamide hydrochloride;
2-[(2E)-2-(aminomethyl)-3-fluoroprop-2-en-1-yl]-4-[4'-(1,3-benzodioxol-5-yl)biphenyl-3-yl]-2,4-dihydro-3H-1,2,4-triazol-3-one hydrochloride;
2-[(2E)-2-(aminomethyl)-3-fluoroprop-2-en-1-yl]-4-[3'-(1,3-benzodioxol-5-yl)biphenyl-3-yl]-2,4-dihydro-3H-1,2,4-triazol-3-one hydrochloride;
4-[4'-(4-acetylpiperazine-1-yl)biphenyl-3-yl]-2-[(2E)-2-(aminomethyl)-3-fluoroprop-2-en-1-yl]-2,4-dihydro-3H-1,2,4-triazol-3-one hydrochloride;
2-[(2E)-2-(aminomethyl)-3-fluoroprop-2-en-1-yl]-4-[4'-(tetrahydro-2H-pyran-4-yl)biphenyl-3-yl]-2,4-dihydro-3H-1,2,4-triazol-3-one hydrochloride;
2-[(2E)-2-(aminomethyl)-3-fluoroprop-2-en-1-yl]-4-[4'-(morpholin-4-yl)biphenyl-3-yl]-2,4-dihydro-3H-1,2,4-triazol-3-one hydrochloride;

2-[(2E)-2-(aminomethyl)-3-fluoroprop-2-en-1-yl]-4-[3'-fluoro-4'-(morpholin-4-yl)biphenyl-3-yl]-2,4-dihydro-3H-1,2,4-triazol-3-one hydrochloride;

2-[(2E)-2-(aminomethyl)-3-fluoroprop-2-en-1-yl]-4-[3'-chloro-4'-(morpholin-4-yl)biphenyl-3-yl]-2,4-dihydro-3H-1,2,4-triazol-3-one hydrochloride;

2-[(2E)-2-(aminomethyl)-3-fluoroprop-2-en-1-yl]-4-[3'-methyl-4'-(morpholin-4-yl)biphenyl-3-yl]-2,4-dihydro-3H-1,2,4-triazol-3-one hydrochloride;

2-[(2E)-2-(aminomethyl)-3-fluoroprop-2-en-1-yl]-4-[4'-(morpholin-4-ylcarbonyl)biphenyl-3-yl]-2,4-dihydro-3H-1,2,4-triazol-3-one hydrochloride;

2-[(2E)-2-(aminomethyl)-3-fluoroprop-2-en-1-yl]-4-[3-(2-methoxypyridin-4-yl)phenyl]-2,4-dihydro-3H-1,2,4-triazol-3-one hydrochloride;

N-[4-(3-{1-[(2Z)-2-(aminomethyl)-3-fluoroprop-2-en-1-yl]-5-oxo-1,5-dihydro-4H-1,2,4-triazol-4-yl}phenyl)pyridin-2-yl]acetamide hydrochloride;

N-[4-(3-{1-[(2E)-2-(aminomethyl)-3-fluoroprop-2-en-1-yl]-5-oxo-1,5-dihydro-4H-1,2,4-triazol-4-yl}phenyl)pyridin-2-yl]acetamide hydrochloride;

2-[(2E)-2-(aminomethyl)-3-fluoroprop-2-en-1-yl]-4-[3-(pyridin-3-yl)phenyl]-2,4-dihydro-3H-1,2,4-triazol-3-one hydrochloride;

2-[(2E)-2-(aminomethyl)-3-fluoroprop-2-en-1-yl]-4-[3-(6-methoxypyridin-3-yl)phenyl]-2,4-dihydro-3H-1,2,4-triazol-3-one hydrochloride;

2-[(2E)-2-(aminomethyl)-3-fluoroprop-2-en-1-yl]-4-{3-[6-(trifluoromethyl)pyridin-3-yl]phenyl}-2,4-dihydro-3H-1,2,4-triazol-3-one hydrochloride;

2-[(2E)-2-(aminomethyl)-3-fluoroprop-2-en-1-yl]-4-[3-(6-chloropyridin-3-yl)phenyl]-2,4-dihydro-3H-1,2,4-triazol-3-one hydrochloride;

2-[(2E)-2-(aminomethyl)-3-fluoroprop-2-en-1-yl]-4-{3-[6-(morpholin-4-yl)pyridin-3-yl]phenyl}-2,4-dihydro-3H-1,2,4-triazol-3-one hydrochloride;

2-[(2E)-2-(aminomethyl)-3-fluoroprop-2-en-1-yl]-4-{3-[6-methoxy-5-(trifluoromethyl)pyridin-3-yl]phenyl}-2,4-dihydro-3H-1,2,4-triazol-3-one hydrochloride;

2-[(2E)-2-(aminomethyl)-3-fluoroprop-2-en-1-yl]-4-{3-[6-hydroxy-5-(trifluoromethyl)pyridin-3-yl]phenyl}-2,4-dihydro-3H-1,2,4-triazol-3-one hydrochloride;

5-(3-{1-[(2E)-2-(aminomethyl)-3-fluoroprop-2-en-1-yl]-5-oxo-1,5-dihydro-4H-1,2,4-triazol-4-yl}phenyl)-1,3-dimethylpyridin-2(1H)-one hydrochloride;

5-(3-{1-[(2E)-2-(aminomethyl)-3-fluoroprop-2-en-1-yl]-5-oxo-1,5-dihydro-4H-1,2,4-triazol-4-yl}phenyl)-1-(propan-2-yl)pyridin-2(1H)-one hydrochloride;

2-[(2E)-2-(aminomethyl)-3-fluoroprop-2-en-1-yl]-4-[3-(2-methylpyrimidin-5-yl)phenyl]-2,4-dihydro-3H-1,2,4-triazol-3-one hydrochloride;

2-[(2Z)-2-(aminomethyl)-3-fluoroprop-2-en-1-yl]-4-[3-(1,3-benzodioxol-5-yl)phenyl]-2,4-dihydro-3H-1,2,4-triazol-3-one hydrochloride;

2-[(2E)-2-(aminomethyl)-3-fluoroprop-2-en-1-yl]-4-[3-(1,3-benzodioxol-5-yl)phenyl]-2,4-dihydro-3H-1,2,4-triazol-3-one hydrochloride;

2-[(2Z)-2-(aminomethyl)-3-fluoroprop-2-en-1-yl]-4-[3-(2,3-dihydro-1,4-benzodioxin-6-yl)phenyl]-2,4-dihydro-3H-1,2,4-triazol-3-one hydrochloride;

2-[(2E)-2-(aminomethyl)-3-fluoroprop-2-en-1-yl]-4-[3-(2,3-dihydro-1,4-benzodioxin-6-yl)phenyl]-2,4-dihydro-3H-1,2,4-triazol-3-one hydrochloride;

2-[(2E)-2-(aminomethyl)-3-fluoroprop-2-en-1-yl]-4-[3-(2,1,3-benzoxadiazol-5-yl)phenyl]-2,4-dihydro-3H-1,2,4-triazol-3-one hydrochloride;

2-[(2E)-2-(aminomethyl)-3-fluoroprop-2-en-1-yl]-4-[3-(1H-indazol-6-yl)phenyl]-2,4-dihydro-3H-1,2,4-triazol-3-one hydrochloride;

2-[(2E)-2-(aminomethyl)-3-fluoroprop-2-en-1-yl]-4-[3-(1H-indol-4-yl)phenyl]-2,4-dihydro-3H-1,2,4-triazol-3-one hydrochloride;

4-[3-(2-amino-1,3-benzothiazol-5-yl)phenyl]-2-[(2E)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-[3-(1H-indol-3-yl)phenyl]-2,4-dihydro-3H-1,2,4-triazol-3-one hydrochloride;

2-[(2E)-2-(aminomethyl)-3-fluoroprop-2-en-1-yl]-4-[3-(1-benzothiophen-2-yl)phenyl]-2,4-dihydro-3H-1,2,4-triazol-3-one hydrochloride;

6-(3-{1-[(2E)-2-(aminomethyl)-3-fluoroprop-2-en-1-yl]-5-oxo-1,5-dihydro-4H-1,2,4-triazol-4-yl}phenyl)-8-methyl-3,4-dihydroquinolin-2(1H)-one hydrochloride;

6-(3-{1-[(2E)-2-(aminomethyl)-3-fluoroprop-2-en-1-yl]-5-oxo-1,5-dihydro-4H-1,2,4-triazol-4-yl}phenyl)-2H-1,4-benzoxazin-3(4H)-one hydrochloride;

2-[(2E)-2-(aminomethyl)-3-fluoroprop-2-en-1-yl]-4-[3-(isoquinolin-4-yl)phenyl]-2,4-dihydro-3H-1,2,4-triazol-3-one hydrochloride;

2-[(2E)-2-(aminomethyl)-3-fluoroprop-2-en-1-yl]-4-[3-(8-methylquinolin-5-yl)phenyl]-2,4-dihydro-3H-1,2,4-triazol-3-one hydrochloride;

2-[(2E)-2-(aminomethyl)-3-fluoroprop-2-en-1-yl]-4-[2-methyl-4'-(methylsulfonyl)biphenyl-3-yl]-2,4-dihydro-3H-1,2,4-triazol-3-one;

N-(3'-{1-[(2E)-2-(aminomethyl)-3-fluoroprop-2-en-1-yl]-5-oxo-1,5-dihydro-4H-1,2,4-triazol-4-yl}-2'-methylbiphenyl-4-yl)acetamide;

2-[(2E)-2-(aminomethyl)-3-fluoroprop-2-en-1-yl]-4-[2-methyl-4'-(1,2-oxazol-3-yl)biphenyl-3-yl]-2,4-dihydro-3H-1,2,4-triazol-3-one;

N-[4-(3-{1-[(2E)-2-(aminomethyl)-3-fluoroprop-2-en-1-yl]-5-oxo-1,5-dihydro-4H-1,2,4-triazol-4-yl}-2-methylphenyl)pyridin-2-yl]acetamide;

2-[(2E)-2-(aminomethyl)-3-fluoroprop-2-en-1-yl]-4-{2-methyl-3-[6-(morpholin-4-yl)pyridin-3-yl]phenyl}-2,4-dihydro-3H-1,2,4-triazol-3-one;

2-[(2E)-2-(aminomethyl)-3-fluoroprop-2-en-1-yl]-4-[3-(1,3-benzodioxol-5-yl)-2-methylphenyl]-2,4-dihydro-3H-1,2,4-triazol-3-one;

2-[(2E)-2-(aminomethyl)-3-fluoroprop-2-en-1-yl]-4-[3-(2,3-dihydro-1,4-benzodioxin-6-yl)-2-methylphenyl]-2,4-dihydro-3H-1,2,4-triazol-3-one;

2-[(2E)-2-(aminomethyl)-3-fluoroprop-2-en-1-yl]-4-[3-(2,1,3-benzoxadiazol-5-yl)-2-methylphenyl]-2,4-dihydro-3H-1,2,4-triazol-3-one;

4-[3-(2-amino-1,3-benzothiazol-5-yl)-2-methylphenyl]-2-[(2E)-2-(aminomethyl)-3-fluoroprop-2-en-1-yl]-2,4-dihydro-3H-1,2,4-triazol-3-one;

2-[(2E)-2-(aminomethyl)-3-fluoroprop-2-en-1-yl]-4-{5-methyl-6-[4-(1H-1,2,4-triazol-3-yl)phenyl]pyridin-3-yl}-2,4-dihydro-3H-1,2,4-triazol-3-one;

2-[(2E)-2-(aminomethyl)-3-fluoroprop-2-en-1-yl]-4-{5-methyl-6-[3-(1H-1,2,4-triazol-3-yl)phenyl]pyridin-3-yl}-2,4-dihydro-3H-1,2,4-triazol-3-one;

2-[(2E)-2-(aminomethyl)-3-fluoroprop-2-en-1-yl]-4-[6-(1,3-benzodioxol-5-yl)-5-methylpyridin-3-yl]-2,4-dihydro-3H-1,2,4-triazol-3-one;

4-[6-(2-amino-1,3-benzothiazol-5-yl)-5-methylpyridin-3-yl]-2-[(2E)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-{4-methyl-6-[4-(methylsulfonyl)phenyl]pyridin-3-yl}-2,4-dihydro-3H-1,2,4-triazol-3-one;

N-[4-(5-{1-[(2E)-2-(aminomethyl)-3-fluoroprop-2-en-1-yl]-5-oxo-1,5-dihydro-4H-1,2,4-triazol-4-yl}-4-methylpyridin-2-yl)phenyl]acetamide;

2-[(2E)-2-(aminomethyl)-3-fluoroprop-2-en-1-yl]-4-{4-methyl-6-[4-(1H-1,2,4-triazol-3-yl)phenyl]pyridin-3-yl}-2,4-dihydro-3H-1,2,4-triazol-3-one;

2-[(2E)-2-(aminomethyl)-3-fluoroprop-2-en-1-yl]-4-{4-methyl-6-[3-(1H-1,2,4-triazol-3-yl)phenyl]pyridin-3-yl}-2,4-dihydro-3H-1,2,4-triazol-3-one;

N-(5-{1-[(2E)-2-(aminomethyl)-3-fluoroprop-2-en-1-yl]-5-oxo-1,5-dihydro-4H-1,2,4-triazol-4-yl}-4-methyl-2,4'-bipyridin-2'-yl)acetamide;

2-[(2E)-2-(aminomethyl)-3-fluoroprop-2-en-1-yl]-4-[4-methyl-6'-(morpholin-4-yl)-2,3'-bipyridin-5-yl]-2,4-dihydro-3H-1,2,4-triazol-3-one;

2-[(2E)-2-(aminomethyl)-3-fluoroprop-2-en-1-yl]-4-[6-(2,1,3-benzoxadiazol-5-yl)-4-methylpyridin-3-yl]-2,4-dihydro-3H-1,2,4-triazol-3-one;

2-[(2E)-2-(aminomethyl)-3-fluoroprop-2-en-1-yl]-4-[6-(1H-indazol-6-yl)-4-methylpyridin-3-yl]-2,4-dihydro-3H-1,2,4-triazol-3-one;

4-[6-(2-amino-1,3-benzothiazol-5-yl)-4-methylpyridin-3-yl]-2-[(2E)-2-(aminomethyl)-3-fluoroprop-2-en-1-yl]-2,4-dihydro-3H-1,2,4-triazol-3-one;

N-[5-(5-{1-[(2E)-2-(aminomethyl)-3-fluoroprop-2-en-1-yl]-5-oxo-1,5-dihydro-4H-1,2,4-triazol-4-yl}-4-methylpyridin-2-yl)-1,3-benzothiazol-2-yl]acetamide;

2-[(2Z)-2-(aminomethyl)-3-fluoroprop-2-en-1-yl]-4-{5-[4-(methylsulfonyl)phenyl]pyridin-2-yl}-2,4-dihydro-3H-1,2,4-triazol-3-one hydrochloride;

N-[4-(6-{1-[(2Z)-2-(aminomethyl)-3-fluoroprop-2-en-1-yl]-5-oxo-1,5-dihydro-4H-1,2,4-triazol-4-yl}pyridin-3-yl)phenyl]acetamide hydrochloride;

2-[(2E)-2-(aminomethyl)-3-fluoroprop-2-en-1-yl]-4-[3-methyl-5-(piperazin-1-yl)pyridin-2-yl]-2,4-dihydro-3H-1,2,4-triazol-3-one;

4-[5-(5-acetylthiophen-2-yl)-3-methylpyridin-2-yl]-2-[(2E)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-{3-methyl-5-[4-(methylsulfonyl)phenyl]pyridin-2-yl}-2,4-dihydro-3H-1,2,4-triazol-3-one hydrochloride;

N-[4-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)phenyl]acetamide hydrochloride;

2-[(2Z)-2-(aminomethyl)-3-fluoroprop-2-en-1-yl]-4-{3-methyl-5-[4-(4H-1,2,4-triazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{3-methyl-5-[4-(4H-1,2,4-triazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{3-methyl-5-[3-(4H-1,2,4-triazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{3-methyl-5-[4-(1,2,5-oxadiazol-3-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{3-methyl-5-[4-(1,2,4-oxadiazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{3-methyl-5-[3-(1,2,4-oxadiazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{5-[4-(5-cyclopropyl-1,2,4-oxadiazol-3-yl)phenyl]-3-methylpyridin-2-yl}-2,4-dihydro-3H-1,2,4-triazol-3-one hydrochloride;

2-[(2E)-2-(aminomethyl)-3-fluoroprop-2-en-1-yl]-4-(3-methyl-5-{4-[5-(propane-2-yl)-1,2,4-oxadiazol-3-yl]phenyl}pyridin-2-yl)-2,4-dihydro-3H-1,2,4-triazol-3-one hydrochloride;

2-[(2E)-2-(aminomethyl)-3-fluoroprop-2-en-1-yl]-4-(3-methyl-5-{3-[5-(propan-2-yl)-1,2,4-oxadiazol-3-yl]phenyl}pyridin-2-yl)-2,4-dihydro-3H-1,2,4-triazol-3-one hydrochloride;

2-[(2E)-2-(aminomethyl)-3-fluoroprop-2-en-1-yl]-4-{3-methyl-5-[3-(1H-tetrazol-5-yl)phenyl]pyridin-2-yl}-2,4-dihydro-3H-1,2,4-triazol-3-one;

2-[(2E)-2-(aminomethyl)-3-fluoroprop-2-en-1-yl]-4-{3-methyl-5-[4-(piperazin-1-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{3-methyl-5-[4-(morpholin-4-ylcarbonyl)phenyl]pyridin-2-yl}-2,4-dihydro-3H-1,2,4-triazol-3-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-2H-1,4-benzoxazin-3(4H)-one hydrochloride;

2-[(2E)-2-(aminomethyl)-3-fluoroprop-2-en-1-yl]-4-[5-methyl-6'-(trifluoromethyl)-3,3'-bipyridin-6-yl]-2,4-dihydro-3H-1,2,4-triazol-3-one hydrochloride;

2-[(2E)-2-(aminomethyl)-3-fluoroprop-2-en-1-yl]-4-[5-methyl-6'-(morpholin-4-yl)-3,3'-bipyridin-6-yl]-2,4-dihydro-3H-1,2,4-triazol-3-one hydrochloride;

2-[(2E)-2-(aminomethyl)-3-fluoroprop-2-en-1-yl]-4-[5-(2H-1,3-benzodioxol-5-yl)-3-methylpyridin-2-yl]-2,4-dihydro-3H-1,2,4-triazol-3-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-1,3-dihydro-2H-indol-2-one;

2-[(2E)-2-(aminomethyl)-3-fluoroprop-2-en-1-yl]-4-[5-(2,1,3-benzoxadiazol-5-yl)-3-methylpyridin-2-yl]-2,4-dihydro-3H-1,2,4-triazol-3-one hydrochloride;

2-[(2E)-2-(aminomethyl)-3-fluoroprop-2-en-1-yl]-4-[5-(1H-indazol-6-yl)-3-methylpyridin-2-yl]-2,4-dihydro-3H-1,2,4-triazol-3-one;

6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-8-methyl-3,4-dihydroquinolin-2(1H)-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-2H-1,4-benzoxazin-3(4H)-one hydrochloride; 7-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-1,4-dihydro-2H-3,1-benzoxazin-2-one hydrochloride;

2-[(2E)-2-(aminomethyl)-3-fluoroprop-2-en-1-yl]-4-{4-methyl-5-[4-(1H-1,2,4-triazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{4-methyl-5-[3-(1H-1,2,4-triazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-[5-(1,3-benzodioxol-5-yl)-4-methylpyridin-2-yl]-2,4-dihydro-3H-1,2,4-triazol-3-one;

2-[(2E)-2-(aminomethyl)-3-fluoroprop-2-en-1-yl]-4-[5-(1H-indazol-6-yl)-4-methylpyridin-2-yl]-2,4-dihydro-3H-1,2,4-triazol-3-one;

4-[5-(2-amino-1,3-benzothiazol-5-yl)-4-methylpyridin-2-yl]-2-[(2E)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-[5-(1,3-benzodioxol-5-yl)-3-fluoropyridin-2-yl]-2,4-dihydro-3H-1,2,4-triazol-3-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-fluoropyridin-3-yl)-1,2-dihydro-3H-indol-3-one;

4-[5-(2-amino-1,3-benzothiazol-5-yl)-3-fluoropyridin-2-yl]-2-[(2E)-2-(aminomethyl)-3-fluoroprop-2-en-1-yl]-2,4-dihydro-3H-1,2,4-triazol-3-one hydrochloride;

2-[(2E)-2-(aminomethyl)-3-fluoroprop-2-en-1-yl]-4-{4-[4-(methylsulfonyl)phenyl]pyridin-2-yl}-2,4-dihydro-3H-1,2,4-triazol-3-one;

N-[4-(2-{1-[(2E)-2-(aminomethyl)-3-fluoroprop-2-en-1-yl]-5-oxo-1,5-dihydro-4H-1,2,4-triazol-4-yl}pyridin-4-yl)phenyl]acetamide;

2-[(2E)-2-(aminomethyl)-3-fluoroprop-2-en-1-yl]-4-{4-[4-(1,2-oxazol-3-yl)phenyl]pyridin-2-yl}-2,4-dihydro-3H-1,2,4-triazol-3-one;

N-(2'-{1-[(2E)-2-(aminomethyl)-3-fluoroprop-2-en-1-yl]-5-oxo-1,5-dihydro-4H-1,2,4-triazol-4-yl}-4,4'-bipyridin-2-yl)acetamide;

2-[(2E)-2-(aminomethyl)-3-fluoroprop-2-en-1-yl]-4-[6-(morpholin-4-yl)-3,4'-bipyridin-2'-yl]-2,4-dihydro-3H-1,2,4-triazol-3-one;

2-[(2E)-2-(aminomethyl)-3-fluoroprop-2-en-1-yl]-4-[4-(1,3-benzodioxol-5-yl)pyridin-2-yl]-2,4-dihydro-3H-1,2,4-triazol-3-one;

2-[(2E)-2-(aminomethyl)-3-fluoroprop-2-en-1-yl]-4-[4-(2,3-dihydro-1,4-benzodioxin-6-yl)pyridin-2-yl]-2,4-dihydro-3H-1,2,4-triazol-3-one; 2-[(2E)-2-(aminomethyl)-3-fluoroprop-2-en-1-yl]-4-[4-(2,1,3-benzoxadiazol-5-yl)pyridin-2-yl]-2,4-dihydro-3H-1,2,4-triazol-3-one;

4-[4-(2-amino-1,3-benzothiazol-5-yl)pyridin-2-yl]-2-[(2E)-2-(aminomethyl)-3-fluoroprop-2-en-1-yl]-2,4-dihydro-3H-1,2,4-triazol-3-one;

2-[(2E)-2-(aminomethyl)-3-fluoroprop-2-en-1-yl]-4-{6-[3-(dimethylamino)phenyl]pyridin-2-yl}-2,4-dihydro-3H-1,2,4-triazol-3-one hydrochloride;

N-[4-(6-{1-[(2E)-2-(aminomethyl)-3-fluoroprop-2-en-1-yl]-5-oxo-1,5-dihydro-4H-1,2,4-triazol-4-yl}pyridin-2-yl)phenyl]acetamide;

2-[(2E)-2-(aminomethyl)-3-fluoroprop-2-en-1-yl]-4-{6-[4-(1,2-oxazol-3-yl)phenyl]pyridin-2-yl}-2,4-dihydro-3H-1,2,4-triazol-3-one;

2-[(2E)-2-(aminomethyl)-3-fluoroprop-2-en-1-yl]-4-{6-[4-(1,2,5-oxadiazol-3-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[4-(5-cyclopropyl-1,2,4-oxadiazol-3-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[3-(5-cyclopropyl-1,2,4-oxadiazol-3-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-(6-{4-[5-(propan-2-yl)-1,2,4-oxadiazol-3-yl]phenyl}pyridin-2-yl)-2,4-dihydro-3H-1,2,4-triazol-3-one;

2-[(2E)-2-(aminomethyl)-3-fluoroprop-2-en-1-yl]-4-(6-{3-[5-(propan-2-yl)-1,2,4-oxadiazol-3-yl]phenyl}pyridin-2-yl)-2,4-dihydro-3H-1,2,4-triazol-3-one;

3-[4-(6-{1-[(2E)-2-(aminomethyl)-3-fluoroprop-2-en-1-yl]-5-oxo-1,5-dihydro-4H-1,2,4-triazol-4-yl}pyridin-2-yl)phenyl]-1,2,4-oxadiazol-5(4H)-one;

2-[(2E)-2-(aminomethyl)-3-fluoroprop-2-en-1-yl]-4-{6-[4-(pyrrolidin-1-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[4-(piperazin-1-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[3-(piperazin-1-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[4-(morpholin-4-ylcarbonyl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-[6'-(trifluoromethyl)-2,3'-bipyridin-6-yl]-2,4-dihydro-3H-1,2,4-triazol-3-one hydrochloride; 2-[(2E)-2-(aminomethyl)-3-fluoroprop-2-en-1-yl]-4-[6'-(dimethylamino)-2,3'-bipyridin-6-yl]-2,4-dihydro-3H-1,2,4-triazol-3-one hydrochloride;

2-[(2E)-2-(aminomethyl)-3-fluoroprop-2-en-1-yl]-4-[6'-(morpholin-4-yl)-2,3'-bipyridin-6-yl]-2,4-dihydro-3H-1,2,4-triazol-3-one;

2-[(2E)-2-(aminomethyl)-3-fluoroprop-2-en-1-yl]-4-(6'-fluoro-5'-methyl-2,3'-bipyridin-6-yl)-2,4-dihydro-3H-1,2,4-triazol-3-one hydrochloride;

2-[(2E)-2-(aminomethyl)-3-fluoroprop-2-en-1-yl]-4-[6'-(dimethylamino)-5'-fluoro-2,3'-bipyridin-6-yl]-2,4-dihydro-3H-1,2,4-triazol-3-one hydrochloride;

2-[(2E)-2-(aminomethyl)-3-fluoroprop-2-en-1-yl]-4-{6-[1-methyl-3-(trifluoromethyl)-1H-pyrazol-5-yl]pyridin-2-yl}-2,4-dihydro-3H-1,2,4-triazol-3-one hydrochloride;

2-[(2E)-2-(aminomethyl)-3-fluoroprop-2-en-1-yl]-4-[6-(1,3-benzodioxol-5-yl)pyridin-2-yl]-2,4-dihydro-3H-1,2,4-triazol-3-one;

2-[(2E)-2-(aminomethyl)-3-fluoroprop-2-en-1-yl]-4-[6-(2,3-dihydro-1,4-benzodioxin-6-yl)pyridin-2-yl]-2,4-dihydro-3H-1,2,4-triazol-3-one;

2-[(2E)-2-(aminomethyl)-3-fluoroprop-2-en-1-yl]-4-[6-(2,1,3-benzoxadiazol-5-yl)pyridin-2-yl]-2,4-dihydro-3H-1,2,4-triazol-3-one;

4-[6-(2-amino-1,3-benzothiazol-5-yl)pyridin-2-yl]-2-[(2E)-2-(aminomethyl)-3-fluoroprop-2-en-1-yl]-2,4-dihydro-3H-1,2,4-triazol-3-one;

6-(6-{1-[(2E)-2-(aminomethyl)-3-fluoroprop-2-en-1-yl]-5-oxo-1,5-dihydro-4H-1,2,4-triazol-4-yl}pyridin-2-yl)-8-methyl-3,4-dihydroquinolin-2(1H)-one hydrochloride;

6-[6-[1-[(E)-2-(aminomethyl)-3-fluoro-allyl]-5-oxo-1,2,4-triazol-4-yl]-2-pyridyl]-1-methyl-3,4-dihydroquinolin-2-one hydrochloride;

6-(3-{1-[(2E)-2-(aminomethyl)-3-fluoroprop-2-en-1-yl]-5-oxo-1,5-dihydro-4H-1,2,4-triazol-4-yl}pyridin-2-yl)-2H-1,4-benzoxazin-3(4H)-one hydrochloride;

7-(6-{1-[(2E)-2-(aminomethyl)-3-fluoroprop-2-en-1-yl]-5-oxo-1,5-dihydro-4H-1,2,4-triazol-4-yl}pyridin-2-yl)-1,4-dihydro-2H-3,1-benzoxazin-2-one hydrochloride;

5-(6-{1-[(2E)-2-(aminomethyl)-3-fluoroprop-2-en-1-yl]-5-oxo-1,5-dihydro-4H-1,2,4-triazol-4-yl}pyridin-2-yl)quinolin-2(1H)-one hydrochloride;

2-[(2E)-2-(aminomethyl)-3-fluoroprop-2-en-1-yl]-4-[6-(4-methyl-3,4-dihydro-2H-1,4-benzoxazin-7-yl)pyridin-2-yl]-2,4-dihydro-3H-1,2,4-triazol-3-one hydrochloride;

2-[(2E)-2-(aminomethyl)-3-fluoroprop-2-en-1-yl]-4-[6-(dibenzo[b,d]furan-4-yl)pyridin-2-yl]-2,4-dihydro-3H-1,2,4-triazol-3-one hydrochloride;

2-[(2E)-2-(aminomethyl)-3-fluoroprop-2-en-1-yl]-4-{6-[4-(5-cyclopropyl-1,2,4-oxadiazol-3-yl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-(2-{4-[5-(propan-2-yl)-1,2,4-oxadiazol-3-yl]phenyl}pyridin-4-yl)-2,4-dihydro-3H-1,2,4-triazol-3-one hydrochloride;

2-[(2E)-2-(aminomethyl)-3-fluoroprop-2-en-1-yl]-4-(2-{3-[5-(propan-2-yl)-1,2,4-oxadiazol-3-yl]phenyl}pyridin-4-yl)-2,4-dihydro-3H-1,2,4-triazol-3-one hydrochloride;

2-[(2E)-2-(aminomethyl)-3-fluoroprop-2-en-1-yl]-4-{2-[4-(morpholin-4-yl)phenyl]pyridin-4-yl}-2,4-dihydro-3H-1,2,4-triazol-3-one hydrochloride;

2-[(2E)-2-(aminomethyl)-3-fluoroprop-2-en-1-yl]-4-{2-[4-(morpholin-4-ylcarbonyl)phenyl]pyridin-4-yl}-2,4-dihydro-3H-1,2,4-triazol-3-one hydrochloride;

2-[(2E)-2-(aminomethyl)-3-fluoroprop-2-en-1-yl]-4-[2-(1,3-benzodioxol-5-yl)pyridin-4-yl]-2,4-dihydro-3H-1,2,4-triazol-3-one hydrochloride;

2-[(2E)-2-(aminomethyl)-3-fluoroprop-2-en-1-yl]-4-{6-[3-(5-cyclopropyl-1,2,4-oxadiazol-3-yl)phenyl]-3-methylpyridin-2-yl}-2,4-dihydro-3H-1,2,4-triazol-3-one hydrochloride;

2-[(2E)-2-(aminomethyl)-3-fluoroprop-2-en-1-yl]-4-{3-methyl-6-[4-(morpholin-4-ylcarbonyl)phenyl]pyridin-2-yl}-2,4-dihydro-3H-1,2,4-triazol-3-one hydrochloride;

2-[(2E)-2-(aminomethyl)-3-fluoroprop-2-en-1-yl]-4-(6'-methoxy-5-methyl-2,3'-bipyridin-6-yl)-2,4-dihydro-3H-1,2,4-triazol-3-one hydrochloride;

2-[(2E)-2-(aminomethyl)-3-fluoroprop-2-en-1-yl]-4-[6-(1,3-benzodioxol-5-yl)-3-methylpyridin-2-yl]-2,4-dihydro-3H-1,2,4-triazol-3-one hydrochloride;

2-[(2E)-2-(aminomethyl)-3-fluoroprop-2-en-1-yl]-4-[6-(1H-indazol-6-yl)-3-methylpyridin-2-yl]-2,4-dihydro-3H-1,2,4-triazol-3-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-methylpyridin-2-yl)-8-methyl-3,4-dihydroquinolin-2(1H)-one hydrochloride;

6-(6-{1-[(2E)-2-(aminomethyl)-3-fluoroprop-2-en-1-yl]-5-oxo-1,5-dihydro-4H-1,2,4-triazol-4-yl}-5-methylpyridin-2-yl)-2H-1,4-benzoxazin-3(4H)-one hydrochloride;

2-[(2E)-2-(aminomethyl)-3-fluoroprop-2-en-1-yl]-4-{5-[4-(methylsulfonyl)phenyl]pyrazin-2-yl}-2,4-dihydro-3H-1,2,4-triazol-3-one;

2-[(2E)-2-(aminomethyl)-3-fluoroprop-2-en-1-yl]-4-{5-[4-(1H-1,2,4-triazol-3-yl)phenyl]pyrazin-2-yl}-2,4-dihydro-3H-1,2,4-triazol-3-one;

2-[(2E)-2-(aminomethyl)-3-fluoroprop-2-en-1-yl]-4-{5-[3-(1H-1,2,4-triazol-3-yl)phenyl]pyrazin-2-yl}-2,4-dihydro-3H-1,2,4-triazol-3-one;

N-[4-(5-{1-[(2E)-2-(aminomethyl)-3-fluoroprop-2-en-1-yl]-5-oxo-1,5-dihydro-4H-1,2,4-triazol-4-yl}pyrazin-2-yl)pyridin-2-yl]acetamide;

2-[(2E)-2-(aminomethyl)-3-fluoroprop-2-en-1-yl]-4-{5-[6-(morpholin-4-yl)pyridin-3-yl]pyrazin-2-yl}-2,4-dihydro-3H-1,2,4-triazol-3-one;

2-[(2E)-2-(aminomethyl)-3-fluoroprop-2-en-1-yl]-4-[5-(2,1,3-benzoxadiazol-5-yl)pyrazin-2-yl]-2,4-dihydro-3H-1,2,4-triazol-3-one;

2-[(2E)-2-(aminomethyl)-3-fluoroprop-2-en-1-yl]-4-[5-(1H-indazol-6-yl)pyrazin-2-yl]-2,4-dihydro-3H-1,2,4-triazol-3-one;

4-[5-(2-amino-1,3-benzothiazol-5-yl)pyrazin-2-yl]-2-[(2E)-2-(aminomethyl)-3-fluoroprop-2-en-1-yl]-2,4-dihydro-3H-1,2,4-triazol-3-one;

N-[5-(5-{1-[(2E)-2-(aminomethyl)-3-fluoroprop-2-en-1-yl]-5-oxo-1,5-dihydro-4H-1,2,4-triazol-4-yl}pyrazin-2-yl)-1,3-benzothiazol-2-yl]acetamide;

2-[(2Z)-2-(aminomethyl)-3-fluoroprop-2-en-1-yl]-4-{5-[4-(methylsulfonyl)phenyl]-1,3-thiazol-2-yl}-2,4-dihydro-3H-1,2,4-triazol-3-one hydrochloride;

2-[(2E)-2-(aminomethyl)-3-fluoroprop-2-en-1-yl]-4-{5-[4-(4H-1,2,4-triazol-3-yl)phenyl]-1,3-thiazol-2-yl}-2,4-dihydro-3H-1,2,4-triazol-3-one;

2-[(2E)-2-(aminomethyl)-3-fluoroprop-2-en-1-yl]-4-{5-[3-(4H-1,2,4-triazol-3-yl)phenyl]-1,3-thiazol-2-yl}-2,4-dihydro-3H-1,2,4-triazol-3-one;

2-[(2E)-2-(aminomethyl)-3-fluoroprop-2-en-1-yl]-4-{5-[4-(4H-1,2,4-oxadiazol-3-yl)phenyl]-1,3-thiazol-2-yl}-2,4-dihydro-3H-1,2,4-triazol-3-one;

2-[(2E)-2-(aminomethyl)-3-fluoroprop-2-en-1-yl]-4-{5-[3-(1H-tetrazol-5-yl)phenyl]-1,3-thiazol-2-yl}-2,4-dihydro-3H-1,2,4-triazol-3-one;

N-[4-(2-{1-[(2E)-2-(aminomethyl)-3-fluoroprop-2-en-1-yl]-5-oxo-1,5-dihydro-4H-1,2,4-triazol-4-yl}-1,3-thiazol-5-yl)pyridin-2-yl]acetamide;

2-[(2Z)-2-(aminomethyl)-3-fluoroprop-2-en-1-yl]-4-[5-(1,3-benzodioxol-5-yl)-1,3-thiazol-2-yl]-2,4-dihydro-3H-1,2,4-triazol-3-one hydrochloride;

6-(2-{1-[(2E)-2-(aminomethyl)-3-fluoroprop-2-en-1-yl]-5-oxo-1,5-dihydro-4H-1,2,4-triazol-4-yl}-1,3-thiazol-5-yl)-1,3-dihydro-2H-indol-2-one;

2-[(2Z)-2-(aminomethyl)-3-fluoroprop-2-en-1-yl]-4-[5-(2,1,3-benzoxadiazol-5-yl)-1,3-thiazol-2-yl]-2,4-dihydro-3H-1,2,4-triazol-3-one hydrochloride;

N-[5-(4-{1-[(2E)-2-(aminomethyl)-3-fluoroprop-2-en-1-yl]-5-oxo-1,5-dihydro-4H-1,2,4-triazol-4-yl}benzyl)-1,3-thiazol-2-yl]acetamide hydrochloride;

2-[(2E)-2-(aminomethyl)-3-fluoroprop-2-en-1-yl]-4-{4-[(E)-2-phenylethenyl]pyridin-2-yl}-2,4-dihydro-3H-1,2,4-triazol-3-one hydrochloride;

2-[(2E)-2-(aminomethyl)-3-fluoroprop-2-en-1-yl]-4-{6-[(E)-2-(thiophen-3-yl)ethenyl]pyridin-2-yl}-2,4-dihydro-3H-1,2,4-triazol-3-one;

2-[(2E)-2-(aminomethyl)-3-fluoroprop-2-en-1-yl]-4-(6-{(E)-2-[4-(trifluoromethyl)phenyl]ethenyl}pyridin-2-yl)-2,4-dihydro-3H-1,2,4-triazol-3-one hydrochloride;

2-[(E)-2-(aminomethyl)-3-fluoro-allyl]-4-[6-[(E)-2-[4-(dimethylamino)phenyl]vinyl]-2-pyridyl]-1,2,4-triazol-3-one hydrochloride;

2-[(E)-2-(aminomethyl)-3-fluoro-allyl]-4-[6-[(E)-2-(3-methyl-1,2-dihydroimidazo[4,5-b]pyridin-6-yl)vinyl]-2-pyridyl]-1,2,4-triazol-3-one hydrochloride;

7-[(E)-2-[6-[1-[(E)-2-(aminomethyl)-3-fluoro-allyl]-5-oxo-1,2,4-triazol-4-yl]-2-pyridyl]vinyl]-1H-pyrido[2,3-b][1,4]oxazin-2-one hydrochloride;

6-[(E)-2-[6-[1-[(E)-2-(aminomethyl)-3-fluoro-allyl]-5-oxo-1,2,4-triazol-4-yl]-2-pyridyl]vinyl]-3H-oxazolo[4,5-b]pyridin-2-one hydrochloride;

2-[(2E)-2-(aminomethyl)-3-fluoroprop-2-en-1-yl]-4-[3-(pyridin-3-ylethynyl)phenyl]-2,4-dihydro-3H-1,2,4-triazol-3-one hydrochloride;

2-[(2E)-2-(aminomethyl)-3-fluoroprop-2-en-1-yl]-4-[4-(pyridin-2-ylethynyl)pyridin-2-yl]-2,4-dihydro-3H-1,2,4-triazol-3-one hydrochloride;

2-[(2E)-2-(aminomethyl)-3-fluoroprop-2-en-1-yl]-4-[4-(pyridin-3-ylethynyl)pyridin-2-yl]-2,4-dihydro-3H-1,2,4-triazol-3-one hydrochloride;

2-[(2E)-2-(aminomethyl)-3-fluoroprop-2-en-1-yl]-4-[4-(pyridin-4-ylethynyl)pyridin-2-yl]-2,4-dihydro-3H-1,2,4-triazol-3-one hydrochloride;

2-[(2E)-2-(aminomethyl)-3-fluoroprop-2-en-1-yl]-4-{6-[(6-methoxypyridin-3-yl)ethynyl]pyridin-2-yl}-2,4-dihydro-3H-1,2,4-triazol-3-one;

2-[(E)-2-(aminomethyl)-3-fluoro-allyl]-4-[6-[2-[6-(dimethylamino)-3-pyridyl]ethynyl]-2-pyridyl]-1,2,4-triazol-3-one;

2-[(E)-2-(aminomethyl)-3-fluoro-allyl]-4-[6-[2-(6-morpholino-3-pyridyl)ethynyl]-2-pyridyl]-1,2,4-triazol-3-one;

2-[(E)-2-(aminomethyl)-3-fluoro-allyl]-4-[6-[2-(3,4-dihydro-2H-1,4-benzoxazin-6-yl)ethynyl]-2-pyridyl]-1,2,4-triazol-3-one;

2-[(E)-2-(aminomethyl)-3-fluoro-allyl]-4-[6-[2-(2,3-dihydro-1H-pyrido[2,3-b][1,4]oxazin-7-yl)ethynyl]-2-pyridyl]-1,2,4-triazol-3-one;

2-[(E)-2-(aminomethyl)-3-fluoro-allyl]-4-[6-[2-(3,4-dihydro-2H-pyrido[3,2-b][1,4]oxazin-7-yl)ethynyl]-2-pyridyl]-1,2,4-triazol-3-one;

2-[(E)-2-(aminomethyl)-3-fluoro-allyl]-4-[6-[2-(2,3-dihydro-1H-pyrido[2,3-b][1,4]oxazin-6-yl)ethynyl]-2-pyridyl]-1,2,4-triazol-3-one;

6-[2-[6-[1-[(E)-2-(aminomethyl)-3-fluoro-allyl]-5-oxo-1,2,4-triazol-4-yl]-2-pyridyl]ethynyl]-3,4-dihydro-1H-quinolin-2-one;

7-[2-[6-[1-[(E)-2-(aminomethyl)-3-fluoro-allyl]-5-oxo-1,2,4-triazol-4-yl]-2-pyridyl]ethynyl]-4H-pyrido[3,2-b][1,4]oxazin-3-one;

2-[(E)-2-(aminomethyl)-3-fluoro-allyl]-4-[6-[2-(3-methylimidazol-4-yl)ethynyl]-2-pyridyl]-1,2,4-triazol-3-one; and 2-[(2E)-2-(aminomethyl)-3-fluoroprop-2-en-1-yl]-4-{6-[(1-methyl-1H-pyrazol-4-yl)ethynyl]pyridin-2-yl}-2,4-dihydro-3H-1,2,4-triazol-3-one hydrochloride.

As for the compound of Formula 1, or an isomer thereof, or a pharmaceutically acceptable salt, the more preferred compound may be a compound selected from the group consisting of the following compounds, or an isomer thereof, or a pharmaceutically acceptable salt thereof:

2-[(2E)-2-(aminomethyl)-3-fluoroprop-2-en-1-yl]-4-(5-bromo-3-methylpyridin-2-yl)-2,4-dihydro-3H-1,2,4-triazol-3-one hydrochloride;

2-[(2E)-2-(aminomethyl)-3-fluoroprop-2-en-1-yl]-4-[4'-(methylsulfanyl)biphenyl-3-yl]-2,4-dihydro-3H-1,2,4-triazol-3-one hydrochloride;

2-[(2E)-2-(aminomethyl)-3-fluoroprop-2-en-1-yl]-4-[5-(2H-1,3-benzodioxol-5-yl)-3-methylpyridin-2-yl]-2,4-dihydro-3H-1,2,4-triazol-3-one hydrochloride;

2-[(2E)-2-(aminomethyl)-3-fluoroprop-2-en-1-yl]-4-6-[4-(1,2-oxazol-3-yl)phenyl]pyridin-2-yl-2,4-dihydro-3H-1,2,4-triazol-3-one;

2-[(2E)-2-(aminomethyl)-3-fluoroprop-2-en-1-yl]-4-[6'-(trifluoromethyl)-2,3'-bipyridin-6-yl]-2,4-dihydro-3H-1,2,4-triazol-3-one hydrochloride; and 2-[(2E)-2-(aminomethyl)-3-fluoroprop-2-en-1-yl]-4-6-[(1-methyl-1H-pyrazol-4-yl)ethynyl]pyridin-2-yl-2,4-dihydro-3H-1,2,4-triazol-3-one hydrochloride.

The compound of Formulae X, 1, 10, 10a, 10b, 11, 11a, 11b, 11c, 11d, 11e, or 12 or a salt thereof may exist as the geometric isomer of a cis or trans structure. Thus, unless indicated otherwise, the compound of Formula 1 or salt thereof comprises both geometric isomers of cis and trans structures.

The compound of Formulae X, 1, 10, 10a, 10b, 11, 11a, 11b, 11c, 11d, 11e, or 12 of the present technology can be in the form of a pharmaceutically acceptable salt. The term "pharmaceutically acceptable salt," as used herein, represents salts or zwitterionic forms of the compounds of the present technology which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by, for example, reacting the appropriate compound in the form of the free base with a suitable acid. Such salts include conventional acid addition salts, e.g., a salt derived from inorganic acid such as hydrochloric acid, bromic acid, sulfuric acid, sulfamic acid, phosphoric acid, or nitric acid and a salt derived from organic acid such as acetic acid, propionic acid, succinic acid, glycolic acid, stearic acid, citric acid, maleic, malonic acid, methanesulfonic acid, tartaric acid, malic acid, phenylacetic acid, glutamic acid, benzoic acid, salicylic acid, 2-acetoxybenzoic acid, fumaric acid, p-toluenesulfonic acid, oxalic acid or trifluoroacetic acid. Further, said salts include conventional metal salt types, e.g. a salt derived from a metal such as lithium, sodium, potassium, magnesium, or calcium. Said acid addition salt or metal salt can be prepared according to conventional methods.

The compound of Formulae X, 1, 10, 10a, 10b, 11, 11a, 11b, 11c, 11d, 11e, or 12 or a salt thereof according to the technology may be prepared by various methods. For example, a compound of Formula 1a, or an isomer thereof, or a salt thereof, wherein A is a substituted aryl or heteroaryl group (i.e., the compound of Formula 1a wherein A is an aryl or heteroaryl group selected from the group consisting of phenyl, pyridine, pyrazine, and thiazole and wherein said aryl or heteroaryl group is optionally substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R) can be prepared by a preparation process comprising the step of reacting a compound of Formula 2 with a compound of Formula 3a or a compound of Formula 3b to obtain a compound of Formula 1aa; and the step of deprotecting said compound of Formula 1aa.

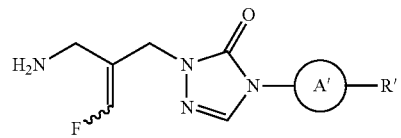

(Formula 1a)

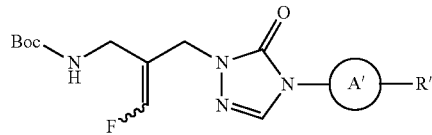

(Formula 1aa)

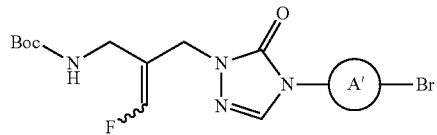

(Formula 2)

Z$_2$—B—R'  (Formula 3a)

HC≡CR'  (Formula 3b)

In said Formulae 1a, 1aa, 2, 3a and 3b, Boc is an amine protecting group (e.g., tert-butoxycarbonyl, 9-fluorenylmethyloxycarbonyl (FMOC), benzyloxycarbonyl(CBZ), triphenylmethyl(trityl), etc.), A' is an aryl or heteroaryl group selected from the group consisting of phenyl, pyridine, pyrazine, and thiazole; Z is hydroxy or $C_{1-3}$ alkoxy, or two Z together with the boron to which they are attached form

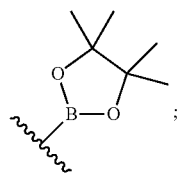 [SMILES: *B1OC(C)(C)C(C)(C)O1]

R' is one to three groups independently selected from the group consisting of —R, —$CH_2$—R, —CH═CH—R, and —C≡C—R; and R is the same as defined above. In some embodiments, R is a substituted or unsubstituted cyclic ring, optionally containing at least one heteroatom, and the cyclic ring is aromatic or non-aromatic. In some embodiments, R is a cyclic ring selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan; wherein said cyclic ring is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$ alkyl sulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, isoxazolyl, oxazolyl, oxadiazolyl, cyclopropyl-oxadiazolyl, $C_{1-6}$ alkyl-oxadiazolyl, and oxadiazol-5-onyl.

The reaction of the compound of Formula 2 above with a commercially available compound of Formula 3a may be carried out via Suzuki reaction. Said reaction can be carried out by using a palladium catalyst. The palladium catalyst includes palladium diacetate (Pd(OAc)$_2$), tris(dibenzylideneacetone)dipalladium (Pd$_2$(dba)$_3$), tetrakis(triphenylphosphine)palladium (Pd(PPh$_3$)$_4$) or palladiumdi[1,1'-bis(diphenylphosphino)ferrocene]dichloride (PdCl$_2$(dppf)$_2$), etc. In the reaction carried out under a palladium catalyst, a ligand and a base can be added in addition to the palladium catalyst. Said ligand includes (S)-2,2-bis(diphenylphospino)-1,1-binaphthyl(BINAP), 1,1'-bis(diphenylphospino)ferrocene (dppf) or (tri-O-tolyl)phosphine(P(O-Tol)$_3$), etc., and said base includes an inorganic base such as cesium carbonate (Cs$_2$CO$_3$), sodium carbonate (Na$_2$CO$_3$), potassium carbonate (K$_2$CO$_3$), potassium fluoride (KF), cesium fluoride (CsF), sodium hydroxide (NaOH), potassium phosphonate (K$_3$PO$_4$), sodium tert-butoxide (tert-BuONa), potassium tert-butoxide (tert-BuOK), or the like. The reaction may be carried out, in a non-polar organic solvent such as benzene or toluene, or a polar solvent such as dioxane, tetrahydrofuran, acetonitrile, 1,2-dimethoxyethane, N,N-dimethylformamide, or the like, at a temperature ranging from 50° C. to 150° C., preferably from 80° C. to 110° C. Other reaction conditions, including e.g., reaction time, may be determined from the reaction conditions for conventional Suzuki reaction (Barbara Czako and Laszlo Kurti, *STRATEGIC APPLICATIONS of NAMED REACTIONS in ORGANIC SYNTHESIS*, 2005). Further, the reaction of the compound of Formula 2 and the commercially available compound of Formula 3b (i.e., an ethyne derivative) can be carried out via Sonogashira coupling reaction using a palladium reagent such as bis(triphenylphosphine)palladium(II) dichloride, tetrakis(triphenylphosphine)palladium(0), etc. and a copper iodide. The coupling reaction may be carried out at room temperature or a heated temperature, e.g., a temperature ranging from 20° C. to 60° C. In addition, in order to improve reaction rate and reaction yield, said coupling reaction can be carried out in the presence of a base such as a diisopropylamine, a triethylamine, etc. and a ligand such as triphenylphosphine, or the like.

Deprotection of the compound of Formula 1aa can be carried out by conventional methods of removing an amine protecting group. For example, said amine protecting group in an organic solvent such as dichloromethane, etc. can be removed in the form of a free amine by using an acid such as trifluoroacetic acid or can be removed in the form of a hydrochloride salt by using hydrogen chloride melt in the organic solvents, diethyl ether, 1,4-dioxane, etc.

The compound of Formula 2 can be prepared according to the following Reaction Scheme 1.

Reaction Scheme 1.

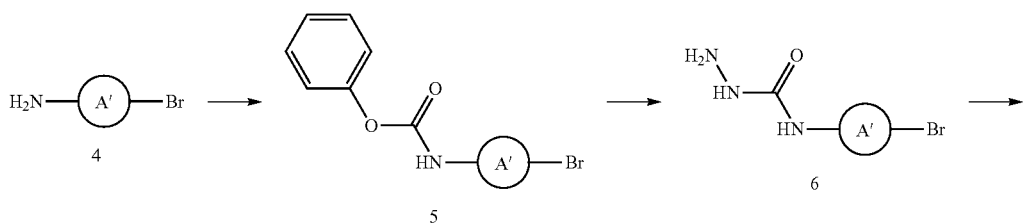

-continued

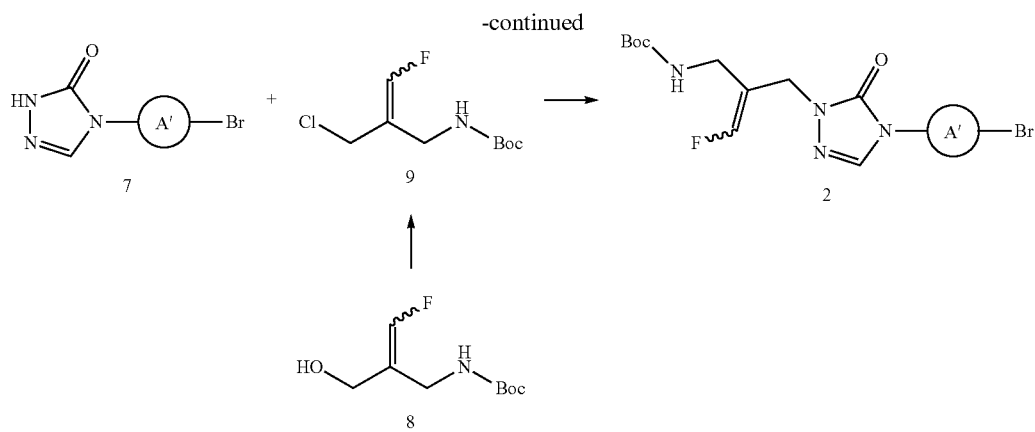

In Reaction Scheme 1, A' and Boc are the same as defined in the above.

The compound of Formula 4 is commercially available. The compound of Formula 4 can be converted to the compound of Formula 5 via nucleophilic acylsubstitution reaction. Said nucleophilic acylsubstitution reaction can be carried out at 0° C. to room temperature by using pyridine or triethylamine, etc. in a solvent such as ethyl acetate, tetrahydrofuran, etc. (Chunquan Sheng; Xiaoying Che; Wenya Wang; Shengzheng Wang; Yongbing Cao; Zhenyuan Miao; Jianzhong Yao; Wannian Zhang, *European Journal of Medicinal Chemistry*, 46, 5276-5282, 2011).

The compound of Formula 5 can be converted to the compound of Formula 6 via hydrazinolysis reaction. The hydrazinolysis reaction can be carried out according to known methods (e.g., WO 2005/014583, etc.).

The compound of Formula 6 can be converted to the compound of Formula 7 via cyclization reaction. The cyclization reaction can be carried out at room temperature to 80° C. by using an acetic acid in N,N-dimethylformamide (Chunquan Sheng; Xiaoying Che; Wenya Wang; Shengzheng Wang; Yongbing Cao; Zhenyuan Miao; Jianzhong Yao; Wannian Zhang, *European Journal of Medicinal Chemistry*, 46, 5276-5282, 2011).

The coupling reaction of the compound of Formula 7 with the compound of Formula 9 can be carried out in the presence of a base and a solvent. Said base may be cesium carbonate, potassium carbonate, sodium carbonate, etc. and said solvent may be an organic solvent such as N,N-dimethylformamide, dioxane, tetrahydrofuran, etc. Further, said reaction can be carried out at room temperature to 100° C.

The compound of Formula 9 can be obtained from chlorination reaction of the commercially available compound of Formula 8. Said chlorination reaction can be carried out in the presence of conventional inorganic bases and organic solvents.

The aryl or heteroaryl triazolone derivatives according to the present technology, i.e., the compound of Formulae X, 1, 10, 10a, 10b, 11, 11a, 11b, 11c, 11d, 11e, or 12 or an isomer thereof, or a pharmaceutically acceptable salt thereof, have a selective inhibitory activity on VAP-1, and thus, can be usefully applied in the prevention or treatment of a disease mediated by VAP-1. Preferably, the compound of Formulae X, 1, 10, 10a, 10b, 11, 11a, 11b, 11c, 11d, 11e, or 12 according to the present technology, or an isomer thereof, or a pharmaceutically acceptable salt thereof can be usefully applied, for example, in the prevention or treatment of nonalcoholic steatohepatitis (NASH).

In some embodiments, provided herein is the use of the aryl or heteroaryl triazolone derivatives according to the present technology, i.e., the compound of Formulae X, 1, 10, 10a, 10b, 11, 11a, 11b, 11c, 11d, 11e, or 12, or an isomer thereof, or a pharmaceutically acceptable salt thereof, in the preparation of a medicament for the prophylaxis and/or treatment of lipid and lipoprotein disorders (such as, but not limited to, hypercholesterolemia, hypertriglyceridemia, and atherosclerosis), of conditions and diseases which result from chronic fatty and fibrotic degeneration of organs due to accumulated lipid and specifically triglyceride accumulation and subsequent activation of profibrotic pathways (such as, but not limited to, NASH and chronic cholestatic conditions in the liver, Glomerulosclerosis and Diabetic Nephropathy in the kidney, Macular Degeneration and Diabetic Retinopathy in the eye and neurodegenerative diseases, such as Alzheimer's Disease in the brain, or Diabetic Neuropathies in the peripheral nervous system), of Type I or Type II Diabetes and clinical complications of Type I and Type II Diabetes (such as, but not limited to, Diabetic Nephropathy, Diabetic Retinopathy, Diabetic Neuropathies, or Peripheral Arterial Occlusive Disease (PAOD)), of chronic intrahepatic or some forms of extrahepatic cholestatic conditions, of liver fibrosis, of acute intraheptic cholestatic conditions, of obstructive or chronic inflammatory disorders that arise out of improper bile composition (such as, but not limited to, cholelithiasis also known as cholesterol gallstones), of gastrointestinal conditions with a reduced uptake of dietary fat and fat-soluble dietary vitamins, of inflammatory bowel diseases, of obesity and metabolic syndrome (combined conditions of dyslipidemia, diabetes and abnormally high body-mass index), of persistent infections by intracellular bacteria or parasitic protozoae, of non-malignant hyperproliferative disorders, of malignant hyperproliferative disorders (such as, but not limited to, different forms of cancer, specifically certain forms of breast, liver or colon cancer, or a disorder selected from the group consisting of hepatocellular carcinoma, colon adenoma, and polyposis), of colon adenocarcinoma and hepatocellular carcinoma in particular, of liver steatosis and associated syndromes, of Hepatitis B infection, of Hepatitis C infection and/or of cholestatic and fibrotic effects that are associated with alcohol-induced cirrhosis or with viral-borne forms of hepatitis, of liver failure or liver malfunction as an outcome of chronic liver diseases or of surgical liver resection, of acute myocardial infarction, of acute stroke, of thrombosis which occurs as an endpoint of chronic obstructive atherosclerosis, of osteoarthritis, of rheumatoid arthritis, of psoriasis, or of cerebral infarction, individually or of any combination thereof.

In some embodiments, the compounds and/or pharmaceutical compositions disclosed herein are used for prophylaxis and/or treatment of chronic intrahepatic conditions, such as Primary Biliary Cirrhosis (PBC), Primary Sclerosing Cholangitis (PSC), progressive familiar cholestasis (PFIC), alcohol-induced cirrhosis and associated cholestasis, and some forms of extrahepatic cholestatic conditions, or liver fibrosis.

In some embodiments, provided herein is a method to treat chronic intrahepatic conditions and/or some forms of extrahepatic cholestatic conditions in a patient in need thereof, the method comprising, consisting essentially of, or consisting of administering to the patient a therapeutically effective amount of a compound or a composition disclosed herein. In some embodiments, the chronic intrahepatic conditions are selected from PBC, PSC, PFIC, and alcohol-induced cirrhosis and associated cholestasis.

In some embodiments, provided herein is a method to treat liver fibrosis in a patient in need thereof, the method comprising, consisting essentially of, or consisting of administering to the patient a therapeutically effective amount of a compound or a composition disclosed herein.

In some embodiments, provided herein is a method to treat a lipid and lipoprotein disorder in a patient in need thereof, the method comprising, consisting essentially of, or consisting of administering to the patient a therapeutically effective amount of a compound or a composition disclosed herein. In some embodiments, the lipid and lipoprotein disorder is selected from hypercholesterolemia, hypertriglyceridemia, and atherosclerosis.

In some embodiments, provided herein is a method to treat a condition or disease which results from chronic fatty and fibrotic degeneration of organs due to accumulated lipid and specifically triglyceride accumulation and subsequent activation of profibrotic pathways in a patient in need thereof, the method comprising, consisting essentially of, or consisting of administering to the patient a therapeutically effective amount of a compound or a composition disclosed herein. In some embodiments, the condition or disease which results from chronic fatty and fibrotic degeneration of organs due to accumulated lipid and specifically triglyceride accumulation and subsequent activation of profibrotic pathways is selected from NASH and chronic cholestatic conditions in the liver, Glomerulosclerosis and Diabetic Nephropathy in the kidney, Macular Degeneration and Diabetic Retinopathy in the eye, and neurodegenerative diseases. In some further embodiments, neurodegenerative diseases are selected from Alzheimer's Disease in the brain, and Diabetic Neuropathies in the peripheral nervous system.

In some embodiments, provided herein is a method to treat Type I or Type II Diabetes and clinical complications of Type I and Type II Diabetes in a patient in need thereof, the method comprising, consisting essentially of, or consisting of administering to the patient a therapeutically effective amount of a compound or a composition disclosed herein. In some embodiments, provided herein is a method to treat Type I Diabetes in a patient in need thereof, the method comprising, consisting essentially of, or consisting of administering to the patient a therapeutically effective amount of a compound or a composition disclosed herein. In some embodiments, provided herein is a method to treat Type II Diabetes in a patient in need thereof, the method comprising, consisting essentially of, or consisting of administering to the patient a therapeutically effective amount of a compound or a composition disclosed herein. In some embodiments, provided herein is a method to treat one or more clinical complications of Type I and Type II Diabetes in a patient in need thereof, the method comprising, consisting essentially of, or consisting of administering to the patient a therapeutically effective amount of a compound or a composition disclosed herein. In some embodiments, the clinical complications of Type I and Type II Diabetes are selected from Diabetic Nephropathy, Diabetic Retinopathy, Diabetic Neuropathies, and Peripheral Arterial Occlusive Disease (PAOD), or any combination thereof.

In some embodiments, provided herein is a method to treat acute intraheptic cholestatic conditions in a patient in need thereof, the method comprising, consisting essentially of, or consisting of administering to the patient a therapeutically effective amount of a compound or a composition disclosed herein.

In some embodiments, provided herein is a method to treat obstructive or chronic inflammatory disorders that arise out of improper bile composition in a patient in need thereof, the method comprising, consisting essentially of, or consisting of administering to the patient a therapeutically effective amount of a compound or a composition disclosed herein. In some embodiments, the obstructive or chronic inflammatory disorders that arise out of improper bile composition is cholelithiasis also known as cholesterol gallstones.

In some embodiments, provided herein is a method to treat gastrointestinal conditions with a reduced uptake of dietary fat and fat-soluble dietary vitamins in a patient in need thereof, the method comprising, consisting essentially of, or consisting of administering to the patient a therapeutically effective amount of a compound or a composition disclosed herein.

In some embodiments, provided herein is a method to treat inflammatory bowel diseases in a patient in need thereof, the method comprising, consisting essentially of, or consisting of administering to the patient a therapeutically effective amount of a compound or a composition disclosed herein.

In some embodiments, provided herein is a method to treat obesity and metabolic syndrome in a patient in need thereof, the method comprising, consisting essentially of, or consisting of administering to the patient a therapeutically effective amount of a compound or a composition disclosed herein.

In some embodiments, provided herein is a method to treat persistent infections by intracellular bacteria or parasitic protozoae in a patient in need thereof, the method comprising, consisting essentially of, or consisting of administering to the patient a therapeutically effective amount of a compound or a composition disclosed herein.

In some embodiments, provided herein is a method to treat non-malignant hyperproliferative disorders in a patient in need thereof, the method comprising, consisting essentially of, or consisting of administering to the patient a therapeutically effective amount of a compound or a composition disclosed herein.

In some embodiments, provided herein is a method to treat malignant hyperproliferative disorders in a patient in need thereof, the method comprising, consisting essentially of, or consisting of administering to the patient a therapeutically effective amount of a compound or a composition disclosed herein. In some embodiments, malignant hyperproliferative disorders are selected from different forms of cancer, specifically certain forms of breast, liver or colon cancer, or a disorder selected from the group consisting of hepatocellular carcinoma, colon adenoma, and polyposis.

In some embodiments, provided herein is a method to treat colon adenocarcinoma in a patient in need thereof, the method comprising, consisting essentially of, or consisting of administering to the patient a therapeutically effective amount of a compound or a composition disclosed herein.

In some embodiments, provided herein is a method to treat hepatocellular carcinoma in a patient in need thereof, the method comprising, consisting essentially of, or consisting of administering to the patient a therapeutically effective amount of a compound or a composition disclosed herein.

In some embodiments, provided herein is a method to treat liver steatosis and associated syndromes in a patient in need thereof, the method comprising, consisting essentially of, or consisting of administering to the patient a therapeutically effective amount of a compound or a composition disclosed herein.

In some embodiments, provided herein is a method to treat Hepatitis B infection in a patient in need thereof, the method comprising, consisting essentially of, or consisting of administering to the patient a therapeutically effective amount of a compound or a composition disclosed herein.

In some embodiments, provided herein is a method to treat Hepatitis C infection in a patient in need thereof, the method comprising, consisting essentially of, or consisting of administering to the patient a therapeutically effective amount of a compound or a composition disclosed herein.

In some embodiments, provided herein is a method to treat cholestatic and fibrotic effects that are associated with alcohol-induced cirrhosis or with viral-borne forms of hepatitis in a patient in need thereof, the method comprising, consisting essentially of, or consisting of administering to the patient a therapeutically effective amount of a compound or a composition disclosed herein.

In some embodiments, provided herein is a method to treat liver failure or liver malfunction as an outcome of chronic liver diseases or of surgical liver resection in a patient in need thereof, the method comprising, consisting essentially of, or consisting of administering to the patient a therapeutically effective amount of a compound or a composition disclosed herein.

In some embodiments, provided herein is a method to treat acute myocardial infarction in a patient in need thereof, the method comprising, consisting essentially of, or consisting of administering to the patient a therapeutically effective amount of a compound or a composition disclosed herein.

In some embodiments, provided herein is a method to treat acute stroke in a patient in need thereof, the method comprising, consisting essentially of, or consisting of administering to the patient a therapeutically effective amount of a compound or a composition disclosed herein.

In some embodiments, provided herein is a method to treat thrombosis which occurs as an endpoint of chronic obstructive atherosclerosis in a patient in need thereof, the method comprising, consisting essentially of, or consisting of administering to the patient a therapeutically effective amount of a compound or a composition disclosed herein.

In some embodiments, provided herein is a method to treat osteoarthritis in a patient in need thereof, the method comprising, consisting essentially of, or consisting of administering to the patient a therapeutically effective amount of a compound or a composition disclosed herein.

In some embodiments, provided herein is a method to treat rheumatoid arthritis in a patient in need thereof, the method comprising, consisting essentially of, or consisting of administering to the patient a therapeutically effective amount of a compound or a composition disclosed herein.

In some embodiments, provided herein is a method to treat psoriasis in a patient in need thereof, the method comprising, consisting essentially of, or consisting of administering to the patient a therapeutically effective amount of a compound or a composition disclosed herein.

In some embodiments, provided herein is a method to treat cerebral infarction in a patient in need thereof, the method comprising, consisting essentially of, or consisting of administering to the patient a therapeutically effective amount of a compound or a composition disclosed herein.

The present technology includes a pharmaceutical composition for selectively inhibiting vascular adhesion protein-1 (VAP-1), comprising a therapeutically effective amount of a compound of Formulae X, 1, 10, 10a, 10b, 11, 11a, 11b, 11c, 11d, 11e, or 12, or an isomer thereof, or a pharmaceutically acceptable salt thereof as an active ingredient. In one embodiment, the present technology provides a pharmaceutical composition for preventing or treating nonalcoholic steatohepatitis (NASH), comprising a therapeutically effective amount of a compound of Formulae X, 1, 10, 10a, 10b, 11, 11a, 11b, 11c, 11d, 11e, or 12 or a pharmaceutically acceptable salt thereof as an active ingredient. In some embodiments, provided herein is a pharmaceutical composition for preventing or treating NASH comprising, consisting essentially of, or consisting of a therapeutically effective amount of a compound of Formulae X, 1, 10, 10a, 10b, 11, 11a, 11b, 11c, 11d, 11e, or 12, or an isomer thereof, or a pharmaceutically acceptable salt thereof, and at least one pharmaceutically acceptable carrier or excipient.

In another aspect, the present technology provides a pharmaceutical composition for preventing or treating diabetic nephropathy comprising, consisting essentially of, or consisting of a therapeutically effective amount of a compound of Formulae X, 1, 10, 10a, 10b, 11, 11a, 11b, 11c, 11d, 11e, or 12, or an isomer thereof, or a pharmaceutically acceptable salt thereof, and at least one pharmaceutically acceptable carrier or excipient.

In another aspect, the present technology provides a pharmaceutical composition for preventing or treating primary sclerosing cholangitis comprising, consisting essentially of, or consisting of a therapeutically effective amount of a compound of Formulae X, 1, 10, 10a, 10b, 11, 11a, 11b, 11c, 11d, 11e, or 12, or an isomer thereof, or a pharmaceutically acceptable salt thereof, and at least one pharmaceutically acceptable carrier or excipient.

In some embodiments, the compounds of the present disclosure may be combined with one or more additional therapies for the prevention or treatment of a disease or condition amenable to treatment by inhibition of VAP-1.

In some embodiments, the compositions disclosed herein contain at least one additional active agent.

Exemplary additional active agents include, but are not limited to, one or more of a(n) ACE inhibitor, Acetyl CoA carboxylase inhibitor, Adenosine A3 receptor agonist, Adiponectin receptor agonist, AKT protein kinase inhibitor, AMP-activated protein kinases (AMPK), Amylin receptor agonist, Angiotensin II AT-1 receptor antagonist, Apoptosis Signaling Kinase 1 inhibitor, Autotaxin inhibitors, Bioactive lipid, Calcitonin agonist, Caspase inhibitor, Caspase-3 stimulator, Cathepsin inhibitor, Caveolin 1 inhibitor, CCR2 chemokine antagonist, CCR3 chemokine antagonist, CCR5 chemokine antagonist, Chloride channel stimulator, CNR1 inhibitor, Cyclin D1 inhibitor, Cytochrome P450 7A1 inhibitor, DGAT1/2 inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, Hedgehog (Hh) modulator, Hepatitis C virus NS3 protease inhibitor, Hepatocyte nuclear factor 4 alpha modulator (HNF4A), Hepatocyte growth factor modulator, HMG CoA reductase inhibitor, IL-10 agonist, IL-17 antagonist, Ileal sodium bile acid cotransporter inhibitor, Insulin sensitizer, integrin modulator, intereukin-1 receptor-associated kinase 4 (IRAK4) inhibitor, Jak2 tyrosine kinase inhibitor, ketohexokinase inhibitors, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Matrix metalloproteinases (MMPs) inhibitor, MEKK-5 protein kinase inhibitor, Membrane copper amine oxidase (VAP-1) inhibitor, Methionine aminopeptidase-2 inhibitor, Methyl CpG binding protein 2 modulator, MicroRNA-21 (miR-21) inhibitor, Mitochondrial uncoupler, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, PDE 3 inhibitor, PDE 4 inhibitor, PDE 5 inhibitor, PDGF receptor beta modulator, Phospholipase C inhibitor, PPAR alpha agonist, PPAR delta agonist, PPAR gamma agonist, PPAR gamma modulator, Protease-activated receptor-2 antagonist, Protein kinase modulator, Rho associated protein kinase inhibitor, Sodium glucose transporter-2 inhibitor, SREBP transcription factor inhibitor, STAT-1 inhibitor, Stearoyl CoA desaturase-1 inhibitor, Suppressor of cytokine signalling-1 stimulator, Suppressor of cytokine signalling-3 stimulator, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, WNT modulators, and YAP/TAZ modulator. Examples of JAK inhibitors include, but are not limited to, filgotonib and tofacitinib. A non-limiting example of an apoptosis signal kinase inhibitor is selonsertib.

The compound of Formulae X, 1, 10, 10a, 10b, 11, 11a, 11b, 11c, 11d, 11e, or 12, or the isomer thereof, or the pharmaceutically acceptable salt thereof, and at least one additional active agent may be administered in any order or even simultaneously. The multiple active agents may be provided in a single, unified form, or in multiple forms (by way of example only, either as a single pill or as two separate pills). One of the active agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

The pharmaceutical composition of the present technology may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

The pharmaceutical composition of the present technology may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition.

Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The composition of the present technology can be administered orally or parenterally, including inhalation, intravenous, intraperitoneal, subcutaneous, rectal and topical routes of administration. Therefore, the composition of the present technology can be formulated into various forms such as tablets, capsules, aqueous solutions, suspensions, or the like. In the case of tablets for oral administration, carriers such as lactose, corn starch, and lubricating agents, e.g. magnesium stearate, can be conventionally added thereto. In the case of capsules for oral administration, lactose and/or dried corn starch can be used as a diluent. When an aqueous suspension is required for oral administration, the active ingredient can be combined with emulsifying and/or suspending agents. If desired, certain sweetening agents and/or flavoring agents can be added thereto. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present technology may be in the form of an aqueous solution containing pharmaceutically acceptable carriers, e.g., saline having a pH level of 7.4. The solutions may be introduced into a patient's intramuscular blood-stream by local bolus injection.

Said aryl or heteroaryl triazolone derivatives, i.e. the compound of Formulae X, 1, 10, 10a, 10b, 11, 11a, 11b, 11c, 11d, 11e, or 12, or an isomer thereof, or a pharmaceutically acceptable salt thereof can be administered to a patient in an effective amount ranging from about 0.001 mg/kg to about 100 mg/kg per day. This includes 0.001, 0.0025, 0.005, 0.0075, 0.01, 0.025, 0.05, 0.075, 0.1, 0.25, 0.5, 0.75, 1, 2, 3, 4, 5, 6, 7, 8, 9, 10, 15, 20, 25, 30, 35, 40, 45, 50, 55, 60, 65, 70, 75, 80, 85, 90, 95, or 100 mg/kg.

Generally, a therapeutically effective amount of the compound of Formulae X, 1, 10, 10a, 10b, 11, 11a, 11b, 11c, 11d, 11e, or 12, or an isomer thereof, or a pharmaceutically acceptable salt thereof, will range from a total daily dosage of about 0.1 mg/day to 1000 mg/day, about 30-720 mg/day, about 60-600 mg/day, or about 100-480 mg/day, or more. In some embodiments, a therapeutically effective amount of the compound of Formulae X, 1, 10, 10a, 10b, 11, 11a, 11b, 11c, 11d, 11e, or 12, or an isomer thereof, or a pharmaceutically acceptable salt thereof, will range from about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, multiple dosages include two, three, or four doses per day.

In some embodiments, the therapeutically effective amount of the compound of Formulae X, 1, 10, 10a, 10b, 11, 11a, 11b, 11c, 11d, 11e, or 12, or an isomer thereof, or a pharmaceutically acceptable salt thereof, is at least 0.1 mg/day, at least 0.5 mg/day, at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, at least 725 mg/day, at least 750 mg/day, at least 775 mg/day, at least 800 mg/day, at least 825 mg/day, at least 850 mg/day, at least 875 mg/day, at least 900 mg/day, at least 925 mg/day, at least 950 mg/day, at least 975 mg/day, or at least 1000 mg/day.

Of course, the dosage may be changed according to the patient's age, weight, susceptibility, symptom, or the efficacy of the compound.

In one embodiment, the present technology provides a method of selectively inhibiting vascular adhesion protein (VAP)-1 in a mammal, comprising administering, to the mammal, a therapeutically effective amount of the compound of Formulae X, 1, 10, 10a, 10b, 11, 11a, 11b, 11c, 11d, 11e, or 12, or an isomer thereof, or a pharmaceutically acceptable salt thereof. In one embodiment, the present technology provides a method for treating nonalcoholic hepatosteatosis (NASH), comprising administering, to a mammal, a therapeutically effective amount of the compound of Formula 1 or a pharmaceutically acceptable salt thereof. In some embodiments, provided herein is a method for treating NASH in a subject in need thereof, the method comprising, consisting essentially of, or consisting of administering to the subject a therapeutically effective amount of a compound of Formulae X, 1, 10, 10a, 10b, 11, 11a, 11b, 11c, 11d, 11e, or 12, or an isomer thereof, or a pharmaceutically acceptable salt thereof. Mammals include, but are not limited to, mice, rodents, rats, simians, humans, farm animals, dogs, cats, sport animals, and pets.

The present technology provides a use of the compound of Formulae X, 1, 10, 10a, 10b, 11, 11a, 11b, 11c, 11d, 11e, or 12 above, or an isomer thereof, or a pharmaceutically acceptable salt thereof for use in the preparation of a medicament for selectively inhibiting a vascular adhesion protein-1 (VAP-1) in mammals. In one embodiment, the present technology provides a use of the compound of Formulae X, 1, 10, 10a, 10b, 11, 11a, 11b, 11c, 11d, 11e, or 12 above, or an isomer thereof, or a pharmaceutically acceptable salt thereof for use in the preparation of a medicament for treating or preventing nonalcoholic hepatosteatosis (NASH).

The following examples and experimental examples are provided for illustration purposes only, and are not intended to limit the scope of the technology.

As will be apparent to those of skill in the art upon reading this disclosure, each of the individual embodiments described and illustrated herein has discrete components and features which may be readily separated from or combined with the features of any of the other several embodiments without departing from the scope or spirit of the present technology. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present technology is not entitled to antedate such publication by virtue of prior technology. Further, the dates of publication provided may be different from the actual publication dates which may need to be independently confirmed.

EXAMPLES

The analyses of the compounds prepared in the following examples were carried out as follows: Nuclear magnetic resonance (NMR) spectrum analysis was carried out using Bruker 400 MHz spectrometer and Agilent 600 MHz spectrometer and chemical shifts thereof were analyzed in ppm. Further, the indicated molecular weights were measured by using liquid chromatography/mass selective detector (MSD) of Agilent 1260 Infinity series equipped with an electrostatic spray interface (by using Single Quadrupole, it indicates a value of m/z in ESI+ (ESI-MS (cation), which is represented by the [M+H]+peak). Column chromatography was carried out on silica gel (Merck, 70-230 mesh). (W. C. Still, *J. Org. Chem.*, 43, 2923, 1978). The abbreviations used in the following examples are as follows: 'methyl' is abbreviated to 'Me'; 'ethyl' is abbreviated to 'Et'; 'phenyl' is abbreviated to 'Ph, tert-tert-butyloxycarbonyl is abbreviated to 'BOC'. Further, the starting materials in each Example are known compounds, which were synthesized according to publications or obtained from Sigma-Aldrich.

Reference Example 1. tert-butyl (Z)-(2-(chloromethyl)-3-fluoroallyl)carbamate 290.0 mg of tert-butyl (Z)-(3-fluoro-2-(hydroxymethyl)allyl)carbamate, 350.2 mg of 4-methylbenzenesulfonyl chloride, and 0.26 mL of triethylamine were dissolved in 5.0 mL of dichloromethane, and the solution was stirred overnight at room temperature. To the reaction mixture, dichloromethane was added. The resulting reaction mixture was washed with distilled water, dried over anhydrous magnesium sulfate, and concentrated under reduced pressure to give a yellow liquid residue. The residue was purified with silica gel column chromatography (developing solvent: n-hexane/ethyl acetate=2/1) to give 312.0 mg of the title compound as a white solid (yield: 98.9%). $^1$H-NMR (CDCl$_3$, 400 MHz) δ 6.63 (d, 1H), 4.73 (bs, 1H), 4.07 (s, 2H), 3.79 (bs, 2H), 1.47 (s, 9H)

Reference Example 2. tert-butyl (E)-(2-(chloromethyl)-3-fluoroallyl)carbamate 440.0 mg of tert-butyl (E)-(3-fluoro-2-(hydroxymethyl)allyl)carbamate, 531.3 mg of 4-methylbenzenesulfonyl chloride, and 0.39 mL of triethylamine were dissolved in 5.0 mL of dichloromethane, and the solution was stirred overnight at room temperature. To the resulting reaction mixture, dichloromethane was added. The reaction mixture was washed with distilled water, dried over anhydrous magnesium sulfate, and then concentrated under reduced pressure to give a yellow liquid residue. The residue was purified with silica gel column chromatography (developing solvent: n-hexane/ethyl acetate=2/1) to give 400.0 mg of the title compound as a white solid (yield: 83.6%). $^1$H-NMR (CDCl$_3$, 400 MHz) δ 6.72 (d, 1H), 4.74 (bs, 1H), 4.05 (s, 2H), 3.98 (s, 2H), 1.44 (s, 9H)

Reference Example 3. 4-(4-bromophenyl)-2,4-dihydro-3H-1,2,4-triazol-3-one

Step 1: phenyl (4-bromophenyl)carbamate 1.0 g of 4-bromoaniline and 0.98 mL of pyridine were dissolved in 10 mL of ethyl acetate. To the resulting solution, 0.77 mL of phenylchloroformate at 0° C. was slowly added, and the solution was stirred at room temperature for 3 hours. To the solution, ethyl acetate was added, and the resulting reaction mixture was washed with 1N hydrochloric acid solution and brine, dried over anhydrous magnesium sulfate, and concentrated under reduced pressure to give 1.4 g of the title compound as a yellow solid (yield: 80%).

Step 2: N-(4-bromophenyl)hydrazine carboxamide 1.4 g of phenyl (4-bromophenyl)carbamate prepared in Step 1 and 480.0 mg of hydrazine hydrate were dissolved in 4.0 mL of tetrahydrofuran and 4.0 mL of ethanol, and the resulting solution was stirred overnight at room temperature. The resulting reaction mixture was concentrated and then washed with ethyl acetate to give 890.0 mg of the title compound as a white solid (yield: 80.0%).

Step 3: 4-(4-bromophenyl)-2,4-dihydro-3H-1,2,4-triazol-3-one 890.0 mg of N-(4-bromophenyl)hydrazine carboxamide prepared in Step 2 and 1.6 g of formamidine acetate were dissolved in 8.9 mL of 1-propanol, and the resulting solution was stirred at room temperature for 30 minutes, and then 1.3 mL of acetic acid was added and stirred at 80° C. for 8 hours. The reaction mixture was cooled to room temperature, distilled water was added to the cooled reaction mixture, and then the reaction mixture was stirred overnight. The resulting crystals were filtered and dried to give 742.8 mg of the title compound as a white solid (yield: 80.2%). MS (ESI) m/z=241.9 (M+H)+

Reference Example 4. 4-(3-bromophenyl)-2,4-dihydro-3H-1,2,4-triazol-3-one 540.0 mg of the title compound (yield: 38.7%) was prepared in the same fashion as Reference Example 3, except that 1.0 g of 3-bromoaniline was used in Step 1 instead of 4-bromoaniline. MS (ESI) m/z=241.5 (M+H)+

Reference Example 5. 4-(4-fluorophenyl)-2,4-dihydro-3H-1,2,4-triazol-3-one 527.0 mg of the title compound (yield: 32.7%) was prepared in the same fashion as Reference Example 3, except that 1.0 g of 4-fluoroaniline was used in Step 1 instead of 4-bromoaniline. MS (ESI) m/z=180.1 (M+H)$^+$

Reference Example 6. 4-(4-(benzyloxy)phenyl)-2,4-dihydro-3H-1,2,4-triazol-3-one 487.0 mg of the title compound (yield: 36.3%) was prepared in the same fashion as Reference Example 3, except that 1.0 g of 4-(benzyloxy)aniline was used in Step 1 instead of 4-bromoaniline. $^1$H-NMR (CDCl$_3$, 400 MHz) δ 9.58 (bs, 1H), 7.62 (s, 1H), 7.33-7.41 (m, 6H), 7.21-7.25 (m, 1H), 7.06 (d, 2H), 5.10 (s, 2H)

Reference Example 7. 4-(3,4-difluorophenyl)-2,4-dihydro-3H-1,2,4-triazol-3-one 492.0 mg of the title compound (yield: 32.2%) was prepared in the same fashion as Reference Example 3, except that 1.0 g of 3,4-difluoroaniline was used in Step 1 instead of 4-bromoaniline. MS (ESI) m/z=198.0 (M+H)$^+$

Reference Example 8. 4-(4-bromo-2-fluorophenyl)-2,4-dihydro-3H-1,2,4-triazol-3-one 443.5 mg of the title compound (yield: 32.7%) was prepared in the same fashion as Reference Example 3, except that 1.0 g of 4-bromo-2-fluoroaniline was used in Step 1 instead of 4-bromoaniline. MS (ESI) m/z=259.9 (M+H)$^+$ Reference Example 9. 4-(4-bromo-3-fluorophenyl)-2,4-dihydro-3H-1,2,4-triazol-3-one 517.3 mg of the title compound (yield: 38.1%) was prepared in the same fashion as Reference Example 3, except that 1.0 g of 4-bromo-3-fluoroaniline was used in Step 1 instead of 4-bromoaniline. MS (ESI) m/z=259.4 (M+H)$^+$ Reference Example 10. 4-(4-bromo-3-methylphenyl)-2,4-dihydro-3H-1,2,4-triazol-3-one 750 mg of the title compound (yield: 55.0%) was prepared in the same fashion as Reference Example 3, except that 1.0 g of 4-bromo-3-methylaniline was used in Step 1 instead of 4-bromoaniline. MS (ESI) m/z=255.2 (M+H)$^+$ Reference Example 11. 4-(3-bromo-2-methylphenyl)-2,4-dihydro-3H-1,2,4-triazol-3-one 5.1 g of the title compound (yield: 69.9%) was prepared in the same fashion as Reference Example 3, except that 5.0 g of 3-bromo-2-methylaniline was used in Step 1 instead of 4-bromoaniline. MS (ESI) m/z=255.2 (M+H)$^+$ Reference Example 12. 4-(4-bromo-3-methoxyphenyl)-2,4-dihydro-3H-1,2,4-triazol-3-one 500.5 mg of the title compound (yield: 37.4%) was prepared in the same fashion as Reference Example 3, except that 1.0 g of 4-bromo-3-methoxyaniline was used in Step 1 instead of 4-bromoaniline. MS (ESI) m/z=271.1 (M+H)$^+$ Reference Example 13. 4-(5-bromo-2-methoxyphenyl)-2,4-dihydro-3H-1,2,4-triazol-3-one 628.5 mg of the title compound (yield: 47.1%) was prepared in the same fashion as Reference Example 3, except that 1.0 g of 5-bromo-2-methoxyaniline was used in Step 1 instead of 4-bromoaniline. MS (ESI) m/z=271.2 (M+H)+

Reference Example 14. 4-(4-bromo-3,5-difluorophenyl)-2,4-dihydro-3H-1,2,4-triazol-3-one 570.0 mg of the title compound (yield: 42.9%) was prepared in the same fashion as Reference Example 3, except that 1.0 g of 4-bromo-3,5-difluoroaniline was used in Step 1 instead of 4-bromoaniline. MS (ESI) m/z=277.8 (M+H)$^+$ Reference Example 15. 4-(4-bromo-2,6-difluorophenyl)-2,4-dihydro-3H-1,2,4-triazol-3-one 530.0 mg of the title compound (yield: 39.9%) was prepared in the same fashion as Reference Example 3, except that 1.0 g of 4-bromo-2,6-difluoroaniline was used in Step 1 instead of 4-bromoaniline. MS (ESI) m/z=277.0 (M+H)$^+$ Reference Example 16. 4-(4-bromo-2,5-difluorophenyl)-2,4-dihydro-3H-1,2,4-triazol-3-one 424.5 mg of the title compound (yield: 32.0%) was prepared in the same fashion as Reference Example 3, except that 1.0 g of 4-bromo-2,5-difluoroaniline was used in Step 1 instead of 4-bromoaniline. MS (ESI) m/z=277.1 (M+H)+

Reference Example 17. 4-(6-bromopyridin-3-yl)-2,4-dihydro-3H-1,2,4-triazol-3-one 500.7 mg of the title compound (yield: 35.9%) was prepared in the same fashion as Reference Example 3, except that 1.0 g of 3-amino-6-bromopyridine was used in Step 1 instead of 4-bromoaniline. MS (ESI) m/z=242.1 (M+H)$^+$ Reference Example 18. 4-(6-bromo-5-methylpyridin-3-yl)-2,4-dihydro-3H-1,2,4-triazol-3-one 362.1 mg of the title compound (yield: 26.5%) was prepared in the same fashion as Reference Example 3, except that 1.0 g of 5-amino-2-bromo-3-picoline was used in Step 1 instead of 4-bromoaniline. MS (ESI) m/z=256.4 (M+H)+

Reference Example 19. 4-(6-bromo-4-methylpyridin-3-yl)-2,4-dihydro-3H-1,2,4-triazol-3-one 4.5 g of the title compound (yield: 66.1%) was prepared in the same fashion as Reference Example 3, except that 5.0 g of 2-bromo-4-methyl-5-aminopyridine was used in Step 1 instead of 4-bromoaniline. MS (ESI) m/z=256.0 (M+H)$^+$ Reference Example 20. 4-(5-bromopyridin-2-yl)-2,4-dihydro-3H-1,2,4-triazol-3-one 526.5 mg of the title compound (yield: 37.8%) was prepared in the same fashion as Reference Example 3, except that 1.0 g of 2-amino-5-bromopyridine was used in Step 1 instead of 4-bromoaniline. MS (ESI) m/z=252.7 (M+H)$^+$ Reference Example 21. 4-(5-bromo-3-methylpyridin-2-yl)-2,4-dihydro-3H-1,2,4-triazol-3-one 1.9 g of the title compound (yield: 69.6%) was prepared in the same fashion as Reference Example 3, except that 2.0 g of 2-amino-5-bromo-3-methylpyridine was used in Step 1 instead of 4-bromoaniline. $^1$H-NMR (DMSO-d$_6$, 400 MHz) δ 8.55 (d, 1H), 8.21 (s, 1H), 8.13 (s, 1H), 2.27 (s, 3H)

Reference Example 22. 4-(5-bromo-4-methylpyridin-2-yl)-2,4-dihydro-3H-1,2,4-triazol-3-one 1.1 g of the title compound (yield: 80.6%) was prepared in the same fashion as Reference Example 3, except that 1.0 g of 2-amino-5-bromo-4-methylpyridine was used in Step 1 instead of 4-bromoaniline. MS (ESI) m/z=256.3 (M+H)$^+$ Reference Example 23. 4-(5-bromo-3-fluoropyridin-2-yl)-2,4-dihydro-3H-1,2,4-triazol-3-one 715.0 mg of the title compound (yield: 52.7%) was prepared in the same fashion as Reference Example 3, except that 1.0 g of 2-amino-5-bromo-3-fluoropyridine was used in Step 1 instead of 4-bromoaniline. MS (ESI) m/z=260.2 (M+H)+

Reference Example 24. 4-(6-bromopyridin-2-yl)-2,4-dihydro-3H-1,2,4-triazol-3-one 6.0 g of the title compound (yield: 86.1%) was prepared in the same fashion as Reference Example 3, except that 5.0 g of 2-amino-6-bromopyridine was used in Step 1 instead of 4-bromoaniline. $^1$H-NMR (MeOD, 400 MHz) δ 8.44 (s, 1H), 8.24 (d, 1H), 7.83 (t, 1H), 7.53 (d, 1H)

Reference Example 25. 4-(4-bromopyridin-2-yl)-2,4-dihydro-3H-1,2,4-triazol-3-one 902.2 mg of the title compound (yield: 64.8%) was prepared in the same fashion as Reference Example 3, except that 1.0 g of 2-amino-4-bromopyridine was used in Step 1 instead of 4-bromoaniline. MS (ESI) m/z=252.1 (M+H)$^+$

Reference Example 26. 4-(2-bromopyridin-4-yl)-2,4-dihydro-3H-1,2,4-triazol-3-one 2.0 g of the title compound (yield: 28.7%) was prepared in the same fashion as Reference Example 3, except that 5.0 g of 4-amino-2-bromopyridine was used in Step 1 instead of 4-bromoaniline. $^1$H-NMR (DMSO-d$_6$, 600 MHz) δ 8.65 (s, 1H), 8.45 (d, 1H), 8.17 (s, 1H), 8.12 (d, 1H), 7.97 (dd, 1H)

Reference Example 27. 4-(6-bromo-3-methylpyridin-2-yl)-2,4-dihydro-3H-1,2,4-triazol-3-one 1.8 g of the title compound (yield: 65.9%) was prepared in the same fashion as Reference Example 3, except that 2.0 g of 2-amino-6-bromo-3-methylpyridine was used in Step 1 instead of 4-bromoaniline. MS (ESI) m/z=256.7 (M+H)$^+$

Reference Example 28. 4-(5-bromopyrazin-2-yl)-2,4-dihydro-3H-1,2,4-triazol-3-one 4.3 g of the title compound (yield: 61.9%) was prepared in the same fashion as Reference Example 3, except that 5.0 g of 2-amino-5-bromopyrazine was used in Step 1 instead of 4-bromoaniline. MS (ESI) m/z=243.4 (M+H)+

Reference Example 29. 4-(5-bromothiazol-2-yl)-2,4-dihydro-3H-1,2,4-triazol-3-one 475.9 mg of the title compound (yield: 34.6%) was prepared in the same fashion as Reference Example 3, except that 1.0 g of 2-amino-5-bromothiazole was used in Step 1 instead of 4-bromoaniline. MS (ESI) m/z=248.0 (M+H)+

Reference Example 30. tert-butyl 4-(3-bromophenyl)-5-oxo-4,5-dihydro-1H-1,2,4-triazole-1-carboxylate 5.0 g of 4-(3-bromophenyl)-2,4-dihydro-3H-1,2,4-triazol-3-one prepared in Reference Example 4 and 2.6 g of sodium carbonate were dissolved in 15.0 mL of 1,4-dioxane and 25.0 mL of distilled water. 5.7 mL of di tert-butyl dicarbonate and 10.0 mL of 1,4-dioxane were added to the resulting solution, and then the solution was stirred overnight at room temperature. The resulting reaction mixture was neutralized with 1N aqueous hydrochloride solution and then crystallized with addition of ethyl acetate. The resulting crystals were filtered, washed with diisopropylether, and then dried to give 5.1 g of the title compound as a white solid (yield: 71.2%). MS (ESI) m/z=241.9 (M+H)$^+$

Reference Example 31. 3-(4-(4,4,5,5-tetramethyl-1,3,2-dioxaborolan-2-yl)phenyl)-1-((2-(trimethylsilyl)ethoxy)methyl)-1H-1,2,4-triazole Step 1: (E)-4-bromo-N-((dimethylamino)methylene)benzamide A reaction mixture of 2.0 g of 4-bromobenzamide and 5.4 g of N,N-dimethylformamide dimethyl acetal was stirred at 90° C. for 15 minutes. The reaction mixture was cooled to room temperature, and 30.0 mL of diethylether was added thereto to give crystals. The resulting crystals were filtered and dried to give 1.89 g of the title compound as a yellow solid (yield: 100.0%).

Step 2: 3-(4-bromophenyl)-1H-1,2,4-triazole 1.5 g of (E)-4-bromo-N-((dimethylamino)methylene)benzamide prepared in Step 1 and 0.3 mL of hydrazine hydrate were dissolved in 15.0 mL acetic acid, and the resulting solution was stirred at 90° C. for 2 hours. The reaction mixture was cooled to room temperature and then 30 mL diethylether was added thereto. The resulting reaction mixture was stirred at room temperature for 1 hour and then additionally stirred at 0° C. for 1 hour to give crystals. The resulting crystals were filtered and dried to obtain 1.57 g of the title compound as a yellow solid (yield: 100.0%). $^1$H-NMR (DMSO-d$_6$, 400 MHz) δ 14.23 (s, 1H), 8.51 (s, 1H), 7.96 (d, 2H), 7.69 (d, 2H)

Step 3: 3-(4-bromophenyl)-1-((2-(trimethylsilyl)ethoxy)methyl)-1H-1,2,4-triazole 1.5 g of 3-(4-bromophenyl)-1H-1,2,4-triazole prepared in Step 2 was dissolved in 5.0 mL of N,N-dimethylformamide, and the resulting reaction mixture was cooled to 0° C. To the reaction mixture, 0.32 g of sodium hydride was added, and then the reaction mixture was stirred for 30 minutes. 1.67 g of (2-(chloromethoxy)ethyl)trimethylsilane was added thereto and the reaction mixture was then stirred at 0° C. for 15 minutes and additionally stirred for 2 hours further. Distilled water was added and the reaction mixture was extracted with dichloromethane. The extract was dried over anhydrous magnesium sulfate and then concentrated under reduced pressure to give a residue as a yellow liquid. The residue was purified with silica gel column chromatography (developing solvent: n-hexane/ethyl acetate=2/1) to give 1.1 g of the title compound as a yellow solid (yield: 46.3%). $^1$H-NMR (CDCl$_3$, 400 MHz) δ 8.25 (s, 1H), 8.01 (d, 2H), 7.58 (d, 2H), 5.52 (s, 2H), 3.69 (t, 2H), 0.96 (t, 2H), 0.00 (s, 9H)

Step 4: 3-(4-(4,4,5,5-tetramethyl-1,3,2-dioxaborolan-2-yl)phenyl)-1-((2-(trimethylsilyl)ethoxy)methyl)-1H-1,2,4-triazole 500.0 mg of 3-(4-bromophenyl)-1-((2-(trimethylsilyl)ethoxy)methyl)-1H-1,2,4-triazole prepared in Step 3, 720.0 mg of bis(pinacolato)diboron, and 420.0 mg of potassium acetate were dissolved in 10.0 mL of 1,4-dioxane. To the resulting solution, 103.0 mg of palladiumdi[1,1'-bis(diphenylphosphino)ferrocene]dichloride (PdCl$_2$(dppf)) and 39.0 mg of 1,1'-bis(diphenylphosphino)ferrocene] (dppf) were added, and the solution was stirred overnight at 95° C. The reaction mixture thus obtained was concentrated, and ethyl acetate was added thereto. The concentrated reaction mixture was washed with distilled water, dried over anhydrous magnesium sulfate, and concentrated under reduced pressure to give a yellow liquid residue. The residue was purified with silica gel column chromatography (developing solvent: n-hexane/ethyl acetate=1/1) to give 403.0 mg of the title compound as a yellow solid (yield: 70.6%). $^1$H-NMR (CDCl$_3$, 400 MHz) δ 8.27 (s, 1H), 8.14 (d, 2H), 7.93 (m, 2H), 5.54 (s, 2H), 3.71 (t, 2H), 1.38 (s, 12H), 0.96 (t, 2H), 0.01 (s, 9H)

Reference Example 32. 3-(3-(4,4,5,5-tetramethyl-1, 3,2-dioxaborolan-2-yl)phenyl)-1-((2-(trimethylsilyl) ethoxy)methyl)-1H-1,2,4-triazole 1.57 g of the title compound as a yellow solid (yield: 66.0%) was prepared in the same fashion as Reference Example 32, except that 2.0 g of 3-bromobenzamide was used in Step 1 instead of 4-bromobenzamide. 41-NMR (CDCl$_3$, 400 MHz) δ 8.59 (s, 1H), 8.27 (s, 1H), 8.21 (d, 2H), 7.84 (d, 2H), 7.45 (t, 2H), 5.53 (s, 2H), 3.69 (t, 2H), 1.35 (s, 12H), 0.96 (t, 2H), 0.01 (s, 9H).

Reference Example 33. tert-butyl (Z)-(2-((4-(4-bromophenyl)-5-oxo-4,5-dihydro-1H-1,2,4-triazol-1-yl)methyl)-3-fluoroallyl)carbamate 20.9 mg of 4-(4-bromophenyl)-2,4-dihydro-3H-1,2,4-triazol-3-one prepared in Reference Example 3 and 23.1 mg of potassium carbonate were dissolved in 0.6 mL of N,N-dimethylformamide. 30.0 mg of tert-butyl (Z)-(2-(chloromethyl)-3-fluoroallyl)carbamate prepared in Reference Example 1 was added to the resulting solution, and then the solution was stirred at 100° C. for 4 hours. The resulting reaction mixture was concentrated, and with the addition of dichloromethane, the concentrated reaction mixture was washed with distilled water, dried over anhydrous magnesium sulfate, and concentrated under reduced pressure to give a yellow liquid residue. The residue was purified with silica gel column chromatography (developing solvent: n-hexane/ethyl acetate=2/1) to give 17.0 mg of the title compound as a colorless liquid (yield: 34.9%). MS (ESI) m/z=328.2 (M+H)+

Reference Example 34. tert-butyl (E)-(2-((4-(4-bromophenyl)-5-oxo-4,5-dihydro-1H-1,2,4-triazol-1-yl)methyl)-3-fluoroallyl)carbamate 16.3 mg of 4-(4-bromophenyl)-2,4-dihydro-3H-1,2,4-triazol-3-one prepared in Reference Example 3 and 23.1 mg of potassium carbonate were dissolved in 0.6 mL of N,N-dimethylforamide. To the resulting solution, 30.0 mg of tert-butyl (E)-(2-(chloromethyl)-3-fluoroallyl)carbamate prepared in Reference Example 2 was added, and the solution was stirred at 100° C. for 4 hours. The resulting reaction mixture was concentrated, and dichloromethane was added thereto. The concentrated reaction mixture was washed with distilled water, dried over anhydrous magnesium sulfate, and concentrated under reduced pressure to give a yellow liquid residue. The residue was purified with silica gel column chromatography (developing solvent: n-hexane/ethyl acetate=2/1) to give 19.0 mg of the title compound as a colorless liquid (yield: 64.7%). MS (ESI) m/z=328.2 (M+H)+

Reference Example 35. tert-butyl (Z)-(2-((4-(4-bromo-2-fluorophenyl)-5-oxo-4,5-dihydro-1H-1,2,4-triazol-1-yl)methyl)-3-fluoroallyl)carbamate 31.0 mg of the title compound as a yellow solid (yield: 84.3%) was prepared in the same fashion as Reference Example 33, except that 21.5 mg of 4-(4-bromo-2-fluorophenyl)-2,4-dihydro-3H-1,2,4-triazol-3-one prepared in Reference Example 8 was used instead of 4-(4-bromophenyl)-2,4-dihydro-3H-1,2,4-triazol-3-one. MS (ESI) m/z=346.1 (M+H)+

Reference Example 36. tert-butyl (E)-(2-((4-(4-bromo-2-fluorophenyl)-5-oxo-4,5-dihydro-1H-1,2,4-triazol-1-yl)methyl)-3-fluoroallyl)carbamate 20.0 mg of the title compound as a white solid (yield: 72.6%) was prepared in the same fashion as Reference Example 34, except that 16.0 mg of 4-(4-bromo-2-fluorophenyl)-2,4-dihydro-3H-1,2,4-triazol-3-one prepared in Reference Example 8 was used instead of 4-(4-bromophenyl)-2,4-dihydro-3H-1,2,4-triazol-3-one. $^1$H-NMR (MeOD, 400 MHz) δ 8.11 (s, 1H), 7.65 (d, 1H), 7.53-7.59 (m, 2H), 7.18 (d, 1H), 4.53 (s, 2H), 3.73 (d, 2H), 1.41 (s, 9H)

Reference Example 37. tert-butyl (Z)-(2-((4-(4-bromo-3-fluoroallyl)-5-oxo-4,5-dihydro-1H-1,2,4-triazol-1-yl)methyl)-3-fluorophenyl)carbamate 81.0 mg of the title compound as a yellow solid (yield: 64.3%) was prepared in the same fashion as Reference Example 33, except that 71.8 mg of 4-(4-bromo-3-fluorophenyl)-2,4-dihydro-3H-1,2,4-triazol-3-one prepared in Reference Example 9 was used instead of 4-(4-bromophenyl)-2,4-dihydro-3H-1,2,4-triazol-3-one. MS (ESI) m/z=346.3 (M+H)+

Reference Example 38. tert-butyl (E)-(2-((4-(4-bromo-3-fluoroallyl)-5-oxo-4,5-dihydro-1H-1,2,4-triazol-1-yl)methyl)-3-fluorophenyl)carbamate 26.0 mg of the title compound as a white solid (yield: 72.6%) was prepared in the same fashion as Reference Example 34, except that 16.0 mg of 4-(4-bromo-3-fluorophenyl)-2,4-dihydro-3H-1,2,4-triazol-3-one prepared in Reference Example 9 was used instead of 4-(4-bromophenyl)-2,4-dihydro-3H-1,2,4-triazol-3-one. 41-NMR (MeOD, 400 MHz) δ 8.34 (s, 1H), 7.71-7.80 (m, 2H), 7.48 (dd, 1H), 7.18 (d, 1H), 4.53 (d, 2H), 3.73 (d, 2H), 1.42 (s, 9H)

Reference Example 39. tert-butyl (Z)-(2-((4-(4-bromo-3-methylphenyl)-5-oxo-4,5-dihydro-1H-1,2, 4-triazol-1-yl)methyl)-3-fluoroallyl)carbamate 79.0 mg of the title compound as a yellow solid (yield: 63.9%) was prepared in the same fashion as Reference Example 33, except that 70.7 mg of 4-(4-bromo-3-methylphenyl)-2,4-dihydro-3H-1,2,4-triazol-3-one prepared in Reference Example 10 was used instead of 4-(4-bromophenyl)-2,4-dihydro-3H-1,2,4-triazol-3-one. MS (ESI) m/z=342.2 (M+H)+

Reference Example 40. tert-butyl (E)-(2-((4-(4-bromo-3-methylphenyl)-5-oxo-4,5-dihydro-1H-1,2, 4-triazol-1-yl)methyl)-3-fluoroallyl)carbamate 26.0 mg of the title compound as a colorless liquid (yield: 95.2%) was prepared in the same fashion as Reference Example 34, except that 16.0 mg of 4-(4-bromo-3-methylphenyl)-2,4-dihydro-3H-1,2,4-triazol-3-one prepared in Reference Example 10 was used instead of 4-(4-bromophenyl)-2,4-dihydro-3H-1,2,4-triazol-3-one. $^1$H-NMR (MeOD, 400 MHz) δ 8.26 (s, 1H), 7.68 (d, 1H), 7.62 (s, 1H), 7.40 (dd, 1H), 7.18 (d, 1H), 4.53 (d, 2H), 3.73 (d, 2H), 2.45 (s, 3H), 1.41 (s, 9H)

Reference Example 41. tert-butyl (Z)-(2-((4-(4-bromo-3-methoxyphenyl)-5-oxo-4,5-dihydro-1H-1,2,4-triazol-1-yl)methyl)-3-fluoroallyl)carbamate 77.0 mg of the title compound as a yellow solid (yield: 60.1%) was prepared in the same fashion as Reference Example 33, except that 75.1 mg of 4-(4-bromo-3-methoxyphenyl)-2,4-dihydro-3H-1,2,4-triazol-3-one prepared in Reference Example 12 was used instead of 4-(4-bromophenyl)-2,4-dihydro-3H-1,2,4-triazol-3-one. MS (ESI) m/z=358.3 (M+H)+

Reference Example 42. tert-butyl (E)-(2-((4-(4-bromo-3-methoxyphenyl)-5-oxo-4,5-dihydro-1H-1,2,4-triazol-1-yl)methyl)-3-fluoroallyl)carbamate 20.0 mg of the title compound as a white solid (yield: 71.0%) was prepared in the same fashion as Reference Example 34, except that 17.0 mg of 4-(4-bromo-3-methoxyphenyl)-2,4-dihydro-3H-1,2,4-triazol-3-one prepared in Reference Example 12 was used instead of 4-(4-bromophenyl)-2,4-dihydro-3H-1,2,4-triazol-3-one. 41-NMR (MeOD, 400 MHz) δ 8.31 (s, 1H), 7.65 (d, 1H), 7.40 (s, 1H), 7.18 (d, 1H), 7.15 (dd, 1H), 4.55 (d, 2H), 3.93 (s, 3H), 3.75 (s, 2H), 1.42 (s, 9H)

Reference Example 43. tert-butyl (Z)-(2-((4-(4-bromo-3,5-difluorophenyl)-5-oxo-4,5-dihydro-1H-1,2,4-triazol-1-yl)methyl)-3-fluoroallyl)carbamate 82.0 mg of the title compound as a yellow solid (yield: 63.2%) was prepared in the same fashion as Reference Example 33, except that 76.8 mg of 4-(4-bromo-3,5-difluorophenyl)-2,4-dihydro-3H-1,2,4-triazol-3-one prepared in Reference Example 14 was used instead of 4-(4-bromophenyl)-2,4-dihydro-3H-1,2,4-triazol-3-one. MS (ESI) m/z=364.6 (M+H)+

Reference Example 44. tert-butyl (E)-(2-((4-(4-bromo-3,5-difluorophenyl)-5-oxo-4,5-dihydro-1H-1,2,4-triazol-1-yl)methyl)-3-fluoroallyl)carbamate 24.0 mg of the title compound as a colorless liquid (yield: 83.9%) was prepared in the same fashion as Reference Example 34, except that 17.0 mg of 4-(4-bromo-3,5-difluorophenyl)-2,4-dihydro-3H-1,2,4-triazol-3-one prepared in Reference Example 14 was used instead of 4-(4-bromophenyl)-2,4-dihydro-3H-1,2,4-triazol-3-one. $^1$H-NMR (MeOD, 400 MHz) δ 8.39 (s, 1H), 7.64 (dd, 2H), 7.18 (d, 1H), 4.53 (d, 2H), 3.73 (d, 2H), 1.42 (s, 9H)

Reference Example 45. tert-butyl (Z)-(2-((4-(4-bromo-2,6-difluorophenyl)-5-oxo-4,5-dihydro-1H-1,2,4-triazol-1-yl)methyl)-3-fluoroallyl)carbamate 9.0 mg of the title compound as a yellow solid (yield: 23.4%) was prepared in the same fashion as Reference Example 33, except that 23.0 mg of 4-(4-bromo-2,6-difluorophenyl)-2,4-dihydro-3H-1,2,4-triazol-3-one prepared in Reference Example 15 was used instead of 4-(4-bromophenyl)-2,4-dihydro-3H-1,2,4-triazol-3-one. MS (ESI) m/z=364.5 (M+H)+

Reference Example 46. tert-butyl (E)-(2-((4-(4-bromo-2,6-difluorophenyl)-5-oxo-4,5-dihydro-1H-1,2,4-triazol-1-yl)methyl)-3-fluoroallyl)carbamate 14.0 mg of the title compound as a white solid (yield: 48.4%) was prepared in the same fashion as Reference Example 34, except that 17.0 mg of 4-(4-bromo-2,6-difluorophenyl)-2,4-dihydro-3H-1,2,4-triazol-3-one prepared in Reference Example 15 was used instead of 4-(4-bromophenyl)-2,4-dihydro-3H-1,2,4-triazol-3-one. 41-NMR (MeOD, 400 MHz) δ 8.10 (s, 1H), 7.57 (d, 2H), 7.18 (d, 1H), 4.55 (d, 2H), 3.73 (d, 2H), 1.41 (s, 9H).

Reference Example 47. tert-butyl (E)-(2-((4-(4-bromo-2,5-difluorophenyl)-5-oxo-4,5-dihydro-1H-1,2,4-triazol-1-yl)methyl)-3-fluoroallyl)carbamate 12.0 mg of the title compound as a white solid (yield: 41.9%) was prepared in the same fashion as Reference Example 34, except that 17.0 mg of 4-(4-bromo-2,5-difluorophenyl)-2,4-dihydro-3H-1,2,4-triazol-3-one prepared in Reference Example 16 was used instead of 4-(4-bromophenyl)-2,4-dihydro-3H-1,2,4-triazol-3-one. $^1$H-NMR (MeOD, 400 MHz) δ 8.15 (s, 1H), 7.79 (dd, 1H), 7.69 (dd, 1H), 7.09 (d, 1H), 7.08 (d, 1H), 4.54 (d, 2H), 4.12 (d, 2H), 1.42 (s, 9H).

Reference Example 48. tert-butyl (E)-(2-((4-(5-bromo-2-methoxy-4-morpholinophenyl)-5-oxo-4,5-dihydro-1H-1,2,4-triazol-1-yl)methyl)-3-fluoroallyl) carbamate Step 1: phenyl (5-bromo-2-methoxy-4-morpholinophenyl)carbamate 1.0 g of 5-bromo-2-methoxy-4-morpholinoaniline and 0.62 mL of pyridine were dissolved in 10.0 mL of ethyl acetate. To the resulting solution, 0.17 mL of phenylchloroformate at 0° C. was slowly added, and the solution was stirred overnight at room temperature. To the solution, ethyl acetate was added, and the resulting mixture was washed with a 1N hydrochloric acid solution and brine, dried over anhydrous magnesium sulfate, and concentrated under reduced pressure to give 0.78 g of the title compound as a yellow solid (yield: 55.0%). $^1$H-NMR (CDCl$_3$, 400 MHz) δ 8.35 (bs, 1H), 7.40 (t, 3H), 7.18-7.26 (m, 3H), 6.63 (s, 1H), 3.92 (s, 3H), 3.88 (d, 4H), 3.02 (d, 4H)

Step 2: N-(5-bromo-2-methoxy-4-morpholinophenyl)hydrazine carboxamide 780 mg of phenyl (5-bromo-2-methoxy-4-morpholinophenyl)carbamate prepared in Step 1 and 186 uL of hydrazine hydrate were dissolved in 2.0 mL of tetrahydrofuran and 2.0 mL of ethanol, and the resulting solution was stirred overnight at 80° C. The resulting reaction mixture was concentrated and then washed with ethyl acetate to give 637 mg of the title compound as a white solid (yield: 96.1%). $^1$H-NMR (DMSO-d$_6$, 400 MHz) δ 8.37 (s, 1H), 7.68 (s, 1H), 6.82 (s, 1H), 4.55 (s, 2H), 3.86 (s, 3H), 3.72 (s, 4H), 2.92 (s, 4H)

Step 3: 4-(5-bromo-2-methoxy-4-morpholinophenyl)-2,4-dihydro-3H-1,2,4-triazol-3-one 637 mg of N-(5-bromo-2-methoxy-4-morpholinophenyl) hydrazine carboxamide prepared in Step 2 and 766 mg of formamidine acetate were dissolved in 10.0 mL of 1-propanol, and the resulting solution was stirred at room temperature for 30 minutes, and then 632 uL of acetic acid was added and stirred at 80° C. for 8 hours. The reaction mixture was cooled to room temperature, distilled water was added to the cooled reaction mixture, and then the reaction mixture was stirred overnight. The resulting crystals were filtered and dried to give 615 mg of the title compound as a white solid (yield: 94.1%). (CDCl$_3$, 400 MHz) δ 9.67 (s, 1H), 7.67 (s, 1H), 7.56 (s, 1H), 6.68 (s, 1H), 3.90 (s, 4H), 3.86 (s, 3H), 3.08 (s, 4H)

Step 4: tert-butyl (E)-(2-((4-(5-bromo-2-methoxy-4-morpholinophenyl)-5-oxo-4,5-dihydro-1H-1,2,4-triazol-1-yl)methyl)-3-fluoroallyl)carbamate 213 mg of 4-(5-bromo-2-methoxy-4-morpholinophenyl)-2,4-dihydro-3H-1,2,4-triazol-3-one prepared in Step 3 and 231 mg of potassium carbonate were dissolved in 3.0 mL of N,N-dimethylformamide. 300 mg of tert-butyl (E)-(2-(chloromethyl)-3-fluoroallyl)carbamate prepared in Reference Example 2 was added to the resulting solution, and the solution was stirred at 100° C. for 4 hours. The resulting reaction mixture was concentrated, and with the addition of dichloromethane, the concentrated reaction mixture was washed with distilled water, dried over anhydrous magnesium sulfate, and concentrated under reduced pressure to give a yellow liquid residue. The residue was purified with silica gel column chromatography (developing solvent: n-hexane/ethyl acetate=2/1) to give 221 mg of the title compound as a colorless liquid (yield: 48.8%). MS (ESI) m/z=443.3 (M+H)+

Reference Example 49. tert-butyl (Z)-(2-((4-(3-bromophenyl)-5-oxo-4,5-dihydro-1H-1,2,4-triazol-1-yl)methyl)-3-fluoroallyl)carbamate 22.0 mg of the title compound as a yellow solid (yield: 62.0%) was prepared in the same fashion as Reference Example 33, except that 20.0 mg of 4-(3-bromophenyl)-2,4-dihydro-3H-1,2,4-triazol-3-one prepared in Reference Example 4 was used instead of 4-(4-bromophenyl)-2,4-dihydro-3H-1,2,4-triazol-3-one. MS (ESI) m/z=328.2 (M+H)+

Reference Example 50. tert-butyl (E)-(2-((4-(3-bromophenyl)-5-oxo-4,5-dihydro-1H-1,2,4-triazol-1-yl)methyl)-3-fluoroallyl)carbamate 27.0 mg of the title compound as a colorless liquid (yield: 100.0%) was prepared in the same fashion as Reference Example 34, except that 15.0 mg of 4-(3-bromophenyl)-2,4-dihydro-3H-1,2,4-triazol-3-one prepared in Reference Example 4 was used instead of 4-(4-bromophenyl)-2,4-dihydro-3H-1,2,4-triazol-3-one. (CDCl$_3$, 400 MHz) δ 7.81 (s, 1H), 7.70 (s, 1H), 7.50-7.53 (m, 2H), 7.35 (t, 1H), 6.76 (d, 1H), 5.20 (bs, 1H), 4.39 (d, 2H), 3.90 (d, 2H), 1.42 (s, 9H)

Reference Example 51. tert-butyl (Z)-(3-fluoro-2-((4-(4-fluorophenyl)-5-oxo-4,5-dihydro-1H-1,2,4-triazol-1-yl)methyl)allyl)carbamate 25.0 mg of the title compound as a colorless liquid (yield: 74.2%) was prepared in the same fashion as Reference Example 33, except that 16.5 mg of 4-(4-fluorophenyl)-2,4-dihydro-3H-1,2,4-triazol-3-one prepared in Reference Example 5 was used instead of 4-(4-bromophenyl)-2,4-dihydro-3H-1,2,4-triazol-3-one. MS (ESI) m/z=267.3 (M+H)+

Reference Example 52. tert-butyl (E)-(3-fluoro-2-((4-(4-fluorophenyl)-5-oxo-4,5-dihydro-1H-1,2,4-triazol-1-yl)methyl)allyl)carbamate 12.0 mg of the title compound as a colorless liquid (yield: 39.0%) was prepared in the same fashion as Reference Example 34, except that 15.0 mg of 4-(4-fluorophenyl)-2,4-dihydro-3H-1,2,4-triazol-3-one prepared in Reference Example 5 was used instead of 4-(4-bromophenyl)-2,4-dihydro-3H-1,2,4-triazol-3-one. MS (ESI) m/z=267.3 (M+H)+

Reference Example 53. tert-butyl (Z)-(2-((4-(4-(benzyloxy)phenyl)-5-oxo-4,5-dihydro-1H-1,2,4-triazol-1-yl)methyl)-3-fluoroallyl)carbamate 37.0 mg of the title compound as a yellow solid (yield: 98.1%) was prepared in the same fashion as Reference Example 33, except that 22.3 mg of 4-(4-(benzyloxy)phenyl)-2,4-dihydro-3H-1,2,4-triazol-3-one prepared in Reference Example 6 was used instead of 4-(4-bromophenyl)-2,4-dihydro-3H-1,2,4-triazol-3-one. MS (ESI) m/z=355.6 (M+H)+

Reference Example 54. tert-butyl (E)-(2-((4-(4-(benzyloxy)phenyl)-5-oxo-4,5-dihydro-1H-1,2,4-triazol-1-yl)methyl)-3-fluoroallyl)carbamate 18.0 mg of the title compound as a colorless liquid (yield: 47.7%) was prepared in the same fashion as Reference Example 34, except that 22.3 mg of 4-(4-(benzyloxy)phenyl)-2,4-dihydro-3H-1,2,4-triazol-3-one prepared in Reference Example 6 was used instead of 4-(4-bromophenyl)-2,4-dihydro-3H-1,2,4-triazol-3-one. MS (ESI) m/z=355.3 (M+H)+

Reference Example 55. tert-butyl (Z)-(2-((4-(3,4-difluorophenyl)-5-oxo-4,5-dihydro-1H-1,2,4-triazol-1-yl)methyl)-3-fluoroallyl)carbamate 25.0 mg of the title compound as a yellow solid (yield: 77.4%) was prepared in the same fashion as Reference Example 33, except that 16.5 mg of 4-(3,4-difluorophenyl)-2,4-dihydro-3H-1,2,4-triazol-3-one prepared in Reference Example 7 was used instead of 4-(4-bromophenyl)-2,4-dihydro-3H-1,2,4-triazol-3-one. MS (ESI) m/z=285.1 (M+H)+

Reference Example 56. tert-butyl (E)-(2-((4-(3,4-difluorophenyl)-5-oxo-4,5-dihydro-1H-1,2,4-triazol-1-yl)methyl)-3-fluoroallyl)carbamate 27.0 mg of the title compound as a colorless liquid (yield: 83.6%) was prepared in the same fashion as Reference Example 34, except that 16.5 mg of 4-(3,4-difluorophenyl)-2,4-dihydro-3H-1,2,4-triazol-3-one prepared in Reference Example 7 was used instead of 4-(4-bromophenyl)-2,4-dihydro-3H-1,2,4-triazol-3-one. MS (ESI) m/z=285.2 (M+H)+

Reference Example 57. tert-butyl (E)-(2-((4-(3-bromo-2-methylphenyl)-5-oxo-4,5-dihydro-1H-1,2,4-triazol-1-yl)methyl)-3-fluoroallyl)carbamate 157.0 mg of the title compound as a yellow solid (yield: 45.2%) was prepared in the same fashion as Reference Example 34, except that 200.0 mg of 4-(3-bromo-2-methylphenyl)-2,4-dihydro-3H-1,2,4-triazol-3-one prepared in Reference Example 11 was used instead of 4-(4-bromophenyl)-2,4-dihydro-3H-1,2,4-triazol-3-one. MS (ESI) m/z=342.3 (M+H)+

Reference Example 58. tert-butyl (Z)-(2-((4-(6-bromopyridin-3-yl)-5-oxo-4,5-dihydro-1H-1,2,4-triazol-1-yl)methyl)-3-fluoroallyl)carbamate 103.0 mg of the title compound as a yellow solid (yield: 86.5%) was prepared in the same fashion as Reference Example 33, except that 67.1 mg of 4-(6-bromopyridin-3-yl)-2,4-dihydro-3H-1,2,4-triazol-3-one prepared in Reference Example 17 was used instead of 4-(4-bromophenyl)-2,4-dihydro-3H-1,2,4-triazol-3-one. MS (ESI) m/z=329.2 (M+H)+

Reference Example 59. tert-butyl (E)-(2-((4-(6-bromopyridin-3-yl)-5-oxo-4,5-dihydro-1H-1,2,4-triazol-1-yl)methyl)-3-fluoroallyl)carbamate 20.0 mg of the title compound as a yellow liquid (yield: 74.2%) was prepared in the same fashion as Reference Example 34, except that 15.0 mg of 4-(6-bromopyridin-3-yl)-2,4-dihydro-3H-1,2,4-triazol-3-one prepared in Reference Example 17 was used instead of 4-(4-bromophenyl)-2,4-dihydro-3H-1,2,4-triazol-3-one. $^1$H-NMR (MeOD, 400 MHz) δ 8.74 (d, 1H), 8.36 (s, 1H), 8.06 (dd, 1H), 7.76 (d, 1H), 7.19 (d, 1H), 4.54 (d, 2H), 3.74 (s, 2H), 1.41 (s, 9H)

Reference Example 60. tert-butyl (Z)-(2-((4-(6-bromo-5-methylpyridin-3-yl)-5-oxo-4,5-dihydro-1H-1,2,4-triazol-1-yl)methyl)-3-fluoroallyl)carbamate 14.0 mg of the title compound as a yellow solid (yield: 37.9%) was prepared in the same fashion as Reference Example 33, except that 21.3 mg of 4-(6-bromo-5-methylpyridin-3-yl)-2,4-dihydro-3H-1,2,4-triazol-3-one prepared in Reference Example 18 was used instead of 4-(4-bromophenyl)-2,4-dihydro-3H-1,2,4-triazol-3-one. MS (ESI) m/z=343.3 (M+H)+

Reference Example 61. tert-butyl (E)-(2-((4-(6-bromo-5-methylpyridin-3-yl)-5-oxo-4,5-dihydro-1H-1,2,4-triazol-1-yl)methyl)-3-fluoroallyl)carbamate 14.0 mg of the title compound as a yellow solid (yield: 50.0%) was prepared in the same fashion as Reference Example 34, except that 16.0 mg of 4-(6-bromo-5-methylpyridin-3-yl)-2,4-dihydro-3H-1,2,4-triazol-3-one prepared in Reference Example 18 was used instead of 4-(4-bromophenyl)-2,4-dihydro-3H-1,2,4-triazol-3-one. $^1$H-NMR (MeOD, 400 MHz) δ 8.58 (d, 1H), 8.35 (s, 1H), 8.07 (d, 1H), 7.19 (d, 1H), 4.55 (d, 2H), 3.75 (s, 1H), 2.46 (s, 3H), 1.41 (s, 9H)

Reference Example 62. tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate 13.2 mg of the title compound as a yellow solid (yield: 47.6%) was prepared in the same fashion as Reference Example 34, except that 16.0 mg of 4-(6-bromo-4-methylpyridin-3-yl)-2,4-dihydro-3H-1,2,4-triazol-3-one prepared in Reference Example 19 was used instead of 4-(4-bromophenyl)-2,4-dihydro-3H-1,2,4-triazol-3-one. MS (ESI) m/z=343.2 (M+H)+

Reference Example 63. tert-butyl (Z)-(2-((4-(5-bromopyridin-2-yl)-5-oxo-4,5-dihydro-1H-1,2,4-triazol-1-yl)methyl)-3-fluoroallyl)carbamate 13.0 mg of the title compound as a yellow solid (yield: 34.3%) was prepared in the same fashion as Reference Example 33, except that 21.3 mg of 4-(5-bromopyridin-2-yl)-2,4-dihydro-3H-1,2,4-triazol-3-one prepared in Reference Example 20 was used instead of 4-(4-bromophenyl)-2,4-dihydro-3H-1,2,4-triazol-3-one. MS (ESI) m/z=329.1 (M+H)+

Reference Example 64. tert-butyl (E)-(2-((4-(5-bromopyridin-2-yl)-5-oxo-4,5-dihydro-1H-1,2,4-triazol-1-yl)methyl)-3-fluoroallyl)carbamate 30.0 mg of the title compound as a white solid (yield: 90.3%) was prepared in the same fashion as Reference Example 34, except that 30.0 mg of 4-(5-bromopyridin-2-yl)-2,4-dihydro-3H-1,2,4-triazol-3-one prepared in Reference Example 20 was used instead of 4-(4-bromophenyl)-2,4-dihydro-3H-1,2,4-triazol-3-one. $^1$H-NMR (MeOD, 400 MHz) δ 8.65 (s, 1H), 8.57 (d, 1H), 8.22 (d, 1H), 8.15 (dd, 1H), 7.19 (d, 1H), 4.53 (d, 2H), 3.73 (d, 2H), 1.42 (s, 9H)

Reference Example 65. tert-butyl (Z)-(2-((4-(5-bromo-3-methylpyridin-2-yl)-5-oxo-4,5-dihydro-1H-1,2,4-triazol-1-yl)methyl)-3-fluoroallyl)carbamate 13.0 mg of the title compound as a yellow solid (yield: 35.2%) was prepared in the same fashion as Reference Example 33, except that 21.3 mg of 4-(5-bromo-3-methylpyridin-2-yl)-2,4-dihydro-3H-1,2,4-triazol-3-one prepared in Reference Example 21 was used instead of 4-(4-bromophenyl)-2,4-dihydro-3H-1,2,4-triazol-3-one. MS (ESI) m/z=343.4 (M+H)+

Reference Example 66. tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate 27.0 mg of the title compound as a colorless liquid (yield: 98.4%) was prepared in the same fashion as Reference Example 34, except that 16.0 mg of 4-(5-bromo-3-methylpyridin-2-yl)-2,4-dihydro-3H-1,2,4-triazol-3-one prepared in Reference Example 21 was used instead of 4-(4-bromophenyl)-2,4-dihydro-3H-1,2,4-triazol-3-one.
$^1$H-NMR (CDCl$_3$, 400 MHz) δ 7.98 (s, 1H), 7.38 (s, 1H), 6.61 (d, 1H), 4.40 (bs, 1H), 3.93-3.97 (m, 2H), 2.11 (s, 3H), 1.45 (s, 9H)

Reference Example 67. tert-butyl (Z)-(2-((4-(5-bromo-4-methylpyridin-2-yl)-5-oxo-4,5-dihydro-1H-1,2,4-triazol-1-yl)methyl)-3-fluoroallyl)carbamate 15.0 mg of the title compound as a yellow solid (yield: 43.2%) was prepared in the same fashion as Reference Example 33, except that 20.0 mg of 4-(5-bromo-4-methylpyridin-2-yl)-2,4-dihydro-3H-1,2,4-triazol-3-one prepared in Reference Example 22 was used instead of 4-(4-bromophenyl)-2,4-dihydro-3H-1,2,4-triazol-3-one. MS (ESI) m/z=343.5 (M+H)+

Reference Example 68. tert-butyl (E)-(2-((4-(5-bromo-4-methylpyridin-2-yl)-5-oxo-4,5-dihydro-1H-1,2,4-triazol-1-yl)methyl)-3-fluoroallyl)carbamate 26.0 mg of the title compound as a white solid (yield: 95.2%) was prepared in the same fashion as Reference Example 34, except that 16.0 mg of 4-(5-bromo-4-methylpyridin-2-yl)-2,4-dihydro-3H-1,2,4-triazol-3-one prepared in Reference Example 22 was used instead of 4-(4-bromophenyl)-2,4-dihydro-3H-1,2,4-triazol-3-one.
$^1$H-NMR (CDCl$_3$, 400 MHz) δ 8.42 (s, 1H), 8.40 (s, 1H), 8.26 (s, 1H), 6.76 (d, 1H), 5.16 (bs, 1H), 4.38 (s, 2H), 3.90 (bs, 2H), 2.47 (s, 3H), 1.41 (s, 9H)

Reference Example 69. tert-butyl (Z)-(2-((4-(5-bromo-3-fluoropyridin-2-yl)-5-oxo-4,5-dihydro-1H-1,2,4-triazol-1-yl)methyl)-3-fluoroallyl)carbamate 12.0 mg of the title compound as a yellow solid (yield: 34.8%) was prepared in the same fashion as Reference Example 33, except that 20.0 mg of 4-(5-bromo-3-fluoropyridin-2-yl)-2,4-dihydro-3H-1,2,4-triazol-3-one prepared in Reference Example 23 was used instead of 4-(4-bromophenyl)-2,4-dihydro-3H-1,2,4-triazol-3-one. MS (ESI) m/z=347.5 (M+H)+

Reference Example 70. tert-butyl (E)-(2-((4-(5-bromo-3-fluoropyridin-2-yl)-5-oxo-4,5-dihydro-1H-1,2,4-triazol-1-yl)methyl)-3-fluoroallyl)carbamate 18.0 mg of the title compound as a yellow solid (yield: 52.2%) was prepared in the same fashion as Reference Example 34, except that 20.0 mg of 4-(5-bromo-3-fluoropyridin-2-yl)-2,4-dihydro-3H-1,2,4-triazol-3-one prepared in Reference Example 23 was used instead of 4-(4-bromophenyl)-2,4-dihydro-3H-1,2,4-triazol-3-one. MS (ESI) m/z=347.4 (M+H)+

Reference Example 71. tert-butyl (E)-(2-((4-(4-bromopyridin-2-yl)-5-oxo-4,5-dihydro-1H-1,2,4-triazol-1-yl)methyl)-3-fluoroallyl)carbamate 17.5 mg of the title compound as a yellow solid (yield: 49.2%) was prepared in the same fashion as Reference Example 34, except that 20.0 mg of 4-(4-bromopyridin-2-yl)-2,4-dihydro-3H-1,2,4-triazol-3-one prepared in Reference Example 25 was used instead of 4-(4-bromophenyl)-2,4-dihydro-3H-1,2,4-triazol-3-one. $^1$H-NAIR (CDCl$_3$, 400 MHz) δ 8.60 (s, 1H), 8.43 (s, 1H), 8.23 (d, 1H), 7.41 (d, 1H), 6.76 (d, 1H), 5.14 (bs, 1H), 4.39 (s, 2H), 3.89 (bs, 2H), 1.41 (s, 9H)

Reference Example 72. tert-butyl (E)-(2-((4-(6-bromopyridin-2-yl)-5-oxo-4,5-dihydro-1H-1,2,4-triazol-1-yl)methyl)-3-fluoroallyl)carbamate 21.3 mg of the title compound as a yellow solid (yield: 59.9%) was prepared in the same fashion as Reference Example 34, except that 20.0 mg of 4-(6-bromopyridin-2-yl)-2,4-dihydro-3H-1,2,4-triazol-3-one prepared in Reference Example 24 was used instead of 4-(4-bromophenyl)-2,4-dihydro-3H-1,2,4-triazol-3-one. $^1$H-NAIR (CDCl$_3$, 400 MHz) δ 8.41 (s, 1H), 8.32 (d, 1H), 7.69 (t, 1H), 7.42 (d, 1H), 6.75 (d, 1H), 5.13 (bs, 1H), 4.38 (s, 2H), 3.88 (bs, 2H), 1.41 (s, 9H)

Reference Example 73. tert-butyl (E)-(2-((4-(2-bromopyridin-4-yl)-5-oxo-4,5-dihydro-1H-1,2,4-triazol-1-yl)methyl)-3-fluoroallyl)carbamate 19.1 mg of the title compound as a yellow solid (yield: 53.7%) was prepared in the same fashion as Reference Example 34, except that 20.0 mg of 4-(2-bromopyridin-4-yl)-2,4-dihydro-3H-1,2,4-triazol-3-one prepared in Reference Example 26 was used instead of 4-(4-bromophenyl)-2,4-dihydro-3H-1,2,4-triazol-3-one. MS (ESI) m/z=329.5 (M+H)+

Reference Example 74. tert-butyl (E)-(2-((4-(6-bromo-3-methylpyridin-2-yl)-5-oxo-4,5-dihydro-1H-1,2,4-triazol-1-yl)methyl)-3-fluoroallyl)carbamate 27.8 mg of the title compound as a yellow solid (yield: 64.1%) was prepared in the same fashion as Reference Example 34, except that 25.0 mg of 4-(6-bromo-3-methylpyridin-2-yl)-2,4-dihydro-3H-1,2,4-triazol-3-one prepared in Reference Example 27 was used instead of 4-(4-bromophenyl)-2,4-dihydro-3H-1,2,4-triazol-3-one. MS (ESI) m/z=343.2 (M+H)+

Reference Example 75. tert-butyl (E)-(2-((4-(5-bromopyrazin-2-yl)-5-oxo-4,5-dihydro-1H-1,2,4-triazol-1-yl)methyl)-3-fluoroallyl)carbamate 20.0 mg of the title compound as a yellow solid (yield: 45.2%) was prepared in the same fashion as Reference Example 34, except that 25.0 mg of 4-(5-bromopyrazin-2-yl)-2,4-dihydro-3H-1,2,4-triazol-3-one prepared in Reference Example 28 was used instead of 4-(4-bromophenyl)-2,4-dihydro-3H-1,2,4-triazol-3-one. MS (ESI) m/z=330.1 (M+H)+

Reference Example 76. tert-butyl (Z)-(2-((4-(5-bromothiazol-2-yl)-5-oxo-4,5-dihydro-1H-1,2,4-triazol-1-yl)methyl)-3-fluoroallyl)carbamate 13.0 mg of the title compound as a yellow solid (yield: 35.4%) was prepared in the same fashion as Reference Example 33, except that 20.9 mg of 4-(5-bromothiazol-2-yl)-2,4-dihydro-3H-1,2,4-triazol-3-one prepared in Reference Example 29 was used instead of 4-(4-bromophenyl)-2,4-dihydro-3H-1,2,4-triazol-3-one. MS (ESI) m/z=335.2 (M+H)+

Reference Example 77. tert-butyl (E)-(2-((4-(5-bromothiazol-2-yl)-5-oxo-4,5-dihydro-1H-1,2,4-triazol-1-yl)methyl)-3-fluoroallyl)carbamate 14.0 mg of the title compound as a white solid (yield: 51.6%) was prepared in the same fashion as Reference Example 34, except that 15.0 mg of 4-(5-bromothiazol-2-yl)-2,4-dihydro-3H-1,2,4-triazol-3-one prepared in Reference Example 29 was used instead of 4-(4-bromophenyl)-2,4-dihydro-3H-1,2,4-triazol-3-one. $^1$H-NMR (MeOD, 400 MHz) δ 8.56 (s, 1H), 7.62 (s, 1H), 7.20 (d, 1H), 4.55 (d, 2H), 3.72 (d, 2H), 1.41 (s, 9H)

Reference Example 78. 3-(4-(4,4,5,5-tetramethyl-1,3,2-dioxaborolan-2-yl)phenyl)-1,2,4-oxadiazole Step 1: 4-bromo-N-hydroxybenzimidamide 5.0 g of 4-bromobenzonitrile, 4.77 g of hydroxylamine hydrochloride, and 7.28 g of sodium carbonate were dissolved in 60.0 mL of 80% ethanol solution, and the resulting solution was refluxed at 80° C. for 7 hours. The reaction mixture was cooled to room temperature and then concentrated under reduced pressure, and to the concentrated reaction mixture, ethyl acetate was added, and the reaction mixture was washed with distilled water. The organic layer thus obtained was dried over anhydrous magnesium sulfate and concentrated under reduced pressure to give a yellow liquid residue. The residue was purified with silica gel column chromatography (developing solvent: n-hexane/ethyl acetate=3/1) to give 5.06 g of the title compound as a yellow liquid (yield: 85.4%).

Step 2: 3-(4-bromophenyl)-1,2,4-oxadiazole 1.0 g of 4-bromo-N-hydroxybenzimidamide prepared in Step 1 was dissolved in 3.0 mL of triethyl orthoformate, and the resulting solution was stirred at 90° C. for 5 hours. The reaction mixture was cooled to room temperature and then concentrated under reduced pressure to give a yellow liquid residue. The residue was purified with silica gel column chromatography (developing solvent: n-hexane/ethyl acetate=2/1) to give 612.0 mg of the title compound as a yellow solid (yield: 57.9%).

Step 3: 3-(4-(4,4,5,5-tetramethyl-1,3,2-dioxaborolan-2-yl)phenyl)-1,2,4-oxadiazole 500.0 mg of 3-(4-bromophenyl)-1,2,4-oxadiazole prepared in Step 2, 1.13 g of bis(pinacolato)diboron and 650.0 mg of potassium acetate were dissolved in 10.0 mL of 1,4-dioxane, and to the resulting solution, 161.0 mg of palladiumdi[1,1'-bis(diphenylphosphino)ferrocene]dichloride (PdCl$_2$(dppf)) and 61.0 mg of 1,1'-bis(diphenylphosphino)ferrocene] (dppf) were added, and the solution was stirred overnight at 95° C. The reaction mixture was concentrated, and ethyl acetate was added thereto, and the reaction was washed with distilled water, dried over anhydrous magnesium sulfate, and concentrated under reduced pressure to give a yellow liquid residue. The residue was purified with silica gel column chromatography (developing solvent: n-hexane/ethyl acetate=1/1) to give 397.0 mg of the title compound as a yellow solid (yield: 65.7%). $^1$H-NMR (CDCl$_3$, 400 MHz) δ 8.77 (s, 1H), 8.12 (d, 2H), 7.94 (d, 2H), 1.37 (s, 12H)

Reference Example 79. 3-(3-(4,4,5,5-tetramethyl-1,3,2-dioxaborolan-2-yl)phenyl)-1,2,4-oxadiazole 325.0 mg of the title compound as a yellow solid (yield: 53.8%) was prepared in the same fashion as Reference Example 78, except that 5.0 g of 3-bromobenzonitrile was used in Step 1 instead of 4-bromobenzonitrile. $^1$H-NMR (CDCl$_3$, 400 MHz) δ 8.76 (s, 1H), 8.56 (s, 1H), 8.21 (d, 1H), 7.95 (d, 1H), 7.51 (t, 1H), 1.36 (s, 12H)

Reference Example 80. 5-cyclopropyl-3-(4-(4,4,5,5-tetramethyl-1,3,2-dioxaborolan-2-yl)phenyl)-1,2,4-oxadiazole Step 1: 4-bromo-N-hydroxybenzimidamide 5.0 g of 4-bromobenzonitrile, 4.77 g of hydroxylamine hydrochloride, and 7.28 g of sodium carbonate were dissolved in 60.0 mL of 80% ethanol solution, and the resulting solution was refluxed at 80° C. for 7 hours. The resulting reaction mixture was cooled to room temperature, and then concentrated under reduced pressure, and to the concentrated reaction mixture, ethyl acetate was added, and the reaction mixture was washed with distilled water. The organic layer thus obtained was dried over anhydrous magnesium sulfate and concentrated under reduced pressure to give a yellow liquid residue. The residue was purified with silica gel column chromatography (developing solvent: n-hexane/ethyl acetate=3/1) to give 5.06 g of the title compound as a yellow liquid (yield: 85.6%).

Step 2: 3-(4-bromophenyl)-5-cyclopropyl-1,2,4-oxadiazole 1.0 g of 4-bromo-N-hydroxybenzimidamide prepared in Step 1 was dissolved in 10.0 mL of dichloromethane, and to the resulting solution, 1.65 mL of triethylamine and 0.71 mL of cyclopropanecarbonyl chloride were added, and the solution was stirred at room temperature for 30 minutes. The reaction mixture was concentrated under reduced pressure and dissolved in toluene, and then re-concentrated to give a residue. The residue was dissolved in 10.0 mL of toluene, and the resulting solution was stirred at 110° C. for 18 hours. The reaction mixture thus obtained was cooled to room temperature and then concentrated under reduced pressure, and dichloromethane was added thereto, and the reaction mixture was washed with distilled water. The organic layer thus obtained was dried over anhydrous magnesium sulfate and concentrated under reduced pressure to give a yellow liquid residue. The residue was purified with silica gel column chromatography (developing solvent: n-hexane/ethyl acetate=2/1) to give 818.0 mg of the title compound as a yellow liquid (yield: 77.1%). MS (ESI) m/z=266.2 (M+H)+

Step 3: 5-cyclopropyl-3-(4-(4,4,5,5-tetramethyl-1,3,2-dioxaborolan-2-yl)phenyl)-1,2,4-oxadiazole 500.0 mg of 3-(4-bromophenyl)-5-cyclopropyl-1,2,4-oxadiazole prepared in Step 2, 1.13 g of bis(pinacolato)diboron, 650.0 mg of potassium acetate were dissolved in 10.0 mL of 1,4-dixoane, 161.0 mg of palladiumdi[1,1'-bis(diphenylphosphino)ferrocene]dichloride (PdCl$_2$(dppf)) and 61.0 mg of 1,1'-bis(diphenylphosphino)ferrocene] (dppf) were added thereto, and the resulting solution was stirred overnight at 95° C. The reaction mixture was concentrated, ethyl acetate was added thereto, and then the reaction mixture was washed with distilled water, dried over anhydrous magnesium sulfate, and concentrated under reduced pressure to obtain a yellow liquid residue. The residue was purified with silica gel column chromatography (developing solvent: n-hexane/ethyl acetate=1/1) to give 403.0 mg of the title compound as a white solid (yield: 58.1%). 41-NMR (CDCl$_3$, 400 MHz) δ 8.35 (d, 2H), 7.89 (d, 2H), 2.25 (m, 1H), 1.35 (m, 2H), 1.30 (m, 2H), 1.26 (s, 12H)

Reference Example 81. 5-cyclopropyl-3-(3-(4,4,5,5-tetramethyl-1,3,2-dioxaborolan-2-yl)phenyl)-1,2,4-oxadiazole 307.0 mg of the title compound as a yellow solid (yield: 44.3%) was prepared in the same fashion as Reference Example 80, except that 5.0 g of 3-bromobenzonitrile was used in Step 1 instead of 4-bromobenzonitrile. MS (ESI) m/z=313.2 (M+H)+

Reference Example 82. 5-isopropyl-3-(4-(4,4,5,5-tetramethyl-1,3,2-dioxaborolan-2-yl)phenyl)-1,2,4-oxadiazole 486.0 mg of the title compound as a white solid (yield: 69.7%) was prepared in the same fashion as Reference Example 80, except that 0.82 mL of isobutyryl chloride was used in Step 2 instead of cyclopropane carbonyl chloride. $^{1}$H-NMR (CDCl$_3$, 400 MHz) δ 8.09 (d, 2H), 7.91 (d, 2H), 3.29 (m, 1H), 1.46 (d, 6H), 1.26 (s, 12H)

Reference Example 83. 5-isopropyl-3-(3-(4,4,5,5-tetramethyl-1,3,2-dioxaborolan-2-yl)phenyl)-1,2,4-oxadiazole 325.0 mg of the title compound as a yellow solid (yield: 46.6%) was prepared in the same fashion as Reference Example 80, except that 5.0 g of 3-bromobenzonitrile was used in Step 1 instead of 4-bromobenzonitrile and 0.82 mL of isobutyryl chloride was used in Step 2 instead of cyclopropane carbonyl chloride. $^{1}$H-NMR (CDCl$_3$, 400 MHz) δ 8.52 (s, 1H), 8.16 (d, 1H), 7.92 (d, 1H), 7.49 (t, 1H), 3.29 (m, 1H), 1.46 (d, 6H), 1.26 (s, 12H)

Reference Example 84. tert-butyl (E)-(2-((4-(4'-bromo-[1,1'-biphenyl]-3-yl)-5-oxo-4,5-dihydro-1H-1,2,4-triazol-1-yl)methyl)-3-fluoroallyl)carbamate Step 1: 4-(3-(4,4,5,5-tetramethyl-1,3,2-dioxaborolan-2-yl)phenyl)-2,4-dihydro-3H-1,2,4-triazol-3-one 2.0 g of 4-(3-bromophenyl)-2,4-dihydro-3H-1,2,4-triazol-3-one prepared in Reference Example 4, 4.0 g of bis(pinacolato)diboron, 3.6 g of potassium acetate, and 303.0 mg of palladiumdi[1,1'-bis(diphenylphosphino)ferrocene]dichloride (PdCl$_2$(dppf)) were dissolved in 20.0 mL of 1,4-dioxane, and the resulting solution was stirred overnight at 95° C. The reaction mixture was concentrated, ethyl acetate was added thereto, and then the reaction mixture was washed with distilled water, dried over anhydrous magnesium sulfate, and concentrated under reduced pressure to obtain a yellow liquid residue. The residue was purified with silica gel column chromatography (developing solvent: n-hexane/ethyl acetate=1/1) to give 1.1 g of the title compound as a yellow liquid (yield: 46.0%). $^{1}$H-NMR (CDCl$_3$, 400 MHz) δ 10.6 (s, 1H), 7.84 (s, 1H), 7.81 (d, 1H), 7.75 (dd, 2H), 7.51 (t, 1H), 1.35 (s, 12H)

Step 2: 4-(4'-bromo-[1,1'-biphenyl]-3-yl)-2,4-dihydro-3H-1,2,4-triazol-3-one 230.0 mg of 4-(3-(4,4,5,5-tetramethyl-1,3,2-dioxaborolan-2-yl)phenyl)-2,4-dihydro-3H-1,2,4-triazol-3-one prepared in Step 1, 226.0 mg of 1-bromo-4-iodobenzene, and 20.0 mg of palladiumdi[1,1'-bis(diphenylphosphino)ferrocene]dichloride (PdCl$_2$(dppf)) were dissolved in 5.0 mL of 1,4-dioxane, and 4.0 mL of 1M aqueous solution of potassium carbonate was added thereto, and the resulting solution was stirred at 100° C. for 3.5 hours. The reaction mixture was concentrated, ethyl acetate was added thereto, and then the reaction mixture was washed with distilled water, dried over anhydrous magnesium sulfate, and concentrated under reduced pressure to obtain a yellow liquid residue. The residue was purified with silica gel column chromatography (developing solvent: n-hexane/ethyl acetate=2/1) to give 90.0 mg of the title compound as a brown solid (yield: 35.0%). MS (ESI) m/z=318.0 (M+H)+

Step 3: tert-butyl (E)-(2-((4-(4'-bromo-[1,1'-biphenyl]-3-yl)-5-oxo-4,5-dihydro-1H-1,2,4-triazol-1-yl)methyl)-3-fluoroallyl)carbamate 90.0 mg of 4-(4'-bromo-[1,1'-biphenyl]-3-yl)-2,4-dihydro-3H-1,2,4-triazol-3-one prepared in Step 2 and 77.0 mg of potassium carbonate were dissolved in 1.0 mL of N,N-dimethylformamide, 101.0 mg of tert-butyl (E)-(2-(chloromethyl)-3-fluoroallyl)carbamate prepared in Reference Example 2 was added thereto, and then the resulting solution was stirred at 80° C. for 3 hours. The reaction mixture was concentrated, ethyl acetate was added thereto, and then the reaction mixture was washed with distilled water, dried over anhydrous magnesium sulfate, and concentrated under reduced pressure to obtain a yellow liquid residue. The residue was purified with silica gel column chromatography (developing solvent: n-hexane/ethyl acetate=2/1) to give 108.0 mg of the title compound as a white solid (yield: 77.0%). $^{1}$H-NMR (CDCl$_3$, 400 MHz) δ 7.76 (d, 2H), 7.55-7.59 (m, 4H), 7.46-7.50 (m, 3H), 6.77 (d, 1H), 5.25 (m, 4H), 4.41 (s, 2H), 3.90 (bs, 2H), 1.41 (s, 9H)

Reference Example 85. tert-butyl (E)-(2-((4-(3'-bromo-[1,1'-biphenyl]-3-yl)-5-oxo-4,5-dihydro-1H-1,2,4-triazol-1-yl)methyl)-3-fluoroallyl)carbamate 151.0 mg of the title compound as a white solid (yield: 73.7%) was prepared in the same fashion as Reference Example 84, except that 132.0 uL of 1-bromo-3-iodobenzene was used in Step 2 instead of 1-bromo-4-iodobenzene. $^{1}$H-NMR (CDCl$_3$, 400 MHz) δ 7.76 (s, 1H), 7.75 (d, 2H), 7.51-7.56 (m, 5H), 7.33 (t, 1H), 6.77 (d, 1H), 5.25 (bs, 1H), 4.41 (s, 2H), 3.91 (bs, 2H), 1.42 (s, 9H)

Reference Example 86. 5-(4,4,5,5-tetramethyl-1,3,2-dioxaborolan-2-yl)benzo[d]thiazol-2-amine 4.0 g of 2-amino-5-bromobenzothiazole, 5.7 g of bis(pinacolato)diboron, and 5.1 g of potassium acetate were dissolved in 40.0 mL of 1,4-dioxane, and 426.0 mg of palladiumdi[1,1'-bis(diphenylphosphino)ferrocene]dichloride (PdCl$_2$(dppf)) was added thereto, and the resulting solution was stirred overnight at 95° C. The reaction mixture was concentrated, ethyl acetate was added thereto, and then the reaction mixture was washed with distilled water, dried over anhydrous magnesium sulfate, and concentrated under reduced pressure to obtain a yellow liquid residue. The residue was purified with silica gel column chromatography (developing solvent: n-hexane/ethyl acetate=2/1) to give 1.9 g of the title compound as a yellow solid (yield: 39.4%). $^{1}$H-NMR (CDCl$_3$, 400 MHz) δ 7.97 (s, 1H), 7.58 (dd, 2H), 5.39 (bs, 2H), 1.36 (s, 12H)

Reference Example 87. N-(5-(4,4,5,5-tetramethyl-1,3,2-dioxaborolan-2-yl)benzo[d]thiazol-2-yl)acetamide Step 1: N-(5-bromobenzo[d]thiazol-2-yl)acetamide 2.0 g of 2-amino-5-bromobenzothiazole was dissolved in 20.0 mL of pyridine, 688 uL of acetyl chloride was added thereto, and the resulting solution was stirred overnight at room temperature. The reaction mixture thus obtained was concentrated, and then ethyl acetate and 1N aqueous solution of hydrogen chloride were added thereto, and the resulting solution was stirred for about 30 minutes. The solid thus obtained was filtered under reduced pressure while it was washed with ethyl acetate, to give 1.18 g of the title compound as a white solid (yield: 49.8%). $^{1}$H-NMR (CDCl$_3$, 400 MHz) δ 9.71 (bs, 1H0, 7.91 (s, 1H), 7.68 (d, 1H), 7.43 (d, 1H), 2.32 (s, 3H)

Step 2: N-(5-(4,4,5,5-tetramethyl-1,3,2-dioxaborolan-2-yl)benzo[d]thiazol-2-yl)acetamide 500.0 mg of N-(5-bromobenzo[d]thiazol-2-yl)acetamide prepared in Step 1, 607.0 mg of bis(pinacolato)diboron, 542.0 mg of potassium acetate, and 45.0 mg of palladiumdi[1,1'-bis(diphenylphosphino)ferrocene]dichloride (PdCl$_2$(dppf)) were dissolved in 5.0 mL of 1,4-dioxane, and the resulting solution was stirred overnight at 95° C. The resulting mixture was concentrated, ethyl acetate was added thereto, and the reaction mixture was washed with distilled water, dried over anhydrous magnesium sulfate, and concentrated under reduced pressure to give a yellow liquid residue. The residue was purified with silica gel column chromatography (developing solvent: n-hexane/ethyl acetate=1/1) to give 492.0 mg of the title compound as a orange solid (yield: 84.0%). $^1$H-NMR (CDCl$_3$, 400 MHz) δ 10.9 (bs, 1H), 8.22 (s, 1H), 7.84 (d, 1H), 7.74 (d, 1H), 2.32 (s, 3H), 1.36 (s, 12H)

Reference Example 88. 5-(3-(4,4,5,5-tetramethyl-1,3,2-dioxaborolan-2-yl)phenyl)-1-((2-(trimethylsilyl)ethoxy)methyl)-1H-tetrazole

Step 1: 5-(3-bromophenyl)-1H-tetrazole 2.00 g of 3-bromobenzonitrile was dissolved in 10.0 mL of dimethylsufoxide and sodium azide and copper sulfate were added thereto, and the resulting solution was stirred at 120° C. for 6 hours. The reaction mixture was cooled to room temperature and 1N aqueous solution of hydrogen chloride was added thereto, and the resulting reaction mixture was washed with water. The reaction mixture was extracted with ethyl acetate, and the resulting extract was dried over anhydrous magnesium sulfate and concentrated under reduced pressure to give 0.97 g of the title compound as a dark yellow liquid (yield: 39.1%).

Step 2: 5-(3-bromophenyl)-1((2-(trimethylsilyl)ethoxy)methyl)-1H-tetrazole 0.97 g of 5-(3-bromophenyl)-1H-tetrazole prepared in Step 1 is dissolved in 3.0 mL of N,N-dimethylforamide, the resulting reaction mixture was cooled to 0° C., and then 0.21 g of sodium hydride was added thereto, and the reaction mixture was stirred for 30 minutes. To the reaction mixture, 1.67 g of (2-(chloromethoxy)ethyl)trimethylsilane was added, and the reaction mixture was stirred at 0° C. for 15 minutes and then additionally stirred at room temperature for 2 hours. To the reaction mixture, distilled water was added, and the reaction mixture was extracted with dichloromethane, and the extract thus obtained was dried over anhydrous magnesium sulfate and concentrated under reduced pressure to obtain a yellow liquid residue. The residue was purified with silica gel column chromatography (developing solvent: n-hexane/ethyl acetate=2/1) to give 0.87 g of the title compound as a yellow solid (yield: 57.6%).

Step 3: 5-(3-(4,4,5,5-tetramethyl-1,3,2-dioxaborolan-2-yl)phenyl)-1-((2-(trimethylsilyl)ethoxy)methyl)-1H-tetrazole 500.0 mg of 5-(3-bromophenyl)-1-((2-(trimethylsilyl)ethoxy)methyl)-1H-tetrazole prepared in Step 2, 710.0 mg of bis(pinacolato)diboron, and 410.0 mg of potassium acetate were dissolved in 10.0 mL of 1,4-dioxane. To the resulting solution, 103.0 mg of palladiumdi[1,1'-bis(diphenylphosphino)ferrocene]dichloride (PdCl$_2$(dppf)) and 80.0 mg of 1,1'-bis(diphenylphosphino)ferrocene] (dppf) were added, and the solution was stirred overnight at 95° C. The reaction mixture thus obtained was concentrated, ethyl acetate was added thereto, and then the reaction mixture was washed with distilled water, dried over anhydrous magnesium sulfate, and concentrated under reduced pressure to obtain a yellow liquid residue. The residue was purified with silica gel column chromatography (developing solvent: n-hexane/ethyl acetate=1/1) to give 333.0 mg of the title compound as a yellow solid (yield: 57.1%). $^1$H-NMR (CDCl$_3$, 400 MHz) δ 8.36 (s, 1H), 8.30 (d, 1H), 7.62 (d, 1H), 7.38 (t, 1H), 5.93 (s, 2H), 3.75 (t, 2H), 0.98 (t, 2H), 0.00 (s, 9H)

Example 1. 2-[(2Z)-2-(aminomethyl)-3-fluoroprop-2-en-1-yl]-4-(4-bromophenyl)-2,4-dihydro-3H-1,2,4-triazol-3-one 17.0 mg of tert-butyl (Z)-(2-((4-(4-bromophenyl)-5-oxo-4,5-dihydro-1H-1,2,4-triazol-1-yl)methyl)-3-fluoroallyl)carbamate prepared in Reference Example 33 was dissolved in 0.9 mL of dichloromethane. 0.2 mL of trifluoroacetic acid was added to the solution, and the solution was stirred at room temperature for 4 hours. The residue obtained by concentration under reduced pressure was dissolved in dichloromethane, and the solution was washed with an aqueous solution of sodium bicarbonate and brine, dried over anhydrous magnesium sulfate, and then concentrated under reduced pressure to give a yellow liquid residue. The residue was purified with silica gel column chromatography (developing solvent: dichloromethane/methanol=10/1) to give 5.6 mg of the title compound as a yellow liquid (yield: 43.0%). $^1$H NMR (MeOD, 400 MHz) δ 8.27 (s, 1H), 7.68 (d, 2H), 7.60 (d, 2H), 7.10 (d, 1H), 4.70 (s, 2H), 3.61 (s, 2H)

Example 2. 2-[(2E)-2-(aminomethyl)-3-fluoroprop-2-en-1-yl]-4-(4-bromophenyl)-2,4-dihydro-3H-1,2,4-triazol-3-one 8.6 mg of the title compound (yield: 59.1%) was prepared in the same fashion as Example 1, except that 19.0 mg of tert-butyl (E)-(2-((4-(4-bromophenyl)-5-oxo-4,5-dihydro-1H-1,2,4-triazol-1-yl)methyl)-3-fluoroallyl)carbamate prepared in Reference Example 34 was used instead of tert-butyl (Z)-(2-((4-(4-bromophenyl)-5-oxo-4,5-dihydro-1H-1,2,4-triazol-1-yl)methyl)-3-fluoroallyl)carbamate. $^1$H-NMR (DMSO-d$_6$, 400 MHz) δ 8.58 (s, 1H), 7.73 (m, 2H), 7.21 (d, 1H), 4.49 (s, 2H), 3.54 (s, 2H)

Example 3. 2-[(2Z)-2-(aminomethyl)-3-fluoroprop-2-en-1-yl]-4-(3-bromophenyl)-2,4-dihydro-3H-1,2,4-triazol-3-one hydrochloride 22.0 mg of tert-butyl (Z)-(2-((4-(3-bromophenyl)-5-oxo-4,5-dihydro-1H-1,2,4-triazol-1-yl)methyl)-3-fluoroallyl)carbamate prepared in Reference Example 49 was dissolved in 0.9 mL of dichloromethane, and 0.2 mL of 4M hydrogen chloride solution in dioxane was added thereto, and the resulting solution was stirred overnight at room temperature. The reaction mixture was concentrated, and the residue thus obtained was washed with ethyl acetate and concentrated under reduced pressure to give 10.3 mg of the yellow title compound (yield: 55.0%). $^1$H-NMR (DMSO-d$_6$, 400 MHz) δ 8.62 (s, 1H), 8.02 (d, 1H), 7.77 (d, 1H), 7.60 (t, 1H), 7.50 (t, 1H), 7.20 (d, 1H), 4.61 (s, 2H), 3.47 (s, 2H)

Example 4. 2-[(2E)-2-(aminomethyl)-3-fluoroprop-2-en-1-yl]-4-(3-bromophenyl)-2,4-dihydro-3H-1,2,4-triazol-3-one hydrochloride 18.0 mg of the title compound (yield: 78.3%) was prepared in the same fashion as Example 3, except that 27.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(3-bromophenyl)-5-oxo-4,5-dihydro-1H-1,2,4-triazol-1-yl)methyl)-3-fluoroallyl)carbamate.
$^1$H-NMR (MeOD, 400 MHz) δ 8.31 (s, 1H), 7.96 (s, 1H), 7.64 (dd, 1H), 7.58 (d, 1H), 7.45 (t, 1H), 7.18 (d, 1H), 4.53 (d, 2H), 3.73 (d, 2H)

Example 5. 2-[(2Z)-2-(aminomethyl)-3-fluoroprop-2-en-1-yl]-4-(4-fluorophenyl)-2,4-dihydro-3H-1,2,4-triazol-3-one 14.6 mg of the title compound (yield: 73.8%) was prepared in the same fashion as Example 1, except that 25.0 mg of tert-butyl (Z)-(3-fluoro-2-((4-(4-fluorophenyl)-5-oxo-4,5-dihydro-1H-1,2,4-triazol-1-yl)methyl)allyl)carbamate prepared in Reference Example 51 was used instead of tert-butyl (Z)-(2-((4-(4-bromophenyl)-5-oxo-4,5-dihydro-1H-1,2,4-triazol-1-yl)methyl)-3-fluoroallyl)carbamate.
$^1$H-NMR (DMSO-d$_6$, 400 MHz) δ 8.53 (s, 1H), 7.72-7.75 (m, 2H), 7.40 (t, 2H), 7.18 (d, 1H), 4.60 (s, 2H), 3.48 (s, 2H)

Example 6. 2-[(2E)-2-(aminomethyl)-3-fluoroprop-2-en-1-yl]-4-(4-fluorophenyl)-2,4-dihydro-3H-1,2,4-triazol-3-one hydrochloride 0.9 mg of the title compound (yield: 9.1%) was prepared in the same fashion as Example 3, except that 12.0 mg of tert-butyl (E)-(3-fluoro-2-((4-(4-fluorophenyl)-5-oxo-4,5-dihydro-1H-1,2,4-triazol-1-yl)methyl)allyl)carbamate prepared in Reference Example 52 was used instead of tert-butyl (Z)-(2-((4-(3-bromophenyl)-5-oxo-4,5-dihydro-1H-1,2,4-triazol-1-yl)methyl)-3-fluoroallyl)carbamate $^1$H-NMR (MeOD, 400 MHz) δ 8.22 (s, 1H), 7.63-7.67 (m, 2H), 7.28 (t, 2H), 7.16 (d, 1H), 4.53 (s, 2H), 3.73 (s, 2H)

Example 7. 2-[(2Z)-2-(aminomethyl)-3-fluoroprop-2-en-1-yl]-4-[4-(benzyloxy)phenyl]-2,4-dihydro-3H-1,2,4-triazol-3-one 20.0 mg of the title compound (yield: 65.6%) was prepared in the same fashion as Example 1, except that 37.0 mg of tert-butyl (Z)-(2-((4-(4-(benzyloxy)phenyl)-5-oxo-4,5-dihydro-1H-1,2,4-triazol-1-yl)methyl)-3-fluoroallyl)carbamate prepared in Reference Example 53 was used instead of tert-butyl (Z)-(2-((4-(4-bromophenyl)-5-oxo-4,5-dihydro-1H-1,2,4-triazol-1-yl)methyl)-3-fluoroallyl)carbamate.
$^1$H-NMR (DMSO-d$_6$, 400 MHz) δ 8.44 (s, 1H), 7.56 (d, 2H), 7.46 (d, 2H), 7.41 (t, 2H), 7.35 (t, 1H), 7.17 (d, 1H), 7.15 (d, 2H), 5.17 (s, 2H), 4.59 (s, 2H), 3.48 (s, 2H)

Example 8. 2-[(2E)-2-(aminomethyl)-3-fluoroprop-2-en-1-yl]-4-[4-(benzyloxy)phenyl]-2,4-dihydro-3H-1,2,4-triazol-3-one hydrochloride 6.4 mg of the title compound (yield: 41.3%) was prepared in the same fashion as Example 3, except that 18.0 mg of tert-butyl (E)-(2-((4-(4-(benzyloxy)phenyl)-5-oxo-4,5-dihydro-1H-1,2,4-triazol-1-yl)methyl)-3-fluoroallyl)carbamate prepared in Reference Example 54 was used instead of tert-butyl (Z)-(2-((4-(3-bromophenyl)-5-oxo-4,5-dihydro-1H-1,2,4-triazol-1-yl)methyl)-3-fluoroallyl)carbamate.
$^1$H-NMR (DMSO-d$_6$, 400 MHz) δ 8.44 (s, 1H), 7.56 (d, 2H), 7.45 (t, 2H), 7.40 (t, 2H), 7.34 (d, 1H), 7.20 (d, 1H), 7.15 (d, 2H), 5.16 (s, 2H), 4.49 (s, 2H), 3.53 (s, 2H)

Example 9. 2-[(2Z)-2-(aminomethyl)-3-fluoroprop-2-en-1-yl]-4-(3,4-difluorophenyl)-2,4-dihydro-3H-1,2,4-triazol-3-one 11.7 mg of the title compound (yield: 58.6%) was prepared in the same fashion as Example 1, except that 25.0 mg of tert-butyl (Z)-(2-((4-(3,4-difluorophenyl)-5-oxo-4,5-dihydro-1H-1,2,4-triazol-1-yl)methyl)-3-fluoroallyl)carbamate prepared in Reference Example 55 was used instead of tert-butyl (Z)-(2-((4-(4-bromophenyl)-5-oxo-4,5-dihydro-1H-1,2,4-triazol-1-yl)methyl)-3-fluoroallyl)carbamate.
(DMSO-d$_6$, 400 MHz) δ 8.58 (s, 1H), 7.89-7.94 (m, 1H), 7.61-7.69 (m, 2H), 7.18 (d, 1H), 4.60 (s, 2H), 3.48 (s, 2H)

Example 10. 2-[(2E)-2-(aminomethyl)-3-fluoroprop-2-en-1-yl]-4-(3,4-difluorophenyl)-2,4-dihydro-3H-1,2,4-triazol-3-one hydrochloride 11.8 mg of the title compound (yield: 52.4%) was prepared in the same fashion as Example 3, except that 27.0 mg of tert-butyl (E)-(2-((4-(3,4-difluorophenyl)-5-oxo-4,5-dihydro-1H-1,2,4-triazol-1-yl)methyl)-3-fluoroallyl)carbamate prepared in Reference Example 56 was used instead of tert-butyl (Z)-(2-((4-(3-bromophenyl)-5-oxo-4,5-dihydro-1H-1,2,4-triazol-1-yl)methyl)-3-fluoroallyl)carbamate.
(DMSO-d$_6$, 400 MHz) δ 8.58 (s, 1H), 7.89-7.94 (m, 1H), 7.63-7.67 (m, 2H), 7.20 (d, 1H), 4.51 (s, 2H), 3.51 (s, 2H)

Example 11. 2-[(2Z)-2-(aminomethyl)-3-fluoroprop-2-en-1-yl]-4-(4-bromo-2-fluorophenyl)-2,4-dihydro-3H-1,2,4-triazol-3-one hydrochloride 15.7 mg of the title compound (yield: 52.4%) was prepared in the same fashion as Example 3, except that 31.0 mg of tert-butyl (Z)-(2-((4-(4-bromo-2-fluorophenyl)-5-oxo-4,5-dihydro-1H-1,2,4-triazol-1-yl)methyl)-3-fluoroallyl)carbamate prepared in Reference Example 35 was used instead of tert-butyl (Z)-(2-((4-(3-bromophenyl)-5-oxo-4,5-dihydro-1H-1,2,4-triazol-1-yl)methyl)-3-fluoroallyl)carbamate.
$^1$H-NMR (DMSO-d$_6$, 400 MHz) δ 8.34 (s, 1H), 7.89 (d, 1H), 7.63 (d, 2H), 7.20 (d, 1H), 4.61 (s, 2H), 3.47 (s, 2H)

Example 12. 2-[(2E)-2-(aminomethyl)-3-fluoroprop-2-en-1-yl]-4-(4-bromo-2-fluorophenyl)-2,4-dihydro-3H-1,2,4-triazol-3-one hydrochloride 12.0 mg of the title compound (yield: 70.0%) was prepared in the same fashion as Example 3, except that 20.0 mg of tert-butyl (E)-(2-((4-(4-bromo-2-fluorophenyl)-5-oxo-4,5-dihydro-1H-1,2,4-triazol-1-yl)methyl)-3-fluoroallyl)carbamate prepared in Reference Example 36 was used instead of tert-butyl (Z)-(2-((4-(3-bromophenyl)-5-oxo-4,5-dihydro-1H-1,2,4-triazol-1-yl)methyl)-3-fluoroallyl)carbamate.
$^1$H-NMR (MeOD, 400 MHz) δ 8.11 (s, 1H), 7.66 (d, 1H), 7.53-7.60 (m, 2H), 7.18 (d, 1H), 4.53 (d, 2H), 3.73 (d, 2H)

Example 13. 2-[(2Z)-2-(aminomethyl)-3-fluoroprop-2-en-1-yl]-4-(4-bromo-3-fluorophenyl)-2,4-dihydro-3H-1,2,4-triazol-3-one 17.2 mg of the title compound (yield: 69.8%) was prepared in the same fashion as Example 1, except that 30.0 mg of tert-butyl (Z)-(2-((4-(4-bromo-3-fluoroallyl)-5-oxo-4,5-dihydro-1H-1,2,4-triazol-1-yl)methyl)-3-fluoroallyl)carbamate prepared in Reference Example 37 was used instead of tert-butyl (Z)-(2-((4-(4-bromophenyl)-5-oxo-4,5-dihydro-1H-1,2,4-triazol-1-yl)methyl)-3-fluoroallyl)carbamate. $^1$H-NMR (DMSO-$d_6$, 400 MHz) δ 8.65 (s, 1H), 7.87-7.93 (m, 2H), 7.64 (m, 1H), 7.18 (d, 1H), 4.60 (s, 2H), 3.48 (s, 2H)

Example 14. 2-[(2E)-2-(aminomethyl)-3-fluoroprop-2-en-1-yl]-4-(4-bromo-3-fluorophenyl)-2,4-dihydro-3H-1,2,4-triazol-3-one hydrochloride 18.0 mg of the title compound (yield: 80.0%) was prepared in the same fashion as Example 3, except that 26.0 mg of tert-butyl (E)-(2-((4-(4-bromo-3-fluoroallyl)-5-oxo-4,5-dihydro-1H-1,2,4-triazol-1-yl)methyl)-3-fluorophenyl)carbamate prepared in Reference Example 38 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (MeOD, 400 MHz) δ 8.34 (s, 1H), 7.72-7.80 (m, 2H), 7.48 (dd, 1H), 7.18 (d, 1H), 4.53 (d, 2H), 3.73 (d, 2H)

Example 15. 2-[(2Z)-2-(aminomethyl)-3-fluoroprop-2-en-1-yl]-4-(4-bromo-3-methylphenyl)-2,4-dihydro-3H-1,2,4-triazol-3-one 18.0 mg of the title compound (yield: 73.2%) was prepared in the same fashion as Example 1, except that 30.0 mg of tert-butyl (Z)-(2-((4-(4-bromo-3-methylphenyl)-5-oxo-4,5-dihydro-1H-1,2,4-triazol-1-yl)methyl)-3-fluoroallyl)carbamate prepared in Reference Example 39 was used instead of tert-butyl (Z)-(2-((4-(4-bromophenyl)-5-oxo-4,5-dihydro-1H-1,2,4-triazol-1-yl)methyl)-3-fluoroallyl)carbamate. $^1$H-NMR (DMSO-$d_6$, 400 MHz) δ 8.55 (s, 1H), 7.74 (t, 2H), 7.53 (m, 1H), 7.18 (d, 1H), 4.59 (s, 2H), 3.48 (s, 2H), 2.40 (s, 3H)

Example 16. 2-[(2E)-2-(aminomethyl)-3-fluoroprop-2-en-1-yl]-4-(4-bromo-3-methylphenyl)-2,4-dihydro-3H-1,2,4-triazol-3-one hydrochloride 12.0 mg of the title compound (yield: 53.9%) was prepared in the same fashion as Example 3, except that 26.0 mg of tert-butyl (E)-(2-((4-(4-bromo-3-methylphenyl)-5-oxo-4,5-dihydro-1H-1,2,4-triazol-1-yl)methyl)-3-fluoroallyl)carbamate prepared in Reference Example 40 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (MeOD, 400 MHz) δ 8.26 (s, 1H), 7.68 (d, 1H), 7.62 (s, 1H), 7.40 (dd, 1H), 7.18 (d, 1H), 4.53 (d, 2H), 3.73 (d, 2H), 2.45 (s, 3H)

Example 17. 2-[(2Z)-2-(aminomethyl)-3-fluoroprop-2-en-1-yl]-4-(4-bromo-3-methoxyphenyl)-2,4-dihydro-3H-1,2,4-triazol-3-one 14.8 mg of the title compound (yield: 59.8%) was prepared in the same fashion as Example 1, except that 30.0 mg of tert-butyl (Z)-(2-((4-(4-bromo-3-methoxyphenyl)-5-oxo-4,5-dihydro-1H-1,2,4-triazol-1-yl)methyl)-3-fluoroallyl)carbamate prepared in Reference Example 41 was used instead of tert-butyl (Z)-(2-((4-(4-bromophenyl)-5-oxo-4,5-dihydro-1H-1,2,4-triazol-1-yl)methyl)-3-fluoroallyl)carbamate. $^1$H-NMR (DMSO-$d_6$, 400 MHz) δ 8.63 (s, 1H), 7.74 (d, 1H), 7.48 (d, 1H), 7.31 (m, 1H), 7.18 (d, 1H), 4.60 (s, 2H), 3.90 (s, 3H) 3.49 (s, 2H)

Example 18. 2-[(2E)-2-(aminomethyl)-3-fluoroprop-2-en-1-yl]-4-(4-bromo-3-methoxyphenyl)-2,4-dihydro-3H-1,2,4-triazol-3-one hydrochloride 13.0 mg of the title compound (yield: 75.5%) was prepared in the same fashion as Example 3, except that 20.0 mg of tert-butyl (E)-(2-((4-(4-bromo-3-methoxyphenyl)-5-oxo-4,5-dihydro-1H-1,2,4-triazol-1-yl)methyl)-3-fluoroallyl) carbamate prepared in Reference Example 42 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (MeOD, 400 MHz) δ 8.32 (s, 1H), 7.65 (d, 1H), 7.40 (d, 1H), 7.18 (d, 1H), 7.15 (dd, 1H), 4.54 (s, 2H), 3.94 (s, 3H), 3.75 (s, 2H)

Example 19. 2-[(2Z)-2-(aminomethyl)-3-fluoroprop-2-en-1-yl]-4-(4-bromo-3,5-difluorophenyl)-2,4-dihydro-3H-1,2,4-triazol-3-one 14.6 mg of the title compound (yield: 58.9%) was prepared in the same fashion as Example 1, except that 30.0 mg of tert-butyl (Z)-(2-((4-(4-bromo-3,5-difluorophenyl)-5-oxo-4,5-dihydro-1H-1,2,4-triazol-1-yl)methyl)-3-fluoroallyl)carbamate prepared in Reference Example 43 was used instead of tert-butyl (Z)-(2-((4-(4-bromophenyl)-5-oxo-4,5-dihydro-1H-1,2,4-triazol-1-yl)methyl)-3-fluoroallyl)carbamate. $^1$H-NMR (DMSO-$d_6$, 400 MHz) δ 8.69 (s, 1H), 7.85 (d, 2H), 7.18 (d, 1H), 4.60 (s, 2H), 3.48 (s, 2H)

Example 20. 2-[(2E)-2-(aminomethyl)-3-fluoroprop-2-en-1-yl]-4-(4-bromo-3,5-difluorophenyl)-2,4-dihydro-3H-1,2,4-triazol-3-one hydrochloride 14.0 mg of the title compound (yield: 67.6%) was prepared in the same fashion as Example 3, except that 24.0 mg of tert-butyl (E)-(2-((4-(4-bromo-3,5-difluorophenyl)-5-oxo-4,5-dihydro-1H-1,2,4-triazol-1-yl)methyl)-3-fluoroallyl)carbamate prepared in Reference Example 44 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (MeOD, 400 MHz) δ 8.39 (s, 1H), 7.64 (dd, 2H), 7.18 (d, 1H), 4.53 (d, 2H), 3.73 (d, 2H)

Example 21. 2-[(2Z)-2-(aminomethyl)-3-fluoroprop-2-en-1-yl]-4-(4-bromo-2,6-difluorophenyl)-2,4-dihydro-3H-1,2,4-triazol-3-one hydrochloride 1.3 mg of the title compound (yield: 16.7%) was prepared in the same fashion as Example 3, except that 9.0 mg of tert-butyl (Z)-(2-((4-(4-bromo-2,6-difluorophenyl)-5-oxo-4,5-dihydro-1H-1,2,4-triazol-1-yl)methyl)-3-fluoroallyl)carbamate prepared in Reference Example 45 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (DMSO-$d_6$, 400 MHz) δ 8.35 (s, 1H), 7.85 (d, 2H), 7.19 (d, 1H), 4.61 (s, 2H), 3.46 (s, 2H)

Example 22. 2-[(2E)-2-(aminomethyl)-3-fluoroprop-2-en-1-yl]-4-(4-bromo-2,6-difluorophenyl)-2,4-dihydro-3H-1,2,4-triazol-3-one hydrochloride 7.0 mg of the title compound (yield: 58.0%) was prepared in the same fashion as Example 3, except that 14.0 mg of tert-butyl (E)-(2-((4-(4-bromo-2,6-difluorophenyl)-5-oxo-4, 5-dihydro-1H-1,2,4-triazol-1-yl)methyl)-3-fluoroallyl)carbamate prepared in Reference Example 46 was used instead of tert-butyl (Z)-(2-((4-(3-bromophenyl)-5-oxo-4,5-dihydro-1H-1,2,4-triazol-1-yl)methyl)-3-fluoroallyl)carbamate. ¹H-NMR (MeOD, 400 MHz) δ 8.10 (s, 1H), 7.55-7.59 (m, 2H), 7.18 (d, 1H), 4.55 (d, 2H), 3.72 (d, 2H)

Example 23. 2-[(2E)-2-(aminomethyl)-3-fluoroprop-2-en-1-yl]-4-(4-bromo-2,5-difluorophenyl)-2,4-dihydro-3H-1,2,4-triazol-3-one hydrochloride 5.0 mg of the title compound (yield: 48.3%) was prepared in the same fashion as Example 3, except that 12.0 mg of tert-butyl (E)-(2-((4-(4-bromo-2,5-difluorophenyl)-5-oxo-4,5-dihydro-1H-1,2,4-triazol-1-yl)methyl)-3-fluoroallyl)carbamate prepared in Reference Example 47 was used instead of tert-butyl (Z)-(2-((4-(3-bromophenyl)-5-oxo-4,5-dihydro-1H-1,2,4-triazol-1-yl)methyl)-3-fluoroallyl)carbamate. ¹H-NMR (MeOD, 400 MHz) δ 8.23 (s, 1H), 7.79 (dd, 1H), 7.69 (dd, 1H), 7.09 (d, 1H), 4.54 (d, 2H), 4.12 (d, 2H)

Example 24. 2-[(2Z)-2-(aminomethyl)-3-fluoroprop-2-en-1-yl]-4-(6-bromopyridin-3-yl)-2,4-dihydro-3H-1,2,4-triazol-3-one 14.8 mg of the title compound (yield: 60.5%) was prepared in the same fashion as Example 1, except that 30.0 mg of tert-butyl (Z)-(2-((4-(6-bromopyridin-3-yl)-5-oxo-4,5-dihydro-1H-1,2,4-triazol-1-yl)methyl)-3-fluoroallyl)carbamate prepared in Reference Example 58 was used instead of tert-butyl (Z)-(2-((4-(4-bromophenyl)-5-oxo-4,5-dihydro-1H-1,2,4-triazol-1-yl)methyl)-3-fluoroallyl)carbamate. ¹H-NMR (DMSO-d₆, 400 MHz) δ 8.80 (s, 1H), 8.64 (s, 1H), 8.15 (d, 1H), 7.87 (d, 1H), 7.18 (d, 1H), 4.60 (s, 2H), 3.48 (s, 2H)

Example 25. 2-[(2E)-2-(aminomethyl)-3-fluoroprop-2-en-1-yl]-4-(6-bromopyridin-3-yl)-2,4-dihydro-3H-1,2,4-triazol-3-one hydrochloride 10.0 mg of the title compound (yield: 53.4%) was prepared in the same fashion as Example 3, except that 20.0 mg of tert-butyl (E)-(2-((4-(6-bromopyridin-3-yl)-5-oxo-4,5-dihydro-1H-1,2,4-triazol-1-yl)methyl)-3-fluoroallyl)carbamate prepared in Reference Example 59 was used instead of tert-butyl (Z)-(2-((4-(3-bromophenyl)-5-oxo-4,5-dihydro-1H-1,2,4-triazol-1-yl)methyl)-3-fluoroallyl)carbamate. ¹H-NMR (MeOD, 400 MHz) δ 8.73 (d, 1H), 8.36 (s, 1H), 8.06 (dd, 1H), 7.76 (d, 1H), 7.19 (d, 1H), 4.54 (d, 2H), 3.74 (s, 2H)

Example 26. 2-[(2Z)-2-(aminomethyl)-3-fluoroprop-2-en-1-yl]-4-(6-bromo-5-methylpyridin-3-yl)-2,4-dihydro-3H-1,2,4-triazol-3-one hydrochloride 4.4 mg of the title compound (yield: 36.7%) was prepared in the same fashion as Example 3, except that 14.0 mg of tert-butyl (Z)-(2-((4-(6-bromo-5-methylpyridin-3-yl)-5-oxo-4,5-dihydro-1H-1,2,4-triazol-1-yl)methyl)-3-fluoroallyl)carbamate prepared in Reference Example 60 was used instead of tert-butyl (Z)-(2-((4-(3-bromophenyl)-5-oxo-4,5-dihydro-1H-1,2,4-triazol-1-yl)methyl)-3-fluoroallyl)carbamate. ¹H-NMR (DMSO-d₆, 400 MHz) δ 8.65 (d, 1H), 8.61 (d, 1H), 8.21 (s, 1H), 7.20 (d, 1H), 4.61 (s, 2H), 3.47 (s, 2H) 2.40 (s, 3H)

Example 27. 2-[(2E)-2-(aminomethyl)-3-fluoroprop-2-en-1-yl]-4-(6-bromo-5-methylpyridin-3-yl)-2,4-dihydro-3H-1,2,4-triazol-3-one hydrochloride 11.0 mg of the title compound (yield: 83.7%) was prepared in the same fashion as Example 3, except that 14.0 mg of tert-butyl (E)-(2-((4-(6-bromo-5-methylpyridin-3-yl)-5-oxo-4,5-dihydro-1H-1,2,4-triazol-1-yl)methyl)-3-fluoroallyl)carbamate prepared in Reference Example 61 was used instead of tert-butyl (Z)-(2-((4-(3-bromophenyl)-5-oxo-4,5-dihydro-1H-1,2,4-triazol-1-yl)methyl)-3-fluoroallyl)carbamate. ¹H-NMR (MeOD, 400 MHz) δ 8.58 (d, 1H), 8.36 (s, 1H), 8.07 (d, 1H), 7.19 (d, 1H), 4.54 (d, 2H), 3.75 (s, 2H), 2.46 (s, 3H)

Example 28. 2-[(2E)-2-(aminomethyl)-3-fluoroprop-2-en-1-yl]-4-(6-bromo-4-methylpyridin-3-yl)-2,4-dihydro-3H-1,2,4-triazol-3-one hydrochloride 11.8 mg of the title compound (yield: 68.9%) was prepared in the same fashion as Example 3, except that 20.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used instead of tert-butyl (Z)-(2-((4-(3-bromophenyl)-5-oxo-4,5-dihydro-1H-1,2,4-triazol-1-yl)methyl)-3-fluoroallyl)carbamate. ¹H-NMR (MeOD, 400 MHz) δ 8.31 (m, 1H), 8.04 (s, 1H), 7.68 (s, 1H), 7.53 (s, 1H), 7.05-7.25 (m, 1H), 4.51 (s, 2H), 3.71 (s, 2H), 2.27 (s, 3H)

Example 29. 2-[(2Z)-2-(aminomethyl)-3-fluoroprop-2-en-1-yl]-4-(5-bromopyridin-2-yl)-2,4-dihydro-3H-1,2,4-triazol-3-one hydrochloride 6.6 mg of the title compound (yield: 59.6%) was prepared in the same fashion as Example 3, except that 13.0 mg of tert-butyl (Z)-(2-((4-(5-bromopyridin-2-yl)-5-oxo-4,5-dihydro-1H-1,2,4-triazol-1-yl)methyl)-3-fluoroallyl)carbamate prepared in Reference Example 63 was used instead of tert-butyl (Z)-(2-((4-(3-bromophenyl)-5-oxo-4,5-dihydro-1H-1,2,4-triazol-1-yl)methyl)-3-fluoroallyl)carbamate. ¹H-NMR (DMSO-d₆, 400 MHz) δ 8.71 (s, 1H), 8.66 (d, 1H), 8.31 (dd, 1H), 8.17 (d, 1H), 7.20 (d, 1H), 4.62 (s, 2H), 3.47 (s, 2H)

Example 30. 2-[(2E)-2-(aminomethyl)-3-fluoroprop-2-en-1-yl]-4-(5-bromopyridin-2-yl)-2,4-dihydro-3H-1,2,4-triazol-3-one hydrochloride 18.0 mg of the title compound (yield: 64.1%) was prepared in the same fashion as Example 3, except that 30.0 mg of tert-butyl (E)-(2-((4-(5-bromopyridin-2-yl)-5-oxo-4,5-dihydro-1H-1,2,4-triazol-1-yl)methyl)-3-fluoroallyl)carbamate prepared in Reference Example 64 was used instead of tert-butyl (Z)-(2-((4-(3-bromophenyl)-5-oxo-4,5-dihydro-1H-1,2,4-triazol-1-yl)methyl)-3-fluoroallyl)carbamate. ¹H-NMR (MeOD, 400 MHz) δ 8.57 (s, 1H), 8.56 (s, 1H), 8.23 (d, 1H), 8.15 (dd, 1H), 7.19 (d, 1H), 4.53 (d, 2H), 3.73 (d, 2H)

Example 31. 2-[(2Z)-2-(aminomethyl)-3-fluoroprop-2-en-1-yl]-4-(5-bromo-3-methylpyridin-2-yl)-2,4-dihydro-3H-1,2,4-triazol-3-one hydrochloride 6.3 mg of the title compound (yield: 56.6%) was prepared in the same fashion as Example 3, except that 13.0 mg of tert-butyl (Z)-(2-((4-(5-bromo-3-methylpyridin-2-yl)-5- oxo-4,5-dihydro-1H-1,2,4-triazol-1-yl)methyl)-3-fluoroallyl)carbamate prepared in Reference Example 65 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (DMSO-$d_6$, 400 MHz) δ 8.59 (s, 1H), 8.33 (s, 1H), 8.27 (s, 1H), 7.19 (d, 1H), 4.60 (s, 2H), 3.46 (s, 2H)

Example 32. 2-[(2E)-2-(aminomethyl)-3-fluoroprop-2-en-1-yl]-4-(5-bromo-3-methylpyridin-2-yl)-2,4-dihydro-3H-1,2,4-triazol-3-one hydrochloride 18.0 mg of the title compound (yield: 71.0%) was prepared in the same fashion as Example 3, except that 27.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (MeOD, 400 MHz) δ 8.50 (s, 1H), 8.13 (d, 2H), 7.19 (d, 1H), 4.54 (d, 2H), 3.74 (s, 2H), 2.35 (s, 3H)

Example 33. 2-[(2Z)-2-(aminomethyl)-3-fluoroprop-2-en-1-yl]-4-(5-bromo-4-methylpyridin-2-yl)-2,4-dihydro-3H-1,2,4-triazol-3-one hydrochloride 7.6 mg of the title compound (yield: 59.2%) was prepared in the same fashion as Example 3, except that 15.0 mg of tert-butyl (Z)-(2-((4-(5-bromo-4-methylpyridin-2-yl)-5-oxo-4,5-dihydro-1H-1,2,4-triazol-1-yl)methyl)-3-fluoroallyl)carbamate prepared in Reference Example 67 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (DMSO-$d_6$, 400 MHz) δ 8.69 (s, 1H), 8.61 (d, 1H), 8.18 (s, 1H), 7.20 (d, 1H), 4.62 (s, 2H), 3.46 (s, 2H) 2.46 (s, 3H)

Example 34. 2-[(2E)-2-(aminomethyl)-3-fluoroprop-2-en-1-yl]-4-(5-bromo-4-methylpyridin-2-yl)-2,4-dihydro-3H-1,2,4-triazol-3-one hydrochloride 17.0 mg of the title compound (yield: 69.7%) was prepared in the same fashion as Example 3, except that 26.0 mg of tert-butyl (E)-(2-((4-(5-bromo-4-methylpyridin-2-yl)-5-oxo-4,5-dihydro-1H-1,2,4-triazol-1-yl)methyl)-3-fluoroallyl)carbamate prepared in Reference Example 68 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (MeOD, 400 MHz) δ 8.59 (s, 1H), 8.52 (s, 1H), 8.21 (s, 1H), 7.19 (d, 1H), 4.53 (d, 2H), 3.73 (d, 2H), 2.49 (s, 3H)

Example 35. 2-[(2Z)-2-(aminomethyl)-3-fluoroprop-2-en-1-yl]-4-(5-bromo-3-fluoropyridin-2-yl)-2,4-dihydro-3H-1,2,4-triazol-3-one hydrochloride 5.9 mg of the title compound (yield: 24.2%) was prepared in the same fashion as Example 3, except that 26.0 mg of tert-butyl (Z)-(2-((4-(5-bromo-3-fluoropyridin-2-yl)-5-oxo-4,5-dihydro-1H-1,2,4-triazol-1-yl)methyl)-3-fluoroallyl) carbamate prepared in Reference Example 69 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (DMSO-$d_6$, 400 MHz) δ 8.66 (s, 1H), 8.58 (d, 1H), 8.38 (s, 1H), 7.20 (d, 1H), 4.61 (s, 2H), 3.47 (s, 2H)

Example 36. 2-[(2E)-2-(aminomethyl)-3-fluoroprop-2-en-1-yl]-4-(5-bromo-3-fluoropyridin-2-yl)-2,4-dihydro-3H-1,2,4-triazol-3-one hydrochloride 5.5 mg of the title compound (yield: 32.5%) was prepared in the same fashion as Example 3, except that 18.0 mg of tert-butyl (E)-(2-((4-(5-bromo-3-fluoropyridin-2-yl)-5-oxo-4,5-dihydro-1H-1,2,4-triazol-1-yl)methyl)-3-fluoroallyl) carbamate prepared in Reference Example 70 was used instead of tert-butyl (Z)-(2-((4-(3-bromophenyl)-5-oxo-4,5-dihydro-1H-1,2,4-triazol-1-yl)methyl)-3-fluoroallyl)carbamate. $^1$H-NMR (MeOD, 400 MHz) δ 8.55 (s, 1H), 8.26 (m, 1H), 8.20 (s, 1H), 7.20 (d, 1H), 4.54 (s, 2H), 3.74 (s, 2H)

Example 37. 2-[(2E)-2-(aminomethyl)-3-fluoroprop-2-en-1-yl]-4-(6-bromopyridin-2-yl)-2,4-dihydro-3H-1,2,4-triazol-3-one 11.4 mg of the title compound (yield: 74.4%) was prepared in the same fashion as Example 1, except that 20.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate. $^1$H-NMR (MeOD, 400 MHz) δ 8.55 (s, 1H), 8.26 (d, 1H), 7.86 (m, 1H), 7.57 (d, 1H), 6.94-7.14 (m, 1H), 4.50 (s, 2H), 3.56 (s, 2H)

Example 38. 2-[(2E)-2-(aminomethyl)-3-fluoroprop-2-en-1-yl]-4-(5-bromopyrazin-2-yl)-2,4-dihydro-3H-1,2,4-triazol-3-one 14.7 mg of the title compound (yield: 95.8%) was prepared in the same fashion as Example 1, except that 20.0 mg of tert-butyl (E)-(2-((4-(5-bromopyrazin-2-yl)-5-oxo-4,5-dihydro-1H-1,2,4-triazol-1-yl)methyl)-3-fluoroallyl)carbamate prepared in Reference Example 75 was used instead of tert-butyl (Z)-(2-((4-(4-bromophenyl)-5-oxo-4,5-dihydro-1H-1,2,4-triazol-1-yl)methyl)-3-fluoroallyl)carbamate. $^1$H-NMR (MeOD, 400 MHz) δ 9.33 (s, 1H), 8.68 (s, 1H), 8.60 (s, 1H), 7.11-7.31 (m, 1H), 4.57 (s, 2H), 3.77 (s, 2H)

Example 39. 2-[(2Z)-2-(aminomethyl)-3-fluoroprop-2-en-1-yl]-4-(1,3-thiazol-2-yl)-2,4-dihydro-3H-1,2,4-triazol-3-one hydrochloride Step 1: tert-butyl (Z)-(3-fluoro-2-((5-oxo-4-(thiazol-2-yl)-4,5-dihydro-1H-1,2,4-triazol-1-yl)methyl)allyl)carbamate 23.0 mg of tert-butyl (Z)-(2-((4-(5-bromothiazol-2-yl)-5-oxo-4,5-dihydro-1H-1,2,4-triazol-1-yl)methyl)-3-fluoroallyl)carbamate prepared in Reference Example 76 was dissolved in 2.0 mL of ethyl acetate, and 5.0 mg of Pd/C was added to the resulting solution, and then the solution was stirred overnight at room temperature in a hydrogen atmosphere in a reaction flask provided with a hydrogen balloon. The reaction mixture thus obtained was filtered through Celite, washed with ethyl acetate, and concentrated under reduced pressure to give a yellow liquid residue. The residue was purified with silica gel column chromatography (developing solvent: n-hexane/ethyl acetate=2/1) to give 10.0 mg of the title compound as a yellow liquid (yield: 53.0%). MS (ESI) m/z=256.4 (M+H)+

Step 2: 2-[(2Z)-2-(aminomethyl)-3-fluoroprop-2-en-1-yl]-4-(1,3-thiazol-2-yl)-2,4-dihydro-3H-1,2,4-triazol-3-one hydrochloride 10.0 mg of tert-butyl (Z)-(3-fluoro-2-((5-oxo-4-(thiazol-2-yl)-4,5-dihydro-1H-1,2,4-triazol-1-yl)methyl)allyl)carbamate prepared in Step 1 was dissolved in 0.3 mL of ethyl acetate, 0.3 mL of 4M hydrogen chloride solution in dioxane was added to the resulting solution, and the solution was stirred overnight at room temperature. The resulting reaction mixture was concentrated to give a residue, and the residue was washed with ethyl acetate and concentrated under reduced pressure to give 2.0 mg of the title compound as a yellow solid (yield: 24.4%). $^1$H-NMR (MeOD, 400 MHz) δ 8.58 (s, 1H), 7.64 (d, 1H), 7.48 (d, 1H), 7.11 (d, 1H), 4.73 (d, 2H), 3.63 (s, 2H)

Example 40. 2-[(2Z)-2-(aminomethyl)-3-fluoroprop-2-en-1-yl]-4-(5-bromo-1,3-thiazol-2-yl)-2,4-dihydro-3H-1,2,4-triazol-3-one hydrochloride 3.5 mg of the title compound (yield: 31.5%) was prepared in the same fashion as Example 3, except that 13.0 mg of tert-butyl (Z)-(2-((4-(5-bromothiazol-2-yl)-5-oxo-4,5-dihydro-1H-1,2,4-triazol-1-yl)methyl)-3-fluoroallyl)carbamate prepared in Reference Example 76 was used instead of tert-butyl (Z)-(2-((4-(3-bromophenyl)-5-oxo-4,5-dihydro-1H-1,2,4-triazol-1-yl)methyl)-3-fluoroallyl)carbamate.
$^1$H-NMR (DMSO-$d_6$, 400 MHz) δ 8.80 (s, 1H), 7.84 (s, 1H), 7.20 (d, 1H), 4.64 (s, 2H), 3.47 (s, 2H)

Example 41. 2-[(2E)-2-(aminomethyl)-3-fluoroprop-2-en-1-yl]-4-(5-bromo-1,3-thiazol-2-yl)-2,4-dihydro-3H-1,2,4-triazol-3-one hydrochloride 9.0 mg of the title compound (yield: 75.3%) was prepared in the same fashion as Example 3, except that 14.0 mg of tert-butyl (E)-(2-((4-(5-bromothiazol-2-yl)-5-oxo-4,5-dihydro-1H-1,2,4-triazol-1-yl)methyl)-3-fluoroallyl)carbamate prepared in Reference Example 77 was used instead of tert-butyl (Z)-(2-((4-(3-bromophenyl)-5-oxo-4,5-dihydro-1H-1,2,4-triazol-1-yl)methyl)-3-fluoroallyl)carbamate.
$^1$H-NMR (MeOD, 400 MHz) δ 8.56 (s, 1H), 7.63 (s, 1H), 7.20 (d, 1H), 4.55 (d, 2H), 3.72 (d, 2H)

Example 42. 4-[4-(5-acetylthiophen-2-yl)phenyl]-2-[(2Z)-2-(aminomethyl)-3-fluoroprop-2-en-1-yl]-2,4-dihydro-3H-1,2,4-triazol-3-one hydrochloride Step 1: tert-butyl (Z)-(2-((4-(4-(5-acetylthiophen-2-yl)phenyl)-5-oxo-4,5-dihydro-1H-1,2,4-triazol-1-yl)methyl)-3-fluoroallyl)carbamate 30.0 mg of tert-butyl (Z)-(2-((4-(4-bromophenyl)-5-oxo-4,5-dihydro-1H-1,2,4-triazol-1-yl)methyl)-3-fluoroallyl)carbamate prepared in Reference Example 33, 35.4 mg of 1-(5-(4,4,5,5-tetramethyl-1,3,2-dioxaborolan-2-yl)thiophen-2-yl)ethan-1-one, and 1.5 mg of palladiumdi[1,1'-bis(diphenylphosphino)ferrocene]dichloride ($PdCl_2$(dppf)) were dissolved in 0.81 mL of 1,4-dioxane. To the resulting solution, 0.27 mL of 1M aqueous solution of potassium carbonate was added, and the solution was stirred overnight at 110° C. The resulting reaction mixture was concentrated, and then with addition of ethyl acetate, the reaction mixture was washed with distilled water, dried over anhydrous magnesium sulfate, and concentrated under reduced pressure to obtain a yellow liquid residue. The residue was purified with silica gel column chromatography (developing solvent: dichloromethane/methanol=20/1) to give 16.1 mg of the title compound as a yellow liquid (yield: 50.1%). MS (ESI) m/z=373.6 (M+H)+

Step 2: 4-[4-(5-acetylthiophen-2-yl)phenyl]-2-[(2Z)-2-(aminomethyl)-3-fluoroprop-2-en-1-yl]-2,4-dihydro-3H-1,2,4-triazol-3-one hydrochloride 16.1 mg of tert-butyl (Z)-(2-((4-(4-(5-acetylthiophen-2-yl)phenyl)-5-oxo-4,5-dihydro-1H-1,2,4-triazol-1-yl)methyl)-3-fluoroallyl)carbamate prepared in Step 1 was dissolved in 0.9 mL of ethyl acetate, and 0.2 mL of 4M hydrogen chloride solution in dioxane was added thereto. The resulting solution was stirred overnight at room temperature. The resulting reaction mixture was concentrated, and the residue thus obtained was washed with ethyl acetate and concentrated under reduced pressure to give 6.3 mg of the title compound as a white solid (yield: 45.2%). $^1$H-NMR (MeOD, 400 MHz) δ 8.34 (s, 1H), 7.88 (m, 3H), 7.77 (d, 2H), 7.56 (d, 1H), 7.10 (d, 1H), 4.72 (s, 2H), 3.62 (s, 2H), 2.58 (s, 3H)

Example 43. 2-[(2E)-2-(aminomethyl)-3-fluoroprop-2-en-1-yl]-4-[3-fluoro-4'-(4H-1,2,4-triazol-3-yl)biphenyl-4-yl]-2,4-dihydro-3H-1,2,4-triazol-3-one Step 1: tert-butyl (E)-(3-fluoro-2-((4-(3-fluoro-4'-(1-((2-(trimethylsilyl)ethoxy)methyl)-1H-1,2,4-triazol-3-yl)-[1,1'-biphenyl]-4-yl)-5-oxo-4,5-dihydro-1H-1,2,4-triazol-1-yl)methyl)allyl)carbamate 15.2 mg of the title compound as a yellow liquid (yield: 20.9%) was prepared in the same fashion as Step 1 in Example 42, except that 30.0 mg of tert-butyl (E)-(2-((4-(4-bromo-2-fluorophenyl)-5-oxo-4,5-dihydro-1H-1,2,4-triazol-1-yl)methyl)-3-fluoroallyl)carbamate prepared in Reference Example 36 was used instead of tert-butyl (Z)-(2-((4-(4-bromophenyl)-5-oxo-4,5-dihydro-1H-1,2,4-triazol-1-yl)methyl)-3-fluoroallyl)carbamate and that 35.2 mg of 3-(4-(4,4,5,5-tetramethyl-1,3,2-dioxaborolan-2-yl)phenyl)-1-((2-(trimethylsilyl)ethoxy)methyl)-1H-1,2,4-triazole prepared in Reference Example 31 was used instead of 1-(5-(4,4,5,5-tetramethyl-1,3,2-dioxaborolan-2-yl)thiophen-2-yl)ethane-1-one.

Step 2: 2-[(2E)-2-(aminomethyl)-3-fluoroprop-2-en-1-yl]-4-[3-fluoro-4'-(4H-1,2,4-triazol-3-yl)biphenyl-4-yl]-2,4-dihydro-3H-1,2,4-triazol-3-one 15.2 mg of tert-butyl (E)-(3-fluoro-2-((4-(3-fluoro-4'-(1-((2-(trimethylsilyl)ethoxy)methyl)-1H-1,2,4-triazol-3-yl)-[1,1'-biphenyl]-4-yl)-5-oxo-4,5-dihydro-1H-1,2,4-triazol-1-yl)methyl)allyl)carbamate prepared in Step 1 was dissolved in 2.0 mL of dichloromethane, and 0.1 mL of trifluoroacetic acid was added thereto. The solution was stirred at room temperature for 4 hours. The residue obtained by concentration under reduced pressure was dissolved in dichloromethane, and the resulting solution was washed with an aqueous solution of sodium bicarbonate and brine, dried over anhydrous magnesium sulfate, and concentrated under reduced pressure to give a yellow liquid residue. The residue was purified with silica gel column chromatography (developing solvent: dichloromethane/methanol=10/1) to give 3.6 mg of the title compound as a yellow liquid (yield: 36.9%).

¹H-NMR (DMSO-d₆, 400 MHz) δ 8.45 (s, 1H), 8.15 (d, 1H), 7.84 (d, 3H), 7.73 (m, 4H), 7.20 (d, 1H), 4.57 (s, 2H), 3.77 (s, 2H)

Example 44. 2-[(2E)-2-(aminomethyl)-3-fluoroprop-2-en-1-yl]-4-[3-fluoro-3'-(4H-1,2,4-triazol-3-yl)biphenyl-4-yl]-2,4-dihydro-3H-1,2,4-triazol-3-one 10.0 mg of the title compound (yield: 36.2%) was prepared in the same fashion as Example 43, except that 35.2 mg of 3-(3-(4,4,5,5-tetramethyl-1,3,2-dioxaborolan-2-yl)phenyl)-1-((2-(trimethylsilyl)ethoxy)methyl)-1H-1,2,4-triazole prepared in Reference Example 32 was used in Step 1 instead of 3-(4-(4,4,5,5-tetramethyl-1,3,2-dioxaborolan-2-yl)phenyl)-1-((2-(trimethylsilyl)ethoxy)methyl)-1H-1,2,4-triazole. ¹H-NMR (MeOD, 400 MHz) δ 8.46 (s, 1H), 8.37 (s, 1H), 8.17 (s, 1H), 8.08 (d, 1H), 7.71-7.81 (m, 4H), 7.63 (t, 1H), 4.57 (s, 2H), 3.77 (s, 2H)

Example 45. 2-[(2E)-2-(aminomethyl)-3-fluoroprop-2-en-1-yl]-4-[4-(1,3-benzodioxol-5-yl)-2-fluorophenyl]-2,4-dihydro-3H-1,2,4-triazol-3-one hydrochloride 13.0 mg of the title compound (yield: 45.6%) was prepared in the same fashion as Example 42, except that 30.0 mg of tert-butyl (E)-(2-((4-(4-bromo-2-fluorophenyl)-5-oxo-4,5-dihydro-1H-1,2,4-triazol-1-yl)methyl)-3-fluoroallyl)carbamate prepared in Reference Example 36 was used instead of tert-butyl (Z)-(2-((4-(4-bromophenyl)-5-oxo-4,5-dihydro-1H-1,2,4-triazol-1-yl)methyl)-3-fluoroallyl)carbamate and 35.2 mg of 2-(benzo[d][1,3]dioxol-5-yl)-4,4,5,5-tetramethyl-1,3,2-dioxaborolan was used instead of 1-(5-(4,4,5,5-tetramethyl-1,3,2-dioxaborolan-2-yl)thiophen-2-yl)ethan-1-one in Step 1. ¹H-NMR (DMSO-d₆, 400 MHz) δ 8.36 (s, 1H), 7.77 (d, 1H), 7.66 (m, 2H), 7.39 (d, 1H), 7.28 (d, 1H), 7.22 (d, 1H), 7.05 (d, 1H), 6.10 (s, 2H), 4.53 (s, 2H), 3.55 (s, 2H)

Example 46. 2-[(2E)-2-(aminomethyl)-3-fluoroprop-2-en-1-yl]-4-[4-(2,1,3-benzooxadiazol-5-yl)-2-fluorophenyl]-2,4-dihydro-3H-1,2,4-triazol-3-one hydrochloride 9.1 mg of the title compound (yield: 32.1%) was prepared in the same fashion as Example 42, except that 30.0 mg of tert-butyl (E)-(2-((4-(4-bromo-2-fluorophenyl)-5-oxo-4,5-dihydro-1H-1,2,4-triazol-1-yl)methyl)-3-fluoroallyl)carbamate prepared in Reference Example 36 was used instead of tert-butyl (Z)-(2-((4-(4-bromophenyl)-5-oxo-4,5-dihydro-1H-1,2,4-triazol-1-yl)methyl)-3-fluoroallyl)carbamate and 35.2 mg of 5-(4,4,5,5-tetramethyl-1,3,2-dioxaborolan-2-yl)benzo[c][1,2,5]oxadiazole was used instead of 1-(5-(4,4,5,5-tetramethyl-1,3,2-dioxaborolan-2-yl)thiophen-2-yl)ethan-1-one in Step 1. ¹H-NMR (DMSO-d₆, 400 MHz) δ 8.51 (s, 1H), 8.42 (s, 1H), 8.21 (d, 1H), 8.08-8.12 (m, 2H), 7.94 (d, 1H), 7.84 (t, 1H), 7.23 (d, 1H), 4.54 (s, 2H), 3.56 (s, 2H)

Example 47. 2-[(2E)-2-(aminomethyl)-3-fluoroprop-2-en-1-yl]-4-[5-bromo-2-methoxy-4-(morpholin-4-yl)phenyl]-2,4-dihydro-3H-1,2,4-triazol-3-one hydrochloride 15.4 mg of the title compound (yield: 58.2%) was prepared in the same fashion as Example 3, except that 30.0 mg of tert-butyl (E)-(2-((4-(5-bromo-2-methoxy-4-morpholino-phenyl)-5-oxo-4,5-dihydro-1H-1,2,4-triazol-1-yl)methyl)-3-fluoroallyl)carbamate prepared in Reference Example 48 was used instead of tert-butyl (Z)-(2-((4-(3-bromophenyl)-5-oxo-4,5-dihydro-1H-1,2,4-triazol-1-yl)methyl)-3-fluoroallyl)carbamate. ¹H-NMR (MeOD, 400 MHz) δ 7.95 (s, 1H), 7.66 (s, 1H), 7.16 (d, 2H), 6.90 (s, 1H), 4.52 (s, 2H), 3.88 (s, 8H), 3.72 (s, 2H), 3.10 (s, 3H)

Example 48. 2-[(2E)-2-(aminomethyl)-3-fluoroprop-2-en-1-yl]-4-[3-(1,2,3,6-tetrahydropyridin-4-yl)phenyl]-2,4-dihydro-3H-1,2,4-triazol-3-one dihydrochloride 1.0 mg of the title compound (yield: 3.5%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 32.0 mg of N-Boc-1,2,3,6-tetrahydropyridine-4-boronic acid pinacol ester was used instead of 1-(5-(4,4,5,5-tetramethyl-1,3,2-dioxaborolan-2-yl)thiophen-2-yl)ethan-1-one in Step 1. MS (ESI) m/z=330.2 (M+H)+

Example 49. 4-[3-(5-acetylthiophen-2-yl)phenyl]-2-[(2E)-2-(aminomethyl)-3-fluoroprop-2-en-1-yl]-2,4-dihydro-3H-1,2,4-triazol-3-one hydrochloride 1.7 mg of the title compound (yield: 5.9%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 18.0 mg of 5-acetyl-2-thiophene boronic acid was used instead of 1-(5-(4,4,5,5-tetramethyl-1,3,2-dioxaborolan-2-yl)thiophen-2-yl)ethan-1-one in Step 1. ¹H-NMR (DMSO-d₆, 400 MHz) δ 8.67 (s, 1H), 8.10 (s, 1H), 7.99 (d, 1H), 7.74-7.80 (m, 3H), 7.62 (t, 1H), 7.22 (d, 1H), 4.51 (s, 2H), 3.56 (s, 2H), 2.56 (s, 3H)

Example 50. 2-[(2E)-2-(aminomethyl)-3-fluoroprop-2-en-1-yl]-4-[4'-(trifluoromethoxy)biphenyl-3-yl]-2,4-dihydro-3H-1,2,4-triazol-3-one hydrochloride 15.2 mg of the title compound (yield: 29.2%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 36.0 mg of 4-(trifluoromethoxy)phenyl boronic acid was used instead of 1-(5-(4,4,5,5-tetramethyl-1,3,2-dioxaborolan-2-yl)thiophen-2-yl)ethan-1-one in Step 1. ¹H-NMR (MeOD, 400 MHz) δ 8.35 (s, 1H), 7.93 (s, 1H), 7.78 (d, 2H), 7.60-7.72 (m, 3H), 7.39 (d, 2H), 7.19 (d, 1H), 4.56 (d, 2H), 3.75 (d, 2H)

Example 51. 2-[(2E)-2-(aminomethyl)-3-fluoroprop-2-en-1-yl]-4-[4'-(dimethylamino)biphenyl-3-yl]-2,4-dihydro-3H-1,2,4-triazol-3-one hydrochloride 22.1 mg of the title compound (yield: 46.8%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 43.0 mg of 4-N,N-dimethyl(amino)phenyl boronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.31 (s, 1H), 7.82 (s, 1H), 7.62 (d, 1H), 7.49-7.58 (m, 3H), 7.47 (d, 1H), 7.19 (d, 1H), 6.85 (d, 2H), 4.56 (d, 2H), 3.76 (d, 2H), 2.98 (s, 6H)

Example 52. 2-[(2E)-2-(aminomethyl)-3-fluoroprop-2-en-1-yl]-4-[4'-(propan-2-ylsulfanyl)biphenyl-3-yl]-2,4-dihydro-3H-1,2,4-triazol-3-one hydrochloride 17.4 mg of the title compound (yield: 42.7%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.0 mg of 4-isopropylthiobenzene boronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.34 (s, 1H), 7.91 (s, 1H), 7.69 (s, 1H), 7.57-7.66 (m, 4H), 7.48 (d, 2H), 7.20 (d, 1H), 4.56 (d, 2H), 3.76 (d, 2H), 1.31 (d, 6H)

Example 53. 2-[(2Z)-2-(aminomethyl)-3-fluoroprop-2-en-1-yl]-4-[4'-(methylsulfonyl)biphenyl-3-yl]-2,4-dihydro-3H-1,2,4-triazol-3-one hydrochloride 6.0 mg of the title compound (yield: 11.7%) was prepared in the same fashion as Example 42, except that 50.0 mg of tert-butyl (Z)-(2-((4-(3-bromophenyl)-5-oxo-4,5-dihydro-1H-1,2,4-triazol-1-yl)methyl)-3-fluoroallyl)carbamate prepared in Reference Example 49 was used instead of tert-butyl (Z)-(2-((4-(4-bromophenyl)-5-oxo-4,5-dihydro-1H-1,2,4-triazol-1-yl)methyl)-3-fluoroallyl)carbamate and 36.0 mg of 4-(methanesulfonyl)phenyl boronic acid was used instead of 1-(5-(4,4,5,5-tetramethyl-1,3,2-dioxaborolan-2-yl)thiophen-2-yl)ethan-1-one in Step 1. $^1$H-NMR (DMSO-$d_6$, 400 MHz) δ 8.68 (d, 1H), 8.04-8.11 (m, 5H), 7.79-7.81 (m, 2H), 7.69 (s, 1H), 7.20 (d, 1H), 4.62 (s, 2H), 3.48 (s, 2H), 2.50 (s, 3H)

Example 54. 2-[(2E)-2-(aminomethyl)-3-fluoroprop-2-en-1-yl]-4-[4'-(methylsulfonyl)biphenyl-3-yl]-2,4-dihydro-3H-1,2,4-triazol-3-one hydrochloride 23.8 mg of the title compound (yield: 46.3%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 44.0 mg of 4-(methanesulfonyl)phenyl boronic acid was used instead of 1-(5-(4,4,5,5-tetramethyl-1,3,2-dioxaborolan-2-yl)thiophen-2-yl)ethan-1-one in Step 1. $^1$H-NMR (DMSO-$d_6$, 400 MHz) δ 8.69 (s, 1H), 8.00-8.06 (m, 5H), 7.83 (d, 1H), 7.78 (d, 1H), 7.68 (t, 1H), 7.21 (d, 1H), 4.53 (d, 2H), 3.54 (s, 2H), 3.27 (s, 3H)

Example 55. 3'-{1-[(2E)-2-(aminomethyl)-3-fluoroprop-2-en-1-yl]-5-oxo-1,5-dihydro-4H-1,2,4-triazol-4-yl}-N,N-dimethylbiphenyl-4-sulfonamide hydrochloride 20.7 mg of the title compound (yield: 47.3%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 44.0 mg of 4-(N,N-dimethylaminosulfonyl)phenyl boronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.38 (s, 1H), 8.01 (s, 1H), 7.86-7.97 (m, 3H), 7.78 (d, 1H), 7.58-7.75 (m, 2H), 7.20 (d, 1H), 4.57 (d, 2H), 3.76 (d, 2H), 2.73 (s, 6H)

Example 56. N-(3'-{1-[(2Z)-2-(aminomethyl)-3-fluoroprop-2-en-1-yl]-5-oxo-1,5-dihydro-4H-1,2,4-triazol-4-yl}biphenyl-4-yl)acetamide hydrochloride 8.0 mg of the title compound (yield: 16.4%) was prepared in the same fashion as Example 42, except that 50.0 mg of tert-butyl (Z)-(2-((4-(3-bromophenyl)-5-oxo-4,5-dihydro-1H-1,2,4-triazol-1-yl)methyl)-3-fluoroallyl)carbamate prepared in Reference Example 49 was used instead of tert-butyl (Z)-(2-((4-(4-bromophenyl)-5-oxo-4,5-dihydro-1H-1,2,4-triazol-1-yl)methyl)-3-fluoroallyl)carbamate and 32.0 mg of 4-acetamidobenzeneboronic acid was used instead of 1-(5-(4,4,5,5-tetramethyl-1,3,2-dioxaborolan-2-yl)thiophen-2-yl)ethan-1-one in Step 1. $^1$H-NMR (DMSO-$d_6$, 400 MHz) δ 10.14 (s, 1H), 8.65 (s, 1H), 7.93 (s, 1H), 7.64-7.72 (m, 6H), 7.58 (t, 1H), 7.20 (d, 1H), 4.62 (s, 2H), 3.48 (s, 2H), 2.07 (s, 3H)

Example 57. N-(3'-{1-[(2E)-2-(aminomethyl)-3-fluoroprop-2-en-1-yl]-5-oxo-1,5-dihydro-4H-1,2,4-triazol-4-yl}biphenyl-4-yl)acetamide hydrochloride 8.0 mg of the title compound (yield: 16.4%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 32.0 mg of 4-acetamidobenzeneboronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.33 (s, 1H), 7.89 (s, 1H), 7.60-7.68 (m, 5H), 7.58 (d, 2H), 7.18 (d, 1H), 4.55 (d, 2H), 3.73 (d, 2H), 2.14 (s, 3H)

Example 58. 2-[(2Z)-2-(aminomethyl)-3-fluoroprop-2-en-1-yl]-4-[4'-(4H-1,2,4-triazol-3-yl)biphenyl-3-yl]-2,4-dihydro-3H-1,2,4-triazol-3-one 7.2 mg of the title compound (yield: 26.2%) was prepared in the same fashion as Example 43, except that 30.0 mg of tert-butyl (Z)-(2-((4-(3-bromophenyl)-5-oxo-4,5-dihydro-1H-1,2,4-triazol-1-yl)methyl)-3-fluoroallyl)carbamate prepared in Reference Example 49 was used in Step 1 instead of tert-butyl (E)-(2-((4-(4-bromo-2-fluorophenyl)-5-oxo-4,5-dihydro-1H-1,2,4-triazol-1-yl)methyl)-3-fluoroallyl)carbamate. (MeOD, 400 MHz) δ 8.43 (s, 1H), 8.36 (s, 1H), 8.13

(d, 2H), 7.99 (s, 1H), 7.83 (d, 2H), 7.76 (d, 1H), 7.65 (d, 2H), 7.07 (d, 1H), 4.74 (s, 2H), 4.57 (s, 3H), 3.57 (s, 2H)

Example 59. 2-[(2E)-2-(aminomethyl)-3-fluoroprop-2-en-1-yl]-4-[4'-(4H-1,2,4-triazol-3-yl)biphenyl-3-yl]-2,4-dihydro-3H-1,2,4-triazol-3-one 1.1 mg of the title compound (yield: 4.0%) was prepared in the same fashion as Example 43, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used in Step 1 instead of tert-butyl (E)-(2-((4-(4-bromo-2-fluorophenyl)-5-oxo-4,5-dihydro-1H-1,2,4-triazol-1-yl)methyl)-3-fluoroallyl)carbamate. $^1$H-NMR (DMSO-$d_6$, 400 MHz) δ 8.71 (s, 1H), 8.65 (m, 1H), 8.15 (d, 1H), 7.63-7.87 (m, 5H), 7.14 (d, 1H), 4.53 (s, 2H), 3.57 (s, 2H)

Example 60. 2-[(2Z)-2-(aminomethyl)-3-fluoroprop-2-en-1-yl]-4-[3'-(4H-1,2,4-triazol-3-yl)biphenyl-3-yl]-2,4-dihydro-3H-1,2,4-triazol-3-one 1.1 mg of the title compound (yield: 4.0%) was prepared in the same fashion as Example 43, except that 30.0 mg of tert-butyl (Z)-(2-((4-(3-bromophenyl)-5-oxo-4,5-dihydro-1H-1,2,4-triazol-1-yl)methyl)-3-fluoroallyl)carbamate prepared in Reference Example 49 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 36.6 mg of 3-(3-(4,4,5,5-tetramethyl-1,3,2-dioxaborolan-2-yl)phenyl)-1-((2-(trimethylsilyl)ethoxy)methyl)-1H-1,2,4-triazole prepared in Reference Example 32 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.46 (s, 1H), 8.37 (d, 2H), 8.05 (d, 1H), 8.00 (s, 1H), 7.80 (t, 2H), 7.59-7.72 (m, 4H), 7.09 (d, 1H), 4.74 (s, 2H), 4.57 (s, 3H), 3.57 (s, 2H)

Example 61. 2-[(2E)-2-(aminomethyl)-3-fluoroprop-2-en-1-yl]-4-[4'-(1,2,4-oxadiazol-3-yl)biphenyl-3-yl]-2,4-dihydro-3H-1,2,4-triazol-3-one 14.9 mg of the title compound (yield: 54.1%) was prepared in the same fashion as Example 43, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 24.8 mg of 3-(4-(4,4,5,5-tetramethyl-1,3,2-dioxaborolan-2-yl)phenyl)-1,2,4-oxadiazole prepared in Reference Example 78 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. 41-NMR (MeOD, 400 MHz) δ 8.37 (s, 1H), 7.99 (s, 1H), 7.83-7.89 (m, 4H), 7.66-7.76 (m, 3H), 7.20 (d, 1H), 4.57 (s, 2H), 3.76 (s, 2H)

Example 62. 2-[(2E)-2-(aminomethyl)-3-fluoroprop-2-en-1-yl]-4-[3'-(1,2,4-oxadiazol-3-yl)biphenyl-3-yl]-2,4-dihydro-3H-1,2,4-triazol-3-one 19.1 mg of the title compound (yield: 69.3%) was prepared in the same fashion as Example 43, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 24.8 mg of 3-(3-(4,4,5,5-tetramethyl-1,3,2-dioxaborolan-2-yl)phenyl)-1,2,4-oxadiazole prepared in Reference Example 79 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. 41-NMR (MeOD, 400 MHz) δ 8.37 (s, 1H), 8.08 (s, 1H), 8.01 (d, 1H), 7.97 (s, 1H), 7.65-7.78 (m, 5H), 7.20 (d, 1H), 4.57 (s, 2H), 3.76 (s, 2H)

Example 63. 2-[(2E)-2-(aminomethyl)-3-fluoroprop-2-en-1-yl]-4-[4'-(5-cyclopropyl-1,2,4-oxadiazol-3-yl)biphenyl-3-yl]-2,4-dihydro-3H-1,2,4-triazol-3-one hydrochloride 10.1 mg of the title compound (yield: 30.7%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.5 mg of 5-cyclopropyl-3-(4-(4,4,5,5-tetramethyl-1,3,2-dioxaborolan-2-yl)phenyl)-1,2,4-oxadiazole prepared in Reference Example 80 was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.37 (s, 1H), 8.12 (d, 2H), 7.99 (s, 1H), 7.84 (d, 2H), 7.77 (d, 1H), 7.65 (m, 2H), 7.21 (d, 1H), 4.57 (s, 2H), 3.76 (s, 2H), 2.35 (s, 1H), 1.28-1.33 (m, 4H)

Example 64. 2-[(2E)-2-(aminomethyl)-3-fluoroprop-2-en-1-yl]-4-{4'-[5-(propan-2-yl)-1,2,4-oxadiazol-3-yl]biphenyl-3-yl}-2,4-dihydro-3H-1,2,4-triazol-3-one hydrochloride 11.6 mg of the title compound (yield: 35.1%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.7 mg of 5-isopropyl-3-(4-(4,4,5,5-tetramethyl-1,3,2-dioxaborolan-2-yl)phenyl)-1,2,4-oxadiazole prepared in Reference Example 82 was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.38 (s, 1H), 8.17 (d, 2H), 8.00 (s, 1H), 7.86 (d, 2H), 7.77 (d, 1H), 7.66 (m, 2H), 7.20 (d, 1H), 4.57 (s, 2H), 3.76 (s, 2H), 3.66 (s, 1H), 3.35 (m, 1H), 1.47 (d, 6H)

Example 65. 2-[(2E)-2-(aminomethyl)-3-fluoroprop-2-en-1-yl]-4-{3'-[5-(propan-2-yl)-1,2,4-oxadiazol-3-yl]biphenyl-3-yl}-2,4-dihydro-3H-1,2,4-triazol-3-one hydrochloride 27.0 mg of the title compound (yield: 81.7%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.7 mg of 5-isopropyl-3-(3-(4,4,5,5-tetramethyl-1,3,2-dioxaborolan-2-yl)phenyl)-1,2,4-oxadiazole prepared in Reference Example 83 was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.36 (d, 2H), 8.09 (d, 1H), 7.99 (s, 1H), 7.87 (d, 1H), 7.76 (d, 1H), 7.62-7.67 (m, 3H), 7.20 (d, 1H), 4.57 (s, 2H), 3.76 (s, 2H), 3.35 (m, 1H), 1.47 (d, 6H)

Example 66. 2-[(2E)-2-(aminomethyl)-3-fluoroprop-2-en-1-yl]-4-[4"-(methylsulfonyl)-1,1':4',1"-terphenyl-3-yl]-2,4-dihydro-3H-1,2,4-triazol-3-one hydrochloride 11.2 mg of the title compound (yield: 36.5%) was prepared in the same fashion as Example 42, except that 30.0 mg of tert-butyl (E)-(2-((4-(4'-bromo-[1,1'-biphenyl]-3-yl)-5-oxo-4,5-dihydro-1H-1,2,4-triazol-1-yl)methyl)-3-fluoroallyl)carbamate prepared in Reference Example 84 was used instead of tert-butyl (Z)-(2-((4-(4-bromophenyl)-5-oxo-4,5-dihydro-1H-1,2,4-triazol-1-yl)methyl)-3-fluoroallyl)carbamate and 18.0 mg of 4-(methanesulfonyl)phenylboronic acid was used instead of 1-(5-(4,4,5,5-tetramethyl-1,3,2-dioxaborolan-2-yl)thiophen-2-yl)ethan-1-one in Step 1. $^1$H-NMR (DMSO-d$_6$, 400 MHz) δ 8.70 (s, 1H), 8.03-8.05 (m, 6H), 7.89-7.93 (m, 3H), 7.76-7.77 (m, 2H), 7.65 (t, 1H), 7.23 (d, 1H), 4.53 (s, 2H), 3.56 (s, 2H), 3.27 (s, 3H)

Example 67. 2-[(2E)-2-(aminomethyl)-3-fluoroprop-2-en-1-yl]-4-[4"-(methylsulfonyl)-1,1':3',1"-terphenyl-3-yl]-2,4-dihydro-3H-1,2,4-triazol-3-one 21.3 mg of the title compound (yield: 74.7%) was prepared in the same fashion as Example 43, except that 30.0 mg of tert-butyl (E)-(2-((4-(3'-bromo-[1,1'-biphenyl]-3-yl)-5-oxo-4,5-dihydro-1H-1,2,4-triazol-1-yl)methyl)-3-fluoroallyl)carbamate prepared in Reference Example 85 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 18.0 mg of 4-(methanesulfonyl)phenylboronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (CDCl$_3$, 600 MHz) δ 8.03 (d, 2H), 7.86 (d, 1H), 7.82 (d, 2H), 7.79 (d, 2H), 7.57-7.67 (m, 5H), 7.51 (d, 1H), 6.74 (d, 1H), 4.47 (d, 2H), 3.46 (s, 2H), 3.10 (s, 3H)

Example 68. N-(3"-{1-[(2E)-2-(aminomethyl)-3-fluoroprop-2-en-1-yl]-5-oxo-1,5-dihydro-4H-1,2,4-triazol-4-yl}-1,1':4',1"-terphenyl-4-yl)acetamide hydrochloride 16.8 mg of the title compound (yield: 57.1%) was prepared in the same fashion as Example 42, except that 30.0 mg of tert-butyl (E)-(2-((4-(4'-bromo-[1,1'-biphenyl]-3-yl)-5-oxo-4,5-dihydro-1H-1,2,4-triazol-1-yl)methyl)-3-fluoroallyl)carbamate prepared in Reference Example 84 was used instead of tert-butyl (Z)-(2-((4-(4-bromophenyl)-5-oxo-4,5-dihydro-1H-1,2,4-triazol-1-yl)methyl)-3-fluoroallyl)carbamate and 16.0 mg of 4-acetamidobenzeneboronic acid was used instead of 1-(5-(4,4,5,5-tetramethyl-1,3,2-dioxaborolan-2-yl)thiophen-2-yl)ethan-1-one in Step 1. $^1$H-NMR (DMSO-d$_6$, 400 MHz) δ 10.09 (s, 1H), 8.69 (s, 1H), 8.02 (s, 1H), 7.70-7.82 (m, 9H), 7.63 (t, 1H), 7.23 (d, 1H), 4.53 (s, 2H), 3.55 (s, 2H), 2.07 (s, 3H)

Example 69. N-(3"-{1-[(2E)-2-(aminomethyl)-3-fluoroprop-2-en-1-yl]-5-oxo-1,5-dihydro-4H-1,2,4-triazol-4-yl}-1,1':3',1"-terphenyl-4-yl)acetamide hydrochloride 8.9 mg of the title compound (yield: 30.2%) was prepared in the same fashion as Example 42, except that 30.0 mg of tert-butyl (E)-(2-((4-(3'-bromo-[1,1'-biphenyl]-3-yl)-5-oxo-4,5-dihydro-1H-1,2,4-triazol-1-yl)methyl)-3-fluoroallyl)carbamate prepared in Reference Example 85 was used instead of tert-butyl (Z)-(2-((4-(4-bromophenyl)-5-oxo-4,5-dihydro-1H-1,2,4-triazol-1-yl)methyl)-3-fluoroallyl)carbamate and 16.0 mg of 4-acetamidobenzeneboronic acid was used instead of 1-(5-(4,4,5,5-tetramethyl-1,3,2-dioxaborolan-2-yl)thiophen-2-yl)ethan-1-one in Step 1. $^1$H-NMR (DMSO-d$_6$, 400 MHz) δ 10.09 (s, 1H), 8.69 (s, 1H), 8.04 (s, 1H), 7.94 (s, 1H), 7.77 (t, 2H), 7.62-7.71 (m, 7H), 7.57 (t, 1H), 7.23 (d, 1H), 4.52 (s, 2H), 3.56 (s, 2H), 2.07 (s, 3H)

Example 70. 2-[(2E)-2-(aminomethyl)-3-fluoroprop-2-en-1-yl]-4-[4'-(1,3-benzodioxol-5-yl)biphenyl-3-yl]-2,4-dihydro-3H-1,2,4-triazol-3-one hydrochloride 15.0 mg of the title compound (yield: 52.3%) was prepared in the same fashion as Example 42, except that 30.0 mg of tert-butyl (E)-(2-((4-(4'-bromo-[1,1'-biphenyl]-3-yl)-5-oxo-4,5-dihydro-1H-1,2,4-triazol-1-yl)methyl)-3-fluoroallyl)carbamate prepared in Reference Example 84 was used instead of tert-butyl (Z)-(2-((4-(4-bromophenyl)-5-oxo-4,5-dihydro-1H-1,2,4-triazol-1-yl)methyl)-3-fluoroallyl)carbamate and 15.0 mg of 3,4-(methylenedioxy)phenylboronic acid was used instead of 1-(5-(4,4,5,5-tetramethyl-1,3,2-dioxaborolan-2-yl)thiophen-2-yl)ethan-1-one in Step 1. $^1$H-NMR (DMSO-d$_6$, 400 MHz) δ 8.18 (s, 1H), 8.02 (s, 1H), 7.70-7.80 (m, 7H), 7.62 (t, 1H), 7.33 (s, 1H), 7.24 (d, 1H), 7.23 (d, 1H), 7.03 (d, 1H), 6.08 (s, 2H), 4.52 (s, 2H), 3.55 (s, 2H)

Example 71. 2-[(2E)-2-(aminomethyl)-3-fluoroprop-2-en-1-yl]-4-[3'-(1,3-benzodioxol-5-yl)biphenyl-3-yl]-2,4-dihydro-3H-1,2,4-triazol-3-one hydrochloride 14.0 mg of the title compound (yield: 48.8%) was prepared in the same fashion as Example 42, except that 30.0 mg of tert-butyl (E)-(2-((4-(3'-bromo-[1,1'-biphenyl]-3-yl)-5-oxo-4,5-dihydro-1H-1,2,4-triazol-1-yl)methyl)-3-fluoroallyl)carbamate prepared in Reference Example 85 was used instead of tert-butyl (Z)-(2-((4-(4-bromophenyl)-5-oxo-4,5-dihydro-1H-1,2,4-triazol-1-yl)methyl)-3-fluoroallyl)carbamate and 15.0 mg of 3,4-(methylenedioxy)phenylboronic acid was used instead of 1-(5-(4,4,5,5-tetramethyl-1,3,2-dioxaborolan-2-yl)thiophen-2-yl)ethan-1-one in Step 1. $^1$H-NMR (DMSO-d$_6$, 400 MHz) δ 8.82 (s, 1H), 8.39 (s, 1H), 8.01 (s, 1H), 7.70-7.80 (m, 2H), 7.61-7.68 (m, 3H), 7.55 (t, 1H), 7.38 (s, 1H), 7.26 (d, 1H), 7.23 (d, 1H), 7.03 (d, 1H), 6.08 (s, 2H), 4.52 (s, 2H), 3.55 (s, 2H)

Example 72. 4-[4'-(4-acetylpiperazine-1-yl)biphenyl-3-yl]-2-[(2E)-2-(aminomethyl)-3-fluoroprop-2-en-1-yl]-2,4-dihydro-3H-1,2,4-triazol-3-one hydrochloride 1.0 mg of the title compound (yield: 3.4%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 26.0 mg of 4-(acetyl-1-piperazinyl)phenylboronic acid was used instead of 1-(5-(4,4,5,5-tetramethyl-1,3,2-dioxaborolan-2-yl)thiophen-2-yl)ethan-1-one in Step 1. MS (ESI) m/z=451.2 (M+H)+

Example 73. 2-[(2E)-2-(aminomethyl)-3-fluoroprop-2-en-1-yl]-4-[4'-(tetrahydro-2H-pyran-4-yl)biphenyl-3-yl]-2,4-dihydro-3H-1,2,4-triazol-3-one hydrochloride 24.2 mg of the title compound (yield: 91.2%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 30.0 mg of 4-(4-tetrahydropyranyl)phenylboronic acid pinacol ester was used instead of 1-(5-(4,4,5,5-tetramethyl-1,3,2-dioxaborolan-2-yl)thiophen-2-yl)ethan-1-one in Step 1. $^1$H-NMR (DMSO-$d_6$, 400 MHz) δ 8.66 (s, 1H), 7.94 (s, 1H), 7.65-7.71 (4H, m), 7.59 (1H, t), 7.39 (2H, d), 7.22 (1H, d), 4.51 (2H, s), 3.97 (2H, d), 3.55 (2H, d), 3.45 (2H, t), 3.79-3.88 (1H, m), 1.71-1.73 (4H, m)

Example 74. 2-[(2E)-2-(aminomethyl)-3-fluoroprop-2-en-1-yl]-4-[4'-(morpholin-4-yl)biphenyl-3-yl]-2,4-dihydro-3H-1,2,4-triazol-3-one hydrochloride 23.7 mg of the title compound (yield: 56.7%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 40.6 mg of 4-morpholinophenylboronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.36 (s, 1H), 7.94 (s, 1H), 7.82 (d, 2H), 7.71 (dt, 1H), 7.60-7.65 (m, 2H), 7.54 (d, 2H), 7.20 (d, 1H), 4.57 (d, 2H), 3.98-4.07 (m, 4H), 3.77 (s, 2H), 3.50-3.61 (m, 4H)

Example 75. 2-[(2E)-2-(aminomethyl)-3-fluoroprop-2-en-1-yl]-4-[3'-fluoro-4'-(morpholin-4-yl)biphenyl-3-yl]-2,4-dihydro-3H-1,2,4-triazol-3-one hydrochloride 24.8 mg of the title compound (yield: 45.7%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 53.0 mg of 3-fluoro-4-morpholinophenylboronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.36 (s, 1H), 7.92 (s, 1H), 7.66-7.75 (m, 1H), 7.59-7.64 (m, 1H), 7.56 (d, 1H), 7.54 (s, 1H), 7.35 (t, 1H), 7.20 (d, 1H), 4.57 (d, 2H), 3.87-4.00 (m, 4H), 3.77 (s, 2H), 3.30-3.32 (m, 4H)

Example 76. 2-[(2E)-2-(aminomethyl)-3-fluoroprop-2-en-1-yl]-4-[3'-chloro-4'-(morpholin-4-yl)biphenyl-3-yl]-2,4-dihydro-3H-1,2,4-triazol-3-one hydrochloride 19.7 mg of the title compound (yield: 43.8%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 45.5 mg of 3-chloro-4-morpholinophenylboronic acid was used instead of 1-(5-(4,4,5,5-tetramethyl-1,3,2-dioxaborolan-2-yl)thiophen-2-yl)ethan-1-one in Step 1. 41-NMR (MeOD, 400 MHz) δ 8.35 (s, 1H), 7.89 (s, 1H), 7.74 (d, 1H), 7.66 (d, 1H), 7.62 (d, 1H), 7.54-7.62 (m, 1H), 7.24 (d, 1H), 7.19 (d, 1H), 4.56 (d, 2H), 3.82-3.94 (m, 4H), 3.76 (d, 1H), 3.66 (s, 1H), 3.04-3.20 (m, 4H)

Example 77. 2-[(2E)-2-(aminomethyl)-3-fluoroprop-2-en-1-yl]-4-[3'-methyl-4'-(morpholin-4-yl)biphenyl-3-yl]-2,4-dihydro-3H-1,2,4-triazol-3-one hydrochloride 18.6 mg of the title compound (yield: 43.2%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 31.0 mg of 3-methyl-4-morpholinophenylboronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.28 (s, 1H), 7.85 (s, 1H), 7.62 (s, 1H), 7.45-7.59 (m, 4H), 7.13 (d, 1H), 6.90 (d, 1H), 4.49 (d, 2H), 3.85 (m, 4H), 3.40 (d, 2H), 2.93 (m, 4H), 2.38 (s, 3H)

Example 78. 2-[(2E)-2-(aminomethyl)-3-fluoroprop-2-en-1-yl]-4-[4'-(morpholin-4-ylcarbonyl)biphenyl-3-yl]-2,4-dihydro-3H-1,2,4-triazol-3-one hydrochloride 21.1 mg of the title compound (yield: 47.6%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 45.0 mg of 4-(morpholin-4-carbonyl)phenylboronic acid pinacol ester was used instead of 1-(5-(4,4,5,5-tetramethyl-1,3,2-dioxaborolan-2-yl)thiophen-2-yl)ethan-1-one in Step 1. MS (ESI) m/z=438.2 (M+H)+

Example 79. 2-[(2E)-2-(aminomethyl)-3-fluoroprop-2-en-1-yl]-4-[3-(2-methoxypyridin-4-yl)phenyl]-2,4-dihydro-3H-1,2,4-triazol-3-one hydrochloride 11.4 mg of the title compound (yield: 41.4%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 16.0 mg of 2-methoxy-4-pyridine boronic acid was used instead of 1-(5-(4,4,5,5-tetramethyl-1,3,2-dioxaborolan-2-yl)thiophen-2-yl)ethan-1-one in Step 1. $^1$H-NMR (DMSO-d$_6$, 400 MHz) δ 8.69 (s, 1H), 8.28 (d, 1H), 8.06 (s, 1H), 7.83 (dd, 2H), 7.65 (t, 1H), 7.38 (d, 1H), 7.21 (d, 1H), 7.20 (s, 1H), 4.52 (s, 2H), 3.91 (s, 3H), 3.54 (d, 2H)

Example 80. N-[4-(3-{1-[(2Z)-2-(aminomethyl)-3-fluoroprop-2-en-1-yl]-5-oxo-1,5-dihydro-4H-1,2,4-triazol-4-yl}phenyl)pyridin-2-yl]acetamide hydrochloride 4.0 mg of the title compound (yield: 8.2%) was prepared in the same fashion as Example 42, except that 50.0 mg of tert-butyl (Z)-(2-((4-(3-bromophenyl)-5-oxo-4,5-dihydro-1H-1,2,4-triazol-1-yl)methyl)-3-fluoroallyl)carbamate prepared in Reference Example 49 was used instead of tert-butyl (Z)-(2-((4-(4-bromophenyl)-5-oxo-4,5-dihydro-1H-1,2,4-triazol-1-yl)methyl)-3-fluoroallyl)carbamate and 47.0 mg of N-(4-(4,4,5,5-tetramethyl-1,3,2-dioxaborolan-2-yl)pyridin-2-yl)acetamide was used instead of 1-(5-(4,4,5,5-tetramethyl-1,3,2-dioxaborolan-2-yl)thiophen-2-yl)ethan-1-one in Step 1. $^1$H-NMR (DMSO-d$_6$, 400 MHz) δ 10.73 (s, 1H), 8.66 (s, 1H), 8.41 (d, 1H), 8.38 (s, 1H), 8.06 (s, 1H), 7.82 (d, 1H), 7.67-7.73 (m, 2H), 7.47 (t, 1H), 7.20 (d, 1H), 4.62 (s, 2H), 3.49 (s, 2H), 2.13 (s, 3H)

Example 81. N-[4-(3-{1-[(2E)-2-(aminomethyl)-3-fluoroprop-2-en-1-yl]-5-oxo-1,5-dihydro-4H-1,2,4-triazol-4-yl}phenyl)pyridin-2-yl]acetamide hydrochloride 8.0 mg of the title compound (yield: 16.3%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 47.0 mg of N-(4-(4,4,5,5-tetramethyl-1,3,2-dioxaborolan-2-yl)pyridin-2-yl)acetamide was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.41 (d, 2H), 8.18 (s, 1H), 7.83-7.89 (m, 4H), 7.77 (d, 1H), 7.20 (d, 1H), 4.57 (d, 2H), 3.76 (s, 2H), 2.33 (s, 3H)

Example 82. 2-[(2E)-2-(aminomethyl)-3-fluoroprop-2-en-1-yl]-4-[3-(pyridin-3-yl)phenyl]-2,4-dihydro-3H-1,2,4-triazol-3-one hydrochloride 26.3 mg of the title compound (yield: 77.7%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 47.0 mg of 3-pyridine boronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 9.11 (s, 1H), 8.77 (d, 1H), 8.73 (s, 1H), 8.28 (s, 1H), 8.00 (s, 2H), 7.69-7.87 (m, 1H), 7.63 (d, 1H), 7.07 (d, 1H), 4.44 (d, 2H), 3.63 (d, 2H)

Example 83. 2-[(2E)-2-(aminomethyl)-3-fluoroprop-2-en-1-yl]-4-[3-(6-methoxypyridin-3-yl)phenyl]-2,4-dihydro-3H-1,2,4-triazol-3-one hydrochloride 2.0 mg of the title compound (yield: 6.2%) was prepared in the same fashion as Example 42, except that 35.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 18.0 mg of 2-methoxy-5-pyridinylboronic acid was used instead of 1-(5-(4,4,5,5-tetramethyl-1,3,2-dioxaborolan-2-yl)thiophen-2-yl)ethane-1-one in Step 1. MS (ESI) m/z=356.2 (M+H)+

Example 84. 2-[(2E)-2-(aminomethyl)-3-fluoroprop-2-en-1-yl]-4-{3-[6-(trifluoromethyl)pyridin-3-yl]phenyl}-2,4-dihydro-3H-1,2,4-triazol-3-one hydrochloride 22.0 mg of the title compound (yield: 54.7%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 26.8 mg of 2-(trifluoromethyl)pyridine-5-boronic acid was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 9.05 (d, 1H), 8.40 (s, 1H), 8.36 (dd, 1H), 8.04-8.08 (m, 1H), 7.94 (d, 1H), 7.76-7.85 (m, 2H), 7.64-7.75 (m, 1H), 7.20 (d, 1H), 4.57 (d, 2H), 3.76 (d, 2H)

Example 85. 2-[(2E)-2-(aminomethyl)-3-fluoroprop-2-en-1-yl]-4-[3-(6-chloropyridin-3-yl)phenyl]-2,4-dihydro-3H-1,2,4-triazol-3-one hydrochloride 19.5 mg of the title compound (yield: 52.6%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 33.6 mg of 2-chloropyridin-5-boronic acid was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.70 (d, 1H), 8.38 (s, 1H), 8.15 (dd, 1H), 7.98 (s, 1H), 7.74 (d, 2H), 7.64-7.71 (m, 1H), 7.58 (d, 1H), 7.19 (d, 1H), 4.56 (d, 2H), 3.76 (d, 2H)

Example 86. 2-[(2E)-2-(aminomethyl)-3-fluoroprop-2-en-1-yl]-4-{3-[6-(morpholin-4-yl)pyridin-3-yl]phenyl}-2,4-dihydro-3H-1,2,4-triazol-3-one hydrochloride 13.0 mg of the title compound (yield: 24.9%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 33.6 mg of 6-morpholinopyridin-3-ylboronic acid was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.38-8.39 (m, 2H), 8.30 (s, 1H), 7.97 (s, 1H), 7.73 (d, 2H), 7.66 (t, 1H), 7.49 (d, 1H), 7.20 (d, 1H), 4.56 (d, 2H), 3.89 (t, 4H), 3.70-3.76 (m, 6H)

Example 87. 2-[(2E)-2-(aminomethyl)-3-fluoroprop-2-en-1-yl]-4-{3-[6-methoxy-5-(trifluoromethyl)pyridin-3-yl]phenyl}-2,4-dihydro-3H-1,2,4-triazol-3-one hydrochloride 23.7 mg of the title compound (yield: 44.0%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 53.0 mg of 2-methoxy-3-(trifluoromethyl)pyridin-5-ylboronic acid was used instead of 1-(5-(4,4,5,5-tetramethyl-1,3,2-dioxaborolan-2-yl)thiophen-2-yl)ethane-1-one in Step 1. MS (ESI) m/z=424.2 (M+H)+

Example 88. 2-[(2E)-2-(aminomethyl)-3-fluoroprop-2-en-1-yl]-4-{3-[6-hydroxy-5-(trifluoromethyl)pyridin-3-yl]phenyl}-2,4-dihydro-3H-1,2,4-triazol-3-one hydrochloride 33.0 mg of the title compound (yield: 63.3%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 53.0 mg of 2-hydroxy-3-(trifluoromethyl)pyridin-5-ylboronic acid was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.35 (s, 1H), 8.29 (s, 1H), 8.06 (s, 1H), 7.85 (s, 1H), 7.59-7.66 (m, 2H), 7.10 (d, 1H), 4.55 (d, 2H), 3.65 (d, 2H)

Example 89. 5-(3-{1-[(2E)-2-(aminomethyl)-3-fluoroprop-2-en-1-yl]-5-oxo-1,5-dihydro-4H-1,2,4-triazol-4-yl}phenyl)-1,3-dimethylpyridin-2(1H)-one hydrochloride 18.6 mg of the title compound (yield: 49.0%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 35.0 mg of 1,3-dimethyl-5-(4,4,5,5-tetramethyl-1,3,2-dioxaborolan-2-yl)pyridin-2(1H)-one was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.35 (s, 1H), 7.94 (s, 1H), 7.81 (s, 2H), 7.48-7.69 (m, 3H), 7.20 (d, 1H), 4.55 (d, 2H), 3.76 (d, 2H), 3.66 (d, 3H), 2.20 (s, 3H)

Example 90. 5-(3-{1-[(2E)-2-(aminomethyl)-3-fluoroprop-2-en-1-yl]-5-oxo-1,5-dihydro-4H-1,2,4-triazol-4-yl}phenyl)-1-(propan-2-yl)pyridin-2(1H)-one hydrochloride 13.0 mg of the title compound (yield: 33.1%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 37.0 mg of 1-isopropyl-6-oxo-1,6-dihydropyridin-3-boronic acid pinacol ester was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.38 (s, 1H), 8.16 (s, 1H), 8.02 (d, 1H), 7.86 (s, 1H), 7.55-7.73 (m, 3H), 7.20 (d, 1H), 6.80 (d, 1H), 5.27 (d, 1H), 4.57 (d, 2H), 3.76 (d, 2H), 1.43-1.57 (m, 6H)

Example 91. 2-[(2E)-2-(aminomethyl)-3-fluoroprop-2-en-1-yl]-4-[3-(2-methylpyrimidin-5-yl)phenyl]-2,4-dihydro-3H-1,2,4-triazol-3-one hydrochloride 9.5 mg of the title compound (yield: 35.9%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 23.0 mg of 2-methylpyrimidine-5-boronic acid pinacol ester was used instead of 1-(5-(4,4,5,5-tetramethyl-1,3,2-dioxaborolan-2-yl)thiophen-2-yl)ethane-1-one in Step 1. $^1$H-NMR (DMSO-$d_6$, 400 MHz) δ 9.09 (s, 1H), 8.68 (s, 1H), 8.10 (s, 1H), 8.04 (s, 1H), 7.84 (dd, 2H), 7.68 (t, 1H), 7.22 (d, 1H), 4.52 (s, 2H), 3.54 (d, 2H), 2.68 (s, 3H)

Example 92. 2-[(2Z)-2-(aminomethyl)-3-fluoroprop-2-en-1-yl]-4-[3-(1,3-benzodioxol-5-yl)phenyl]-2,4-dihydro-3H-1,2,4-triazol-3-one hydrochloride 6.0 mg of the title compound (yield: 12.7%) was prepared in the same fashion as Example 42, except that 50.0 mg of tert-butyl (Z)-(2-((4-(3-bromophenyl)-5-oxo-4,5-dihydro-1H-1,2,4-triazol-1-yl)methyl)-3-fluoroallyl)carbamate prepared in Reference Example 49 was used instead of tert-butyl (Z)-(2-((4-(4-bromophenyl)-5-oxo-4,5-dihydro-1H-1,2,4-triazol-1-yl)methyl)-3-fluoroallyl)carbamate and 24.0 mg of 3,4-(methylenedioxy)phenyl boronic acid was used instead of 1-(5-(4,4,5,5-tetramethyl-1,3,2-dioxaborolan-2-yl)thiophen-2-yl)ethane-1-one in Step 1. $^1$H-NMR (DMSO-$d_6$, 400 MHz) δ 8.66 (s, 1H), 7.88 (s, 1H), 7.68 (d, 1H), 7.62 (d, 1H), 7.56 (t, 1H), 7.34 (d, 1H), 7.22 (dd, 1H), 7.20 (d, 1H), 7.03 (d, 1H), 6.08 (s, 2H), 4.62 (s, 2H), 3.48 (s, 2H)

Example 93. 2-[(2E)-2-(aminomethyl)-3-fluoroprop-2-en-1-yl]-4-[3-(1,3-benzodioxol-5-yl)phenyl]-2,4-dihydro-3H-1,2,4-triazol-3-one hydrochloride 12.4 mg of the title compound (yield: 26.2%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 24.0 mg of 3,4-(methylenedioxy)phenyl boronic acid was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.72 (s, 1H), 7.88 (s, 1H), 7.69 (d, 1H), 7.63 (d, 1H), 7.56 (t, 1H), 7.34 (d, 1H), 7.23 (dd, 1H), 7.22 (d, 1H), 7.04 (d, 1H), 6.08 (s, 2H), 4.52 (d, 2H), 3.56 (d, 2H)

Example 94. 2-[(2Z)-2-(aminomethyl)-3-fluoroprop-2-en-1-yl]-4-[3-(2,3-dihydro-1,4-benzodioxin-6-yl)phenyl]-2,4-dihydro-3H-1,2,4-triazol-3-one hydrochloride 7.0 mg of the title compound (yield: 14.3%) was prepared in the same fashion as Example 42, except that 50.0 mg of tert-butyl (Z)-(2-((4-(3-bromophenyl)-5-oxo-4,5-dihydro-1H-1,2,4-triazol-1-yl)methyl)-3-fluoroallyl)carbamate prepared in Reference Example 49 was used instead of tert-butyl (Z)-(2-((4-(4-bromophenyl)-5-oxo-4,5-dihydro-1H-1,2,4-triazol-1-yl)methyl)-3-fluoroallyl)carbamate and 32.0 mg of 1,4-benzodioxane-6-boronic acid was used instead of 1-(5-(4,4,5,5-tetramethyl-1,3,2-dioxaborolan-2-yl)thiophen-2-yl)ethane-1-one in Step 1. $^1$H-NMR (DMSO-d$_6$, 400 MHz) δ 8.65 (s, 1H), 7.88 (s, 1H), 7.67 (d, 1H), 7.61 (d, 1H), 7.55 (t, 1H), 7.25 (d, 1H), 7.20 (d, 1H), 7.19 (d, 1H), 6.97 (d, 1H), 4.62 (s, 2H), 4.28 (s, 4H), 3.48 (s, 2H)

Example 95. 2-[(2E)-2-(aminomethyl)-3-fluoroprop-2-en-1-yl]-4-[3-(2,3-dihydro-1,4-benzodioxin-6-yl)phenyl]-2,4-dihydro-3H-1,2,4-triazol-3-one hydrochloride 5.0 mg of the title compound (yield: 22.2%) was prepared in the same fashion as Example 42, except that 23.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 14.0 mg of 1,4-benzodioxane-6-boronic acid was used instead of 1-(5-(4,4,5,5-tetramethyl-1,3,2-dioxaborolan-2-yl)thiophen-2-yl)ethane-1-one in Step 1. $^1$H-NMR (DMSO-d$_6$, 400 MHz) δ 8.65 (s, 1H), 7.88 (s, 1H), 7.67 (d, 1H), 7.61 (d, 1H), 7.55 (t, 1H), 7.25 (d, 1H), 7.22 (d, 1H), 7.20 (dd, 1H), 6.97 (d, 1H), 4.51 (d, 2H), 4.28 (s, 4H), 3.54 (s, 2H)

Example 96. 2-[(2E)-2-(aminomethyl)-3-fluoroprop-2-en-1-yl]-4-[3-(2,1,3-benzooxadiazol-5-yl)phenyl]-2,4-dihydro-3H-1,2,4-triazol-3-one hydrochloride 8.0 mg of the title compound (yield: 17.0%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 44.0 mg of benzo[c][1,2,5]oxadiazole-5-boronic acid pinacol ester was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.08 (s, 1H), 8.05 (s, 1H), 8.02 (s, 1H), 7.93 (d, 1H), 7.91 (d, 1H), 7.84 (d, 1H), 7.77 (d, 1H), 7.70 (t, 1H), 7.21 (d, 1H), 4.57 (d, 2H), 3.77 (d, 2H)

Example 97. 2-[(2E)-2-(aminomethyl)-3-fluoroprop-2-en-1-yl]-4-[3-(1H-indazol-6-yl)phenyl]-2,4-dihydro-3H-1,2,4-triazol-3-one hydrochloride 4.0 mg of the title compound (yield: 12.2%) was prepared in the same fashion as Example 42, except that 35.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 19.0 mg of 1H-indazole-6-boronic acid was used instead of 1-(5-(4,4,5,5-tetramethyl-1,3,2-dioxaborolan-2-yl)thiophen-2-yl)ethane-1-one in Step 1. MS (ESI) m/z=365.2 (M+H)+

Example 98. 2-[(2E)-2-(aminomethyl)-3-fluoroprop-2-en-1-yl]-4-[3-(1H-indol-4-yl)phenyl]-2,4-dihydro-3H-1,2,4-triazol-3-one hydrochloride 4.0 mg of the title compound (yield: 13.4%) was prepared in the same fashion as Example 42, except that 35.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 29.0 mg of indole-4-boronic acid pinacol ester was used instead of 1-(5-(4,4,5,5-tetramethyl-1,3,2-dioxaborolan-2-yl)thiophen-2-yl)ethane-1-one in Step 1. MS (ESI) m/z=364.2 (M+H)+

Example 99. 4-[3-(2-amino-1,3-benzothiazol-5-yl)phenyl]-2-[(2E)-2-(aminomethyl)-3-fluoroprop-2-en-1-yl]-2,4-dihydro-3H-1,2,4-triazol-3-one hydrochloride 5.0 mg of the title compound (yield: 9.9%) was prepared in the same fashion as Example 42, except that 50.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 50.0 mg of 5-(4,4,5,5-tetramethyl-1,3,2-dioxaborolan-2-yl)benzo[d]thiazol-2-amine prepared in Reference Example 86 was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.36 (s, 1H), 7.97 (s, 1H), 7.84 (d, 1H), 7.73 (d, 2H), 7.61-7.66 (m, 3H), 7.20 (d, 1H), 4.56 (d, 2H), 3.76 (s, 2H)

Example 100. 2-[(2E)-2-(aminomethyl)-3-fluoroprop-2-en-1-yl]-4-[3-(1H-indol-3-yl)phenyl]-2,4-dihydro-3H-1,2,4-triazol-3-one hydrochloride 4.0 mg of the title compound (yield: 12.2%) was prepared in the same fashion as Example 42, except that 35.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 31.0 mg of 1-Boc-indole-3-boronic acid was used instead of 1-(5-(4,4,5,5-tetramethyl-1,3,2-dioxaborolan-2-yl)thiophen-2-yl)ethane-1-one in Step 1. MS (ESI) m/z=364.2 (M+H)+

Example 101. 2-[(2E)-2-(aminomethyl)-3-fluoroprop-2-en-1-yl]-4-[3-(1-benzothiophen-2-yl)phenyl]-2,4-dihydro-3H-1,2,4-triazol-3-one hydrochloride 14.7 mg of the title compound (yield: 37.7%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 25.0 mg of benzo[b]thiophen-2-ylboronic acid was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.37 (s, 1H), 8.09 (s, 1H), 7.74-7.96 (m, 3H), 7.52-7.68 (m, 2H), 7.33-7.49 (m, 2H), 7.20 (d, 1H), 4.57 (d, 2H), 3.76 (d, 2H)

Example 102. 6-(3-{1-[(2E)-2-(aminomethyl)-3-fluoroprop-2-en-1-yl]-5-oxo-1,5-dihydro-4H-1,2,4-triazol-4-yl}phenyl)-8-methyl-3,4-dihydroquinolin-2(1H)-one hydrochloride 15.2 mg of the title compound (yield: 48.8%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 30.0 mg of 8-methyl-2-oxo-1,2,3,4-tetrahydroquinoline-6-boronic acid pinacol ester was used instead of 1-(5-(4,4,5,5-tetramethyl-1,3,2-dioxaborolan-2-yl)thiophen-2-yl)ethane-1-one in Step 1. $^1$H-NMR (DMSO-$d_6$, 400 MHz) δ 9.57 (s, 1H), 8.64 (s, 1H), 7.90 (s, 1H), 7.64 (d, 2H), 7.56 (t, 1H), 7.41 (d, 2H), 7.22 (d, 1H), 4.51 (s, 2H), 3.56 (s, 2H), 2.92-2.95 (m, 2H), 2.42-2.49 (m, 2H), 2.29 (s, 3H)

Example 103. 6-(3-{1-[(2E)-2-(aminomethyl)-3-fluoroprop-2-en-1-yl]-5-oxo-1,5-dihydro-4H-1,2,4-triazol-4-yl}phenyl)-2H-1,4-benzoxazin-3(4H)-one hydrochloride 13.3 mg of the title compound (yield: 32.9%) was prepared in the same fashion as Example 42, except that 40.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 39.0 mg of 6-(4,4,5,5-tetramethyl-1,3,2-dioxaborolan-2-yl)-2H-benzo[b][1,4]oxazin-3(4H)-one was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.33 (s, 1H), 7.86 (s, 1H), 7.49-7.70 (m, 3H), 7.24-7.36 (m, 2H), 7.19 (s, 1H), 7.07 (d, 1H), 7.06 (s, 1H), 4.62 (d, 2H), 4.56 (s, 2H), 3.76 (d, 2H)

Example 104. 2-[(2E)-2-(aminomethyl)-3-fluoroprop-2-en-1-yl]-4-[3-(isoquinolin-4-yl)phenyl]-2,4-dihydro-3H-1,2,4-triazol-3-one hydrochloride 11.6 mg of the title compound (yield: 40.2%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 18.0 mg of isoquinoline-4-boronic acid was used instead of 1-(5-(4,4,5,5-tetramethyl-1,3,2-dioxaborolan-2-yl)thiophen-2-yl)ethane-1-one in Step 1. 41-NMR (DMSO-$d_6$, 400 MHz) δ 9.65 (s, 1H), 8.67 (s, 1H), 8.61 (s, 1H), 8.43 (d, 1H), 7.91-8.01 (m, 5H), 7.76 (t, 1H), 7.61 (d, 1H), 7.20 (d, 1H), 4.52 (d, 2H), 3.53 (d, 2H)

Example 105. 2-[(2E)-2-(aminomethyl)-3-fluoroprop-2-en-1-yl]-4-[3-(8-methylquinolin-5-yl)phenyl]-2,4-dihydro-3H-1,2,4-triazol-3-one hydrochloride 4.0 mg of the title compound (yield: 13.4%) was prepared in the same fashion as Example 42, except that 30.0 mg of tert-butyl (E)-(2-((4-(3-bromophenyl)-5-oxo-4,5-dihydro-1H-1,2,4-triazol-1-yl)methyl)-3-fluoroallyl)carbamate prepared in Reference Example 50 was used instead of tert-butyl (Z)-(2-((4-(4-bromophenyl)-5-oxo-4,5-dihydro-1H-1,2,4-triazol-1-yl)methyl)-3-fluoroallyl)carbamate and 20.0 mg of 8-methyl-5-quinoline boronic acid was used instead of 1-(5-(4,4,5,5-tetramethyl-1,3,2-dioxaborolan-2-yl)thiophen-2-yl)ethane-1-one in Step 1. MS (ESI) m/z=390.2 (M+H)+

Example 106. 2-[(2E)-2-(aminomethyl)-3-fluoroprop-2-en-1-yl]-4-[2-methyl-4'-(methylsulfonyl)biphenyl-3-yl]-2,4-dihydro-3H-1,2,4-triazol-3-one 19.3 mg of the title compound (yield: 73.5%) was prepared in the same fashion as Example 43, except that 30.0 mg of tert-butyl (E)-(2-((4-(3-bromo-2-methylphenyl)-5-oxo-4,5-dihydro-1H-1,2,4-triazol-1-yl)methyl)-3-fluoroallyl)carbamate prepared in Reference Example 57 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 34.0 mg of 4-(methanesulfonyl)phenylboronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. 41-NMR (MeOD, 400 MHz) δ 8.07 (s, 1H), 8.05 (d, 2H), 7.64 (d, 2H), 7.45 (m, 3H), 7.09-7.29 (m, 1H), 4.57 (s, 2H), 3.77 (s, 2H), 3.18 (s, 3H), 2.10 (s, 3H)

Example 107. N-(3'-{1-[(2E)-2-(aminomethyl)-3-fluoroprop-2-en-1-yl]-5-oxo-1,5-dihydro-4H-1,2,4-triazol-4-yl}-2'-methylbiphenyl-4-yl)acetamide 14.7 mg of the title compound (yield: 58.8%) was prepared in the same fashion as Example 43, except that 30.0 mg of tert-butyl (E)-(2-((4-(3-bromo-2-methylphenyl)-5-oxo-4,5-dihydro-1H-1,2,4-triazol-1-yl)methyl)-3-fluoroallyl)carbamate prepared in Reference Example 57 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 30.4 mg of 4-acetylamidobenzene boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.04 (s, 1H), 7.65 (d, 2H), 7.40 (m, 2H), 7.09-7.33 (m, 1H), 7.29 (m, 4H), 4.57 (s, 2H), 3.76 (s, 2H), 2.15 (s, 3H), 2.10 (s, 3H)

Example 108. 2-[(2E)-2-(aminomethyl)-3-fluoroprop-2-en-1-yl]-4-[2-methyl-4'-(1,2-oxazol-3-yl)biphenyl-3-yl]-2,4-dihydro-3H-1,2,4-triazol-3-one 11.3 mg of the title compound (yield: 44.1%) was prepared in the same fashion as Example 43, except that 30.0 mg of tert-butyl (E)-(2-((4-(3-bromo-2-methylphenyl)-5-oxo-4,5-dihydro-1H-1,2,4-triazol-1-yl)methyl)-3-fluoroallyl)carbamate prepared in Reference Example 57 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 46.1 mg of 3-(4-(4,4,5,5-tetramethyl-1,3,2-dioxaborolan-2-yl)phenyl)-isoxazole was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.75 (s, 1H), 8.0 (s, 1H), 7.97 (d, 2H), 7.50 (d, 2H), 7.45 (s, 2H), 7.39 (m, 1H), 7.10-7.39 (m, 1H), 6.98 (s, 1H), 4.58 (s, 2H), 3.76 (s, 2H), 2.13 (s, 3H)

Example 109. N-[4-(3-{1-[(2E)-2-(aminomethyl)-3-fluoroprop-2-en-1-yl]-5-oxo-1,5-dihydro-4H-1,2,4-triazol-4-yl}-2-methylphenyl)pyridin-2-yl]acetamide 15.2 mg of the title compound (yield: 58.8%) was prepared in the same fashion as Example 43, except that 30.0 mg of tert-butyl (E)-(2-((4-(3-bromo-2-methylphenyl)-5-oxo-4,5-dihydro-1H-1,2,4-triazol-1-yl)methyl)-3-fluoroallyl)carbamate prepared in Reference Example 57 was used instead of 44.6 mg of tert-butyl (E)-(2-((4-(4-bromo-2-fluorophenyl)-5-oxo-4,5-dihydro-1H-1,2,4-triazol-1-yl)methyl)-3-fluoroallyl)carbamate and 44.6 mg of N-(4-(4,4,5,5,-tetramethyl-1,3,2-dioxaborolan-2-yl)pyridin-2-yl)acetamide was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.37 (m, 1H), 8.09 (m, 2H), 7.43 (m, 3H), 7.09-7.29 (m, 2H), 4.57 (s, 2H), 3.76 (s, 2H), 2.19 (s, 3H), 2.13 (s, 3H)

Example 110. 2-[(2E)-2-(aminomethyl)-3-fluoroprop-2-en-1-yl]-4-{2-methyl-3-[6-(morpholin-4-yl)pyridin-3-yl]phenyl}-2,4-dihydro-3H-1,2,4-triazol-3-one 17.0 mg of the title compound (yield: 58.8%) was prepared in the same fashion as Example 43, except that 30.0 mg of tert-butyl (E)-(2-((4-(3-bromo-2-methylphenyl)-5-oxo-4,5-dihydro-1H-1,2,4-triazol-1-yl)methyl)-3-fluoroallyl)carbamate prepared in Reference Example 57 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 49.3 mg of 6-(morpholin-4-yl)pyridin-3-boronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.05 (s, 2H), 7.86 (d, 1H), 7.42 (m, 3H), 7.09-7.29 (m, 1H), 7.21 (d, 1H), 4.57 (s, 2H), 3.86 (m, 4H), 3.76 (s, 2H), 3.65 (m, 4H), 2.13 (s, 3H)

Example 111. 2-[(2E)-2-(aminomethyl)-3-fluoroprop-2-en-1-yl]-4-[3-(1,3-benzodioxol-5-yl)-2-methylphenyl]-2,4-dihydro-3H-1,2,4-triazol-3-one 13.0 mg of the title compound (yield: 44.1%) was prepared in the same fashion as Example 43, except that 30.0 mg of tert-butyl (E)-(2-((4-(3-bromo-2-methylphenyl)-5-oxo-4,5-dihydro-1H-1,2,4-triazol-1-yl)methyl)-3-fluoroallyl)carbamate prepared in Reference Example 57 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 28.2 mg of 3,4-(methylenedioxy)phenylboronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.03 (s, 1H), 7.37 (s, 2H), 7.32 (m, 1H), 7.08-7.29 (m, 1H), 6.90 (m, 1H), 6.79 (m, 2H), 5.99 (s, 2H), 4.57 (s, 2H), 3.76 (s, 2H), 2.09 (s, 3H)

Example 112. 2-[(2E)-2-(aminomethyl)-3-fluoroprop-2-en-1-yl]-4-[3-(2,3-dihydro-1,4-benzodioxin-6-yl)-2-methylphenyl]-2,4-dihydro-3H-1,2,4-triazol-3-one 15.0 mg of the title compound (yield: 58.8%) was prepared in the same fashion as Example 43, except that 30.0 mg of tert-butyl (E)-(2-((4-(3-bromo-2-methylphenyl)-5-oxo-4,5-dihydro-1H-1,2,4-triazol-1-yl)methyl)-3-fluoroallyl)carbamate prepared in Reference Example 57 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 30.4 mg of 1,4-benzodioxane-6-boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.03 (s, 1H), 7.35 (m, 2H), 7.28 (m, 1H), 7.06-7.26 (m, 1H), 6.91 (m, 1H), 6.80 (m, 2H), 4.56 (s, 2H), 4.27 (s, 4H), 3.72 (s, 2H), 2.09 (s, 3H)

Example 113. 2-[(2E)-2-(aminomethyl)-3-fluoroprop-2-en-1-yl]-4-[3-(2,1,3-benzooxadiazol-5-yl)-2-methylphenyl]-2,4-dihydro-3H-1,2,4-triazol-3-one 21.0 mg of the title compound (yield: 88.2%) was prepared in the same fashion as Example 43, except that 30.0 mg of tert-butyl (E)-(2-((4-(3-bromo-2-methylphenyl)-5-oxo-4,5-dihydro-1H-1,2,4-triazol-1-yl)methyl)-3-fluoroallyl)carbamate prepared in Reference Example 57 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 41.8 mg of benzo[c][1,2,5]oxadiazole-5-boronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.08 (s, 1H), 8.00 (d, 1H), 7.87 (s, 1H), 7.52 (m, 4H), 7.10-7.30 (m, 1H), 4.58 (s, 2H), 3.77 (s, 2H), 2.15 (s, 3H)

Example 114. 4-[3-(2-amino-1,3-benzothiazol-5-yl)-2-methylphenyl]-2-[(2E)-2-(aminomethyl)-3-fluoroprop-2-en-1-yl]-2,4-dihydro-3H-1,2,4-triazol-3-one 13.0 mg of the title compound (yield: 44.1%) was prepared in the same fashion as Example 43, except that 30.0 mg of tert-butyl (E)-(2-((4-(3-bromo-2-methylphenyl)-5-oxo-4,5-dihydro-1H-1,2,4-triazol-1-yl)methyl)-3-fluoroallyl)carbamate prepared in Reference Example 57 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 46.9 mg of 5-(4,4,5,5-tetramethyl-1,3,2-dioxaborolan-2-yl)benzo[d]thiazol-2-amine prepared in Reference Example 86 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.06 (s, 1H), 7.73 (d, 1H), 7.41 (s, 2H), 7.38 (s, 2H), 7.29 (s, 1H), 7.15 (d, 1H), 7.09 (s, 1H), 4.57 (s, 2H), 3.76 (s, 2H), 2.11 (s, 3H)

Example 115. 2-[(2E)-2-(aminomethyl)-3-fluoroprop-2-en-1-yl]-4-{5-methyl-6-[4-(1H-1,2,4-triazol-3-yl)phenyl]pyridin-3-yl}-2,4-dihydro-3H-1,2,4-triazol-3-one 15.0 mg of the title compound (yield: 58.8%) was prepared in the same fashion as Example 43, except that 30.0 mg of tert-butyl (E)-(2-((4-(6-bromo-5-methylpyridin-3-yl)-5-oxo-4,5-dihydro-1H-1,2,4-triazol-1-yl)methyl)-3-fluoroallyl)carbamate prepared in Reference Example 61 was used in Step 1 instead of tert-butyl (E)-(2-((4-(4-bromo-2-fluorophenyl)-5-oxo-4,5-dihydro-1H-1,2,4-triazol-1-yl)methyl)-3-fluoroallyl)carbamate. $^1$H-NMR (MeOD, 400 MHz) δ 9.15 (d, 1H), 8.86 (s, 1H), 8.61 (d, 1H), 8.55 (s, 1H), 8.27 (m, 2H), 7.78 (d, 2H), 7.12-7.32 (m, 1H), 4.60 (s, 2H), 3.79 (s, 2H), 2.56 (s, 3H)

Example 116. 2-[(2E)-2-(aminomethyl)-3-fluoroprop-2-en-1-yl]-4-{5-methyl-6-[3-(1H-1,2,4-triazol-3-yl)phenyl]pyridin-3-yl}-2,4-dihydro-3H-1,2,4-triazol-3-one 11.1 mg of the title compound (yield: 44.1%) was prepared in the same fashion as Example 43, except that 30.0 mg of tert-butyl (E)-(2-((4-(6-bromo-5-methylpyridin-3-yl)-

5-oxo-4,5-dihydro-1H-1,2,4-triazol-1-yl)methyl)-3-fluoroallyl)carbamate prepared in Reference Example 61 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 68.2 mg of 3-(3-(4,4,5,5-tetramethyl-1,3,2-dioxaborolan-2-yl)phenyl)-1-((2-(trimethylsilyl)ethoxy)methyl)-1H-1,2,4-triazole prepared in Reference Example 32 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 9.04 (s, 1H), 8.74 (s, 1H), 8.18-8.26 (m, 6H), 7.12-7.32 (m, 1H)

Example 117. 2-[(2E)-2-(aminomethyl)-3-fluoroprop-2-en-1-yl]-4-[6-(1,3-benzodioxol-5-yl)-5-methylpyridin-3-yl]-2,4-dihydro-3H-1,2,4-triazol-3-one 23.2 mg of the title compound (yield: 88.2%) was prepared in the same fashion as Example 43, except that 30.0 mg of tert-butyl (E)-(2-((4-(6-bromo-5-methylpyridin-3-yl)-5-oxo-4,5-dihydro-1H-1,2,4-triazol-1-yl)methyl)-3-fluoroallyl)carbamate prepared in Reference Example 61 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 27.8 mg of 3,4-(methylenedioxy)phenylboronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 9.22 (d, 1H), 8.08 (s, 1H), 8.59 (s, 1H), 7.16-7.31 (m, 1H), 7.10-7.18 (m, 3H), 6.13 (s, 2H), 4.59 (d, 2H), 3.78 (s, 2H), 2.57 (s, 3H)

Example 118. 4-[6-(2-amino-1,3-benzothiazol-5-yl)-5-methylpyridin-3-yl]-2-[(2E)-2-(aminomethyl)-3-fluoroprop-2-en-1-yl]-2,4-dihydro-3H-1,2,4-triazol-3-one hydrochloride 21.2 mg of the title compound (yield: 73.5%) was prepared in the same fashion as Example 42, except that 30.0 mg of tert-butyl (E)-(2-((4-(6-bromo-5-methylpyridin-3-yl)-5-oxo-4,5-dihydro-1H-1,2,4-triazol-1-yl)methyl)-3-fluoroallyl)carbamate prepared in Reference Example 61 was used instead of tert-butyl (Z)-(2-((4-(4-bromophenyl)-5-oxo-4,5-dihydro-1H-1,2,4-triazol-1-yl)methyl)-3-fluoroallyl)carbamate and 46.9 mg of 5-(4,4,5,5-tetramethyl-1,3,2-dioxaborolan-2-yl)benzo[d]thiazol-2-amine prepared in Reference Example 86 was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 9.16 (s, 1H), 8.62 (s, 1H), 8.55 (s, 1H), 8.06 (d, 1H), 7.79 (s, 1H), 7.63 (m, 1H), 7.12-7.32 (m, 1H), 4.59 (d, 2H), 3.78 (s, 2H), 2.53 (s, 3H)

Example 119. 2-[(2E)-2-(aminomethyl)-3-fluoroprop-2-en-1-yl]-4-{4-methyl-6-[4-(methylsulfonyl)phenyl]pyridin-3-yl}-2,4-dihydro-3H-1,2,4-triazol-3-one 29.3 mg of the title compound (yield: 100%) was prepared in the same fashion as Example 43, except that 30.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 34.0 mg of 4-(methanesulfonyl)phenylboronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.62 (s, 1H), 8.33 (d, 2H), 8.14 (s, 1H), 8.08 (m, 3H), 7.11-7.31 (m, 1H), 4.58 (s, 2H), 3.78 (s, 2H), 3.18 (s, 3H), 2.42 (s, 3H)

Example 120. N-[4-(5-{1-[(2E)-2-(aminomethyl)-3-fluoroprop-2-en-1-yl]-5-oxo-1,5-dihydro-4H-1,2,4-triazol-4-yl}-4-methylpyridin-2-yl)phenyl]acetamide 21.0 mg of the title compound (yield: 73.5%) was prepared in the same fashion as Example 43, except that 30.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 30.4 mg of 4-acetamidobenzene boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.50 (s, 1H), 8.1.0 (s, 1H), 8.00 (d, 2H), 7.90 (s, 1H), 7.71 (d, 2H), 7.10-7.30 (m, 1H), 4.57 (d, 2H), 3.31 (s, 2H), 2.40 (s, 3H), 2.16 (s, 3H)

Example 121. 2-[(2E)-2-(aminomethyl)-3-fluoroprop-2-en-1-yl]-4-{4-methyl-6-[4-(1H-1,2,4-triazol-3-yl)phenyl]pyridin-3-yl}-2,4-dihydro-3H-1,2,4-triazol-3-one 6.1 mg of the title compound (yield: 22.1%) was prepared in the same fashion as Example 43, except that 30.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used in Step 1 instead of tert-butyl (E)-(2-((4-(4-bromo-2-fluorophenyl)-5-oxo-4,5-dihydro-1H-1,2,4-triazol-1-yl)methyl)-3-fluoroallyl)carbamate. (MeOD, 400 MHz) δ 8.79 (s, 1H), 8.40 (s, 1H), 8.35 (s, 1H), 8.14 (d, 2H), 8.09 (m, 1H), 7.64 (d, 2H), 6.89-7.09 (m, 1H), 4.50 (m, 2H), 3.51 (s, 2H), 2.43 (s, 3H)

Example 122. 2-[(2E)-2-(aminomethyl)-3-fluoroprop-2-en-1-yl]-4-{4-methyl-6-[3-(1H-1,2,4-triazol-3-yl)phenyl]pyridin-3-yl}-2,4-dihydro-3H-1,2,4-triazol-3-one 18.9 mg of the title compound (yield: 68.4%) was prepared in the same fashion as Example 43, except that 30.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 68.2 mg of 3-(3-(4,4,5,5-tetramethyl-1,3,2-dioxaborolan-2-yl)phenyl)-1-((2-(trimethylsilyl)ethoxy)methyl)-1H-1,2,4-triazole prepared in Reference Example 32 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.73 (s, 1H), 8.59 (s, 1H), 8.44 (brs, 1H), 8.13 (m, 3H), 8.03 (s, 1H), 7.63 (m, 1H), 7.11-7.31 (m, 1H), 4.58 (s, 2H), 3.79 (s, 2H), 2.42 (s, 3H)

Example 123. N-(5-{1-[(2E)-2-(aminomethyl)-3-fluoroprop-2-en-1-yl]-5-oxo-1,5-dihydro-4H-1,2,4-triazol-4-yl}-4-methyl-2,4'-bipyridin-2'-yl)acetamide 37.3 mg of the title compound (yield: 100%) was prepared in the same fashion as Example 43, except that 30.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 44.6 mg of N-(4-(4,4,5,5,-tetramethyl-1,3,2-dioxaborolan-2-yl)pyridin-2-yl)acetamide was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.72 (s, 1H), 8.62 (s, 1H), 8.41 (d, 1H), 8.14 (s, 1H), 8.02 (s, 1H), 7.74 (m, 1H), 7.10-7.31 (m, 1H), 4.58 (d, 2H), 3.78 (s, 2H), 2.41 (s, 3H), 2.22 (s, 3H)

Example 124. 2-[(2E)-2-(aminomethyl)-3-fluoroprop-2-en-1-yl]-4-[4-methyl-6'-(morpholin-4-yl)-2,3'-bipyridin-5-yl]-2,4-dihydro-3H-1,2,4-triazol-3-one 29.2 mg of the title compound (yield: 100%) was prepared in the same fashion as Example 43, except that 30.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 49.3 mg of 6-(morpholin-4-yl)pyridine-3-boronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.79 (s, 1H), 8.50 (s, 1H), 8.33 (d, 1H), 8.10 (s, 1H), 7.88 (s, 1H), 7.10-7.30 (m, 1H), 7.04 (d, 1H), 4.57 (s, 2H), 3.83 (m, 4H), 3.78 (s, 2H), 3.64 (m, 4H), 2.37 (s, 3H)

Example 125. 2-[(2E)-2-(aminomethyl)-3-fluoroprop-2-en-1-yl]-4-[6-(2,1,3-benzooxadiazol-5-yl)-4-methylpyridin-3-yl]-2,4-dihydro-3H-1,2,4-triazol-3-one 32.5 mg of the title compound (yield: 100%) was prepared in the same fashion as Example 43, except that 30.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 41.8 mg of benzo[c][1,2,5]oxadiazole-5-boronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.64 (s, 1H), 8.58 (s, 1H), 8.33 (d, 1H), 8.15 (s, 2H), 8.02 (d, 1H), 7.11-7.31 (m, 1H), 4.59 (s, 2H), 3.80 (s, 2H), 3.30 (s, 3H)

Example 126. 2-[(2E)-2-(aminomethyl)-3-fluoroprop-2-en-1-yl]-4-[6-(1H-indazol-6-yl)-4-methylpyridin-3-yl]-2,4-dihydro-3H-1,2,4-triazol-3-one 6.6 mg of the title compound (yield: 25.6%) was prepared in the same fashion as Example 43, except that 30.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 27.5 mg of indazole-6-boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.60 (s, 1H), 8.25 (s, 1H), 8.16 (s, 1H), 8.13 (s, 1H), 8.05 (s, 1H), 7.84-7.94 (m, 2H), 7.13-7.34 (m, 1H), 4.61 (s, 2H), 3.81 (s, 2H), 2.44 (s, 3H)

Example 127. 4-[6-(2-amino-1,3-benzothiazol-5-yl)-4-methylpyridin-3-yl]-2-[(2E)-2-(aminomethyl)-3-fluoroprop-2-en-1-yl]-2,4-dihydro-3H-1,2,4-triazol-3-one 21.7 mg of the title compound (yield: 77.6%) was prepared in the same fashion as Example 43, except that 30.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 46.9 mg of 5-(4,4,5,5-tetramethyl-1,3,2-dioxaborolan-2-yl)benzo[d]thiazol-2-amine prepared in Reference Example 86 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.53 (s, 1H), 8.12 (s, 1H), 8.04 (s, 1H), 7.95 (s, 1H), 7.71-7.76 (m, 2H), 7.10-7.30 (m, 1H), 4.58 (d, 2H), 3.78 (s, 2H), 2.39 (s, 3H)

Example 128. N-[5-(5-{1-[(2E)-2-(aminomethyl)-3-fluoroprop-2-en-1-yl]-5-oxo-1,5-dihydro-4H-1,2,4-triazol-4-yl}-4-methylpyridin-2-yl)-1,3-benzothiazol-2-yl]acetamide 24.2 mg of the title compound (yield: 78.5%) was prepared in the same fashion as Example 43, except that 30.0 mg of tert-butyl (E)-(2-((4-(6-bromo-4-methylpyridin-3-yl)-5-oxo-4,5-dihydro-1H-1,2,4-triazol-1-yl)methyl)-3-fluoroallyl)carbamate prepared in Reference Example 62 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 54.1 mg of N-(5-(4,4,5,5-tetramethyl-1,3,2-dioxaborolan-2-yl)benzo[d]thiazol-2-yl)acetamide prepared in Reference Example 87 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.56 (s, 1H), 8.40 (s, 1H), 8.13 (s, 1H), 7.98-8.01 (m, 3H), 7.11-7.31 (m, 1H), 4.59 (d, 2H), 3.78 (s, 2H), 2.40 (s, 3H), 2.28 (s, 3H)

Example 129. 2-[(2Z)-2-(aminomethyl)-3-fluoroprop-2-en-1-yl]-4-{5-[4-(methylsulfonyl)phenyl]pyridin-2-yl}-2,4-dihydro-3H-1,2,4-triazol-3-one hydrochloride 5.1 mg of the title compound (yield: 16.6%) was prepared in the same fashion as Example 42, except that 30.0 mg of tert-butyl (Z)-(2-((4-(5-bromopyridin-2-yl)-5-oxo-4,5-dihydro-1H-1,2,4-triazol-1-yl)methyl)-3-fluoroallyl)carbamate prepared in Reference Example 63 was used instead of tert-butyl (Z)-(2-((4-(4-bromophenyl)-5-oxo-4,5-dihydro-1H-1,2,4-triazol-1-yl)methyl)-3-fluoroallyl)carbamate and 18.2 mg of (4-(methylsulfonyl)phenyl)boronic acid was used instead of 1-(5-(4,4,5,5-tetramethyl-1,3,2-dioxaborolan-2-yl)thiophen-2-yl)ethane-1-one in Step 1. MS (ESI) m/z=404.1 (M+H)+

Example 130. N-[4-(6-{1-[(2Z)-2-(aminomethyl)-3-fluoroprop-2-en-1-yl]-5-oxo-1,5-dihydro-4H-1,2,4-triazol-4-yl}pyridin-3-yl)phenyl]acetamide hydrochloride 2.5 mg of the title compound (yield: 8.5%) was prepared in the same fashion as Example 42, except that 30.0 mg of tert-butyl (Z)-(2-((4-(5-bromopyridin-2-yl)-5-oxo-4,5-dihydro-1H-1,2,4-triazol-1-yl)methyl)-3-fluoroallyl)carbamate prepared in Reference Example 63 was used instead of tert-butyl (Z)-(2-((4-(4-bromophenyl)-5-oxo-4,5-dihydro-1H-1,2,4-triazol-1-yl)methyl)-3-fluoroallyl)carbamate and 16.3 mg of (4-acetamidophenyl)boronic acid was used instead of 1-(5-(4,4,5,5-tetramethyl-1,3,2-dioxaborolan-2-yl)thiophen-2-yl)ethane-1-one in Step 1. MS (ESI) m/z=383.2 (M+H)+

Example 131. 2-[(2E)-2-(aminomethyl)-3-fluoroprop-2-en-1-yl]-4-[3-methyl-5-(piperazin-1-yl)pyridin-2-yl]-2,4-dihydro-3H-1,2,4-triazol-3-one 40.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66, 41.9 mg of 1-Boc-piperazine, 8.2 mg of bis(dibenzylideneacetone)palladium(0) (Pd(dba)$_2$), 10.4 mg of Xantphos, and 87.9 mg of cesium carbonate were dissolved in 1.0 mL of 1,4-dioxane, and the resulting solution was stirred overnight at 96° C. The filtrate obtained by filtration of the reaction mixture with a celite pad was concentrated under reduced pressure to give a brown liquid residue. The residue was purified with silica gel column chromatography (developing solution: n-hexane/ethyl acetate=1/1) to give a compound as a white solid, and the compound thus obtained was dissolved in 1.0 mL of dichloromethane, 0.5 mL of trifluoroacetic acid was added to the resulting solution, and the solution was stirred overnight at room temperature. The residue obtained by concentration under reduced pressure was dissolved in dichloromethane, and the solution thus obtained was washed with an aqueous solution of sodium bicarbonate and brine, dried over anhydrous magnesium sulfate, and concentrated under reduced pressure to give a yellow liquid residue. The residue was purified with silica gel column chromatography (developing solution: dichloromethane/methanol=90/1) to give 4.7 mg of the title compound as a yellow liquid (yield: 15.0%). $^1$H-NMR (MeOD, 400 MHz) δ 8.17 (s, 1H), 8.08 (s, 1H), 7.54 (s, 1H), 7.10-7.30 (m, 1H), 4.57 (s, 2H), 3.77 (s, 2H), 3.59 (m, 4H), 3.40 (m, 4H), 2.31 (s, 3H)

Example 132. 4-[5-(5-acetylthiophen-2-yl)-3-methylpyridin-2-yl]-2-[(2E)-2-(aminomethyl)-3-fluoroprop-2-en-1-yl]-2,4-dihydro-3H-1,2,4-triazol-3-one hydrochloride 2.2 mg of the title compound (yield: 7.6%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used in Step 1 instead of tert-butyl (Z)-(2-((4-(4-bromophenyl)-5-oxo-4,5-dihydro-1H-1,2,4-triazol-1-yl)methyl)-3-fluoroallyl)carbamate. $^1$H-NMR (MeOD, 400 MHz) δ 8.77 (s, 1H), 8.24 (s, 1H), 8.17 (s, 1H), 7.91 (d, 1H), 7.68 (d, 1H), 7.18 (d, 1H), 4.61 (s, 2H), 4.55 (s, 2H), 3.74 (s, 2H), 2.60 (s, 3H), 2.42 (s, 3H)

Example 133. 2-[(2E)-2-(aminomethyl)-3-fluoroprop-2-en-1-yl]-4-{3-methyl-5-[4-(methylsulfonyl)phenyl]pyridin-2-yl}-2,4-dihydro-3H-1,2,4-triazol-3-one hydrochloride 4.0 mg of the title compound (yield: 13.0%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 17.6 mg of (4-(methylsulfonyl)phenyl)boronic acid was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.76 (s, 1H), 8.27 (s, 1H), 8.19 (s, 1H), 8.11 (d, 2H), 8.00 (d, 1H), 7.19 (d, 1H), 4.58 (d, 4H), 3.74 (s, 2H), 3.18 (s, 3H), 2.45 (s, 3H)

Example 134. N-[4-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)phenyl]acetamide hydrochloride 3.1 mg of the title compound (yield: 10.5%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 15.8 mg of (4-acetamidophenyl)boronic acid was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.66 (s, 1H), 8.16 (d, 2H), 7.71 (m, 4H), 7.15 (d, 1H), 4.61 (s, 6H), 4.56 (s, 2H), 3.70 (s, 2H)

Example 135. 2-[(2Z)-2-(aminomethyl)-3-fluoroprop-2-en-1-yl]-4-{3-methyl-5-[4-(4H-1,2,4-triazol-3-yl)phenyl]pyridin-2-yl}-2,4-dihydro-3H-1,2,4-triazol-3-one 13.2 mg of the title compound (yield: 47.8%) was prepared in the same fashion as Example 43, except that 30.0 mg of tert-butyl (Z)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 65 was used in Step 1 instead of tert-butyl (E)-(2-((4-(4-bromo-2-fluorophenyl)-5-oxo-4,5-dihydro-1H-1,2,4-triazol-1-yl)methyl)-3-fluoroallyl)carbamate. $^1$H-NMR (MeOD, 400 MHz) δ 8.74 (s, 1H), 8.45 (s, 1H), 8.24 (s, 1H), 8.19 (d, 3H), 7.87 (d, 2H), 7.10 (d, 1H), 4.75 (s, 2H), 4.57 (s, 2H), 3.62 (s, 2H), 2.44 (s, 3H)

Example 136. 2-[(2E)-2-(aminomethyl)-3-fluoroprop-2-en-1-yl]-4-{3-methyl-5-[4-(4H-1,2,4-triazol-3-yl)phenyl]pyridin-2-yl}-2,4-dihydro-3H-1,2,4-triazol-3-one 1.3 mg of the title compound (yield: 4.7%) was prepared in the same fashion as Example 43, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used in Step 1 instead of tert-butyl (E)-(2-((4-(4-bromo-2-fluorophenyl)-5-oxo-4,5-dihydro-1H-1,2,4-triazol-1-yl)

methyl)-3-fluoroallyl)carbamate. ¹H-NMR (DMSO-d₆, 400 MHz) δ 8.81 (s, 1H), 8.40 (s, 1H), 8.31 (s, 1H), 7.85-8.19 (m, 8H), 7.15 (d, 1H), 4.53 (s, 2H), 3.56 (s, 2H), 2.38 (s, 3H)

Example 137. 2-[(2E)-2-(aminomethyl)-3-fluoro-prop-2-en-1-yl]-4-{3-methyl-5-[3-(4H-1,2,4-triazol-3-yl)phenyl]pyridin-2-yl}-2,4-dihydro-3H-1,2,4-triazol-3-one 8.8 mg of the title compound (yield: 31.8%) was prepared in the same fashion as Example 43, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 35.4 mg of 3-(3-(4,4,5,5-tetramethyl-1,3,2-dioxaborolan-2-yl)phenyl)-1-((2-(trimethyl silyl)ethoxy)methyl)-1H-1,2,4-triazole prepared in Reference Example 32 was used instead of 3-(4-(4,4,5,5-tetramethyl-1,3,2-dioxaborolan-2-yl)phenyl)-1-((2-(trimethyl silyl)ethoxy)methyl)-1H-1,2,4-triazol e in Step 1. ¹H-NMR (DMSO-d₆, 400 MHz) δ 8.82 (s, 1H), 8.42 (d, 2H), 8.34 (s, 1H), 8.14 (d, 3H), 7.89 (m, 1H), 7.71 (t, 1H), 7.17 (d, 1H), 4.56 (s, 2H), 3.60 (s, 2H), 2.43 (s, 3H)

Example 138. 2-[(2E)-2-(aminomethyl)-3-fluoro-prop-2-en-1-yl]-4-{3-methyl-5-[4-(1,2,5-oxadiazol-3-yl)phenyl]pyridin-2-yl}-2,4-dihydro-3H-1,2,4-triazol-3-one hydrochloride 5.1 mg of the title compound (yield: 16.9%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 24.0 mg of 3-(4-(4,4,5,5-tetramethyl-1,3,2-dioxaborolan-2-yl)phenyl)-1,2,5-oxadiazole was used instead of 1-(5-(4,4,5,5-tetramethyl-1,3,2-dioxaborolan-2-yl)thiophen-2-yl)ethane-1-one in Step 1. ¹H-NMR (MeOD, 400 MHz) δ 8.74 (s, 1H), 8.24 (s, 1H), 8.19 (s, 1H), 7.94 (d, 2H), 7.86 (d, 2H), 7.20 (d, 1H), 4.57 (s, 2H), 3.77 (s, 2H), 2.44 (s, 3H)

Example 139. 2-[(2E)-2-(aminomethyl)-3-fluoro-prop-2-en-1-yl]-4-{3-methyl-5-[4-(1,2,4-oxadiazol-3-yl)phenyl]pyridin-2-yl}-2,4-dihydro-3H-1,2,4-triazol-3-one 5.0 mg of the title compound (yield: 18.0%) was prepared in the same fashion as Example 43, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 35.4 mg of 3-(4-(4,4,5,5-tetramethyl-1,3,2-dioxaborolan-2-yl)phenyl)-1,2,4-oxadiazole prepared in Reference Example 78 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.73 (d, 1H), 8.24 (d, 1H), 8.19 (s, 1H), 7.90 (m, 4H), 7.20 (d, 1H), 4.57 (s, 2H), 3.77 (s, 2H), 2.45 (s, 3H)

Example 140. 2-[(2E)-2-(aminomethyl)-3-fluoro-prop-2-en-1-yl]-4-{3-methyl-5-[3-(1,2,4-oxadiazol-3-yl)phenyl]pyridin-2-yl}-2,4-dihydro-3H-1,2,4-triazol-3-one 4.3 mg of the title compound (yield: 10.0%) was prepared in the same fashion as Example 43, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 35.4 mg of 3-(3-(4,4,5,5-tetramethyl-1,3,2-dioxaborolan-2-yl)phenyl)-1,2,4-oxadiazole prepared in Reference Example 79 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (DMSO-d₆, 400 MHz) δ 8.83 (s, 1H), 8.39 (s, 1H), 8.35 (s, 1H), 8.18 (d, 1H), 7.94 (d, 1H), 7.75 (t, 1H), 7.23 (d, 1H), 4.53 (s, 2H), 3.56 (s, 2H), 2.38 (s, 3H)

Example 141. 2-[(2E)-2-(aminomethyl)-3-fluoro-prop-2-en-1-yl]-4-{5-[4-(5-cyclopropyl-1,2,4-oxadiazol-3-yl)phenyl]-3-methylpyridin-2-yl}-2,4-dihydro-3H-1,2,4-triazol-3-one hydrochloride 2.1 mg of the title compound (yield: 5.9%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 27.5 mg of 5-cyclopropyl-3-(4-(4,4,5,5-tetramethyl-1,3,2-dioxaborolan-2-yl)phenyl)-1,2,4-oxadiazole prepared in Reference Example 80 was used instead of 1-(5-(4,4,5,5-tetramethyl-1,3,2-dioxaborolan-2-yl)thiophen-2-yl)ethane-1-one in Step 1. ¹H-NMR (MeOD, 400 MHz) δ 8.74 (s, 1H), 8.11-8.24 (m, 4H), 7.88 (d, 2H), 7.19 (d, 1H), 4.57 (s, 2H), 3.74 (s, 2H), 2.44 (s, 3H), 2.35 (s, 1H), 1.28-1.32 (m, 4H)

Example 142. 2-[(2E)-2-(aminomethyl)-3-fluoro-prop-2-en-1-yl]-4-(3-methyl-5-{4-[5-(propan-2-yl)-1,2,4-oxadiazol-3-yl]phenyl}pyridin-2-yl)-2,4-dihydro-3H-1,2,4-triazol-3-one hydrochloride 6.4 mg of the title compound (yield: 18.0%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 27.7 mg of 5-isopropyl-3-(4-(4,4,5,5-tetramethyl-1,3,2-dioxaborolan-2-yl)phenyl)-1,2,4-oxadiazole prepared in Reference Example 82 was used instead of 1-(5-(4,4,5,5-tetramethyl-1,3,2-dioxaborolan-2-yl)thiophen-2-yl)ethane-1-one in Step 1. ¹H-NMR (MeOD, 400 MHz) δ 8.75 (s, 1H), 8.19-8.25 (m, 4H), 7.90 (d, 2H), 7.21 (d, 1H), 4.58 (s, 2H), 3.77 (s, 2H), 3.35 (m, 1H), 2.45 (s, 3H), 1.48 (d, 6H)

Example 143. 2-[(2E)-2-(aminomethyl)-3-fluoro-prop-2-en-1-yl]-4-(3-methyl-5-{3-[5-(propan-2-yl)-1,2,4-oxadiazol-3-yl]phenyl}pyridin-2-yl)-2,4-dihydro-3H-1,2,4-triazol-3-one hydrochloride 15.1 mg of the title compound (yield: 42.5%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 27.7 mg of 5-isopropyl-3-(3-(4,4,5,5-tetramethyl-1,3,2-dioxaborolan-2-yl)phenyl)-1,2,4-oxadiazole prepared in Reference Example 83 was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.74 (s, 1H), 8.38 (s, 1H), 8.24 (s, 1H), 8.20 (s, 1H), 8.15 (d, 1H), 7.91 (d, 1H), 7.69 (t, 1H), 7.21 (d, 1H), 4.58 (s, 2H), 3.77 (s, 2H), 3.35 (m, 1H), 2.45 (s, 3H), 1.47 (d, 6H)

Example 144. 2-[(2E)-2-(aminomethyl)-3-fluoroprop-2-en-1-yl]-4-{3-methyl-5-[3-(1H-tetrazol-5-yl)phenyl]pyridin-2-yl}-2,4-dihydro-3H-1,2,4-triazol-3-one 2.9 mg of the title compound (yield: 10.5%) was prepared in the same fashion as Example 43, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 35.4 mg of 5-(3-(4,4,5,5-tetramethyl-1,3,2-dioxaborolan-2-yl)phenyl)-1-((2-(trimethylsilyl)ethoxy)methyl)-1H-tetrazole in Reference Example 88 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.77 (s, 1H), 8.41 (s, 1H), 8.26 (s, 1H), 8.20 (s, 1H), 8.12 (d, 1H), 7.95 (t, 1H), 7.21 (d, 1H), 4.58 (s, 2H), 3.77 (s, 2H), 2.46 (s, 3H)

Example 145. 2-[(2E)-2-(aminomethyl)-3-fluoroprop-2-en-1-yl]-4-{3-methyl-5-[4-(piperazin-1-yl)phenyl]pyridin-2-yl}-2,4-dihydro-3H-1,2,4-triazol-3-one hydrochloride 5.3 mg of the title compound (yield: 17.0%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 34.2 mg of tert-butyl 4-(4-(4,4,5,5-tetramethyl-1,3,2-dioxaborolan-2-yl)phenyl)piperazine-1-carboxylate was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.65 (s, 1H), 8.15 (d, 2H), 7.69 (d, 2H), 7.20 (d, 1H), 7.18 (d, 2H), 4.57 (s, 2H), 3.76 (s, 2H), 3.52 (s, 4H), 3.41 (s, 4H), 2.40 (s, 3H)

Example 146. 2-[(2E)-2-(aminomethyl)-3-fluoroprop-2-en-1-yl]-4-{3-methyl-5-[4-(morpholin-4-ylcarbonyl)phenyl]pyridin-2-yl}-2,4-dihydro-3H-1,2,4-triazol-3-one hydrochloride 5.2 mg of the title compound (yield: 15.6%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.0 mg of morpholino(4-(4,4,5,5-tetramethyl-1,3,2-dioxaborolan-2-yl)phenyl)methanone was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.72 (s, 1H), 8.22 (d, 2H), 7.84 (d, 2H), 7.60 (d, 2H), 7.21 (d, 1H), 4.58 (s, 2H), 3.77 (s, 6H), 3.66 (s, 2H), 3.52 (s, 2H), 2.44 (s, 3H)

Example 147. (E)-N-(6-(1-(2-(aminomethyl)-3-fluoroallyl)-5-oxo-1,5-dihydro-4H-1,2,4-triazol-4-yl)-5-methyl-[3,4'-bipyridin]-2'-yl)acetamide hydrochloride 2.9 mg of the title compound (yield: 9.1%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 23.1 mg of (2-acetamidopyridin-4-yl)boronic acid was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.87 (s, 1H), 8.46 (d, 1H), 8.39 (d, 1H), 8.22 (s, 1H), 7.90 (d, 1H), 7.86 (s, 1H), 7.20 (d, 1H), 4.58 (d, 2H), 3.77 (s, 2H), 2.50 (s, 3H), 2.36 (s, 3H)

Example 148. 2-[(2E)-2-(aminomethyl)-3-fluoroprop-2-en-1-yl]-4-[5-methyl-6'-(trifluoromethyl)-3,3'-bipyridin-6-yl]-2,4-dihydro-3H-1,2,4-triazol-3-one hydrochloride 4.8 mg of the title compound (yield: 15.9%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 24.1 mg of 5-(4,4,5,5-tetramethyl-1,3,2-dioxaborolan-2-yl)-2-(trifluoromethyl)pyridine was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 9.09 (s, 1H), 8.80 (s, 1H), 8.41 (d, 1H), 8.32 (s, 1H), 8.20 (s, 1H), 7.97 (d, 1H), 7.21 (d, 1H), 4.58 (s, 2H), 3.77 (s, 2H), 2.47 (s, 3H)

Example 149. 2-[(2E)-2-(aminomethyl)-3-fluoroprop-2-en-1-yl]-4-[5-methyl-6'-(morpholin-4-yl)-3,3'-bipyridin-6-yl]-2,4-dihydro-3H-1,2,4-triazol-3-one hydrochloride 5.5 mg of the title compound (yield: 17.5%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 18.3 mg of (6-morpholinopyridin-3-yl)boronic acid was used instead of 1-(5-(4,4,5,5-tetramethyl-1,3,2- dioxaborolan-2-yl)thiophen-2-yl)ethane-1-one in Step 1. MS (ESI) m/z=426.5 (M+H)+

Example 150. 2-[(2E)-2-(aminomethyl)-3-fluoro-prop-2-en-1-yl]-4-[5-(2H-1,3-benzodioxol-5-yl)-3-methylpyridin-2-yl]-2,4-dihydro-3H-1,2,4-triazol-3-one hydrochloride 9.1 mg of the title compound (yield: 31.9%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 35.4 mg of 2-(benzo[d][1,3]dioxol-5-yl)-4,4,5,5-tetramethyl-1,3,2-dioxaborolan was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.60 (s, 1H), 8.16 (s, 1H), 8.08 (s, 1H), 7.21 (m, 2H), 7.10 (d, 1H), 6.96 (d, 1H), 6.03 (s, 2H), 4.57 (s, 2H), 3.75 (s, 2H), 2.40 (s, 3H)

Example 151. 6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-1,3-dihydro-2H-indol-2-one 3.3 mg of the title compound (yield: 12.3%) was prepared in the same fashion as Example 43, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 22.8 mg of (2-oxoindol-6-yl)boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. 41-NMR (MeOD, 400 MHz) δ 8.62 (s, 1H), 8.12 (s, 1H), 8.11 (d, 1H), 7.36 (m, 2H), 7.20 (s, 1H), 6.93 (d, 1H), 4.51 (s, 2H), 3.44 (s, 2H), 2.40 (s, 3H)

Example 152. 2-[(2E)-2-(aminomethyl)-3-fluoro-prop-2-en-1-yl]-4-[5-(2,1,3-benzooxadiazol-5-yl)-3-methylpyridin-2-yl]-2,4-dihydro-3H-1,2,4-triazol-3-one hydrochloride 5.9 mg of the title compound (yield: 20.8%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 21.7 mg of benzo[c][1,2,5]oxadiazol-5-ylboronic acid was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.83 (s, 1H), 8.33 (s, 1H), 8.29 (s, 1H), 8.20 (s, 1H), 8.08 (d, 1H), 7.93 (d, 1H), 7.21 (d, 1H), 4.58 (d, 2H), 3.78 (s, 2H), 2.47 (s, 3H)

Example 153. 2-[(2E)-2-(aminomethyl)-3-fluoro-prop-2-en-1-yl]-4-[5-(1H-indazol-6-yl)-3-methylpyridin-2-yl]-2,4-dihydro-3H-1,2,4-triazol-3-one 7.1 mg of the title compound (yield: 27.5%) was prepared in the same fashion as Example 43, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 27.5 mg of indazole-6-boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.76 (s, 1H), 8.26 (s, 1H), 8.21 (s, 1H), 8.14 (s, 1H), 7.96 (d, 1H), 7.88 (s, 1H), 7.53 (d, 1H), 7.12-7.33 (m, 1H), 4.60 (s, 2H), 3.79 (s, 2H), 2.47 (s, 3H)

Example 154. 6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-8-methyl-3,4-dihydroquinolin-2(1H)-one hydrochloride 4.7 mg of the title compound (yield: 15.1%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 25.3 mg of 8-methyl-6-(4,4,5,5-tetramethyl-1,3,2-dioxaborolan-2-yl)-3,4-dihydroquinolin-2(1H)-one was used instead of 1-(5-(4,4,5,5-tetramethyl-1,3,2-dioxaborolan-2-yl)thiophen-2-yl)ethane-1-one in Step 1. $^1$H-NMR (MeOD, 400 MHz) δ 8.64 (s, 1H), 8.16 (s, 1H), 8.13 (s, 1H), 7.43 (s, 2H), 7.20 (d, 1H), 4.57 (s, 2H), 3.76 (s, 2H), 3.04 (t, 2H), 2.61 (t, 2H), 2.40 (s, 3H), 2.35 (s, 3H)

Example 155. 6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-2H-1,4-benzoxazin-3 (4H)-one hydrochloride 4.9 mg of the title compound (yield: 16.1%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 24.3 mg of 6-(4,4,5,5-tetramethyl-1,3,2-dioxaborolan-2-yl)-2H-benzo[b][1,4]oxazin-3(4H)-one was used instead of 1-(5-(4,4,5,5-tetramethyl-1,3,2-dioxaborolan-2-yl)thiophen-2-yl)ethane-1-one in Step 1. $^1$H-NMR (DMSO-$d_6$, 400 MHz) δ 10.89 (s, 1H), 8.59 (s, 1H), 8.36 (s, 1H), 8.09 (s, 1H), 7.32 (s, 1H), 7.24 (s, 1H), 7.20 (d, 1H), 7.11 (s, 1H), 4.64 (s, 2H), 4.54 (s, 2H), 3.64 (s, 2H), 2.34 (s, 3H)

Example 156. 7-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-1,4-dihydro-2H-3,1-benzoxazin-2-one hydrochloride 4.2 mg of the title compound (yield: 13.8%) was prepared in the same fashion as Example 42, except that 30.0 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (Z)-(2-((4-(4-bromophenyl)-5-oxo-4,5-dihydro-1H-1,2,4-triazol-1-yl)methyl)-3-fluoroallyl)carbamate and 24.3 mg of 7-(4,4,5,5-tetramethyl-1,3,2-dioxaborolan-2-yl)-1,4-dihydro-2H-benzo[d][1,3]oxazin-2-one was used instead of 1-(5-(4,4,5,5-tetramethyl-1,3,2-dioxaborolan-2-yl)thiophen-2-yl)ethane-1-one in Step 1. ¹H-NMR (MeOD, 400 MHz) δ 8.64 (s, 1H), 8.18 (s, 2H), 8.13 (s, 1H), 7.41 (d, 1H), 7.35 (d, 1H), 7.20 (d, 1H), 7.18 (s, 1H), 5.39 (s, 2H), 4.57 (s, 2H), 3.76 (s, 2H), 2.42 (s, 3H)

Example 157. 2-[(2E)-2-(aminomethyl)-3-fluoroprop-2-en-1-yl]-4-{4-methyl-5-[4-(1H-1,2,4-triazol-3-yl)phenyl]pyridin-2-yl}-2,4-dihydro-3H-1,2,4-triazol-3-one 19.3 mg of the title compound (yield: 69.8%) was prepared in the same fashion as Example 43, except that 30.0 mg of tert-butyl (E)-(2-((4-(5-bromo-4-methylpyridin-2-yl)-5-oxo-4,5-dihydro-1H-1,2,4-triazol-1-yl)methyl)-3-fluoroallyl)carbamate prepared in Reference Example 68 was used in Step 1 instead of tert-butyl (E)-(2-((4-(4-bromo-2-fluorophenyl)-5-oxo-4,5-dihydro-1H-1,2,4-triazol-1-yl)methyl)-3-fluoroallyl)carbamate. 41-NMR (MeOD, 400 MHz) δ 8.61 (s, 1H), 8.40 (brs, 1H), 8.30 (s, 1H), 8.13 (m, 3H), 7.50 (m, 2H), 7.07-7.28 (m, 1H), 4.53 (s, 2H), 3.74 (s, 2H), 2.39 (s, 3H)

Example 158. 2-[(2E)-2-(aminomethyl)-3-fluoroprop-2-en-1-yl]-4-{4-methyl-5-[3-(1H-1,2,4-triazol-3-yl)phenyl]pyridin-2-yl}-2,4-dihydro-3H-1,2,4-triazol-3-one 23.0 mg of the title compound (yield: 83.2%) was prepared in the same fashion as Example 43, except that 30.0 mg of tert-butyl (E)-(2-((4-(5-bromo-4-methylpyridin-2-yl)-5-oxo-4,5-dihydro-1H-1,2,4-triazol-1-yl)methyl)-3-fluoroallyl)carbamate prepared in Reference Example 68 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 68.2 mg of 3-(3-(4,4,5,5-tetramethyl-1,3,2-dioxaborolan-2-yl)phenyl)-1-((2-(trimethylsilyl)ethoxy)methyl)-1H-1,2,4-triazole prepared in Reference Example 32 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.64 (s, 1H), 8.44 (brs, 1H), 8.33 (s, 1H), 8.19 (s, 1H), 8.09 (m, 1H), 8.04 (s, 1H), 7.63 (m, 1H), 7.48 (m, 1H), 7.10-7.31 (m, 1H), 4.57 (s, 2H), 3.78 (s, 2H), 2.42 (s, 3H)

Example 159. 2-[(2E)-2-(aminomethyl)-3-fluoroprop-2-en-1-yl]-4-[5-(1,3-benzodioxol-5-yl)-4-methylpyridin-2-yl]-2,4-dihydro-3H-1,2,4-triazol-3-one 11.7 mg of the title compound (yield: 44.9%) was prepared in the same fashion as Example 43, except that 30.0 mg of tert-butyl (E)-(2-((4-(5-bromo-4-methylpyridin-2-yl)-5-oxo-4,5-dihydro-1H-1,2,4-triazol-1-yl)methyl)-3-fluoroallyl)carbamate prepared in Reference Example 68 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 27.8 mg of 3,4-(methylenedioxy)phenylboronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.61 (s, 1H), 8.24 (s, 1H), 8.12 (s, 1H), 7.03-7.24 (m, 1H), 6.95 (m, 1H), 6.82 (m, 2H), 4.54 (s, 2H), 3.68 (s, 2H), 2.38 (s, 3H), 6.02 (s, 2H)

Example 160. 2-[(2E)-2-(aminomethyl)-3-fluoroprop-2-en-1-yl]-4-[5-(1H-indazol-6-yl)-4-methylpyridin-2-yl]-2,4-dihydro-3H-1,2,4-triazol-3-one 6.1 mg of the title compound (yield: 23.6%) was prepared in the same fashion as Example 43, except that 30.0 mg of tert-butyl (E)-(2-((4-(5-bromo-4-methylpyridin-2-yl)-5-oxo-4,5-dihydro-1H-1,2,4-triazol-1-yl)methyl)-3-fluoroallyl)carbamate prepared in Reference Example 68 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 27.5 mg of indazole-6-boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.67 (s, 1H), 8.37 (s, 1H), 8.21 (s, 1H), 8.14 (s, 1H), 7.92 (d, 1H), 7.54 (s, 1H), 7.33 (s, 1H), 7.18 (d, 1H), 7.13 (s, 1H), 4.59 (s, 2H), 3.79 (s, 2H), 2.43 (s, 3H)

Example 161. 4-[5-(2-amino-1,3-benzothiazol-5-yl)-4-methylpyridin-2-yl]-2-[(2E)-2-(aminomethyl)-3-fluoroprop-2-en-1-yl]-2,4-dihydro-3H-1,2,4-triazol-3-one hydrochloride 28.9 mg of the title compound (yield: 94.9%) was prepared in the same fashion as Example 42, except that 30.0 mg of tert-butyl (E)-(2-((4-(5-bromo-4-methylpyridin-2-yl)-5-oxo-4,5-dihydro-1H-1,2,4-triazol-1-yl)methyl)-3-fluoroallyl)carbamate prepared in Reference Example 68 was used instead of tert-butyl (Z)-(2-((4-(4-bromophenyl)-5-oxo-4,5-dihydro-1H-1,2,4-triazol-1-yl)methyl)-3-fluoroallyl)carbamate and 46.9 mg of 5-(4,4,5,5-tetramethyl-1,3,2-dioxaborolan-2-yl)benzo[d]thiazol-2-amine prepared in Reference Example 86 was used instead of 1-(5-(4,4,5,5-tetramethyl-1,3,2-dioxaborolan-2-yl)thiophen-2-yl)ethane-1-one in Step 1. ¹H-NMR (MeOD, 400 MHz) δ 8.65 (s, 1H), 8.34 (s, 1H), 8.23 (s, 1H), 7.95 (d, 1H), 7.55 (s, 1H), 7.46 (d, 1H), 7.11-7.31 (s, 1H), 4.57 (d, 2H), 3.77 (s, 1H), 2.41 (s, 3H)

Example 162. 2-[(2E)-2-(aminomethyl)-3-fluoroprop-2-en-1-yl]-4-[5-(1,3-benzodioxol-5-yl)-3-fluoropyridin-2-yl]-2,4-dihydro-3H-1,2,4-triazol-3-one hydrochloride 8.1 mg of the title compound (yield: 28.5%) was prepared in the same fashion as Example 42, except that 30.0 mg of tert-butyl (E)-(2-((4-(5-bromo-3-fluoropyridin-2-yl)-5-oxo-4,5-dihydro-1H-1,2,4-triazol-1-yl)methyl)-3-fluoroallyl)carbamate prepared in Reference Example 70 was used instead of tert-butyl (Z)-(2-((4-(4-bromophenyl)-5-oxo-4,5-dihydro-1H-1,2,4-triazol-1-yl)methyl)-3-fluoroallyl)carbamate and 27.8 mg of 3,4-(methylenedioxy)phenylboronic acid was used instead of 1-(5-(4,4,5,5-tetramethyl-1,3,2-dioxaborolan-2-yl)thiophen-2-yl)ethane-1-one in Step 1. ¹H-NMR (MeOD, 400 MHz) δ 8.63 (s, 1H), 8.22 (s, 1H), 8.09 (d, 1H), 7.10-7.30 (m, 2+1H), 6.97 (d, 1H), 6.04 (s, 2H), 4.56 (d, 2H), 3.76 (s, 2H)

Example 163. 6-(6-{1-[(2E)-2-(aminomethyl)-3-fluoroprop-2-en-1-yl]-5-oxo-1,5-dihydro-4H-1,2,4-triazol-4-yl}-5-fluoropyridin-3-yl)-1,2-dihydro-3H-indol-3-one 3.5 mg of the title compound (yield: 13.1%) was prepared in the same fashion as Example 43, except that 30.0 mg of tert-butyl (E)-(2-((4-(5-bromo-3-fluoropyridin-2-yl)-5-oxo-4,5-dihydro-1H-1,2,4-triazol-1-yl)methyl)-3-fluoroallyl)carbamate prepared in Reference Example 70 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 44.0 mg of 6-(4,4,5,5-tetramethyl-1,3,2-dioxaborolan-2-yl)indol-3-one was used instead of 3-(4-(4, 4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.68 (s, 1H), 8.26 (m, 1H), 8.15 (m, 1H), 7.40 (m, 1H), 7.31 (m, 1H), 7.28 (m, 1H), 7.11 (m, 1H), 4.57 (s, 2H), 3.77 (s, 2H), 3.61 (s, 2H)

Example 164. 4-[5-(2-amino-1,3-benzothiazol-5-yl)-3-fluoropyridin-2-yl]-2-[(2E)-2-(aminomethyl)-3-fluoroprop-2-en-1-yl]-2,4-dihydro-3H-1,2,4-triazol-3-one hydrochloride 11.6 mg of the title compound (yield: 38.3%) was prepared in the same fashion as Example 42, except that 30.0 mg of tert-butyl (E)-(2-((4-(5-bromo-3-fluoropyridin-2-yl)-5-oxo-4,5-dihydro-1H-1,2,4-triazol-1-yl)methyl)-3-fluoroallyl)carbamate prepared in Reference Example 70 was used instead of tert-butyl (Z)-(2-((4-(4-bromophenyl)-5-oxo-4,5-dihydro-1H-1,2,4-triazol-1-yl)methyl)-3-fluoroallyl)carbamate and 46.9 mg of 5-(4,4,5,5-tetramethyl-1,3,2-dioxaborolan-2-yl)benzo[d]thiazol-2-amine prepared in Reference Example 86 was used instead of 1-(5-(4,4,5,5-tetramethyl-1,3,2-dioxaborolan-2-yl)thiophen-2-yl)ethane-1-one in Step 1. ¹H-NMR (MeOD, 400 MHz) δ 8.76 (s, 1H), 8.26 (m, 2H), 7.98 (d, 1H), 7.85 (s, 1H), 7.76 (d, 1H), 7.11-7.31 (m, 1H), 4.57 (d, 2H), 3.77 (s, 2H)

Example 165. 2-[(2E)-2-(aminomethyl)-3-fluoroprop-2-en-1-yl]-4-{4-[4-(methylsulfonyl)phenyl]pyridin-2-yl}-2,4-dihydro-3H-1,2,4-triazol-3-one 15.3 mg of the title compound (yield: 54.2%) was prepared in the same fashion as Example 43, except that 30.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 34.0 mg of 4-(methanesulfonyl)phenylboronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.69 (s, 1H), 8.59 (m, 2H), 8.13 (m, 2H), 8.03 (m, 2H), 7.72 (m, 1H), 7.11-7.31 (m, 1H), 4.58 (s, 2H), 3.77 (s, 2H), 3.19 (s, 3H)

Example 166. N-[4-(2-{1-[(2E)-2-(aminomethyl)-3-fluoroprop-2-en-1-yl]-5-oxo-1,5-dihydro-4H-1,2,4-triazol-4-yl}pyridin-4-yl)phenyl]acetamide 11.7 mg of the title compound (yield: 43.7%) was prepared in the same fashion as Example 43, except that 30.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 30.4 mg of 4-acetylamidobenzene boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.65 (s, 1H), 8.48 (s, 2H), 7.74 (s, 4H), 7.64 (m, 1H), 7.10-7.31 (m, 1H), 4.57 (s, 2H), 3.77 (s, 2H), 2.16 (s, 3H)

Example 167. 2-[(2E)-2-(aminomethyl)-3-fluoroprop-2-en-1-yl]-4-{4-[4-(1,2-oxazol-3-yl)phenyl]pyridin-2-yl}-2,4-dihydro-3H-1,2,4-triazol-3-one 12.7 mg of the title compound (yield: 46.2%) was prepared in the same fashion as Example 43, except that 30.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 46.1 mg of 3-(4-(4,4,5,5-tetramethyl-1,3,2-dioxaborolan-2-yl)phenyl)-isoxazole was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.76 (s, 1H), 8.67 (s, 1H), 8.55 (m, 2H), 8.02 (m, 2H), 7.91 (m, 2H), 7.71 (m, 1H), 7.11-7.31 (m, 1H), 7.00 (s, 1H), 4.58 (s, 2H), 3.78 (s, 2H)

Example 168. N-(2'-{1-[(2E)-2-(aminomethyl)-3-fluoroprop-2-en-1-yl]-5-oxo-1,5-dihydro-4H-1,2,4-triazol-4-yl}-4,4'-bipyridin-2-yl)acetamide 14.2 mg of the title compound (yield: 52.9%) was prepared in the same fashion as Example 43, except that 30.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 44.6 mg of N-(4-(4,4,5,5,-tetramethyl-1,3,2-dioxaborolan-2-yl)pyridin-2-yl)acetamide was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.68 (s, 1H), 8.58 (s, 2H), 8.50 (s, 1H), 8.43 (m, 1H), 7.69 (m, 1H), 7.47 (m, 1H), 7.31 (s, 1H), 7.11-7.31 (m, 1H), 4.58 (s, 2H), 3.77 (s, 2H), 2.22 (s, 3H)

Example 169. 2-[(2E)-2-(aminomethyl)-3-fluoroprop-2-en-1-yl]-4-[6-(morpholin-4-yl)-3,4'-bipyridin-2'-yl]-2,4-dihydro-3H-1,2,4-triazol-3-one 14.9 mg of the title compound (yield: 51.7%) was prepared in the same fashion as Example 43, except that 30.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 49.3 mg of 6-(morpholin-4-yl)pyridine-3-boronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.65 (s, 1H), 8.55 (s, 1H), 8.46 (m, 2H), 8.09 (d, 1H), 7.63 (m, 1H), 7.10-7.31 (m, 1H), 7.06 (d, 1H), 4.57 (s, 2H), 3.82 (m, 4H), 3.77 (s, 2H), 3.65 (m, 4H)

Example 170. 2-[(2E)-2-(aminomethyl)-3-fluoroprop-2-en-1-yl]-4-[4-(1,3-benzodioxol-5-yl)pyridin-2-yl]-2,4-dihydro-3H-1,2,4-triazol-3-one 17.8 mg of the title compound (yield: 68.8%) was prepared in the same fashion as Example 43, except that 30.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 28.2 mg of 3,4-(methylenedioxy)phenylboronic acid was used instead of 3-(4-(4,4,5,5-tetramethyl-1,3,2-dioxaborolan-2-yl)phenyl)-1-((2-(trimethylsilyl)ethoxy)

methyl)-1H-1,2,4-triazole in Step 1. ¹H-NMR (MeOD, 400 MHz) δ 8.63 (s, 1H), 8.44 (m, 1H), 8.41 (s, 1H), 7.56 (m, 1H), 7.10-7.30 (m, 3H), 6.97 (d, 1H), 6.04 (s, 2H), 4.57 (s, 2H), 3.77 (s, 2H)

Example 171. 2-[(2E)-2-(aminomethyl)-3-fluoroprop-2-en-1-yl]-4-[4-(2,3-dihydro-1,4-benzodioxin-6-yl)pyridin-2-yl]-2,4-dihydro-3H-1,2,4-triazol-3-one 19.3 mg of the title compound (yield: 71.9%) was prepared in the same fashion as Example 43, except that 30.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 30.4 mg of 1,4-benzodioxan-6-boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.63 (s, 1H), 8.43 (m, 2H), 7.56 (m, 1H), 7.10-7.30 (m, 3H), 6.97 (d, 1H), 4.56 (s, 2H), 4.30 (s, 4H), 3.77 (s, 2H)

Example 172. 2-[(2E)-2-(aminomethyl)-3-fluoroprop-2-en-1-yl]-4-[4-(2,1,3-benzooxadiazol-5-yl)pyridin-2-yl]-2,4-dihydro-3H-1,2,4-triazol-3-one 20.0 mg of the title compound (yield: 77.8%) was prepared in the same fashion as Example 43, except that 30.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 41.8 mg of benzo[c][1,2,5]oxadiazol-5-boronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.69 (s, 1H), 8.62 (s, 2H), 8.35 (s, 1H), 8.11 (d, 1H), 7.93 (m, 1H), 7.78 (m, 1H), 7.11-7.32 (m, 1H), 5.59 (s, 2H), 3.78 (s, 2H)

Example 173. 4-[4-(2-amino-1,3-benzothiazol-5-yl)pyridin-2-yl]-2-[(2E)-2-(aminomethyl)-3-fluoroprop-2-en-1-yl]-2,4-dihydro-3H-1,2,4-triazol-3-one 17.4 mg of the title compound (yield: 62.5%) was prepared in the same fashion as Example 43, except that 30.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 46.9 mg of 5-(4,4,5,5-tetramethyl-1,3,2-dioxaborolan-2-yl)benzo[d]thiazol-2-amine prepared in Reference Example 86 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.66 (s, 1H), 8.54 (s, 1H), 8.51 (m, 1H), 7.76 (m, 2H), 7.68 (m, 1H), 7.49 (m, 1H), 7.10-7.30 (s, 1H), 4.57 (s, 2H), 3.76 (s, 2H)

Example 174. 2-[(2E)-2-(aminomethyl)-3-fluoroprop-2-en-1-yl]-4-{6-[3-(dimethylamino)phenyl]pyridin-2-yl}-2,4-dihydro-3H-1,2,4-triazol-3-one hydrochloride 5.1 mg of the title compound (yield: 18.0%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 15.0 mg of (3-(dimethylamino)phenyl)boronic acid was used instead of 1-(5-(4,4,5,5-tetramethyl-1,3,2-dioxaborolan-2-yl)thiophen-2-yl)ethan-1-one in Step 1. ¹H-NMR (MeOD, 400 MHz) δ 8.94 (s, 1H), 8.54 (s, 1H), 8.30 (t, 2H), 8.12 (t, 1H), 8.02 (d, 1H), 7.76 (s, 2H), 7.21 (d, 1H), 4.58 (s, 2H), 3.77 (s, 2H), 3.39 (s, 6H)

Example 175. N-[4-(6-{1-[(2E)-2-(aminomethyl)-3-fluoroprop-2-en-1-yl]-5-oxo-1,5-dihydro-4H-1,2,4-triazol-4-yl}pyridin-2-yl)phenyl]acetamide 14.7 mg of the title compound (yield: 54.8%) was prepared in the same fashion as Example 43, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 30.4 mg of 4-acetylamidobenzene boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.79 (s, 1H), 8.06-8.13 (m, 3H), 7.97 (m, 1H), 7.84 (d, 1H), 7.70 (d, 2H), 7.10-7.30 (m, 1H), 4.55 (s, 2H), 3.76 (s, 2H), 2.15 (s, 3H)

Example 176. 2-[(2E)-2-(aminomethyl)-3-fluoroprop-2-en-1-yl]-4-{6-[4-(1,2-oxazol-3-yl)phenyl]pyridin-2-yl}-2,4-dihydro-3H-1,2,4-triazol-3-one 10.7 mg of the title compound (yield: 39.0%) was prepared in the same fashion as Example 43, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 46.1 mg of 3-(4-(4,4,5,5-tetramethyl-1,3,2-dioxaborolan-2-yl)phenyl)-isoxazole was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 8.83 (s, 1H), 8.75 (s, 1H), 8.23 (m, 3H), 8.06 (m, 1H), 7.93-8.00 (m, 3H), 7.11-7.31 (m, 1H), 6.98 (s, 1H), 4.57 (s, 2H), 3.78 (s, 2H)

Example 177. 2-[(2E)-2-(aminomethyl)-3-fluoroprop-2-en-1-yl]-4-{6-[4-(1,2,5-oxadiazol-3-yl)phenyl]pyridin-2-yl}-2,4-dihydro-3H-1,2,4-triazol-3-one hydrochloride 7.1 mg of the title compound (yield: 23.6%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 24.7 mg of 3-(4-(4,4,5,5-tetramethyl-1,3,2-dioxaborolan-2-yl)phenyl)-1,2,5-oxadiazole was used instead of 1-(5-(4,4,5,5-tetramethyl-1,3,2-dioxaborolan-2-yl)thiophen-2-yl)ethan-1-one in Step 1. ¹H-NMR (MeOD, 400 MHz) δ 8.86

(s, 1H), 8.25 (t, 3H), 8.07 (t, 1H), 7.96 (d, 1H), 7.91 (d, 2H), 7.19 (d, 1H), 4.57 (s, 2H), 3.74 (s, 2H)

Example 178. 2-[(2E)-2-(aminomethyl)-3-fluoroprop-2-en-1-yl]-4-{6-[4-(5-cyclopropyl-1,2,4-oxadiazol-3-yl)phenyl]pyridin-2-yl}-2,4-dihydro-3H-1,2,4-triazol-3-one hydrochloride 17.1 mg of the title compound (yield: 52.0%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.4 mg of 5-cyclopropyl-3-(4-(4,4,5,5-tetramethyl-1,3,2-dioxaborolan-2-yl)phenyl)-1,2,4-oxadiazole prepared in Reference Example 80 was used instead of 1-(5-(4,4,5,5-tetramethyl-1,3,2-dioxaborolan-2-yl)thiophen-2-yl)ethan-1-one in Step 1. MS (ESI) m/z=434.4 (M+H)+

Example 179. 2-[(2E)-2-(aminomethyl)-3-fluoroprop-2-en-1-yl]-4-{6-[3-(5-cyclopropyl-1,2,4-oxadiazol-3-yl)phenyl]pyridin-2-yl}-2,4-dihydro-3H-1,2,4-triazol-3-one hydrochloride 8.6 mg of the title compound (yield: 26.1%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.4 mg of 5-cyclopropyl-3-(3-(4,4,5,5-tetramethyl-1,3,2-dioxaborolan-2-yl)phenyl)-1,2,4-oxadiazole prepared in Reference Example 81 was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.90 (s, 1H), 8.74 (s, 1H), 8.23-8.30 (m, 2H), 8.06-8.11 (m, 2H), 7.96 (d, 1H), 7.65 (t, 1H), 7.21 (d, 1H), 4.58 (s, 2H), 3.77 (s, 2H), 2.37 (m, 1H), 1.30-1.35 (m, 4H)

Example 180. 2-[(2E)-2-(aminomethyl)-3-fluoroprop-2-en-1-yl]-4-(6-{4-[5-(propan-2-yl)-1,2,4-oxadiazol-3-yl]phenyl}pyridin-2-yl)-2,4-dihydro-3H-1,2,4-triazol-3-one 3.9 mg of the title compound (yield: 12.8%) was prepared in the same fashion as Example 43, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 28.6 mg of 5-isopropyl-3-(4-(4,4,5,5-tetramethyl-1,3,2-dioxaborolan-2-yl)phenyl)-1,2,4-oxadiazole prepared in Reference Example 82 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (CDCl$_3$, 400 MHz) δ 8.62 (s, 1H), 8.33 (d, 1H), 8.22 (d, 2H), 8.13 (d, 2H), 7.95 (t, 1H), 7.76 (d, 1H), 6.75 (d, 1H), 4.49 (s, 2H), 3.45 (s, 2H), 3.32 (m, 1H), 1.49 (d, 6H)

Example 181. 2-[(2E)-2-(aminomethyl)-3-fluoroprop-2-en-1-yl]-4-(6-{3-[5-(propan-2-yl)-1,2,4-oxadiazol-3-yl]phenyl}pyridin-2-yl)-2,4-dihydro-3H-1,2,4-triazol-3-one 6.5 mg of the title compound (yield: 21.3%) was prepared in the same fashion as Example 43, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 28.6 mg of 5-isopropyl-3-(3-(4,4,5,5-tetramethyl-1,3,2-dioxaborolan-2-yl)phenyl)-1,2,4-oxadiazole prepared in Reference Example 83 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (CDCl$_3$, 400 MHz) δ 8.70 (s, 1H), 8.65 (s, 1H), 8.33 (d, 1H), 8.17 (d, 2H), 7.95 (t, 1H), 7.79 (d, 1H), 7.62 (t, 1H), 6.75 (d, 1H), 4.48 (s, 2H), 3.45 (s, 2H), 3.32 (m, 1H), 1.49 (d, 6H)

Example 182. 3-[4-(6-{1-[(2E)-2-(aminomethyl)-3-fluoroprop-2-en-1-yl]-5-oxo-1,5-dihydro-4H-1,2,4-triazol-4-yl}pyridin-2-yl)phenyl]-1,2,4-oxadiazol-5(4H)-one hydrochloride 4.8 mg of the title compound (yield: 15.4%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 26.2 mg of 3-(4-(4,4,5,5-tetramethyl-1,3,2-dioxaborolan-2-yl)phenyl)-1,2,4-oxadiazol-5(4H)-one was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.87 (s, 1H), 8.34 (d, 2H), 8.27 (d, 1H), 8.09 (t, 1H), 8.00 (d, 1H), 7.94 (d, 2H), 7.21 (d, 1H), 4.57 (s, 2H), 3.77 (s, 2H)

Example 183. 2-[(2E)-2-(aminomethyl)-3-fluoroprop-2-en-1-yl]-4-{6-[4-(pyrrolidin-1-yl)phenyl]pyridin-2-yl}-2,4-dihydro-3H-1,2,4-triazol-3-one hydrochloride 4.9 mg of the title compound (yield: 16.2%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 17.1 mg of (4-(pyrrolidin-1-yl)phenyl)boronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.83 (s, 1H), 8.23 (d, 2H), 8.16 (d, 1H), 8.02 (t, 1H), 7.89 (d, 1H), 7.38 (d, 2H), 7.21 (d, 1H), 4.57 (s, 2H), 3.76 (s, 2H), 3.67 (s, 4H), 2.24 (s, 4H)

Example 184. 2-[(2E)-2-(aminomethyl)-3-fluoroprop-2-en-1-yl]-4-{6-[4-(piperazin-1-yl)phenyl]pyridin-2-yl}-2,4-dihydro-3H-1,2,4-triazol-3-one hydrochloride 8.2 mg of the title compound (yield: 26.3%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 40.8 mg of tert-butyl 4-(4-(4,4,5,5-tetramethyl-1,3,2-dioxaborolan-2-yl)phenyl)piperazin-1-carboxylate was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.80 (s, 1H), 8.09 (d, 3H), 7.98 (t, 1H), 7.82 (d, 1H), 7.21 (d, 1H), 7.15 (d, 2H), 4.57 (s, 2H), 3.76 (s, 2H), 3.55 (s, 4H), 3.41 (s, 4H)

Example 185. 2-[(2E)-2-(aminomethyl)-3-fluoro-prop-2-en-1-yl]-4-{6-[3-(piperazin-1-yl)phenyl]pyridin-2-yl}-2,4-dihydro-3H-1,2,4-triazol-3-one hydrochloride 6.6 mg of the title compound (yield: 21.1%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 35.1 mg of tert-butyl 4-(3-(4,4,5,5-tetramethyl-1,3,2-dioxaborolan-2-yl)phenyl)piperazin-1-carboxylate was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.84 (s, 1H), 8.19 (d, 1H), 8.04 (t, 1H), 7.91 (d, 1H), 7.82 (s, 1H), 7.72 (d, 1H), 7.45 (t, 1H), 7.20 (d, 1H), 7.18 (d, 1H), 4.58 (s, 2H), 3.77 (s, 2H), 3.57 (s, 4H), 3.45 (s, 4H)

Example 186. 2-[(2E)-2-(aminomethyl)-3-fluoro-prop-2-en-1-yl]-4-{6-[4-(morpholin-4-ylcarbonyl)phenyl]pyridin-2-yl}-2,4-dihydro-3H-1,2,4-triazol-3-one hydrochloride 9.3 mg of the title compound (yield: 28.0%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 33.3 mg of morpholino(4-(4,4,5,5-tetramethyl-1,3,2-dioxaborolan-2-yl)phenyl)methanone was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.85 (s, 1H), 8.25 (d, 3H), 8.07 (t, 1H), 7.96 (d, 1H), 7.58 (d, 2H), 7.21 (d, 1H), 4.57 (s, 2H), 3.77 (s, 6H), 3.66 (s, 2H), 3.51 (s, 2H)

Example 187. 2-[(2E)-2-(aminomethyl)-3-fluoro-prop-2-en-1-yl]-4-[6'-(trifluoromethyl)-2,3'-bipyridin-6-yl]-2,4-dihydro-3H-1,2,4-triazol-3-one hydrochloride 6.3 mg of the title compound (yield: 20.9%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 24.9 mg of 5-(4,4,5,5-tetramethyl-1,3,2-dioxaborolan-2-yl)-2-(trifluoromethyl)pyridine was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 9.46 (s, 1H), 8.89 (s, 1H), 8.76 (d, 1H), 8.35 (d, 1H), 8.15 (t, 1H), 8.07 (d, 1H), 7.96 (d, 1H), 7.21 (d, 1H), 4.57 (s, 2H), 3.77 (s, 2H), 3.41 (s, 4H)

Example 188. 2-[(2E)-2-(aminomethyl)-3-fluoro-prop-2-en-1-yl]-4-[6'-(dimethylamino)-2,3'-bipyridin-6-yl]-2,4-dihydro-3H-1,2,4-triazol-3-one hydrochloride 16.2 mg of the title compound (yield: 47.0%) was prepared in the same fashion as Example 42, except that 40.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 35.0 mg of 6-(dimethylamino)pyridin-3-boronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.88 (s, 1H), 8.77 (dd, 1H), 8.60-8.70 (m, 1H), 8.28 (d, 1H), 8.10 (t, 1H), 7.92 (d, 1H), 7.39 (d, 1H), 7.20 (d, 1H), 4.57 (d, 2H), 3.76 (d, 2H), 3.39 (s, 6H)

Example 189. 2-[(2E)-2-(aminomethyl)-3-fluoro-prop-2-en-1-yl]-4-[6'-(morpholin-4-yl)-2,3'-bipyridin-6-yl]-2,4-dihydro-3H-1,2,4-triazol-3-one 15.3 mg of the title compound (yield: 53.1%) was prepared in the same fashion as Example 43, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 49.3 mg of 6-(morpholin-4-yl)pyridin-3-boronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.81 (s, 2H), 8.50 (d, 1H), 8.17 (m, 1H), 8.03 (m, 1H), 7.84 (m, 1H), 7.10-7.30 (s, 1H), 7.16 (d, 1H), 4.57 (s, 2H), 3.84 (m, 4H), 3.77 (s, 2H), 3.67 (m, 4H)

Example 190. 2-[(2E)-2-(aminomethyl)-3-fluoro-prop-2-en-1-yl]-4-(6'-fluoro-5'-methyl-2,3'-bipyridin-6-yl)-2,4-dihydro-3H-1,2,4-triazol-3-one hydrochloride 17.1 mg of the title compound (yield: 46.4%) was prepared in the same fashion as Example 42, except that 40.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 25.0 mg of 2-fluoro-3-methylpyridin-5-boronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.86 (s, 1H), 8.75 (s, 1H), 8.52 (d, 1H), 8.25 (d, 1H), 8.07 (t, 1H), 7.93 (d, 1H), 7.21 (d, 1H), 4.57 (d, 2H), 3.76 (d, 2H), 2.39 (s, 3H)

Example 191. 2-[(2E)-2-(aminomethyl)-3-fluoro-prop-2-en-1-yl]-4-[6'-(dimethylamino)-5'-fluoro-2,3'-bipyridin-6-yl]-2,4-dihydro-3H-1,2,4-triazol-3-one hydrochloride 15.7 mg of the title compound (yield: 43.4%) was prepared in the same fashion as Example 42, except that 40.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 42.4 mg of 2-(N,N-dimethylamino)-3-fluoropyridin-5-boronic acid pinacol ester was used instead of 1-(5-(4,4,5,5-tetramethyl-1,3,2-dioxaborolan-2-yl)thiophen-2-yl) ethan-1-one in Step 1. $^1$H-NMR (MeOD, 400 MHz) δ 8.91 (s, 1H), 8.65 (dd, 1H), 8.54 (s, 1H), 8.29 (d, 1H), 8.10 (t, 1H), 7.93 (d, 1H), 7.20 (d, 1H), 4.56 (d, 2H), 3.76 (d, 2H), 3.45 (d, 6H)

Example 192. 2-[(2E)-2-(aminomethyl)-3-fluoroprop-2-en-1-yl]-4-{6-[1-methyl-3-(trifluoromethyl)-1H-pyrazol-5-yl]pyridin-2-yl}-2,4-dihydro-3H-1,2,4-triazol-3-one hydrochloride 14.8 mg of the title compound (yield: 36.5%) was prepared in the same fashion as Example 42, except that 40.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 25.0 mg of 1-methyl-3-trifluoromethyl-1H-pyrazol-5-boronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.68 (s, 1H), 8.30 (d, 1H), 8.11 (t, 1H), 7.81 (d, 1H), 7.21 (d, 1H), 7.17 (s, 1H), 4.57 (d, 2H), 4.29 (s, 3H), 3.76 (d, 2H)

Example 193. 2-[(2E)-2-(aminomethyl)-3-fluoroprop-2-en-1-yl]-4-[6-(1,3-benzodioxol-5-yl)pyridin-2-yl]-2,4-dihydro-3H-1,2,4-triazol-3-one 16.8 mg of the title compound (yield: 65.0%) was prepared in the same fashion as Example 43, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 28.2 mg of 3,4-(methylenedioxy)phenylboronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.77 (s, 1H), 8.10 (m, 1H), 7.95 (m, 1H), 7.77 (d, 1H), 7.64 (m, 1H), 7.26 (s, 1H), 7.30 (s, 1H), 7.10 (s, 1H), 6.93 (d, 1H), 6.03 (s, 2H), 4.56 (s, 2H), 3.77 (s, 2H)

Example 194. 2-[(2E)-2-(aminomethyl)-3-fluoroprop-2-en-1-yl]-4-[6-(2,3-dihydro-1,4-benzodioxin-6-yl)pyridin-2-yl]-2,4-dihydro-3H-1,2,4-triazol-3-one 15.3 mg of the title compound (yield: 57.0%) was prepared in the same fashion as Example 43, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 30.4 mg of 1,4-benzodioxan-6-boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.72 (s, 1H), 8.06 (m, 2H), 7.93 (d, 1H), 7.73 (d, 1H), 7.58 (m, 2H), 7.29 (s, 1H), 7.09 (s, 1H), 6.91 (d, 1H), 4.55 (s, 2H), 4.28 (s, 4H), 3.76 (s, 2H)

Example 195. 2-[(2E)-2-(aminomethyl)-3-fluoroprop-2-en-1-yl]-4-[6-(2,1,3-benzooxadiazol-5-yl) pyridin-2-yl]-2,4-dihydro-3H-1,2,4-triazol-3-one 23.0 mg of the title compound (yield: 89.4%) was prepared in the same fashion as Example 43, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 41.8 mg of benzo[c][1,2,5]oxadiazol-5-boronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.90 (s, 1H), 8.69 (s, 1H), 8.33-8.41 (m, 2H), 8.14 (m, 2H), 8.05 (d, 1H), 7.12-7.32 (m, 1H), 4.58 (s, 2H), 3.78 (s, 2H)

Example 196. 4-[6-(2-amino-1,3-benzothiazol-5-yl) pyridin-2-yl]-2-[(2E)-2-(aminomethyl)-3-fluoroprop-2-en-1-yl]-2,4-dihydro-3H-1,2,4-triazol-3-one 1.0 mg of the title compound (yield: 3.6%) was prepared in the same fashion as Example 43, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 46.9 mg of 5-(4,4,5,5-tetramethyl-1,3,2-dioxaborolan-2-yl)benzo[d]thiazol-2-amine prepared in Reference Example 86 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.83 (s, 1H), 8.18 (m, 1H), 8.13 (s, 1H), 8.04 (m, 1H), 7.91 (m, 1H), 7.86 (m, 1H), 7.72 (m, 1H), 6.97-7.18 (m, 1H), 4.54 (s, 2H), 3.59 (s, 2H)

Example 197. 6-(6-{1-[(2E)-2-(aminomethyl)-3-fluoroprop-2-en-1-yl]-5-oxo-1,5-dihydro-4H-1,2,4-triazol-4-yl}pyridin-2-yl)-8-methyl-3,4-dihydroquinolin-2(1H)-one hydrochloride 5.5 mg of the title compound (yield: 18.2%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 26.2 mg of 8-methyl-6-(4,4,5,5-tetramethyl-1,3,2-dioxaborolan-2-yl)-3,4-dihydroquinolin-2(1H)-one was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.84 (s, 1H), 8.12 (d, 1H), 7.99 (t, 1H), 7.84 (s, 2H), 7.20 (d, 1H), 4.56 (s, 2H), 3.76 (s, 2H), 3.05 (m, 2H), 2.61 (m, 2H), 2.36 (s, 3H), 1.30 (m, 4H)

Example 198. 6-[6-[1-[(E)-2-(aminomethyl)-3-fluoro-allyl]-5-oxo-1,2,4-triazol-4-yl]-2-pyridyl]-1-methyl-3,4-dihydroquinolin-2-one hydrochloride 97.0 mg of the title compound (yield: 96.5%) was prepared in the same fashion as Example 42, except that 97.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 84.0 mg of 1-(methyl-2-oxo-1,2,3,4-tetrahydroquinolin-6-yl)boronic acid pinacol ester was used instead of 1-(5-(4,4,5,5-tetramethyl-1,3,2-dioxaborolan-2-yl)thiophen-2-yl)ethan-1-one in Step 1. MS (ESI) m/z=409.2 (M+H)+

Example 199. 6-(3-{1-[(2E)-2-(aminomethyl)-3-fluoroprop-2-en-1-yl]-5-oxo-1,5-dihydro-4H-1,2,4-triazol-4-yl}pyridin-2-yl)-2H-1,4-benzoxazin-3(4H)-one hydrochloride 2.4 mg of the title compound (yield: 7.7%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 25.1 mg of 6-(4,4,5,5-tetramethyl-1,3,2-dioxaborolan-2-yl)-2H-benzo[b][1,4]oxazin-3(4H)-one was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.79 (s, 1H), 8.15 (d, 1H), 8.01 (t, 1H), 7.81 (d, 1H), 7.74 (m, 2H), 7.21 (d, 1H), 7.07 (d, 1H), 4.65 (s, 2H), 4.57 (s, 2H), 3.77 (s, 2H), 3.66 (s, 2H), 1.31 (m, 3H)

Example 200. 7-(6-{1-[(2E)-2-(aminomethyl)-3-fluoroprop-2-en-1-yl]-5-oxo-1,5-dihydro-4H-1,2,4-triazol-4-yl}pyridin-2-yl)-1,4-dihydro-2H-3,1-benzoxazin-2-one hydrochloride 7.7 mg of the title compound (yield: 25.4%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 25.2 mg of 7-(4,4,5,5-tetramethyl-1,3,2-dioxaborolan-2-yl)-1,4-dihydro-2H-benzo[d][1,3]oxazin-2-one was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.79 (s, 1H), 8.22 (d, 1H), 8.04 (t, 1H), 7.87 (d, 1H), 7.81 (d, 1H), 7.68 (s, 1H), 7.32 (d, 1H), 7.19 (d, 1H), 5.39 (s, 2H), 4.57 (s, 2H), 3.74 (s, 2H)

Example 201. 5-(6-{1-[(2E)-2-(aminomethyl)-3-fluoroprop-2-en-1-yl]-5-oxo-1,5-dihydro-4H-1,2,4-triazol-4-yl}pyridin-2-yl)quinolin-2(1H)-one hydrochloride 21.7 mg of the title compound (yield: 59.2%) was prepared in the same fashion as Example 42, except that 40.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 38.0 mg of 5-(4,4,5,5-tetramethyl-1,3,2-dioxaborolan-2-yl)quinolin-2H-one was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.57 (s, 1H), 8.43 (d, 1H), 8.33 (d, 1H), 8.15 (t, 1H), 7.70-7.76 (m, 1H), 7.67 (d, 1H), 7.54 (dd, 2H), 7.20 (d, 1H), 6.75 (d, 1H), 4.57 (d, 2H), 3.77 (d, 2H)

Example 202. 2-[(2E)-2-(aminomethyl)-3-fluoroprop-2-en-1-yl]-4-[6-(4-methyl-3,4-dihydro-2H-1,4-benzoxazin-7-yl)pyridin-2-yl]-2,4-dihydro-3H-1,2,4-triazol-3-one hydrochloride 8.2 mg of the title compound (yield: 27.1%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 25.0 mg of 4-methyl-7-(4,4,5,5-tetramethyl-1,3,2-dioxaborolan-2-yl)-3,4-dihydro-2H-benzo[b][1,4]oxazine was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.76 (s, 1H), 8.03 (s, 1H), 7.93 (s, 1H), 7.75 (s, 1H), 7.63 (d, 1H), 7.56 (s, 1H), 7.20 (d, 1H), 6.88 (s, 1H), 4.56 (s, 2H), 4.33 (s, 2H), 3.76 (s, 2H), 3.35 (s, 1H), 3.02 (s, 3H)

Example 203. 2-[(2E)-2-(aminomethyl)-3-fluoroprop-2-en-1-yl]-4-[6-(dibenzo[b,d]furan-4-yl)pyridin-2-yl]-2,4-dihydro-3H-1,2,4-triazol-3-one hydrochloride 22.4 mg of the title compound (yield: 53.1%) was prepared in the same fashion as Example 42, except that 40.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 30.0 mg of 4-(dibenzofuranyl)boronic acid pinacol ester was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.84 (s, 1H), 8.48 (d, 1H), 8.36 (d, 1H), 8.23 (d, 1H), 8.05-8.17 (m, 3H), 7.69 (d, 1H), 7.53 (q, 2H), 7.42 (t, 1H), 7.22 (d, 1H), 4.58 (d, 2H), 3.78 (d, 2H)

Example 204. 2-[(2E)-2-(aminomethyl)-3-fluoroprop-2-en-1-yl]-4-{6-[4-(5-cyclopropyl-1,2,4-oxadiazol-3-yl)phenyl]pyridin-2-yl}-2,4-dihydro-3H-1,2,4-triazol-3-one hydrochloride 1.9 mg of the title compound (yield: 5.8%) was prepared in the same fashion as Example 42, except that 30.0 mg of tert-butyl (E)-(2-((4-(2-bromopyridin-4-yl)-5-oxo-4,5-dihydro-1H-1,2,4-triazol-1-yl)methyl)-3-fluoroallyl)carbamate prepared in Reference Example 73 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.4 mg of 5-cyclopropyl-3-(3-(4,4,5,5-tetramethyl-1,3,2-dioxaborolan-2-yl)phenyl)-1,2,4-oxadiazole prepared in Reference Example 81 was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.89 (d, 1H), δ 8.81 (s, 1H), 8.71 (s, 1H), 8.65 (s, 1H), 8.40 (s, 1H), 8.29 (d, 1H), 8.16 (d, 1H), 7.79 (d, 1H), 7.22 (d, 1H), 4.59 (s, 2H), 3.77 (s, 2H)

Example 205. 2-[(2E)-2-(aminomethyl)-3-fluoroprop-2-en-1-yl]-4-(2-{4-[5-(propan-2-yl)-1,2,4-oxadiazol-3-yl]phenyl}pyridin-4-yl)-2,4-dihydro-3H-1,2,4-triazol-3-one hydrochloride 6.1 mg of the title compound (yield: 18.5%) was prepared in the same fashion as Example 42, except that 30.0 mg of tert-butyl (E)-(2-((4-(2-bromopyridin-4-yl)-5-oxo-4,5-dihydro-1H-1,2,4-triazol-1-yl)methyl)-3-fluoroallyl)carbamate prepared in Reference Example 73 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.6 mg of 5-isopropyl-3-(4-(4,4,5,5-tetramethyl-1,3,2-dioxaborolan-2-yl)phenyl)-1,2,4-oxadiazole prepared in Reference Example 82 was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.94 (d, 1H), 8.88 (s, 1H), 8.82 (s, 1H), 8.58 (d, 1H), 8.36 (d, 2H), 8.16 (d, 2H), 7.22 (d, 1H), 4.61 (s, 2H), 3.76 (s, 2H), 3.35 (m, 1H), 1.48 (d, 6H)

Example 206. 2-[(2E)-2-(aminomethyl)-3-fluoroprop-2-en-1-yl]-4-(2-{3-[5-(propan-2-yl)-1,2,4-oxadiazol-3-yl]phenyl}pyridin-4-yl)-2,4-dihydro-3H-1,2,4-triazol-3-one hydrochloride 15.1 mg of the title compound (yield: 45.9%) was prepared in the same fashion as Example 42, except that 30.0 mg of tert-butyl (E)-(2-((4-(2-bromopyridin-4-yl)-5-oxo-4,5-dihydro-1H-1,2,4-triazol-1-yl)methyl)-3-fluoroallyl)carbamate prepared in Reference Example 73 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.6 mg of 5-isopropyl-3-(3-(4,4,5,5-tetramethyl-1,3,2-dioxaborolan-2-yl)phenyl)-1,2,4-oxadiazole prepared in Reference Example 83 was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.93 (s, 1H), 8.85 (s, 1H), 8.79 (s, 1H), 8.69 (s, 1H), 8.52 (s, 1H), 8.37 (d, 1H), 8.18 (d, 1H), 7.85 (t, 1H), 7.22 (d, 1H), 4.60 (s, 2H), 3.77 (s, 2H), 3.38 (m, 1H), 1.48 (d, 6H)

Example 207. 2-[(2E)-2-(aminomethyl)-3-fluoroprop-2-en-1-yl]-4-{2-[4-(morpholin-4-yl)phenyl]pyridin-4-yl}-2,4-dihydro-3H-1,2,4-triazol-3-one hydrochloride 14.2 mg of the title compound (yield: 45.4%) was prepared in the same fashion as Example 42, except that 30.0 mg of tert-butyl (E)-(2-((4-(2-bromopyridin-4-yl)-5-oxo-4,5-dihydro-1H-1,2,4-triazol-1-yl)methyl)-3-fluoroallyl)carbamate prepared in Reference Example 73 was used instead of tert-butyl (Z)-(2-((4-(4-bromophenyl)-5-oxo-4,5-dihydro-1H-1,2,4-triazol-1-yl)methyl)-3-fluoroallyl)carbamate and 26.3 mg of 4-(4-(4,4,5,5-tetramethyl-1,3,2-dioxaborolan-2-yl)phenyl)morpholine was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.86 (s, 1H), 8.74 (d, 2H), 8.41 (s, 1H), 7.94 (d, 2H), 7.23 (d, 2H), 7.22 (d, 1H), 4.59 (s, 2H), 3.85 (s, 4H), 3.76 (s, 2H), 3.41 (s, 4H)

Example 208. 2-[(2E)-2-(aminomethyl)-3-fluoroprop-2-en-1-yl]-4-{2-[4-(morpholin-4-ylcarbonyl)phenyl]pyridin-4-yl}-2,4-dihydro-3H-1,2,4-triazol-3-one hydrochloride 15.0 mg of the title compound (yield: 45.1%) was prepared in the same fashion as Example 42, except that 30.0 mg of tert-butyl (E)-(2-((4-(2-bromopyridin-4-yl)-5-oxo-4,5-dihydro-1H-1,2,4-triazol-1-yl)methyl)-3-fluoroallyl)carbamate prepared in Reference Example 73 was used instead of tert-butyl (Z)-(2-((4-(4-bromophenyl)-5-oxo-4,5-dihydro-1H-1,2,4-triazol-1-yl)methyl)-3-fluoroallyl)carbamate and 33.3 mg of morpholino(4-(4,4,5,5-tetramethyl-1,3,2-dioxaborolan-2-yl)phenyl)methanone was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.93-9.03 (m, 1H), 8.88 (s, 1H), 8.82 (s, 1H), 8.60 (d, 1H), 8.10 (d, 1H), 7.75 (d, 1H), 7.22 (d, 1H), 4.60 (s, 2H), 3.77 (s, 5H), 3.66 (s, 2H), 3.48 (s, 1H)

Example 209. 2-[(2E)-2-(aminomethyl)-3-fluoroprop-2-en-1-yl]-4-[2-(1,3-benzodioxol-5-yl)pyridin-4-yl]-2,4-dihydro-3H-1,2,4-triazol-3-one hydrochloride 4.0 mg of the title compound (yield: 14.1%) was prepared in the same fashion as Example 42, except that 30.0 mg of tert-butyl (E)-(2-((4-(2-bromopyridin-4-yl)-5-oxo-4,5-dihydro-1H-1,2,4-triazol-1-yl)methyl)-3-fluoroallyl)carbamate prepared in Reference Example 73 was used instead of tert-butyl (Z)-(2-((4-(4-bromophenyl)-5-oxo-4,5-dihydro-1H-1,2,4-triazol-1-yl)methyl)-3-fluoroallyl)carbamate and 15.1 mg of benzo[d][1,3]dioxol-5-yl boronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.85 (s, 1H), δ 8.81 (d, 1H), 8.70 (s, 1H), 8.52 (d, 1H), 7.55 (d, 1H), 7.50 (s, 1H), 7.22 (d, 1H), 7.12 (s, 1H), 6.16 (s, 2H), 4.59 (s, 2H), 3.76 (s, 2H)

Example 210. 2-[(2E)-2-(aminomethyl)-3-fluoroprop-2-en-1-yl]-4-{6-[3-(5-cyclopropyl-1,2,4-oxadiazol-3-yl)phenyl]-3-methylpyridin-2-yl}-2,4-dihydro-3H-1,2,4-triazol-3-one hydrochloride 9.7 mg of the title compound (yield: 29.6%) was prepared in the same fashion as Example 42, except that 30.0 mg of tert-butyl (E)-(2-((4-(6-bromo-3-methylpyridin-2-yl)-5-oxo-4,5-dihydro-1H-1,2,4-triazol-1-yl)methyl)-3-fluoroallyl)carbamate prepared in Reference Example 74 was used instead of tert-butyl (Z)-(2-((4-(4-bromophenyl)-5-oxo-4,5-dihydro-1H-1,2,4-triazol-1-yl)methyl)-3-fluoroallyl)carbamate and 27.5 mg of 5-cyclopropyl-3-(3-(4,4,5,5-tetramethyl-1,3,2-dioxaborolan-2-yl)phenyl)-1,2,4-oxadiazole prepared in Reference Example 81 was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.68 (s, 1H), 8.27 (s, 1H), 8.21 (d, 1H), 7.98-8.10 (m, 3H), 7.63 (t, 1H), 7.21 (d, 1H), 4.58 (s, 2H), 3.78 (s, 2H), 2.40 (s, 3H), 2.30 (s, 1H), 1.23-1.33 (m, 4H)

Example 211. 2-[(2E)-2-(aminomethyl)-3-fluoroprop-2-en-1-yl]-4-{3-methyl-6-[4-(morpholin-4-ylcarbonyl)phenyl]pyridin-2-yl}-2,4-dihydro-3H-1,2,4-triazol-3-one hydrochloride 6.1 mg of the title compound (yield: 18.4%) was prepared in the same fashion as Example 42, except that 30.0 mg of tert-butyl (E)-(2-((4-(6-bromo-3-methylpyridin-2-yl)-5-oxo-4,5-dihydro-1H-1,2,4-triazol-1-yl)methyl)-3-fluoroallyl)carbamate prepared in Reference Example 74 was used instead of tert-butyl (Z)-(2-((4-(4-bromophenyl)-5-oxo-4,5-dihydro-1H-1,2,4-triazol-1-yl)methyl)-3-fluoroallyl)carbamate and 28.0 mg of morpholino(4-(4,4,5,5-tetramethyl-1,3,2-dioxaborolan-2-yl)phenyl)methanone was used instead of 1-(5-(4,4,5,5-tetramethyl-1,3,2-dioxaborolan-2-yl)thiophen-2-yl)ethan-1-one in Step 1. ¹H-NMR (MeOD, 400 MHz) δ 8.25 (s, 1H), 8.15 (d, 2H), 8.02 (m, 2H), 7.55 (d, 2H), 7.21 (d, 1H), 4.58 (s, 2H), 3.77 (s, 6H), 3.66 (s, 4H), 3.45 (s, 2H), 2.40 (s, 3H)

Example 212. 2-[(2E)-2-(aminomethyl)-3-fluoroprop-2-en-1-yl]-4-(6'-methoxy-5-methyl-2,3'-bipyridin-6-yl)-2,4-dihydro-3H-1,2,4-triazol-3-one hydrochloride 10.4 mg of the title compound (yield: 37.7%) was prepared in the same fashion as Example 42, except that 30.0 mg of tert-butyl (E)-(2-((4-(6-bromo-3-methylpyridin-2-yl)-5-oxo-4,5-dihydro-1H-1,2,4-triazol-1-yl)methyl)-3-fluoroallyl)carbamate prepared in Reference Example 74 was used instead of tert-butyl (Z)-(2-((4-(4-bromophenyl)-5-oxo-4,5-dihydro-1H-1,2,4-triazol-1-yl)methyl)-3-fluoroallyl)carbamate and 13.5 mg of (6-methoxypyridin-3-yl)boronic acid was used instead of 1-(5-(4,4,5,5-tetramethyl-1,3,2-dioxaborolan-2-yl)thiophen-2-yl)ethan-1-one in Step 1. ¹H-NMR (MeOD, 400 MHz) δ 8.89 (s, 1H), 8.65 (d, 1H), 8.26 (s, 1H), 8.00 (s, 2H), 7.23 (d, 1H), 7.21 (d, 1H), 4.57 (s, 2H), 4.10 (s, 3H), 3.77 (s, 2H), 2.40 (s, 3H)

Example 213. 2-[(2E)-2-(aminomethyl)-3-fluoroprop-2-en-1-yl]-4-[6-(1,3-benzodioxol-5-yl)-3-methylpyridin-2-yl]-2,4-dihydro-3H-1,2,4-triazol-3-one hydrochloride 16.9 mg of the title compound (yield: 59.4%) was prepared in the same fashion as Example 42, except that 30.0 mg of tert-butyl (E)-(2-((4-(6-bromo-3-methylpyridin-2-yl)-5-oxo-4,5-dihydro-1H-1,2,4-triazol-1-yl)methyl)-3-fluoroallyl)carbamate prepared in Reference Example 74 was used instead of tert-butyl (Z)-(2-((4-(4-bromophenyl)-5-oxo-4,5-dihydro-1H-1,2,4-triazol-1-yl)methyl)-3-fluoroallyl)carbamate and 14.6 mg of benzo[d][1,3]dioxol-5-yl boronic acid was used instead of 1-(5-(4,4,5,5-tetramethyl-1,3,2-dioxaborolan-2-yl)thiophen-2-yl)ethan-1-one in Step 1. ¹H-NMR (MeOD, 400 MHz) δ 8.23 (s, 1H), 7.88 (s, 2H), 7.55 (d, 2H), 7.21 (d, 1H), 6.92 (d, 1H), 6.01 (s, 1H), 4.57 (s, 2H), 3.76 (s, 2H), 2.35 (s, 3H)

Example 214. 2-[(2E)-2-(aminomethyl)-3-fluoroprop-2-en-1-yl]-4-[6-(1H-indazol-6-yl)-3-methylpyridin-2-yl]-2,4-dihydro-3H-1,2,4-triazol-3-one hydrochloride 2.9 mg of the title compound (yield: 10.3%) was prepared in the same fashion as Example 42, except that 30.0 mg of tert-butyl (E)-(2-((4-(6-bromo-3-methylpyridin-2-yl)-5-oxo-4,5-dihydro-1H-1,2,4-triazol-1-yl)methyl)-3-fluoroallyl)carbamate prepared in Reference Example 74 was used instead of tert-butyl (Z)-(2-((4-(4-bromophenyl)-5-oxo-4,5-dihydro-1H-1,2,4-triazol-1-yl)methyl)-3-fluoroallyl)carbamate and 14.3 mg of indazol-6-boronic acid was used instead of 1-(5-(4,4,5,5-tetramethyl-1,3,2-dioxaborolan-2-yl)thiophen-2-yl)ethan-1-one in Step 1. ¹H-NMR (MeOD, 400 MHz) δ 8.20-8.34 (m, 3H), 8.08 (s, 1H), 8.00 (d, 1H), 7.90 (s, 2H), 7.21 (d, 1H), 4.59 (s, 2H), 3.78 (s, 2H), 2.41 (s, 3H)

Example 215. 6-(6-{1-[(2E)-2-(aminomethyl)-3-fluoroprop-2-en-1-yl]-5-oxo-1,5-dihydro-4H-1,2,4-triazol-4-yl}-5-methylpyridin-2-yl)-8-methyl-3,4-dihydroquinolin-2(1H)-one hydrochloride 2.1 mg of the title compound (yield: 6.8%) was prepared in the same fashion as Example 42, except that 30.0 mg of tert-butyl (E)-(2-((4-(6-bromo-3-methylpyridin-2-yl)-5-oxo-4,5-dihydro-1H-1,2,4-triazol-1-yl)methyl)-3-fluoroallyl)carbamate prepared in Reference Example 74 was used instead of tert-butyl (Z)-(2-((4-(4-bromophenyl)-5-oxo-4,5-dihydro-1H-1,2,4-triazol-1-yl)methyl)-3-fluoroallyl)carbamate and 25.3 mg of 8-methyl-6-(4,4,5,5-tetramethyl-1,3,2-dioxaborolan-2-yl)-3,4-dihydroquinolin-2(1H)-one was used instead of 1-(5-(4,4,5,5-tetramethyl-1,3,2-dioxaborolan-2-yl)thiophen-2-yl)ethan-1-one in Step 1. ¹H-NMR (MeOD, 400 MHz) δ 8.23 (s, 1H), 7.91 (s, 2H), 7.74 (s, 2H), 7.21 (d, 1H), 4.58 (s, 2H), 3.77 (s, 2H), 3.05 (t, 2H), 2.61 (t, 2H), 2.34 (d, 6H)

Example 216. 6-(6-{1-[(2E)-2-(aminomethyl)-3-fluoroprop-2-en-1-yl]-5-oxo-1,5-dihydro-4H-1,2,4-triazol-4-yl}-5-methylpyridin-2-yl)-2H-1,4-benzoxazin-3(4H)-one hydrochloride 5.8 mg of the title compound (yield: 19.1%) was prepared in the same fashion as Example 42, except that 30.0 mg of tert-butyl (E)-(2-((4-(6-bromo-3-methylpyridin-2-yl)-5-oxo-4,5-dihydro-1H-1,2,4-triazol-1-yl)methyl)-3-fluoroallyl)carbamate prepared in Reference Example 74 was used instead of tert-butyl (Z)-(2-((4-(4-bromophenyl)-5-oxo-4,5-dihydro-1H-1,2,4-triazol-1-yl)methyl)-3-fluoroallyl)carbamate and 24.3 mg of 6-(4,4,5,5-tetramethyl-1,3,2-dioxaborolan-2-yl)-2H-benzo[b][1,4]oxazin-3(4H)-one was used instead of 1-(5-(4,4,5,5-tetramethyl-1,3,2-dioxaborolan-2-yl)thiophen-2-yl)ethan-1-one in Step 1. ¹H-NMR (MeOD, 400 MHz) δ 8.22 (s, 1H), 7.90 (m, 2H), 7.66 (d, 1H), 7.61 (s, 1H), 7.21 (d, 1H), 7.04 (s, 1H), 4.63 (s, 2H), 4.58 (s, 2H), 3.77 (s, 2H), 2.37 (s, 3H)

Example 217. 2-[(2E)-2-(aminomethyl)-3-fluoroprop-2-en-1-yl]-4-{5-[4-(methylsulfonyl)phenyl]pyrazin-2-yl}-2,4-dihydro-3H-1,2,4-triazol-3-one 19.9 mg of the title compound (yield: 70.4%) was prepared in the same fashion as Example 43, except that 30.0 mg of tert-butyl (E)-(2-((4-(5-bromopyrazin-2-yl)-5-oxo-4,5-dihydro-1H-1,2,4-triazol-1-yl)methyl)-3-fluoroallyl)carbamate prepared in Reference Example 75 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 36.0 mg of 4-(methanesulfonyl)phenylboronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. ¹H-NMR (MeOD, 400 MHz) δ 9.58 (s, 1H), 9.09 (s, 1H), 8.65 (s, 1H), 8.35 (d, 2H), 8.08 (d, 2H), 7.11-7.31 (m, 1H), 4.58 (s, 2H), 3.79 (s, 2H), 3.31 (s, 3H)

Example 218. 2-[(2E)-2-(aminomethyl)-3-fluoroprop-2-en-1-yl]-4-{5-[4-(1H-1,2,4-triazol-3-yl)phenyl]pyrazin-2-yl}-2,4-dihydro-3H-1,2,4-triazol-3-one 15.4 mg of the title compound (yield: 56.0%) was prepared in the same fashion as Example 43, except that 30.0 mg of tert-butyl (E)-(2-((4-(5-bromopyrazin-2-yl)-5-oxo-4,5-dihydro-1H-1,2,4-triazol-1-yl)methyl)-3-fluoroallyl)carbamate prepared in Reference Example 75 was used in Step 1 instead of tert-butyl (E)-(2-((4-(4-bromo-2-fluorophenyl)-5-oxo-4,5-dihydro-1H-1,2,4-triazol-1-yl)methyl)-3-fluoroallyl)carbamate. ¹H-NMR (MeOD, 400 MHz) δ 9.55 (s, 1H), 9.07 (s, 1H), 8.64 (s, 1H), 8.45 (brs, 1H), 8.17-8.25 (m, 4H), 7.11-7.31 (m, 1H), 4.57 (s, 2H), 3.78 (s, 2H)

Example 219. 2-[(2E)-2-(aminomethyl)-3-fluoroprop-2-en-1-yl]-4-{5-[3-(1H-1,2,4-triazol-3-yl)phenyl]pyrazin-2-yl}-2,4-dihydro-3H-1,2,4-triazol-3-one 13.7 mg of the title compound (yield: 49.8%) was prepared in the same fashion as Example 43, except that 30.0 mg of tert-butyl (E)-(2-((4-(5-bromopyrazin-2-yl)-5-oxo-4,5-dihydro-1H-1,2,4-triazol-1-yl)methyl)-3-fluoroallyl)carbamate prepared in Reference Example 75 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 72.3 mg of 3-(3-(4,4,5,5-tetramethyl-1,3,2-dioxaborolan-2-yl)phenyl)-1-((2-(trimethylsilyl)ethoxy)methyl)-1H-1,2,4-triazole prepared in Reference Example 32 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 9.55 (s, 1H), 9.07 (s, 1H), 8.77 (s, 1H), 8.64 (s, 1H), 8.46 (brs, 1H), 8.13-8.21 (m, 2H), 7.65 (m, 1H), 7.11-7.32 (m, 1H), 4.58 (s, 2H), 3.78 (s, 2H)

Example 220. N-[4-(5-{1-[(2E)-2-(aminomethyl)-3-fluoroprop-2-en-1-yl]-5-oxo-1,5-dihydro-4H-1,2,4-triazol-4-yl}pyrazin-2-yl)pyridin-2-yl]acetamide 8.7 mg of the title compound (yield: 32.4%) was prepared in the same fashion as Example 43, except that 30.0 mg of tert-butyl (E)-(2-((4-(5-bromopyrazin-2-yl)-5-oxo-4,5-dihydro-1H-1,2,4-triazol-1-yl)methyl)-3-fluoroallyl)carbamate prepared in Reference Example 75 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 45.9 mg of N-(4-(4,4, 5,5, -tetramethyl-1,3,2-dioxaborolan-2-yl)pyridin-2-yl)acetamide was used instead of 3-(4-(4,4,5,5-tetramethyl-1,3,2-dioxaborolan-2-yl)phenyl)-1-((2-(trimethyl silyl)ethoxy)methyl)-1H-1,2,4-triazole in Step 1. $^1$H-NMR (MeOD, 400 MHz) δ 9.62 (s, 1H), 9.08 (s, 1H), 8.79 (s, 1H), 8.67 (s, 1H), 8.44 (d, 1H), 7.88 (m, 1H), 7.11-7.31 (m, 1H), 4.58 (s, 2H), 3.77 (s, 2H), 2.22 (s, 3H)

Example 221. 2-[(2E)-2-(aminomethyl)-3-fluoroprop-2-en-1-yl]-4-{5-[6-(morpholin-4-yl)pyridin-3-yl]pyrazin-2-yl}-2,4-dihydro-3H-1,2,4-triazol-3-one 5.7 mg of the title compound (yield: 19.8%) was prepared in the same fashion as Example 43, except that 30.0 mg of tert-butyl (E)-(2-((4-(5-bromopyrazin-2-yl)-5-oxo-4,5-dihydro-1H-1,2,4-triazol-1-yl)methyl)-3-fluoroallyl)carbamate prepared in Reference Example 75 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 37.4 mg of 6-(morpholin-4-yl)pyridin-3-boronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 9.44 (s, 1H), 8.93 (d, 1H), 8.86 (s, 1H), 8.61 (s, 1H), 8.29 (d, 1H), 7.10-7.31 (m, 1H), 6.96 (d, 1H), 4.57 (s, 2H), 3.81 (m, 4H), 3.74 (s, 2H), 3.63 (m, 4H)

Example 222. 2-[(2E)-2-(aminomethyl)-3-fluoroprop-2-en-1-yl]-4-[5-(2,1,3-benzooxadiazol-5-yl)pyrazin-2-yl]-2,4-dihydro-3H-1,2,4-triazol-3-one 13.6 mg of the title compound (yield: 52.8%) was prepared in the same fashion as Example 43, except that 30.0 mg of tert-butyl (E)-(2-((4-(5-bromopyrazin-2-yl)-5-oxo-4,5-dihydro-1H-1,2,4-triazol-1-yl)methyl)-3-fluoroallyl)carbamate prepared in Reference Example 75 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 44.3 mg of benzo[c][1,2,5]oxadiazol-5-boronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 9.67 (s, 1H), 9.25 (s, 1H), 8.71 (m, 2H), 8.39 (d, 1H), 8.11 (d, 1H), 7.14-7.34 (m, 1H), 4.60 (s, 2H), 3.80 (s, 2H)

Example 223. 2-[(2E)-2-(aminomethyl)-3-fluoroprop-2-en-1-yl]-4-[5-(1H-indazol-6-yl)pyrazin-2-yl]-2,4-dihydro-3H-1,2,4-triazol-3-one 3.8 mg of the title compound (yield: 14.8%) was prepared in the same fashion as Example 43, except that 30.0 mg of tert-butyl (E)-(2-((4-(5-bromopyrazin-2-yl)-5-oxo-4,5-dihydro-1H-1,2,4-triazol-1-yl)methyl)-3-fluoroallyl)carbamate prepared in Reference Example 75 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 29.2 mg of indazol-6-boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 9.56 (s, 1H), 9.10 (s, 1H), 8.64 (s, 1H), 8.31 (s, 1H), 8.12 (s, 1H), 7.92 (m, 2H), 7.12-7.32 (m, 1H), 4.58 (s, 2H), 3.77 (s, 2H)

Example 224. 4-[5-(2-amino-1,3-benzothiazol-5-yl)pyrazin-2-yl]-2-[(2E)-2-(aminomethyl)-3-fluoroprop-2-en-1-yl]-2,4-dihydro-3H-1,2,4-triazol-3-one 8.1 mg of the title compound (yield: 29.1%) was prepared in the same fashion as Example 43, except that 30.0 mg of tert-butyl (E)-(2-((4-(5-bromopyrazin-2-yl)-5-oxo-4,5-dihydro-1H-1,2,4-triazol-1-yl)methyl)-3-fluoroallyl)carbamate prepared in Reference Example 75 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 50.0 mg of 5-(4,4,5,5-tetramethyl-1,3,2-dioxaborolan-2-yl)benzo[d]thiazol-2-amine prepared in Reference Example 86 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 9.50 (s, 1H), 9.01 (s, 1H), 8.63 (s, 1H), 8.10 (s, 1H), 7.83 (m, 1H), 7.74 (m, 1H), 7.11-7.31 (m, 1H), 4.57 (s, 2H), 3.77 (s, 2H)

Example 225. N-[5-(5-{1-[(2E)-2-(aminomethyl)-3-fluoroprop-2-en-1-yl]-5-oxo-1,5-dihydro-4H-1,2,4-triazol-4-yl}pyrazin-2-yl)-1,3-benzothiazol-2-yl]acetamide 5.1 mg of the title compound (yield: 16.6%) was prepared in the same fashion as Example 43, except that 30.0 mg of tert-butyl (E)-(2-((4-(5-bromopyrazin-2-yl)-5-oxo-4,5-dihydro-1H-1,2,4-triazol-1-yl)methyl)-3-fluoroallyl)carbamate prepared in Reference Example 75 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 57.3 mg of N-(5-(4,4,5,5-tetramethyl-1,3,2-dioxaborolan-2-yl)benzo[d]thiazol-2-yl)acetamide prepared in Reference Example 87 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 9.51 (s, 1H), 9.03 (s, 1H), 8.63 (s, 1H), 8.41 (s, 1H), 7.97-8.04 (m, 2H), 7.12-0.32 (m, 1H), 4.58 (s, 2H), 3.78 (s, 2H), 2.28 (s, 3H)

Example 226. 2-[(2Z)-2-(aminomethyl)-3-fluoroprop-2-en-1-yl]-4-{5-[4-(methylsulfonyl)phenyl]-1,3-thiazol-2-yl}-2,4-dihydro-3H-1,2,4-triazol-3-one hydrochloride 28.5 mg of the title compound (yield: 55.6%) was prepared in the same fashion as Example 42, except that 50.0 mg of tert-butyl (Z)-(2-((4-(5-bromothiazol-2-yl)-5-oxo-4,5-dihydro-1H-1,2,4-triazol-1-yl)methyl)-3-fluoroallyl)carbamate prepared in Reference Example 76 was used instead of tert-butyl (Z)-(2-((4-(4-bromophenyl)-5-oxo-4,5-dihydro-1H-1,2,4-triazol-1-yl)methyl)-3-fluoroallyl)carbamate and 35.0 mg of 4-(methanesulfonyl)phenylboronic acid was used instead of 1-(5-(4,4,5,5-tetramethyl-1,3,2-dioxaborolan-2-yl)thiophen-2-yl)ethan-1-one in Step 1. MS (ESI) m/z=410.1 (M+H)+

Example 227. 2-[(2E)-2-(aminomethyl)-3-fluoroprop-2-en-1-yl]-4-{5-[4-(4H-1,2,4-triazol-3-yl)phenyl]-1,3-thiazol-2-yl}-2,4-dihydro-3H-1,2,4-triazol-3-one 4.6 mg of the title compound (yield: 16.7%) was prepared in the same fashion as Example 43, except that 30.0 mg of tert-butyl (E)-(2-((4-(5-bromothiazol-2-yl)-5-oxo-4,5-dihydro-1H-1,2,4-triazol-1-yl)methyl)-3-fluoroallyl)carbamate prepared in Reference Example 77 was used in Step 1 instead of tert-butyl (E)-(2-((4-(4-bromo-2-fluorophenyl)-5-oxo-4,5-dihydro-1H-1,2,4-triazol-1-yl)methyl)-3-fluoroallyl)carbamate. $^1$H-NMR (MeOD, 400 MHz) δ 8.61 (s, 1H), 8.44 (s, 1H), 8.10 (d, 2H), 8.00 (s, 1H), 7.79 (d, 2H), 7.20 (d, 1H), 4.58 (s, 2H), 3.74 (s, 2H)

Example 228. 2-[(2E)-2-(aminomethyl)-3-fluoroprop-2-en-1-yl]-4-{5-[3-(4H-1,2,4-triazol-3-yl)phenyl]-1,3-thiazol-2-yl}-2,4-dihydro-3H-1,2,4-triazol-3-one 3.5 mg of the title compound (yield: 12.7%) was prepared in the same fashion as Example 43, except that 30.0 mg of tert-butyl (E)-(2-((4-(5-bromothiazol-2-yl)-5-oxo-4,5-dihydro-1H-1,2,4-triazol-1-yl)methyl)-3-fluoroallyl)carbamate prepared in Reference Example 77 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 36.0 mg of 3-(3-(4,4,5,5-tetramethyl-1,3,2-dioxaborolan-2-yl)phenyl)-1-((2-(trimethylsilyl)ethoxy)methyl)-1H-1,2,4-triazole prepared in Reference Example 32 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.62 (s, 1H), 8.46 (s, 1H), 8.34 (s, 1H), 8.03 (d, 1H), 7.99 (s, 1H), 7.75 (d, 1H), 7.58 (t, 1H), 7.20 (d, 1H), 4.58 (s, 2H), 3.73 (s, 2H)

Example 229. 2-[(2E)-2-(aminomethyl)-3-fluoroprop-2-en-1-yl]-4-{5-[4-(4H-1,2,4-oxadiazol-3-yl)phenyl]-1,3-thiazol-2-yl}-2,4-dihydro-3H-1,2,4-triazol-3-one 9.1 mg of the title compound (yield: 33.0%) was prepared in the same fashion as Example 43, except that 30.0 mg of tert-butyl (E)-(2-((4-(5-bromothiazol-2-yl)-5-oxo-4,5-dihydro-1H-1,2,4-triazol-1-yl)methyl)-3-fluoroallyl)carbamate prepared in Reference Example 77 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 36.0 mg of 3-(4-(4,4,5,5-tetramethyl-1,3,2-dioxaborolan-2-yl)phenyl)-1,2,4-oxadiazole prepared in Reference Example 78 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. 41-NMR (MeOD, 400 MHz) δ 8.62 (s, 1H), 8.09 (s, 1H), 7.82 (m, 4H), 7.21 (d, 1H), 4.58 (s, 2H), 3.75 (s, 2H)

Example 230. 2-[(2E)-2-(aminomethyl)-3-fluoroprop-2-en-1-yl]-4-{5-[3-(1H-tetrazol-5-yl)phenyl]-1,3-thiazol-2-yl}-2,4-dihydro-3H-1,2,4-triazol-3-one 4.3 mg of the title compound (yield: 15.6%) was prepared in the same fashion as Example 43, except that 30.0 mg of tert-butyl (E)-(2-((4-(5-bromothiazol-2-yl)-5-oxo-4,5-dihydro-1H-1,2,4-triazol-1-yl)methyl)-3-fluoroallyl)carbamate prepared in Reference Example 77 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 36.0 mg of 5-(3-(4,4,5,5-tetramethyl-1,3,2-dioxaborolan-2-yl)phenyl)-1-((2-(trimethylsilyl)ethoxy)methyl)-1H-tetrazole prepared in Reference Example 88 was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.62 (s, 1H), 8.34 (s, 1H), 8.02 (s, 2H), 7.86 (d, 1H), 7.67 (t, 1H), 7.22 (d, 1H), 4.59 (s, 2H), 3.77 (s, 2H)

Example 231. N-[4-(2-{1-[(2E)-2-(aminomethyl)-3-fluoroprop-2-en-1-yl]-5-oxo-1,5-dihydro-4H-1,2,4-triazol-4-yl}-1,3-thiazol-5-yl)pyridin-2-yl]acetamide 1.2 mg of the title compound (yield: 4.5%) was prepared in the same fashion as Example 43, except that 30.0 mg of tert-butyl (E)-(2-((4-(5-bromothiazol-2-yl)-5-oxo-4,5-dihydro-1H-1,2,4-triazol-1-yl)methyl)-3-fluoroallyl)carbamate prepared in Reference Example 77 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 23.5 mg of (2-acetamido-pyridin-4-yl)boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.63 (s, 1H), 8.33 (t, 2H), 8.15 (s, 1H), 7.41 (d, 1H), 7.21 (d, 1H), 4.58 (s, 2H), 3.75 (s, 2H), 2.21 (s, 3H)

Example 232. 2-[(2Z)-2-(aminomethyl)-3-fluoroprop-2-en-1-yl]-4-[5-(1,3-benzodioxol-5-yl)-1,3-thiazol-2-yl]-2,4-dihydro-3H-1,2,4-triazol-3-one hydrochloride 5.2 mg of the title compound (yield: 18.3%) was prepared in the same fashion as Example 42, except that 30.0 mg of tert-butyl (Z)-(2-((4-(5-bromothiazol-2-yl)-5-oxo-4,5-dihydro-1H-1,2,4-triazol-1-yl)methyl)-3-fluoroallyl)carbamate prepared in Reference Example 76 was used instead of tert-butyl (Z)-(2-((4-(4-bromophenyl)-5-oxo-4,5-dihydro-1H-1,2,4-triazol-1-yl)methyl)-3-fluoroallyl)carbamate and 23.0 mg of 3,4-(methylenedioxy)phenylboronic acid was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.52 (s, 1H), 7.73 (s, 1H), 7.05-7.21 (m, 2H), 6.89 (d, 1H), 6.88 (d, 1H), 6.00 (s, 2H), 4.69 (d, 2H), 3.23 (d, 2H)

Example 233. 6-(2-{1-[(2E)-2-(aminomethyl)-3-fluoroprop-2-en-1-yl]-5-oxo-1,5-dihydro-4H-1,2,4-triazol-4-yl}-1,3-thiazol-5-yl)-1,3-dihydro-2H-indol-2-one 1.5 mg of the title compound (yield: 5.6%) was prepared in the same fashion as Example 43, except that 30.0 mg of tert-butyl (E)-(2-((4-(5-bromothiazol-2-yl)-5-oxo-4,5-dihydro-1H-1,2,4-triazol-1-yl)methyl)-3-fluoroallyl)carbamate prepared in Reference Example 77 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 23.3 mg of (2-oxoindolin-6-yl)boronic acid was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.58 (s, 1H), 7.85 (s, 1H), 7.31 (m, 2H), 7.15 (s, 1H), 7.08 (d, 1H), 4.55 (s, 2H), 3.59 (s, 2H), 2.17 (t, 2H), 1.60 (s, 2H)

Example 234. 2-[(2Z)-2-(aminomethyl)-3-fluoroprop-2-en-1-yl]-4-[5-(2,1,3-benzooxadiazol-5-yl)-1,3-thiazol-2-yl]-2,4-dihydro-3H-1,2,4-triazol-3-one hydrochloride 14.4 mg of the title compound (yield: 30.6%) was prepared in the same fashion as Example 42, except that 50.0 mg of tert-butyl (Z)-(2-((4-(5-bromothiazol-2-yl)-5-oxo-4,5-dihydro-1H-1,2,4-triazol-1-yl)methyl)-3-fluoroallyl)carbamate prepared in Reference Example 76 was used instead of tert-butyl (Z)-(2-((4-(4-bromophenyl)-5-oxo-4,5-dihydro-1H-1,2,4-triazol-1-yl)methyl)-3-fluoroallyl)carbamate and 43.0 mg of benzo[c][1,2,5]oxadiazol-5-boronic acid pinacol ester was used instead of 1-(5-(4,4,5,5-tetramethyl-1,3,2-dioxaborolan-2-yl)thiophen-2-yl)ethan-1-one in Step 1. $^1$H-NMR (DMSO-d$_6$, 400 MHz) δ 8.88 (s, 1H), 8.51 (s, 1H), 8.36 (s, 1H), 7.96-8.21 (m, 3H), 7.22 (d, 1H), 4.67 (d, 2H), 3.37-3.56 (d, 2H)

Example 235. N-[5-(4-{1-[(2E)-2-(aminomethyl)-3-fluoroprop-2-en-1-yl]-5-oxo-1,5-dihydro-4H-1,2,4-triazol-4-yl}benzyl)-1,3-thiazol-2-yl]acetamide hydrochloride Step 1: 4-(4-nitrobenzyl)thiazol-2-amine hydrobromide 3.0 g of 4-nitrophenyl acetone was added to 6.0 mL of acetic acid, and 3.0 mL of 48% aqueous solution of hydrogen bromide was added to the resulting solution. The reaction mixture thus obtained was cooled to 0° C., 5.4 g of bromine dissolved in 4.8 mL of acetic acid was added, and the reaction mixture was stirred at room temperature for 4 hours. 30.0 mL of acetone was further added to the reaction mixture, and the reaction mixture was stirred overnight at room temperature. The reaction mixture was concentrated and dissolved in 140.0 mL of ethanol and then added with 4.7 g of thiourea and refluxed at 80° C. for 3 hours. The reaction mixture thus obtained was concentrated and then washed with acetonitrile to give 4.0 g of the title compound as a white solid (yield: 79.1%). $^1$H-NMR (DMSO-d$_6$, 400 MHz) δ 8.82 (bs, 2H), 8.22 (d, 2H), 7.55 (d, 2H), 6.60 (s, 1H), 4.05 (s, 2H)

Step 2: N-(4-(4-nitrobenzyl)thiazol-2-yl)acetamide 4.0 g of 4-(4-nitrobenzyl)thiazol-2-amine hydrobromide prepared in Step 1 was dissolved in 40.0 mL of dichloromethane, the resulting reaction mixture was cooled to 0° C., and then 4.6 mL of pyridine and 1.4 mL of acetyl chloride were added thereto, and the reaction mixture was stirred at 0° C. for 3 hours. To the reaction mixture, 1N of hydrochloric acid solution and distilled water were added. The reaction mixture was washed with an aqueous solution of sodium hydrogen carbonate, dried with anhydrous magnesium sulfate, and concentrated under reduced pressure to give a yellow liquid residue. The residue was washed with acetonitrile to give 0.9 g of the title compound as a white solid (yield: 25.2%). $^1$H-NMR (DMSO-d$_6$, 400 MHz) δ 12.08 (s, 1H), 8.17 (d, 2H), 7.50 (d, 2H), 6.92 (s, 1H), 4.09 (s, 2H), 2.08 (s, 3H)

Step 3: N-(5-(4-aminobenzyl)thiazol-2-yl)acetamide 926.0 mg of N-(4-(4-nitrobenzyl)thiazol-2-yl)acetamide prepared in Step 2 was dissolved in 18.5 mL of methanol and 4.6 mL of N,N-dimethylformamide, 667.0 mg of Pd/C was added to the resulting solution, and then the solution was stirred at room temperature for 2 hours via hydrogenation using a hydrogen balloon. The reaction mixture thus obtained was filtered with a celite pad and the resulting filtrate was concentrated under reduced pressure, and then it was crystallized with acetonitrile and diethylether to give crystals. The crystals thus obtained were filtered and dried to give 495.0 mg of the title compound as a white solid (yield: 59.9%). $^1$H-NMR (DMSO-d$_6$, 400 MHz) δ 12.02 (s, 1H), 6.87 (d, 2H), 6.65 (s, 1H), 6.47 (d, 2H), 4.86 (s, 2H), 3.72 (s, 2H), 2.08 (s, 3H)

Step 4: phenyl (4-((2-acetamidothiazol-5-yl)methyl) phenyl)carbamate 495.0 mg of N-(5-(4-aminobenzyl)thiazol-2-yl)acetamide prepared in Step 3 and 0.36 mL of pyridine were dissolved in 5.0 mL of ethyl acetate, 0.41 mL of phenylchloroformic acid at 0° C. was slowly added and the solution was stirred overnight at room temperature. To the solution, ethyl acetate was added, and the resulting mixture was washed with a 1N hydrochloric acid solution and brine, dried over anhydrous magnesium sulfate, and concentrated under reduced pressure to give 735.0 mg of the title compound as a white solid (yield: 100.0%). $^1$H-NMR (DMSO-d$_6$, 400 MHz) δ 12.03 (bs, 1H), 10.14 (s, 1H), 8.88 (d, 2H), 8.48 (t, 1H), 7.97 (d, 2H), 7.40-7.44 (m, 4H), 7.26 (d, 1H), 3.88 (s, 2H), 2.09 (s, 3H)

Step 5: N-(4-((2-acetamidothiazol-5-yl)methyl)phenyl)hydrazine carboxamide 735.0 mg of phenyl (4-((2-acetamidothiazol-5-yl)methyl) phenyl)carbamate prepared in Step 4 and 0.23 mL of a hydrazine hydrate were dissolved in 4.0 mL of tetrahydrofuran and 4.0 mL of ethanol, and the resulting solution was stirred overnight at room temperature. The reaction mixture thus obtained was concentrated and washed with ethyl acetate to give 440.0 mg of the title compound as a white solid (yield: 72.0%). $^1$H-NMR (DMSO-d$_6$, 400 MHz) δ 12.03 (s, 1H), 8.53 (s, 1H), 7.40 (d, 2H), 7.33 (s, 1H), 7.09 (d, 2H), 6.73 (s, 1H), 4.37 (bs, 2H), 3.84 (s, 2H), 2.08 (s, 3H)

Step 6: N-(5-(4-(5-oxo-1,5-dihydro-4H-1,2,4-triazol-4-yl)benzyl)thiazol-2-yl)acetamide 440.0 mg of N-(4-((2-acetamidothiazol-5-yl)methyl)phenyl)hydrazine carboxamide prepared in Step 5 and 600.0 mg of formamidine acetate were dissolved in 5.0 mL of 1-propanol, and the resulting solution was stirred at room temperature for 30 minutes, and thereafter 1.0 mL of acetic acid was added thereto and the solution was stirred at 80° C. for 3 hours. The reaction mixture was cooled to room temperature, distilled water was added to the cooled reaction mixture, and then the reaction mixture was stirred overnight. The crystals thus obtained were filtered and dried to give 375.0 mg of the title compound as a yellow solid (yield: 83.3%). $^1$H-NMR (DMSO-$d_6$, 400 MHz) δ 12.03 (d, 1H), 11.94 (s, 1H), 8.31 (s, 1H), 7.56 (d, 2H), 7.37 (d, 2H), 6.83 (s, 1H), 3.97 (s, 2H), 2.08 (s, 3H)

Step 7: tert-butyl (E)-(2-((4-(4-(2-acetamidothiazol-5-yl)methyl)phenyl)-5-oxo-4,5-dihydro-1H-1,2,4-triazol-1-yl)methyl)-3-fluoroallyl)carbamate 100.0 mg of N-(5-(4-(5-oxo-1,5-dihydro-4H-1,2,4-triazol-4-yl)benzyl)thiazol-2-yl)acetamide prepared in Step 6 and 53.0 mg of potassium carbonate were dissolved in 1.0 mL of N,N-dimethylformamide, and 92.0 mg of tert-butyl (E)-(2-(chloromethyl)-3-fluoroallyl)carbamate prepared in Reference Example 2 was added thereto, and the resulting solution was stirred at 60° C. for 1 hour. The resulting reaction mixture was concentrated, and then with addition of ethyl acetate, the reaction mixture was washed with distilled water, dried over anhydrous magnesium sulfate, and concentrated under reduced pressure to obtain a yellow liquid residue. The residue was purified with silica gel column chromatography (developing solvent: n-hexane/ethyl acetate=1/1) to give 35.0 mg of the title compound a colorless liquid (yield: 21.9%). $^1$H-NMR (CDCl$_3$, 400 MHz) δ 8.96 (bs, 1H), 7.66 (s, 1H), 7.45 (d, 2H), 7.33 (d, 2H), 6.75 (d, 1H), 6.53 (s, 1H), 5.31 (bs, 1H), 4.38 (d, 2H), 4.00 (s, 2H), 3.88 (bs, 2H), 2.22 (s, 3H), 1.42 (s, 9H)

Step 8: N-[5-(4-{1-[(2E)-2-(aminomethyl)-3-fluoroprop-2-en-1-yl]-5-oxo-1,5-dihydro-4H-1,2,4-triazol-4-yl}benzyl)-1,3-thiazol-2-yl]acetamide hydrochloride 35.0 mg of tert-butyl (E)-(2-((4-(4-((2-acetamidothiazol-5-yl)methyl)phenyl)-5-oxo-4,5-dihydro-1H-1,2,4-triazol-1-yl)methyl)-3-fluoroallyl)carbamate prepared in Step 7 was dissolved in 0.5 mL of ethyl acetate, 0.2 mL of 4M hydrogen chloride solution in dioxane was added thereto, and the resulting solution was stirred overnight at room temperature. The reaction mixture was concentrated, and then the residue thus obtained was washed with ethyl acetate and concentrated under reduced pressure to give 15.0 mg of the title compound as a yellow solid (yield: 26.3%). MS (ESI) m/z=403.1 (M+H)+

Example 236. 2-[(2E)-2-(aminomethyl)-3-fluoroprop-2-en-1-yl]-4-{4-[(E)-2-phenylethenyl]pyridin-2-yl}-2,4-dihydro-3H-1,2,4-triazol-3-one hydrochloride 3.0 mg of the title compound (yield: 11.0%) was prepared in the same fashion as Example 42, except that 30.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl (Z)-(2-((4-(4-bromophenyl)-5-oxo-4,5-dihydro-1H-1,2,4-triazol-1-yl)methyl)-3-fluoroallyl)carbamate and 16.0 mg of trans-2-vinylphenylboronic acid pinacol ester was used instead of 1-(5-(4,4,5,5-tetramethyl-1,3,2-dioxaborolan-2-yl)thiophen-2-yl)ethan-1-one in Step 1. $^1$H-NMR (MeOD, 400 MHz) δ 8.63 (s, 1H), 8.41-8.42 (m, 1H), 8.35 (s, 1H), 7.64 (d, 2H), 7.55 (d, 2H), 7.40 (d, 2H), 7.27-7.36 (m, 2H), 7.17 (d, 1H), 4.57 (s, 2H), 3.76 (s, 2H)

Example 237. 2-[(2E)-2-(aminomethyl)-3-fluoroprop-2-en-1-yl]-4-{6-[(E)-2-(thiophen-3-yl)ethenyl]pyridin-2-yl}-2,4-dihydro-3H-1,2,4-triazol-3-one 13.0 mg of the title compound (yield: 52.0%) was prepared in the same fashion as Example 43, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 23.0 uL of trans-2-(thiophen-3-yl)vinylboronic acid pinacol ester was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. MS (ESI) m/z=358.1 (M+H)+

Example 238. 2-[(2E)-2-(aminomethyl)-3-fluoroprop-2-en-1-yl]-4-(6-{(E)-2-[4-(trifluoromethyl)phenyl]ethenyl}pyridin-2-yl)-2,4-dihydro-3H-1,2,4-triazol-3-one Hydrochloride 17.4 mg of the title compound (yield: 54.5%) was prepared in the same fashion as Example 42, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 23.0 mg of trans-2-[4-(trifluoromethyl)phenyl]vinylboronic acid was used instead of 1-(5-(4,4,5,5-tetramethyl-1,3,2-dioxaborolan-2-yl)thiophen-2-yl)ethan-1-one in Step 1. $^1$H-NMR (DMSO-$d_6$, 400 MHz) δ 9.04 (s, 1H), 8.12 (d, 1H), 8.05 (d, 1H), 7.97-8.02 (m, 1H), 7.93 (d, 2H), 7.79 (d, 2H), 7.54 (s, 1H), 7.51 (d, 1H), 7.23 (d, 1H), 4.54 (s, 2H), 3.55 (d, 2H)

Example 239. 2-[(E)-2-(aminomethyl)-3-fluoroallyl]-4-[6-[(E)-2-[4-(dimethylamino)phenyl]vinyl]-2-pyridyl]-1,2,4-triazol-3-one hydrochloride 48.2 mg of the title compound (yield: 49.5%) was prepared in the same fashion as Example 42, except that 97.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 80.0 mg of N,N-dimethyl-4-[(E)-2-(4,4,5,5-tetramethyl-1,3,2-dioxaborolan-2-yl)vinyl]aniline was used instead of 1-(5-(4,4,5,5-tetramethyl-1,3,2-dioxaborolan-2-yl)thiophen-2-yl)ethan-1-one in Step 1. MS (ESI) m/z=395.3 (M+H)+

Example 240. 2-[(E)-2-(aminomethyl)-3-fluoroallyl]-4-[6-[(E)-2-(3-methyl-1,2-dihydroimidazo[4,5-b]pyridin-6-yl)vinyl]-2-pyridyl]-1,2,4-triazol-3-one hydrochloride 7.4 mg of the title compound (yield: 7.4%) was prepared in the same fashion as Example 42, except that 97.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 84.0 mg of 3-methyl-6-[(E)-2-(4,4,5,5-tetramethyl-1,3,2-dioxaborolan-2-yl)vinyl]-1,2-dihydroimidazo[4,5-b]pyridine was used instead of 1-(5-(4,4,5,5-tetramethyl-1,3,2-dioxaborolan-2-yl)thiophen-2-yl)ethan-1-one in Step 1. MS (ESI) m/z=408.2 (M+H)+

Example 241. 7-[(E)-2-[6-[1-[(E)-2-(aminomethyl)-3-fluoro-allyl]-5-oxo-1,2,4-triazol-4-yl]-2-pyridyl]vinyl]-1H-pyrido[2,3-b][1,4]oxazin-2-one hydrochloride 31.7 mg of the title compound (yield: 30.5%) was prepared in the same fashion as Example 42, except that 97.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 89.0 mg of 7-[(E)-2-(tetramethyl-1,3,2-dioxaborolan-2-yl)ethynyl]-1H,2H,3H-pyrido[2,3-b][1,4]oxazin-2-one was used instead of 1-(5-(4,4,5,5-tetramethyl-1,3,2-dioxaborolan-2-yl)thiophen-2-yl)ethan-1-one in Step 1. MS (ESI) m/z=424.1 (M+H)+

Example 242. 6-[(E)-2-[6-[1-[(E)-2-(aminomethyl)-3-fluoro-allyl]-5-oxo-1,2,4-triazol-4-yl]-2-pyridyl]vinyl]-3H-oxazolo[4,5-b]pyridin-2-one hydrochloride 9.8 mg of the title compound (yield: 9.7%) was prepared in the same fashion as Example 42, except that 97.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 85.0 mg of 6-[(E)-2-(tetramethyl-1,3,2-dioxaborolan-2-yl)ethynyl]-2H,3H[1,3]oxazolo[4,5-b]pyridin-2-one was used instead of 1-(5-(4,4,5,5-tetramethyl-1,3,2-dioxaborolan-2-yl)thiophen-2-yl)ethan-1-one in Step 1. MS (ESI) m/z=410.1 (M+H)+

Example 243. 2-[(2E)-2-(aminomethyl)-3-fluoroprop-2-en-1-yl]-4-[3-(pyridin-3-ylethynyl)phenyl]-2,4-dihydro-3H-1,2,4-triazol-3-one hydrochloride

Step 1: tert-butyl 5-oxo-4-(3-(pyridin-3-ylethynyl)phenyl)-4,5-dihydro-1H-1,2,4-triazol-1-carboxylate 100.0 mg of tert-butyl 4-(3-bromophenyl)-5-oxo-4,5-dihydro-1H-1,2,4-triazol-1-carboxylate prepared in Reference Example 30, 75.0 mg of 3-ethynylpyridine, 17.0 mg of tetrakis(triphenylphosphine)palladium (Pd(PPh$_3$)$_4$), and 6.0 mg of copper iodide were dissolved in 1.0 mL of N,N-dimethylformamide, 0.12 mL of triethylamine was added thereto, and the resulting solution was stirred overnight at 100° C. The resulting reaction mixture was concentrated, and then with addition of ethyl acetate, the reaction mixture was washed with distilled water, dried over anhydrous magnesium sulfate, and concentrated under reduced pressure to obtain a yellow liquid residue. The residue was purified with silica gel column chromatography (developing solvent: n-hexane/ethyl acetate=1/1) to give 25.0 mg of the title compound as a yellow liquid (yield: 23.8%). $^1$H-NMR (CDCl$_3$, 400 MHz) δ 8.77 (s, 1H), 8.58 (d, 1H), 7.82 (d, 2H), 7.72 (s, 1H), 7.48-7.58 (m, 3H), 7.32 (t, 1H), 1.66 (s, 9H)

Step 2: 4-(3-(pyridin-3-ylethynyl)phenyl)-2,4-dihydro-3H-1,2,4-triazol-3-one 25.0 mg of tert-butyl 5-oxo-4-(3-(pyridin-3-yl ethynyl)phenyl)-4,5-dihydro-1H-1,2,4-triazol-1-carboxylate prepared in Step 1 was dissolved in 0.5 mL of dichloromethane, 80.0 uL of trifluoroacetic acid was added thereto, and then the resulting solution was stirred overnight at room temperature. The reaction mixture was concentrated under reduced pressure to give 18.1 mg of the title compound as a yellow solid (yield: 100.0%). $^1$H-NMR (MeOD, 400 MHz) δ 8.86 (s, 1H), 8.65 (d, 1H), 8.26 (d, 1H), 8.19 (s, 1H), 7.93 (s, 1H), 7.70 (t, 2H), 7.56-7.63 (m, 2H)

Step 3: tert-butyl (E)-(3-fluoro-2-((5-oxo-4-(3-(pyridin-3-ylethynyl)phenyl)-4,5-dihydro-1H-1,2,4-triazol-1-yl)methyl)allyl)carbamate 18.1 mg of 4-(3-(pyridin-3-ylethynyl)phenyl)-2,4-dihydro-3H-1,2,4-triazol-3-one prepared in Step 2 and 19.0 mg of potassium carbonate were dissolved in 1.0 mL of N,N-dimethylformamide, 22.0 mg of tert-butyl (E)-(2-(chloromethyl)-3-fluoroallyl)carbamate prepared in Reference Example 2 was added thereto, and the resulting solution was stirred at 90° C. for 3.5 hours. The resulting reaction mixture was concentrated, and then with addition of ethyl acetate, the reaction mixture was washed with distilled water, dried over anhydrous magnesium sulfate, and concentrated under reduced pressure to obtain a yellow liquid residue. The residue was purified with silica gel column chromatography (developing solvent: n-hexane/ethyl acetate=1/2) to give 15.0 mg of the title compound as a colorless liquid (yield: 47.8%). MS (ESI) m/z=350.1 (M+H)+

Step 4: 2-[(2E)-2-(aminomethyl)-3-fluoroprop-2-en-1-yl]-4-[3-(pyridin-3-ylethynyl)phenyl]-2,4-dihydro-3H-1,2,4-triazol-3-one hydrochloride 15.0 mg of tert-butyl (E)-(3-fluoro-2-((5-oxo-4-(3-(pyridin-3-ylethynyl)phenyl)-4,5-dihydro-1H-1,2,4-triazol-1-yl)methyl)allyl)carbamate prepared in Step 3 was dissolved in 0.35 mL of ethyl acetate, 0.3 mL of 4M hydrogen chloride solution in dioxane was added thereto, and the resulting solution was stirred overnight at room temperature. The reaction mixture was concentrated, and the residue thus obtained was washed with ethyl acetate and concentrated under reduced pressure to give 4.8 mg of the title compound as a white solid (yield: 37.3%). $^1$H-NMR (MeOD, 400 MHz) δ 9.18 (s, 1H), 8.86 (d, 1H), 8.76 (d, 1H), 8.35 (s, 1H), 8.13 (t, 1H), 8.03 (s, 1H), 7.79 (d, 1H), 7.69 (d, 1H), 7.62 (t, 1H), 7.19 (d, 1H), 4.56 (s, 2H), 3.76 (s, 2H)

Example 244. 2-[(2E)-2-(aminomethyl)-3-fluoroprop-2-en-1-yl]-4-[4-(pyridin-2-ylethynyl)pyridin-2-yl]-2,4-dihydro-3H-1,2,4-triazol-3-one hydrochloride

Step 1: tert-butyl (E)-(3-fluoro-2-((5-oxo-4-(4-(pyridin-2-ylethynyl)pyridin-2-yl)-4,5-dihydro-1H-1,2,4-triazol-1-yl)methyl)allyl)carbamate 26.0 mg of the title compound as a yellow solid (yield: 100%) was prepared in the same fashion as Example 243, except that 25.0 mg of tert-butyl (E)-(2-((4-(4-bromopyridin-2-yl)-5-oxo-4,5-dihydro-1H-1,2,4-triazol-1-yl)methyl)-3-fluoroallyl)carbamate prepared in Reference Example 71 was used instead of tert-butyl 4-(3-bromophenyl)-5-oxo-4,5-dihydro-1H-1,2,4-triazol-1-carboxylate and 15.0 mg of 2-ethynylpyridine was used instead of 3-ethynylpyridine in Step 1. MS (ESI) m/z=351.2 (M+H)+

Step 2: 2-[(2E)-2-(aminomethyl)-3-fluoroprop-2-en-1-yl]-4-[4-(pyridin-2-ylethynyl)pyridin-2-yl]-2,4-dihydro-3H-1,2,4-triazol-3-one hydrochloride 26.0 mg of tert-butyl (E)-(3-fluoro-2-((5-oxo-4-(4-(pyridin-2-ylethynyl)pyridin-2-yl)-4,5-dihydro-1H-1,2,4-triazol-1-yl)methyl)allyl)carbamate prepared in Step 1 was dissolved in 0.5 mL of ethyl acetate, 0.25 mL of 4M hydrogen chloride solution in dioxane was added thereto, and the resulting solution was stirred overnight at room temperature. The reaction mixture was concentrated, and the residue thus obtained was washed with ethyl acetate and concentrated under reduced pressure to give 13.1 mg of the title compound as a yellow solid (yield: 58.7%). $^1$H-NMR (DMSO-$d_6$, 400 MHz) δ 8.82 (s, 1H), 8.66 (s, 1H), 8.62 (d, 1H), 8.58 (d, 1H), 8.00 (d, 2H), 7.73 (d, 1H), 7.51 (dd, 1H), 7.24 (d, 1H), 4.53 (s, 2H), 3.53 (d, 2H)

Example 245. 2-[(2E)-2-(aminomethyl)-3-fluoroprop-2-en-1-yl]-4-[4-(pyridin-3-ylethynyl)pyridin-2-yl]-2,4-dihydro-3H-1,2,4-triazol-3-one hydrochloride 9.8 mg of the title compound (yield: 43.9%) was prepared in the same fashion as Example 244, except that 15.0 mg of 3-ethynylpyridine was used in Step 1 instead of 2-ethynylpyridine. $^1$H-NMR (DMSO-$d_6$, 400 MHz) δ 8.89 (s, 1H), 8.72 (s, 1H), 8.68 (dd, 1H), 8.59 (d, 1H), 8.32 (s, 1H), 8.11-8.14 (m, 1H), 7.60 (dd, 1H), 7.54 (dd, 1H), 7.22 (d, 1H), 4.53 (s, 2H), 3.56 (d, 2H)

Example 246. 2-[(2E)-2-(aminomethyl)-3-fluoroprop-2-en-1-yl]-4-[4-(pyridin-4-ylethynyl)pyridin-2-yl]-2,4-dihydro-3H-1,2,4-triazol-3-one hydrochloride 2.5 mg of the title compound (yield: 48.5%) was prepared in the same fashion as Example 244, except that 20.0 mg of 4-ethynylpyridine was used in Step 1 instead of 2-ethynylpyridine. $^1$H-NMR (DMSO-$d_6$, 400 MHz) δ 8.90 (d, 1H), 8.80 (s, 2H), 8.61 (d, 1H), 8.06 (d, 1H), 7.75 (dd, 1H), 7.61 (dd, 1H), 7.22 (d, 1H), 4.53 (s, 2H), 3.53 (d, 2H)

Example 247. 2-[(2E)-2-(aminomethyl)-3-fluoroprop-2-en-1-yl]-4-{6-[(6-methoxypyridin-3-yl)ethynyl]pyridin-2-yl}-2,4-dihydro-3H-1,2,4-triazol-3-one Step 1: tert-butyl (E)-(2-((4-(6-((6-methoxypyridin-3-yl)ethynyl)pyridin-2-yl)-5-oxo-4,5-dihydro-1H-1,2,4-triazol-1-yl)methyl)-3-fluoroallyl)carbamate 34.0 mg of the title compound as a yellow solid (yield: 100%) was prepared in the same fashion as Example 244, except that 30.0 mg of tert-butyl (E)-(2-((4-(6-bromopyridin-2-yl)-5-oxo-4,5-dihydro-1H-1,2,4-triazol-1-yl)methyl)-3-fluoroallyl)carbamate prepared in Reference Example 72 was used instead of tert-butyl (E)-(2-((4-(4-bromopyridin-2-yl)-5-oxo-4,5-dihydro-1H-1,2,4-triazol-1-yl)methyl)-3-fluoroallyl)carbamate and 23.0 mg of 5-ethynyl-2-methoxypyridine was used instead of 2-ethynylpyridine in Step 1. MS (ESI) m/z=381.1 (M+H)+

Step 2: 2-[(2E)-2-(aminomethyl)-3-fluoroprop-2-en-1-yl]-4-{6-[(6-methoxypyridin-3-yl)ethynyl]pyridin-2-yl}-2,4-dihydro-3H-1,2,4-triazol-3-one 34.0 mg of tert-butyl (E)-(2-((4-(6-((6-methoxypyridin-3-yl)ethynyl)pyridin-2-yl)-5-oxo-4,5-dihydro-1H-1,2,4-triazol-1-yl)methyl)-3-fluoroallyl)carbamate prepared in Step 1 was dissolved in 0.5 mL of dichloromethane, 72.0 uL of trifluoroacetic acid was added thereto, and the resulting solution was stirred at room temperature for 3 hours. The residue obtained by concentration under reduced pressure was dissolved in dichloromethane, and the solution thus obtained was washed with an aqueous solution of sodium bicarbonate and brine, dried over anhydrous magnesium sulfate, and concentrated under reduced pressure to give a yellow liquid residue. The residue was purified with silica gel column chromatography (developing solvent: dichloromethane/methanol=10/1) to give 25.0 mg of the title compound as a yellow solid (yield: 92.9%). $^1$H-NMR (DMSO-$d_6$, 400 MHz) δ 8.67 (s, 1H), 8.48 (s, 1H), 8.20 (d, 1H), 8.07 (t, 1H), 7.95 (d, 1H), 7.64 (d, 1H), 6.98 (d, 1H), 6.93 (d, 1H), 4.44 (s, 2H), 3.90 (s, 3H), 3.28 (s, 2H)

Example 248. 2-[(E)-2-(aminomethyl)-3-fluoroallyl]-4-[6-[2-[6-(dimethylamino)-3-pyridyl]ethynyl]-2-pyridyl]-1,2,4-triazol-3-one 26.0 mg of the title compound (yield: 98.8%) was prepared in the same fashion as Example 247, except that 43.0 mg of 5-ethynyl-N,N-dimethylpyridin-2-amine was used in Step 1 instead of 5-ethynyl-2-methoxypyridine. MS (ESI) m/z=394.2 (M+H)$^+$ Example 249. 2-[(E)-2-(aminomethyl)-3-fluoroallyl]-4-[6-[2-(6-morpholino-3-pyridyl)ethynyl]-2-pyridyl]-1,2,4-triazol-3-one 28.0 mg of the title compound (yield: 62.6%) was prepared in the same fashion as Example 247, except that 55.0 mg of 4-(5-ethynylpyridin-2-yl)morpholine was used in Step 1 instead of 5-ethynyl-2-methoxypyridine. $^1$H-NMR (MeOD, 400 MHz) δ 8.66 (s, 1H), 8.34 (s, 1H), 8.20 (d, 1H), 7.95 (t, 1H), 7.70 (d, 1H), 7.52 (d, 1H), 7.20 (d, 1H), 6.82 (d, 1H), 4.55 (m, 2H), 3.77-3.78 (m, 6H), 3.59 (s, 4H)

Example 250. 2-[(E)-2-(aminomethyl)-3-fluoroallyl]-4-[6-[2-(3,4-dihydro-2H-1,4-benzoxazin-6-yl)ethynyl]-2-pyridyl]-1,2,4-triazol-3-one 33.0 mg of the title compound (yield: 54.1%) was prepared in the same fashion as Example 247, except that 76.0 mg of tert-butyl 6-ethynyl-2H-benzo[b][1,4]oxazin-4(3H)-carboxylate was used in Step 1 instead of 5-ethynyl-2-methoxypyridine. $^1$H-NMR (MeOD, 400 MHz) δ 8.64 (s, 1H), 8.17 (d, 1H), 7.93 (t, 1H), 7.48 (d, 1H), 7.19 (d, 1H), 6.80 (d, 2H), 6.69 (d, 1H), 4.54 (s, 2H), 4.22 (s, 2H), 3.75 (s, 2H), 3.35 (s, 2H)

Example 251. 2-[(E)-2-(aminomethyl)-3-fluoroallyl]-4-[6-[2-(2,3-dihydro-1H-pyrido[2,3-b][1,4]oxazin-7-yl)ethynyl]-2-pyridyl]-1,2,4-triazol-3-one 27.0 mg of the title compound (yield: 71.6%) was prepared in the same fashion as Example 247, except that 47.0 mg of 7-ethynyl-2,3-dihydro-1H-pyrido[2,3-b][1,4]oxazine was used in Step 1 instead of 5-ethynyl-2-methoxypyridine. $^1$H-NMR (DMSO-d$_6$, 400 MHz) δ 8.69 (s, 1H), 8.08-8.17 (m, 2H), 7.62 (d, 2H), 7.21 (d, 1H), 7.04 (s, 1H), 6.36 (s, 1H), 4.49 (s, 2H), 4.30 (bs, 2H), 3.53 (s, 2H), 3.29 (bs, 2H)

Example 252. 2-[(E)-2-(aminomethyl)-3-fluoro-allyl]-4-[6-[2-(3,4-dihydro-2H-pyrido[3,2-b][1,4]oxazin-7-yl)ethynyl]-2-pyridyl]-1,2,4-triazol-3-one 21.0 mg of the title compound (yield: 55.7%) was prepared in the same fashion as Example 247, except that 47.0 mg of 7-ethynyl-2H,3H,4H-pyrido[3,2-b][1,4]oxazine was used in Step 1 instead of 5-ethynyl-2-methoxypyridine. $^1$H-NMR (MeOD, 400 MHz) δ 8.64 (s, 1H), 8.18 (d, 1H), 7.93 (t, 1H), 7.79 (s, 1H), 7.49 (d, 1H), 7.20 (d, 1H), 7.10 (s, 1H), 4.54 (s, 2H), 4.18 (s, 2H), 3.75 (s, 2H), 3.54 (s, 2H)

Example 253. 2-[(E)-2-(aminomethyl)-3-fluoro-allyl]-4-[6-[2-(2,3-dihydro-1H-pyrido[2,3-b][1,4]oxazin-6-yl)ethynyl]-2-pyridyl]-1,2,4-triazol-3-one 30.0 mg of the title compound (yield: 79.5%) was prepared in the same fashion as Example 247, except that 47.0 mg of 6-ethynyl-2,3-dihydro-1H-pyrido[2,3-b][1,4]oxazine was used in Step 1 instead of 5-ethynyl-2-methoxypyridine. $^1$H-NMR (DMSO-d$_6$, 400 MHz) δ 8.71 (s, 1H), 8.14 (d, 1H), 8.03 (t, 1H), 7.57 (d, 1H), 7.22 (d, 1H), 7.11-7.12 (m, 1H), 6.87 (d, 1H), 6.76 (s, 1H), 4.49 (s, 2H), 4.26 (bs, 2H), 3.53 (s, 2H), 3.33 (bs, 2H)

Example 254. 6-[2-[6-[1-[(E)-2-(aminomethyl)-3-fluoro-allyl]-5-oxo-1,2,4-triazol-4-yl]-2-pyridyl]ethynyl]-3,4-dihydro-1H-quinolin-2-one 29.0 mg of the title compound (yield: 71.9%) was prepared in the same fashion as Example 247, except that 50.0 mg of 6-ethynyl-1,2,3,4-tetrahydroquinolin-2-one was used in Step 1 instead of 5-ethynyl-2-methoxypyridine. MS (ESI) m/z=419.1 (M+H)+

Example 255. 7-[2-[6-[1-[(E)-2-(aminomethyl)-3-fluoro-allyl]-5-oxo-1,2,4-triazol-4-yl]-2-pyridyl]ethynyl]-4H-pyrido[3,2-b][1,4]oxazin-3-one 6.0 mg of the title compound (yield: 14.6%) was prepared in the same fashion as Example 247, except that 51.0 mg of 7-ethynyl-2H,3H,4H-pyrido[3,2-b][1,4]oxazin-3-one was used in Step 1 instead of 5-ethynyl-2-methoxypyridine. MS (ESI) m/z=422.1 (M+H)+

Example 256. 2-[(E)-2-(aminomethyl)-3-fluoro-allyl]-4-[6-[2-(3-methylimidazol-4-yl)ethynyl]-2-pyridyl]-1,2,4-triazol-3-one 21.0 mg of the title compound (yield: 86.9%) was prepared in the same fashion as Example 247, except that 31.0 mg of 5-ethynyl-1-methyl-1H-imidazole was used in Step 1 instead of 5-ethynyl-2-methoxypyridine. $^1$H-NMR (DMSO-d$_6$, 400 MHz) δ 8.69 (s, 1H), 8.40 (s, 1H), 8.22 (d, 1H), 8.06-8.13 (m, 2H), 7.76 (s, 1H), 7.71 (d, 1H), 7.21 (d, 1H), 4.49 (s, 2H), 3.81 (s, 3H), 3.46 (s, 2H)

Example 257. 2-[(2E)-2-(aminomethyl)-3-fluoro-prop-2-en-1-yl]-4-{6-[(1-methyl-1H-pyrazol-4-yl)ethynyl]pyridin-2-yl}-2,4-dihydro-3H-1,2,4-triazol-3-one hydrochloride 4.9 mg of the title compound (yield: 14.3%) was prepared in the same fashion as Example 42, except that 30.0 mg of tert-butyl (E)-(2-((4-(6-bromopyridin-2-yl)-5-oxo-4,5-di-hydro-1H-1,2,4-triazol-1-yl)methyl)-3-fluoroallyl)carbamate prepared in Reference Example 72 was used instead of tert-butyl (Z)-(2-((4-(4-bromophenyl)-5-oxo-4,5-dihydro-1H-1,2,4-triazol-1-yl)methyl)-3-fluoroallyl)carbamate and 17.0 mg of 1-methyl-4-[(4,4,5,5-tetramethyl-1,3,2-dioxaborolan-2-yl)ethynyl]-1H-pyrazole was used instead of 1-(5-(4,4,5,5-tetramethyl-1,3,2-dioxaborolan-2-yl)thiophen-2-yl)ethan-1-one in Step 1. $^1$H-NMR (DMSO-d$_6$, 400 MHz) δ 8.69 (s, 1H), 8.19 (s, 1H), 8.15 (d, 1H), 8.05 (t, 1H), 7.78 (s, 1H), 7.56 (d, 1H), 7.22 (d, 1H), 4.52 (d, 2H), 3.88 (s, 3H), 3.52 (s, 2H)

Example 258. 7-[2-[6-[1-[(E)-2-(aminomethyl)-3-fluoro-allyl]-5-oxo-1,2,4-triazol-4-yl]-2-pyridyl]ethynyl]-1H-pyrido[2,3-b][1,4]oxazin-2-one 12 mg of the title compound (yield: 15.2%) was prepared in the same fashion as Example 247, except that 81 mg of 7-ethynyl-1H,2H,3H-pyrido[2,3-b][1,4]oxazin-2-one was used in Step 1 instead of 5-ethynyl-2-methoxypyridine. $^1$H-NMR (MeOD, 400 MHz) δ 8.66 (s, 1H), 8.27 (d, 1H), 8.04 (s, 1H), 8.00 (t, 1H), 7.59 (d, 1H), 7.41 (s, 1H), 7.20 (d, 1H), 4.89 (s, 2H), 4.54 (d, 2H), 3.75 (s, 2H)

Example 259. 2-[(E)-2-(aminomethyl)-3-fluoro-allyl]-4-[3-methyl-5-(6-piperazin-1-yl-3-pyridyl)-2-pyridyl]-1,2,4-triazol-3-one 46 mg of the title compound (yield: 93.3%) was prepared in the same fashion as Example 43, except that 50 mg of tert-butyl (E)-(2-((4-(5-bromo-3-methylpyridin-2-yl)-5-oxo-4,5-dihydro-1H-1,2,4-triazol-1-yl)methyl)-3-fluoroallyl)carbamate prepared in Reference Example 66 was used instead of tert-butyl (E)-(2-((4-(4-bromo-2-fluorophenyl)-5-oxo-4,5-dihydro-1H-1,2,4-triazol-1-yl)methyl)-3-fluoroallyl)carbamate and 57 mg of tert-butyl 4-[5-(4,4,5,5-tetramethyl-1,3,2-dioxaborolan-2-yl)-2-pyridyl]piperazin-1-carboxylate was used instead of 3-(4-(4,4,5,5-tetramethyl-1,3,2-dioxaborolan-2-yl)phenyl)-1-((2-(trimethylsilyl)ethoxy)methyl)-1H-1,2,4-triazole in Step 1. $^1$H-NMR (MeOD, 400 MHz) δ 8.64 (s, 1H), 8.55 (s, 1H), 8.16 (s, 1H), 8.13 (s, 1H), 8.00 (d, 1H), 7.20 (d, 1H), 7.06 (d, 1H), 4.58 (s, 2H), 3.91 (s, 4H), 3.77 (s, 2H), 3.35 (s, 4H), 2.41 (s, 3H)

Compounds from the Examples are shown in Table 1.

TABLE 1

| EX No | Structure | Chemical Name |
|---|---|---|
| 1 | 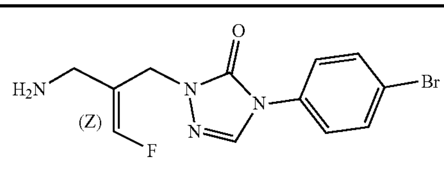 | 2-[(2Z)-2-(aminomethyl)-3-fluoroprop-2-en-1-yl]-4-(4-bromophenyl)-2,4-dihydro-3H-1,2,4-triazol-3-one |

TABLE 1-continued

| EX No | Structure | Chemical Name |
|---|---|---|
| 2 | 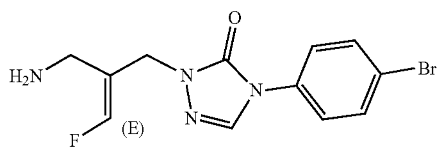 [SMILES: NC/C(=C\F)Cn1ncn(-c2ccc(Br)cc2)c1=O] | 2-[(2E)-2-(aminomethyl)-3-fluoroprop-2-en-1-yl]-4-(4-bromophenyl)-2,4-dihydro-3H-1,2,4-triazol-3-one |
| 3 | 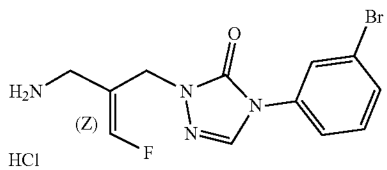 [SMILES: NC/C(=C/F)Cn1ncn(-c2cccc(Br)c2)c1=O ; Cl] | 2-[(2Z)-2-(aminomethyl)-3-fluoroprop-2-en-1-yl]-4-(3-bromophenyl)-2,4-dihydro-3H-1,2,4-triazol-3-one hydrochloride |
| 4 | 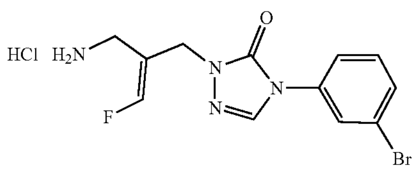 [SMILES: Cl ; NC/C(=C\F)Cn1ncn(-c2cccc(Br)c2)c1=O] | 2-[(2E)-2-(aminomethyl)-3-fluoroprop-2-en-1-yl]-4-(3-bromophenyl)-2,4-dihydro-3H-1,2,4-triazol-3-one hydrochloride |
| 5 | 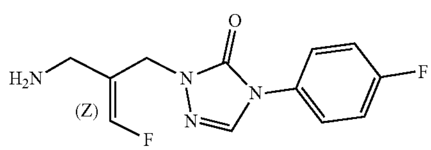 | 2-[(2Z)-2-(aminomethyl)-3-fluoroprop-2-en-1-yl]-4-(4-fluorophenyl)-2,4-dihydro-3H-1,2,4-triazol-3-one |
| 6 | 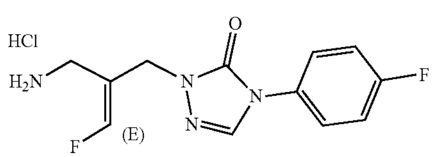 [SMILES: Cl ; NC/C(=C\F)Cn1ncn(-c2ccc(F)cc2)c1=O] | 2-[(2E)-2-(aminomethyl)-3-fluoroprop-2-en-1-yl]-4-(4-fluorophenyl)-2,4-dihydro-3H-1,2,4-triazol-3-one hydrochloride |
| 7 | 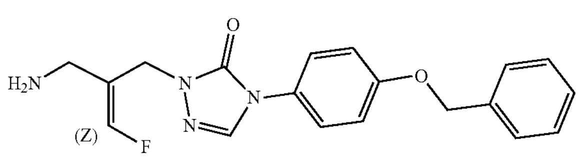 [SMILES: NC/C(=C/F)Cn1ncn(-c2ccc(OCc3ccccc3)cc2)c1=O] | 2-[(2Z)-2-(aminomethyl)-3-fluoroprop-2-en-1-yl]-4-[4-(benzyloxy)phenyl]-2,4-dihydro-3H-1,2,4-triazol-3-one |
| 8 | 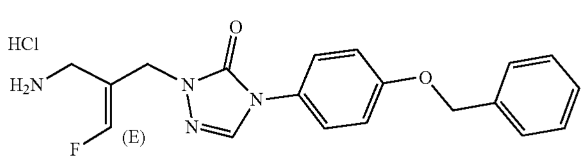 [SMILES: Cl ; NC/C(=C\F)Cn1ncn(-c2ccc(OCc3ccccc3)cc2)c1=O] | 2-[(2E)-2-(aminomethyl)-3-fluoroprop-2-en-1-yl]-4-[4-(benzyloxy)phenyl]-2,4-dihydro-3H-1,2,4-triazol-3-one hydrochloride |
| 9 | 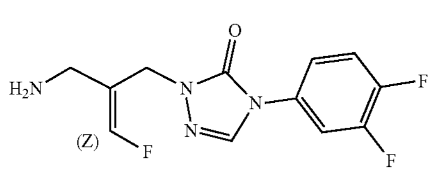 [SMILES: NC/C(=C/F)Cn1ncn(-c2ccc(F)c(F)c2)c1=O] | 2-[(2Z)-2-(aminomethyl)-3-fluoroprop-2-en-1-yl]-4-(3,4-difluorophenyl)-2,4-dihydro-3H-1,2,4-triazol-3-one |

TABLE 1-continued

| EX No | Structure | Chemical Name |
|---|---|---|
| 10 | 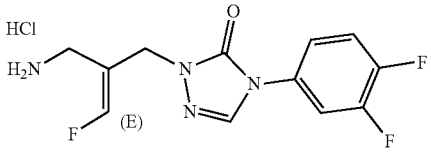 [SMILES: Cl ; NC/C(=C\F)Cn1ncn(-c2ccc(F)c(F)c2)c1=O] | 2-[(2E)-2-(aminomethyl)-3-fluoroprop-2-en-1-yl]-4-(3,4-difluorophenyl)-2,4-dihydro-3H-1,2,4-triazol-3-one hydrochloride |
| 11 | 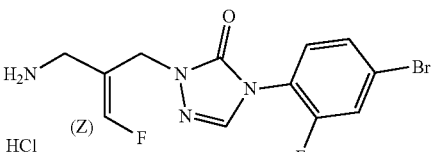 [SMILES: NC/C(=C/F)Cn1ncn(-c2ccc(Br)c(F)c2)c1=O] | 2-[(2Z)-2-(aminomethyl)-3-fluoroprop-2-en-1-yl]-4-(4-bromo-2-fluorophenyl)-2,4-dihydro-3H-1,2,4-triazol-3-one hydrochloride |
| 12 | 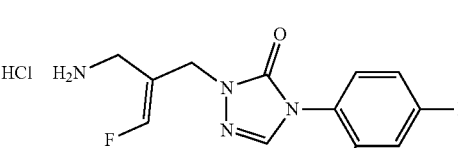 | 2-[(2E)-2-(aminomethyl)-3-fluoroprop-2-en-1-yl]-4-(4-bromo-2-fluorophenyl)-2,4-dihydro-3H-1,2,4-triazol-3-one hydrochloride |
| 13 | 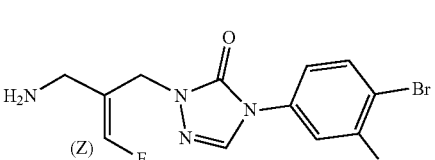 | 2-[(2Z)-2-(aminomethyl)-3-fluoroprop-2-en-1-yl]-4-(4-bromo-3-fluorophenyl)-2,4-dihydro-3H-1,2,4-triazol-3-one |
| 14 | 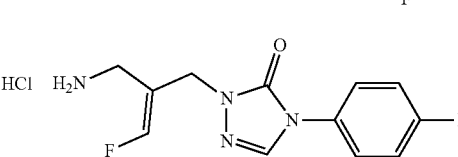 | 2-[(2E)-2-(aminomethyl)-3-fluoroprop-2-en-1-yl]-4-(4-bromo-3-fluorophenyl)-2,4-dihydro-3H-1,2,4-triazol-3-one hydrochloride |
| 15 | 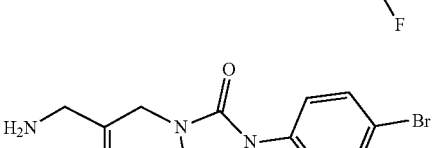 | 2-[(2Z)-2-(aminomethyl)-3-fluoroprop-2-en-1-yl]-4-(4-bromo-3-methylphenyl)-2,4-dihydro-3H-1,2,4-triazol-3-one |
| 16 | 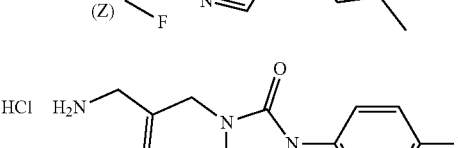 | 2-[(2E)-2-(aminomethyl)-3-fluoroprop-2-en-1-yl]-4-(4-bromo-3-methylphenyl)-2,4-dihydro-3H-1,2,4-triazol-3-one hydrochloride |
| 17 | 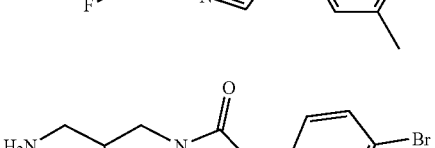 | 2-[(2Z)-2-(aminomethyl)-3-fluoroprop-2-en-1-yl]-4-(4-bromo-3-methoxyphenyl)-2,4-dihydro-3H-1,2,4-triazol-3-one |
| 18 | 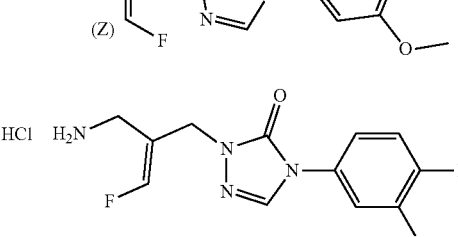 | 2-[(2E)-2-(aminomethyl)-3-fluoroprop-2-en-1-yl]-4-(4-bromo-3-methoxyphenyl)-2,4-dihydro-3H-1,2,4-triazol-3-one hydrochloride |

TABLE 1-continued

| EX No | Structure | Chemical Name |
|---|---|---|
| 19 | 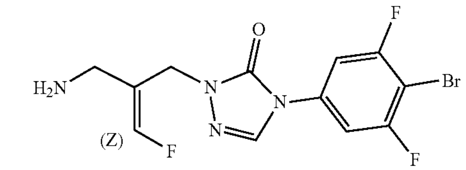 [SMILES: NC/C(=C/F)Cn1ncn(-c2cc(F)c(Br)c(F)c2)c1=O] | 2-[(2Z)-2-(aminomethyl)-3-fluoroprop-2-en-1-yl]-4-(4-bromo-3,5-difluorophenyl)-2,4-dihydro-3H-1,2,4-triazol-3-one |
| 20 | 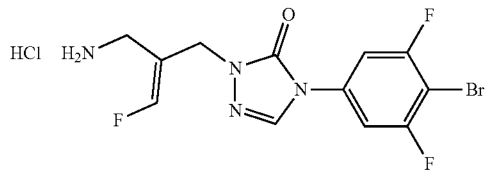 [SMILES: Cl ; NC/C(=C\F)Cn1ncn(-c2cc(F)c(Br)c(F)c2)c1=O] | 2-[(2E)-2-(aminomethyl)-3-fluoroprop-2-en-1-yl]-4-(4-bromo-3,5-difluorophenyl)-2,4-dihydro-3H-1,2,4-triazol-3-one hydrochloride |
| 21 | 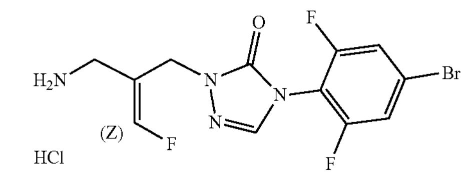 [SMILES: Cl ; NC/C(=C/F)Cn1ncn(-c2c(F)cc(Br)cc2F)c1=O] | 2-[(2Z)-2-(aminomethyl)-3-fluoroprop-2-en-1-yl]-4-(4-bromo-2,6-difluorophenyl)-2,4-dihydro-3H-1,2,4-triazol-3-one hydrochloride |
| 22 | 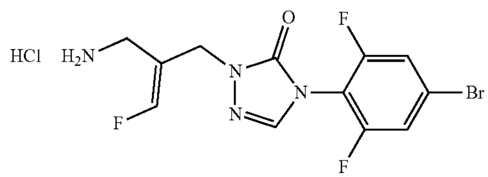 [SMILES: Cl ; NC/C(=C\F)Cn1ncn(-c2c(F)cc(Br)cc2F)c1=O] | 2-[(2E)-2-(aminomethyl)-3-fluoroprop-2-en-1-yl]-4-(4-bromo-2,6-difluorophenyl)-2,4-dihydro-3H-1,2,4-triazol-3-one hydrochloride |
| 23 | 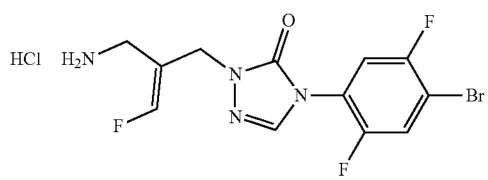 [SMILES: Cl ; NC/C(=C\F)Cn1ncn(-c2cc(F)c(Br)cc2F)c1=O] | 2-[(2E)-2-(aminomethyl)-3-fluoroprop-2-en-1-yl]-4-(4-bromo-2,5-difluorophenyl)-2,4-dihydro-3H-1,2,4-triazol-3-one hydrochloride |
| 24 | 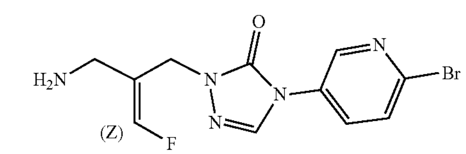 [SMILES: NC/C(=C/F)Cn1ncn(-c2ccc(Br)nc2)c1=O] | 2-[(2Z)-2-(aminomethyl)-3-fluoroprop-2-en-1-yl]-4-(6-bromopyridin-3-yl)-2,4-dihydro-3H-1,2,4-triazol-3-one |
| 25 | 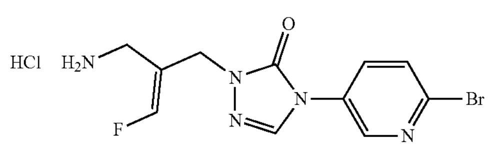 [SMILES: Cl ; NC/C(=C\F)Cn1ncn(-c2ccc(Br)nc2)c1=O] | 2-[(2E)-2-(aminomethyl)-3-fluoroprop-2-en-1-yl]-4-(6-bromopyridin-3-yl)-2,4-dihydro-3H-1,2,4-triazol-3-one hydrochloride |
| 26 | 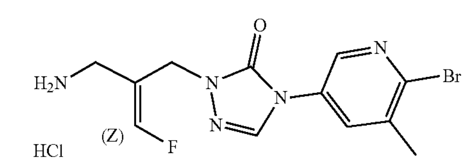 [SMILES: Cl ; Cc1cc(-n2cnn(C/C(=C\F)CN)c2=O)cnc1Br] | 2-[(2Z)-2-(aminomethyl)-3-fluoroprop-2-en-1-yl]-4-(6-bromo-5-methylpyridin-3-yl)-2,4-dihydro-3H-1,2,4-triazol-3-one hydrochloride |
| 27 | 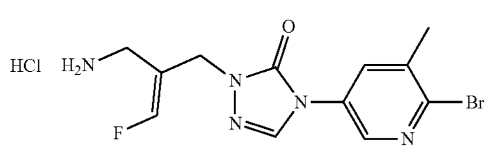 [SMILES: Cl ; Cc1cc(-n2cnn(C/C(=C/F)CN)c2=O)cnc1Br] | 2-[(2E)-2-(aminomethyl)-3-fluoroprop-2-en-1-yl]-4-(6-bromo-5-methylpyridin-3-yl)-2,4-dihydro-3H-1,2,4-triazol-3-one hydrochloride |

TABLE 1-continued

| EX No | Structure | Chemical Name |
|---|---|---|
| 28 | 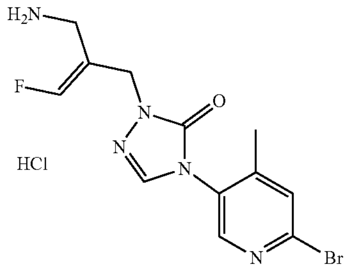 [SMILES: Cc1cc(Br)ncc1-n1cnn(C/C(=C/F)CN)c1=O ; Cl] | 2-[(2E)-2-(aminomethyl)-3-fluoroprop-2-en-1-yl]-4-(6-bromo-4-methylpyridin-3-yl)-2,4-dihydro-3H-1,2,4-triazol-3-one hydrochloride |
| 29 | 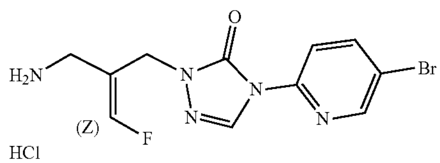 [SMILES: NC/C(=C/F)Cn1ncn(-c2ccc(Br)cn2)c1=O ; Cl] | 2-[(2Z)-2-(aminomethyl)-3-fluoroprop-2-en-1-yl]-4-(5-bromopyridin-2-yl)-2,4-dihydro-3H-1,2,4-triazol-3-one hydrochloride |
| 30 | 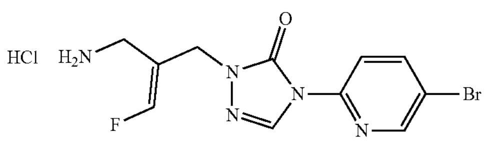 [SMILES: Cl ; NC/C(=C\F)Cn1ncn(-c2ccc(Br)cn2)c1=O] | 2-[(2E)-2-(aminomethyl)-3-fluoroprop-2-en-1-yl]-4-(5-bromopyridin-2-yl)-2,4-dihydro-3H-1,2,4-triazol-3-one hydrochloride |
| 31 | 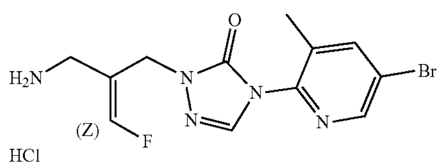 [SMILES: Cc1cc(Br)cnc1-n1cnn(C/C(=C\F)CN)c1=O ; Cl] | 2-[(2Z)-2-(aminomethyl)-3-fluoroprop-2-en-1-yl]-4-(5-bromo-3-methylpyridin-2-yl)-2,4-dihydro-3H-1,2,4-triazol-3-one hydrochloride |
| 32 | 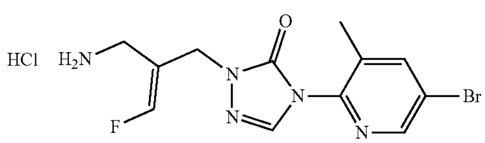 [SMILES: Cl ; Cc1cc(Br)cnc1-n1cnn(C/C(=C/F)CN)c1=O] | 2-[(2E)-2-(aminomethyl)-3-fluoroprop-2-en-1-yl]-4-(5-bromo-3-methylpyridin-2-yl)-2,4-dihydro-3H-1,2,4-triazol-3-one hydrochloride |
| 33 | 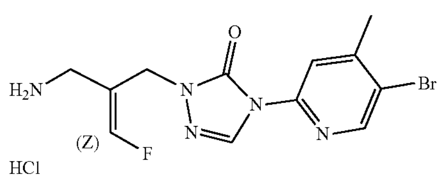 [SMILES: Cc1cc(-n2cnn(C/C(=C\F)CN)c2=O)ncc1Br ; Cl] | 2-[(2Z)-2-(aminomethyl)-3-fluoroprop-2-en-1-yl]-4-(5-bromo-4-methylpyridin-2-yl)-2,4-dihydro-3H-1,2,4-triazol-3-one hydrochloride |
| 34 | 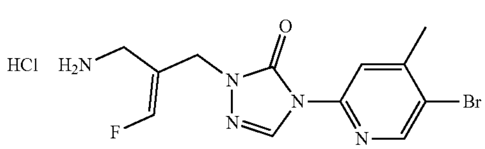 [SMILES: Cl ; Cc1cc(-n2cnn(C/C(=C/F)CN)c2=O)ncc1Br] | 2-[(2E)-2-(aminomethyl)-3-fluoroprop-2-en-1-yl]-4-(5-bromo-4-methylpyridin-2-yl)-2,4-dihydro-3H-1,2,4-triazol-3-one hydrochloride |
| 35 | 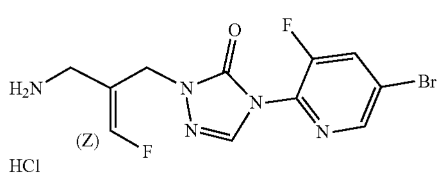 [SMILES: NC/C(=C/F)Cn1ncn(-c2ncc(Br)cc2F)c1=O ; Cl] | 2-[(2Z)-2-(aminomethyl)-3-fluoroprop-2-en-1-yl]-4-(5-bromo-3-fluoropyridin-2-yl)-2,4-dihydro-3H-1,2,4-triazol-3-one hydrochloride |
| 36 | 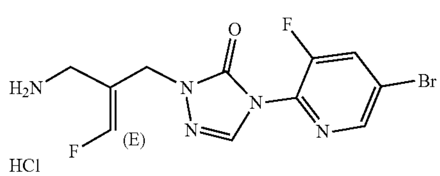 [SMILES: NC/C(=C\F)Cn1ncn(-c2ncc(Br)cc2F)c1=O ; Cl] | 2-[(2E)-2-(aminomethyl)-3-fluoroprop-2-en-1-yl]-4-(5-bromo-3-fluoropyridin-2-yl)-2,4-dihydro-3H-1,2,4-triazol-3-one hydrochloride |

TABLE 1-continued

| EX No | Structure | Chemical Name |
|---|---|---|
| 37 | 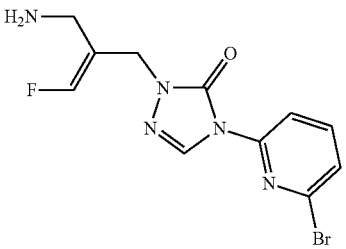 [SMILES: NC/C(=C\F)Cn1ncn(-c2cccc(Br)n2)c1=O] | 2-[(2E)-2-(aminomethyl)-3-fluoroprop-2-en-1-yl]-4-(6-bromopyridin-2-yl)-2,4-dihydro-3H-1,2,4-triazol-3-one |
| 38 | 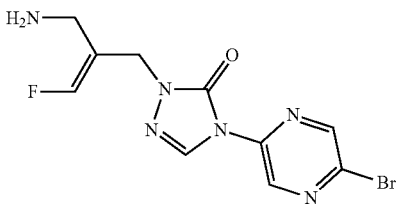 [SMILES: NC/C(=C\F)Cn1ncn(-c2cnc(Br)cn2)c1=O] | 2-[(2E)-2-(aminomethyl)-3-fluoroprop-2-en-1-yl]-4-(5-bromopyrazin-2-yl)-2,4-dihydro-3H-1,2,4-triazol-3-one |
| 39 | 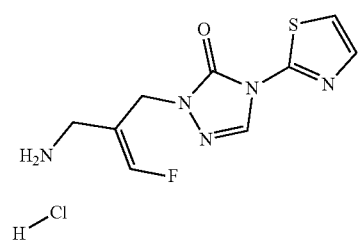 | 2-[(2Z)-2-(aminomethyl)-3-fluoroprop-2-en-1-yl]-4-(1,3-thiazol-2-yl)-2,4-dihydro-3H-1,2,4-triazol-3-one hydrochloride |
| 40 | 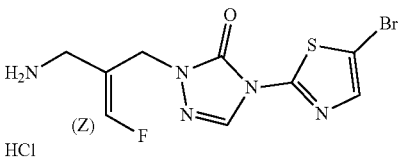 [SMILES: NC/C(=C/F)Cn1ncn(-c2ncc(Br)s2)c1=O ; Cl] | 2-[(2Z)-2-(aminomethyl)-3-fluoroprop-2-en-1-yl]-4-(5-bromo-1,3-thiazol-2-yl)-2,4-dihydro-3H-1,2,4-triazol-3-one hydrochloride |
| 41 | 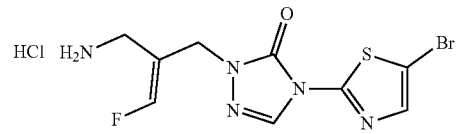 [SMILES: Cl ; NC/C(=C\F)Cn1ncn(-c2ncc(Br)s2)c1=O] | 2-[(2E)-2-(aminomethyl)-3-fluoroprop-2-en-1-yl]-4-(5-bromo-1,3-thiazol-2-yl)-2,4-dihydro-3H-1,2,4-triazol-3-one hydrochloride |
| 42 | 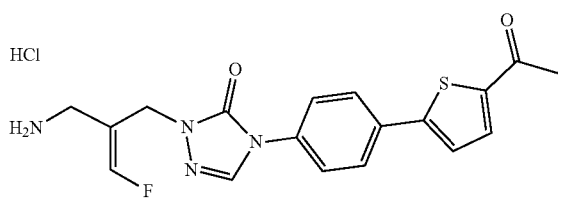 [SMILES: Cl ; CC(=O)c1ccc(-c2ccc(-n3cnn(C/C(=C\F)CN)c3=O)cc2)s1] | 4-[4-(5-acetylthiophen-2-yl)phenyl]-2-[(2Z)-2-(aminomethyl)-3-fluoroprop-2-en-1-yl]-2,4-dihydro-3H-1,2,4-triazol-3-one hydrochloride |
| 43 | 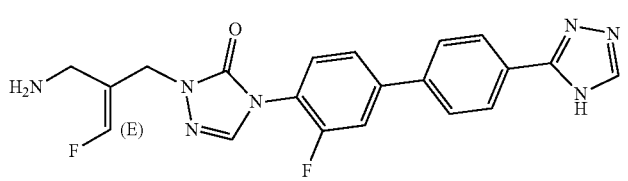 [SMILES: NC/C(=C\F)Cn1ncn(-c2ccc(-c3ccc(-c4nnc[nH]4)cc3)cc2F)c1=O] | 2-[(2E)-2-(aminomethyl)-3-fluoroprop-2-en-1-yl]-4-[3-fluoro-4'-(4H-1,2,4-triazol-3-yl)biphenyl-4-yl]-2,4-dihydro-3H-1,2,4-triazol-3-one |

TABLE 1-continued

| EX No | Structure | Chemical Name |
|---|---|---|
| 44 | 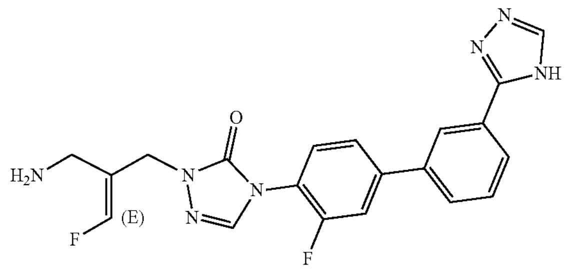 [SMILES: NC/C(=C\F)Cn1ncn(-c2ccc(-c3cccc(-c4nnc[nH]4)c3)cc2F)c1=O] | 2-[(2E)-2-(aminomethyl)-3-fluoroprop-2-en-1-yl]-4-[3-fluoro-3'-(4H-1,2,4-triazol-3-yl)biphenyl-4-yl]-2,4-dihydro-3H-1,2,4-triazol-3-one |
| 45 | 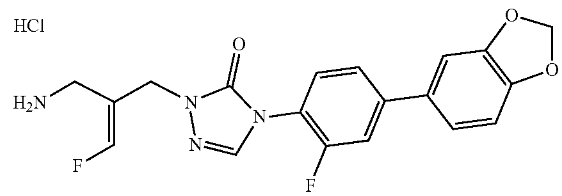 [SMILES: Cl ; NC/C(=C\F)Cn1ncn(-c2ccc(-c3ccc4c(c3)OCO4)cc2F)c1=O] | 2-[(2E)-2-(aminomethyl)-3-fluoroprop-2-en-1-yl]-4-[4-(1,3-benzodioxol-5-yl)-2-fluorophenyl]-2,4-dihydro-3H-1,2,4-triazol-3-one hydrochloride |
| 46 | 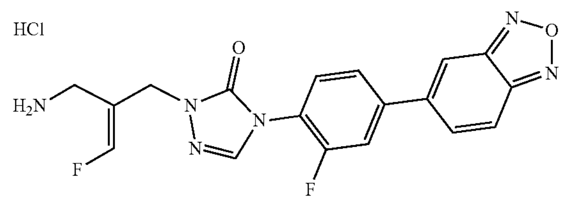 [SMILES: Cl ; NC/C(=C\F)Cn1ncn(-c2ccc(-c3ccc4nonc4c3)cc2F)c1=O] | 2-[(2E)-2-(aminomethyl)-3-fluoroprop-2-en-1-yl]-4-[4-(2,1,3-benzoxadiazol-5-yl)-2-fluorophenyl]-2,4-dihydro-3H-1,2,4-triazol-3-one hydrochloride |
| 47 | 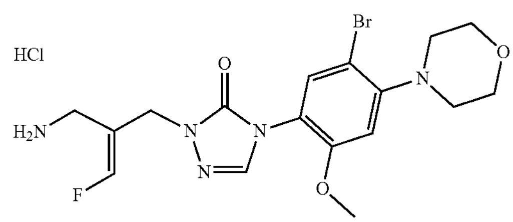 [SMILES: Cl ; COc1cc(N2CCOCC2)c(Br)cc1-n1cnn(C/C(=C/F)CN)c1=O] | 2-[(2E)-2-(aminomethyl)-3-fluoroprop-2-en-1-yl]-4-[5-bromo-2-methoxy-4-(morpholin-4-yl)phenyl]-2,4-dihydro-3H-1,2,4-triazol-3-one hydrochloride |
| 48 | 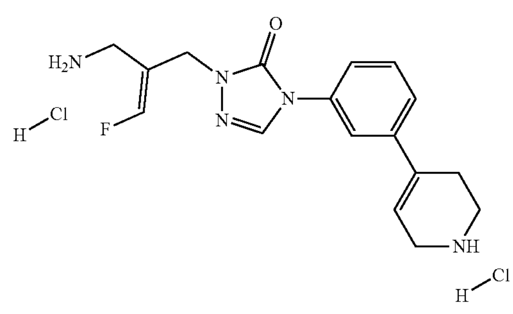 | 2-[(2E)-2-(aminomethyl)-3-fluoroprop-2-en-1-yl]-4-[3-(1,2,3,6-tetrahydropyridin-4-yl)phenyl]-2,4-dihydro-3H-1,2,4-triazol-3-one dihydrochloride |
| 49 | 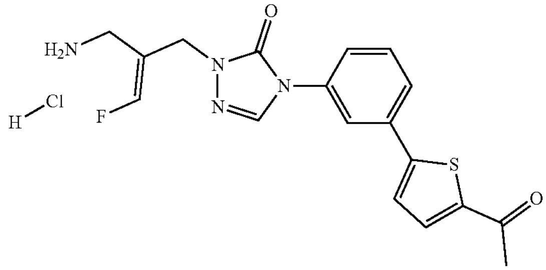 | 4-[3-(5-acetylthiophen-2-yl)phenyl]-2-[(2E)-2-(aminomethyl)-3-fluoroprop-2-en-1-yl]-2,4-dihydro-3H-1,2,4-triazol-3-one hydrochloride |

TABLE 1-continued

| EX No | Structure | Chemical Name |
|---|---|---|
| 50 | 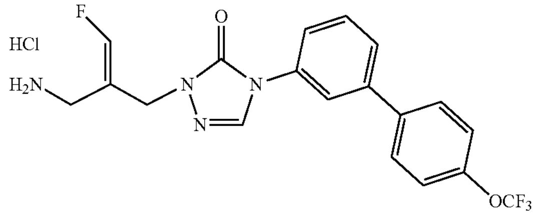 [SMILES: Cl ; NC/C(=C\F)Cn1ncn(-c2cccc(-c3ccc(OC(F)(F)F)cc3)c2)c1=O] | 2-[(2E)-2-(aminomethyl)-3-fluoroprop-2-en-1-yl]-4-[4'-(trifluoromethoxy)biphenyl-3-yl]-2,4-dihydro-3H-1,2,4-triazol-3-one hydrochloride |
| 51 | 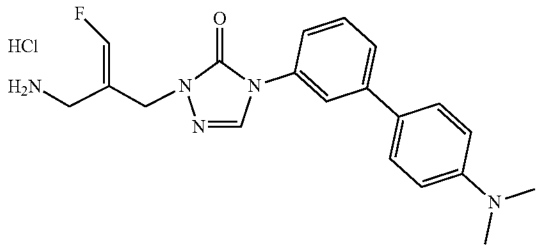 [SMILES: Cl ; CN(C)c1ccc(-c2cccc(-n3cnn(C/C(=C/F)CN)c3=O)c2)cc1] | 2-[(2E)-2-(aminomethyl)-3-fluoroprop-2-en-1-yl]-4-[4'-(dimethylamino)biphenyl-3-yl]-2,4-dihydro-3H-1,2,4-triazol-3-one hydrochloride |
| 52 | 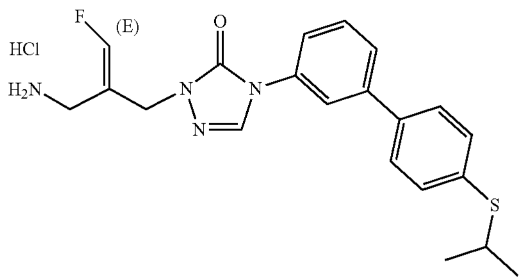 [SMILES: Cl ; CC(C)Sc1ccc(-c2cccc(-n3cnn(C/C(=C/F)CN)c3=O)c2)cc1] | 2-[(2E)-2-(aminomethyl)-3-fluoroprop-2-en-1-yl]-4-[4'-(propan-2-ylsulfanyl)biphenyl-3-yl]-2,4-dihydro-3H-1,2,4-triazol-3-one hydrochloride |
| 53 | 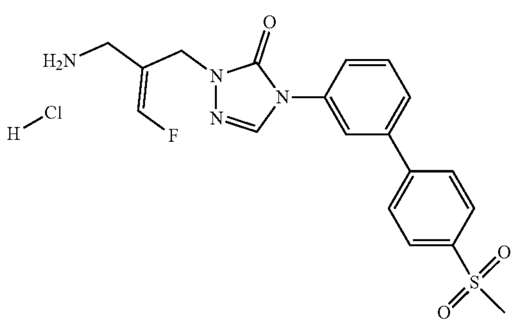 | 2-[(2Z)-2-(aminomethyl)-3-fluoroprop-2-en-1-yl]-4-[4'-(methylsulfonyl)biphenyl-3-yl]-2,4-dihydro-3H-1,2,4-triazol-3-one hydrochloride |
| 54 | 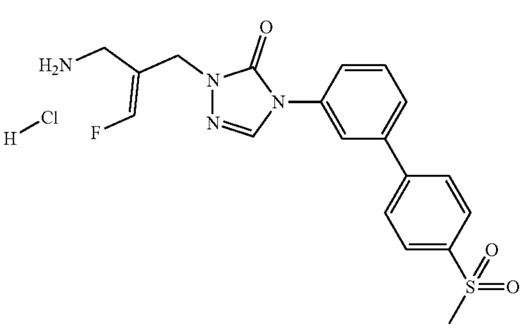 | 2-[(2E)-2-(aminomethyl)-3-fluoroprop-2-en-1-yl]-4-[4'-(methylsulfonyl)biphenyl-3-yl]-2,4-dihydro-3H-1,2,4-triazol-3-one hydrochloride |

TABLE 1-continued

| EX No | Structure | Chemical Name |
|---|---|---|
| 55 | 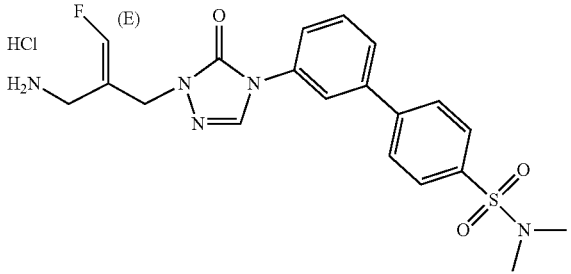 [SMILES: Cl ; CN(C)S(=O)(=O)c1ccc(-c2cccc(-n3cnn(C/C(=C/F)CN)c3=O)c2)cc1] | 3'-{1-[(2E)-2-(aminomethyl)-3-fluoroprop-2-en-1-yl]-5-oxo-1,5-dihydro-4H-1,2,4-triazol-4-yl}-N,N-dimethyl-biphenyl-4-sulfonamide hydrochloride |
| 56 | 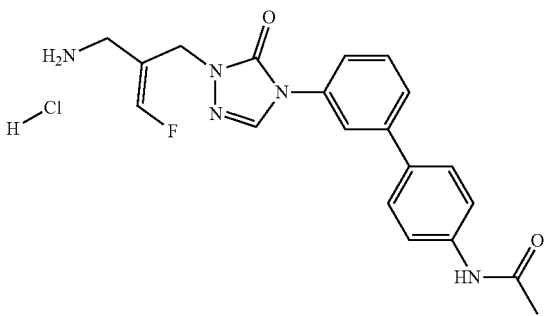 | N-(3'-{1-[(2Z)-2-(aminomethyl)-3-fluoroprop-2-en-1-yl]-5-oxo-1,5-dihydro-4H-1,2,4-triazol-4-yl}biphenyl-4-yl)acetamide hydrochloride |
| 57 | 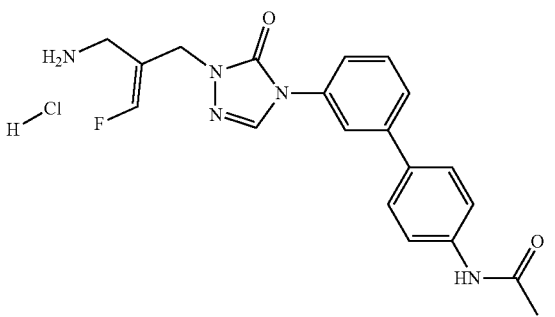 | N-(3'-{1-[(2E)-2-(aminomethyl)-3-fluoroprop-2-en-1-yl]-5-oxo-1,5-dihydro-4H-1,2,4-triazol-4-yl}biphenyl-4-yl)acetamide hydrochloride |
| 58 | 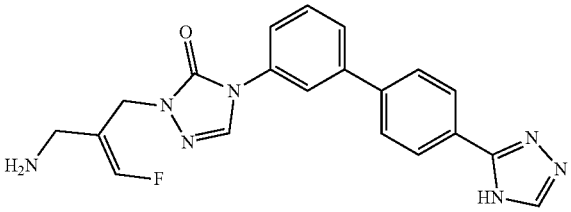 [SMILES: NC/C(=C/F)Cn1ncn(-c2cccc(-c3ccc(-c4nnc[nH]4)cc3)c2)c1=O] | 2-[(2Z)-2-(aminomethyl)-3-fluoroprop-2-en-1-yl]-4-[4'-(4H-1,2,4-triazol-3-yl)biphenyl-3-yl]-2,4-dihydro-3H-1,2,4-triazol-3-one |
| 59 | 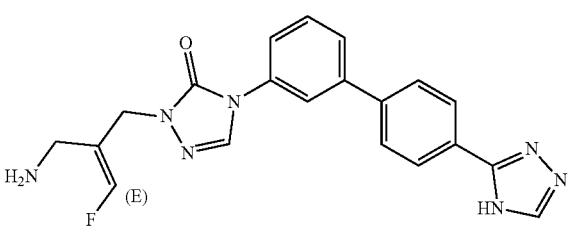 [SMILES: NC/C(=C\F)Cn1ncn(-c2cccc(-c3ccc(-c4nnc[nH]4)cc3)c2)c1=O] | 2-[(2E)-2-(aminomethyl)-3-fluoroprop-2-en-1-yl]-4-[(4'-(4H-1,2,4-triazol-3-yl)biphenyl-3-yl]-2,4-dihydro-3H-1,2,4-triazol-3-one |
| 60 | 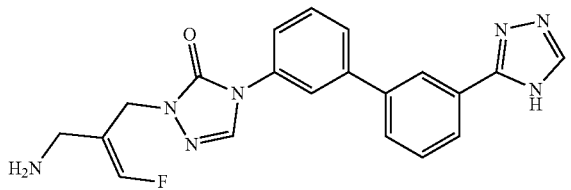 [SMILES: NC/C(=C/F)Cn1ncn(-c2cccc(-c3cccc(-c4nnc[nH]4)c3)c2)c1=O] | 2-[(2Z)-2-(aminomethyl)-3-fluoroprop-2-en-1-yl]-4-[3'-(4H-1,2,4-triazol-3-yl)biphenyl-3-yl]-2,4-dihydro-3H-1,2,4-triazol-3-one |

TABLE 1-continued

| EX No | Structure | Chemical Name |
|---|---|---|
| 61 | 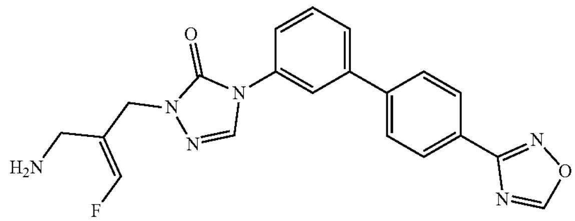 [SMILES: NC/C(=C\F)Cn1ncn(-c2cccc(-c3ccc(-c4ncon4)cc3)c2)c1=O] | 2-[(2E)-2-(aminomethyl)-3-fluoroprop-2-en-1-yl]-4-[4'-(1,2,4-oxadiazol-3-yl)biphenyl-3-yl]-2,4-dihydro-3H-1,2,4-triazol-3-one |
| 62 | 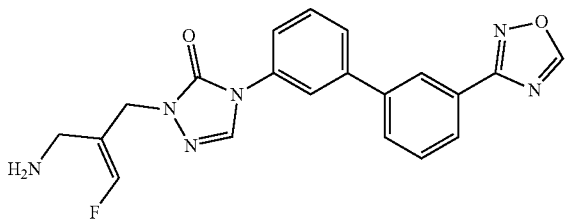 [SMILES: NC/C(=C\F)Cn1ncn(-c2cccc(-c3cccc(-c4ncon4)c3)c2)c1=O] | 2-[(2E)-2-(aminomethyl)-3-fluoroprop-2-en-1-yl]-4-[3'-(1,2,4-oxadiazol-3-yl)biphenyl-3-yl]-2,4-dihydro-3H-1,2,4-triazol-3-one |
| 63 | 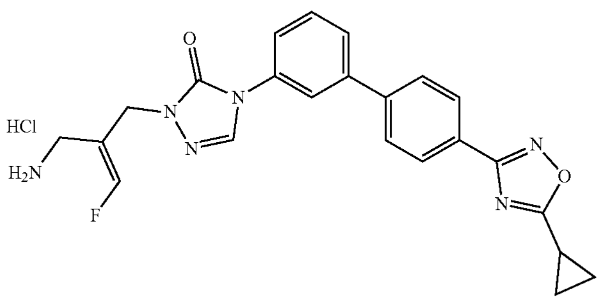 [SMILES: Cl ; NC/C(=C\F)Cn1ncn(-c2cccc(-c3ccc(-c4noc(C5CC5)n4)cc3)c2)c1=O] | 2-[(2E)-2-(aminomethyl)-3-fluoroprop-2-en-1-yl]-4-[4'-(5-cyclopropyl-1,2,4-oxadiazol-3-yl)biphenyl-3-yl]-2,4-dihydro-3H-1,2,4-triazol-3-one hydrochloride |
| 64 | 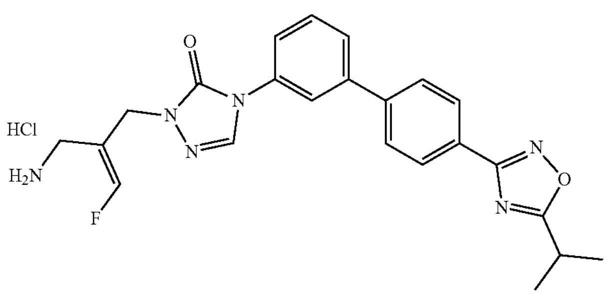 [SMILES: Cl ; CC(C)c1nc(-c2ccc(-c3cccc(-n4cnn(C/C(=C/F)CN)c4=O)c3)cc2)no1] | 2-[(2E)-2-(aminomethyl)-3-fluoroprop-2-en-1-yl]-4-{4'-[5-(propan-2-yl)-1,2,4-oxadiazol-3-yl[biphenyl-3-yl}-2,4-dihydro-3H-1,2,4-triazol-3-one hydrochloride |
| 65 | 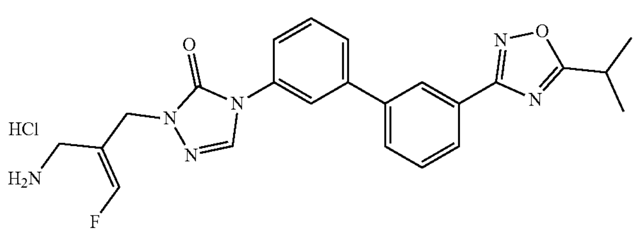 [SMILES: Cl ; CC(C)c1nc(-c2cccc(-c3cccc(-n4cnn(C/C(=C/F)CN)c4=O)c3)c2)no1] | 2-[(2E)-2-(aminomethyl)-3-fluoroprop-2-en-1-yl]-4-{3'-[5-(propan-2-yl)-1,2,4-oxadiazol-3-yl[biphenyl-3-yl}-2,4-dihydro-3H-1,2,4-triazol-3-one hydrochloride |

TABLE 1-continued

| EX No | Structure | Chemical Name |
|---|---|---|
| 66 | 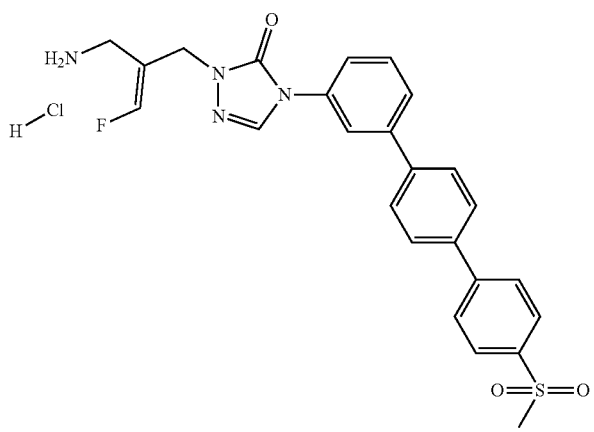 | 2-[(2E)-2-(aminomethyl)-3-fluoroprop-2-en-1-yl]-4-[4''-(methylsulfonyl)-1,1':4',1''-terphenyl-3-yl]-2,4-dihydro-3H-1,2,4-triazol-3-one hydrochloride |
| 67 | 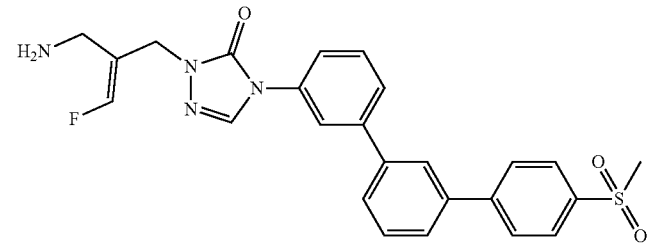 [SMILES: CS(=O)(=O)c1ccc(-c2cccc(-c3cccc(-n4cnn(C/C(=C/F)CN)c4=O)c3)c2)cc1] | 2-[(2E)-2-(aminomethyl)-3-fluoroprop-2-en-1-yl]-4-[4''-(methylsulfonyl)-1,1':3',1''-terphenyl-3-yl]-2,4-dihydro3H-1,2,4-triazol-3-one |
| 68 | 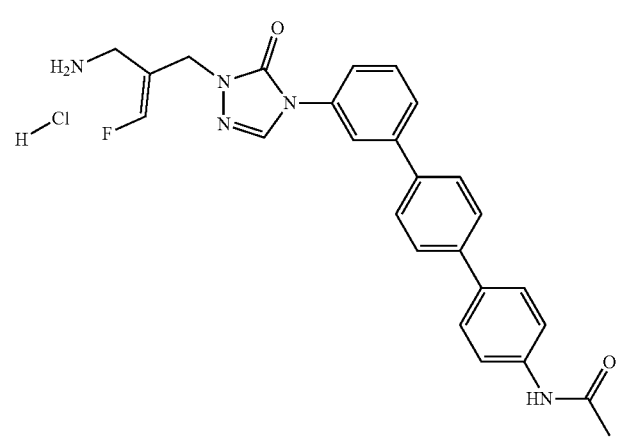 | N-(3''-{1-[(2E)-2-(aminomethyl)-3-fluoroprop-2-en-1-yl]-5-oxo-1,5-dihydro-4H-1,2,4-triazol-4-yl}-1,1':4', 1''-terphenyl-4-yl)acetamide hydrochloride |
| 69 | 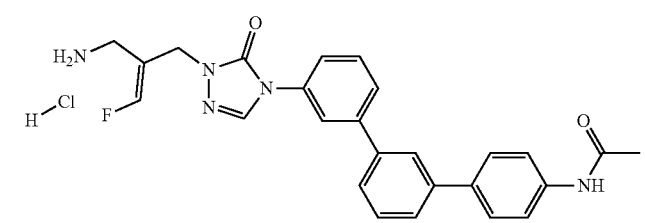 | N-(3''-{1-[(2E)-2-(aminomethyl)-3-fluoroprop-2-en-1-yl]-5-oxo-1,5-dihydro-4H-1,2,4-triazol-4-yl}-1,1':3',1''-terphenyl-4-yl)acetamide hydrochloride |

TABLE 1-continued

| EX No | Structure | Chemical Name |
|---|---|---|
| 70 | 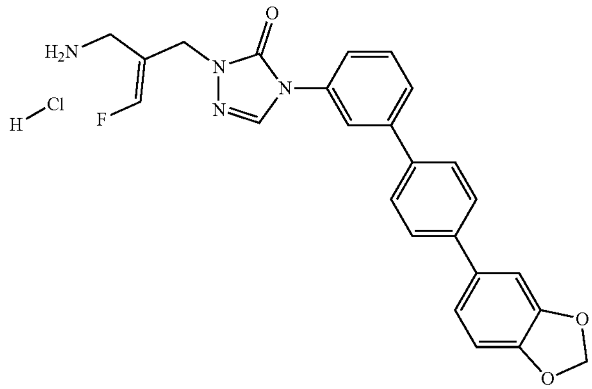 | 2-[(2E)-2-(aminomethyl)-3-fluoroprop-2-en-1-yl]-4-[4'-(1,3-benzodioxol-5-yl)biphenyl-3-yl]-2,4-dihydro-3H-1,2,4-triazol-3-one hydrochloride |
| 71 | 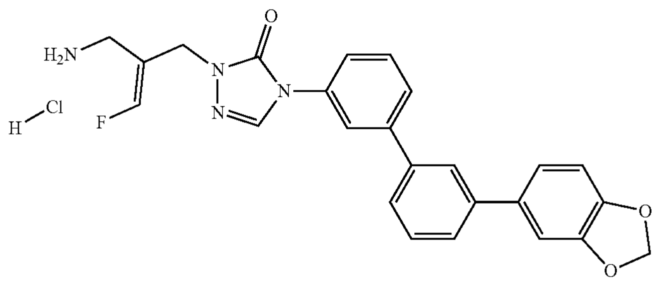 | 2-[(2E)-2-(aminomethyl)-3-fluoroprop-2-en-1-yl]-4-[3'-(1,3-benzodioxol-5-yl)biphenyl-3-yl]-2,4-dihydro-3H-1,2,4-triazol-3-one hydrochloride |
| 72 | 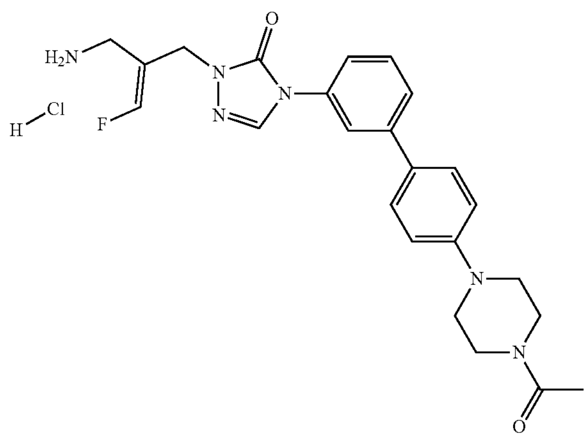 | 4-[4'-(4-acetylpiperazin-1-yl)biphenyl-3-yl]-2-[(2E)-2-(aminomethyl)-3-fluoroprop-2-en-1-yl]-2,4-dihydro-3H-1,2,4-triazol-3-one hydrochloride |
| 73 | 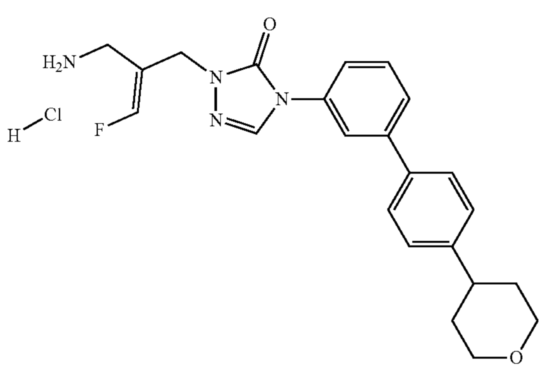 | 2-[(2E)-2-(aminomethyl)-3-fluoroprop-2-en-1-yl]-4-[4'-(tetrahydro-2H-pyran-4-yl)biphenyl-3-yl]-2,4-dihydro-3H-1,2,4-triazol-3-one hydrochloride |

TABLE 1-continued

| EX No | Structure | Chemical Name |
|---|---|---|
| 74 | 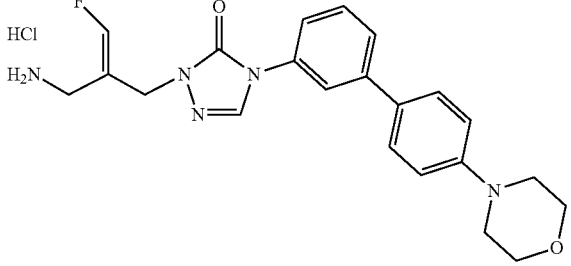 | 2-[(2E)-2-(aminomethyl)-3-fluoroprop-2-en-1-yl]-4-[4'-(morpholin-4-yl)biphenyl-3-yl]-2,4-dihydro-3H-1,2,4-triazol-3-one hydrochloride |
| 75 | 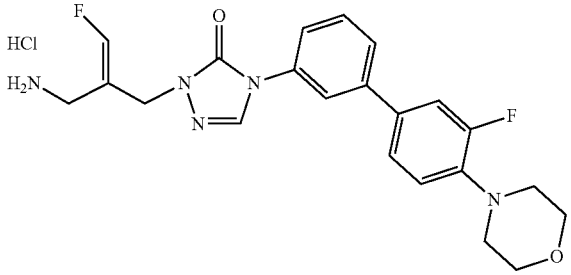 | 2-[(2E)-2-(aminomethyl)-3-fluoroprop-2-en-1-yl]-4-[3'-fluoro-4'-(morpholin-4-yl)biphenyl-3-yl]-2,4-dihydro-3H-1,2,4-triazol-3-one hydrochloride |
| 76 | 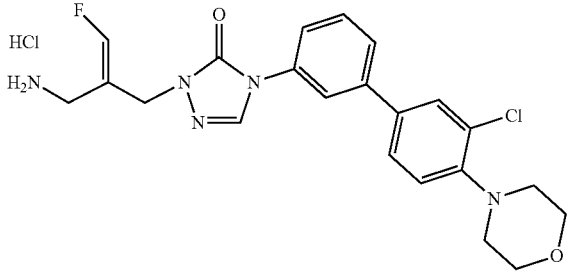 [SMILES: Cl ; NC/C(=C\F)Cn1ncn(-c2cccc(-c3ccc(N4CCOCC4)c(F)c3)c2)c1=O] | 2-[(2E)-2-(aminomethyl)-3-fluoroprop-2-en-1-yl]-4-[3'-chloro-4'-(morpholin-4-yl)biphenyl-3-yl]-2,4-dihydro-3H-1,2,4-triazol-3-one hydrochloride |
| 77 | 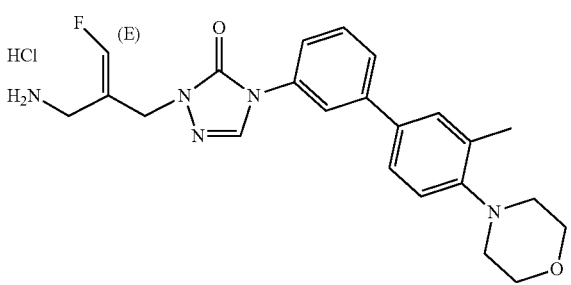 [SMILES: Cl ; Cc1cc(-c2cccc(-n3cnn(C/C(=C/F)CN)c3=O)c2)ccc1N1CCOCC1] | 2-[(2E)-2-(aminomethyl)-3-fluoroprop-2-en-1-yl]-4-[3'-methyl-4'-(morpholin-4-yl)biphenyl-3-yl]-2,4-dihydro-3H-1,2,4-triazol-3-one hydrochloride |
| 78 | 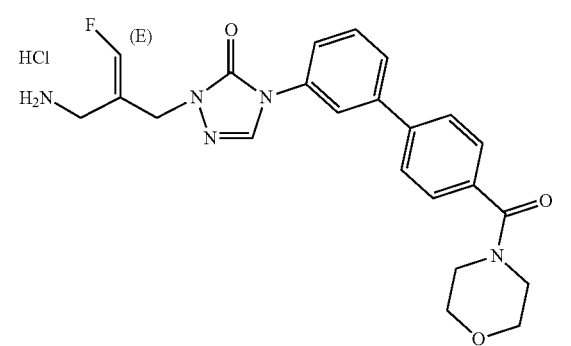 [SMILES: Cl ; NC/C(=C\F)Cn1ncn(-c2cccc(-c3ccc(C(=O)N4CCOCC4)cc3)c2)c1=O] | 2-[(2E)-2-(aminomethyl)-3-fluoroprop-2-en-1-yl]-4-[4'-(morpholin-4-ylcarbonyl)biphenyl-3-yl]-2,4-dihydro-3H-1,2,4-triazol-3-one hydrochloride |

TABLE 1-continued

| EX No | Structure | Chemical Name |
|---|---|---|
| 79 | 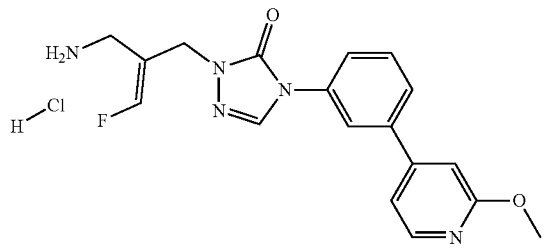 | 2-[(2E)-2-(aminomethyl)-3-fluoroprop-2-en-1-yl]-4-[3-(2-methoxypyridin-4-yl)phenyl]-2,4-dihydro-3H-1,2,4-triazol-3-one hydrochloride |
| 80 | 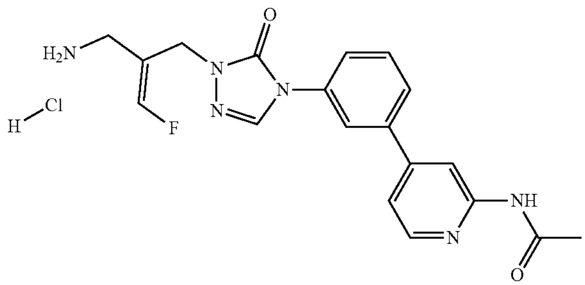 | N-[4-(3-{1-[(2Z)-2-(aminomethyl)-3-fluoroprop-2-en-1-yl]-5-oxo-1,5-dihydro-4H-1,2,4-triazol-4-yl}phenyl)pyridin-2-yl]acetamide hydrochloride |
| 81 | 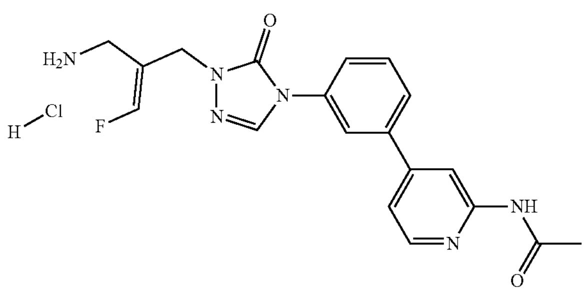 | N-[4-(3-{1-[(2E)-2-(aminomethyl)-3-fluoroprop-2-en-1-yl]-5-oxo-1,5-dihydro-4H-1,2,4-triazol-4-yl}phenyl)pyridin-2-yl]acetamide hydrochloride |
| 82 | 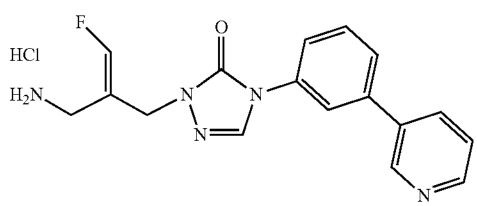 [SMILES: Cl ; NC/C(=C\F)Cn1ncn(-c2cccc(-c3cccnc3)c2)c1=O] | 2-[(2E)-2-(aminomethyl)-3-fluoroprop-2-en-1-yl]-4-[3-(pyridin-3-yl)phenyl]-2,4-dihydro-3H-1,2,4-triazol-3-one hydrochloride |
| 83 | 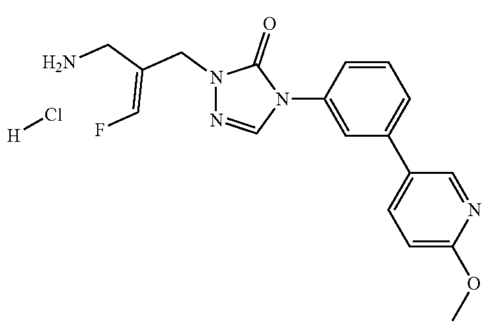 | 2-[(2E)-2-(aminomethyl)-3-fluoroprop-2-en-1-yl]-4-[3-(6-methoxypyridin-3-yl)phenyl]-2,4-dihydro-3H-1,2,4-triazol-3-one hydrochloride |
| 84 | 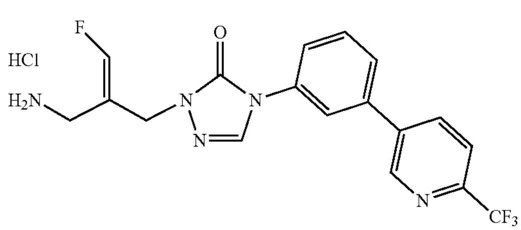 [SMILES: Cl ; NC/C(=C\F)Cn1ncn(-c2cccc(-c3ccc(C(F)(F)F)nc3)c2)c1=O] | 2-[(2E)-2-(aminomethyl)-3-fluoroprop-2-en-1-yl]-4-{3-[6-(trifluoromethyl)pyridin-3-yl]phenyl}-2,4-dihydro-3H-1,2,4-triazol-3-one hydrochloride |

TABLE 1-continued

| EX No | Structure | Chemical Name |
| --- | --- | --- |
| 85 | 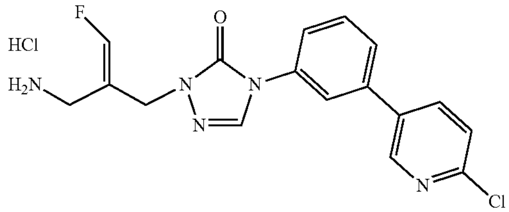 [SMILES: Cl ; NC/C(=C\F)Cn1ncn(-c2cccc(-c3ccc(Cl)nc3)c2)c1=O] | 2-[(2E)-2-(aminomethyl)-3-fluoroprop-2-en-1-yl]-4-[3-(6-chloropyridin-3-yl)phenyl]-2,4-dihydro-3H-1,2,4-triazol-3-one hydrochloride |
| 86 | 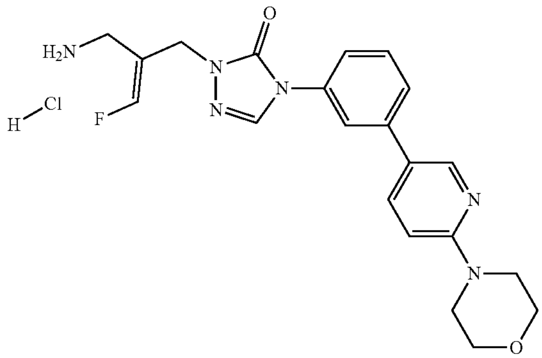 | 2-[(2E)-2-(aminomethyl)-3-fluoroprop-2-en-1-yl]-4-{3-[6-(morpholin-4-yl)pyridin-3-yl]phenyl}-2,4-dihydro-3H-1,2,4-triazol-3-one hydrochloride |
| 87 | 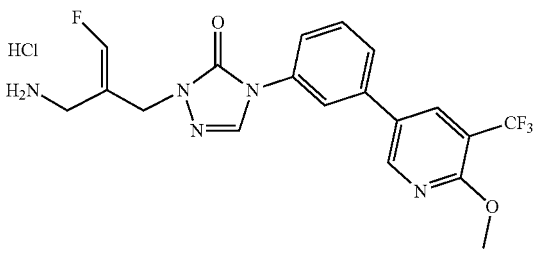 [SMILES: Cl ; COc1ncc(-c2cccc(-n3cnn(C/C(=C/F)CN)c3=O)c2)cc1C(F)(F)F] | 2-[(2E)-2-(aminomethyl)-3-fluoroprop-2-en-1-yl]-4-{3-[6-methoxy-5-(trifluoromethyl)pyridin-3-yl]phenyl}-2,4-dihydro-3H-1,2,4-triazol-3-one hydrochloride |
| 88 | 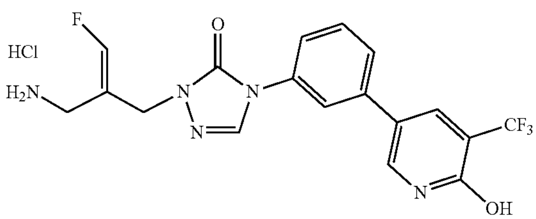 [SMILES: Cl ; NC/C(=C\F)Cn1ncn(-c2cccc(-c3cnc(O)c(C(F)(F)F)c3)c2)c1=O] | 2-[(2E)-2-(aminomethyl)-3-fluoroprop-2-en-1-yl]-4-{3-[6-hydroxy-5-(trifluoromethyl)pyridin-3-yl]phenyl}-2,4-dihydro-3H-1,2,4-triazol-3-one hydrochloride |
| 89 | 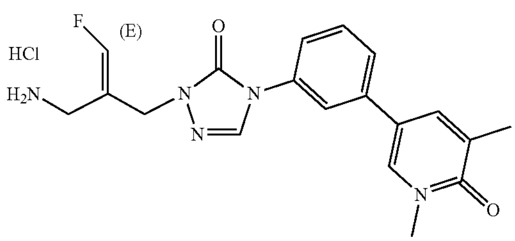 | 5-(3-{1-[(2E)-2-(aminomethyl)-3-fluoroprop-2-en-1-yl]-5-oxo-1,5-dihydro-4H-1,2,4-triazol-4-yl}phenyl)-1,3-dimethylpyridin-2(1H)-one hydrochloride |
| 90 | 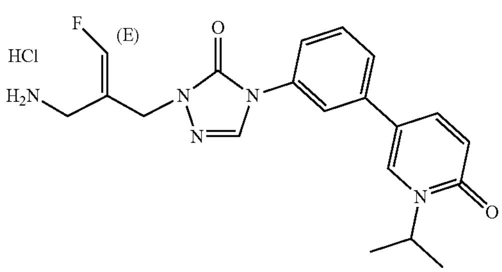 | 5-(3-{1-[(2E)-2-(aminomethyl)-3-fluoroprop-2-en-1-yl]-5-oxo-1,5-dihydro-4H-1,2,4-triazol-4-yl}phenyl)-1-(propan-2-yl)pyridin-2(1H)-one hydrochloride |

TABLE 1-continued

| EX No | Structure | Chemical Name |
|---|---|---|
| 91 | 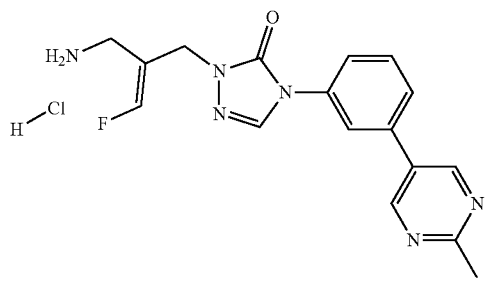 | 2-[(2E)-2-(aminomethyl)-3-fluoroprop-2-en-1-yl]-4-[3-(2-methylpyrimidin-5-yl)phenyl]-2,4-dihydro-3H-1,2,4-triazol-3-one hydrochloride |
| 92 | 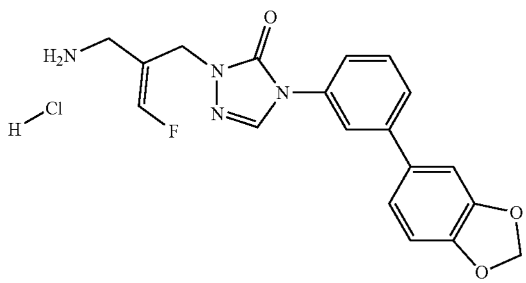 | 2-[(2Z)-2-(aminomethyl)-3-fluoroprop-2-en-1-yl]-4-[3-(1,3-benzodioxol-5-yl)phenyl]-2,4-dihydro-3H-1,2,4-triazol-3-one hydrochloride |
| 93 | 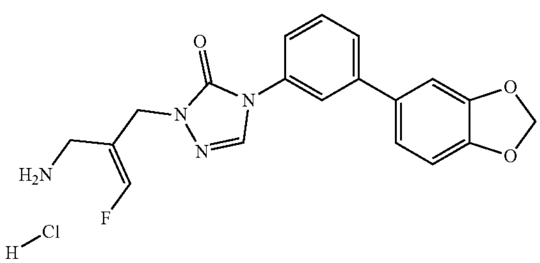 | 2-[(2E)-2-(aminomethyl)-3-fluoroprop-2-en-1-yl]-4-[3-(1,3-benzodioxol-5-yl)phenyl]-2,4-dihydro-3H-1,2,4-triazol-3-one hydrochloride |
| 94 | 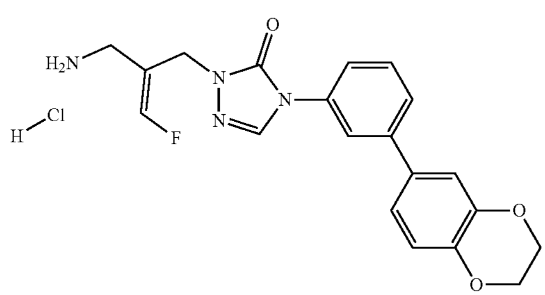 | 2-[(2Z)-2-(aminomethyl)-3-fluoroprop-2-en-1-yl]-4-[3-(2,3-dihydro-1,4-benzodioxin-6-yl)phenyl]-2,4-dihydro-3H-1,2,4-triazol-3-one hydrochloride |
| 95 | 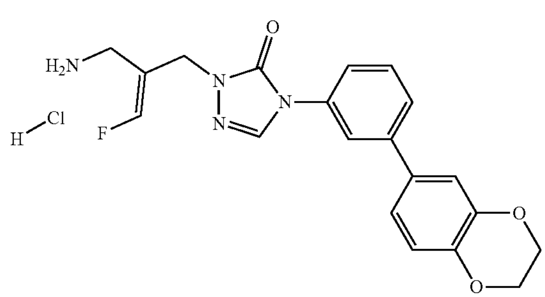 | 2-[(2E)-2-(aminomethyl)-3-fluoroprop-2-en-1-yl]-4-[3-(2,3-dihydro-1,4-benzodioxin-6-yl)phenyl]-2,4-dihydro-3H-1,2,4-triazol-3-one hydrochloride |

TABLE 1-continued

| EX No | Structure | Chemical Name |
|---|---|---|
| 96 | 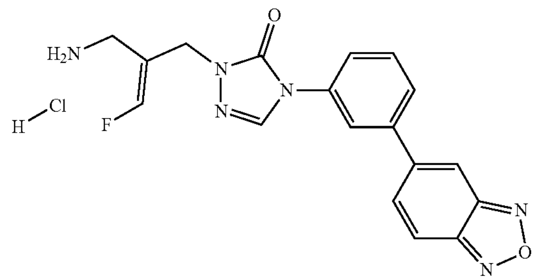 | 2-[(2E)-2-(aminomethyl)-3-fluoroprop-2-en-1-yl]-4-[3-(2,1,3-benzoxadiazol-5-yl)phenyl]-2,4-dihydro-3H-1,2,4-triazol-3-one hydrochloride |
| 97 | 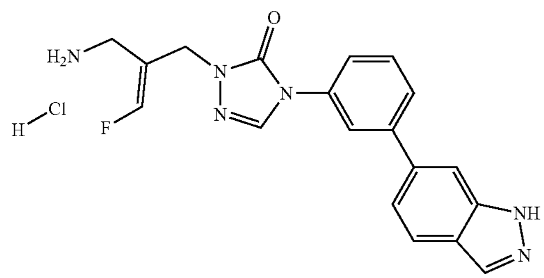 | 2-[(2E)-2-(aminomethyl)-3-fluoroprop-2-en-1-yl]-4-[3-(1H-indazol-6-yl)phenyl]-2,4-dihydro-3H-1,2,4-triazol-3-one hydrochloride |
| 98 | 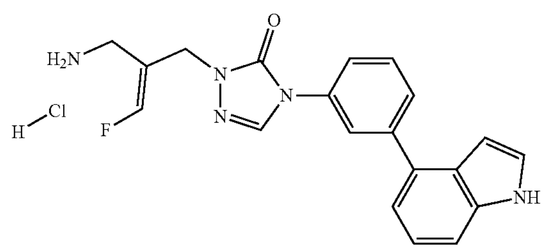 | 2-[(2E)-2-(aminomethyl)-3-fluoroprop-2-en-1-yl]-4-[3-(1H-indol-4-yl)phenyl]-2,4-dihydro-3H-1,2,4-triazol-3-one hydrochloride |
| 99 | 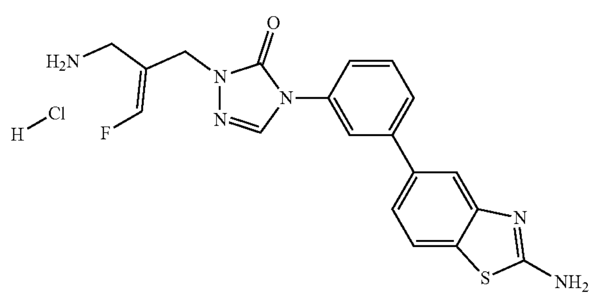 | 4-[3-(2-amino-1,3-benzothiazol-5-yl)phenyl]-2-[(2E)-2-(aminomethyl)-3-fluoroprop-2-en-1-yl]-2,4-dihydro-3H-1,2,4-triazol-3-one hydrochloride |
| 100 | 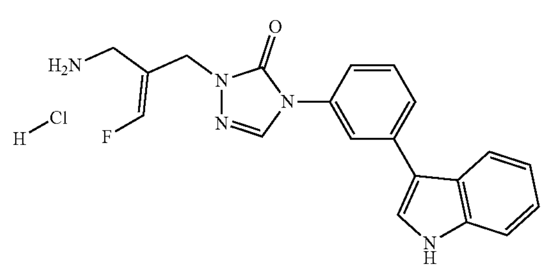 | 2-[(2E)-2-(aminomethyl)-3-fluoroprop-2-en-1-yl]-4-[3-(1H-indol-3-yl)phenyl]-2,4-dihydro-3H-1,2,4-triazol-3-one hydrochloride |
| 101 | 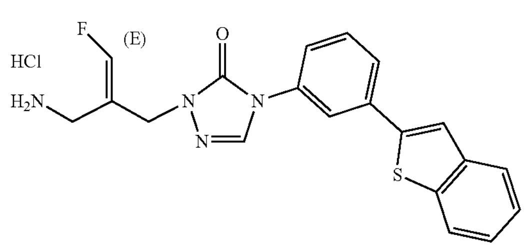 [SMILES: Cl ; NC/C(=C\F)Cn1ncn(-c2cccc(-c3cc4ccccc4s3)c2)c1=O] | 2-[(2E)-2-(aminomethyl)-3-fluoroprop-2-en-1-yl]-4-[3-(1-benzothiophen-2-yl)phenyl]-2,4-dihydro-3H-1,2,4-triazol-3-one hydrochloride |

TABLE 1-continued

| EX No | Structure | Chemical Name |
|---|---|---|
| 102 | 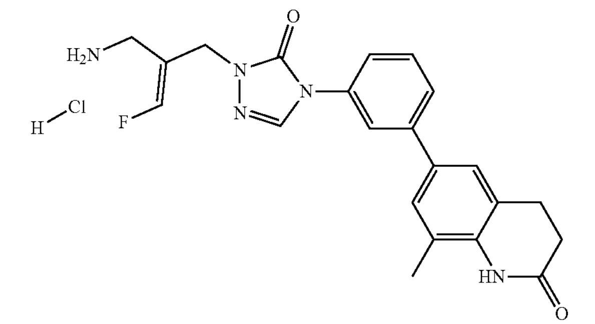 | 6-(3-{1-[(2E)-2-(aminomethyl)-3-fluoroprop-2-en-1-yl]-5-oxo-1,5-dihydro-4H-1,2,4-triazol-4-yl}phenyl)-8-methyl-3,4-dihydroquinolin-2(1H)-one hydrochloride |
| 103 | 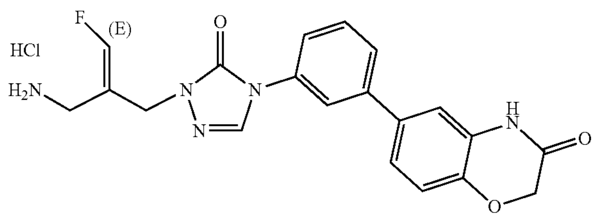 [SMILES: Cl ; NC/C(=C\F)Cn1ncn(-c2cccc(-c3ccc4c(c3)NC(=O)CO4)c2)c1=O] | 6-(3-{1-[(2E)-2-(aminomethyl)-3-fluoroprop-2-en-1-yl]-5-oxo-1,5-dihydro-4H-1,2,4-triazol-4-yl}phenyl)-2H-1,4-benzoxazin-3-(4H)-one hydrochloride |
| 104 | 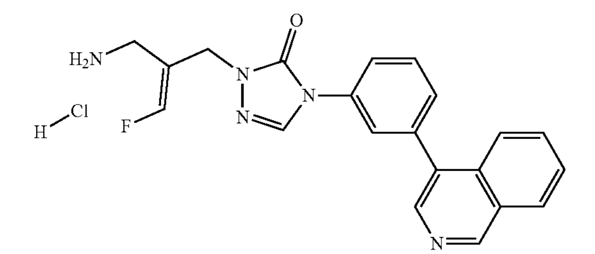 | 2-[(2E)-2-(aminomethyl)-3-fluoroprop-2-en-1-yl]-4-[3-(isoquinolin-4-yl)phenyl]-2,4-dihydro-3H-1,2,4-triazol-3-one hydrochloride |
| 105 | 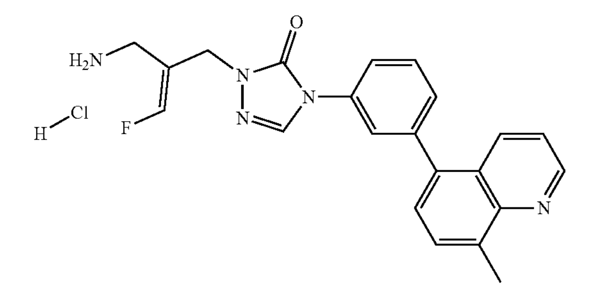 | 2-[(2E)-2-(aminomethyl)-3-fluoroprop-2-en-1-yl]-4-[3-(8-methylquinolin-5-yl)phenyl]-2,4-dihydro-3H-1,2,4-triazol-3-one hydrochloride |
| 106 | 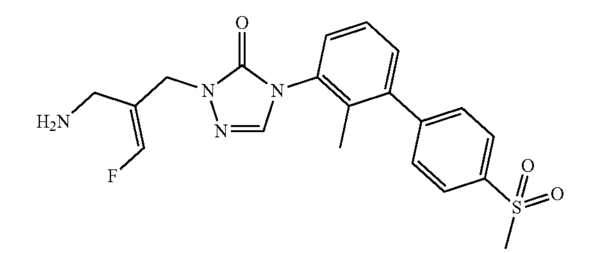 [SMILES: Cc1c(-c2ccc(S(C)(=O)=O)cc2)cccc1-n1cnn(C/C(=C/F)CN)c1=O] | 2-[(2E)-2-(aminomethyl)-3-fluoroprop-2-en-1-yl]-4-[2-methyl-4'-(methylsulfonyl)biphenyl-3-yl]-2,4-dihydro-3H-1,2,4-triazol-3-one |
| 107 | 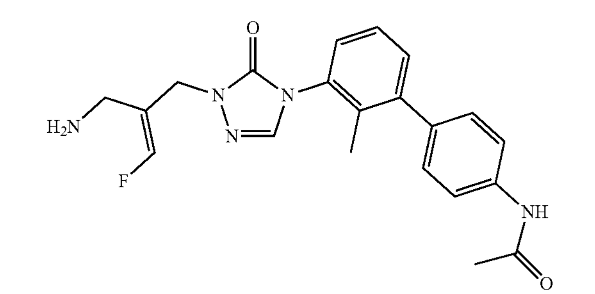 [SMILES: CC(=O)Nc1ccc(-c2cccc(-n3cnn(C/C(=C/F)CN)c3=O)c2C)cc1] | N-(3'-{1-[(2E)-2-(aminomethyl)-3-fluoroprop-2-en-1-yl]-5-oxo-1,5-dihydro-4H-1,2,4-triazol-4-yl}-2'-methylbiphenyl-4-yl)acetamide |

TABLE 1-continued

| EX No | Structure | Chemical Name |
|---|---|---|
| 108 | 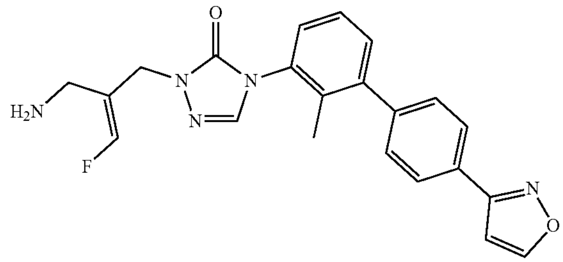 [SMILES: Cc1c(-c2ccc(-c3ccon3)cc2)cccc1-n1cnn(C/C(=C/F)CN)c1=O] | 2-[(2E)-2-(aminomethyl)-3-fluoroprop-2-en-1-yl]-4-[2-methyl-4'-(1,2-oxazol-3-yl)biphenyl-3-yl]-2,4-dihydro-3H-1,2,4-triazol-3-one |
| 109 | 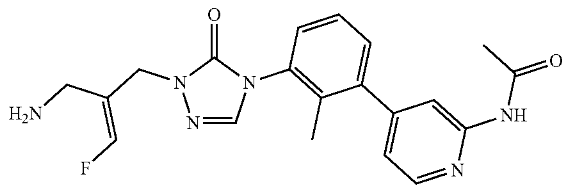 [SMILES: CC(=O)Nc1cc(-c2cccc(-n3cnn(C/C(=C/F)CN)c3=O)c2C)ccn1] | N-[4-(3-{1-[(2E)-2-(aminomethyl)-3-fluoroprop-2-en-1-yl]-5-oxo-1,5-dihydro-4H-1,2,4-triazol-4-yl}-2-methylphenyl)pyridin-2-yl]acetamide |
| 110 | 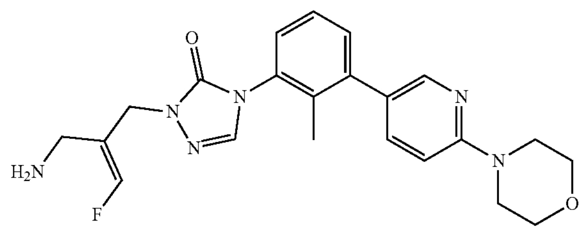 [SMILES: Cc1c(-c2ccc(N3CCOCC3)nc2)cccc1-n1cnn(C/C(=C/F)CN)c1=O] | 2-[(2E)-2-(aminomethyl)-3-fluoroprop-2-en-1-yl]-4-{2-methyl-3-[6-(morpholin-4-yl)pyridin-3-yl]phenyl}-2,4-dihydro-3H-1,2,4-triazol-3-one |
| 111 | 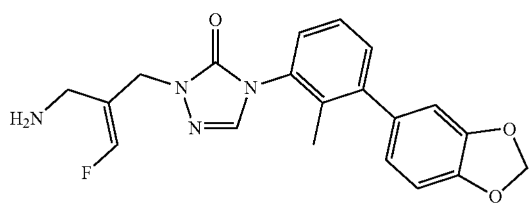 [SMILES: Cc1c(-c2ccc3c(c2)OCO3)cccc1-n1cnn(C/C(=C/F)CN)c1=O] | 2-[(2E)-2-(aminomethyl)-3-fluoroprop-2-en-1-yl]-4-[3-(1,3-benzodioxol-5-yl)-2-methylphenyl]-2,4-dihydro-3H-1,2,4-triazol-3-one |
| 112 | 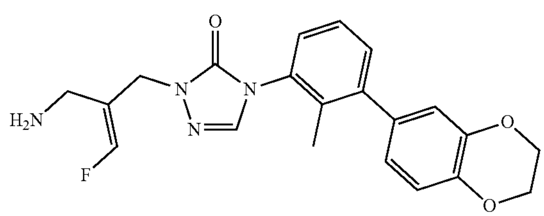 [SMILES: Cc1c(-c2ccc3c(c2)OCCO3)cccc1-n1cnn(C/C(=C/F)CN)c1=O] | 2-[(2E)-2-(aminomethyl)-3-fluoroprop-2-en-1-yl]-4-[3-(2,3-dihydro-1,4-benzodioxin-6-yl)-2-methylphenyl]-2,4-dihydro-3H-1,2,4-triazol-3-one |
| 113 | 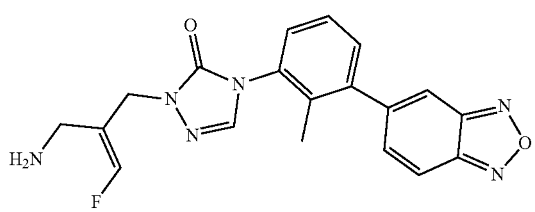 [SMILES: Cc1c(-c2ccc3nonc3c2)cccc1-n1cnn(C/C(=C/F)CN)c1=O] | 2-[(2E)-2-(aminomethyl)-3-fluoroprop-2-en-1-yl]-4-[3-(2,1,3-benzoxadiazol-5-yl)-2-methylphenyl]-2,4-dihydro-3H-1,2,4-triazol-3-one |
| 114 | 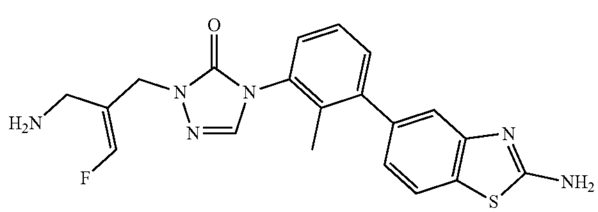 [SMILES: Cc1c(-c2ccc3sc(N)nc3c2)cccc1-n1cnn(C/C(=C/F)CN)c1=O] | 4-[3-(2-amino-1,3-benzothiazol-5-yl)-2-methylphenyl]-2-[(2E)-2-(aminomethyl)-3-fluoroprop-2-en-1-yl]-2,4-dihydro-3H-1,2,4-triazol-3-one |

TABLE 1-continued

| EX No | Structure | Chemical Name |
| --- | --- | --- |
| 115 | 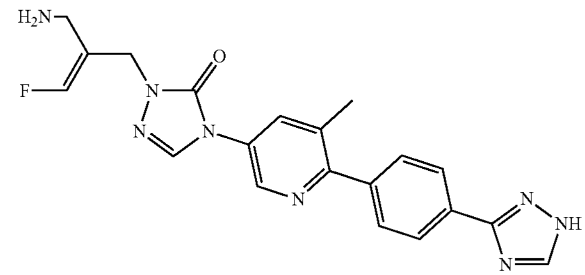 [SMILES: Cc1cc(-n2cnn(C/C(=C/F)CN)c2=O)cnc1-c1ccc(-c2nc[nH]n2)cc1] | 2-[(2E)-2-(aminomethyl)-3-fluoroprop-2-en-1-yl]-4-{5-methyl-6-[4-(1H-1,2,4-triazol-3-yl)phenyl]pyridin-3-yl}-2,4-dihydro-3H-1,2,4-triazol-3-one |
| 116 | 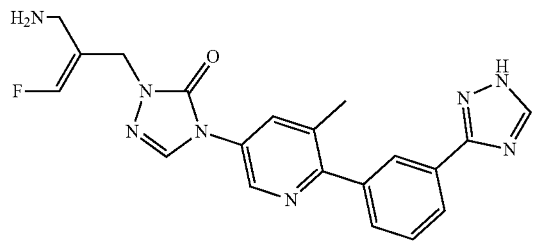 [SMILES: Cc1cc(-n2cnn(C/C(=C/F)CN)c2=O)cnc1-c1cccc(-c2nc[nH]n2)c1] | 2-[(2E)-2-(aminomethyl)-3-fluoroprop-2-en-1-yl]-4-{5-methyl-6-[3-(1H-1,2,4-triazol-3-yl)phenyl]pyridin-3-yl}-2,4-dihydro-3H-1,2,4-triazol-3-one |
| 117 | 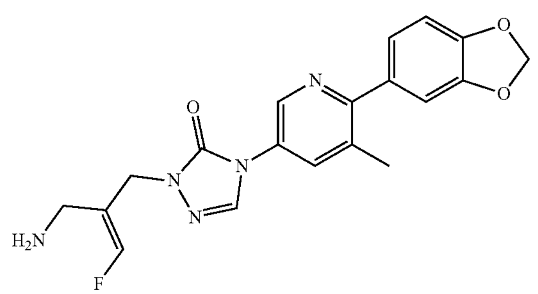 [SMILES: Cc1cc(-n2cnn(C/C(=C/F)CN)c2=O)cnc1-c1ccc2c(c1)OCO2] | 2-[(2E)-2-(aminomethyl)-3-fluoroprop-2-en-1-yl]-4-[6-(1,3-benzodioxol-5-yl)-5-methylpyridin-3-yl]-2,4-dihydro-3H-1,2,4-triazol-3-one |
| 118 | 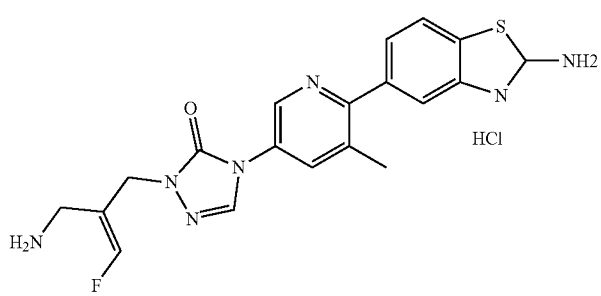 [SMILES: Cc1cc(-n2cnn(C/C(=C/F)CN)c2=O)cnc1-c1ccc2c(c1)NC(N)S2 ; Cl] | 4-[6-(2-amino-1,3-benzothiazol-5-yl)-5-methylpyridin-3-yl]-2-[(2E)-2-(aminomethyl)-3-fluoroprop-2-en-1-yl]-2,4-dihydro-3H-1,2,4-triazol-3-one hydrochloride |
| 119 | 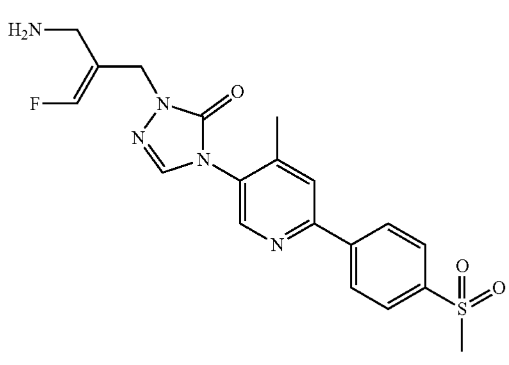 [SMILES: Cc1cc(-c2ccc(S(C)(=O)=O)cc2)ncc1-n1cnn(C/C(=C/F)CN)c1=O] | 2-[(2E)-2-(aminomethyl)-3-fluoroprop-2-en-1-yl]-4-[4-methyl-6-[4-(methylsulfonyl)phenyl]pyridin-3-yl}-2,4-dihydro-3H-1,2,4-triazol-3-one |

TABLE 1-continued

| EX No | Structure | Chemical Name |
|---|---|---|
| 120 | 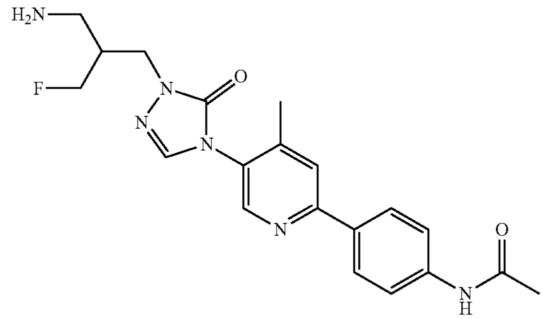 [SMILES: CC(=O)Nc1ccc(-c2cc(C)c(-n3cnn(CC(CN)CF)c3=O)cn2)cc1] | N-[4-(5-{1[(2E)-2-(aminomethyl)-3-fluoroprop-2-en-1-yl]-5-oxo-1,5-dihydro-4H-1,2,4-triazol-4-yl}-4-methylpyridin-2-yl)phenyl]acetamide |
| 121 | 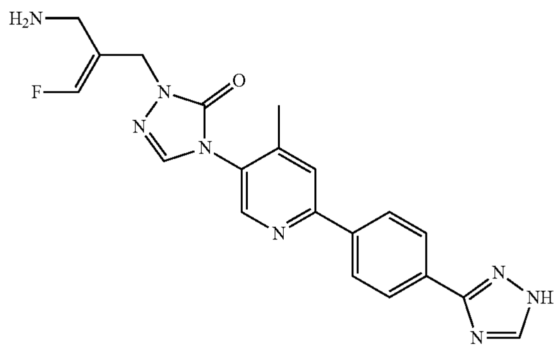 [SMILES: Cc1cc(-c2ccc(-c3nc[nH]n3)cc2)ncc1-n1cnn(C/C(=C/F)CN)c1=O] | 2-[(2E)-2-(aminomethyl)-3-fluoroprop-2-en-1-yl]-4-{4-methyl-6-[4-(1H-1,2,4-triazol-3-yl)phenyl]pyridin-3-yl}-2,4-dihydro-3H-1,2,4-triazol-3-one |
| 122 | 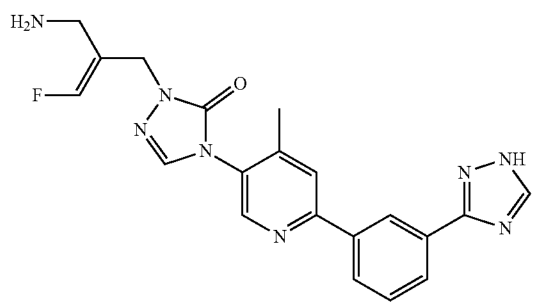 [SMILES: Cc1cc(-c2cccc(-c3nc[nH]n3)c2)ncc1-n1cnn(C/C(=C/F)CN)c1=O] | 2-[(2E)-2-(aminomethyl)-3-fluoroprop-2-en-1-yl]-4-{4-methyl-6-[3-(1H-1,2,4-triazol-3-yl)phenyl]pyridin-3-yl}-2,4-dihydro-3H-1,2,4-triazol-3-one |
| 123 | 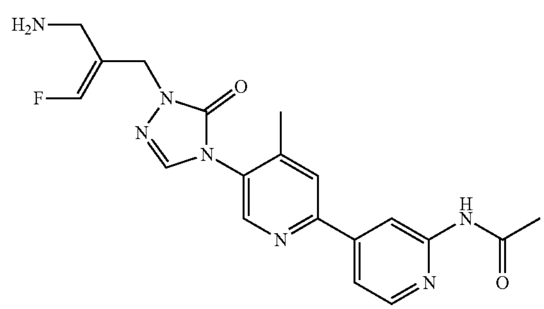 [SMILES: CC(=O)Nc1cc(-c2cc(C)c(-n3cnn(C/C(=C/F)CN)c3=O)cn2)ccn1] | N-(5-{1-[(2E)-2-(aminomethyl)-3-fluoroprop-2-en-1-yl]-5-oxo-1,5-dihydro-4H-1,2,4-triazol-4-yl}-4-methyl-2,4'-bipyridin-2'-yl)acetamide |

TABLE 1-continued

| EX No | Structure | Chemical Name |
|---|---|---|
| 124 | 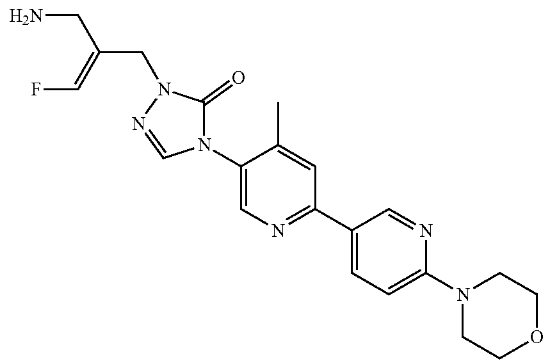 [SMILES: Cc1cc(-c2ccc(N3CCOCC3)nc2)ncc1-n1cnn(C/C(=C/F)CN)c1=O] | 2-[(2E)-2-(aminomethyl)-3-fluoroprop-2-en-1-yl]-4-[4-methyl-6'-(morpholin-4-yl)-2,3'-bipyridin-5-yl]-2,4-dihydro-3H-1,2,4-triazol-3-one |
| 125 | 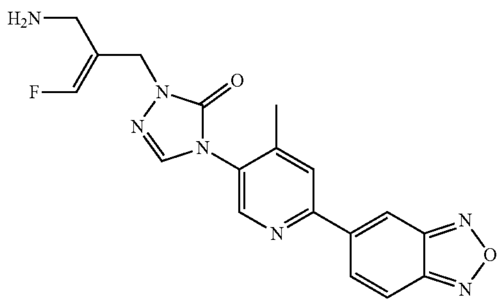 [SMILES: Cc1cc(-c2ccc3nonc3c2)ncc1-n1cnn(C/C(=C/F)CN)c1=O] | 2-[(2E)-2-(aminomethyl)-3-fluoroprop-2-en-1-yl]-4-[6-(2,1,3-benzoxadiazol-5-yl)-4-methylpyridin-3-yl]-2,4-dihydro-3H-1,2,4-triazol-3-one |
| 126 | 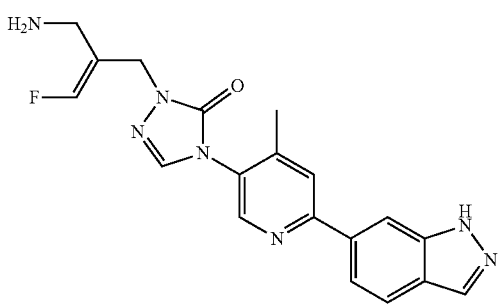 [SMILES: Cc1cc(-c2ccc3cn[nH]c3c2)ncc1-n1cnn(C/C(=C/F)CN)c1=O] | 2-[(2E)-2-(aminomethyl)-3-fluoroprop-2-en-1-yl]-4-[6-(1H-indazol-6-yl)-4-methylpyridin-3-yl]-2,4-dihydro-3H-1,2,4-triazol-3-one |
| 127 | 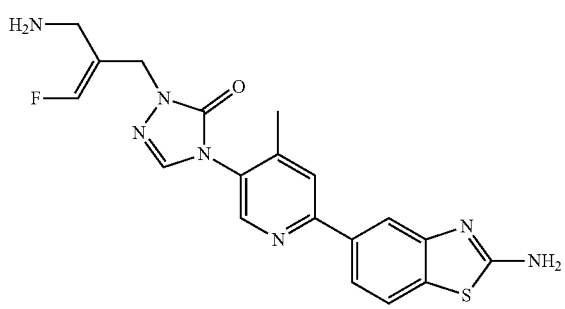 [SMILES: Cc1cc(-c2ccc3sc(N)nc3c2)ncc1-n1cnn(C/C(=C/F)CN)c1=O] | 4-[6-(2-amino-1,3-benzothiazol-5-yl)-4-methylpyridin-3-yl]-2-[(2E)-2-(aminomethyl)-3-fluoroprop-2-en-1-yl]-2,4-dihydro-3H-1,2,4-triazol-3-one |
| 128 | 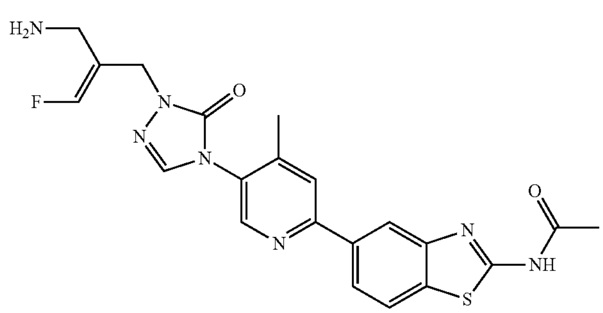 [SMILES: CC(=O)Nc1nc2cc(-c3cc(C)c(-n4cnn(C/C(=C/F)CN)c4=O)cn3)ccc2s1] | N-[5-(5-{1-[(2E)-2-(aminomethyl)-3-fluoroprop-2-en-1-yl]-5-oxo-1,5-dihydro-4H-1,2,4-triazol-4-yl}-4-methylpyridin-2-yl)-1,3-benzothiazol-2-yl]acetamide |

TABLE 1-continued

| EX No | Structure | Chemical Name |
|---|---|---|
| 129 | 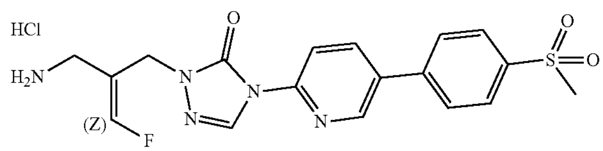 [SMILES: Cl ; CS(=O)(=O)c1ccc(-c2ccc(-n3cnn(C/C(=C\F)CN)c3=O)nc2)cc1] | 2-[(2Z)-2-(aminomethyl)-3-fluoroprop-2-en-1-yl]-4-{5-[4-(methylsulfonyl)phenyl]pyridin-2-yl}-2,4-dihydro-3H-1,2,4-triazol-3-one hydrochloride |
| 130 | 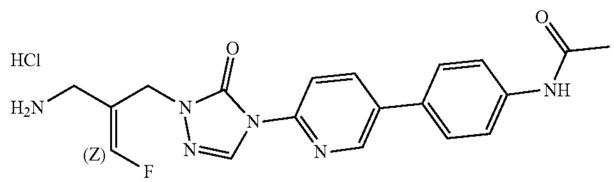 [SMILES: Cl ; CC(=O)Nc1ccc(-c2ccc(-n3cnn(C/C(=C\F)CN)c3=O)nc2)cc1] | N-[4-(6-{1-[(2Z)-2-(aminomethyl)-3-fluoroprop-2-en-1-yl]-5-oxo-1,5-dihydro-4H-1,2,4-triazol-4-yl}pyridin-3-yl)phenyl]acetamide hydrochloride |
| 131 | 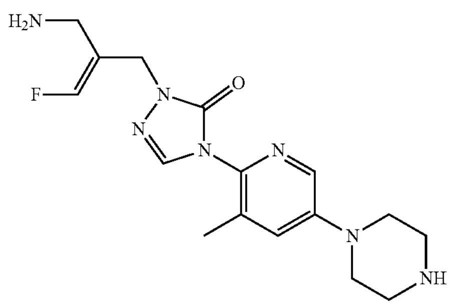 [SMILES: Cc1cc(N2CCNCC2)cnc1-n1cnn(C/C(=C/F)CN)c1=O] | 2-[(2E)-2-(aminomethyl)-3-fluoroprop-2-en-1-yl]-4-[3-methyl-5-(piperazin-1-yl)pyridin-2-yl]-2,4-dihydro-3H-1,2,4-triazol-3-one |
| 132 | 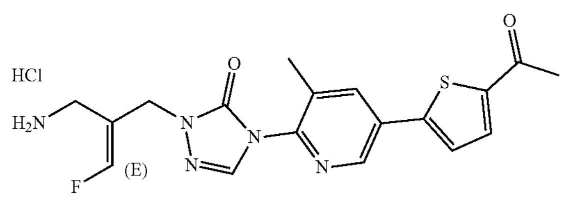 [SMILES: Cl ; CC(=O)c1ccc(-c2cnc(-n3cnn(C/C(=C/F)CN)c3=O)c(C)c2)s1] | 4-[5-(5-acetylthiophen-2-yl)-3-methylpyridin-2-yl]-2-[(2E)-2-(aminomethyl)-3-fluoroprop-2-en-1-yl]-2,4-dihydro-3H-1,2,4-triazol-3-one hydrochloride |
| 133 | 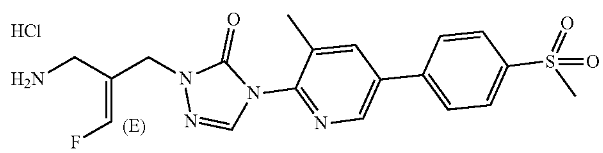 [SMILES: Cl ; Cc1cc(-c2ccc(S(C)(=O)=O)cc2)cnc1-n1cnn(C/C(=C/F)CN)c1=O] | 2-[(2E)-2-(aminomethyl)-3-fluoroprop-2-en-1-yl]-4-{3-methyl-5-[4-(methylsulfonyl)phenyl]pyridin-2-yl}-2,4-dihydro-3H-1,2,4-triazol-3-one hydrochloride |
| 134 | 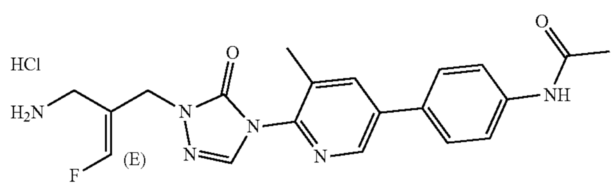 [SMILES: Cl ; CC(=O)Nc1ccc(-c2cnc(-n3cnn(C/C(=C/F)CN)c3=O)c(C)c2)cc1] | N-[4-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)phenyl]acetamide hydrochloride |
| 135 | 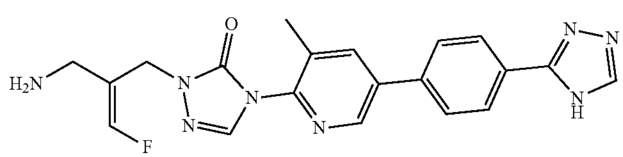 [SMILES: Cc1cc(-c2ccc(-c3nnc[nH]3)cc2)cnc1-n1cnn(C/C(=C\F)CN)c1=O] | 2-[(2Z)-2-(aminomethyl)-3-fluoroprop-2-en-1-yl]-4-{3-methyl-5-[4-(4H-1,2,4-triazol-3-yl)phenyl]pyridin-2-yl}-2,4-dihydro-3H-1,2,4-triazol-3-one |
| 136 | 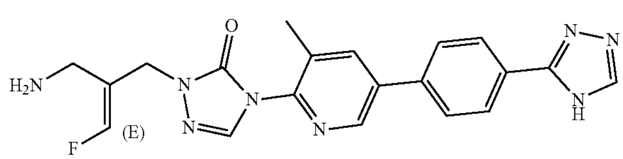 [SMILES: Cc1cc(-c2ccc(-c3nnc[nH]3)cc2)cnc1-n1cnn(C/C(=C/F)CN)c1=O] | 2-[(2E)-2-(aminomethyl)-3-fluoroprop-2-en-1-yl]-4-{3-methyl-5-[4-(4H-1,2,4-triazol-3-yl)phenyl]pyridin-2-yl}-2,4-dihydro-3H-1,2,4-triazol-3-one |

TABLE 1-continued

| EX No | Structure | Chemical Name |
|---|---|---|
| 137 | 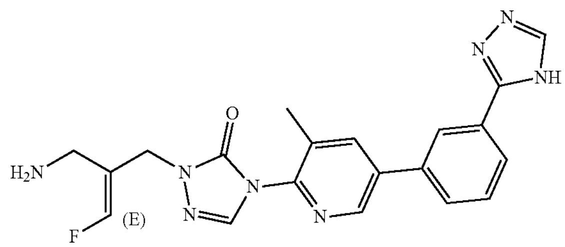 [SMILES: Cc1cc(-c2cccc(-c3nnc[nH]3)c2)cnc1-n1cnn(C/C(=C/F)CN)c1=O] | 2-[(2E)-2-(aminomethyl)-3-fluoroprop-2-en-1-yl]-4-{3-methyl-5-[3-(4H-1,2,4-triazol-3-yl)phenyl]pyridin-2-yl}-2,4-dihydro-3H-1,2,4-triazol-3-one |
| 138 | 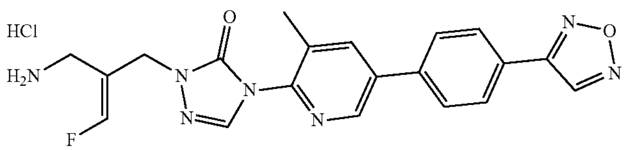 [SMILES: Cl ; Cc1cc(-c2ccc(-c3cnon3)cc2)cnc1-n1cnn(C/C(=C/F)CN)c1=O] | 2-[(2E)-2-(aminomethyl)-3-fluoroprop-2-en-1-yl]-4-{3-methyl-5-[4-(1,2,5-oxadiazol-3-yl)phenyl]pyridin-2-yl}-2,4-dihydro-3H-1,2,4-triazol-3-one hydrochloride |
| 139 | 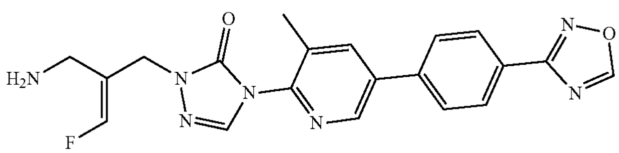 [SMILES: Cc1cc(-c2ccc(-c3ncon3)cc2)cnc1-n1cnn(C/C(=C/F)CN)c1=O] | 2-[(2E)-2-(aminomethyl)-3-fluoroprop-2-en-1-yl]-4-{3-methyl-5-[4-(1,2,4-oxadiazol-3-yl)phenyl]pyridin-2-yl}-2,4-dihydro-3H-1,2,4-triazol-3-one |
| 140 | 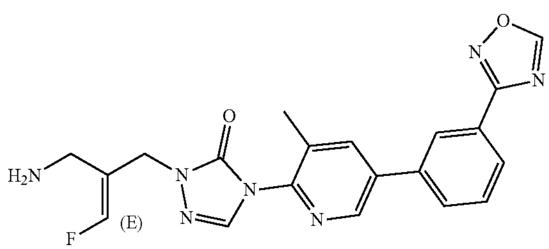 [SMILES: Cc1cc(-c2cccc(-c3ncon3)c2)cnc1-n1cnn(C/C(=C/F)CN)c1=O] | 2-[(2E)-2-(aminomethyl)-3-fluoroprop-2-en-1-yl]-4-{3-methyl-5-[3-(1,2,4-oxadiazol-3-yl)phenyl]pyridin-2-yl}-2,4-dihydro-3H-1,2,4-triazol-3-one |
| 141 | 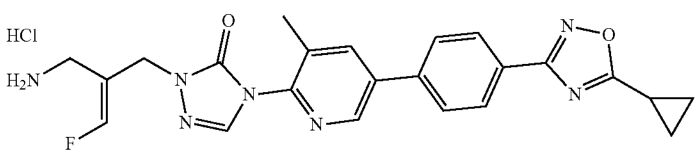 [SMILES: Cl ; Cc1cc(-c2ccc(-c3noc(C4CC4)n3)cc2)cnc1-n1cnn(C/C(=C/F)CN)c1=O] | 2-[(2E)-2-(aminomethyl)-3-fluoroprop-2-en-1-yl]-4-{5-[4-(5-cyclopropyl-1,2,4-oxadiazol-3-yl)phenyl]-3-methylpyridin-2-yl}-2,4-dihydro-3H-1,2,4-triazol-3-onehydrochloride |
| 142 | 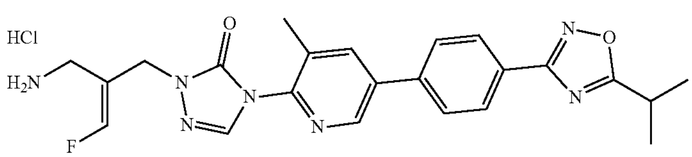 [SMILES: Cl ; Cc1cc(-c2ccc(-c3noc(C(C)C)n3)cc2)cnc1-n1cnn(C/C(=C/F)CN)c1=O] | 2-[(2E)-2-(aminomethyl)-3-fluoroprop-2-en-1-yl]-4-(3-methyl-5-{4-[5-(propan-2-yl)-1,2,4-oxadiazol-3-yl]phenyl}pyridin-2-yl)-2,4-dihydro-3H-1,2,4-triazol-3-one hydrochloride |
| 143 | 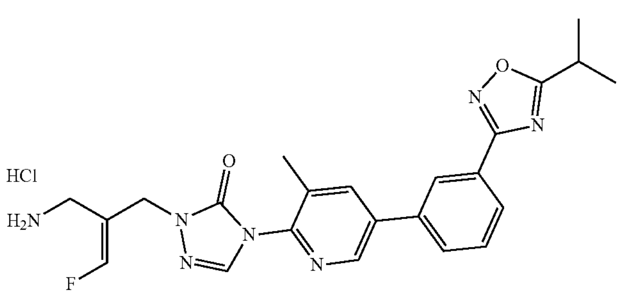 [SMILES: Cl ; Cc1cc(-c2cccc(-c3noc(C(C)C)n3)c2)cnc1-n1cnn(C/C(=C/F)CN)c1=O] | 2-[(2E)-2-(aminomethyl)-3-fluoroprop-2-en-1-yl]-4-(3-methyl-5-{3-[5-(propan-2-yl)-1,2,4-oxadiazol-3-yl]phenyl}pyridin-2-yl)-2,4-dihydro-3H-1,2,4-triazol-3-one hydrochloride |

TABLE 1-continued

| EX No | Structure | Chemical Name |
|---|---|---|
| 144 | 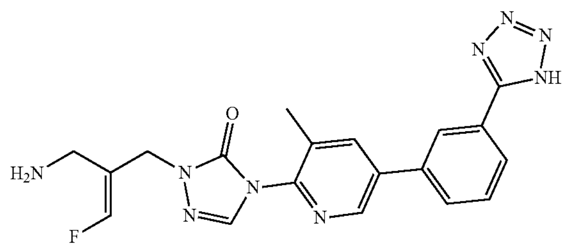 [SMILES: Cc1cc(-c2cccc(-c3nnn[nH]3)c2)cnc1-n1cnn(C/C(=C/F)CN)c1=O] | 2-[(2E)-2-(aminomethyl)-3-fluoroprop-2-en-1-yl]-4-{3-methyl-5-[3-(1H-tetrazol-5-yl)phenyl]pyridin-2-yl}-2,4-dihydro-3H-1,2,4-triazol-3-one |
| 145 | 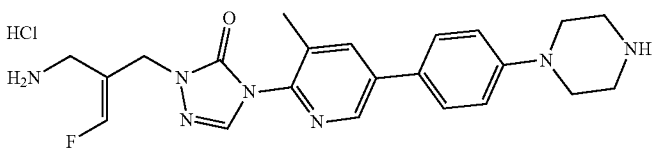 [SMILES: Cl ; Cc1cc(-c2ccc(N3CCNCC3)cc2)cnc1-n1cnn(C/C(=C/F)CN)c1=O] | 2-[(2E)-2-(aminomethyl)-3-fluoroprop-2-en-1-yl]-4-{3-methyl-5-[4-(piperazin-1-yl)phenyl]pyridin-2-yl}-2,4-dihydro-3H-1,2,4-triazol-3-one hydrochloride |
| 146 | 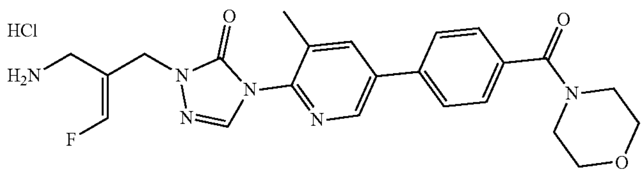 [SMILES: Cl ; Cc1cc(-c2ccc(C(=O)N3CCOCC3)cc2)cnc1-n1cnn(C/C(=C/F)CN)c1=O] | 2-[(2E)-2-(aminomethyl)-3-fluoroprop-2-en-1-yl]-4-{3-methyl-5-[4-(morpholin-4-ylcarbonyl)phenyl]pyridin-2-yl}-2,4-dihydro-3H-1,2,4-triazol-3-one hydrochloride |
| 147 | 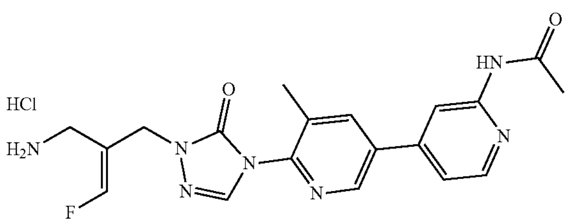 [SMILES: Cl ; CC(=O)Nc1cc(-c2cnc(-n3cnn(C/C(=C/F)CN)c3=O)c(C)c2)ccn1] | (E)-N-(6-(1-(2-(aminomethyl)-3-fluoroallyl)-5-oxo-1,5-dihydro-4H-1,2,4-triazol-4-yl)-5-methyl-[3,4'-bipyridin]-2'-yl)acetamide hydrochloride |
| 148 | 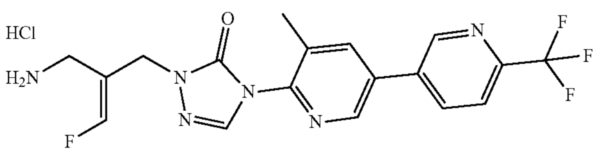 [SMILES: Cl ; Cc1cc(-c2ccc(C(F)(F)F)nc2)cnc1-n1cnn(C/C(=C/F)CN)c1=O] | 2-[(2E)-2-(aminomethyl)-3-fluoroprop-2-en-1-yl]-4-[5-methyl-6'-(trifluoromethyl)-3,3'-bipyridin-6-yl]-2,4-dihydro-3H-1,2,4-triazol-3-one hydrochloride |
| 149 | 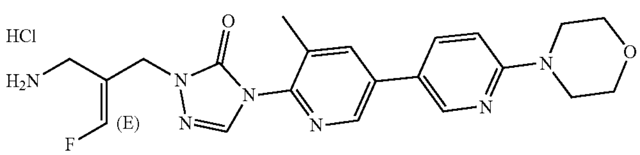 [SMILES: Cl ; Cc1cc(-c2ccc(N3CCOCC3)nc2)cnc1-n1cnn(C/C(=C/F)CN)c1=O] | 2-[(2E)-2-(aminomethyl)-3-fluoroprop-2-en-1-yl]-4-[5-methyl-6'-(morpholin-4-yl)-3,3'-bipyridin-6-yl]-2,4-dihydro-3H-1,2,4-triazol-3-one hydrochloride |
| 150 | 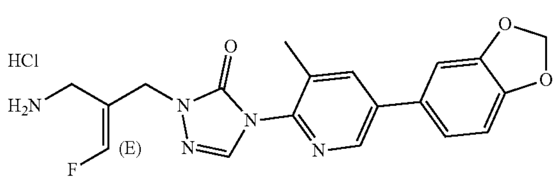 [SMILES: Cl ; Cc1cc(-c2ccc3c(c2)OCO3)cnc1-n1cnn(C/C(=C/F)CN)c1=O] | 2-[(2E)-2-(aminomethyl)-3-fluoroprop-2-en-1-yl]-4-[5-(2H-1,3-benzodioxol-5-yl)-3-methylpyridin-2-yl]-2,4-dihydro-3H-1,2,4-triazol-3-one hydrochloride |
| 151 | 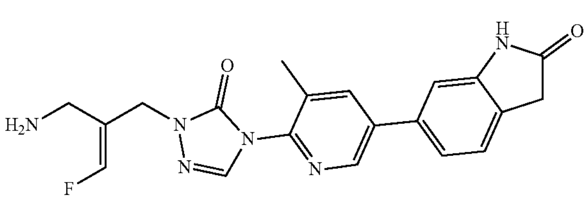 [SMILES: Cc1cc(-c2ccc3c(c2)NC(=O)C3)cnc1-n1cnn(C/C(=C/F)CN)c1=O] | 6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-1,3-dihydro-2H-indol-2-one |

TABLE 1-continued

| EX No | Structure | Chemical Name |
|---|---|---|
| 152 | 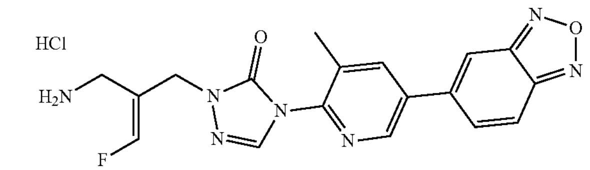 [SMILES: Cl ; Cc1cc(-c2ccc3nonc3c2)cnc1-n1cnn(C/C(=C/F)CN)c1=O] | 2-[(2E)-2-(aminomethyl)-3-fluoroprop-2-en-1-yl]-4-[5-(2,1,3-benzoxadiazol-5-yl)-3-methylpyridin-2-yl]-2,4-dihydro-3H-1,2,4-triazol-3-one hydrochloride |
| 153 | 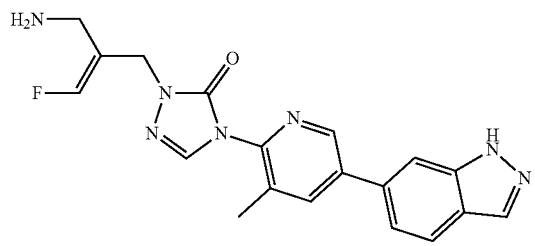 [SMILES: Cc1cc(-c2ccc3cn[nH]c3c2)cnc1-n1cnn(C/C(=C/F)CN)c1=O] | 2-[(2E)-2-(aminomethyl)-3-fluoroprop-2-en-1-yl]-4-[5-(1H-indazol-6-yl)-3-methylpyridin-2-yl]-2,4-dihydro-3H-1,2,4-triazol-3-one |
| 154 | 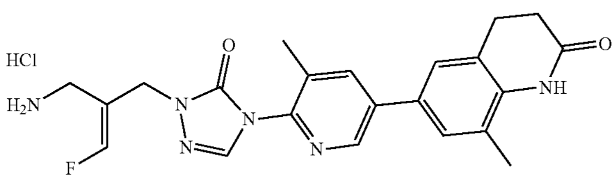 [SMILES: Cl ; Cc1cc(-c2cc(C)c3c(c2)CCC(=O)N3)cnc1-n1cnn(C/C(=C/F)CN)c1=O] | 6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-8-methyl-3,4-dihydroquinolin-2(1H)-one hydrochloride |
| 155 | 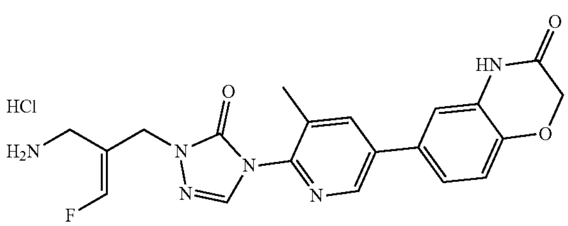 [SMILES: Cl ; Cc1cc(-c2ccc3c(c2)NC(=O)CO3)cnc1-n1cnn(C/C(=C/F)CN)c1=O] | 6-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-2H-1,4-benzoxazin-3(4H)-one hydrochloride |
| 156 | 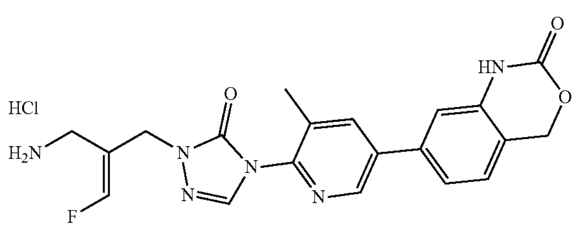 [SMILES: Cl ; Cc1cc(-c2ccc3c(c2)NC(=O)OC3)cnc1-n1cnn(C/C(=C/F)CN)c1=O] | 7-(6-{1-[(2E)-2-(aminomethyl)-3-fluoroprop-2-en-1-yl]-5-oxo-1,5-dihydro-4H-1,2,4-triazol-4-yl}-5-methylpyridin-3-yl)-1,4-dihydro-2H-3,1-benzoxazin-2-one hydrochloride |
| 157 | 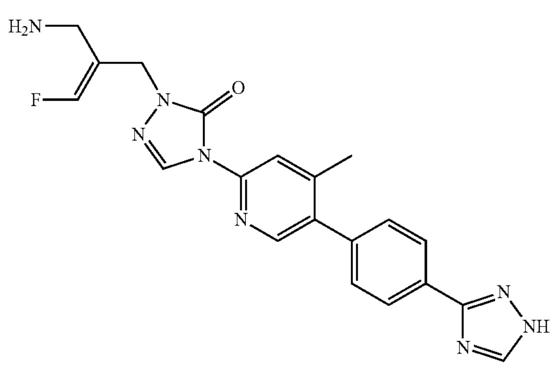 [SMILES: Cc1cc(-n2cnn(C/C(=C/F)CN)c2=O)ncc1-c1ccc(-c2nc[nH]n2)cc1] | 2-[(2E)-2-(aminomethyl)-3-fluoroprop-2-en-1-yl]-4-{4-methyl-5-[4-(1H-1,2,4-triazol-3-yl)phenyl]pyridin-2-yl}-2,4-dihydro-3H-1,2,4-triazol-3-one |

TABLE 1-continued

| EX No | Structure | Chemical Name |
|---|---|---|
| 158 | 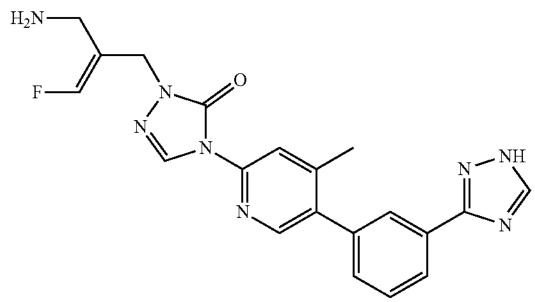 [SMILES: Cc1cc(-n2cnn(C/C(=C/F)CN)c2=O)ncc1-c1cccc(-c2nc[nH]n2)c1] | 2-[(2E)-2-(aminomethyl)-3-fluoroprop-2-en-1-yl]-4-{4-methyl-5-[3-(1H-1,2,4-triazol-3-yl)phenyl]pyridin-2-yl}-2,4-dihydro-3H-1,2,4-triazol-3-one |
| 159 | 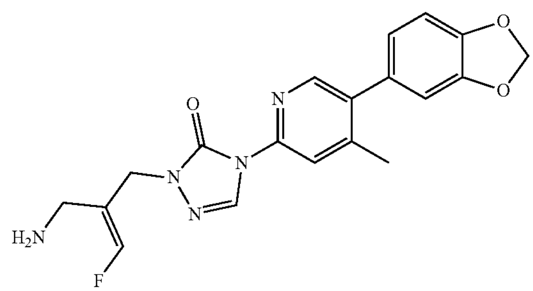 [SMILES: Cc1cc(-n2cnn(C/C(=C/F)CN)c2=O)ncc1-c1ccc2c(c1)OCO2] | 2-[(2E)-2-(aminomethyl)-3-fluoroprop-2-en-1-yl]-4-[5-(1,3-benzodioxol-5-yl)-4-methylpyridin-2-yl]-2,4-dihydro-3H-1,2,4-triazol-3-one |
| 160 | 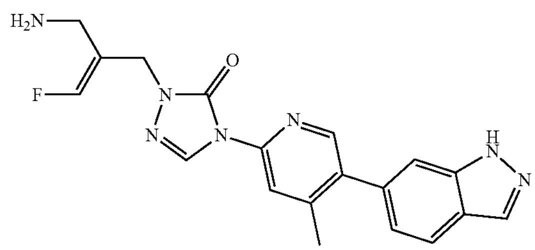 [SMILES: Cc1cc(-n2cnn(C/C(=C/F)CN)c2=O)ncc1-c1ccc2cn[nH]c2c1] | 2-[(2E)-2-(aminomethyl)-3-fluoroprop-2-en-1-yl]-4-[5-(1H-indazol-6-yl)-4-methylpyridin-2-yl]-2,4-dihydro-3H-1,2,4-triazol-3-one |
| 161 | 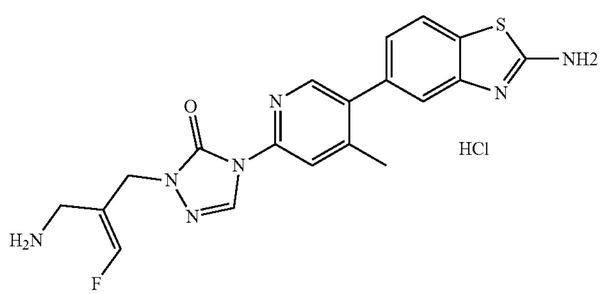 [SMILES: Cc1cc(-n2cnn(C/C(=C/F)CN)c2=O)ncc1-c1ccc2sc(N)nc2c1 ; Cl] | 4-[5-(2-amino-1,3-benzothiazol-5-yl)-4-methylpyridin-2-yl]-2-[(2E)-2-(aminomethyl)-3-fluoroprop-2-en-1-yl]-2,4-dihydro-3H-1,2,4-triazol-3-one hydrochloride |
| 162 | 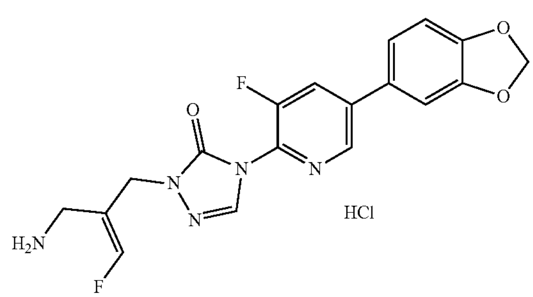 [SMILES: NC/C(=C\F)Cn1ncn(-c2ncc(-c3ccc4c(c3)OCO4)cc2F)c1=O ; Cl] | 2-[(2E)-2-(aminomethyl)-3-fluoroprop-2-en-1-yl]-4-[5-(1,3-benzodioxol-5-yl)-3-fluoropyridin-2-yl]-2,4-dihydro-3H-1,2,4-triazol-3-one hydrochloride |

TABLE 1-continued

| EX No | Structure | Chemical Name |
|---|---|---|
| 163 | 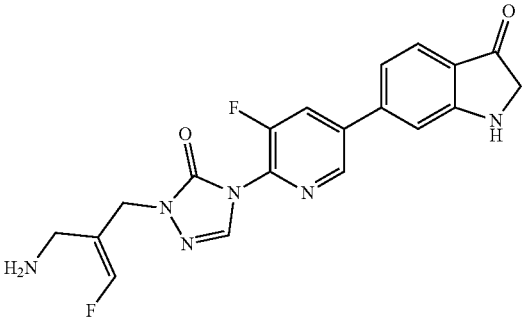 [SMILES: NC/C(=C\F)Cn1ncn(-c2ncc(-c3ccc4c(c3)NCC4=O)cc2F)c1=O] | 6-(6-{1-[(2E)-2-(aminomethyl)-3-fluoroprop-2-en-1-yl]-5-oxo-1,5-dihydro-4H-1,2,4-triazol-4-yl}-5-fluoropyridin-3-yl)-1,2-dihydro-3H-indol-3-one |
| 164 | 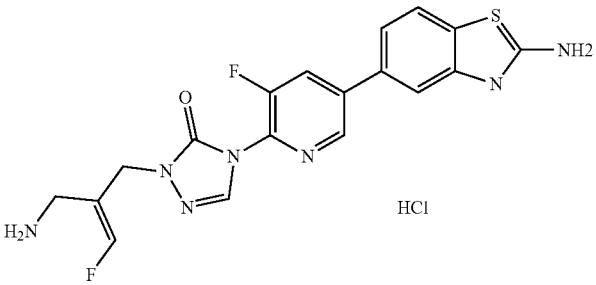 | 4-[5-(2-amino-1,3-benzothiazol-5-yl)-3-fluoropyridin-2-yl]-2-[(2E)-2-(aminomethyl)-3-fluoroprop-2-en-1-yl]-2,4-dihydro-3H-1,2,4-triazol-3-one hydrochloride |
| 165 | 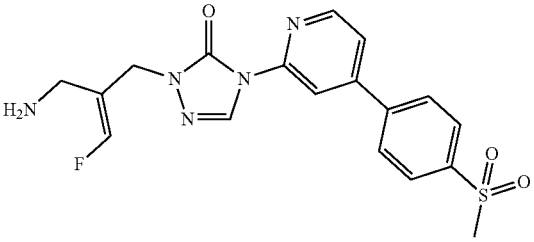 [SMILES: CS(=O)(=O)c1ccc(-c2ccnc(-n3cnn(C/C(=C/F)CN)c3=O)c2)cc1] | 2-[(2E)-2-(aminomethyl)-3-fluoroprop-2-en-1-yl]-4-{4-[4-(methylsulfonyl)phenyl]pyridin-2-yl}-2,4-dihydro-3H-1,2,-triazol-3-one |
| 166 | 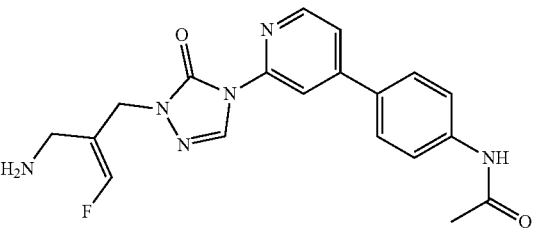 [SMILES: CC(=O)Nc1ccc(-c2ccnc(-n3cnn(C/C(=C/F)CN)c3=O)c2)cc1] | N-[4-(2-{1-[(2E)-2-(aminomethyl)-3-fluoroprop-2-en-1-yl]-5-oxo-1,5-dihydro-4H-1,2,4-triazol-4-yl}pyridin-4-yl)phenyl]acetamide |
| 167 | 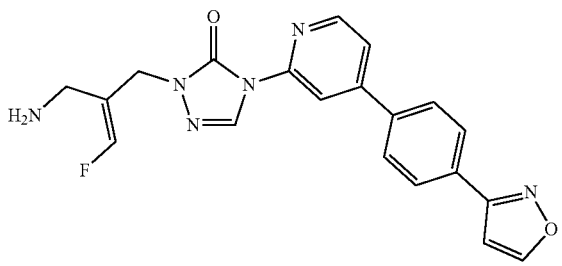 [SMILES: NC/C(=C\F)Cn1ncn(-c2cc(-c3ccc(-c4ccon4)cc3)ccn2)c1=O] | 2-[(2E)-2-(aminomethyl)-3-fluoroprop-2-en-1-yl]-4-{4-[4-(1,2-oxazol-3-yl)phenyl]pyridin-2-yl}-2,4-dihydro-3H-1,2,4-triazol-3-one |
| 168 | 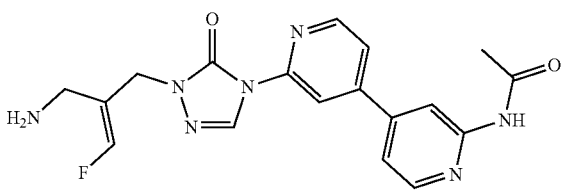 [SMILES: CC(=O)Nc1cc(-c2ccnc(-n3cnn(C/C(=C/F)CN)c3=O)c2)ccn1] | N-(2'-{1-[(2E)-2-(aminomethyl)-3-fluoroprop-2-en-1-yl]-5-oxo-1,5-dihydro-4H-1,2,4-triazol-4-yl}-4,4'-bipyridin-2-yl)acetamide |

TABLE 1-continued

| EX No | Structure | Chemical Name |
|---|---|---|
| 169 | 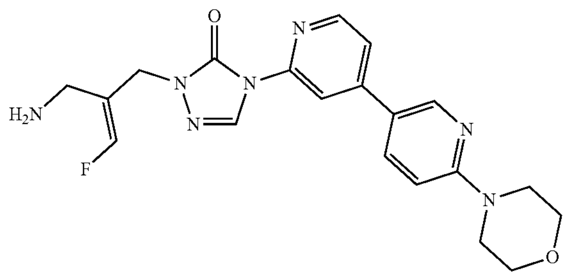 [SMILES: NC/C(=C\F)Cn1ncn(-c2cc(-c3ccc(N4CCOCC4)nc3)ccn2)c1=O] | 2-[(2E)-2-(aminomethyl)-3-fluoroprop-2-en-1-yl]-4-[6-(morpholin-4-yl)-3,4'-bipyridin-2'-yl]-2,4-dihydro-3H-1,2,4-triazol-3-one |
| 170 | 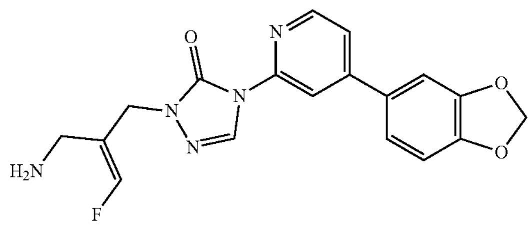 [SMILES: NC/C(=C\F)Cn1ncn(-c2cc(-c3ccc4c(c3)OCO4)ccn2)c1=O] | 2-[(2E)-2-(aminomethyl)-3-fluoroprop-2-en-1-yl]-4-[4-(1,3-benzodioxol-5-yl)pyridin-2-yl]-2,4-dihydro-3H-1,2,4-triazol-3-one |
| 171 | 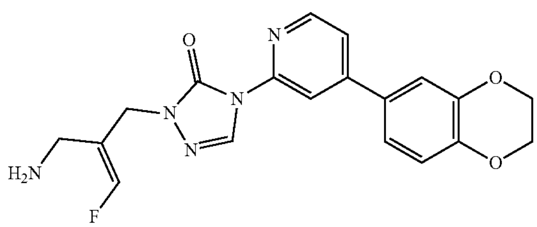 [SMILES: NC/C(=C\F)Cn1ncn(-c2cc(-c3ccc4c(c3)OCCO4)ccn2)c1=O] | 2-[(2E)-2-(aminomethyl)-3-fluoroprop-2-en-1-yl]-4-[4-(2,3-dihydro-1,4-benzodioxin-6-yl)pyridin-2-yl]-2,4-dihydro-3H-1,2,4-triazol-3-one |
| 172 | 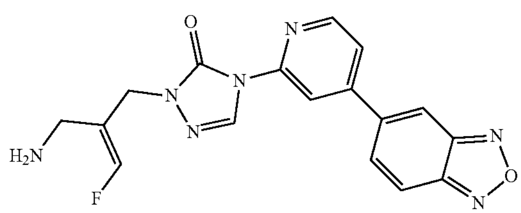 [SMILES: NC/C(=C\F)Cn1ncn(-c2cc(-c3ccc4nonc4c3)ccn2)c1=O] | 2-[(2E)-2-(aminomethyl)-3-fluoroprop-2-en-1-yl]-4-[4-(2,1,3-benzoxadiazol-5-yl)pyridin-2-yl]-2,4-dihydro-3H-1,2,4-triazol-3-one |
| 173 | 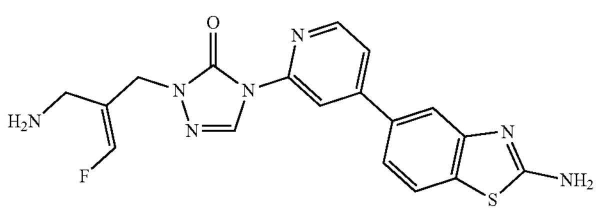 [SMILES: NC/C(=C\F)Cn1ncn(-c2cc(-c3ccc4sc(N)nc4c3)ccn2)c1=O] | 4-[4-(2-amino-1,3-benzothiazol-5-yl)pyridin-2-yl]-2-[(2E)-2-(aminomethyl)-3-fluoroprop-2-en-1-yl]-2,4-dihydro-3H-1,2,4-triazol-3-one |
| 174 | 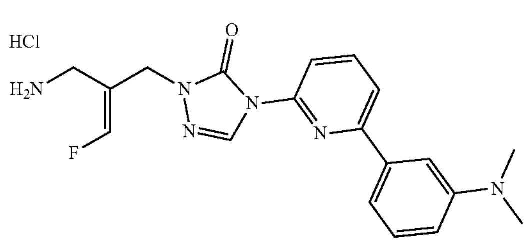 [SMILES: Cl ; CN(C)c1cccc(-c2cccc(-n3cnn(C/C(=C/F)CN)c3=O)n2)c1] | 2-[(2E)-2-(aminomethyl)-3-fluoroprop-2-en-1-yl]-4-{6-[3-(dimethylamino)phenyl]pyridin-2-yl}-2,4-dihydro-3H-1,2,4-triazol-3-one hydrochloride |

TABLE 1-continued

| EX No | Structure | Chemical Name |
|---|---|---|
| 175 | 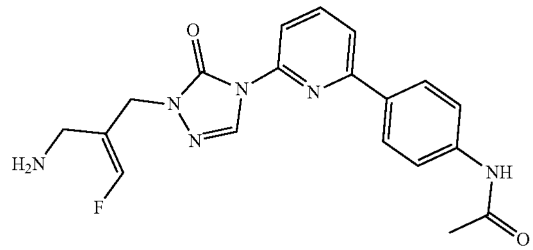 [SMILES: CC(=O)Nc1ccc(-c2cccc(-n3cnn(C/C(=C/F)CN)c3=O)n2)cc1] | N-[4-(6-{1-[(2E)-2-(aminomethyl)-3-fluoroprop-2-en-1-yl]-5-oxo-1,5-dihydro-4H-1,2,4-triazol-4-yl}pyridin-2-yl)phenyl]acetamide |
| 176 | 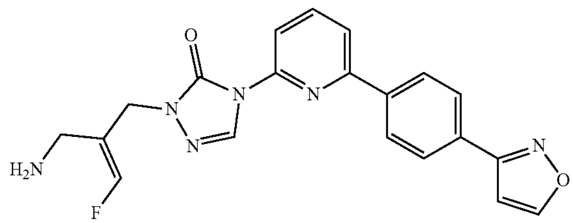 [SMILES: NC/C(=C\F)Cn1ncn(-c2cccc(-c3ccc(-c4ccon4)cc3)n2)c1=O] | 2-[(2E)-2-(aminomethyl)-3-fluoroprop-2-en-1-yl]-4-{6-[4-(1,2-oxazol-3-yl)phenyl]pyridin-2-yl}-2,4-dihydro-3H-1,2,4-triazol-3-one |
| 177 | 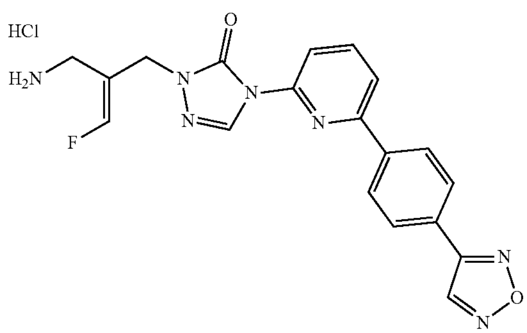 [SMILES: Cl ; NC/C(=C\F)Cn1ncn(-c2cccc(-c3ccc(-c4cnon4)cc3)n2)c1=O] | 2-[(2E)-2-(aminomethyl)-3-fluoroprop-2-en-1-yl]-4-{6-[4-(1,2,5-oxadiazol-3-yl)phenyl]pyridin-2-yl}-2,4-dihydro-3H-1,2,4-triazol-3-one hydrochloride |
| 178 | 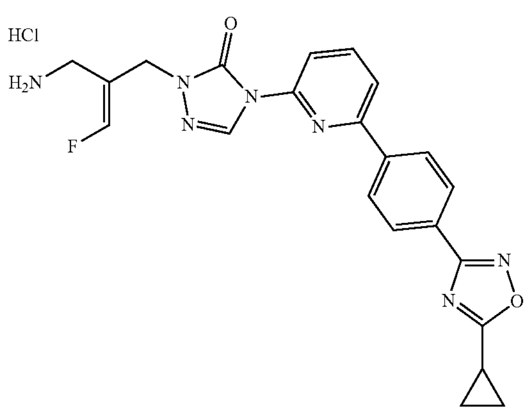 [SMILES: Cl ; NC/C(=C\F)Cn1ncn(-c2cccc(-c3ccc(-c4noc(C5CC5)n4)cc3)n2)c1=O] | 2-[(2E)-2-(aminomethyl)-3-fluoroprop-2-en-1-yl]-4-{6-[4-(5-cyclopropyl-1,2,4-oxadiazol-3-yl)phenyl]pyridin-2-yl}-2,4-dihydro-3H-1,2,4-triazol-3-one hydrochloride |
| 179 | 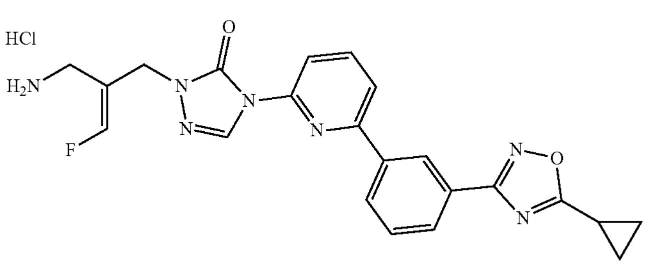 [SMILES: Cl ; NC/C(=C\F)Cn1ncn(-c2cccc(-c3cccc(-c4noc(C5CC5)n4)c3)n2)c1=O] | 2-[(2E)-2-(aminomethyl)-3-fluoroprop-2-en-1-yl]-4-{6-[3-(5-cyclopropyl-1,2,4-oxadiazol-3-yl)phenyl]pyridin-2-yl}-2,4-dihydro-3H-1,2,4-triazol-3-one hydrochloride |

TABLE 1-continued

| EX No | Structure | Chemical Name |
|---|---|---|
| 180 | 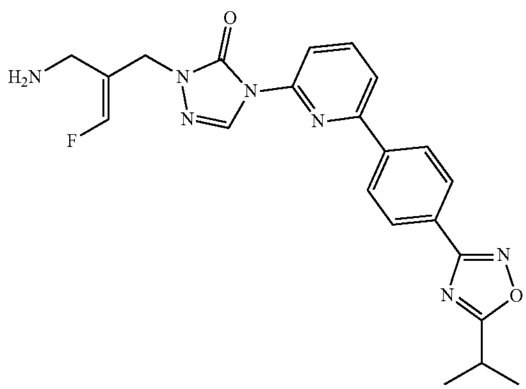 [SMILES: CC(C)c1nc(-c2ccc(-c3cccc(-n4cnn(C/C(=C/F)CN)c4=O)n3)cc2)no1] | 2-[(2E)-2-(aminomethyl)-3-fluoroprop-2-en-1-yl]-4-(6-{4-[5-(propan-2-yl)-1,2,4-oxadiazol-3-yl]phenyl}pyridin-2-yl)-2,4-dihydro-3H-1,2,4-triazol-3-one |
| 181 | 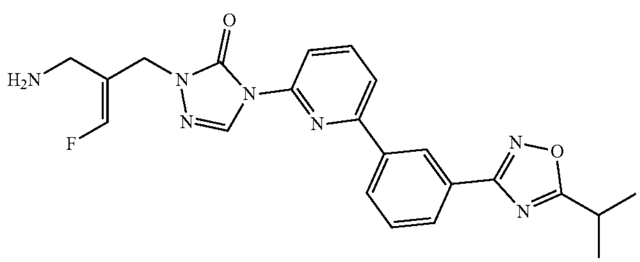 [SMILES: CC(C)c1nc(-c2cccc(-c3cccc(-n4cnn(C/C(=C/F)CN)c4=O)n3)c2)no1] | 2-[(2E)-2-(aminomethyl)-3-fluoroprop-2-en-1-yl]-4-(6-{3-[5-(propan-2-yl)-1,2,4-oxadiazol-3-yl]phenyl}pyridin-2-yl)-2,4-dihydro-3H-1,2,4-triazol-3-one |
| 182 | 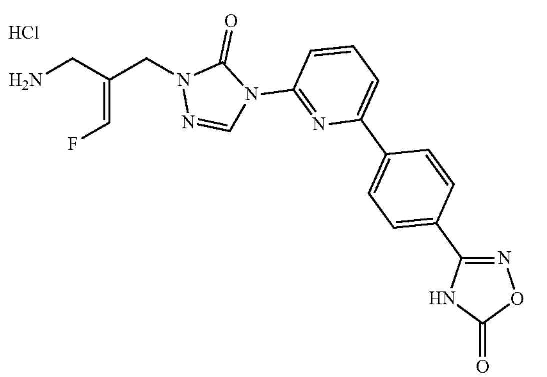 [SMILES: Cl ; NC/C(=C\F)Cn1ncn(-c2cccc(-c3ccc(-c4noc(=O)[nH]4)cc3)n2)c1=O] | 3-[4-(6-{1-[(2E)-2-(aminomethyl)-3-fluoroprop-2-en-1-yl]-5-oxo-1,5-dihydro-4H-1,2,4-triazol-4-yl}pyridin-2-yl)phenyl]-1,2,4-oxoadizol-5(4H)-one hydrochloride |
| 183 | 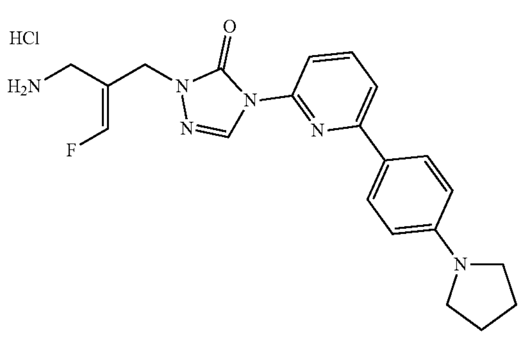 [SMILES: Cl ; NC/C(=C\F)Cn1ncn(-c2cccc(-c3ccc(N4CCCC4)cc3)n2)c1=O] | 2-[(2E)-2-(aminomethyl)-3-fluoroprop-2-en-1-yl]-4-{6-[4-(pyrrolidin-1-yl)phenyl]pyridin-2-yl}-2,4-dihydro-3H-1,2,4-triazol-3-one hydrochloride |

US 11,492,335 B2

TABLE 1-continued

| EX No | Structure | Chemical Name |
|---|---|---|
| 184 | 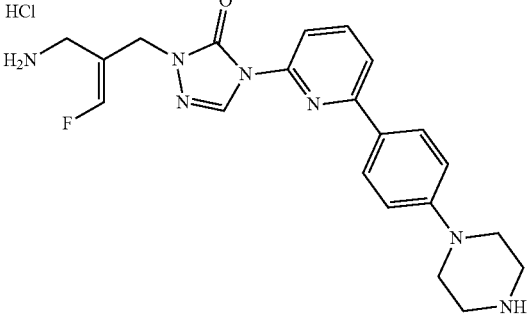 | 2-[(2E)-2-(aminomethyl)-3-fluoroprop-2-en-1-yl]-4-{6-[4-(piperazin-1-yl)phenyl]pyridin-2-yl}-2,4-dihydro-3H-1,2,4-triazol-3-one hydrochloride |
| 185 | 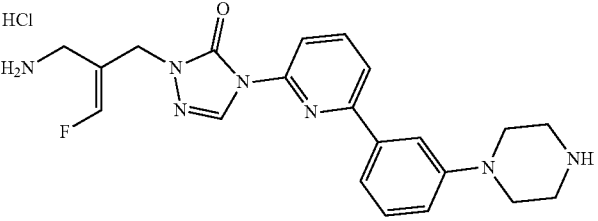 [SMILES: Cl ; NC/C(=C\F)Cn1ncn(-c2cccc(-c3cccc(N4CCNCC4)c3)n2)c1=O] | 2-[(2E)-2-(aminomethyl)-3-fluoroprop-2-en-1-yl]-4-{6-[4-(piperazin-1-yl)phenyl]pyridin-2-yl}-2,4-dihydro-3H-1,2,4-triazol-3-one hydrochloride |
| 186 | 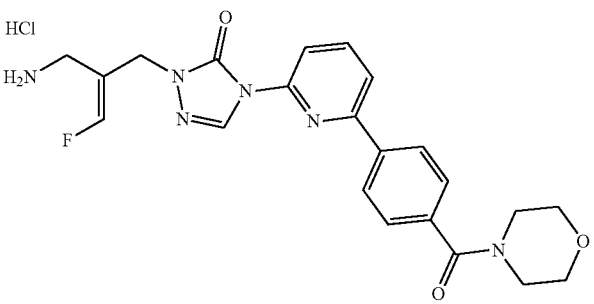 [SMILES: Cl ; NC/C(=C\F)Cn1ncn(-c2cccc(-c3ccc(C(=O)N4CCOCC4)cc3)n2)c1=O] | 2-[(2E)-2-(aminomethyl)-3-fluoroprop-2-en-1-yl]-4-{6-[4-(morpholin-4-ylcarbonyl)phenyl]pyridin-2-yl}-2,4-dihydro-3H-1,2,4-triazol-3-one hydrochloride |
| 187 | 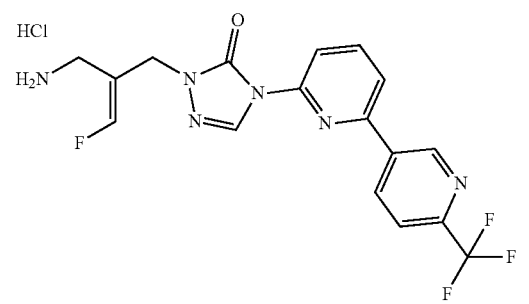 [SMILES: Cl ; NC/C(=C\F)Cn1ncn(-c2cccc(-c3ccc(C(F)(F)F)nc3)n2)c1=O] | 2-[(2E)-2-(aminomethyl)-3-fluoroprop-2-en-1-yl]-4-[6'-(trifluoromethyl)-2,3'-bipyridin-6-yl]-2,4-dihydro-3H-1,2,4-triazol-3-one hydrochloride |
| 188 | 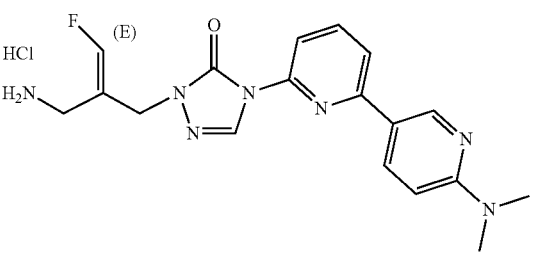 [SMILES: Cl ; CN(C)c1ccc(-c2cccc(-n3cnn(C/C(=C/F)CN)c3=O)n2)cn1] | 2-[(2E)-2-(aminomethyl)-3-fluoroprop-2-en-1-yl]-4-[6'-(dimethylamino)-2,3'-bipyridin-6-yl]-2,4-dihydro-3H-1,2,4-triazol-3-one hydrochloride |

TABLE 1-continued

| EX No | Structure | Chemical Name |
|---|---|---|
| 189 | 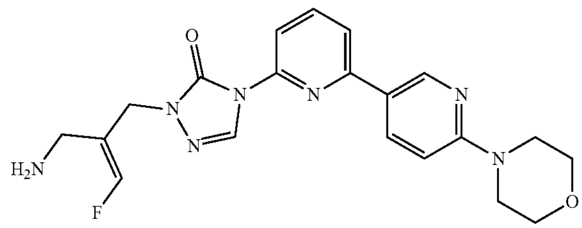 [SMILES: NC/C(=C\F)Cn1ncn(-c2cccc(-c3ccc(N4CCOCC4)nc3)n2)c1=O] | 2-[(2E)-2-(aminomethyl)-3-fluoroprop-2-en-1-yl]-4-[6'-(morpholin-4-yl)-2,3'-bipyridin-6-yl]-2,4-dihydro-3H-1,2,4-triazol-3-one |
| 190 | 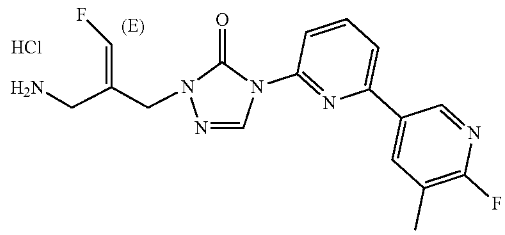 [SMILES: Cl ; Cc1cc(-c2cccc(-n3cnn(C/C(=C/F)CN)c3=O)n2)cnc1F] | 2-[(2E)-2-(aminomethyl)-3-fluoroprop-2-en-1-yl]-4-(6'-fluoro-5'-methyl-2,3'-bipyridin-6-yl)-2,4-dihydro-3H-1,2,4-triazol-3-one hydrochloride |
| 191 | 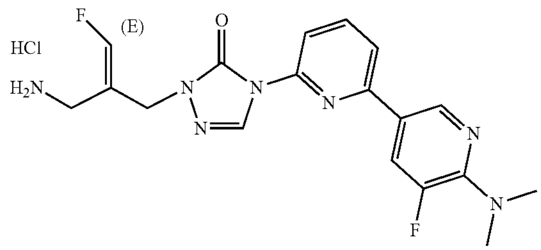 [SMILES: Cl ; CN(C)c1ncc(-c2cccc(-n3cnn(C/C(=C/F)CN)c3=O)n2)cc1F] | 2-[(2E)-2-(aminomethyl)-3-fluoroprop-2-en-1-yl]-4-[6'-(dimethylamino)-5'-fluoro-2,3'-bipyridin-6-yl]-2,4-dihydro-3H-1,2,4-triazol-3-one hydrochloride |
| 192 | 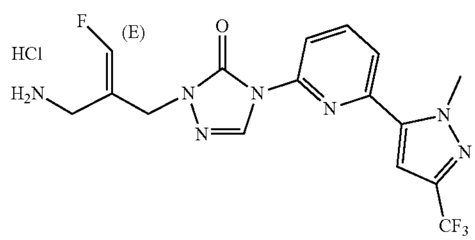 [SMILES: Cl ; Cn1nc(C(F)(F)F)cc1-c1cccc(-n2cnn(C/C(=C/F)CN)c2=O)n1] | 2-[(2E)-2-(aminomethyl)-3-fluoroprop-2-en-1-yl]-4-{6-[1-methyl-3-(trifluoromethyl)-1H-pyrazol-5-yl]pyridin-2-yl}-2,4-dihydro-3H-1,2,4-triazol-3-one hydrochloride |
| 193 | 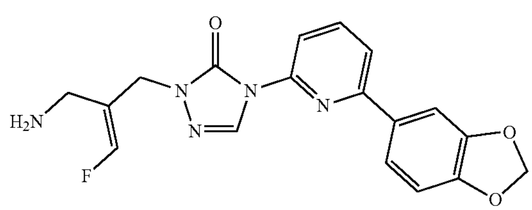 [SMILES: NC/C(=C\F)Cn1ncn(-c2cccc(-c3ccc4c(c3)OCO4)n2)c1=O] | 2-[(2E)-2-(aminomethyl)-3-fluoroprop-2-en-1-yl]-4-[6-(1,3-benzodioxol-5-yl)pyridin-2-yl]-2,4-dihydro-3H-1,2,4-triazol-3-one |
| 194 | 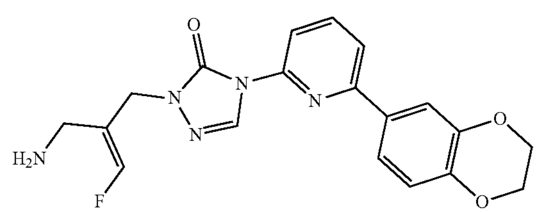 [SMILES: NC/C(=C\F)Cn1ncn(-c2cccc(-c3ccc4c(c3)OCCO4)n2)c1=O] | 2-[(2E)-2-(aminomethyl)-3-fluoroprop-2-en-1-yl]-4-[6-(2,3-dihydro-1,4-benzodioxin-6-yl)pyridin-2-yl]-2,4-dihydro-3H-1,2,4-triazol-3-one |
| 195 | 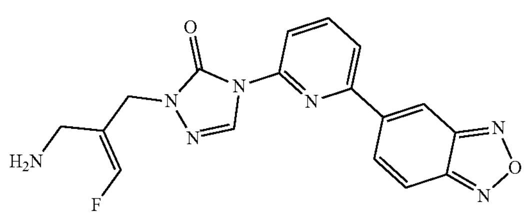 [SMILES: NC/C(=C\F)Cn1ncn(-c2cccc(-c3ccc4nonc4c3)n2)c1=O] | 2-[(2E)-2-(aminomethyl)-3-fluoroprop-2-en-1-yl]-4-[6-(2,1,3-benzoxadiazol-5-yl)pyridin-2-yl]-2,4-dihydro-3H-1,2,4-triazol-3-one |

TABLE 1-continued

| EX No | Structure | Chemical Name |
|---|---|---|
| 196 | 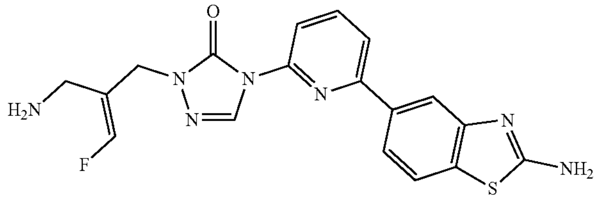 [SMILES: NC/C(=C\F)Cn1ncn(-c2cccc(-c3ccc4sc(N)nc4c3)n2)c1=O] | 4-[6-(2-amino-1,3-benzothiazol-5-yl)pyridin-2-yl]-2-[(2E)-2-(aminomethyl)-3-fluoroprop-2-en-1-yl]-2,4-dihydro-3H-1,2,4-triazol-3-one |
| 197 | 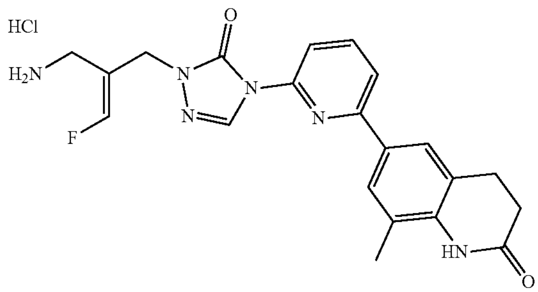 [SMILES: Cl ; Cc1cc(-c2cccc(-n3cnn(C/C(=C/F)CN)c3=O)n2)cc2c1NC(=O)CC2] | 6-(6-{1-[(2E)-2-(aminomethyl)-3-fluoroprop-2-en-1-yl]-5-oxo-1,5-dihydro-4H-1,2,4-triazol-4-yl}pyridin-2-yl)-8-methyl-3,4-dihydroquinolin-2(1H)-one hydrochloride |
| 198 | 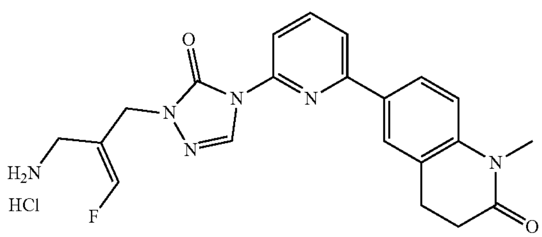 [SMILES: Cl ; CN1C(=O)CCc2cc(-c3cccc(-n4cnn(C/C(=C/F)CN)c4=O)n3)ccc21] | 6-[6-[1-[(E)-2-(aminomethyl)-3-fluoro-allyl]-5-oxo-1,2,4-triazol-4-yl]-2-pyridyl]-1-methyl-3,4-dihydroquinolin-2-one hydrochloride |
| 199 | 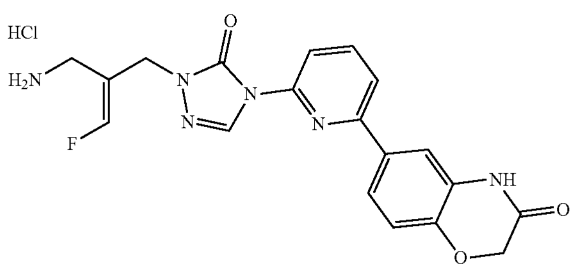 [SMILES: Cl ; NC/C(=C\F)Cn1ncn(-c2cccc(-c3ccc4c(c3)NC(=O)CO4)n2)c1=O] | 6-(3-{1-[(2E)-2-(aminomethyl)-3-fluoroprop-2-en-1-yl]-5-oxo-1,5-dihydro-4H-1,2,4-triazol-4-yl}pyridine-2-yl)-2H-1,4-benzoxazin-3(4H)-one hydrochloride |
| 200 | 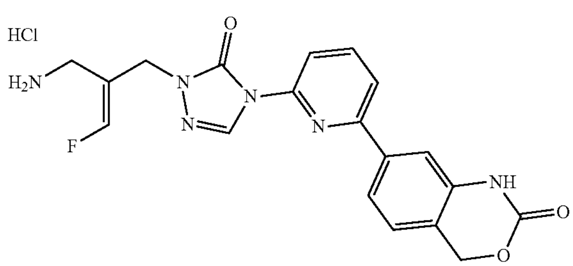 [SMILES: Cl ; NC/C(=C\F)Cn1ncn(-c2cccc(-c3ccc4c(c3)NC(=O)OC4)n2)c1=O] | 7-(6-{1-[(2E)-2-(aminomethyl)-3-fluoroprop-2-en-1-yl]-5-oxo-1,5-dihydro-4H-1,2,4-triazol-4-yl}pyridin-2-yl)-1,4-dihydro-2H-3,1-benzoxazin-2-one hydrochloride |
| 201 | 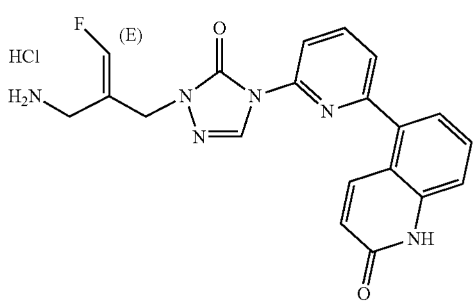 [SMILES: Cl ; NC/C(=C\F)Cn1ncn(-c2cccc(-c3cccc4[nH]c(=O)ccc34)n2)c1=O] | 5-(6-{1-[(2E)-2-(aminomethyl)-3-fluoroprop-2-en-1-yl]-5-oxo-1,5-dihydro-4H-1,2,4-triazol-4-yl}pyridin-2-yl)quinolin-2(1H)-one hydrochloride |

TABLE 1-continued

| EX No | Structure | Chemical Name |
|---|---|---|
| 202 | 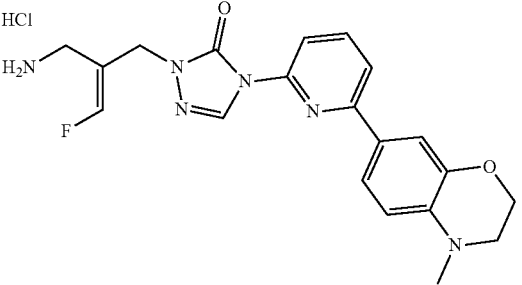 [SMILES: Cl ; CN1CCOc2cc(-c3cccc(-n4cnn(C/C(=C/F)CN)c4=O)n3)ccc21] | 2-[(2E)-2-(aminomethyl)-3-fluoroprop-2-en-1-yl]-4-[6-(4-methyl-3,4-dihydro-2H-1,4-benzoxazin-7-yl)pyridin-2-yl]-2,4-dihydro-3H-1,2,4-triazol-3-one hydrochloride |
| 203 | 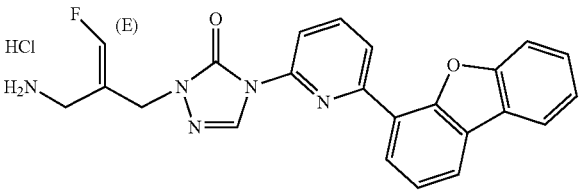 [SMILES: Cl ; NC/C(=C\F)Cn1ncn(-c2cccc(-c3cccc4c3oc3ccccc34)n2)c1=O] | 2-[(2E)-2-(aminomethyl)-3-fluoroprop-2-en-1-yl]-4-[6-(dibenzo[b,d]furan-4-yl)pyridin-2-yl]-2,4-dihydro-3H-1,2,4-triazol-3-one hydrochloride |
| 204 | 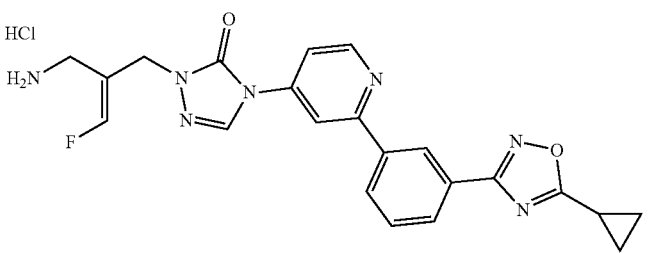 [SMILES: Cl ; NC/C(=C\F)Cn1ncn(-c2ccnc(-c3cccc(-c4noc(C5CC5)n4)c3)c2)c1=O] | 2-[(2E)-2-(aminomethyl)-3-fluoroprop-2-en-1-yl]-4{6-[4-(5-cyclopropyl-1,2,4-oxadiazol-3-yl)phenyl]pyridin-2-yl}-2,4-dihydro-3H-1,2,4-triazol-3-one hydrochloride |
| 205 | 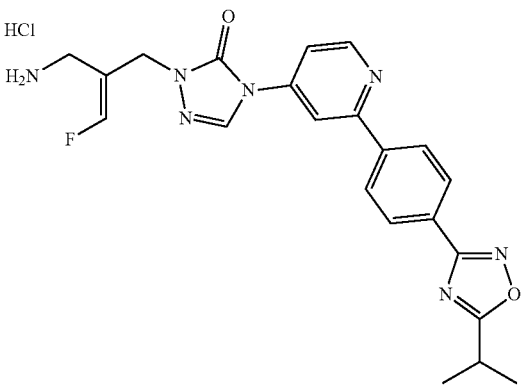 | 2-[(2E)-2-(aminomethyl)-3-fluoroprop-2-en-1-yl]-4-(2-{4-[5-(propan-2-yl)-1,2,4-oxadiazol-3-yl]phenyl}pyridin-4-yl)-2,4-dihydro-3H-1,2,4-triazol-3-one hydrochloride |
| 206 | 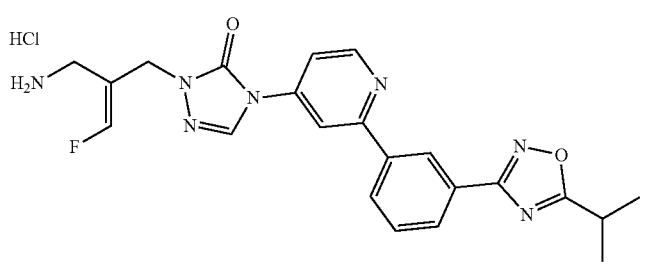 [SMILES: Cl ; CC(C)c1nc(-c2cccc(-c3cc(-n4cnn(C/C(=C/F)CN)c4=O)ccn3)c2)no1] | 2-[(2E)-2-(aminomethyl)-3-fluoroprop-2-en-1-yl]-4-(2-{3-[5-(propan-2-yl)-1,2,4-oxadiazol-3-yl]phenyl}pyridin-4-yl)-2,4-dihydro-3H-1,2,4-triazol-3-one hydrochloride |

| EX No | Structure | Chemical Name |
|---|---|---|
| 207 | 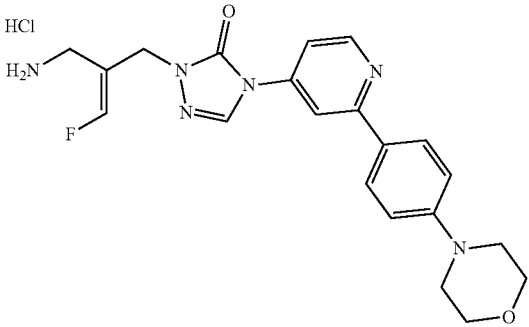 [SMILES: Cl ; NC/C(=C\F)Cn1ncn(-c2ccnc(-c3ccc(N4CCOCC4)cc3)c2)c1=O] | 2-[(2E)-2-(aminomethyl)-3-fluoroprop-2-en-1-yl]-4-{2-[4-(morpholin-4-yl)phenyl]pyridin-4-yl}-2,4-dihydro-3H-1,2,4-triazol-3-one hydrochloride |
| 208 | 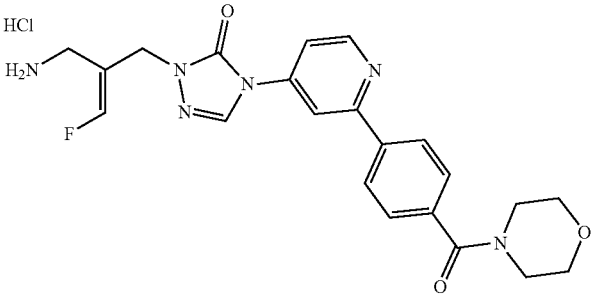 [SMILES: Cl ; NC/C(=C\F)Cn1ncn(-c2ccnc(-c3ccc(C(=O)N4CCOCC4)cc3)c2)c1=O] | 2-[(2E)-2-(aminomethyl)-3-fluoroprop-2-en-1-yl]-4-{2-[4-(morpholin-4-ylcarbonyl)phenyl]pyridin-4-yl}-2,4-dihydro-3H-1,2,4-triazol-3-one hydrochloride |
| 209 | 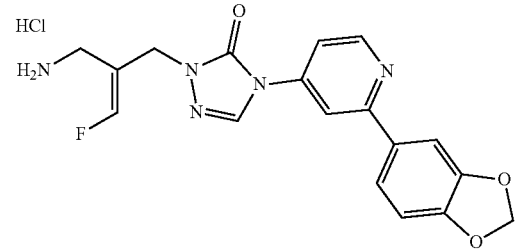 [SMILES: Cl ; NC/C(=C\F)Cn1ncn(-c2ccnc(-c3ccc4c(c3)OCO4)c2)c1=O] | 2-[(2E)-2-(aminomethyl)-3-fluoroprop-2-en-1-yl]-4-[2-(1,3-benzodioxol-5-yl)pyridin-4-yl]-2,4-dihydro-3H-1,2,4-triazol-3-one hydrochloride |
| 210 | 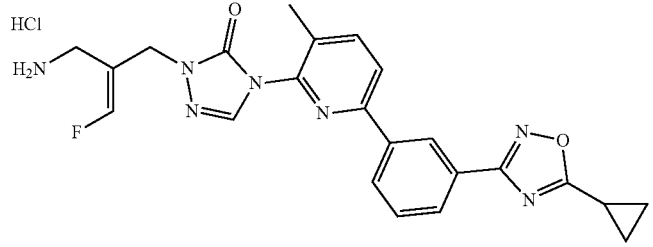 | 2-[(2E)-2-(aminomethyl)-3-fluoroprop-2-en-1-yl]-4-{6-[3-(5-cyclopropyl-1,2,4-oxadiazol-3-yl)phenyl]-3-methylpyridin-2-yl}-2,4-dihydro-3H-1,2,4-triazol-3-one hydrochloride |
| 211 | 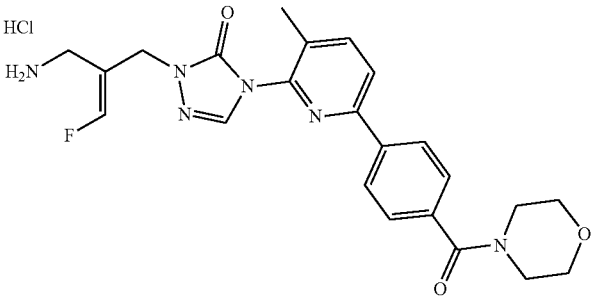 [SMILES: Cl ; Cc1ccc(-c2ccc(C(=O)N3CCOCC3)cc2)nc1-n1cnn(C/C(=C/F)CN)c1=O] | 2-[(2E)-2-(aminomethyl)-3-fluoroprop-2-en-1-yl]-4-{3-methyl-6-[4-(morpholin-4-ylcarbonyl)phenyl]pyridin-2-yl}-2,4-dihydro-3H-1,2,4-triazol-3-one hydrochloride |

| EX No | Structure | Chemical Name |
|---|---|---|
| 212 | 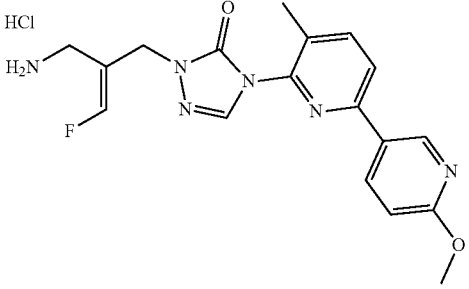 [SMILES: Cl ; COc1ccc(-c2ccc(C)c(-n3cnn(C/C(=C/F)CN)c3=O)n2)cn1] | 2-[(2E)-2-(aminomethyl)-3-fluoroprop-2-en-1-yl]-4-(6'-methoxy-5-methyl-2,3'-bipyridin-6-yl)-2,4-dihydro-3H-1,2,4-triazol-3-one hydrochloride |
| 213 | 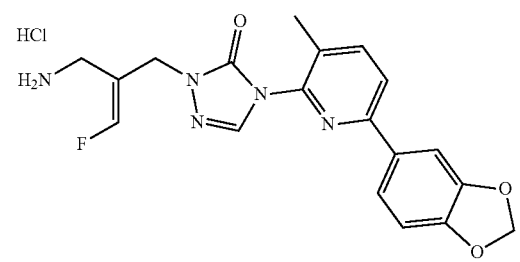 [SMILES: Cl ; Cc1ccc(-c2ccc3c(c2)OCO3)nc1-n1cnn(C/C(=C/F)CN)c1=O] | 2-[(2E)-2-(aminomethyl)-3-fluoroprop-2-en-1-yl]-4-[6-(1,3-benzodioxol-5-yl)-3-methylpyridin-2-yl]-2,4-dihydro-3H-1,2,4-triazol-3-one hydrochloride |
| 214 | 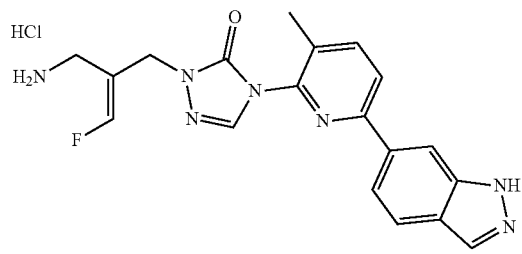 [SMILES: Cl ; Cc1ccc(-c2ccc3cn[nH]c3c2)nc1-n1cnn(C/C(=C/F)CN)c1=O] | 2-[(2E)-2-(aminomethyl)-3-fluoroprop-2-en-1-yl]-4-[6-(1H-indazol-6-yl)-3-methylpyridin-2-yl]-2,4-dihydro-3H-1,2,4-triazol-3-one hydrochloride |
| 215 | 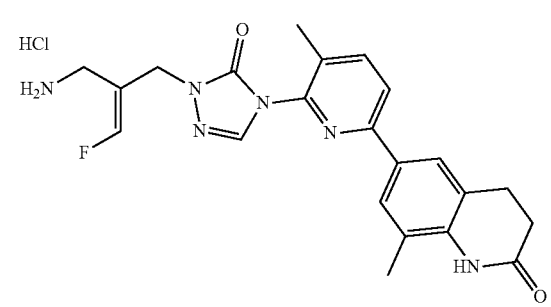 [SMILES: Cl ; Cc1ccc(-c2cc(C)c3c(c2)CCC(=O)N3)nc1-n1cnn(C/C(=C/F)CN)c1=O] | 6-(6-{1-[(2E)-2-(aminomethyl)-3-fluoroprop-2-en-1-yl]-5-oxo-1,5-dihydro-4H-1,2,4-triazol-4-yl}-5-methylpyridin-2-yl)-8-methyl-3,4-dihydroquinolin-2(1H)-one hydrochloride |
| 216 | 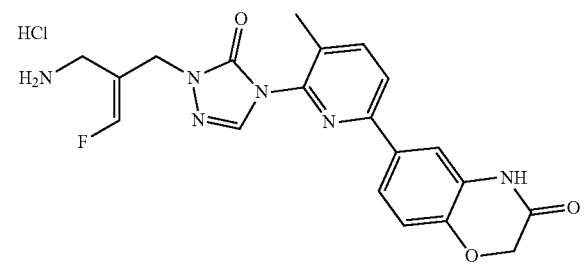 [SMILES: Cl ; Cc1ccc(-c2ccc3c(c2)NC(=O)CO3)nc1-n1cnn(C/C(=C/F)CN)c1=O] | 6-(6-{1-[(2E)-2-(aminomethyl)-3-fluoroprop-2-en-1-yl]-5-oxo-1,5-dihydro-4H-1,2,4-triazol-4-yl}-5-methylpyridin-2-yl)-2H-1,4-benzoxazin-3(4H)-one hydrochloride |

TABLE 1-continued

| EX No | Structure | Chemical Name |
|---|---|---|
| 217 | 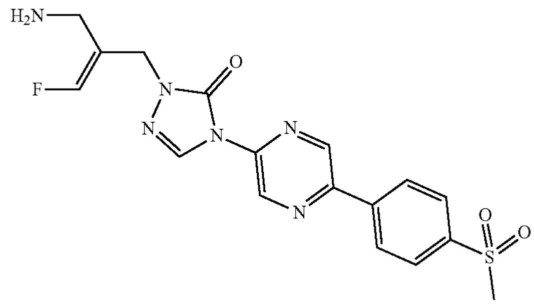 [SMILES: CS(=O)(=O)c1ccc(-c2cnc(-n3cnn(C/C(=C/F)CN)c3=O)cn2)cc1] | 2-[(2E)-2-(aminomethyl)-3-fluoroprop-2-en-1-yl]-4-{5-[4-(methylsulfonyl)phenyl]pyrazin-2-yl}-2,4-dihydro-3H-1,2,4-triazol-3-one |
| 218 | 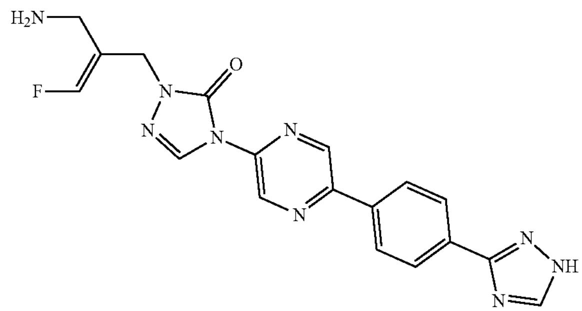 [SMILES: NC/C(=C\F)Cn1ncn(-c2cnc(-c3ccc(-c4nc[nH]n4)cc3)cn2)c1=O] | 2-[(2E)-2-(aminomethyl)-3-fluoroprop-2-en-1-yl]-4-{5-[4-(1H-1,2,4-triazol-3-yl)phenyl]pyrazin-2-yl}-2,4-dihydro-3H-1,2,4-triazol-3-one |
| 219 | 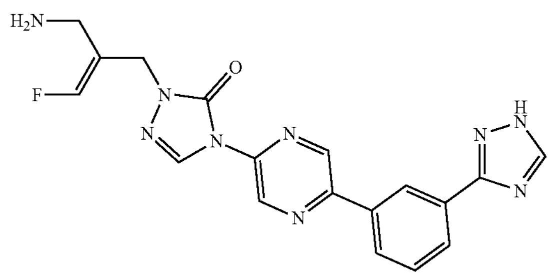 [SMILES: NC/C(=C\F)Cn1ncn(-c2cnc(-c3cccc(-c4nc[nH]n4)c3)cn2)c1=O] | 2-[(2E)-2-(aminomethyl)-3-fluoroprop-2-en-1-yl]-4-{5-[3-(1H-1,2,4-triazol-3-yl)phenyl]pyrazin-2-yl}-2,4-dihydro-3H-1,2,4-triazol-3-one |
| 220 | 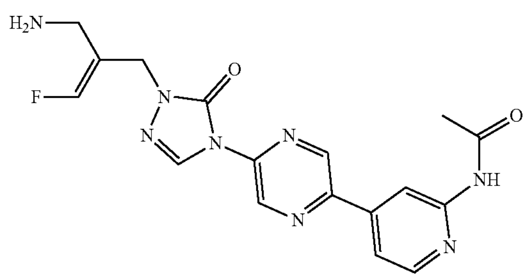 [SMILES: CC(=O)Nc1cc(-c2cnc(-n3cnn(C/C(=C/F)CN)c3=O)cn2)ccn1] | N-[4-(5-{1-[(2E)-2-(aminomethyl)-3-fluoroprop-2-en-1-yl]-5-oxo-1,5-dihydro-4H-1,2,4-triazol-4-yl}pyrazin-2-yl)pyridin-2-yl]acetamide |
| 221 | 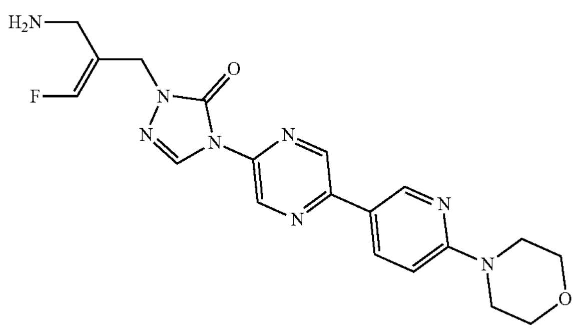 [SMILES: NC/C(=C\F)Cn1ncn(-c2cnc(-c3ccc(N4CCOCC4)nc3)cn2)c1=O] | 2-[(2E)-2-(aminomethyl)-3-fluoroprop-2-en-1-yl]-4-{5-[6-(morpholin-4-yl)pyridin-3-yl]pyrazin-2-yl}-2,4-dihydro-3H-1,2,4-triazol-3-one |

TABLE 1-continued

| EX No | Structure | Chemical Name |
|---|---|---|
| 222 | 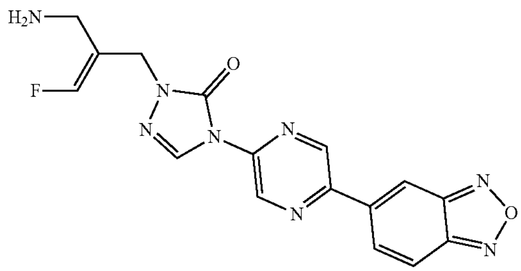 [SMILES: NC/C(=C\F)Cn1ncn(-c2cnc(-c3ccc4nonc4c3)cn2)c1=O] | 2-[(2E)-2-(aminomethyl)-3-fluoroprop-2-en-1-yl]-4-[5-(2,1,3-benzoxadiazol-5-yl)pyrazin-2-yl]-2,4-dihydro-3H-1,2,4-triazol-3-one |
| 223 | 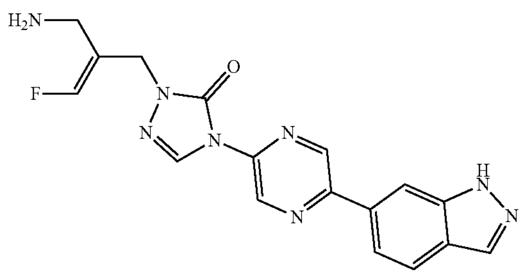 [SMILES: NC/C(=C\F)Cn1ncn(-c2cnc(-c3ccc4cn[nH]c4c3)cn2)c1=O] | 2-[(2E)-2-(aminomethyl)-3-fluoroprop-2-en-1-yl]-4-[5-(1H-indazol-6-yl)pyrazin-2-yl]-2,4-dihydro-3H-1,2,4-triazol-3-one |
| 224 | 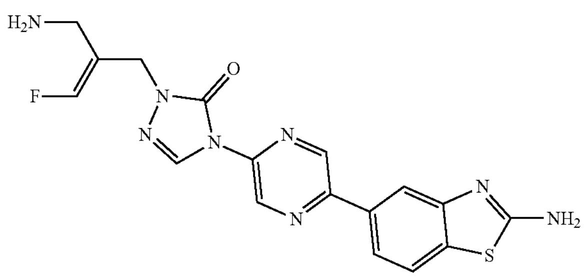 [SMILES: NC/C(=C\F)Cn1ncn(-c2cnc(-c3ccc4sc(N)nc4c3)cn2)c1=O] | 4-[5-(2-amino-1,3-benzothiazol-5-yl)pyrazin-2-yl]-2-[(2E)-2-(aminomethyl)-3-fluoroprop-2-en-1-yl]-2,4-dihydro-3H-1,2,4-triazol-3-one |
| 225 | 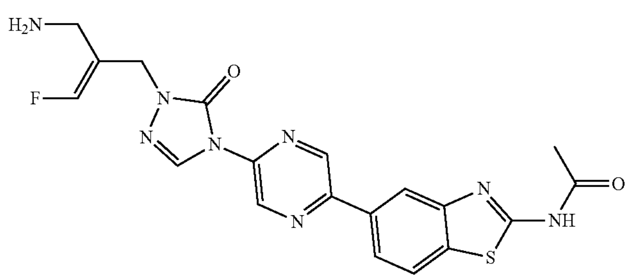 [SMILES: CC(=O)Nc1nc2cc(-c3cnc(-n4cnn(C/C(=C/F)CN)c4=O)cn3)ccc2s1] | N-[5-(5-{1-[(2E)-2-(aminomethyl)-3-fluoroprop-2-en-1-yl]-5-oxo-1,5-dihydro-4H-1,2,4-triazol-4-yl}pyrazin-2-yl)-1,3-benzothiazol-2-yl]acetamide |
| 226 | 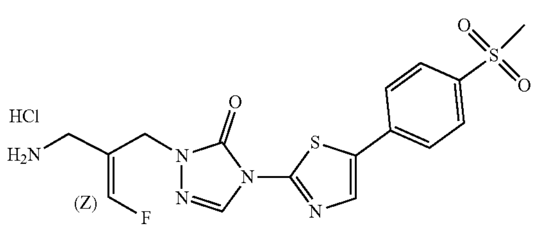 [SMILES: Cl ; CS(=O)(=O)c1ccc(-c2cnc(-n3cnn(C/C(=C\F)CN)c3=O)s2)cc1] | 2-[(2Z)-2-(aminomethyl)-3-fluoroprop-2-en-1-yl]-4-{5-[4-(methylsulfonyl)phenyl]-1,3-thiazol-2-yl}-2,4-dihydro-3H-1,2,4-triazol-3-one hydrochloride |
| 227 | 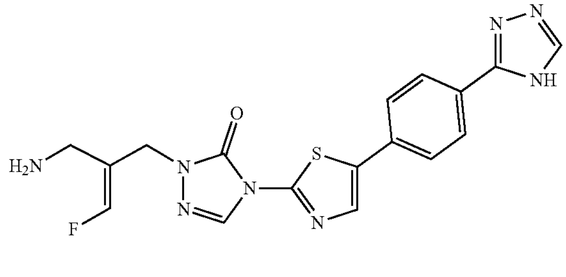 [SMILES: NC/C(=C\F)Cn1ncn(-c2ncc(-c3ccc(-c4nnc[nH]4)cc3)s2)c1=O] | 2-[(2E)-2-(aminomethyl)-3-fluoroprop-2-en-1-yl]-4-{5-[4-(4H-1,2,4-triazol-3-yl)phenyl]-1,3-thiazol-2-yl}-2,4-dihydro-3H-1,2,4-triazol-3-one |

TABLE 1-continued

| EX No | Structure | Chemical Name |
|---|---|---|
| 228 | 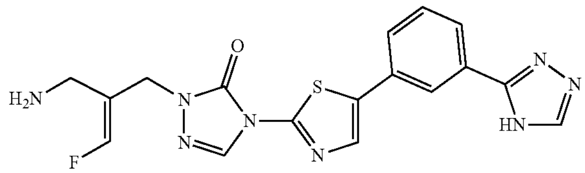 [SMILES: NC/C(=C\F)Cn1ncn(-c2ncc(-c3cccc(-c4nnc[nH]4)c3)s2)c1=O] | 2-[(2E)-2-(aminomethyl)-3-fluoroprop-2-en-1-yl]-4-{5-[3-(4H-1,2,4-triazol-3-yl)phenyl]-1,3-thiazol-2-yl}-2,4-dihydro-3H-1,2,4-triazol-3-one |
| 229 | 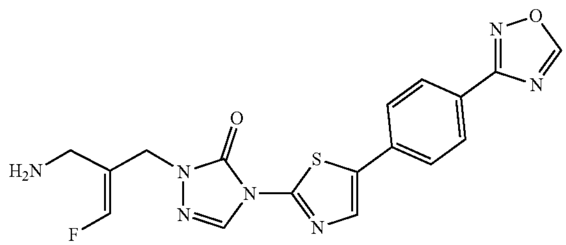 [SMILES: NC/C(=C\F)Cn1ncn(-c2ncc(-c3ccc(-c4ncon4)cc3)s2)c1=O] | 2-[(2E)-2-(aminomethyl)-3-fluoroprop-2-en-1-yl]-4-{5-[4-(4H-1,2,4-oxadiazol-3-yl)phenyl]-1,3-thiazol-2-yl}-2,4-dihydro-3H-1,2,4-triazol-3-one |
| 230 | 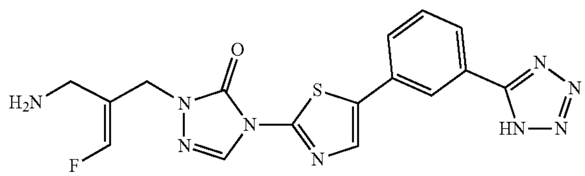 [SMILES: NC/C(=C\F)Cn1ncn(-c2ncc(-c3cccc(-c4nnn[nH]4)c3)s2)c1=O] | 2-[(2E)-2-(aminomethyl)-3-fluoroprop-2-en-1-yl]-4-{5-[3-(1H-tetrazol-5-yl)phenyl]-1,3-thiazol-2-yl}-2,4-dihydro-3H-1,2,4-triazol-3-one |
| 231 | 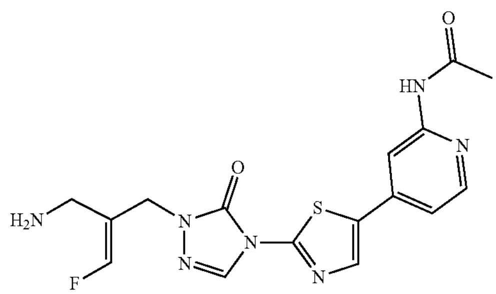 [SMILES: CC(=O)Nc1cc(-c2cnc(-n3cnn(C/C(=C/F)CN)c3=O)s2)ccn1] | N-[4-(2-{1-[(2E)-2-(aminomethyl)-3-fluoroprop-2-en-1-yl]-5-oxo-1,5-dihydro-4H-1,2,4-triazol-4-yl}-1,3-thiazol-5-yl)pyridin-2-yl]acetamide |
| 232 | 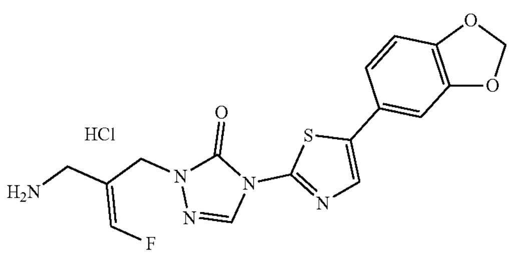 [SMILES: NC/C(=C/F)Cn1ncn(-c2ncc(-c3ccc4c(c3)OCO4)s2)c1=O ; Cl] | 2-[(2Z)-2-(aminomethyl)-3-fluoroprop-2-en-1-yl]-4-[5-(1,3-benzodioxol-5-yl)-1,3-thiazol-2-yl]-dihydro-3H-1,2,4-triazol-3-one hydrochloride |
| 233 | 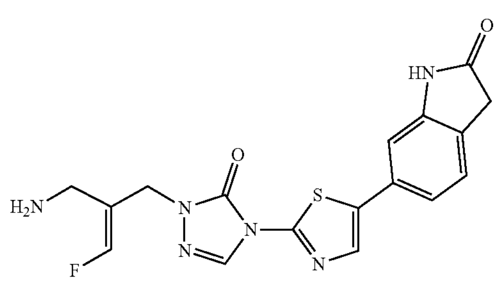 [SMILES: NC/C(=C\F)Cn1ncn(-c2ncc(-c3ccc4c(c3)NC(=O)C4)s2)c1=O] | 6-(2-{1-[(2E)-2-(aminomethyl)-3-fluoroprop-2-en-1-yl]-5-oxo-1,5-dihydro-4H-1,2,4-triazol-4-yl}-1,3-thiazol-5-yl)-1,3-dihydro-2H-indol-2-one |
| 234 | | 2-[(2Z)-2-(aminomethyl)-3-fluoroprop-2-en-1-yl]-4-[5-(2,1,3-benzoxadiazol-5-yl)-1,3-thiazol-2-yl]-2,4-dihydro-3H-1,2,4-triazol-3-one hydrochloride |

US 11,492,335 B2

TABLE 1-continued

| EX No | Structure | Chemical Name |
|---|---|---|
| 235 | | N-[5-(4-{1-[(2E)-2-(aminomethyl)-3-fluoroprop-2-en-1-yl]-5-oxo-1,5-dihydro-4H-1,2,4-triazol-4-yl}benzyl)-1,3-thiazol- 2-yl]acetamide hydrochloride |
| 236 | | 2-[(2E)-2-(aminomethyl)-3-fluoroprop-2-en-1-yl]-4-{4-[(E)-2-phenylethenyl]pyridin-2-yl}-2,4-dihydro-3H-1,2,4-triazol-3-one hydrochloride |
| 237 | | 2-[(2E)-2-(aminomethyl)-3-fluoroprop-2-en-1-yl]-4-{6-[(E)-2-(thiophen-3-yl)ethenyl]pyridin-2-yl}-2,4-dihydro-3H-1,2,4-triazol-3-one |
| 238 | | 2-[(2E)-2-(aminomethyl)-3-fluoroprop-2-en-1-yl]-4-(6-{(E)-2-[4-(trifluoromethyl)phenyl]ethenyl}pyridin-2-yl)-2,4-dihydro-3H-1,2,4-triazol-3-one hydrochloride |
| 239 | 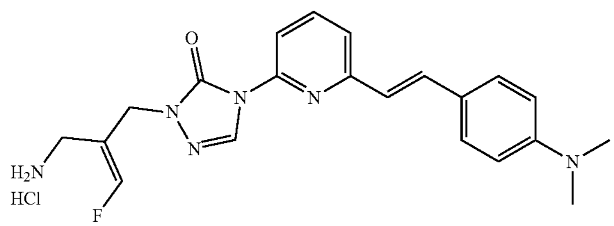 [SMILES: Cl ; CN(C)c1ccc(/C=C/c2cccc(-n3cnn(C/C(=C/F)CN)c3=O)n2)cc1] | 2-[(E)-2-(aminomethyl)-3-fluoro-allyl]-4-(6-[(E)-2-[4-(dimethylamino)phenyl]vinyl]-2-pyridyl]-1,2,4-triazol-3-one hydrochloride |
| 240 | 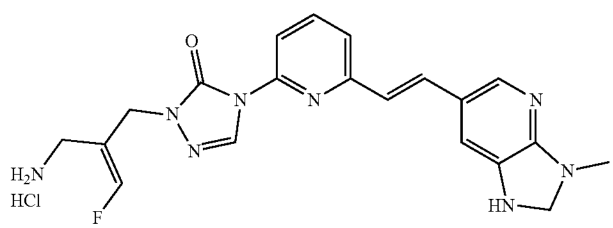 [SMILES: Cl ; CN1CNc2cc(/C=C/c3cccc(-n4cnn(C/C(=C/F)CN)c4=O)n3)cnc21] | 2-[(E)-2-(aminomethyl)-3-fluoro-allyl]-4-[6-[(E)-2-(3-methyl-1,2-dihydroimidazo[4,5-b]pyridin-6-yl)vinyl]-2-pyridyl]-1,2,4-triazol-3-one hydrochloride |
| 241 | 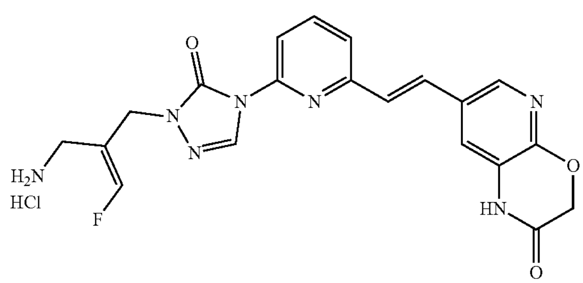 [SMILES: Cl ; NC/C(=C\F)Cn1ncn(-c2cccc(/C=C/c3cnc4c(c3)NC(=O)CO4)n2)c1=O] | 7-[(E)-2-[6-[1-[(E)-2-(aminomethyl)-3-fluoro-allyl]-5-oxo-1,2,4-triazol-4-yl]-2-pyridyl]vinyl]-1H-pyrido[2,3-b][1,4]oxazin-2-one hydrochloride |
| 242 | 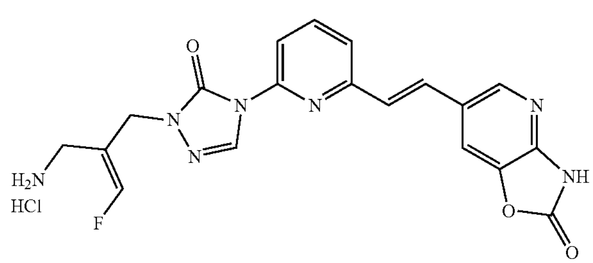 [SMILES: Cl ; NC/C(=C\F)Cn1ncn(-c2cccc(/C=C/c3cnc4[nH]c(=O)oc4c3)n2)c1=O] | 6-[(E)-2-[6-[1-[(E)-2-(aminomethyl)-3-fluoro-allyl]-5-oxo-1,2,4-triazol-4-yl]-2-pyridyl]vinyl]-3H-oxazolo[4,5-b]pyridin-2-one hydrochloride |
| 243 | | 2-[(2E)-2-(aminomethyl)-3-fluoroprop-2-en-1-yl]-4-[3-(pyridin-3-ylethynyl)phenyl]-2,4-dihydro-3H-1,2,4-triazol-4-one hydrochloride |
| 244 | | 2-[(2E)-2-(aminomethyl)-3-fluoroprop-2-en-1-yl]-4-[4-(pyridin-2-ylethynyl)pyridin-2-yl]-2,4-dihydro-3H-1,2,4-triazol-3-one hydrochloride |
| 245 | | 2-[(2E)-2-(aminomethyl)-3-fluoroprop-2-en-1-yl]-4-[4-(pyridin-3-ylethynyl)pyridin-2-yl]-2,4-dihydro-3H-1,2,4-triazol-3-one hydrochloride |

TABLE 1-continued

| EX No | Structure | Chemical Name |
|---|---|---|
| 246 | | 2-[(2E)-2-(aminomethyl)-3-fluoroprop-2-en-1-yl]-4-[4-(pyridin-4-ylethynyl)pyridin-2-yl]-2,4-dihydro-3H-1,2,4-triazol-3-one hydrochloride |
| 247 | 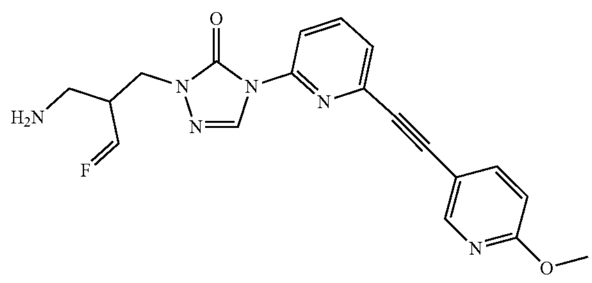 | 2-[(2E)-2-(aminomethyl)-3-fluoroprop-2-en-1-yl]-4-{6-[(6-methoxypyridin-3-yl)ethynyl]pyridin-2-yl}-2,4-dihydro-3H-1,2,4-triazol-3-one |
| 248 | 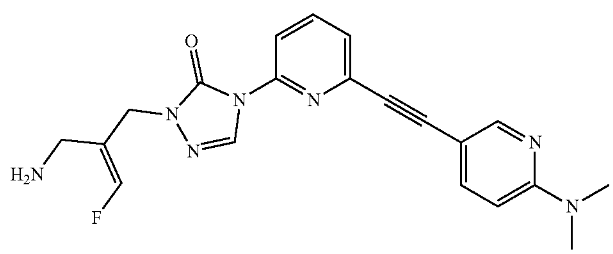 [SMILES: CN(C)c1ccc(C#Cc2cccc(-n3cnn(C/C(=C/F)CN)c3=O)n2)cn1] | 2-[(E)-2-(aminomethyl)-3-fluoro-allyl]-4-[6-[2-[6-(dimethylamino)-3-pyridyl]ethynyl]-2-pyridyl]-1,2,4-triazol-3-one |
| 249 | 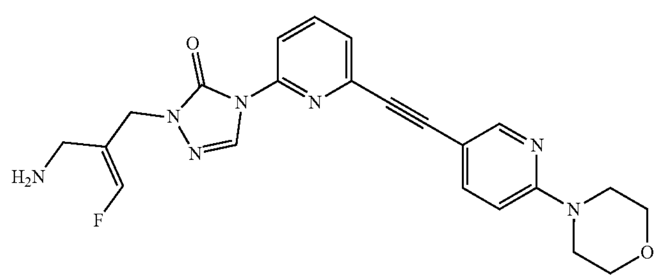 [SMILES: NC/C(=C\F)Cn1ncn(-c2cccc(C#Cc3ccc(N4CCOCC4)nc3)n2)c1=O] | 2-[(E)-2-(aminomethyl)-3-fluoro-allyl]-4-[6-[2-(6-morpholino-3-pyridyl)ethynyl]-2-pyridyl]-1,2,4-triazol-3-one |
| 250 | 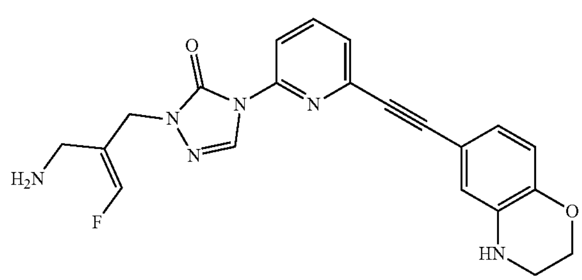 [SMILES: NC/C(=C\F)Cn1ncn(-c2cccc(C#Cc3ccc4c(c3)NCCO4)n2)c1=O] | 2-[(E)-2-(aminomethyl)-3-fluoro-allyl]-4-[6-[2-(3,4-dihydro-2H-1,4-benzoxazin-6-yl)ethynyl]-2-pyridyl]-1,2,4-triazol-3-one |
| 251 | 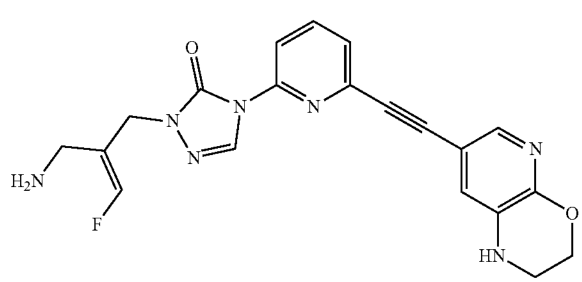 [SMILES: NC/C(=C\F)Cn1ncn(-c2cccc(C#Cc3cnc4c(c3)NCCO4)n2)c1=O] | 2-[(E)-2-(aminomethyl)-3-fluoro-allyl]-4-[6-[2-(2,3-dihydro-1H-pyrido[2,3-b][1,4]oxazin-7-yl)ethynyl]-2-pyridyl]-1,2,4-triazol-3-one |

TABLE 1-continued

| EX No | Structure | Chemical Name |
|---|---|---|
| 252 | 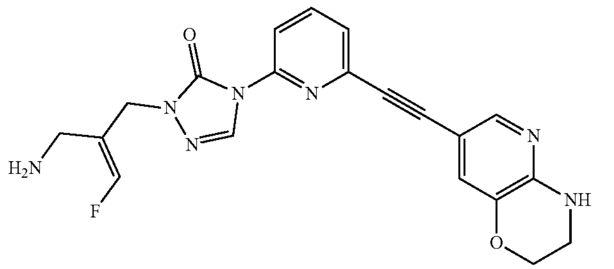 [SMILES: NC/C(=C\F)Cn1ncn(-c2cccc(C#Cc3cnc4c(c3)OCCN4)n2)c1=O] | 2-[(E)-2-(aminomethyl)-3-fluoro-allyl]-4-[6-[2-(3,4-dihydro-2H-pyrido[3,2-b][1,4]oxazin-7-yl)ethynyl]-2-pyridyl]-1,2,4-triazol-3-one |
| 253 | 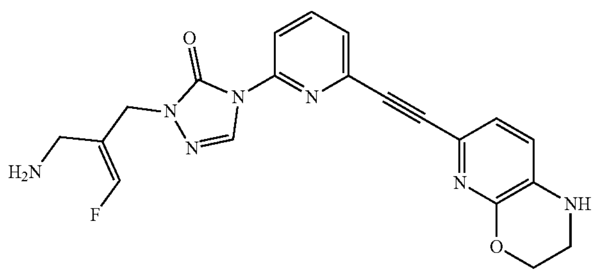 [SMILES: NC/C(=C\F)Cn1ncn(-c2cccc(C#Cc3ccc4c(n3)OCCN4)n2)c1=O] | 2-[(E)-2-(aminomethyl)-3-fluoro-allyl]-4-[6-[2-(2,3-dihydro-1H-pyrido[2,3-b][1,4]oxazin-6-yl)ethynyl]-2-pyridyl]-1,2,4-triazol-3-one |
| 254 | 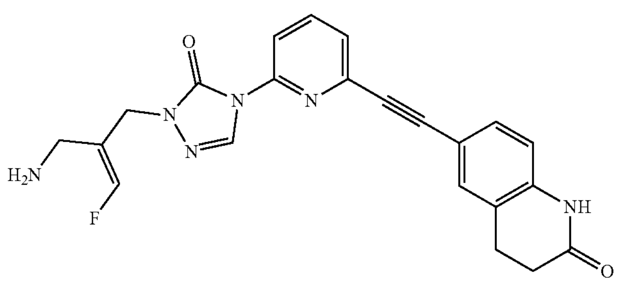 [SMILES: NC/C(=C\F)Cn1ncn(-c2cccc(C#Cc3ccc4c(c3)CCC(=O)N4)n2)c1=O] | 6-[2-[6-[1-[(E)-2-(aminomethyl)-3-fluoro-allyl]-5-oxo-1,2,4-triazol-4-yl]-2-pyridyl]ethynyl]-3,4-dihydro-1H-quinolin-2-one |
| 255 | 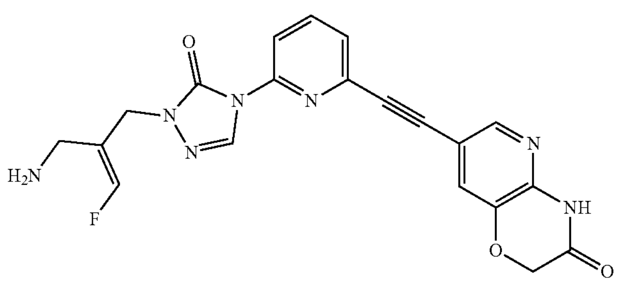 [SMILES: NC/C(=C\F)Cn1ncn(-c2cccc(C#Cc3cnc4c(c3)OCC(=O)N4)n2)c1=O] | 7-[2-[6-[1-[(E)-2-(aminomethyl)-3-fluoro-allyl]-5-oxo-1,2,4-triazol-4-yl]-2-pyridyl]ethynyl]-4H-pyrido[3,2-b][1,4]oxazin-3-one |
| 256 | 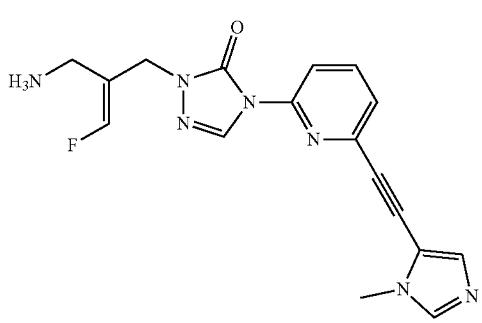 [SMILES: Cn1cncc1C#Cc1cccc(-n2cnn(C/C(=C/F)CN)c2=O)n1] | 2-[(E)-2-(aminomethyl)-3-fluoro-allyl]-4-[6-[2-(3-methylimidazol-4-yl)ethynyl]-2-pyridyl]-1,2,4-triazol-3-one |

TABLE 1-continued

| EX No | Structure | Chemical Name |
|---|---|---|
| 257 | 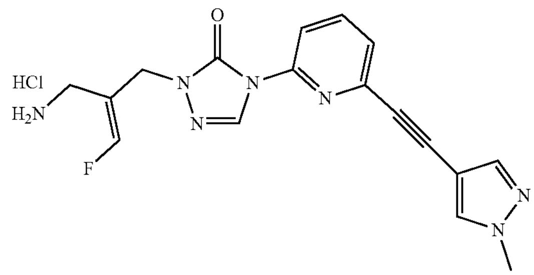 [SMILES: Cl ; Cn1cc(C#Cc2cccc(-n3cnn(C/C(=C/F)CN)c3=O)n2)cn1] | 2-[(2E)-2-(aminomethyl)-3-fluoroprop-2-en-1-yl]-4-{6-[(1-methyl-1H-pyrazol-4-yl)ethynyl]pyridin-2-yl}-2,4-dihydro-3H-1,2,4-triazol-3-one hydrochloride |
| 258 | 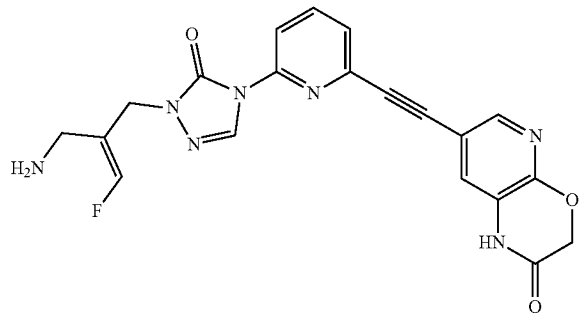 [SMILES: NC/C(=C\F)Cn1ncn(-c2cccc(C#Cc3cnc4c(c3)NC(=O)CO4)n2)c1=O] | 7-[2-[6-[1-[(E)-2-(aminomethyl)-3-fluoro-allyl]-5-oxo-1,2,4-triazol-4-yl]-2-pyridyl]ethynyl]-1H-pyrido[2,3-b][1,4]oxazin-2-one |
| 259 | 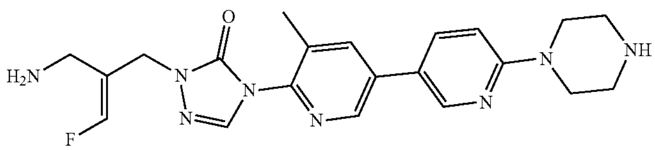 [SMILES: Cc1cc(-c2ccc(N3CCNCC3)nc2)cnc1-n1cnn(C/C(=C/F)CN)c1=O] | 2-[(E)-2-(aminomethyl)-3-fluoro-allyl]-4-[3-methyl-5-(6-piperazin-1-yl-3-pyridyl)-2-pyridyl]-1,2,4-triazol-3-one |

Experimental Example 1: Activity Evaluation with Respect to Amine Oxidases

The compounds according to the present technology were evaluated in terms of activity on recombinant human VAP-1 (R&D systems) by measuring the level of hydrogen peroxide in horseradish peroxidase (HRP)-coupled reaction using Amplex Red Hydrogen Peroxide Assay Kit (Molecular Probes, Invitrogen, USA). The experiment was carried out at room temperature using benzylamine as a substrate. In the HRP-coupled reaction, hydrogen peroxide oxidation of 10-acetyl-3,7-dihydroxyphenoxazine (Amplex Red reagent) produces resorufin, which is a highly fluorescent compound. Briefly, the test compound was dissolved in dimethyl sulfoxide (DMSO) at a concentration of 20 mM. The dose-response assessment was made by 1:3 serial dilution in DMSO, thereby creating an 8 point curve. The concentration of the upper part was controlled according to the efficacy of the compounds, followed by dilution with a reaction buffer solution to obtain a final DMSO concentration less than 1%. To each well of a 96 black well plate, human VAP-1 purified in 50 mM sodium phosphate buffer solution (pH7.4) was added. The test compounds dissolved in DMSO were incubated with the human VAP-1 enzymes at 37° C. for 30 minutes. After 30-minute incubation, each well is added with a reaction mixture containing 200 uM Amplex Red reagent prepared from 50 mM sodium phosphate buffer solution (pH 7.4), 1 mM benzylamine, and 1 U/mL HRP. Fluorescence intensity was measured at several time points during 1-2 hours using a microplate reader (Flexstation3, Molecular Devices) under the wavelength condition exciting at 544 nm and reading the emission at 590 nm. The inhibitory effect of the compounds was measured as a decrease (%) in the signal rate as compared to the control group without any inhibitor (only diluted DMSO). Data was fixed to a logistic model with four variables and $IC_{50}$ value was calculated using GraphPad Prism program.

In addition, the compounds according to the present technology were evaluated in terms of activity on a recombinant human MAO-A (monoamine oxidase-A, Sigma-Aldrich) and a recombinant human MAO-B (monoamine oxidase-B, Sigma-Aldrich) by using as substrates, 0.5 mM tyramine and 1 mM benzylamine, respectively, with a method similar to the activity evaluation method for recombinant human VAP-1. The compounds according to the present technology were also evaluated in terms of activity on a recombinant human DAO (diamine oxidase, R&D systems) by using as a substrate 1 mM putrescine with a method similar to the activity evaluation method for recombinant human VAP-1.

The results obtained by evaluating the activity against the enzymes as above are shown in Tables 2 and 3 below.

TABLE 2

| | Inhibitory Activity ($IC_{50}$, nM) | | | |
|---|---|---|---|---|
| Example | human VAP-1 | MAO-A | MAO-B | DAO |
| 1 | 17 | | | |
| 2 | 0.9 | 2900 | 86 | 120 |
| 3 | 2.5 | 3500 | 121 | 542 |
| 4 | 1.2 | >100,000 | 175 | 90 |
| 5 | 3.8 | 1600 | 260 | 1,100 |
| 6 | 3.7 | >100,000 | >10,000 | 1,100 |

TABLE 2-continued

Inhibitory Activity (IC$_{50}$, nM)

| Example | human VAP-1 | MAO-A | MAO-B | DAO |
|---|---|---|---|---|
| 7 | 0.88 | 2,100 | 8 | 47 |
| 8 | 0.6 | 54,000 | 10 | 38 |
| 9 | 5.4 | 2100 | 85 | 290 |
| 10 | 2.4 | >100,000 | 1,612 | 100 |
| 11 | 1.5 | 200 | 12 | 209 |
| 12 | 0.75 | 1,500 | 281 | 38 |
| 13 | 2.3 | 155 | 3.3 | 67 |
| 14 | 0.96 | 5,200 | 35 | 38 |
| 15 | 2.2 | 710 | 9.8 | 85 |
| 16 | 0.74 | 32,000 | 141 | 12 |
| 17 | 2.7 | >100,000 | 406 | 31 |
| 18 | 1.4 | >100,000 | 58 | 21 |
| 19 | 3.3 | 10,000 | 4.4 | 13 |
| 20 | 2.2 | >100,000 | >10,000 | 15 |
| 21 | 7.3 | 400 | 25 | 333 |
| 22 | 1.4 | 12,000 | 146 | 420 |
| 23 | 2.2 | 5,200 | 142 | 32 |
| 24 | 4.6 | 6,600 | 17 | 26 |
| 25 | 2.4 | >100,000 | 2,300 | 25 |
| 26 | 5.3 | >100,000 | 9.4 | 14 |
| 27 | 2.5 | >100,000 | 63 | 5.4 |
| 28 | 45 | | | 1,100 |
| 29 | 1.2 | 2,600 | 28 | 25 |
| 30 | 0.61 | 1,900 | 1,700 | 13 |
| 31 | 47 | | | |
| 32 | 2.2 | 93,000 | 51 | >100,000 |
| 33 | 31 | | | |
| 34 | 0.6 | 6,100 | 363 | 13 |
| 35 | 6.6 | 1,500 | 503 | 14 |
| 36 | 1.2 | >100,000 | 3,353 | 23 |
| 37 | 1.8 | >100,000 | >10,000 | 16 |
| 38 | 4.4 | 19,600 | 112 | <100 |
| 39 | 1.7 | 5,700 | 2,100 | 30 |
| 40 | 1.1 | 80 | 619 | 25 |
| 41 | 0.6 | 780 | 174 | 17 |
| 42 | 0.47 | 18,400 | <0.01 | 1 |
| 43 | 0.62 | >100,000 | 196 | <100 |
| 44 | 1.3 | 68,300 | 65 | <100 |
| 45 | 0.21 | 198 | <10 | 1.6 |
| 46 | 0.32 | 120 | <10 | 0.76 |
| 47 | 2.8 | | | 1200 |
| 48 | 0.56 | >100,000 | >10,000 | 0.79 |
| 49 | 0.2 | >100,000 | 800 | 2.1 |
| 50 | 1 | >10,000 | 510 | <100* |
| 51 | 2.0 | >100,000 | 5,600 | >10,000 |
| 52 | 1.2 | 50,000 | 3,600 | 24 |
| 53 | 2.5 | | | <30 |
| 54 | 0.4 | >100,000 | >10,000 | <100 |
| 55 | 0.3 | >100,000 | 1,500 | 1 |
| 56 | 0.75 | 5,100 | >10,000 | 110 |
| 57 | 0.38 | 1,250 | >10,000 | <100 |
| 58 | 0.63 | >100,000 | >10,000 | <100 |
| 59 | 0.62 | >100,000 | >10,000 | <100 |
| 60 | 1.3 | | | <100 |
| 61 | 0.65 | 62,000 | 998 | <100 |
| 62 | 0.53 | >100,000 | 117 | <100 |
| 63 | 1 | >100,000 | >10,000 | <30 |
| 64 | 3.2 | 6,030 | >10,000 | <30 |
| 65 | 0.93 | >100,000 | >10,000 | <30 |
| 66 | 0.66 | >100,000 | >10,000 | 3.9 |
| 67 | 0.77 | >100,000 | >10,000 | 11 |
| 68 | 0.82 | 37,800 | >10,000 | 2.7 |
| 69 | 0.63 | 4,910 | 1,097 | 11 |
| 70 | 0.63 | >100,000 | 1,620 | <30 |
| 71 | 1 | 17,300 | 240 | <30 |
| 72 | 1.1 | 4,890 | 1,455 | 59 |
| 73 | 0.98 | >100,000 | >10,000 | 67 |
| 74 | 0.84 | >100,000 | >10,000 | 282 |
| 75 | 0.93 | >100,000 | >10,000 | <100* |
| 76 | 0.64 | >100,000 | >10,000 | <100* |
| 77 | 0.8 | >100,000 | >10,000 | 18 |
| 78 | 1 | >100,000 | >10,000 | 0.2 |
| 79 | 0.47 | >100,000 | 7900 | 2.2 |
| 80 | 1.1 | >100,000 | >10,000 | 12 |
| 81 | 0.54 | >100,000 | 7,520 | <100 |
| 82 | 0.8 | >100,000 | 18,000 | <100* |
| 83 | 0.88 | >100,000 | 2,460 | <30 |
| 84 | 0.78 | >100,000 | 3,000 | <10 |
| 85 | 0.62 | >100,000 | 1,800 | <10 |
| 86 | 0.62 | >100,000 | 1,230 | <100 |
| 87 | 1 | >100,000 | 22 | <100* |
| 88 | 1.1 | >100,000 | 9,600 | <10 |
| 89 | 0.6 | >100,000 | >10,000 | 4.7 |
| 90 | 1.4 | >100,000 | >10,000 | 19 |
| 91 | 1.5 | | | 13 |
| 92 | 1.1 | 9,6900 | 1,350 | 41 |
| 93 | 0.48 | >10,000 | 221 | <100 |
| 94 | 2 | >100,000 | 2,630 | 120 |
| 95 | 0.69 | >100,000 | 1,460 | 37 |
| 96 | 0.51 | >100,000 | 390 | <100 |
| 97 | 0.68 | 22,500 | >10,000 | <30 |
| 98 | 4.7 | 76,400 | 9,320 | 68 |
| 99 | 0.82 | >100,000 | 6,424 | <100 |
| 100 | 0.92 | 39,300 | 162 | 27 |
| 101 | 0.9 | 58,000 | 300 | 34 |
| 102 | 0.2 | >100,000 | >10,000 | 28 |
| 103 | 0.6 | 26,500 | 1,200 | 2.5 |
| 104 | 3 | | | 54 |
| 105 | 0.83 | 65,200 | 9,640 | 180 |
| 106 | 4.7 | >100,000 | >10,000 | 310 |
| 107 | 2.8 | >100,000 | >10,000 | no inhibitory activity |
| 108 | 2.2 | >100,000 | >10,000 | 3,500 |
| 109 | 8.1 | | | 740 |
| 110 | 4.2 | | no inhibitory activity | no inhibitory activity |
| 111 | 2.8 | | no inhibitory activity | no inhibitory activity |
| 112 | 2.5 | | no inhibitory activity | no inhibitory activity |
| 113 | 2.3 | | | <1000** |
| 114 | 3.1 | >100,000 | >10,000 | no inhibitory activity |
| 115 | 1.5 | >100,000 | 980 | <100 |
| 116 | 0.72 | >100,000 | 6,020 | <100 |
| 117 | 0.21 | >100,000 | 32 | 2.5 |
| 118 | 0.34 | >100,000 | 3,040 | 1.7 |
| 119 | 0.94 | | | <100 |
| 120 | 1.4 | >100,000 | >10,000 | 110 |
| 121 | 0.7 | >100,000 | 456 | <100 |
| 122 | 0.77 | | | <100 |
| 123 | 1.3 | >100,000 | 3,220 | <100 |
| 124 | 0.89 | >100,000 | >10,000 | <100 |
| 125 | 1.2 | | | <100 |
| 126 | 0.87 | >100,000 | 133 | <100 |
| 127 | 1.6 | >100,000 | 617 | <100 |
| 128 | 0.82 | | | <100 |
| 129 | 0.45 | >100,000 | 10 | <1 |
| 130 | 0.39 | 26,000 | 20 | 1-10 |
| 131 | 8.2 | | | 4,200 |
| 132 | 0.54 | 62,000 | 850 | 280 |
| 133 | 0.84 | >100,000 | >10,000 | 220 |
| 134 | 0.55 | >100,000 | >10,000 | 1,200 |
| 135 | 3.2 | | | 520 |
| 136 | 0.62 | | | 6,100 |
| 137 | 0.5 | 34,000 | 3,790 | 120 |
| 138 | 0.7 | 84,000 | 1,100 | 240 |
| 139 | 0.53 | >100,000 | 394 | 370 |
| 140 | 0.79 | 3,400 | 3,100 | 13,000 |
| 141 | 0.88 | >100,000 | 7,090 | 110 |
| 142 | 0.63 | >100,000 | 4,720 | 57 |
| 143 | 0.43 | 112,000 | 5,340 | 12 |
| 144 | 3.3 | | | 1,400 |
| 145 | 0.9 | >100,000 | >10,000 | 13,000 |
| 146 | 0.7 | >100,000 | >10,000 | 17,000 |
| 147 | 0.55 | >10,000 | >10,000 | 450 |
| 148 | 0.4 | 160,000 | >10,000 | 35 |
| 149 | 0.5 | >100,000 | >10,000 | 490 |
| 150 | 0.35 | 4,800 | 170 | 480 |

*IC$_{50}$ value is between 10 and 100 nM; **IC$_{50}$ value is between 300 and 1000 nM.

TABLE 3

| Example | human VAP-1 | MAO-A | MAO-B | DAO |
|---|---|---|---|---|
| 151 | 0.52 | >10,000 | >10,000 | 98 |
| 152 | 0.5 | 7,420 | 314 | 1,300 |
| 153 | 0.39 | 96,000 | 703 | 640 |
| 154 | 0.3 | >100,000 | 3,000 | 190 |
| 155 | 0.3 | 16,000 | 4,400 | 87 |
| 156 | 0.3 | >100,000 | 26,000 | 38 |
| 157 | 0.3 | >100,000 | 3,790 | <100 |
| 158 | 0.18 | 9,600 | 1,940 | <100 |
| 159 | 0.21 | 1,510 | 74 | 1.8 |
| 160 | 0.37 | 46,200 | 137 | <100 |
| 161 | 6.5 | 6,240 | 3,140 | 2 |
| 162 | 1.6 | 3,140 | 17 | 1.6 |
| 163 | 0.56 | >100,000 | 740 | 1.3 |
| 164 | 0.25 | >100,000 | 183 | 1.4 |
| 165 | 1.9 | >100,000 | >10,000 | <30 |
| 166 | 0.23 | 20,700 | 2,420 | <30 |
| 167 | 1 | >100,000 | >10,000 | <30 |
| 168 | 0.39 | >100,000 | 159 | <30 |
| 169 | 0.28 | >100,000 | >10,000 | <30 |
| 170 | 0.74 | >100,000 | 235 | <100* |
| 171 | 0.84 | >100,000 | 1540 | <30 |
| 172 | 0.67 | >100,000 | 9070 | <30 |
| 173 | 0.41 | >100,000 | >10000 | 5.9 |
| 174 | 2.2 | >100,000 | 710 | 1,100 |
| 175 | 0.44 | 1,470 | >10,000 | <30 |
| 176 | 0.83 | 7,900 | 3,320 | <30 |
| 177 | 0.5 | >100,000 | 1,900 | 2.6 |
| 178 | 1.4 | 74,000 | 5,490 | <10 |
| 179 | 1.1 | 270,000 | 390 | 3.1 |
| 180 | 2.8 | 120,000 | 180 | 1.4 |
| 181 | 1.9 | >100,000 | 880 | 2.1 |
| 182 | 23 | | | |
| 183 | 2.5 | 13,000 | >10,000 | 350 |
| 184 | 1.4 | 14,000 | >10,000 | 110 |
| 185 | 2.4 | >100,000 | >10,000 | 2.5 |
| 186 | 0.91 | >100,000 | >10,000 | <10 |
| 187 | 0.45 | >100,000 | 940 | <10 |
| 188 | 0.6 | >100,000 | 23,000 | 4 |
| 189 | 0.53 | >100,000 | >10,000 | <30 |
| 190 | 0.6 | >100,000 | 190 | 5 |
| 191 | 0.5 | >100,000 | 1,200 | 19 |
| 192 | 1.4 | >100,000 | 250 | 0.4 |
| 193 | 2.5 | >100,000 | 1,160 | 38 |
| 194 | 1.2 | >100,000 | 2,710 | 2.9 |
| 195 | 0.66 | >100,000 | 620 | <30 |
| 196 | 1.1 | >100,000 | >10000 | 11 |
| 197 | 0.08 | 81,000 | 250 | 2.6 |
| 198 | 2.9 | >100,000 | >10,000 | 130 |
| 199 | 4.6 | >100,000 | 1,900 | <100** |
| 200 | 0.2 | >100,000 | 1,100 | 1.6 |
| 201 | 1.3 | >100,000 | >10,000 | 17 |
| 202 | 1.0 | >100,000 | 1,300 | 240 |
| 203 | 1.8 | 12,000 | 73 | 3 |
| 204 | 0.87 | >100,000 | 85 | <10 |
| 205 | 1 | >100,000 | 240 | <10 |
| 206 | 0.7 | >100,000 | 110 | <10 |
| 207 | 0.45 | >100,000 | 1,400 | <10 |
| 208 | 0.89 | >100,000 | >10,000 | <10 |
| 209 | 0.63 | >100,000 | 17 | <10 |
| 210 | 52 | >100,000 | >10,000 | 4,400 |
| 211 | 49 | >100,000 | >10,000 | 3,500 |
| 212 | 45 | >100,000 | >10,000 | 2,200 |
| 213 | 29 | >100,000 | >10,000 | 1,800 |
| 214 | 23 | >100,000 | >100,000 | 1,400 |
| 215 | 14 | 96,000 | 3,500 | 290 |
| 216 | 88 | >100,000 | >10,000 | 4,200 |
| 217 | 2.2 | >100,000 | 110 | <100 |
| 218 | 1.9 | >100,000 | 49 | <100 |
| 219 | 2.3 | >100,000 | 41 | <100 |
| 220 | 1.8 | >100,000 | 396 | <100 |
| 221 | 1.9 | >100,000 | 650 | <100 |
| 222 | 0.94 | 770 | 22 | <100 |
| 223 | 2.2 | 21,700 | 10.5 | <100 |
| 224 | 1.3 | >100,000 | 49 | <100 |
| 225 | 1 | >100,000 | 53 | <100 |
| 226 | 1.4 | >100000 | 11.4 | <100 |

TABLE 3-continued

| Example | human VAP-1 | MAO-A | MAO-B | DAO |
|---|---|---|---|---|
| 227 | 0.61 | >100,000 | 164 | 0.24 |
| 228 | 0.38 | >100,000 | 9.2 | <100 |
| 229 | 0.98 | 130 | 12 | <100 |
| 230 | 0.53 | | | 2.7 |
| 231 | 0.94 | | | 0.086 |
| 232 | 0.78 | 24 | <100 | <100 |
| 233 | 1.7 | | | 1.2 |
| 234 | 0.98 | <100 | 10.1 | <100 |
| 235 | 0.43 | >100,000 | 2,580 | <100 |
| 236 | 0.8 | >10,000 | 16 | 6.4 |
| 237 | 2.4 | 20,000 | <100 | 170 |
| 238 | 0.9 | 34,000 | 1,600 | 15 |
| 239 | 1.6 | >100,000 | 230 | 1,600 |
| 240 | 1 | >100,000 | >10,000 | 4 |
| 241 | 0.5 | >100,000 | >10,000 | 1 |
| 242 | 1.5 | >100,000 | >10,000 | 21 |
| 243 | 0.6 | >100,000 | 940 | 18 |
| 244 | 0.8 | >100,000 | 100 | 12 |
| 245 | 0.9 | >100,000 | 300 | 11 |
| 246 | 0.5 | >100,000 | 130 | 12 |
| 247 | 0.3 | >100,000 | 4300 | 14 |
| 248 | 0.5 | >100,000 | >10,000 | 36 |
| 249 | 0.4 | >100,000 | 2,000 | 8 |
| 250 | 0.7 | >100,000 | >10,000 | 74 |
| 251 | 0.3 | >100,000 | >10,000 | 21 |
| 252 | 0.6 | >100,000 | >10,000 | 53 |
| 253 | 0.5 | >100,000 | >10,000 | 34 |
| 254 | 0.2 | >100,000 | >10,000 | 35 |
| 255 | 0.2 | >100,000 | 6,100 | 20 |
| 256 | 0.3 | >100,000 | >10,000 | 27 |
| 257 | 0.4 | >100,000 | 5,700 | 90 |
| 258 | 0.2 | >100,000 | 59,000 | 1.3 |
| 259 | 1.4 | >100,000 | >100,000 | 29,000 |

*$IC_{50}$ value is between 30 and 100 nM; **$IC_{50}$ value is between 10 and 100 nM.

From the results of Tables 2 and 3 above, it can be seen that the compounds according to the present technology generally have excellent selective inhibitory activity on VAP-1 among various amine oxidases.

Para. A. A compound of Formula X, or an isomer thereof, or a pharmaceutically acceptable salt thereof:

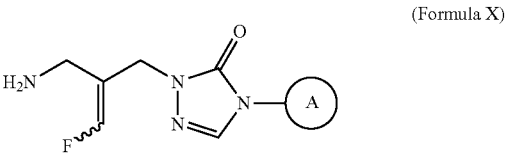

(Formula X)

wherein

A is an aryl or heteroaryl group, said heteroaryl group has 1 to 5 heteroatom ring members chosen from O, N, or S, and said aryl or heteroaryl group is optionally substituted with one to three substituents chosen from $C_{1-3}$ alkyl, $C_{1-3}$ alkoxy, halogen, benzyloxy, —R, —$CH_2$—R, —CH=CH—R, and —C≡C—R; and R is substituted or unsubstituted cyclic ring, optionally containing 1 to 5 heteroatom ring members chosen from O, N, or S, and the cyclic ring is aromatic or non-aromatic.

Para. B. The compound of Para. A, wherein A is selected from phenyl, naphthalene, pyridine, pyrimidine, pyrazine, triazine, thiazole, thiophene, pyrrole, pyrazole, imidazole, triazole, tetrazole, furan, oxazole, isoxazole, oxadiazole, and thiadiazole.

Para. C. The compound of Para. A or Para. B, wherein A is selected from phenyl, pyridine, pyrazine, and thiazole.

Para. D. A compound of Formula 1 below (Formula 1)

or an isomer thereof, or a pharmaceutically acceptable salt thereof;
wherein
A is an aryl or heteroaryl group selected from the group consisting of phenyl, pyridine, pyrazine, and thiazole,
wherein said aryl or heteroaryl group is optionally substituted with one to three substituents selected from the group consisting of $C_{1-3}$ alkyl, $C_{1-3}$ alkoxy, halogen, benzyloxy, —R, —CH$_2$—R, —CH=CH—R, and —C≡C—R,
wherein said R is a cyclic ring selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan,
wherein said cyclic ring is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$ alkyl sulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, oxazolyl, oxadiazolyl, cyclopropyl-oxadiazolyl, $C_{1-6}$ alkyl-oxadiazolyl, and oxadiazol-5-onyl.

Para. E. The compound, or an isomer thereof, or a pharmaceutically acceptable salt thereof, of any one of Paras. A-D, wherein A is pyridine.

Para. F. The compound, or an isomer thereof, or a pharmaceutically acceptable salt thereof, of any one of Paras. A-D, wherein said aryl or heteroaryl group is substituted with one or two substituents selected from the group consisting of $C_{1-3}$ alkyl, halogen, —R, and —C≡C—R.

Para. G. The compound, or an isomer thereof, or a pharmaceutically acceptable salt thereof, of any one of Paras. A-F, wherein said R is a cyclic ring selected from the group consisting of benzene, pyridine, and pyrazole.

Para. H. The compound, or an isomer thereof, or a pharmaceutically acceptable salt thereof, of Para. G, wherein said cyclic ring is unsubstituted; or substituted with a substituent selected from the group consisting of $C_{1-6}$ alkyl, trifluoromethyl, and oxazolyl.

Para. I. The compound, or an isomer thereof, or a pharmaceutically acceptable salt thereof, of any one of Paras. A-D, wherein
A is pyridine,
wherein said pyridine is substituted with one or two substituents selected from the group consisting of $C_{1-3}$ alkyl, halogen, —R, and —C≡C—R,
wherein said R is a cyclic ring selected from the group consisting of benzene, pyridine, and pyrazole,
wherein said cyclic ring is unsubstituted; or substituted with a substituent selected from the group consisting of $C_{1-6}$ alkyl, trifluoromethyl, and oxazolyl.

Para. J. The compound, or an isomer thereof, or a pharmaceutically acceptable salt thereof, of any one of Paras. A-D, which is selected from Table 1, or an isomer thereof, or a pharmaceutically acceptable salt thereof.

Para. K. A compound of Formula 10:

(Formula 10)

or an isomer thereof, or a pharmaceutically acceptable salt thereof,
wherein
R is a substituted or unsubstituted cyclic ring, optionally containing at least one heteroatom, and the cyclic ring is aromatic or non-aromatic; and
$R^a$ is hydrogen, $C_{1-3}$ alkyl, $C_{1-3}$ alkoxy, or halogen.

Para. L. The compound of Para. K of Formula 10a:

(Formula 10a)

or an isomer thereof, or a pharmaceutically acceptable salt thereof.

Para. M. The compound of Para. K of Formula 10b:

(Formula 10b)

or an isomer thereof, or a pharmaceutically acceptable salt thereof.

Para. N. A compound of Formula 11:

(Formula 11)

or an isomer thereof, or a pharmaceutically acceptable salt thereof,
wherein
R is a substituted or unsubstituted cyclic ring, optionally containing at least one heteroatom, and the cyclic ring is aromatic or non-aromatic; and
$R^a$ is hydrogen, $C_{1-3}$ alkyl, $C_{1-3}$ alkoxy, or halogen.

Para. O. The compound of Para. N of Formula 11a:

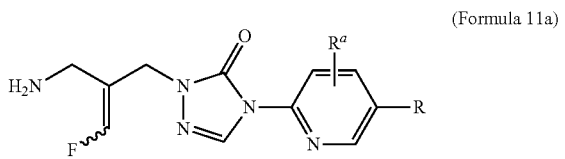
(Formula 11a)

or an isomer thereof, or a pharmaceutically acceptable salt thereof.

Para. P. The compound of Para. N of Formula 11b:

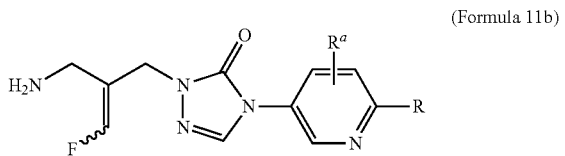
(Formula 11b)

or an isomer thereof, or a pharmaceutically acceptable salt thereof.

Para. Q. The compound of Para. N of Formula 11c:

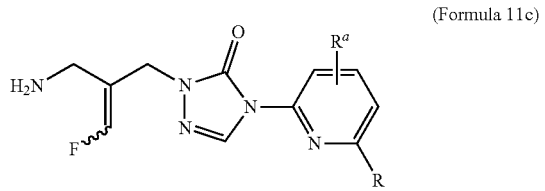
(Formula 11c)

or an isomer thereof, or a pharmaceutically acceptable salt thereof.

Para. R. The compound of Para. N of Formula 11d:

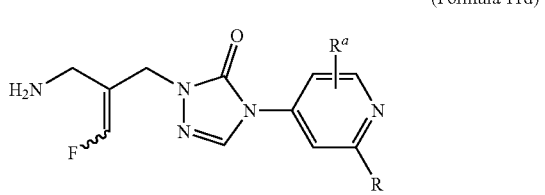
(Formula 11d)

or an isomer thereof, or a pharmaceutically acceptable salt thereof.

Para. S. The compound of Para. N of Formula 11e:

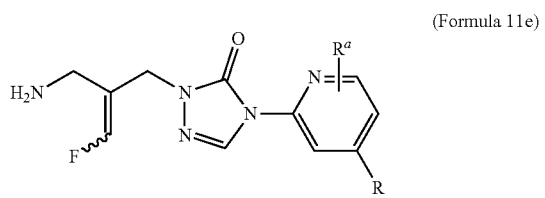
(Formula 11e)

or an isomer thereof, or a pharmaceutically acceptable salt thereof.

Para. T. A compound of Formula 12:

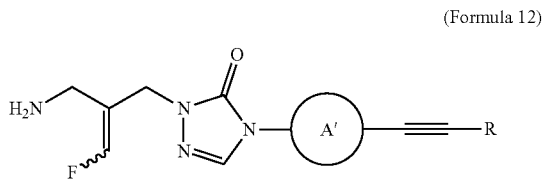
(Formula 12)

or an isomer thereof, or a pharmaceutically acceptable salt thereof,
wherein
A' is pyridine; and
R is a substituted or unsubstituted cyclic ring, optionally containing at least one heteroatom, and the cyclic ring is aromatic or non-aromatic.

Para. U. The compound of any one of Paras. A-C or K-T, or an isomer thereof, or a pharmaceutically acceptable salt thereof, wherein R is selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan; and
R is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$alkylsulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, isoxazolyl, oxazolyl, oxadiazolyl, cyclopropyl-oxadiazolyl, $C_{1-6}$ alkyl-oxadiazolyl, and oxadiazol-5-onyl.

Para. V. A pharmaceutical composition comprising, consisting essentially of, or consisting of the compound according to any one of Paras. A-U, or an isomer thereof, or a pharmaceutically acceptable salt thereof, and at least one pharmaceutically acceptable excipient.

Para. W. A method of selectively inhibiting vascular adhesion protein (VAP-1), comprising administering, to a mammal, a therapeutically effective amount of the compound, or the isomer thereof, or a pharmaceutically acceptable salt thereof according to any one of Paras. A-U.

Para. X. A method of selectively inhibiting vascular adhesion protein (VAP-1), consisting essentially of or consisting of administering, to a mammal, a therapeutically effective amount of the compound, or the isomer thereof, or a pharmaceutically acceptable salt thereof according to any one of Paras. A-U.

Para. Y. A method of selectively inhibiting vascular adhesion protein (VAP-1), comprising administering, to a mammal, a therapeutically effective amount of the composition according to Para. V.

Para. Z. A method of treating NASH in a subject in need thereof, the method comprising, consisting essentially of, or consisting of administering to the subject a therapeutically effective amount of the compound according to any one of Paras. A-U, or an isomer thereof, or a pharmaceutically acceptable salt thereof, or a therapeutically effective amount of the pharmaceutical composition according to Para. V.

Para. AA. Use of the compound according to any one of Paras. A-U, or an isomer thereof, or a pharmaceutically acceptable salt thereof, for the manufacture of a medicament for the treatment of NASH.

Para. AB. A compound according any one of Paras. A-U, or an isomer thereof, or a pharmaceutically acceptable salt thereof, for use in treating NASH.

Para. AC. A composition according to Para. V for use in treating NASH.

Para. AD. A compound according any one of Paras. A-U, or an isomer thereof, or a pharmaceutically acceptable salt thereof, for use in selectively inhibiting VAP-1.

Para. AE. A composition according to Para. V for use in selectively inhibiting VAP-1.

Para. AF. A method of treating a disease mediated by VAP-1 in a subject in need thereof, the method comprising, consisting essentially of, or consisting of administering to the subject a therapeutically effective amount of the compound according to any one of Paras. A-U, or an isomer thereof, or a pharmaceutically acceptable salt thereof, or a therapeutically effective amount of the pharmaceutical composition according to Para. V.

Para. AG. The method of Para. AF, wherein the disease mediated by VAP-1 is selected from the group consisting of lipid and lipoprotein disorders, conditions and diseases which result from chronic fatty and fibrotic degeneration of organs due to accumulated lipid and specifically triglyceride accumulation and subsequent activation of profibrotic pathways, Type I or Type II Diabetes and clinical complications of Type I and Type II Diabetes, chronic intrahepatic or some forms of extrahepatic cholestatic conditions, liver fibrosis, acute intraheptic cholestatic conditions, obstructive or chronic inflammatory disorders that arise out of improper bile composition, gastrointestinal conditions with a reduced uptake of dietary fat and fat-soluble dietary vitamins, inflammatory bowel diseases, obesity and metabolic syndrome (combined conditions of dyslipidemia, diabetes and abnormally high body-mass index), persistent infections by intracellular bacteria or parasitic protozoae, non-malignant hyperproliferative disorders, malignant hyperproliferative disorders, colon adenocarcinoma and hepatocellular carcinoma in particular, liver steatosis and associated syndromes, Hepatitis B infection, Hepatitis C infection and/or of cholestatic and fibrotic effects that are associated with alcohol-induced cirrhosis or with viral-borne forms of hepatitis, liver failure or liver malfunction as an outcome of chronic liver diseases or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

Para. AH. A method of preparing a compound of Formula 1a, or an isomer thereof, or a pharmaceutically acceptable salt thereof,

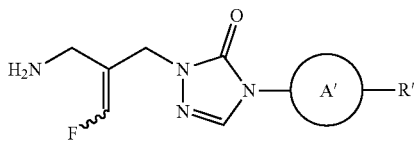

(Formula 1a)

the method comprising
(a) reacting a compound of Formula 2 with a compound of Formula 3a or a compound of Formula 3b to obtain a compound of Formula 1aa;

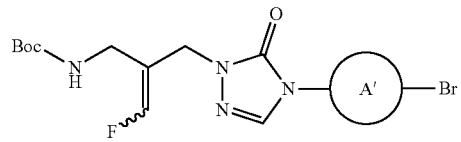

(Formula 2)

Z$_2$—B—R'  (Formula 3a)

HC≡CR'  (Formula 3b)

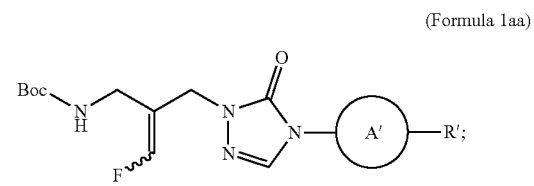

(Formula 1aa)

wherein
Boc is an amine protecting group;
A' is an aryl or heteroaryl group selected from the group consisting of phenyl, pyridine, pyrazine, and thiazole;
Z is hydroxy or C$_{1-3}$ alkoxy, or two Z together with the boron to which they are attached form

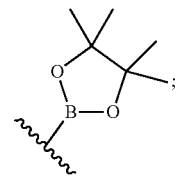 [SMILES: *B1OC(C)(C)C(C)(C)O1]

R' is one to three groups independently selected from the group consisting of —R, —CH$_2$—R, —CH=CH—R, and —C≡C—R; and R is a substituted or unsubstituted cyclic ring, optionally containing at least one heteroatom, and the cyclic ring is aromatic or non-aromatic; and (b) removing Boc from the compound of Formula 1aa under reaction conditions to obtain the compound of Formula 1a, or the isomer thereof, or the pharmaceutically acceptable salt thereof.

Para. AI. The method of Para. AH, wherein the cyclic ring is selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan;

wherein said cyclic ring is optionally substituted with one or two substituents selected from the group consisting of hydroxy, halogen, C$_{1-6}$ alkyl, trifluoromethyl, C$_{1-6}$ alkoxy, trifluoromethoxy, amino, mono- or di-C$_{1-6}$ alkylamino, C$_{1-6}$ alkylcarbonylamino, $C_{1-6}$ alkylthio, mono- or di-$C_{1-6}$ alkylaminosulfonyl, $C_{1-6}$ alkyl sulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, isoxazolyl, oxazolyl, oxadiazolyl, cyclopropyl-oxadiazolyl, $C_{1-6}$ alkyl-oxadiazolyl, and oxadiazol-5-onyl.

What is claimed is:

1. A compound of Formula X, or a stereoisomer or a tautomer thereof, or a pharmaceutically acceptable salt thereof:

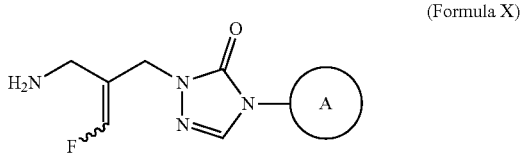

(Formula X)

wherein

A is thiazole optionally substituted with one to three substituents chosen from $C_{1-3}$ alkyl, $C_{1-3}$ alkoxy, halogen, benzyloxy, —R, —CH$_2$—R, —CH=CH—R, and —C≡C—R; and R is substituted or unsubstituted cyclic ring, optionally containing 1 to 5 heteroatom ring members independently chosen from O, N, and S, and the cyclic ring is aromatic or non-aromatic.

2. The compound, or a stereoisomer or a tautomer thereof, or a pharmaceutically acceptable salt thereof, according to claim 1, wherein A is

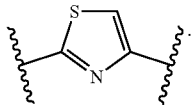

3. The compound, or a stereoisomer or a tautomer thereof, or a pharmaceutically acceptable salt thereof, according to claim 1, wherein said R is a cyclic ring selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan, and R is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$ alkyl sulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, isoxazolyl, oxazolyl, oxadiazolyl, cyclopropyl-oxadiazolyl, $C_{1-6}$ alkyl-oxadiazolyl, and oxadiazol-5-onyl.

4. A pharmaceutical composition comprising the compound according to claim 1, or a stereoisomer or a tautomer thereof, or a pharmaceutically acceptable salt thereof, and at least one pharmaceutically acceptable excipient.

5. A method of selectively inhibiting vascular adhesion protein (VAP-1), comprising administering, to a mammal in need thereof, a therapeutically effective amount of the compound according to claim 1, or a stereoisomer or a tautomer thereof, or a pharmaceutically acceptable salt thereof.

6. A method of treating NASH in a subject in need thereof, the method comprising administering to the subject a therapeutically effective amount of the compound according to claim 1, or a stereoisomer or a tautomer thereof, or a pharmaceutically acceptable salt thereof.

7. A method of treating a disease mediated by VAP-1 in a subject in need thereof, the method comprising administering to the subject a therapeutically effective amount of the compound according to claim 1, or a stereoisomer or a tautomer thereof, or a pharmaceutically acceptable salt thereof.

8. The method according to claim 7, wherein the disease mediated by VAP-1 is selected from the group consisting of a lipid disorder, lipoprotein disorder, condition or disease which results from chronic fatty or fibrotic degeneration of organs due to accumulated lipid, triglyceride accumulation and subsequent activation of a profibrotic pathway, Type I Diabetes, Type II Diabetes, clinical complication of Type I or Type II Diabetes, chronic intrahepatic cholestatic condition, extrahepatic cholestatic condition, liver fibrosis, acute intrahepatic cholestatic condition, obstructive or chronic inflammatory disorder that arises out of improper bile composition, gastrointestinal condition with a reduced uptake of dietary fat or fat-soluble dietary vitamin, inflammatory bowel disease, obesity, metabolic syndrome, combined conditions of dyslipidemia, diabetes and abnormally high body-mass index, persistent infection by intracellular bacteria or parasitic protozoae, non-malignant hyperproliferative disorder, malignant hyperproliferative disorders, colon adenocarcinoma and hepatocellular carcinoma, liver steatosis or associated syndrome, Hepatitis B infection, Hepatitis C infection, cholestatic and fibrotic effects that are associated with alcohol-induced cirrhosis or with viral-borne forms of hepatitis, liver failure or liver malfunction as an outcome of chronic liver disease or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

9. A compound of Formula X, or a stereoisomer or a tautomer thereof, or a pharmaceutically acceptable salt thereof:

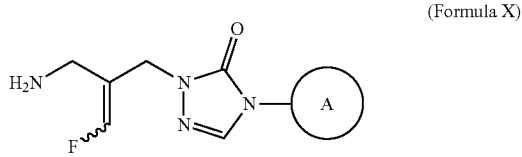

(Formula X)

wherein

A is pyrazine optionally substituted with one to three substituents chosen from $C_{1-3}$ alkyl, $C_{1-3}$ alkoxy, halogen, benzyloxy, —R, —CH$_2$—R, —CH=CH—R, and —C≡C—R; and R is substituted or unsubstituted cyclic ring, optionally containing 1 to 5 heteroatom ring members independently chosen from O, N, and S, and the cyclic ring is aromatic or non-aromatic.

10. The compound, or a stereoisomer or a tautomer thereof, or a pharmaceutically acceptable salt thereof, according to claim 9, wherein said R is a cyclic ring selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan, and R is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$ alkyl sulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, isoxazolyl, oxazolyl, oxadiazolyl, cyclopropyl-oxadiazolyl, $C_{1-6}$ alkyl-oxadiazolyl, and oxadiazol-5-onyl.

11. A pharmaceutical composition comprising the compound according to claim 9, or a stereoisomer or a tautomer thereof, or a pharmaceutically acceptable salt thereof, and at least one pharmaceutically acceptable excipient.

12. A method of selectively inhibiting vascular adhesion protein (VAP-1), comprising administering, to a mammal in need thereof, a therapeutically effective amount of the compound according to claim 9, or a stereoisomer or a tautomer thereof, or a pharmaceutically acceptable salt thereof.

13. A method of treating NASH in a subject in need thereof, the method comprising administering to the subject a therapeutically effective amount of the compound according to claim 9, or a stereoisomer or a tautomer thereof, or a pharmaceutically acceptable salt thereof.

14. A method of treating a disease mediated by VAP-1 in a subject in need thereof, the method comprising administering to the subject a therapeutically effective amount of the compound according to claim 9, or a stereoisomer or a tautomer thereof, or a pharmaceutically acceptable salt thereof.

15. The method according to claim 14, wherein the disease mediated by VAP-1 is selected from the group consisting of a lipid disorder, lipoprotein disorder, condition or disease which results from chronic fatty or fibrotic degeneration of organs due to accumulated lipid, triglyceride accumulation and subsequent activation of a profibrotic pathway, Type I Diabetes, Type II Diabetes, clinical complication of Type I or Type II Diabetes, chronic intrahepatic cholestatic condition, extrahepatic cholestatic condition, liver fibrosis, acute intrahepatic cholestatic condition, obstructive or chronic inflammatory disorder that arises out of improper bile composition, gastrointestinal condition with a reduced uptake of dietary fat or fat-soluble dietary vitamin, inflammatory bowel disease, obesity, metabolic syndrome, combined conditions of dyslipidemia, diabetes and abnormally high body-mass index, persistent infection by intracellular bacteria or parasitic protozoae, non-malignant hyperproliferative disorder, malignant hyperproliferative disorders, colon adenocarcinoma and hepatocellular carcinoma, liver steatosis or associated syndrome, Hepatitis B infection, Hepatitis C infection, cholestatic and fibrotic effects that are associated with alcohol-induced cirrhosis or with viral-borne forms of hepatitis, liver failure or liver malfunction as an outcome of chronic liver disease or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

16. A method of preparing a compound of Formula 1a, or a stereoisomer or a tautomer thereof, or a pharmaceutically acceptable salt thereof,

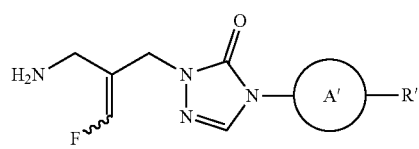

(Formula 1a)

the method comprising
(a) reacting a compound of Formula 2 with a compound of Formula 3a or a compound of Formula 3b to obtain a compound of Formula 1aa;

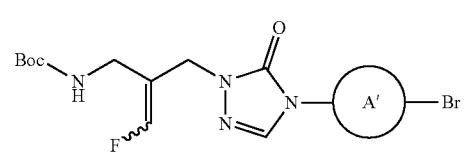

(Formula 2)

$(Z)_2$—B—R'     (Formula 3a)

HC≡CR     (Formula 3b)

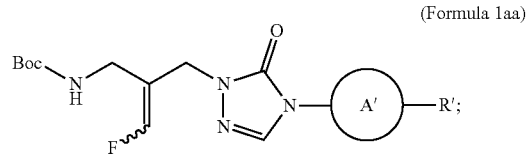

(Formula 1aa)

wherein
Boc is an amine protecting group;
A' is an aryl or heteroaryl group selected from the group consisting of phenyl, pyridine, pyrazine, and thiazole;
Z is hydroxy or $C_{1-3}$ alkoxy, or two Z together with the boron to which they are attached form

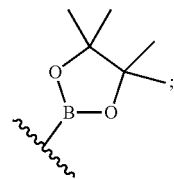 [SMILES: *B1OC(C)(C)C(C)(C)O1]

R' is one to three groups independently selected from the group consisting of —R, —CH$_2$—R, —CH=CH—R, and —C≡C—R; and R is a substituted or unsubstituted cyclic ring, optionally containing at least one heteroatom, and the cyclic ring is aromatic or non-aromatic; and (b) removing Boc from the compound of Formula 1aa under reaction conditions to obtain the compound of Formula 1a, or the stereoisomer or tautomer thereof, or the pharmaceutically acceptable salt thereof.

17. The method according to claim 16, wherein the cyclic ring is selected from the group consisting of benzene, phenylbenzene, pyridine, tetrahydropyridine, pyridin-2-one, pyrimidine, thiophene, thiazole, imidazole, pyrazole, piperazine, morpholine, benzodioxole, benzoxadiazole, benzothiophene, benzothiazole, 2,3-dihydro-benzodioxine, indazole, indole, 1,3-dihydroindol-2-one, 1,2-dihydroindol-3-one, quinoline, isoquinoline, quinolin-2-one, 3,4-dihydroquinolin-2-one, 3,4-dihydro-1,4-benzoxazine, 1,4-benzoxazin-3-one, 3,1-benzoxazin-2-one, 2,3-dihydro-imidazo[4,5-b]pyridine, oxazolo[4,5-b]pyridin-2-one, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, and dibenzo[b,d]furan;

wherein said cyclic ring is optionally substituted with one or two substituents selected from the group consisting of hydroxy, halogen, $C_{1-6}$ alkyl, trifluoromethyl, $C_{1-6}$ alkoxy, trifluoromethoxy, amino, mono- or di-$C_{1-6}$ alkylamino, $C_{1-6}$ alkylcarbonylamino, $C_{1-6}$ alkylthio, mono- or di-$C_{1-6}$ alkylaminosulfonyl, $C_{1-6}$ alkyl sulfonyl, $C_{1-6}$ alkylcarbonyl, morpholinylcarbonyl, benzodioxolyl, pyrrolidinyl, piperazinyl, acetylpiperazinyl, morpholinyl, tetrahydropyranyl, triazolyl, tetrazolyl, isoxazolyl, oxazolyl, oxadiazolyl, cyclopropyl-oxadiazolyl, $C_{1-6}$ alkyl-oxadiazolyl, and oxadiazol-5-onyl.

* * * * *